(12) United States Patent
Nadzan et al.

(10) Patent No.: US 10,428,344 B2
(45) Date of Patent: Oct. 1, 2019

(54) NUCLEOTIDE SEQUENCES AND CORRESPONDING POLYPEPTIDES CONFERRING MODIFIED PHENOTYPE CHARACTERISTICS IN PLANTS

(71) Applicant: CERES, INC., Thousand Oaks, CA (US)

(72) Inventors: Gregory Nadzan, Woodland Hills, CA (US); Richard Schneeberger, Carlsbad, CA (US); Han Suk Kim, Camarillo, CA (US); David Van-dinh Dang, San Diego, CA (US); Kenneth A. Feldmann, Tucson, AZ (US); Roger Pennell, Malibu, CA (US); Shing Kwok, Woodland Hills, CA (US); Hongyu Zhang, Thousand Oaks, CA (US); Cory Christensen, Sherwood, CA (US); Jack Okamuro, Oak Park, CA (US); Fasong Zhou, Oxnard, CA (US); Wuyi Wang, Newbury Park, CA (US); Emilio Margolles-Clark, Miami, FL (US); Gerard Magpantay, Calabasas, CA (US); Julissa Sosa, Northridge, CA (US); Nestor Apuya, Culver City, CA (US); Kerstin Piccolo, Woodland Hills, CA (US); Bonnie Hund, Denver, CO (US); Nickolai Alexandrov, Thousand Oaks, CA (US); Vyacheslav Brover, Simi Valley, CA (US); Peter Mascia, Thousand Oaks, CA (US)

(73) Assignee: CERES, INC., Thousand Oaks, CA (US)

( * ) Notice: Subject to any disclaimer, the term of this patent is extended or adjusted under 35 U.S.C. 154(b) by 810 days.

(21) Appl. No.: 14/627,544

(22) Filed: Feb. 20, 2015

(65) Prior Publication Data

US 2015/0259699 A1 Sep. 17, 2015

Related U.S. Application Data

(60) Continuation-in-part of application No. 13/644,359, filed on Oct. 4, 2012, now Pat. No. 9,777,287, which is a continuation-in-part of application No. 13/465,846, filed on May 7, 2012, now abandoned, which is a division of application No. 10/572,827, filed as application No. PCT/US03/25997 on Aug. 18, 2003, now Pat. No. 8,193,409, application No. 14/627,544, which is a continuation-in-part of application No. 14/175,856, filed on Feb. 7, 2014, now abandoned, which is an application for the reissue of Pat. No. 8,110,724, filed as application No. PCT/US2007/006651 on Mar. 14, 2007, said application No. 13/644,359 is a continuation-in-part of application No. 11/779,266, filed on Jul. 17, 2007, now abandoned, which is a continuation-in-part of application No. 11/778,060, filed on Jul. 15, 2007, now abandoned, which is a continuation-in-part of application No. 11/248,547, filed on Oct. 12, 2005, now Pat. No. 7,244,879, said application No. 13/644,359 is a continuation-in-part of application No. 12/514,991, filed as application No. PCT/US2007/085007 on Nov. 16, 2007, now abandoned, said application No. 13/644,359 is a continuation-in-part of application No. 12/445,005, filed as application No. PCT/US2007/081301 on Oct. 12, 2007, now abandoned, said application No. 13/644,359 is a continuation-in-part of application No. 12/515,707, filed as application No. PCT/US2007/085439 on Nov. 21, 2007, now abandoned, said application No. 13/644,359 is a continuation-in-part of application No. 12/615,920, filed on Nov. 10, 2009, now Pat. No. 8,471,099, which is a continuation of application No.

(Continued)

(51) Int. Cl.
*C12Q 1/6895* (2018.01)
*C12N 15/82* (2006.01)
*C07K 14/415* (2006.01)

(52) U.S. Cl.
CPC ........ *C12N 15/8271* (2013.01); *C07K 14/415* (2013.01); *C12N 15/8261* (2013.01); *C12Q 1/6895* (2013.01); *Y02A 40/146* (2018.01)

(58) Field of Classification Search
CPC .................................................. C07K 14/415
See application file for complete search history.

(56) References Cited

U.S. PATENT DOCUMENTS 7,635,800 B2   12/2009 Ratcliffe et al.

FOREIGN PATENT DOCUMENTS

WO    WO 2004/031349    4/2004

OTHER PUBLICATIONS

Bowie et al., "Deciphering the Message in Protein Sequences: Tolerance to Amino Acid Substitutions," *Science* 247:1306-1310, 1990.

(Continued)

*Primary Examiner* — Johnny F Railey, II
(74) *Attorney, Agent, or Firm* — Dentons US LLP

(57) ABSTRACT

Methods and materials for modulating low-nitrogen tolerance levels in plants are disclosed. For example, nucleic acids encoding low nitrogen tolerance-modulating polypeptides are disclosed as well as methods for using such nucleic acids to transform plant cells. Also disclosed are plants having increased low-nitrogen tolerance levels and plant products produced from plants having increased low-nitrogen tolerance levels.

15 Claims, 169 Drawing Sheets

Specification includes a Sequence Listing.

Related U.S. Application Data

11/114,963, filed on Apr. 25, 2005, now Pat. No. 7,696,409, said application No. 13/644,359 is a continuation-in-part of application No. 12/605,261, filed on Oct. 23, 2009, now abandoned, which is a division of application No. 11/298,391, filed on Dec. 8, 2005, now Pat. No. 7,663,027, said application No. 13/644,359 is a continuation-in-part of application No. 12/377,106, filed as application No. PCT/US2007/075747 on Aug. 10, 2007, now abandoned, said application No. 13/644,359 is a continuation-in-part of application No. 12/541,607, filed on Aug. 14, 2009, now abandoned, which is a continuation of application No. 11/140,347, filed on May 27, 2005, now Pat. No. 7,576,260, said application No. 13/644,359 is a continuation-in-part of application No. 13/184,361, filed on Jul. 15, 2011, now Pat. No. 8,962,921, which is a division of application No. 11/140,450, filed on May 27, 2005, now Pat. No. 8,022,273, said application No. 13/644,359 is a continuation-in-part of application No. 11/654,357, filed on Jan. 16, 2007, now abandoned, said application No. 13/644,359 is a continuation-in-part of application No. 13/465,841, filed on May 7, 2012, now Pat. No. 9,765,355, which is a division of application No. 11/858,117, filed on Sep. 19, 2007, now abandoned, which is a continuation-in-part of application No. PCT/US2007/006544, filed on Mar. 14, 2007, said application No. 13/644,359 is a continuation-in-part of application No. 12/918,609, filed as application No. PCT/US2009/034638 on Feb. 20, 2009, now abandoned, said application No. 13/644,359 is a continuation-in-part of application No. 12/922,143, filed as application No. PCT/US2009/037025 on Mar. 12, 2009, now abandoned, said application No. 13/644,359 is a continuation-in-part of application No. 11/241,685, filed on Sep. 30, 2005, now Pat. No. 8,481,814, said application No. 13/644,359 is a continuation-in-part of application No. 12/863,773, filed as application No. PCT/US2009/031609 on Jan. 21, 2009, now abandoned, said application No. 13/644,359 is a continuation-in-part of application No. 12/282,342, filed as application No. PCT/US2007/006544 on Mar. 14, 2007, now Pat. No. 8,324,454, said application No. 13/644,359 is a continuation-in-part of application No. 12/776,319, filed on May 7, 2010, now abandoned, which is a division of application No. 11/324,093, filed on Dec. 29, 2005, now Pat. No. 7,803,983, which is a continuation-in-part of application No. 11/172,740, filed on Jun. 30, 2005, now Pat. No. 7,396,979, said application No. 13/644,359 is a continuation-in-part of application No. 12/911,698, filed on Oct. 25, 2010, now Pat. No. 9,914,935, which is a division of application No. 11/324,098, filed on Dec. 29, 2005, now Pat. No. 7,884,261, which is a continuation-in-part of application No. 11/172,740, filed on Jun. 30, 2005, now Pat. No. 7,396,979, said application No. 13/644,359 is a continuation-in-part of application No. 13/609,176, filed on Sep. 10, 2012, now abandoned, which is a division of application No. 12/139,269, filed on Jun. 13, 2008, now abandoned, which is a division of application No. 11/172,740, filed on Jun. 30, 2005, now Pat. No. 7,396,979.

(60) Provisional application No. 60/782,428, filed on Mar. 14, 2006, provisional application No. 60/821,639, filed on Aug. 7, 2006, provisional application No. 60/859,467, filed on Nov. 16, 2006, provisional application No. 60/851,585, filed on Oct. 12, 2006, provisional application No. 60/860,296, filed on Nov. 21, 2006, provisional application No. 60/564,659, filed on Apr. 23, 2004, provisional application No. 60/635,115, filed on Dec. 8, 2004, provisional application No. 60/635,140, filed on Dec. 8, 2004, provisional application No. 60/837,434, filed on Aug. 11, 2006, provisional application No. 60/575,309, filed on May 27, 2004, provisional application No. 60/575,253, filed on May 27, 2004, provisional application No. 60/778,568, filed on Mar. 1, 2006, provisional application No. 60/758,831, filed on Jan. 13, 2006, provisional application No. 60/782,735, filed on Mar. 14, 2006, provisional application No. 61/030,152, filed on Feb. 20, 2008, provisional application No. 61/036,396, filed on Mar. 13, 2008, provisional application No. 60/615,080, filed on Sep. 30, 2004, provisional application No. 61/022,786, filed on Jan. 22, 2008, provisional application No. 60/583,621, filed on Jun. 30, 2004, provisional application No. 60/584,829, filed on Jun. 30, 2004, provisional application No. 60/584,800, filed on Jun. 30, 2004.

(56) References Cited

OTHER PUBLICATIONS

Eddy, "What is a hidden Markov model?", *Nature Biotechnology* 22:1315-1316, 2004.
Mcconnell et al., "Role of PHABULOSA and PHAVOLUTA in determining radial patterning in shoots," *Nature* 411:709-713, 2001.
GenBank Accession No. DR750626, dated Feb. 15, 2011.
Yanagisawa, "The Dof family of plant transcription factors," *TRENDS in Plant Science* 7:555-560, 2002.

Figure 1

| SEQ_ID_NO_21 | MTNLYLT | 8 |
| SEQ_ID_NO_36 | MNPLA | 5 |
| SEQ_ID_NO_47 | MSLMIV F | 8 |
| SEQ_ID_NO_4 | MENRR SSGGSGWWVC VLP L FTKDGPAYF HSSSDDVSAW | 39 |
| SEQ_ID_NO_46 | | 0 |
| SEQ_ID_NO_39 | MDSSPSTQ DCGGWL LYVS LAAKC G GDPCRVVGFV | 34 |
| SEQ_ID_NO_40 | MDMDSSPSTQ DCGGWL LYVS LAAKC G GDPCRVVGFV | 36 |
| SEQ_ID_NO_27 | MAPSE KC-GWL LYVS LAAKCCGNGD GKPYRVVGFV | 34 |
| SEQ_ID_NO_29 | MAPPTE DC-GWL LYLS LAAKC GDPQRL LGFA | 30 |
| SEQ_ID_NO_38 | MAPSE DC-GWL LYLS LAAKC GDPHRL LGFA | 29 |
| SEQ_ID_NO_3 | MAT KLDTSSLLLA LLSKC SL LTQTNL ALSL | 30 |
| SEQ_ID_NO_25 | MST NI-DNLMI FA LASKC TQENI AYSL | 26 |
| SEQ_ID_NO_22 | MTS HI DDNLMI A LTSKC TQENL AWVL | 27 |
| SEQ_ID_NO_6 | MGS DI-ESVML FA LASKC KA FSQQNTAWP | 29 |
| SEQ_ID_NO_10 | MRT DI-DSFWI FA LASKC RA FTQENL AWSL | 29 |

| SEQ_ID_NO_21 | LLPT FIFLIVLVLS RRRNNR | 28 |
| SEQ_ID_NO_36 | LIFC TALFCI LLYH FL TRRSVR | 27 |
| SEQ_ID_NO_47 | VTIV AAI LTNRLLN LI KKPTLP | 30 |
| SEQ_ID_NO_4 | RQWPLY ALL IVAMCAVLVS MLSPGGCAWA GRH KRGRVA | 78 |
| SEQ_ID_NO_46 | | 0 |
| SEQ_ID_NO_39 | AMAV VAFAMTSLLH MLSPGPAWG RYWW NRRGGLG | 69 |
| SEQ_ID_NO_40 | AMAV VAFAMTSLLH MLSPGPAWG RYWW NRRGGLG | 71 |
| SEQ_ID_NO_27 | VVLL AAFVVTSLLH MASQGGAAWG RYWW RRKGLG | 68 |
| SEQ_ID_NO_29 | AVEV AACVVTSLLH MASPGGPAWG WYWW TRRAGLG | 65 |
| SEQ_ID_NO_38 | AVLA TAFVVTALLH MASPGGPAWG RYWW TRRAGLG | 64 |
| SEQ_ID_NO_3 | LVAS LASL ALSLFF MSHPGGPAWG KYFL HRRQTT | 65 |
| SEQ_ID_NO_25 | LIMA LLWI TMTFFY MSHPGGPAWG KYYYSSNYST TKTNNKNNLN | 70 |
| SEQ_ID_NO_22 | LIMG SLML TMTFYY MSHPGGPAWG KYYT YSPPLS | 61 |
| SEQ_ID_NO_6 | LIIA LAWL VMTI VY MWHPGGPAWS KYRF KKCAIT | 63 |
| SEQ_ID_NO_10 | LIIG LAWI VVTLIY MAYPGGPAWG KYKL KNTSLT | 63 |

Figure 1 (continued)

| | | | | | | | |
|---|---|---|---|---|---|---|---|
| SEQ_ID_NO_21 | L-------- | ----PPGPNP | APIIGNLPHM | -GPKPHQTLA | AMVTT---YG | | 61 |
| SEQ_ID_NO_36 | L-------- | ----PPGPKP | WPIVGNLPHL | -GPVPHHSIA | ALAKT---YG | | 60 |
| SEQ_ID_NO_47 | L-------- | ----PPGPSP | WPIVGNLPHM | -GPVPHHALA | ALALK---HG | | 63 |
| SEQ_ID_NO_4 | -------- | ----IPGPKG | APIIGSLMDM | SVGLPHRKLE | SLARL-HGAK | | 113 |
| SEQ_ID_NO_46 | -------- | ---------- | ---------- | ---------- | ---------- | | 0 |
| SEQ_ID_NO_39 | IAAA----- | ----IPGPRG | LPVLGSMSLM | -AGLAHRKLA | AAAGGSPARR | | 108 |
| SEQ_ID_NO_40 | IAAA----- | ----IPGPRG | LPVLGSMSLM | -AGLAHRKLA | AAAGGSPARR | | 110 |
| SEQ_ID_NO_27 | IGEAR---- | ----IPGPRG | FPVIGSMGLM | -TGLAHRKLA | AAAAGNVRRR | | 108 |
| SEQ_ID_NO_29 | VRAA----- | ----IPGPRG | LPVVGSMGLM | -TGLAHRKLS | AAAEROASRR | | 105 |
| SEQ_ID_NO_38 | GAA------ | ----IPGPRG | LPVLGSMGLM | -TGLAHRKLA | AAAGK--ARR | | 101 |
| SEQ_ID_NO_3 | V-------- | ----IPGPRG | LPFVGSMSLM | SNTLAHRC| | ATAEK-FRAE | | 101 |
| SEQ_ID_NO_25 | SSTKPSTTTS | SSIFIPGPKG | YPLFGSMNLM | SSSLAHHRIA | STAKT-CKAT | | 119 |
| SEQ_ID_NO_22 | I-------- | ----IPGPKG | FPLIGSMGLM | -TGLAHHRIA | AAAAT-CRAK | | 96 |
| SEQ_ID_NO_6 | TINKP----- | ----IPGPRG | LPLIGSMNMV | ANSLAHHL|A | TIAKT-CKAK | | 103 |
| SEQ_ID_NO_10 | ISNP------ | ----IPGPRG | FPITGSMKLM | -TSLAHHKIA | AAADA-CKAR | | 101 |

| | | | | | | | |
|---|---|---|---|---|---|---|---|
| SEQ_ID_NO_21 | PLHLRLGFA | DVYVAASKSV | AEQFLKVHDA | NFASRPPNSG | AKHMAYNYQD | | 111 |
| SEQ_ID_NO_36 | PLMHLRMGFV | DVYVAASASV | AADFLKTHDA | NFSNRPPNSG | AKHIAYNYQD | | 110 |
| SEQ_ID_NO_47 | PLMILQLGFV | DVIVAASASV | AEQFLKVHDA | NFSSRPPNSG | AKYIAYNYQD | | 113 |
| SEQ_ID_NO_4 | QLMSFSLGCT | PAVITSDPEV | ARELL-TBP | HFANRPLKQS | AQQLLFG-RA | | 160 |
| SEQ_ID_NO_46 | --MAFSVGLT | RFIVSSHPKT | AKEIL-SGP | AFADRPIKES | AYELLFN-RA | | 45 |
| SEQ_ID_NO_39 | RLMALSLGET | RVVVTADPGV | ARELL-ASA | AFADRPVKES | AYGMLFH-RA | | 155 |
| SEQ_ID_NO_40 | RLMALSLGET | RVVVTADPGV | ARELL-ASA | AFADRPVKES | AYGMLFH-RA | | 157 |
| SEQ_ID_NO_27 | RLMSFSMGET | RVVVTADPDV | ARELL-AGP | AFADRPVKES | AYGLMFH-RA | | 155 |
| SEQ_ID_NO_29 | RLMAFSLGET | RVVVTADLDV | ARELL-ASA | AFADRPVKES | AYGLLFH-RA | | 152 |
| SEQ_ID_NO_38 | RLMAFSLGET | RVVVTADPDV | ARELL-ASA | TFADRPVKES | AYGLLFH-RA | | 148 |
| SEQ_ID_NO_3 | RLMAFSLGET | RVIVTCNPDV | AKEIL-NSP | VFADRPVKES | AYSLMFN-RA | | 148 |
| SEQ_ID_NO_25 | RLMAFSLGDT | RAMVTCNPDV | AKEIL-HSS | VFADRPIKES | AYSLMFN-RA | | 166 |
| SEQ_ID_NO_22 | RLMAFSLGDT | RVIVTCHPDV | AKEIL-NSS | VFADRPVKES | AYSLMFN-RA | | 143 |
| SEQ_ID_NO_6 | RLMAFSLGDT | RVIVTCNPEV | AKEIL-NSS | VFADRPVKES | AYSLMFN-RA | | 150 |
| SEQ_ID_NO_10 | RLMAFSLGDT | RVIVTCNPDV | AKEIL-NSS | VFADRPVKES | AYSLMFN-RA | | 148 |

Figure 1 (continued)

| | | | | | | | |
|---|---|---|---|---|---|---|---|
| SEQ_ID_NO_21 | LVFAPYGDRM | RMLRKISSVH | LFSAKALEDF | KHVRQEEVGT | LMRE---LARA | | 159 |
| SEQ_ID_NO_36 | LVFAPYGPRM | RMLRKICSVH | LFSGDALDDF | RHIRQEEVLA | LMRA---LARE | | 158 |
| SEQ_ID_NO_47 | LVFAPYGPRM | RLLRKISYVH | MFSSKALDDF | RHIRQDEVAR | LIRN---LSNS | | 161 |
| SEQ_ID_NO_4 | IGFAPNGGYW | RLLRRIASAH | LFAPRRIAAH | EAGRQADVVA | MLDD---IQKE | | 208 |
| SEQ_ID_NO_46 | MGFAPFGDYW | RNLRRISSTY | LFSPRRVSSF | EKQRSEIGEG | MVRD---MKRM | | 93 |
| SEQ_ID_NO_39 | IGFAPYGTYW | RALRRVASTH | LFSPRQVSAS | AAQRAVIARD | MVEAMRSAAA | | 205 |
| SEQ_ID_NO_40 | IGFAPYGTYW | RALRRVASTH | LFSPRQVSAS | AAQRAVIARQ | MVEAMRSAAA | | 207 |
| SEQ_ID_NO_27 | IGFAPYGAYW | RTLRRVSSSH | LFSPRQVAAS | AAQRAVIAHQ | MVDA---MRPV | | 203 |
| SEQ_ID_NO_29 | IGFAPHGAYW | RALRRVASAH | LFSPRQIAAS | AAQRAAIARQ | MVDA---TITA | | 200 |
| SEQ_ID_NO_38 | IGFAPHGAYW | RALRRVASAH | LFSPRQIAAS | AAQRAVIARD | MVDAMMNEQG | | 198 |
| SEQ_ID_NO_3 | IGFAPYGVYW | QTLRKIASNH | LFSPKQIKRS | ETQRSVIANQ | IVKC---LTKQ | | 196 |
| SEQ_ID_NO_25 | IGFAPYGVYW | RTLRKISTNII | LFSPMQIKSS | GPQRSEAIID | MIDL---FRNR | | 214 |
| SEQ_ID_NO_22 | IGFASYGVYW | RSLRRIASNH | LFCPRQIKAS | ELQRSDAAD | MVHI---LNNK | | 191 |
| SEQ_ID_NO_6 | IGFAPYGVYW | RELRRIAATH | LFCPKQIKNS | EEDRRFIADE | MVNL---FGRH | | 188 |
| SEQ_ID_NO_10 | IGFAPYGVYW | RTLRKIASTH | LFCPKQIKAA | ESQRLQLASQ | MVST---FNDR | | 196 |

| | | | | | | | |
|---|---|---|---|---|---|---|---|
| SEQ_ID_NO_21 | NTKP---VNL | GQLVNMCVLN | ALGREMGRR | LFGAD----- | ADHKAEEFRS | | 201 |
| SEQ_ID_NO_36 | GQTP---VKL | GQLLNVCTTN | ALGRVMLGRR | VFGDGSGG-- | EDPKADEFKE | | 203 |
| SEQ_ID_NO_47 | GSKA---ANL | GQMLNVCTTN | ALARYMLGRR | VFNEGNGGCE | CDPRADEFKS | | 208 |
| SEQ_ID_NO_4 | YHSK-GVVRV | RRHLQGAALN | NIMGSVFGRR | FDMSH----- | ENEEVKKLRE | | 252 |
| SEQ_ID_NO_46 | MERN-GVNEV | RRMLHYGBLN | NIMLTVFGKK | FOF------- | AKDEGLELEL | | 135 |
| SEQ_ID_NO_39 | AAAG-GGVAA | RPFLKRASLH | NVMASVFGRK | YELAAP---- | ESEETAELRS | | 250 |
| SEQ_ID_NO_40 | AAAG-GGVAA | RPFLKRASLH | NVMASVFGRK | YELAAP---- | ESEETAELRS | | 252 |
| SEQ_ID_NO_27 | GGAGVKHVEA | RRFLKRASLH | NVMASVFGRR | YELDEA---- | GSGEAAELKS | | 249 |
| SEQ_ID_NO_29 | AAHA-PVVVA | RRFLKRASLH | NVMASVFGRR | YDLMA----- | DSREAEELKA | | 244 |
| SEQ_ID_NO_38 | AAAP-GVVTA | RRFLKRASLH | SVMASVFGRR | YELLQAAD-- | GGEEAAELQS | | 245 |
| SEQ_ID_NO_3 | SNIK-GLCFA | RDLIKIASLN | NMMCSVFGKE | YELEE----- | EHEEVSELRE | | 240 |
| SEQ_ID_NO_25 | HLHG-GFC-V | RDVLKKASLN | NMMCSVFGQR | FKIDE----- | VNERMMELSG | | 257 |
| SEQ_ID_NO_22 | RHRS---LRV | RQVLKKASLS | NMMCSVFGQE | YKLHD----- | PNSGMEDLGI | | 233 |
| SEQ_ID_NO_6 | GHER--SFIV | REVVKRASLN | NMMVSIFGRK | YKLDC----- | DNNEYDELRG | | 241 |
| SEQ_ID_NO_10 | EKSS---FSV | REVLKRASLN | NMMCSVFGRE | YKLDS----- | FNNEVEELRA | | 238 |

Figure 1 (continued)

| | | | | | | | |
|---|---|---|---|---|---|---|---|
| SEQ_ID_NO_21 | MVTEMMALAG | VFNIGDFVPA | LDCLDLQGVA | GKMKRLHKRF | DAFLSSLEE | 251 |
| SEQ_ID_NO_36 | MVVELMVLAG | VFNIGDFVPA | LEWLDLQGVA | SKMKKLHARF | DAFLGAVEE | 253 |
| SEQ_ID_NO_47 | MVVELMVLAG | VFNIGDFVPS | LEWLDIQGVQ | SKMKKLHKRF | DSFLTSIED | 258 |
| SEQ_ID_NO_4 | MVDEGFQLLG | AFNWADHLPW | LRPLDPLRIH | ARCARLVPRV | TTFYSNIEQ | 302 |
| SEQ_ID_NO_46 | ILKEGYELLG | IFNWGDHLPL | LGWLDLQSVR | RRCRTLVAKV | NVFVKKIDE | 185 |
| SEQ_ID_NO_39 | MVDEGYDLLG | QLNWSDHLPW | LAPFDLQKTR | SRCSSLVPRV | NRFVTRIDE | 300 |
| SEQ_ID_NO_40 | MVDEGYDLLG | QLNWSDHLPW | LAPFDLKKTR | SRCSSLVPRV | NRFVTRIDE | 302 |
| SEQ_ID_NO_27 | LVDEGYDLLG | QLNWSDHLPW | LARFDLQKIR | SRCSALVPRV | NRFVGRIDE | 299 |
| SEQ_ID_NO_29 | LVDEGYDLLG | QLNWSDHLPW | LARFDLQKTR | ARCCALVPRV | NRFVGNIGE | 294 |
| SEQ_ID_NO_38 | LVDQGYDLLG | QLNWSDHLPW | LARFDLQRTR | ARCAALVPRV | NRFVGRIDE | 295 |
| SEQ_ID_NO_3 | LVEEGYDLLG | TLNWTDHLPW | LSEFDPQRIR | SRCSNLVPKV | NRFVNRISD | 290 |
| SEQ_ID_NO_25 | LVEQGYDLLG | GLNWGDHLPF | LKDFDVQKIR | FSCSELVPKV | NRFVGSISD | 307 |
| SEQ_ID_NO_22 | LVDQGYDLLG | LFNWADHLPF | LAHFDAQNIR | FRCSNLVPMV | NRFVGTIAE | 283 |
| SEQ_ID_NO_6 | LVDEGYDLLG | TLNWSDHLPW | LADFDPQNIR | VRCSNLVPKV | NGFVGGIAQ | 291 |
| SEQ_ID_NO_10 | LVEEGYDLLG | TLNWSDHLPW | LADFDPQKIR | FRCSNLVPKV | NRFVSRLAE | 288 |

| | | | | | | |
|---|---|---|---|---|---|---|
| SEQ_ID_NO_21 | HEAMK----N | GQDQKHTDML | STLISLK--- | -GTDFDGEG | GTLTDTEIKA | 292 |
| SEQ_ID_NO_36 | HKISG----S | AGSERHVDLL | STLISLKDNA | DGEGG----- | -KLTDVEIKA | 293 |
| SEQ_ID_NO_47 | HMVSK----- | --SEKHNDLL | STLLSLKEKV | DEDGD----- | -KLNDTEIKA | 295 |
| SEQ_ID_NO_4 | HRREE---QR | RESGDQCDFV | DVLLSLQ--- | -GED------ | -KLDEEDMIA | 338 |
| SEQ_ID_NO_46 | HKRRA-NGVG | IDEGEGEDFV | DVLLGLE--- | -EKD------ | -RLSESDMVA | 223 |
| SEQ_ID_NO_39 | HRARL----S | LAVDAAVDFT | DVLLSLH--- | --GGD----- | -KLSDADMVA | 335 |
| SEQ_ID_NO_40 | HRARL----S | LAVDAAVDFT | DVLLSLH--- | --GGD----- | -KLSDADMVA | 337 |
| SEQ_ID_NO_27 | HRAAL----N | DDDDAVVDFT | DVLLSLQ--- | --GSD----- | -KLSDADMIA | 334 |
| SEQ_ID_NO_29 | HRARL---GR | GGDTAVMDFT | DVLLSLQ--- | --GDD----- | -KLSDADMIA | 330 |
| SEQ_ID_NO_38 | HRAARLHLGG | DGAAAVDFT | DVLLSLQ--- | --GSD----- | -RLSDADMIA | 334 |
| SEQ_ID_NO_3 | HREQT----- | --RDSPSDFV | DVLLSLD--- | --GPD----- | -KLSDPDIIA | 322 |
| SEQ_ID_NO_25 | HRADK----- | --NGTNKDFV | HVLLSLQ--- | --EPD----- | -KLSDSDMIA | 339 |
| SEQ_ID_NO_22 | HRASK----- | --TETNRDFV | DVLLSLP--- | --EPD----- | -QLSDSDMIA | 315 |
| SEQ_ID_NO_6 | HRART----- | --NEEARDLV | DVLLSLQ--- | --GAD----- | -KLSDSDMIA | 323 |
| SEQ_ID_NO_10 | HRALT----- | --RSENPDFV | DVLLSLQ--- | --GHD----- | -KLSDSDMIA | 320 |

Figure 1 (continued)

| | | | | | | | |
|---|---|---|---|---|---|---|---|
| SEQ_ID_NO_21 | LLLNMFTAGT | DTSASTVOWA | AELIRHPEI | MRKAQEELDS | VV- | GRGRPIN | 341 |
| SEQ_ID_NO_36 | LLLNLFTAGT | DTGSSTVEWA | AELIRHPEM | MAQAQQELDA | VV- | GRGRLVT | 342 |
| SEQ_ID_NO_47 | LLLNMFTAGT | DTSSSTTEWA | AELIKNPKL | MIRIQNELDT | VV- | GRDRLVT | 344 |
| SEQ_ID_NO_4 | VLWEMIFRGT | DTTALLTEWT | MAELVLHPEA | QKKAQAELDA | VV- | GHDRSVK | 397 |
| SEQ_ID_NO_46 | VLWEMIFRGT | DTVAILLEWT | LARMVLHPDI | QSKAQVEIDS | VV- | DSSRPVL | 272 |
| SEQ_ID_NO_39 | VLWEMIFRGT | DTVAVLIEWV | AARLVLHQDV | QARVHDELDR | VV- | GSDRAVT | 384 |
| SEQ_ID_NO_40 | VLWEMIFRGT | DTVAVLIEWV | AARLVLHQDV | QARVHDELDR | VV- | GSDRAVT | 386 |
| SEQ_ID_NO_27 | VLWEMIFRGT | DTVAVVIEWV | LARLMLHQDV | QARVHEELDR | VV- | GPNRAVT | 383 |
| SEQ_ID_NO_29 | VLWEMIFRGT | DTVAVLIEWV | LARLVLHQDV | QSKVQEELDR | VV- | GLGQAVT | 379 |
| SEQ_ID_NO_38 | VLWEMIFRGT | DTVAVLMEWV | LARLVLHQDV | QRRVQEELDR | VV- | GPGRAVT | 383 |
| SEQ_ID_NO_3 | VLWEMIFRGT | DTVAVLIEW | LARMVLHPDI | QSIVHNELDQ | IV- | GRSRAVE | 371 |
| SEQ_ID_NO_25 | VLWEMIFRGT | DTVAVLIEW | LARLVIHPDV | QKKVQTELDE | VASGESCAIT | | 389 |
| SEQ_ID_NO_22 | VLWEMIFRGT | DTVAVLIEW | LARMALHPHV | QSKVQEELDA | VV- | GKARAVA | 364 |
| SEQ_ID_NO_6 | VLWEMIFRGT | DTVAVLIEW | LARIVVHPDV | QSRVHDELDK | VV- | GKSKAVY | 372 |
| SEQ_ID_NO_10 | VLWEMIFRGT | DTVAVLIEW | LARMVLHPDV | QSKVHDELYK | VV- | GRSRAVA | 369 |

| | | | | | | | |
|---|---|---|---|---|---|---|---|
| SEQ_ID_NO_21 | ESDLSQLPYL | QAVIKENFRL | HPPTPLLSLP | HIASESCEI- | NGYHIPKGST | | 389 |
| SEQ_ID_NO_36 | DLDLPKLTYL | QAIVKETFRL | HPSTPLLSLP | RMAAESCEI- | NGYHIPKNAT | | 390 |
| SEQ_ID_NO_47 | EDDLTHLPYL | EAVIKETFRL | HPSTPLLSLP | RVATNSCEI- | FNYHIPKGAT | | 392 |
| SEQ_ID_NO_4 | DSDIPKLPYI | QAVVKEALRM | HPPGPLLSWA | RLSTEDVNMG | DGMCVPAGTT | | 437 |
| SEQ_ID_NO_46 | DSDIQRLPYL | QSIVKETLRM | HPPGPLLSWA | RLAIHDVPV- | DGHMPAGTT | | 321 |
| SEQ_ID_NO_39 | ESDASKLVYL | QAVIKEVLRL | HPPGPLLSWA | RLATSDVHV- | GGFLPSGTT | | 433 |
| SEQ_ID_NO_40 | ESDASKLVYL | QAVIKEVLRL | HPPGPLLSWA | RLATSDVHV- | GGFLPSGTT | | 435 |
| SEQ_ID_NO_27 | ESDAASLVFL | QAVVKEVLRL | HPPGPLLSWA | RLATSDVHV- | DGLHVPAGTT | | 432 |
| SEQ_ID_NO_29 | ESDTASLPYL | QAVIKEVLRL | HPPGPLLSWA | RLATSDVYV- | SGYLVPAGTT | | 428 |
| SEQ_ID_NO_38 | EPDGASLAYL | HAVIREVLRL | HPPGPLLSWA | RLATSDVHV- | GGYLVPAGTT | | 432 |
| SEQ_ID_NO_3 | ESDVVSLVYL | TAVVKEVLRL | HPPGPLLSWA | RLAITDTII- | DGRRVPAGTT | | 420 |
| SEQ_ID_NO_25 | EEDVAAMVYL | PAVIKEVLRL | HPPGPLLSWA | RLAITDTTI- | DGYHVPAGTT | | 438 |
| SEQ_ID_NO_22 | EDDVAVMTYL | PVVKEVLRL | HPPGPLLSWA | RLSINDTTI- | DGYHVPAGTT | | 413 |
| SEQ_ID_NO_6 | ESDVMNLTYL | MAVIKEVLRL | HPPGPLLSWA | RLAITDTTV- | DGYHVPKGTM | | 421 |
| SEQ_ID_NO_10 | ESDITAMVYL | QAVVKEVLRL | HPPGPLLSWA | RLAITDTTL- | DGYHVPKGTT | | 418 |

Figure 1 (continued)

| | | | | | | | |
|---|---|---|---|---|---|---|---|
| SEQ_ID_NO_21 | LLINIWAIAR | DPDQMSDPLT | FRPERFLPGG | EKA-G----- | VDVKGNDFEL | 433 |
| SEQ_ID_NO_36 | LLVNVWAIAR | DPEVWEEPLE | FRPNRFLPGG | ERP-N----- | ADVRGNDFEV | 434 |
| SEQ_ID_NO_47 | LLVNVWAISR | DPKEWTNPLE | FKPERFLPGG | EKF-D----- | VDIRGNDFEV | 436 |
| SEQ_ID_NO_4 | AMVNMWSITH | DPNEWESPYE | FRPERFVVFE | GGE-E----- | VDVRGNDLRL | 481 |
| SEQ_ID_NO_46 | AMVNMWAITH | DECNWAEPNK | FNPDRFIDED | ---------- | VNILGSDLRL | 361 |
| SEQ_ID_NO_39 | AMVNMWAITH | DPAVWPDPNE | FKPERFVAGP | SSDQA---AE | FPIMGSDLRL | 480 |
| SEQ_ID_NO_40 | AMVNMWAITH | DPAVWPDPNE | FKPERFVAGP | SSDQA---TE | FPIMGSDLRL | 482 |
| SEQ_ID_NO_27 | AMVNMWAITH | DPTVWKPAE | FKPERFLGGS | SSDHAAAGAE | FSVTGSDLRL | 482 |
| SEQ_ID_NO_29 | AMVNMWAITH | DPSLWPEPME | FRPERFMGPA | AED------- | VPIMGSDLRL | 471 |
| SEQ_ID_NO_38 | AMVNMWAITH | DPAVWPDPAE | FKPERFAAGS | PGDEA----- | FPVMGSDLRL | 477 |
| SEQ_ID_NO_3 | AMVNMWAIAH | DPHVWENPLE | FKPERFVAKE | GEV-E----- | FSVLGSDLRL | 464 |
| SEQ_ID_NO_25 | AMVNMWAISR | DPDVWRNPLE | FNPERFVSEG | AE-------- | FSVLGSDLRL | 480 |
| SEQ_ID_NO_22 | AMVNTWAICR | DPHVWKDPLE | FMPERFVTAG | GDA-E----- | FSILGSDPRL | 457 |
| SEQ_ID_NO_6 | AVVNMWAIAR | DPQEMADPTE | FVPDRFVAKT | GEV-E----- | FSVLGSDLRL | 465 |
| SEQ_ID_NO_10 | AMVNMWAISR | DPEFMEDPLE | FMPERFVVTK | EDVLE----- | FSVLGSDLRL | 463 |

| | | | | | | | |
|---|---|---|---|---|---|---|---|
| SEQ_ID_NO_21 | IPFGAGRRIC | AGLSLGLRTI | QLLTATLVHG | FEWELAGGVT | -PEKLNMEET | 482 |
| SEQ_ID_NO_36 | IPFGAGRRIC | AGMSLGLRMV | HLLTATLVHA | FNWELPEGQV | -AEKLNMDEA | 483 |
| SEQ_ID_NO_47 | IPFGAGRRIC | AGMSLGLRMV | QLLTATLAHA | YDWELENGLS | -PEKLNMDEA | 485 |
| SEQ_ID_NO_4 | APFGAGRRVC | PGKALGLATV | NLWAKLLHH | FEWLPHAEL | --HPVDLSEV | 527 |
| SEQ_ID_NO_46 | APFGSGKRVC | PGKTMALAAV | HLMLAQLLKS | FKLLLPSR-- | --NGVDLSEC | 406 |
| SEQ_ID_NO_39 | APFGSGRRSC | PGKSLAIATV | GFWVATLLHE | FDWLPLSDK- | -SRGVDLSEV | 528 |
| SEQ_ID_NO_40 | APFGSGRRSC | PGKSLAIATV | GFWVATLLHE | FDWLPLSDK- | -SRGVDLSEV | 530 |
| SEQ_ID_NO_27 | APFGSGRRSC | PGKSLAIATV | GFWVATLLHE | FEWTPPSSDG | -SGGVDLSEV | 531 |
| SEQ_ID_NO_29 | APFGSGRRSC | PGKSLAVATV | GFWVATLLYE | FKWLPPSDEP | RGGGVDLSEV | 521 |
| SEQ_ID_NO_38 | APFGSGRRVC | PGKSLAMATV | AFWVATLLHE | FEWLPASSDE | PPRGVDLSEV | 527 |
| SEQ_ID_NO_3 | APFGSGRRVC | PGKNLGLTTV | TFWIATLLHE | FEWLTPSDE | --KTVSLSEK | 511 |
| SEQ_ID_NO_25 | APFGSGRRSC | PGKNLGLATV | TFWVAKLLHE | FEWLPLDE | -VNGVDLTEV | 527 |
| SEQ_ID_NO_22 | APFGSGRRAC | PGKTLGWATV | NFWVASLLHE | FEWVPSDE | --KGVDLTEV | 503 |
| SEQ_ID_NO_6 | APFGSGRRTC | PGKNLGLTTV | SFWVATLLHE | FEWLPSDQ | --NSVDLSEV | 511 |
| SEQ_ID_NO_10 | APFGSGRRTC | PGKTLGITTV | TFWVASLLHE | YEWVPGEE | --NNVDLSEV | 509 |

Figure 1 (continued)

| | | | | |
|---|---|---|---|---|
| SEQ_ID_NO_21 | YGTTLQRAVP | VVHPKLRLD | MSAYGLGSA | 511 |
| SEQ_ID_NO_36 | YGLTLQRAAP | MVHPRPRLS | PQVFGK--- | 509 |
| SEQ_ID_NO_47 | YQLTLQRAVP | LAHPRPRLS | PHLYL---- | 510 |
| SEQ_ID_NO_4 | LKLSCEMARP | HCVPVTRVP | FAKFSD--- | 553 |
| SEQ_ID_NO_46 | LKMSLEMKNP | VCVAVPRFE | --------- | 428 |
| SEQ_ID_NO_39 | LKLSCEMATP | EARLRPRRK | VMSV----- | 552 |
| SEQ_ID_NO_40 | LKLSCEMATP | EARLRPRRK | V-------- | 551 |
| SEQ_ID_NO_27 | LRLSCEMAAP | EARLRPRRA | V-------- | 552 |
| SEQ_ID_NO_29 | LRLSCEMAAP | EARVVPRHA | VC------- | 543 |
| SEQ_ID_NO_38 | LRLSCEMAAP | EARLVPRRA | V-------- | 548 |
| SEQ_ID_NO_3 | LRLSCEMANP | AAKLRPRRS | FSV------ | 534 |
| SEQ_ID_NO_25 | LRLSCEMANP | TVQVRPRR- | --------- | 546 |
| SEQ_ID_NO_22 | LKLSCEMANP | TVKVRPRRG | --------- | 523 |
| SEQ_ID_NO_6 | LKLSCEMANP | KVRIRPRRK | LT------- | 533 |
| SEQ_ID_NO_10 | LRLSCEMANP | TVKVRPRRS | SQSPLY--- | 535 |

Figure 2

```
SEQ_ID_NO_67  ----------  MQLQPAVAN-  ---------P  NTPSGAA---  ----------  17
SEQ_ID_NO_65  MDTSHWPQGI  GLVKAVEPS-  -----KPVPT  ERKPRPQ---  ----KEQ---  34
SEQ_ID_NO_63  MGMDSSGQQ   QQMSNQSLES  MLTCSKGE-Q  DKKPKPP---  ----QPE---  39
SEQ_ID_NO_73  -----MDQQQ  QEMSSQTLES  MLVCTKPDQD  DKKPRPA---  ----EQQ---  35
SEQ_ID_NO_69  ------MQEE  PGRRPVPPF-  -----AGVDL  RRPKGYP---  -VAVAKEERP  34
SEQ_ID_NO_70  -------MQE  AGRRPAPQF-  -----AGVDL  RRPKGYPAAA  QLTPAAEEAA  37
SEQ_ID_NO_71  -------MQE  AGRRPAPQF-  -----AGVDL  RRPKGYPAAA  QLTPAAEEAA  37
SEQ_ID_NO_64  -----MPSSD  SGESRRSK--  ---------P  QNRPGAP---  --APEQE---  27
SEQ_ID_NO_75  -------MEA  GQVPDGRAL-  -----MAAVT  TTGGGGR---  ----EPE---  27
SEQ_ID_NO_51  -------MQD  ----PTGFH-  ---------Q  MKAPAFQ---  ----EQEQQ-  21
SEQ_ID_NO_53  -------MQD  ----PSTAF-  ---------H  TIKPQFP---  ----EQE---  19
SEQ_ID_NO_60  -------MQD  ----PLTLF-  ---------Q  PMKPHEP---  ----EQE---  18
SEQ_ID_NO_58  -------MQE  DLTSAAAYYH  HQSMIMTAKQ  QQQPELP---  ----EQE---  33
SEQ_ID_NO_49  -------MQD  ----PAAYY-  -QTMMAKQQQ  QQQPQFA---  ----EQE---  27

SEQ_ID_NO_67  ---REQCPRC  ASHDTKFCYY  NNYNTSQPRH  FCRACRRYWT  LGGSLRNVPI  64
SEQ_ID_NO_65  ---AINCPRC  NSTNTKFCYY  NNYSLSQPRY  FCKTCRRYWT  EGGSLRNVPV  81
SEQ_ID_NO_63  ---ALKCPRC  DSNNTKFCYY  NNYSLSQPRY  FCKSCRRYWT  KGGTLRNVPV  86
SEQ_ID_NO_73  ---PQKCPRC  DSANTKFCYY  NNYSLTQPRY  FCKSCRRYWT  KGGTLRNVPV  82
SEQ_ID_NO_69  APGGDPCPRC  GSRDTKFCYY  NNYNTSQPRH  LCKSCRRYWT  KGGSLRNVPV  84
SEQ_ID_NO_70  AGVGDPCPRC  ESRDTKFCYY  NNYNTSQPRH  FCKSCRRYWT  KGGSLRNVPV  87
SEQ_ID_NO_71  AGVGDPCPRC  ESRDTKFCYY  NNYNTSQPRH  FCKSCRRYWT  KGGSLRNVPV  87
SEQ_ID_NO_64  ---NLPCPRC  DSTNTKFCYY  NNYNYSQPRH  LCKACRRYWT  HGGTLRDIPV  74
SEQ_ID_NO_75  ---GLPCPRC  ESVNTKFCYY  NNYNLSQPRY  FCKTCRRYWT  ROGALRNVPV  74
SEQ_ID_NO_51  ---QLKCPRC  DSTNTKFCYY  NNYNLSQPRH  FCKNCRRYWT  KGGALRNIPV  69
SEQ_ID_NO_53  ---QLKCPRC  DSNNTKFCYY  NNYNLSQPRH  FCKNCKRYWT  KGGALRNIPV  66
SEQ_ID_NO_60  ---QLKCPRC  DSTNTKFCYY  NNYNLSQPRH  FCKNCRRYWT  KGGALRNIPV  65
SEQ_ID_NO_58  ---QLNCPRC  ASPNTKFCYY  NNYNLSQPRH  FCKNCRRYWT  KGGSLRNIPV  80
SEQ_ID_NO_49  ---QLKCPRC  DSPNTKFCYY  NNYNLSQPRH  FCKSCRRYWT  KGGALRNVPV  74
```

Figure 2 (continued)

| | | | | | | |
|---|---|---|---|---|---|---|
| SEQ_ID_NO_67 | GGSTRKRLRP | APQQTMRRPP | VHFGAP---P | PPPMPA---- | ---------- | 97 |
| SEQ_ID_NO_65 | GGGSRKNKRB | SSSSNNSSSS | ---TBS---S | YKKIPDLT-- | ---------- | 113 |
| SEQ_ID_NO_63 | GGGCRKNKRB | SSASSKRSQD | ----QPFQTN | PNPLTCFPSL | SYDSNDLTLA | 132 |
| SEQ_ID_NO_73 | GGGCRKNKKL | SSTTSAKRSS | QDNISPNISN | PIPSYDSSTD | LSLAFARLQK | 132 |
| SEQ_ID_NO_69 | GGGTRKSSSS | SSSSSAAAAA | ----TTTTTS | TSPGAAPK-- | -ATKRSKNSK | 127 |
| SEQ_ID_NO_70 | GGGSRKSSTS | SSSSSAAAAA | ----SS---S | SSPSSPAK-- | -SPKRSKNSK | 127 |
| SEQ_ID_NO_71 | GGGSRKSSTS | SSAAAAAAS | -----S---S | SSPSSPAK-- | -SPKRSKNSK | 126 |
| SEQ_ID_NO_64 | GGGTRKNAKR | SRTHHVAVTS | ----SS---S | SSAVT----  | ---------- | 102 |
| SEQ_ID_NO_75 | GGNTRKATPA | TGRRKRSTPA | -----P---V | NVTVPAP--- | ---------- | 103 |
| SEQ_ID_NO_51 | GGGTRKGTKR | SSSSTNKPKR | ----CP---N | PSPDPTPNQK | -IPDPSPPPP | 110 |
| SEQ_ID_NO_53 | GGGSRKNTKR | SSNTKRANPD | -----P---N | PDPVKPTR-- | ---------- | 96 |
| SEQ_ID_NO_60 | GGGSRKNTKR | SSSSNNNTKR | ---------- | ASPSPPVS-- | ---------- | 93 |
| SEQ_ID_NO_58 | GGGTRKNSSK | RSSVGSSSSA | ----PS---S | SSPKSKTV-- | ---------- | 111 |
| SEQ_ID_NO_49 | GGGSRKNATK | RSTSSSSSAS | ----SP---S | NSSQNKKT-- | ---------- | 105 |

| | | | | | | |
|---|---|---|---|---|---|---|
| SEQ_ID_NO_67 | -QSHSQQAPQ | GGLLSSLFAF | GAAPLFEGRV | GF----D-- | LGLGLPGLSQ | 139 |
| SEQ_ID_NO_65 | -IPTSSQNPK | IINEPHDLNL | AFNPSATSNF | SNISEFMA-- | LPLMNPNSTT | 160 |
| SEQ_ID_NO_63 | LARLQKGHLG | FDHEHDFSIL | GNQTNTSCGI | LNN------ | HGNNHSSNNQ | 175 |
| SEQ_ID_NO_73 | QTNAHLEIDQ | EHDNNNMSMM | YNFGNNCTBT | TELDALRGG- | FLENAPNHPG | 181 |
| SEQ_ID_NO_69 | RRRVAPAPDP | AAPGTDASTA | DVASTAPSTV | ---------- | AASEKPSATE | 167 |
| SEQ_ID_NO_70 | RRRVSPPPPD | PAP------- | APPPPTTADA | ---------- | ADVAAPTAPE | 160 |
| SEQ_ID_NO_71 | RRRVSPPPPD | PVP------- | APPPPTTADA | ---------- | ADVAAPTAPE | 159 |
| SEQ_ID_NO_64 | -SAPEQNYP  | ---------- | SMTPIQGGSF | PY-------- | GGVDGEGKQN | 132 |
| SEQ_ID_NO_75 | -ATASPPPPP | ALHGGSLLRP | YGGGGGSGLL | SFAAPALASP | LAAADPDRRL | 152 |
| SEQ_ID_NO_51 | KSSSSSMFPQ | QIVLNSGAQN | SDSDIDSTRM | -Y----L-- | LPVDHQDGKM | 152 |
| SEQ_ID_NO_53 | -RVADSSSSS | ATSSTSGQQL | AGNGNQDPTR | VY-------- | GVEADPDRKI | 137 |
| SEQ_ID_NO_60 | -SAPAPEPDP | TRI------- | ---------- | ---------- | GPTPVVG--- | 112 |
| SEQ_ID_NO_58 | -AVSDQESRT | TGN------- | SGQEMDPTRM | LY----G-- | LPVGDPS--- | 143 |
| SEQ_ID_NO_49 | -KNPDPDPDP | RNS------- | QKPDLDPTRM | LY----G-- | FPLSDQDVKG | 140 |

Figure 2 (continued)

| SEQ_ID_NO_67 | VGLGGGAG-- | --E-------- | --FGLHSLGL | RGGHAGT--- | -----SA--- | 165 |
|---|---|---|---|---|---|---|
| SEQ_ID_NO_65 | SFMSSIMP-- | --QLSDSNNI | M-YSSSSTGL | PNLHDLK--- | -----PTLNF | 197 |
| SEQ_ID_NO_63 | GFFEALMG-- | --SDNNVQNL | YYMGEVDNGN | ANGNGNGEMM | LPYDHEMSIA | 221 |
| SEQ_ID_NO_73 | LFIIINMYNYA | NMGQLVENGE | MGMSYQQDQM | SIGTSTTMMT | TIVKQEMCNM | 231 |
| SEQ_ID_NO_69 | HAAAAVAT- | --EKPPAAPP | VSVGAFADTS | PAPDAGG--- | ---------- | 200 |
| SEQ_ID_NO_70 | DTTKKAPE-- | --DLTAAAAT | QPAVALGLGV | ADGGGGG--- | -----K---- | 194 |
| SEQ_ID_NO_71 | ATTKKAPE-- | --DLTAAAAT | QPAVALGLGV | ADGGGGG--- | ---------- | 192 |
| SEQ_ID_NO_64 | MSVCGSFT- | --SLLNNNPQ | QNSGFLALGG | FGLGLGH--- | -----GL--- | 167 |
| SEQ_ID_NO_75 | LDFGGSFT- | --SLIAPGVA | DYGVHFSAGF | LMGGLAP--- | -----AALPR | 190 |
| SEQ_ID_NO_51 | MDIGGSFS- | --SLLASTGQ | --FGNLLEGF | NSNGSSGL-- | -----KT--L | 186 |
| SEQ_ID_NO_53 | LDMGGSFS- | --SLLASSGQ | --FQSIFEGL | DSGGSGL--- | -----KMVRM | 173 |
| SEQ_ID_NO_60 | ---GGSFS- | --SLLASSGH | LGLGNLLEGL | NSSGSNL--- | -----KTVQM | 147 |
| SEQ_ID_NO_58 | ---GGRFS- | --SLLVSNMQ | QIRGVNYET- | ---GSG---- | ---------- | 168 |
| SEQ_ID_NO_49 | MEIGGSFS- | --SLLANNMQ | --LGLGGGGI | MLDGSG---- | ---------- | 170 |

| SEQ_ID_NO_67 | ---------- | ---------- | PMLMPTAFL | D--------- | -NGNVDTMKV | 184 |
|---|---|---|---|---|---|---|
| SEQ_ID_NO_65 | SL--DGFDNN | -----NGYGS | LQGE-TAGKK | LFFPLDDLKN | VSTPNDDHEF | 239 |
| SEQ_ID_NO_63 | TTQAVTVTTM | KQEMCNVREQ | NEKRVLLGFP | WQFNNGDTNM | AEMDH----- | 266 |
| SEQ_ID_NO_73 | ARSTEGHDLN | -----NSNNN | NKV--LCGFP | WQQMNGDHHV | NNMNTNDFEY | 274 |
| SEQ_ID_NO_69 | ----GGVREL | -----LPHPS | RFEM-PSGCN | LG-------- | ---------- | 222 |
| SEQ_ID_NO_70 | ----EHLDTS | ------P--- | -FEM-PSGCD | L--------- | ---------- | 210 |
| SEQ_ID_NO_71 | ---KEHLDTS | ------P--- | -FEM-PSGCD | L--------- | ---------- | 209 |
| SEQ_ID_NO_64 | ----GDMGFG | ------IGR- | --EMSFPGMM | DGSNMGVPVV | SSGIGNSWQL | 204 |
| SEQ_ID_NO_75 | AP--GSVAA | -----PPPPP | QQQP-TVSQA | L--------- | ---------- | 213 |
| SEQ_ID_NO_51 | NHFGGNFDSG | -----CEMDQ | NSGR-DPLFG | E--------- | SSKNGESYLD | 221 |
| SEQ_ID_NO_53 | GGFGEDLNAG | -----PSR-- | ------NPGLD | LQGSSNNNTT | NDGGGESY-- | 209 |
| SEQ_ID_NO_60 | EEFGENVSSG | -----PVADP | DSGR-NPGLE | MD-------- | SNGNAENFLS | 183 |
| SEQ_ID_NO_58 | ---------- | ---------- | ---M-YPGME | LG-------- | ---------- | 176 |
| SEQ_ID_NO_49 | ---------- | ---------- | --MDHPGMG | LGL------- | ---------- | 180 |

Figure 2 (continued)

| | | | | | | | |
|---|---|---|---|---|---|---|---|
| SEQ_ID_NO_67 | ----SGGGAA | AMWAPEFSPA | PTVADVGGNG | MFHGGAQIMG | QL | 222 |
| SEQ_ID_NO_65 | D------EQN | RGQAAESHGF | WNG------- | WLGGGS---- | -- | 262 |
| SEQ_ID_NO_63 | -------LGR | AGWNGLTSSW | GHGL------ | LNSPLM---- | -- | 289 |
| SEQ_ID_NO_73 | STN----KQS | WNGFGGSSNW | HGL------- | INSPLM---- | -- | 299 |
| SEQ_ID_NO_69 | -------PPY | WGWGTSVFAD | TDPA------ | LFLNLP---- | -- | 245 |
| SEQ_ID_NO_70 | ---------G | PYWPTGVFAD | TDPS------ | LFLNLP---- | -- | 231 |
| SEQ_ID_NO_71 | ---------G | PYWPTGVFAD | TDPS------ | LFLNLP---- | -- | 230 |
| SEQ_ID_NO_64 | EGGE---TGF | VGGGGDCFSW | PGLA------ | ISTPGNGLK- | -- | 234 |
| SEQ_ID_NO_75 | -------PEG | MVW---SMGW | PDLS------ | L--------- | -- | 228 |
| SEQ_ID_NO_51 | V---QGGRDT | SCWGGDSNGW | PDLS------ | YTPGSSLRR | -- | 252 |
| SEQ_ID_NO_53 | -------LQG | GEWGNSNNGW | PGLA------ | YTPGSSFQ- | -- | 235 |
| SEQ_ID_NO_60 | LQN----GDS | SCW-NGTSGW | SHLA------ | FTPGSSFQ- | -- | 211 |
| SEQ_ID_NO_58 | -------LGS | GIRRNDDAAL | TDLA------ | MNRVEKN--- | -- | 200 |
| SEQ_ID_NO_49 | -------RRT | EPGNNNNNPW | TDLA------ | MNRAEKN--- | -- | 204 |

Figure 3

```
SEQ_ID_NO_88                                            RRVQ C--LMRRFYR  ---GSRTFGV    23
SEQ_ID_NO_95   MTSL-----  ----QSFLAL KPAAAGWAAG ARPAAAPQSR RARVSACLAA    40
SEQ_ID_NO_90   MNSL-----  ----QSFLAV APVK--PAAA A--ARLPSSR RARVSACLAT    36
SEQ_ID_NO_93   MNSL-----  ----QSFLAL NPPAAAAALG G--ARLRPSR ---VTACLAT    35
SEQ_ID_NO_80   MGSL-----  ----KLFPSF SLSV--SPAT N--LRRPLNN GR-VNASLNM    35
SEQ_ID_NO_87   MGAVYFSQSC YKPRQFNLE RESTLVGRCP V--VCLRCRR V--VSACLNV    46
SEQ_ID_NO_77   MASL-----  ---GQITLPR APS---SEIG L--LRRRFER PI-IRTRIGF    35
SEQ_ID_NO_92   MASL-----  ---GQITLPR APS---LQKG L--LRRP-- ---IRTPIRF    30
SEQ_ID_NO_78   MTSL-----  ----QYFSLN RPV---FPAT H--LHRPGIR HLQVSACANV    35
SEQ_ID_NO_82   MGSL-----  ----QHFLNS PISVPFSPNL N--HRRSFF- ---LRACLNL    34

SEQ_ID_NO_88   ATQPNA---  ---------- ----SSGSQT IIDKEFQHSA HNNHPLPIVF    55
SEQ_ID_NO_95   PPPPPT---  -TAASAVGPA RRELSAASRA VMDDEARYLV GTYKRSRVVF    85
SEQ_ID_NO_90   PAPAPT---  -----APAAA RRELSAASRA VMADEAKYIV GTYKRAQVVF    77
SEQ_ID_NO_93   PTPTPPPPTS APLAPAAAAA RRELSAASRA VVEDEARYIV GTYNRSRVVL    85
SEQ_ID_NO_80   DVEAPN---  ---------P LKLKSNGSNE VIEKDAKFIV GTYARAPVVL    72
SEQ_ID_NO_87   DVDAPN---  -------TGN TTSEKKKTKD VIEMEGMYLV GTYARTPVVL    85
SEQ_ID_NO_77   NGRIAS---  -VLTNAGDQA VSVKASVSQK VIEEEAKVI V GTYARAPVVL    80
SEQ_ID_NO_92   NGRIAS---  -VLTNAG--- -SVKASVSQK VIEEEAKVLV GTYARAPVVL    71
SEQ_ID_NO_78   EVQAPS---  ---------- SYKKDGVSKE VMEAAGRVLV GTYARVPVVL    71
SEQ_ID_NO_82   DVHAPD---  --------SV KPKTHLKSRE VMEMEGKVLV GTYARNPVVI    72

SEQ_ID_NO_88   AHAKGSAVWD PEGNKYIDFL SGYSAVNQGH CHPKILKALK NQAGRLTVSS   105
SEQ_ID_NO_95   EYSRGCKLYD VDGREYLDMS AGIAVTALGH ADPDVCATIA EQSGKIVHVS   135
SEQ_ID_NO_90   VAGRGCKLYD IDGREYLDMA AGIAVNALGH GDPDVDAAAA DQRGRLVHAS   127
SEQ_ID_NO_93   VAGRGCKLYD ADGREYLDMA AGIAVNALGH ADPDWAAVS  AQAATLVHAS   135
SEQ_ID_NO_80   SSGKGCKLYD PEGREFLDCA AGIAVNALGH GDPDWRAVT  EQASILTHVS   122
SEQ_ID_NO_87   ERGEGCKLYD VEGNEYLDLS AGIAVNALGH GDADWLKAVV EQAGTLTHTS   135
SEQ_ID_NO_77   SSGKGCKLFD PEGKEYLDCA SGIAVNALGH GDPDWLRAVT EQAGVLAHVS   130
SEQ_ID_NO_92   SSGKGCKLMD AEGKEYLDCA SGIAVNALGH GDPDWLQAVT DQASVLSHVS   121
SEQ_ID_NO_78   SRSKGCKLYD PEGREYLDLS AGIAVNVLGH ADSDWLRAVT EQAATLTHVS   121
SEQ_ID_NO_82   SSGKGCKLYD PEGREYLDCT SGIAVNALGH GDPDWKAVV  EQANLLTHVS   122
```

Figure 3 (continued)

| | | | | | | | |
|---|---|---|---|---|---|---|---|
| SEQ_ID_NO_88 | RAFYNDRFPV | FAEYSTALFG | YDMVLPINTG | AEGVETALKL | ARKWGYDKKK | | 155 |
| SEQ_ID_NO_95 | NVFYTIPQVE | LAKRLVEVSF | ADRAFFASTG | TEANEAAIKF | SRK--FQRVA | | 193 |
| SEQ_ID_NO_90 | NVGYTVPOVE | LAKRLVEASF | ADRAFFANSG | TEANEAAIKF | ARK--YQRVA | | 175 |
| SEQ_ID_NO_93 | NVQYTVPQVA | LAKRLVEASF | ADRVFFANTG | TEANEAAIKF | ARK--FQRVA | | 183 |
| SEQ_ID_NO_80 | NAYYSIPQL- | ---------- | ---------- | ---------- | ---------- | | 130 |
| SEQ_ID_NO_87 | NIFHTIPQVE | LAKRLVASSF | ADRVFFANSG | TEANEAAIKF | ARK--YQRHT | | 183 |
| SEQ_ID_NO_77 | NVYYTIPQIE | LAKRLVASSF | ADRVFFCNSG | TEANEAAIKF | SRK--FQRFT | | 178 |
| SEQ_ID_NO_92 | NVYYTIPQIE | LAKRLVASSF | ADRVFFCNSG | TEANEAAIKF | SRK--FQRFT | | 169 |
| SEQ_ID_NO_78 | NVFYSIPQVE | LAKRLVASSF | ADRVFFSNSG | TEANEAAIKF | ARK--FQRFT | | 169 |
| SEQ_ID_NO_82 | NVFYSVPQVE | LAKRLVACSF | ADRVFFTNSG | TEANEAAIKF | ARK--YQRFT | | 170 |

| | | | | | | | |
|---|---|---|---|---|---|---|---|
| SEQ_ID_NO_88 | IPNDEAL--- | IVSCCGCFNG | RTLGVISMSC | DNEATRCFGP | LIPGHLKVDF | | 202 |
| SEQ_ID_NO_95 | HPDSDDPPME | FLAFSSSFHG | RTMGAVALTS | KSQYREPFAP | VMPGVTFVDY | | 233 |
| SEQ_ID_NO_90 | HPNGDAPITE | FMSFTNCFHG | RTIGSLALTS | KVQYREPFEP | VMPGSTFVEY | | 224 |
| SEQ_ID_NO_93 | RPDGDAPITE | FMSFTNCFHG | RTMGSLALTS | KVQYREPFAP | VMPGATFAEY | | 232 |
| SEQ_ID_NO_80 | ---------- | ---------- | ---------- | ---------- | ---------- | | 130 |
| SEQ_ID_NO_87 | TSNGKVPATE | FIAFSNCFHG | RTLGALALTS | KVQYRMPFEP | VMPGVTFLEY | | 233 |
| SEQ_ID_NO_77 | HPEDKEVATG | FIAFTNSFHG | RTLGALALTS | KEQYRTPFEP | IMPGVTFLEY | | 228 |
| SEQ_ID_NO_92 | HPEDKEVATS | FIAFTNSFHG | RTLGALALTS | KEQYRTPFEP | IMPGVTFLEY | | 219 |
| SEQ_ID_NO_78 | RPDEKQPATE | FVSFSNSFHG | RTMGSLALTS | KENYRSPFEP | VMPGVTFLEY | | 219 |
| SEQ_ID_NO_82 | NPEKQQA-TE | FISFSNSFHG | RTMGALALTS | KEQYRFPFEP | VMPGVNFLEY | | 219 |

| | | | | | | | |
|---|---|---|---|---|---|---|---|
| SEQ_ID_NO_88 | GDAEALEKIL | KEKGDAIAAF | ILEPIQGEAG | VKIPPDGYLK | AVRDLCSKYN | | 252 |
| SEQ_ID_NO_95 | GDLEAAKKFI | --QSGRVAAV | FVEPVQGEGG | HSATQEFLQ | GLREACDEAG | | 281 |
| SEQ_ID_NO_90 | GNLEEAKKVI | --QSGKIAAV | FVEPVQGEGG | HSATNEFLQ | GLRDACDEAG | | 272 |
| SEQ_ID_NO_93 | GNLEEAKKVI | --QSGKIAAV | FVEPVQGEGG | HSATKEFLQ | GLRDACDEAG | | 280 |
| SEQ_ID_NO_80 | ---------- | ---------- | ---------- | ---------- | ---------- | | 130 |
| SEQ_ID_NO_87 | GNAQAAVELI | --KQGKIAAV | FVEPIQGEGG | YSATKEFLQ | SLRNACDETG | | 281 |
| SEQ_ID_NO_77 | GNIQAATDLI | --RSGKIAAV | FVEPIQGEGG | YSATKEFLQ | SLRSACDAAG | | 276 |
| SEQ_ID_NO_92 | GNTQAATDLI | --RSGKIAAV | FVEPIQGEGG | VYSATKEFLQ | SLRSACDAAG | | 267 |
| SEQ_ID_NO_78 | GNIEAATQLI | --QRRKIAAV | FVEPIQGEGG | VYSATKEFLY | ALRKACDDSG | | 267 |
| SEQ_ID_NO_82 | GDVQAATELI | --KSGRIAAV | FVEPIQGEGG | YSATKEFLQ | SLRSACDDAG | | 267 |

Figure 3 (continued)

| | | | | | | | |
|---|---|---|---|---|---|---|---|
| SEQ_ID_NO_88 | VLMIADEIQT | GLARTGKMLA | CEWEEVRPDV | VVLGKALGGG | I PVSAVLAD | 302 |
| SEQ_ID_NO_95 | ALLVFDEVQC | GFGRTGYLWA | HEAYGVEPDI | MTLAKPLANG | -I PIGVVLVK | 330 |
| SEQ_ID_NO_90 | ALLVFDEVQC | GLGRTGYLWA | HEVYGVLPDI | MTLAKPLANG | -LPIGVALVT | 321 |
| SEQ_ID_NO_93 | ALLVFDEVQC | GLGRTGYLWA | YEAYGVLPDI | MTLAKPLAGG | -LPIGVVLVT | 329 |
| SEQ_ID_NO_80 | -------VQC | GLGRTGYLWA | HEAYGVFPDM | MTLAKPLAGG | -LPIGATLVS | 172 |
| SEQ_ID_NO_87 | ALLVFDEVQC | GLGRSGFLWA | HEAYGVFPDM | MTLAKPLAGG | -LPIGALLVT | 330 |
| SEQ_ID_NO_77 | SLLVFDEVQC | GLGRTGLMWA | YEAFGVTPDI | MTVAKPLAGG | -LPIGAVLVT | 325 |
| SEQ_ID_NO_92 | SLLVFDEVQC | GLGRTGNLWA | YEAFGVTPDI | MTVAKPLAGG | -LPIGAVLVT | 316 |
| SEQ_ID_NO_78 | TLLVFDEVQC | GLGRTGYLWA | HELYDVFPDI | MTLAKPLAGG | -LPIGAVLVT | 316 |
| SEQ_ID_NO_82 | SLLVFDEVQC | GLGRTGYLWA | HEAYGVVPDI | MTLAKPLAGG | -LPIGAALVS | 316 |

| | | | | | | | |
|---|---|---|---|---|---|---|---|
| SEQ_ID_NO_88 | KEVMLCIKPG | QHGSTFGGNP | LASAVAIABL | EVIKEERLAE | RSTKLGGELL | 352 |
| SEQ_ID_NO_95 | EKVAAAINYG | DHGTTFGGGP | LADQTAITVF | DKIMKPGFLA | EVSKKGENFK | 380 |
| SEQ_ID_NO_90 | EKVAAAIHYG | DHGTTFGGGP | FVCHAALATL | DKIQKPGFLA | EVTKKGEYFK | 371 |
| SEQ_ID_NO_93 | EKVASAINFG | DHGTTFGGGP | LVCQAALTTL | DKIQKPGFLA | EVAKKGENFK | 379 |
| SEQ_ID_NO_80 | ERVASAIAHG | DHGSTFAGSP | FVCSAAICVF | NKISNPSFLS | SVLKKGDYMK | 222 |
| SEQ_ID_NO_87 | ERVASAINYG | DHGSTFAGSP | LVCSAALAVL | DKISKPDFLS | SVSKKGLYFK | 380 |
| SEQ_ID_NO_77 | EKVAETINYG | DHGSTFAGSP | LVCSAAIAVM | DKVSKPSFLS | SVSNKGRYFR | 375 |
| SEQ_ID_NO_92 | EKVAETIKYG | DHGSTFAGNP | LVCSAAIAVF | DKVSKSSFLA | SVSSKGLYFK | 366 |
| SEQ_ID_NO_78 | ERVASAITYG | DHGTTFAGGP | LVCKAALTVL | DKILRPGFLA | SVSKKGHYFK | 366 |
| SEQ_ID_NO_82 | EKVAAAIKYG | DHGSTFAGGP | LVCNAAIAVL | DKISKPGFLA | SVSEKGQYFK | 366 |

| | | | | | | | |
|---|---|---|---|---|---|---|---|
| SEQ_ID_NO_88 | GLLEKIQKQY | PDHVKEVRGR | GLFIGVELNS | ESLSPVSFFE | LSEKLKDRGV | 402 |
| SEQ_ID_NO_95 | QLLRTKLSGN | P-HVKEVRGV | GLLVGIELD- | -----VPAGP | LVDACLDAGV | 423 |
| SEQ_ID_NO_90 | QLLKTKLGGN | P-HVKEIRGA | GLIVGIELD- | -----VPAGP | LVDACLDAGV | 414 |
| SEQ_ID_NO_93 | QLLSTKLSGN | A-HVKEIRGI | GLIVGIELD- | -----VPAGP | LVDACLDRGV | 422 |
| SEQ_ID_NO_80 | ELLNQKLGGN | P-HVKEIRGW | GLMIGIELD- | -----VSASP | LVDACRNSGL | 265 |
| SEQ_ID_NO_87 | ELLREKLGEN | R-HVKEIRGV | GLIIGIDLD- | -----VPASP | LVDACRSSGL | 423 |
| SEQ_ID_NO_77 | DLLVKKLGGN | S-YVKEVRGE | GLIIGVELD- | -----VPASS | LVDACRDSGL | 418 |
| SEQ_ID_NO_92 | DLLVKKLGGN | L-HVKEVRGE | GLIIGVELD- | -----VPAGP | LVDACRDSGL | 409 |
| SEQ_ID_NO_78 | EMLINKLGGN | S-HVREVRGV | GLIVGIELD- | -----VSASP | LVNACLNSGL | 409 |
| SEQ_ID_NO_82 | ELLHKLGGN | S-HVREVRGL | GLIIGIELD- | -----VSASP | LVDACRDSSL | 409 |

Figure 3 (continued)

| | | | | | | |
|---|---|---|---|---|---|---|
| SEQ_ID_NO_88 | LAKST-HDTI | RFTPPLCIS | ADEIQQGSKA | LADVLEIDLP | MLKKMKPKDA | 451 |
| SEQ_ID_NO_95 | LVLTAGKGNV | VRLVPPLIIS | EKELEHA--- | -ADVIRDCLP | VLDVAAA--- | 466 |
| SEQ_ID_NO_90 | FLLTAGKGNV | VRLVPALIVS | EKELEQA--- | -AEVIRECLP | ALEASTS--- | 457 |
| SEQ_ID_NO_93 | IVLTAGKGNV | VRLVPPLIIS | EKELEQA--- | -AEVIRDCLP | ALDASTS--- | 465 |
| SEQ_ID_NO_80 | LVLTAGKGNV | VRLVPPLIIS | EEELKHA--- | -AEILHFCLP | ALDNSN---- | 307 |
| SEQ_ID_NO_87 | LVLTAGKGNV | VRLVPPLIIT | EKELEQA--- | -AGILCDTLP | VLDN------ | 463 |
| SEQ_ID_NO_77 | LILTAGKGNV | VRIVPPLVIS | EEEIERA--- | -VEIMADNLT | ALD------- | 457 |
| SEQ_ID_NO_92 | LILTAGKGNV | VRIVPPLIIS | EEEIERA--- | -VEIIFHDLT | ALD------- | 448 |
| SEQ_ID_NO_78 | LVLTAGKGNV | VRIVPPLIIT | EQELEKA--- | -AEILLQCLP | ALDRHG---- | 451 |
| SEQ_ID_NO_82 | LILTAGKGNV | VRLVPPLIIS | EQELERA--- | -AEIILECLP | ALDKTS---- | 451 |

| | | | |
|---|---|---|---|
| SEQ_ID_NO_88 | APPAGPSACD | RCGRVYYG | 469 |
| SEQ_ID_NO_95 | ---------- | -------- | 466 |
| SEQ_ID_NO_90 | ---------- | -------- | 457 |
| SEQ_ID_NO_93 | ---------- | -------- | 465 |
| SEQ_ID_NO_80 | ---------- | -------- | 307 |
| SEQ_ID_NO_87 | ---------- | -------- | 463 |
| SEQ_ID_NO_77 | ---------- | -------- | 457 |
| SEQ_ID_NO_92 | ---------- | -------- | 448 |
| SEQ_ID_NO_78 | ---------- | -------- | 451 |
| SEQ_ID_NO_82 | ---------- | -------- | 451 |

Figure 4

| SEQ_ID | Sequence alignment (block 1) | len |
|---|---|---|
| SEQ_ID_NO_101 | -MSETEAAPV VA------- -----PAAEA APAAEAPK-- AKAPKAKAPK | 34 |
| SEQ_ID_NO_102 | --MATTEAVE EP------- ----VPVEAT ANEDAKPTE- EKPAKEKKPK | 35 |
| SEQ_ID_NO_150 | --MASTDPPA DT------V PAEPVANEDV KAAEEKP--- VKAPKEKKVK | 38 |
| SEQ_ID_NO_118 | --MAFDTPVS AP------- -----YVPEV TERKSKRG-- TKAAAVKVPK | 32 |
| SEQ_ID_NO_145 | --MATTVAIE TP------- --------AFT PVAVDPPA-- AKPAKAKKAK | 31 |
| SEQ_ID_NO_149 | --MSAAVAIE TP------- -----AFAPV PVARDEPV-- AKPGKVTKAK | 33 |
| SEQ_ID_NO_144 | --MATDETTD PR------- ---------- ------PV-- AKSKKAKAPK | 22 |
| SEQ_ID_NO_125 | --MSTDVAAD VP----APEV EVAADPVVET TAEAAAGD-- AKPAKETKAK | 42 |
| SEQ_ID_NO_137 | --MATEVAET PA------- ---PLAEAVP ETPAEAPA-- APAAEANST- | 34 |
| SEQ_ID_NO_146 | --MATDVAAT EP------- -----EVAAE EAAAAAPETT ATAGDSKPAK | 35 |
| SEQ_ID_NO_147 | --MATDVAAT EP------- -----EVAAE EAAAAAPETT ATAGDSKPAK | 35 |
| SEQ_ID_NO_119 | -MAAVEDPIV PM----EGV EEEVPVTVTE APEEAPP-- AEDPAPKKGK | 42 |
| SEQ_ID_NO_100 | --MSIEEENV PT------T VDSGAADTTV KSPEKKPA-- AKGGKSKKTT | 39 |
| SEQ_ID_NO_113 | --MSTEEETK VV------- --VESGDAEA TVTEKKPA-- AKGGAKAKKT | 36 |
| SEQ_ID_NO_104 | --MATEEPAV VA------- -DPAPETEED KTAETKAT-- SKSGRAKKTK | 37 |
| SEQ_ID_NO_108 | --MSSDEPTV AV------- -DGSTEPTSA EPADDKPA-- AKPSRAKKTK | 37 |
| SEQ_ID_NO_116 | MTSSVEEPTV SAVEQTIYEE PAAVDPLPPV VNESDEPT-- AAKPKL---- | 43 |
| SEQ_ID_NO_117 | --MASEEPTT VAVEQPIVEE PEAVDTFPPV VNESEEPT-- AKPKKAPKL- | 44 |
| SEQ_ID_NO_122 | --MATEEPLV VT-----EIV TEAVVVEAEP AKEENSPA-- AEPDEPKKEK | 41 |
| SEQ_ID_NO_120 | --MATEEPVI VN------E VVEEQAAPET VKDEANPP-- AKSGKAKKET | 39 |

| SEQ_ID | Sequence alignment (block 2) | len |
|---|---|---|
| SEQ_ID_NO_101 | QPKAPKAPKE PKAPKEKKPK AAPTHPPYE MVKDAITTLK ERNGSSLPAL | 84 |
| SEQ_ID_NO_102 | TP----KEKK PRAAKGS--K PPAAHPPYVQ MIAEAITALK ERGGSSPYAI | 79 |
| SEQ_ID_NO_150 | TP----KEKK PKAAKGS--K PPPAHPPYFQ MISEAIVALK ERGGSSPYAI | 82 |
| SEQ_ID_NO_118 | ------EKKK VIAAKKPKSK GTSSHPSFFE MISDAISTLK ERTGSSQYAI | 76 |
| SEQ_ID_NO_145 | VP----KEKK ASVAKL---- -PALHPTYLE MISEAIASLK ERTGSSQIAI | 71 |
| SEQ_ID_NO_149 | AP----KEKK ASVAKKP--- --ALHPIYLE MISEAIASLK ERTGSSQYAI | 74 |
| SEQ_ID_NO_144 | EA----RAKK AAAPRKP--- --BAHPPYAE MIKEAITTLK ERTGSSPYAI | 63 |
| SEQ_ID_NO_125 | AA----KAKK PSAPRKP--R ATPAHPTYAE MVSEAITALK ERTGSSQYAI | 86 |
| SEQ_ID_NO_137 | ------KAKK ASAPKK---R ANPTHPPYAE MISEAVTSLK ERTGSSQYAI | 75 |
| SEQ_ID_NO_146 | EA----KAKK AAAPRKA--R STATHPPYAE MISEAIATLK ERTGSSQYAI | 79 |
| SEQ_ID_NO_147 | EA----KAKK AAAPRKA--R STATHPPYAE MISEAIATLK ERTGSSQYAI | 79 |
| SEQ_ID_NO_119 | EL----KPKK AAAPRKP--R SAPAHPFYLE MITDAITSLK ERTGSSQQAI | 86 |
| SEQ_ID_NO_100 | TAKATKKPVK AAAPTKK--K TTSSHPTYEE MIKDAIVTLK ERTGSSQYAI | 87 |
| SEQ_ID_NO_113 | PA----KKKP AAAPRKL--R TTSSHPPYEE MIKDAIVTLK ERTGSSQYAI | 79 |
| SEQ_ID_NO_104 | EP----KTKK AAAPRKP--R AAPTHPPYEE MIKDAIVTLK ERTGSSQYAI | 81 |
| SEQ_ID_NO_108 | EP----KAKK APAPKKPRHR TPSSHPPYEE MIKDAIVTLK EKTGSSQYAI | 83 |
| SEQ_ID_NO_116 | ------KAPK EPKPRKPASK NTRTHPTYEE MVTDAIVTLK EKNGSSYAL | 87 |
| SEQ_ID_NO_117 | ------EPKA KKAPAKP--- --RTHPTYEE MVKEAIVALK ERNGSSQYAI | 83 |
| SEQ_ID_NO_122 | EI----EAKK PAAPRK---R NPPTHPSYFE MIKDAIVTLK DKTGSSQHAI | 84 |
| SEQ_ID_NO_120 | ------KAKK PAAPRKR--S ATPTHPFYFE MIKDAIVTLK ERTGSSQHAI | 81 |

Figure 4 (continued)

| SEQ_ID_NO_101 | KKFIENKYGK | DIHDKNFAKT | LSQVVKTFVK | GGKLVKVKGS | FKLSE---- | 129 |
|---|---|---|---|---|---|---|
| SEQ_ID_NO_102 | AKFLGDKY-K | ADLPPNFKKQ | LNVQLKNLTK | SGKLTKVKAS | YKLTA---- | 123 |
| SEQ_ID_NO_150 | AKFLSEKY-K | SDLPPVFKKK | LNVQLRNLTN | SGKLTKVKGS | YKLAE---- | 126 |
| SEQ_ID_NO_118 | NKFVEDKH-K | Q-LPSNFRKL | LLFHLKKLVA | SGKLVKVKNS | FKLPS---- | 119 |
| SEQ_ID_NO_145 | SKFVENKH-K | AHLPANFKKL | LLVQLRKLTA | AGKLTKVKNS | YKISA---- | 115 |
| SEQ_ID_NO_149 | AKFVEDKH-K | SHLPANFKKL | LLVQLQKLTA | AGKLTKVKNS | YKISA---- | 118 |
| SEQ_ID_NO_144 | GKFIEDKH-K | AHLPSNFRKI | LFLQLKKLAA | AGKLTKVKSS | YKLST---- | 107 |
| SEQ_ID_NO_125 | AKFVEDKH-K | AHLPANFRKI | LSVQLKKLVA | SGKLTKVKAS | YKLSA---- | 130 |
| SEQ_ID_NO_137 | AKFVEDKH-K | DKLPPNFRKL | LLGQLKKLVA | AGKLTKVKNS | YKLPA---- | 119 |
| SEQ_ID_NO_146 | GKFLEDKH-K | DHLPSNFRKQ | LLVQIKKLVA | AGKLTKVKNS | YKLPP---- | 123 |
| SEQ_ID_NO_147 | GKFLEDKH-K | DHLPSNFRKQ | LLVQIKKLVA | AGKLTKVKNS | YKLPP---- | 123 |
| SEQ_ID_NO_119 | QKFLEAKH-K | D-LPAVFRKM | LSNNLKKLVA | AGKLVKVKAS | YKLPS---- | 129 |
| SEQ_ID_NO_100 | QKFIEEKH-K | S-LPPTFRKL | LLVNLKRLVA | SEKLVKVKAS | FKIPS---A- | 131 |
| SEQ_ID_NO_113 | QKFIEEKQ-K | S-LPPTFRKL | LLVNLRRLVA | SGKLVKVKAS | FKIPS---- | 122 |
| SEQ_ID_NO_104 | AKFIEEKQ-K | N-LPGNFKKL | LLVHLKKLVA | AGKLVKVKAS | YKLPS---A- | 125 |
| SEQ_ID_NO_108 | TKFLEEKH-K | Q-LPSNFKKL | LLFHLKKLVL | SDKIVKVKGS | FKLPS---- | 126 |
| SEQ_ID_NO_116 | AKFIEEKH-K | N-LPANFKKI | LLVQIKKLVA | SGKLVKVKGS | YKLPA---KS | 132 |
| SEQ_ID_NO_117 | AKFIEEKH-K | Q-LPSNFKKL | LLVQIRKLVA | SGKLVKVKAS | YKLPA---- | 126 |
| SEQ_ID_NO_122 | TKFIEDKQ-K | N-LPSNFRKL | LLVQLKKLVA | SGKLVKVKSS | YKLPA-AR- | 129 |
| SEQ_ID_NO_120 | TKFIEEKQ-K | S-LPSNFKKL | LLTQLKKFVA | SEKLVKVKNS | YKLPSGSKP- | 128 |

| SEQ_ID_NO_101 | ---ALKAKAK | KSTPKK-AKA | DG----EAKP | KK-SE-AKPK | ----KAEAVK | 165 |
|---|---|---|---|---|---|---|
| SEQ_ID_NO_102 | -----PKAPA | APKPKK-EKK | TVAKKKAPKP | KV-PA-AKPK | -APAAKAAKP | 164 |
| SEQ_ID_NO_150 | ----KEKKAD | APKPKT-EKK | PA----AKKP | KA-PA-AKAP | -AKAPSKAS | 163 |
| SEQ_ID_NO_118 | -------ARA | APAPAL-AKK | PT----IPKP | KV------- | --AAKPKTAK | 147 |
| SEQ_ID_NO_145 | ---KPTTAT | KPKKTS-AKS | TT----VAKP | KS-AA-AKPK | -STAAKVKK | 152 |
| SEQ_ID_NO_149 | ---KPTPAA | KPKSA----- | ------AVKP | KS-AA-TKLK | -SAAKKVKK | 149 |
| SEQ_ID_NO_144 | ---IVHAAPA | EPKS------ | ------AAGP | KK-PA-AVQT | -KLKAKAKP | 138 |
| SEQ_ID_NO_125 | --------AAA | KPKP------ | ------AAKK | KPAAK-KKAP | -AKKTATKT | 158 |
| SEQ_ID_NO_137 | ----RAPAAA | KPKPKS-KTA | ------VKKP | KA-------- | --GAKKPKAA | 148 |
| SEQ_ID_NO_146 | ---TRAPAAA | KPKAKP-AAA | A----KPKP | KPKAA-AKPK | -AAAKPKAK | 161 |
| SEQ_ID_NO_147 | ---TRAPAAA | KPKAKP-AAA | A----KPKP | KPKAA-AKPK | -AAAKPKAK | 161 |
| SEQ_ID_NO_119 | -AKSSAPAKK | KPAAAP-AKK | KA----AAAP | AKKKT-AAAP | -KKKAAAAP | 170 |
| SEQ_ID_NO_100 | -RSAATPKPA | APVKKK-ATV | VA----KPKG | KV-AA-AVAP | -AKAKAAAK | 171 |
| SEQ_ID_NO_113 | --AAKPAATT | KPVNKK-PAA | A-----VTKP | KG-----KAP | -AKAKPAAK | 157 |
| SEQ_ID_NO_104 | -RSSKTATAA | SAPAKK-KTA | TT----KSKS | KP--AL-SKPK | -EGKSTKAT | 164 |
| SEQ_ID_NO_108 | ---AKSSAPA | KPAAASPAKK | KTATAAKPKA | KSKPAYSKAK | ETKSAKSTAK | 173 |
| SEQ_ID_NO_116 | AAPAKKPAAA | KPKPKPKAKA | PVAKAPAAKS | KAKAA-PAKA | KAKAKAKAAP | 181 |
| SEQ_ID_NO_117 | -KSSAAKPAK | KPAAAK-SKA | KPKAKAATKS | KAKPA-AKAK | --PAAKAKPA | 171 |
| SEQ_ID_NO_122 | -SAAPKAAAT | APAKKK-PGA | KPKAT-KAKP | KPKPK-TVAP | -KAKTATKP | 173 |
| SEQ_ID_NO_120 | -AAAAVPAKK | KPAAAK-SKP | AAKPKAAVKP | KAKPA-AKAK | --PAAKAKPA | 173 |

Figure 4 (continued)

| | | | | | | | |
|---|---|---|---|---|---|---|---|
| SEQ_ID_NO_101 | KTKAPKEKVE | RPKKEKKEKV | EKKKATPKAE | KPKK----AA | TPKSAGKKK- | | 210 |
| SEQ_ID_NO_102 | KAAKKAAPAK | PAAPAPP--- | ------KKEE | KPAA-AA-PK | KAAPAAKPKK | | 203 |
| SEQ_ID_NO_150 | KPAAPKKAEK | PVAPKK---A | AAPKKAAKPA | APKAAAPKAK | KPAAAAKP-- | | 208 |
| SEQ_ID_NO_118 | IGAKPKAKAK | VAAKTKA--T | TKTVA----- | ---------- | KKIPAAKPKA | | 180 |
| SEQ_ID_NO_145 | A--------- | ----------A | VKPKPKSAAV | KPKAEPA-AP | KPKAVSKPKA | | 183 |
| SEQ_ID_NO_149 | AAVKPKPKSA | ----------A | VKPKAPAVNM | KSKP-A-AL | KPNTVTKSKT | | 187 |
| SEQ_ID_NO_144 | AAAASKTKAK | IATTAKA--K | SKHVASTVKP | KPKA-A-AA | KPRVAPKRKS | | 183 |
| SEQ_ID_NO_125 | KAKAPAKKA- | ----------A | AKPKA-KAPA | KPKA----AA | KPKAAAKPKA | | 193 |
| SEQ_ID_NO_137 | TKPKPKAKAK | SPAKAKP--A | AKPKA-AAKP | KPAA----A | KPKAAAKPKA | | 190 |
| SEQ_ID_NO_146 | APAKSKAAAK | PKAAAKP--A | AKPKAAAKPK | SPAK-P-AA | KPKAAPKAKA | | 206 |
| SEQ_ID_NO_147 | APAKSKAAAK | PKAAAKP--A | AKPKAAAKPK | SPAK-P-AA | KPKAAPKAKA | | 206 |
| SEQ_ID_NO_119 | KKKAPVAKAK | PAAKPKAKAV | VKPKA-KAAV | KPKA-KP-AA | KPAAKAKPA- | | 216 |
| SEQ_ID_NO_100 | GTKKPAAKVV | AKAKV----T | AKPKAKVTAA | KPKS----K | SVAAVSKTKA | | 212 |
| SEQ_ID_NO_113 | GAKKPAAAAK | PKAKT----T | ATTKA-AAKP | KPKT----K | SVAAVSKTKA | | 197 |
| SEQ_ID_NO_104 | PKAKAKTKTT | SKAKSKP--A | AKPKA---TS | KAKAAPA-KT | KAVASVKPKT | | 208 |
| SEQ_ID_NO_108 | SPAKSKAAAK | PKAKPKAA-A | AKPKV-TAKA | KPKA-AP-AK | AKTSVAKPKA | | 219 |
| SEQ_ID_NO_116 | AKAKPAAKAK | PAAKAKP--A | AKAKP-VAKA | KPKAKAP-VA | KANAVPVA-- | | 225 |
| SEQ_ID_NO_117 | AKAKPAAKAK | PAAKAKP--A | AKAKPAAKPV | KTAAAKP-AA | KAKPAAKPKA | | 218 |
| SEQ_ID_NO_122 | KAKQRQVKAK | LVAKAKP--A | VKPKA----- | -----AA-VA | VPKAAEKPKE | | 209 |
| SEQ_ID_NO_120 | AKAKPAAKAK | PAAKAKP--A | AKAKP-VAKA | KPKA-AA-AA | KPKAAVKPKA | | 218 |

| | | | | | | | |
|---|---|---|---|---|---|---|---|
| SEQ_ID_NO_101 | -ATPKPKAAP | ---------- | ---------- | ------K | SPAKKDAKPK | KATPSKKAAP | 240 |
| SEQ_ID_NO_102 | -PAAKPKKAA | ---------- | ---------- | ------- | ---TPKKPAP | KPKPAKKAAT | 229 |
| SEQ_ID_NO_150 | -AAPKRSST- | ---------- | ---------- | ------- | ---HTAAKPA | APKAAKKPTP | 233 |
| SEQ_ID_NO_118 | KTAGKPKTVA | ---------- | ---------- | ------A | KPAKVAKTAA | VASPGKKKAV | 211 |
| SEQ_ID_NO_145 | -VAPKPKTAG | ---------- | ---------- | ------- | -PAKKAKTSA | KPSPSKKAAP | 211 |
| SEQ_ID_NO_149 | -VALKGKTAG | ---------- | ---------- | ------- | RPAKAAKTSV | KAAPGKKAAP | 216 |
| SEQ_ID_NO_144 | PVKPKPKPKP | ---------- | ---------- | ------- | RPTRAAKTAA | KDSPGKKAAK | 213 |
| SEQ_ID_NO_125 | KAAAKPKAAA | ---------- | ------KPKG | RPAKAAKTSA | KDAPGKKAPA | | 227 |
| SEQ_ID_NO_137 | KPAAKAKPKA | ------VAA | KPKPAAKKAG | RPAKAAKTSA | KDTPGKKAAP | | 233 |
| SEQ_ID_NO_146 | KPAAKPKAKA | APKPKAAVVT | KTKATSAPAR | RPAKAAKTSA | KDTPSKKAAP | | 256 |
| SEQ_ID_NO_147 | KPAAKPKAKA | APKPKAAAVT | KTKATSAPAR | RPAKAAKTSA | KDTPSKKAAP | | 256 |
| SEQ_ID_NO_119 | -AKAKPAAKP | ---------- | ----KAK---A | KPAKVARTST | RTTPGKKAPA | | 249 |
| SEQ_ID_NO_100 | -VAAKPKAKE | ---------- | ---------- | RPAKASRTST | RTSPGKKVAA | | 241 |
| SEQ_ID_NO_113 | -VAAKPKAKE | ---------- | ---------- | RPVKASRTST | RTSPGKKAAA | | 226 |
| SEQ_ID_NO_104 | TAATKPKAAA | ---------- | ----KPK---D | KPVKASRTST | RTSPGKRAAA | | 242 |
| SEQ_ID_NO_108 | -APAKPKAKE | ---------- | ---------- | RPAKASRTST | RTSPGKKAAA | | 248 |
| SEQ_ID_NO_116 | -AKAKPAAKA | ---------- | ---KPAAKAKPAA | RPAKASRTST | RTSPGKRAAA | | 264 |
| SEQ_ID_NO_117 | AAKAKPAAKA | ---------- | ---KPAAKAKPAA | KPAKAARTST | RTSPAAAAAA | | 258 |
| SEQ_ID_NO_122 | -TPVKTKAAA | ---------- | ---KP--KAK--E | KPAKVARTAT | RSTPSRKAAP | | 244 |
| SEQ_ID_NO_120 | -APAKTKAAV | ---------- | ---KPNLKAK--T | TTAKVAKTAT | RTTPSRKAAP | | 255 |

Figure 4 (continued)

```
SEQ_ID_NO_101    - - KKAPAKKS  T- PKAKEA- -  - - - - - - - - - - -  - - - - - - - - - - -  - - - - - - - - - - -   255
SEQ_ID_NO_102    - - - - - - - - - -  - - PKKKAG- -  - - - - - - - - - - -  - - - - - - - - - - -  - - - - RPI- -       237
SEQ_ID_NO_150    - - - - - - - - - -  - - - KKAG- -   - - - - - - - - - - -  - - - - - - - - - - -  - - - - GA- - -      239
SEQ_ID_NO_118    - - - - - PVKKV  K- TVKSPA- -  - - - - - - - - - - -  - - - - - - - - - - -  - - - - - - - - - - -   223
SEQ_ID_NO_145    - - - - VASKKA  K- PVKKATA-   - - - - - - - - - - -  - - - - - - - - - - -  - - - - - - - - - - -   225
SEQ_ID_NO_149    - - - - VALKKA  K- AGKKVTT-   - - - - - - - - - - -  - - - - - - - - - - -  - - - - - - - - - - -   230
SEQ_ID_NO_144    - - - - RSSSRS  A- PTKKPK- -  - - - - - - - - - - -  - - - - - - - - - - -  - - - - PAVKKA            232
SEQ_ID_NO_125    - - - - AAAPKK  A- AARKPPT-   - - - - - - - - - -  KRSTPVKKAA  PAKKAAPAKK   261
SEQ_ID_NO_137    - - - - - AKKPA  A- AAKKAPA-   - - - - - - - - - -  KKAAPAKKA-  - - - - PTPSRK   261
SEQ_ID_NO_146    - - - - AAKKPA  A- AAKKAPA-   - - - - - - - - - -  KKAAPAKKA-  - - - - AAPARK   285
SEQ_ID_NO_147    - - - - AAKKPA  A- AAKKAPA-   - - - - - - - - - -  KKAAPAKKA-  - - - - AAPARK   285
SEQ_ID_NO_119    KPAAAPVKKA  T- PVKKATAT  PVKKAAPVKK  AAPAKGKSV-  - - - - KTPVKR    293
SEQ_ID_NO_100    - - - - - PAKKV  A- VTKKAP- -  - - - - - - - - - - -  - - - AKSAKV-  - - - - KSPAKR    265
SEQ_ID_NO_113    - - - - PAKKAA  AAATKKAP- -  - - - - - - - - - - -  - - - AKSVKV-  - - - - KSPAKR    252
SEQ_ID_NO_104    - - PKPAAKKA  P- AAKKAP- -  - - - - - - - - - -  AKSVKPKSV-  - - - - KSPAKK    272
SEQ_ID_NO_108    - - TKVAPKKA  A- TPKKAP- -  - - - - - - - - - -  AKTVKLKSV-  - - - - KTPTKK    278
SEQ_ID_NO_116    - - AKPAVKKA  ATPVKKAVPA  - - - - - - - - - -  KKAATPVKK-  - - - - AAPARK    297
SEQ_ID_NO_117    - - PKPAAKKA  A- PVKKTPV-   - - - - - - - - - -  KAAAKAKTA-  - - - - KSPAKK    289
SEQ_ID_NO_122    - - - KPVAKKV  P- VKKAAPA-   - - - - - - - - - -  AKSVKAKTA-  - - - - KSPAKR    274
SEQ_ID_NO_120    - - KATPAKKE  - - PVKKAP- -  - - - - - - - - - - -  - - - - - AKNV-  - - - - KSPAKK    279

SEQ_ID_NO_101    - - - KSKGKK   261
SEQ_ID_NO_102    - - - AKKAKK   243
SEQ_ID_NO_150    - - - AKKAKK   245
SEQ_ID_NO_118    - - - GKRTRK   229
SEQ_ID_NO_145    - - - PKKAKK   231
SEQ_ID_NO_149    - - - PKKAKK   236
SEQ_ID_NO_144    AAAKKKAKK    241
SEQ_ID_NO_125    APAAKKAKK    270
SEQ_ID_NO_137    VP- SRKAKK   269
SEQ_ID_NO_146    VP- ARKAKK   293
SEQ_ID_NO_147    VP- ARKAKK   293
SEQ_ID_NO_119    TSARKAGKK    302
SEQ_ID_NO_100    AS- TRKAKK   273
SEQ_ID_NO_113    ASTRKK- -    258
SEQ_ID_NO_104    AT- SRRGKK   280
SEQ_ID_NO_108    AA- VKKGKK   286
SEQ_ID_NO_116    APAKRGGRK    306
SEQ_ID_NO_117    AA- AKRGKK   297
SEQ_ID_NO_122    AS- ARKGRK   282
SEQ_ID_NO_120    AT- PKRGRK   287
```

Figure 5

| | | | | | | | | |
|---|---|---|---|---|---|---|---|---|
| SEQ_ID_NO_164 | MENM----- | KMNNDERFA- | ------QKGV | PVHSQVMKIK | QESEKIVDWS | | | 37 |
| SEQ_ID_NO_158 | MENN----- | SSNDDSRGRN | GDGDHGYVGF | PIHSQVIKIR | QEFDKIKHPS | | | 44 |
| SEQ_ID_NO_154 | MEQKKISSSS | SSNNNAVIRD | EDE---YKGV | PIHSQVMKIK | QEFEKIKHPS | | | 47 |
| SEQ_ID_NO_152 | MENK----- | TDNGN----- | ------EDGP | IIHSQVEKIK | KEFEKIRQPS | | | 33 |
| SEQ_ID_NO_162 | MENK----- | TNNGN----- | ------EDG- | PKHSQVVKIK | REFEKISQPS | | | 32 |

| | | | | | | |
|---|---|---|---|---|---|---|
| SEQ_ID_NO_164 | PGKPEIRSVL | REISTRQLSR | SPLGISGDPI | SVGES | | 71 |
| SEQ_ID_NO_158 | LQQLEVRGVV | KCRINRQRSR | SPLGLAERPI | SVGN- | | 78 |
| SEQ_ID_NO_154 | LQQPDMRRVL | REITTRQRSR | SPLGLAERPI | SVGNS | | 81 |
| SEQ_ID_NO_152 | LQQPEMRRVL | SEIKRRQRSR | SPLGLGERSI | SVGN- | | 67 |
| SEQ_ID_NO_162 | LKQPEMRRVL | SEITRRQRSR | SPLGLGERSI | SVGH- | | 66 |

Figure 6

| SEQ_ID | col1 | col2 | col3 | col4 | col5 | col6 | len |
|---|---|---|---|---|---|---|---|
| SEQ_ID_NO_184 | | | | | MG | L | 3 |
| SEQ_ID_NO_168 | | | | MS | LS PTQVLQG | LLGEFHSRRL | 22 |
| SEQ_ID_NO_177 | | | | ME | YPRRTLLH-- | ---------- | 10 |
| SEQ_ID_NO_181 | | | | MG | TPLRMPHMST | CSNVAPAP-- | 20 |
| SEQ_ID_NO_182 | | | | MA | MSPHDQHEHE | PDHAHRSP-- | 20 |
| SEQ_ID_NO_183 | | | | MA | MSPHDQHEHE | PDHAHRSP-- | 20 |
| SEQ_ID_NO_170 | | | | MR | PAPLEAEAAA | ANSHLSP--- | 20 |
| SEQ_ID_NO_166 | | | | MR | LLVAEA---- | ---------- | 9 |
| SEQ_ID_NO_174 | MWMMI SQEGQ | RSNPI IYHNN | IHLLCEVDQK | REKASVIVLK | IQTKHPNPES | | 50 |

| SEQ_ID | c1 | c2 | c3 | c4 | c5 | c6 | len |
|---|---|---|---|---|---|---|---|
| SEQ_ID_NO_184 | ------SSLP | GPSEGMLCVI | LVN------- | TALSISFKG | VRSVLHVLG | | 40 |
| SEQ_ID_NO_168 | LLTP--TTAS | PPSSEHHNS | SDLYTRNNSF | DANIVMVLSV | LLCALICSLG | | 70 |
| SEQ_ID_NO_177 | --TPFSGHPS | GPSQPLDGAT | A---TDGSNF | DANVVMILAV | LLCALICALG | | 55 |
| SEQ_ID_NO_181 | --APEAPRAP | PSSPL----- | ---------L | DYDVVVILAA | MLCALVCALG | | 53 |
| SEQ_ID_NO_182 | ------SNGT | AATSTIATNR | WGPYSGAGDF | ASNMAVILAA | LLAALALALA | | 64 |
| SEQ_ID_NO_183 | ------SNGT | AATSTIATNR | WGPYSGAGDF | ASNMAVILAA | LLAALALALA | | 64 |
| SEQ_ID_NO_170 | --PPLHSRAP | SCDPQVHSCK | WAPYSNSNDF | GANTAMILI | LLCALICALV | | 68 |
| SEQ_ID_NO_166 | --SPLSSLAA | TPTCNSHTCR | WKPYSNSTDF | TANASVLLIL | VISALICALS | | 56 |
| SEQ_ID_NO_174 | FKTSLEPLSP | PLSPHSLCR | WKPYSNSSEF | QANASVLLIL | FVSALICSLS | | 99 |

| SEQ_ID | c1 | c2 | c3 | c4 | c5 | c6 | len |
|---|---|---|---|---|---|---|---|
| SEQ_ID_NO_184 | IRLSQSSSSP | SSVTASSEIP | ASEPFDFRVS | HPESFLEEFR | NKTPTLRYS | | 90 |
| SEQ_ID_NO_168 | LNSIIRCALR | CSSLIASESG | ATTSSRLANK | ---GVKRKAL | KTFPTYNYS | | 116 |
| SEQ_ID_NO_177 | LNSIVRCALR | CSSRVVGPE | PNQVTRLVQS | ---GLRRKAL | RAMPVLVYS | | 101 |
| SEQ_ID_NO_181 | LNSMLQCVVR | CTRRAVADPV | GWADRRABA | ---GLKREDV | VALPVVTYS | | 99 |
| SEQ_ID_NO_182 | LNAAVRYLLR | RHRRARQQPA | AAAAAAEDPE | KPPVQEADPP | PPPPALVYSA | | 114 |
| SEQ_ID_NO_183 | LNAAVRYLLR | RHRRARQQPA | AAAAAAEDPE | KPPVQEADPP | PPPPALVYSA | | 114 |
| SEQ_ID_NO_170 | LNTAIRAFLR | SNNNNSSDRL | GELEEDRKPK | --DEADMATL | VLATTQVYS | | 115 |
| SEQ_ID_NO_166 | LYAAIRCFLR | --------PT | LETEDDHKPD | --PEAAASST | PTTPTLVYS | | 95 |
| SEQ_ID_NO_174 | LCAAIRCFLR | PN------L | QTDDNFHKPD | --PEEDVSST | VPTPTLVYS | | 139 |

| SEQ_ID | c1 | c2 | c3 | c4 | c5 | c6 | len |
|---|---|---|---|---|---|---|---|
| SEQ_ID_NO_184 | LCRCKKHEDN | ECSVCLSKFE | EDSEINKLK- | -C----GIL | FIKTCLEKW | | 132 |
| SEQ_ID_NO_168 | ADLKLPGLDS | ECIICLSDFT | AGDRVRLLPK | -C----NHG | FHVRCIDKW | | 159 |
| SEQ_ID_NO_177 | PGLRINAANP | TCAICLSDFE | AGEHVRVLPK | -C----NHG | FHVRCIDRW | | 144 |
| SEQ_ID_NO_181 | -ASPPAAAAA | GCAICLSDFA | DGERMRVLPV | -C----GHR | FHVVCIDRW | | 141 |
| SEQ_ID_NO_182 | AGTKLAGALA | ECAICLAEFV | DGDTYRVMPC | WCQEIPLESG | LRFACIKVYQ | | 163 |
| SEQ_ID_NO_183 | AGTKLAGALA | ECAICLAEFV | DGDTYRVMPV | -C----GHG | FHARCIERW | | 156 |
| SEQ_ID_NO_170 | AGMKLGGVEA | DCAICLSEFV | EGEGRVLGR | -C----DHG | FHVLCIEKW | | 158 |
| SEQ_ID_NO_166 | SDLELAGAEA | ECAICLSEFE | QGESIQVLEK | -C----QHG | FHVKCIHKW | | 138 |
| SEQ_ID_NO_174 | SDLELAGADA | ECAICLSEFE | PGESIHVLEK | -C----HHG | FHIKCIHKW | | 182 |

Figure 6 (continued)

| SEQ_ID_NO_184 | | -L-DYWN TC PLCRT-PLVV | | | | ----------V | 150 |
|---|---|---|---|---|---|---|---|
| SEQ_ID_NO_168 | | -L--SAHSSC PKCRH-CLVD | TCDKIVGCT- | --QASSSEPP | | | 192 |
| SEQ_ID_NO_177 | | -L--LARSTC PTCRQ-SLFG | VPQKASGCSE | ASRAAEPEPA | | | 180 |
| SEQ_ID_NO_181 | | -L--ASHKSC PTCRR-RLSS | | | | --------ES | 159 |
| SEQ_ID_NO_182 | TGPFNVEAAN | LL--PTPGIC TTCRF-VYRG | MVKHLHFL-- | --YGDWRD L | | | 206 |
| SEQ_ID_NO_183 | | -LAGGRRSSC PTCRA-PAAT | | | | --------PP | 176 |
| SEQ_ID_NO_170 | | -L--SSHSSC PTCRRSCLAS | SPSSPEPDNC | SAGNGHDSNS | | | 195 |
| SEQ_ID_NO_166 | | -L--STRSSC PTCRT-SIFS | | | | | 154 |
| SEQ_ID_NO_174 | | -L--SSRSSC PTCRT-SIFS | | | | --QNTLDSAT | 206 |

| SEQ_ID_NO_184 | AAAEDQKQLS | SNVW----- | ---- | 164 |
|---|---|---|---|---|
| SEQ_ID_NO_168 | PVQETI LSII | TPVDREGFIH | SYR- | 215 |
| SEQ_ID_NO_177 | PAPAPARSVL | VPLRPEGLVT | HYDF | 204 |
| SEQ_ID_NO_181 | GGGHRHL QYL | TAV----- | ---- | 172 |
| SEQ_ID_NO_182 | ACFVKGKKNT | NS------- | ---- | 218 |
| SEQ_ID_NO_183 | GATATEPAAV | AP------- | ---- | 188 |
| SEQ_ID_NO_170 | SQSAEPERAA | DNLSTNGNLP | V--- | 216 |
| SEQ_ID_NO_166 | QHSETPSSHI | NA------- | ---- | 166 |
| SEQ_ID_NO_174 | SAVAPSTNEI | NA------- | ---- | 218 |

Figure 7

```
SEQ_ID_NO_194    MLKSKSCREE MRSSS AYK- YHCLTNGGTP EAVAAPSPTN PQLPVMLRSY    49
SEQ_ID_NO_199    -MAAADYDRA YRPYAPSSAA DYDRPYRNE- ---------- ------VPY      32
SEQ_ID_NO_204    -MAAADADYE YRAYG-APA- DHDRPYHG-  ---------- RE----VVPY     31
SEQ_ID_NO_186    ---MANYYE- -PPAS-GNRR DAYKGYNS-- -G-------- ---------SF    25
SEQ_ID_NO_201    ---MD--RS- -KSYA-GGR- MQIEPYYD-- -G----GGAR PD----FRSY     30
SEQ_ID_NO_203    ---MDDFRS- -RSFN-DGK- MQLEVYGSRR SGAVPAPPVL HD----YRSY     39
SEQ_ID_NO_188    ---MEHFRS- -KSCR-EGR- IEMEGYDEDK AA----PTNM QD----LRSY     35
SEQ_ID_NO_196    ---MEEFRS- -KSYG-DGR- MQIEAYRS-  -------ANI QD----LRCY     39
SEQ_ID_NO_197    ---MEDYNKQ IRPYG-NSCM MQMEGYYG-  -A----TNPN YD----IRSY     35
SEQ_ID_NO_193    ---MEDYNRQ -RAYG-DTG- MQIOPYHG-  -G----GPGT GD---FRKY      33

SEQ_ID_NO_194    S-------- TSTYS---- ---------- ----PHKNPT TVRDNPNS-K           70
SEQ_ID_NO_199    G-------- DRRIDLVVKP PPP------- ----TRSPPP PLPVTKSG--          60
SEQ_ID_NO_204    G-------- DRRIDVVVKP PGTTTTTT-- ----TRSPPP PLPVTKVG-G          65
SEQ_ID_NO_186    D-------- DSSGDQSQ-- ---------- ----TNDYQL KIKKSKSVPN          50
SEQ_ID_NO_201    SYSAGGSGMG TSSYAYQYEY S--------- ----GAGAGE EMKRSKS--           64
SEQ_ID_NO_203    S-------- -ASYFYTYD- ---------- ----GSGVGY GDFKGKPDHG          64
SEQ_ID_NO_188    S-------- -VSYAVSVCP N--------- ----QSGKEG KMKKGKSN--          60
SEQ_ID_NO_196    S-------- -ASYASSVHP TTTTTTTQT QMGGNNNNEA KFKKGKST--           68
SEQ_ID_NO_197    S-------- DFSYAQTCRG ---------- ----PNNKDL KLKKGKSI-S          61
SEQ_ID_NO_193    S-------- -TSYA----- ---------- ----TENNIX NLKKEKS---          52

SEQ_ID_NO_194    SNGKVKKGL- --KEAEIQRK KRVAAYNVYG VEGKVKGSIR KNFKWEKETC         117
SEQ_ID_NO_199    GGGGIGSAWC F-SDPEVKRR RRVASYKAYS VEGKVKASFR RGFRWIKDKC         109
SEQ_ID_NO_204    GGGGMGSAWC F-SDPEMKRR RRVASYKAYS VEGKVKSSLR RGFRWIKAKC         114
SEQ_ID_NO_186    ADRAASRSWS F-SDPESRRK RRVAGYKVYS VELKMKGSIR KSFKWEKDL-          97
SEQ_ID_NO_201    ----KRRML ALADPDMERK KRVAAYKAYG VEGKMKGSFR KSFKWIKDRY         109
SEQ_ID_NO_203    SSABNKGGRV F-KDPEFQRK RRVASYKAYA VEGKVKGSLR RSLRWFKDKY         113
SEQ_ID_NO_188    -LESSKSWS F-NDPELQRK RRVANYKVYA IEGKMKGSLR KSFRWIKDTC         108
SEQ_ID_NO_196    -NGSTSKSWS F-SDPELQRK KRVASYKVYA VEGKLKGSLR KSFKWLKDRC         116
SEQ_ID_NO_197    SRSSISKSWS FGDDPEFQRK KRVASYKMYS VEGKVKGSFR KSFKWLKNRY         111
SEQ_ID_NO_193    ---ARSKSWG I-TDPELQRK KRVASYKMYS VEGKVKGSFR KSFRWLKQRY          96
```

Figure 7 (continued)

| | | |
|---|---|---|
| SEQ_ID_NO_194 | SNAVNGLM- ........... ........ . | 125 |
| SEQ_ID_NO_199 | TGFIHG--- ........... ........ - | 115 |
| SEQ_ID_NO_204 | SELIHGWYGS LLLPLSFSLD DFIITSKQAL S | 145 |
| SEQ_ID_NO_186 | ---IGIS-- ........... ........ . | 102 |
| SEQ_ID_NO_201 | LNLVYGWS-- ........... ........ - | 117 |
| SEQ_ID_NO_203 | TRAVYGWW- ........... ........ . | 121 |
| SEQ_ID_NO_188 | TQVVYGWR-- ........... ........ - | 116 |
| SEQ_ID_NO_196 | NRVVYG--- ........... ........ - | 122 |
| SEQ_ID_NO_197 | WHVVYSLM- ........... ........ - | 119 |
| SEQ_ID_NO_193 | TQVVYGWW- ........... ........ . | 106 |

Figure 8

| | | | | | |
|---|---|---|---|---|---|
| SEQ_ID_NO_216 | MGKGEAWWNG | QRIGRYWPTY | VASDASCTDS | CNYRGPYSAS | KCRKNCEKPS | 50 |
| SEQ_ID_NO_208 | ---------- | ---------- | -----METLQ | CRHQHVFIL | ---------E | 15 |
| SEQ_ID_NO_214 | ---------- | ---------- | ----MDTTHS | CRRG--YIL | ---------E | 14 |

| | | | | | |
|---|---|---|---|---|---|
| SEQ_ID_NO_216 | QTLYHVPRSW | LKPSGNILVL | FEFRGGDPTQ | ISIVTKQTES | LCAHVSDSHP | 100 |
| SEQ_ID_NO_208 | LVLFHS-SL | FVLASKIDVS | DDARGIRIDG | ---GDKRFLT | NSPQHSKEHA | 60 |
| SEQ_ID_NO_214 | LVLSVS-SV | FGLASNMSIS | NDTSGNKTDS | FFESQSTSTE | WGTDMGDKYI | 62 |

| | | | | | |
|---|---|---|---|---|---|
| SEQ_ID_NO_216 | PPVDLWNSET | ESGRKVGPVL | SLTCPHDNQV | ISSIKFASYG | TPLSTCGNFY | 150 |
| SEQ_ID_NO_208 | -------ACT | NEEPDLGPLT | RISCNEPEYV | LTKINFADYG | NPTGTCGHFR | 103 |
| SEQ_ID_NO_214 | -------MCT | ESNMEIPWM- | -ISCKKSKEV | FTRINFADYG | NPSGKCEHYR | 103 |

| | | | | | |
|---|---|---|---|---|---|
| SEQ_ID_NO_216 | HGRCSSNKAL | SIVQKACIGS | SSCSVGVSBD | TFGDP-CRGM | AKSLAVEATC | 199 |
| SEQ_ID_NO_208 | RDNCGARATM | RIVKKNCLGK | EKCHLLVTDE | MFGPSKCKGA | PM-LAVETTC | 152 |
| SEQ_ID_NO_214 | HGNCGAKTTM | EVAKKNCLGK | HDCVFKVSDE | MFGTSHCKKE | AK-FFVQLTC | 152 |

| | | |
|---|---|---|
| SEQ_ID_NO_216 | A-- | 200 |
| SEQ_ID_NO_208 | TIA | 155 |
| SEQ_ID_NO_214 | TKA | 155 |

Figure 9

| | | | | | | | |
|---|---|---|---|---|---|---|---|
| SEQ_ID_NO_218 | ----MDEEAA | KPRDSTVNQQ | H--------- | ---------- | QYY | YGTFQGVANF | 30 |
| SEQ_ID_NO_225 | ----MDEEAA | KPRDTTTNQQ | Q--------- | ---------- | QYY | YGTFQGVANY | 30 |
| SEQ_ID_NO_227 | -MGQGEEDKS | KGFADEAGTH | H--------- | ---------- | Q | YGTFQGVSNY | 31 |
| SEQ_ID_NO_220 | ----MSQDEK | NPAVVDHQH | H--------- | ---------- | Q | YGTFQGVSNY | 28 |
| SEQ_ID_NO_222 | ----MSDQEK | NRGVVVDHRH | HEDQPPPPPL | -----PPQPQ | | YGTFQGVANY | 40 |
| SEQ_ID_NO_231 | MAGEMPDADG | KPRSASSGFQ | PSAPPQPQ-- | ------AQQYQ | | YGTFGA---- | 39 |
| SEQ_ID_NO_230 | -MGGGREEEA | ASKL-VGYSS | GDLPPSAPPH | LQGCDPQQYQ | | YGTFQ----- | 42 |
| SEQ_ID_NO_229 | -MGGGDEQEA | DAGKSGGYSS | SGLPPSEP- | ------SQQYG | | YGTFQG---- | 38 |
| SEQ_ID_NO_1052 | -MGGRHEAEA | DGGKAGGYSS | SGLPPSEAPH | LQGCPSQEYG | | YGTFQG---- | 45 |

| | | | | | | | |
|---|---|---|---|---|---|---|---|
| SEQ_ID_NO_218 | PTPAPPPQFM | QPQHPITTF | ---PGHAY- | ---------Q | NLQGHG---- | | 61 |
| SEQ_ID_NO_225 | PPPAPPP--- | LPHQPIVTSP | LLPP------ | ---------- | ---------- | | 51 |
| SEQ_ID_NO_227 | PPPRPL---- | QNSPPVTGFP | QPSAPPRV-- | ---------Y | D-SAPP---- | | 60 |
| SEQ_ID_NO_220 | PPPPPPP--- | QHHGPAIGFP | QPVPPPGL-- | ---------H | EPSAPP---- | | 59 |
| SEQ_ID_NO_222 | PPPS------ | --QSHVIGFP | QPVPPPGL-- | ---------- | --TAEP---- | | 64 |
| SEQ_ID_NO_231 | PSSAPG---- | ENPQPAVGFP | QPAPPPGL-- | ---------R | HYPQPPPPSY | | 74 |
| SEQ_ID_NO_230 | PPPHHHAASG | ELARPPVGFP | QPAPPPGFAG | ASGGGGHYHH | HHQQQP---- | | 88 |
| SEQ_ID_NO_229 | SRAGSG---- | EFRKPPVGFP | QPAPPPGF-- | --QGGG---Y | HNQQQP---- | | 73 |
| SEQ_ID_NO_1052 | P--------- | --RQPPVGFP | QPAPPPGF-- | --SGGG---Y | HNQQKP---- | | 73 |

| | | | | | | | |
|---|---|---|---|---|---|---|---|
| SEQ_ID_NO_218 | ---------- | ---GGVNYAQ | GFPVVVPDVT | -VVEVRP--M | IEHELPCCGL | | 95 |
| SEQ_ID_NO_225 | ---------- | --------VH | GYQTLQEYT | -VVEVRP--M | REHDVPCCGF | | 79 |
| SEQ_ID_NO_227 | ---------- | -------IIYAH | GYQTVPVHG | -IAEGRPVHV | RQRRLPCCGI | | 92 |
| SEQ_ID_NO_220 | ---------- | ----PQVYPQ | GYQTVPGYA | -VAEGRP--V | RERRLPCCGI | | 91 |
| SEQ_ID_NO_222 | ---------- | -------YAQ | GYQTVPGYA | -VAEGRP--V | RQRRLPCCGC | | 93 |
| SEQ_ID_NO_231 | AVYPPLPPQT | YPAAAPYYAL | GYQAVQGYL | PVVEGRP--V | RMRRLPFCGL | | 121 |
| SEQ_ID_NO_230 | ---------- | YAPAEPYYAQ | GYQTSPGYG | S)AEGRP--V | RMRRLPCCGL | | 125 |
| SEQ_ID_NO_229 | ---------- | YTPEEPYYAQ | GYQAVPGYG | QVAEGRP--V | RMRRLPCCGL | | 110 |
| SEQ_ID_NO_1052 | ---------- | YAPAEPYYAQ | GYQAVPGYG | PVAEGRP--V | RMRRLPCCGL | | 110 |

| | | | | | | | |
|---|---|---|---|---|---|---|---|
| SEQ_ID_NO_218 | GMGWFLFIMG | FLFGGIPWYL | GAFIVLVT-S | VDHREKAGYV | ACSIA----- | | 139 |
| SEQ_ID_NO_225 | GMGWFLFIMG | FLFGGIPWYL | GAVIILFTLS | VDHREKAGYV | ACSVA----- | | 123 |
| SEQ_ID_NO_227 | GLGWFLFIVG | FFLGAIPWYV | GMFIMIVGRR | DHREKPGYI | ACTIA----- | | 137 |
| SEQ_ID_NO_220 | GFGWFLFIIG | FFLGAIPWYI | GLFVLLCA-R | DYREKPGYI | ACTIA----- | | 135 |
| SEQ_ID_NO_222 | GVGWFLFIIG | FFLGAIPWYI | GLFIIACM_R | DPREKPGYV | ACTIALRKHL | | 142 |
| SEQ_ID_NO_231 | GMGWFLFIIG | FFLAAIPWYI | GAFVLICVRV | HDYREKPGYV | ACTIA----- | | 166 |
| SEQ_ID_NO_230 | GLGWLLFIAG | FFLAAIPWYV | GAFILICVRV | HDYREKPGYV | ACTVA----- | | 170 |
| SEQ_ID_NO_229 | GLGWCLFITG | FFLAAIPWYI | GAFIMICVRV | HDHREKPGYV | ACTIAVSS-- | | 158 |
| SEQ_ID_NO_1052 | GLGWCLFITG | FFLAAIPWYI | GAFIIICVRV | HDQREKPGYV | ACTIA----- | | 155 |

Figure 9 (continued)

| | | | |
|---|---|---|---|
| SEQ_ID_NO_218 | ---------- ---------- S | VVYLI AVMLG MTGD N W | 158 |
| SEQ_ID_NO_226 | ---------- ---------- S | VVYLI AVMLG MAGN N W | 143 |
| SEQ_ID_NO_227 | ---------- ---------- A | LATI AVI LG VTKGAE DW | 156 |
| SEQ_ID_NO_220 | ---------- ---------- A | VLATI AI I LG VTKGI D DF | 153 |
| SEQ_ID_NO_222 | VEHECHI EI R CLLHNLCVK A | LATI AI I LG ATKGAD EW | 180 |
| SEQ_ID_NO_231 | ---------- ---------- A | SLAAI AI LLG VTRGEE I W | 185 |
| SEQ_ID_NO_230 | ---------- ---------- A | VI AAI VI PLG LTKGAH VW | 189 |
| SEQ_ID_NO_229 | ---------- ---------- F | LL QCNL TVY FTSGI --- | 174 |
| SEQ_ID_NO_1052 | ---------- ---------- A | VVAAVAI LLG VTKGTH VW | 174 |

Figure 10

```
SEQ_ID_NO_244    MEYQRTNNLS  LAFQFFRKAF  EMCDSDPLLF  NEYGVLRYRQ  G-NYEEAVEN    49
SEQ_ID_NO_234    MEYMRTHSYK  LADQFFMQAK  AICPSDPLVY  NELGVVAYHM  K-EYGKAVRW    49
SEQ_ID_NO_236    MEYMRTHSYK  LAEQFFMQAK  TICPSDPLVY  NELGVVAYNM  K-EYNKAVLW    49
SEQ_ID_NO_241    MQYVRMHNFK  LAEQFFTQAK  SICPSDPLIH  NELGVVAYNM  KEEYQKAVSY    50
SEQ_ID_NO_242    MQYLRMHNFK  LAEQFFTQAK  SICPSDPLIY  NEMGVVAYNM  K-EYQKAVQW    49

SEQ_ID_NO_244    FERALDLAPK  PMGSRWESLI  VNLAQAFRKI  GRYDEAIATF  DSALLISPRN    99
SEQ_ID_NO_234    FEKTLAHIPS  ALTESMEPTV  VNLAHAYRKL  RKDREAISYY  ERALTLSTKS    99
SEQ_ID_NO_236    FEKTLKHIPS  -LSQLMEPTV  INLAHAYRKL  KIYHEAISCY  ERALALSTRS    98
SEQ_ID_NO_241    YAKALTFPTK  SLSL----AF  AGLAYIYHLM  DDFEMAINYY  HKALWLKPDD    95
SEQ_ID_NO_242    FELTLEHTSS  SLNEMWEPTL  VNLGHARRKL  KKYQKAISYY  EKALTFQTKS    99

SEQ_ID_NO_244    ASTYAALAFT  YQMKSRCSEP  VSLGLAIEYY  HKALSLRADD  AFSQHHLELA   149
SEQ_ID_NO_234    LSTYSGLAYT  YHLQGNFS--  ----AAISYY  HKALNLKPDD  QFCTEMLNVA   143
SEQ_ID_NO_236    LSTYAGLAYT  YHLQDNFT--  ----AAITCY  HKALNLKPDD  QFCTEMLSLA   142
SEQ_ID_NO_241    QFCTDMLIYA  LESICQIT--  ----------  ----------  ----------A  114
SEQ_ID_NO_242    LSAFAGLAYT  YHLMAMYH--  ----V-----  HRA-------  ----EVLQLL   127

SEQ_ID_NO_244    LIDQSAITIP  RHQQVEWDTM  FPKVEDINAV  TPTFGIASSP  QGGILFPTPS   199
SEQ_ID_NO_234    LMDE------  ----------  ----------  ----------  ----------   147
SEQ_ID_NO_236    LVDE------  ----------  ----------  ----------  ----------   146
SEQ_ID_NO_241    RRKP------  ----------  ----------  ----------  ----------   118
SEQ_ID_NO_242    TKEP------  ----------  ----------  ----------  ----------   131

SEQ_ID_NO_244    PHSFQGTPTF  GQTPFSARVD  RMDESVDMDQ  SVDMDESE      237
SEQ_ID_NO_234    ----------  CQNGVDSKV-  ----------  ------ELC     159
SEQ_ID_NO_236    ----------  GRRGIDPKI-  ----------  ------EFR     158
SEQ_ID_NO_241    ----------  GRGLLTAIGG  ----------  ------VTC     131
SEQ_ID_NO_242    ----------  GR--------  ----------  ---------     133
```

| SEQ_ID | | | | | |
|---|---|---|---|---|---|
| SEQ_ID_NO_268 | ---MEEQCAA | AAGGG---GG | GGGASMCANG | CGFFGSEATK | KLCSKCYRDQ | 44 |
| SEQ_ID_NO_298 | ---MAER-QE | VSG------- | GMAAPMCANA | CGFFGSAATK | NLCSKCYK-- | 37 |
| SEQ_ID_NO_260 | ---MSSEQNN | STSFP----- | PTEPKLCDNG | CGFFGSPSNM | NLCSKCYR-- | 40 |
| SEQ_ID_NO_249 | ---MAEE-HR | CQA------- | P----QLCANN | CGFFGSPTTC | NLCSECYR-- | 34 |
| SEQ_ID_NO_255 | ---MAEEQHR | CQE------- | P----RLCVNN | CGFFGSPATC | NLCSKCYG-- | 35 |
| SEQ_ID_NO_265 | ---MAEE-HR | CQA------- | ----AQRLCANN | CGFFGSPAMC | NLCSKCYR-- | 35 |
| SEQ_ID_NO_262 | ---MAEE-HR | CQA------- | PEGHRLCSNN | CGFFGSPATM | NLCSKCYR-- | 37 |
| SEQ_ID_NO_251 | ---MAEE-HR | CQA------- | PEGHRLCVNN | CGFFGSPATM | NLCSKCYR-- | 37 |
| SEQ_ID_NO_246 | ---MAEE-HR | CET------- | PEGHRLCVNN | CGFFGSSATM | NLCSNCYR-- | 37 |
| SEQ_ID_NO_274 | ---MAEE-HP | CQT------- | PEGHRLCVNN | CGFFGSSATM | NLCSNCYG-- | 37 |
| SEQ_ID_NO_248 | MAQRDKEETE | MKV------- | SESLSLCINN | CGFSGNPATK | NMCQSCYK-- | 41 |
| SEQ_ID_NO_279 | ---MAQESWK | QESEETRVHA | PEAPILCINN | CGFFGSSMTN | NMCSKCYR-- | 45 |
| SEQ_ID_NO_296 | ---MAQESWK | QESHA----- | PEAPILCINN | CGFFGSSMTN | NMCSKCYR-- | 40 |
| SEQ_ID_NO_270 | ---MDHDKTG | CQSP------ | PEGPKLCINN | CGFFGSAATM | NMCSKCHK-- | 39 |
| SEQ_ID_NO_267 | ---MEQNETG | CQVP------ | PDAPMLCVNN | CGFFGSAATM | NPCSKCHK-- | 39 |
| SEQ_ID_NO_277 | ---MEHEETG | CQPH------ | PEGPILCVNN | CGFFGSVATR | NMCSKCHK-- | 39 |
| SEQ_ID_NO_286 | ---MEHKETG | CQQ------- | PKGPILCINN | CGFFGSAATM | NMCSKCHK-- | 38 |
| SEQ_ID_NO_290 | ---MEHKETG | CQQ------- | PEGPILCINN | CGFFGSAATM | NMCSKCHK-- | 38 |

FIG. 11

| SEQ_ID | | | | | |
|---|---|---|---|---|---|
| SEQ_ID_NO_268 | LKAAPSSPPA | APDLVANEEE | EASTAAAAAA | DEQLALCSSG | CGFFGSKETN | 94 |
| SEQ_ID_NO_298 | ---------- | --EHLIKTAK | QEASAAVVVG | GAIVKCAADG | CGFFGSSATN | 75 |
| SEQ_ID_NO_260 | ---------- | --SLRAEEDQ | TAVAKAAVEK | GLKLPSCSLI | TAPAPKQ-PL | 77 |
| SEQ_ID_NO_249 | ---------- | --GLQLKEQQ | SSSAKQAFNH | TLVPSSSSLP | ------SS | 64 |
| SEQ_ID_NO_255 | ---------- | --DLRQSCPL | NCLLAPSSSA | SVSSFSSP- | -------- | 61 |
| SEQ_ID_NO_265 | ---------- | --DLQMKEQR | SSSAKLVLNQ | TLIPQCSNSG | SLDTG-I-HP | 72 |
| SEQ_ID_NO_262 | ---------- | --DLRLKEEE | QAKTKSTIET | ALSGSSSATV | -------T | 66 |
| SEQ_ID_NO_251 | ---------- | --DLCLKEQE | ASSIKSALSS | SPSSSSTVV- | -------- | 64 |
| SEQ_ID_NO_246 | ---------- | --DLCLKQQQ | QASMKSTVES | SLSPVIAPV- | -------- | 64 |
| SEQ_ID_NO_274 | ---------- | --DLCLKNQQ | QASMKSTVES | SLSAASPPS- | -------- | 64 |
| SEQ_ID_NO_248 | ---------- | --ISTGI | MTQPALTFSG | KEKARSSFLR | ------LP | 68 |
| SEQ_ID_NO_279 | ---------- | --DFI----- | KLMEAPVVEK | KVTTSASSS- | -------- | 67 |
| SEQ_ID_NO_296 | ---------- | --DFV---KL | MEMDAPVVDK | KLITTASS | -------- | 63 |
| SEQ_ID_NO_270 | ---------- | --TILFQQEQ | GAKLASAVSG | SPSNILKETF | ------TA | 69 |
| SEQ_ID_NO_267 | ---------- | --DLMLKQQQ | TELAASSIGS | IANGGSSSPG | KEPQSAIT- | 75 |
| SEQ_ID_NO_277 | ---------- | --DMMLKEEQ | AKLAASSFGN | IVNGTSNSNG | NEPV---VA | 73 |
| SEQ_ID_NO_286 | ---------- | --EMIMKQEQ | AKLAASSIDS | IVNGGDSGKE | PIIAG---RA | 73 |
| SEQ_ID_NO_290 | ---------- | --EMIMKQEQ | AKLAASSIDS | IVNGGDSGKE | PIIAG---RA | 73 |

FIG. 11 (continued)

| | | | | | |
|---|---|---|---|---|---|
| SEQ_ID_NO_268 | NMCSKCYRDH | LKATSPLFSS | SSSPATAGTT | DITVPIAPAT | TAPTPSLKGK | 144 |
| SEQ_ID_NO_298 | NMCSGCYMDF | LKDAH----- | ---------- | DKVVVLAAEK | QPAAAQISAA | 116 |
| SEQ_ID_NO_260 | E--------- | ---------- | -TKPASV | ETVVIAETSS | VPPVATSCDE | 104 |
| SEQ_ID_NO_249 | S--------- | ---------- | -SARSSF | SASLPAKEEP | SAGTKETKVV | 91 |
| SEQ_ID_NO_255 | ---------- | ---------- | -TVDVIK | NCIAPVLVVE | GDEKGEFKAE | 87 |
| SEQ_ID_NO_265 | S--------- | ---------- | -STGPSV | MIVSSSTPTV | ELVAAAAGPS | 99 |
| SEQ_ID_NO_262 | A--------- | ---------- | -TAVVAS | SVESPSAPVE | SLPCPPVLIS | 93 |
| SEQ_ID_NO_251 | ---------- | ---------- | -ESISQV | PLLALHEVNR | ESAVPEIASA | 90 |
| SEQ_ID_NO_246 | ---------- | ---------- | -LENYAA | ELETPTTKKT | EEKKPIQIPT | 90 |
| SEQ_ID_NO_274 | ---------- | ---------- | -SPEIQS | ISTSTIAPVV | QIYAAEIQIE | 90 |
| SEQ_ID_NO_248 | E--------- | ---------- | -RSDYCR | -RDLITQDD | KKGIDDDQAK | 93 |
| SEQ_ID_NO_279 | ---------- | ---------- | -TAPLET | KRDDAPAAAA | TEAVAEKQAE | 93 |
| SEQ_ID_NO_296 | ---------- | ---------- | -STVPFE | TAKQDDTVPD | AAAMDDKQPA | 89 |
| SEQ_ID_NO_270 | D--------- | ---------- | -LVDAGT | KSIEPVAVSV | QAVAEVVAPE | 96 |
| SEQ_ID_NO_267 | ---------- | ---------- | -TVHVDA | GSSDSMIVSM | QASHESLLNE | 101 |
| SEQ_ID_NO_277 | A--------- | ---------- | -GVDVQA | HLVEPKTISL | QPSFSFGSGS | 100 |
| SEQ_ID_NO_286 | E--------- | ---------- | -VAVAQV | EVKTLVAQPA | EIAGPSEGVT | 100 |
| SEQ_ID_NO_290 | E--------- | ---------- | -VAVAQV | EVKTLVAQPA | EIAGPSEGVT | 100 |

FIG. 11 (continued)

| | | | | | | |
|---|---|---|---|---|---|---|
| SEQ_ID_NO_268 | EEEATAAISS | SAAAAAKPNR | CVACRKKVGL | LGFECRCGGT | FCSTHRHADK | 194 |
| SEQ_ID_NO_298 | TSSTAPAA-- | -VKAAAAPNR | CASCRKKVGL | LGFPCRCGGT | FCALHRYAEK | 183 |
| SEQ_ID_NO_260 | SEP------- | --SKPARPNR | CFSCNKKVGV | MGFKCKCGST | FCGSHRYPEK | 145 |
| SEQ_ID_NO_249 | EEE------- | --EVQVTPNR | CLSCKKRVGL | TGFKCRCGMV | FCGIHRYPST | 132 |
| SEQ_ID_NO_255 | PTV------- | --VPQQKPNR | CLTCRRRVGL | TGFNCRCGMV | FCGTHRYPEQ | 129 |
| SEQ_ID_NO_265 | EAE------- | --PPKVQPNR | CGTCRRRVGL | TGFKCRCGLT | LCGTHRYPEQ | 140 |
| SEQ_ID_NO_262 | PDI------- | --AAPVQANR | CGACRKRVGL | TGFKCRCGTT | FCGSHRYPEK | 134 |
| SEQ_ID_NO_251 | AEQ------- | -RSQQQPNR | CMVCRKRVGL | TGFRCKCGVT | FCGSHRYPEN | 131 |
| SEQ_ID_NO_246 | EQP------- | --SPPQRPNR | CTVCRKRVGL | TGFMCRCGTT | FCGTHRYPEV | 131 |
| SEQ_ID_NO_274 | KQI------- | --QQQRPNR | CTVCRKRVGL | TGFMCRCGTT | FCGTHRYPEV | 130 |
| SEQ_ID_NO_248 | NDSTTIKI-- | -VEKKQEVNR | CSGCRRKVGL | TGFRCRCGDM | FCSEHRYSDR | 140 |
| SEQ_ID_NO_279 | QEP------- | --PKPPSNR | CLTCRKKVGL | TGFLCRCGDT | FCSTHRYTDS | 133 |
| SEQ_ID_NO_296 | QEP------- | --PKPPSNR | CTTCNKRVGL | TGFQCRCGGT | FCSLHRYTDS | 129 |
| SEQ_ID_NO_270 | EAA------- | --AKPKEGPSR | CSACRKRVGL | TGFKCRCGDL | FCHTHRYADV | 138 |
| SEQ_ID_NO_267 | NNV------- | --IVKEVPPNR | CTTCRKRVGL | TGFNCRCGHL | FCAVHRYSDK | 143 |
| SEQ_ID_NO_277 | GGG------- | GEAKPEGPNR | CGTCRKRVGL | TGFNCRCGNL | FCAMHRYSDK | 143 |
| SEQ_ID_NO_286 | VNP------- | --KGREGPNR | CSTCRKRVGL | TGFNCRCGNL | YCAMHRYSDK | 141 |
| SEQ_ID_NO_290 | VNP------- | --KGREGPNR | CSTCRKRVGL | TGFNCRCGNL | YCAMHRYSDK | 141 |

FIG. 11 (continued)

| | | | | |
|---|---|---|---|---|
| SEQ_ID_NO_268 | HACTFDFKKS | DREKIAKENP | LIVAPKITKF | 224 |
| SEQ_ID_NO_298 | HACDFDFKAA | GREKIAKNNP | LVVAAKINKI | 193 |
| SEQ_ID_NO_260 | HECSFDFKEV | GRGAIAKANP | VVKADKVQRI | 175 |
| SEQ_ID_NO_249 | TCLCF---- | ---------- | ---------- | 137 |
| SEQ_ID_NO_255 | HDCEFDFKSL | GKEQIAKANP | VVKGEKLQRI | 159 |
| SEQ_ID_NO_265 | HGCGFDFKSM | GREEIKKANP | VVKGEKLNKI | 170 |
| SEQ_ID_NO_262 | HACGFDFKAV | GREEIARANP | VIKGEKLRRI | 164 |
| SEQ_ID_NO_251 | HGCTFDFKKV | GREEIARANP | LVKAEKLEKI | 161 |
| SEQ_ID_NO_246 | HGCTFDFKSA | GREEIAKANP | LVIAAKLQKI | 161 |
| SEQ_ID_NO_274 | HGCTFDFKSA | GREEIAKANP | LVVAAKLQKI | 160 |
| SEQ_ID_NO_248 | HDCSFDYKAA | GRESIARQNP | VVKAAKLIRL | 170 |
| SEQ_ID_NO_279 | HQCTFDYKKV | AREQIAKQNP | VVIAEKLNKI | 163 |
| SEQ_ID_NO_296 | HECTFDYKKV | AREQIAKQNP | VVKADKLDKI | 159 |
| SEQ_ID_NO_270 | HNCSFDYHVA | AQEAIAKANP | VVKAEKLDKI | 168 |
| SEQ_ID_NO_267 | HDCPFDYRSA | AQDAIAKANP | VVKADKLDKL | 173 |
| SEQ_ID_NO_277 | HDCPYDYHTA | ARDVIAKANP | VVKADKLEKI | 173 |
| SEQ_ID_NO_286 | HDCQFDYRTA | ARDAIAKANP | VVKAEKLDKI | 171 |
| SEQ_ID_NO_290 | HDCQFDYRTA | ARDAIAKANP | VVKAEKLDKI | 171 |

```
SEQ_ID_NO_310    -------MAE AKGAAAPLL- --LAREDGRR RGGMGGATWA Q--TLGNVVV   37
SEQ_ID_NO_316    MGFGMG-NDG ASSSSSRLDP APLLPHHGSA GGEIG--LSS QPKTFANVFI   47
SEQ_ID_NO_325    MGFGMGNNNG ASSSSSRLDP APLLPHHGSG SREVG--LSS QPKTFANVFI   48
SEQ_ID_NO_312    MGF----DKE ASSSSSRLDA APLLPQHG-- GGGAGGHLSS QPKTFANVFI   44
SEQ_ID_NO_319    MGL----HKE ASSSSSRLDA APLLPHHGHG GGGAGHHLSS QPKTFANVFI   46
SEQ_ID_NO_321    MGL----HKE ASSSSSRLDA APLLPHHGHG GGGAGHHLSS QPKTFANVFI   46
SEQ_ID_NO_300    MGF----QNE ASSSSYTLKI PPPAREDTPL LGK-GPPLSS QFKTFANVFI   45
SEQ_ID_NO_302    MGFG---RKK ASSSAKTF-- --PPREDTPL IAK-STPLSS QSKTFANVFI   42

SEQ_ID_NO_310    SIVGTGVLGL PYAFRAAGWV AGSLGMAAAG FATLYCMLLL MDCKDKLQEE   87
SEQ_ID_NO_316    AVVGAGVLGL PYTFSHTGWA AGSLLLFAVA VLTFYCMMLL VACRRLAD-   96
SEQ_ID_NO_325    AVVGAGVLGL PYTFSHTGWA AGTLLLFSVA ALTFYCMMLL VACRRLAD-   97
SEQ_ID_NO_312    AVVGSGVLGL PYTFSRTGWA AGTLLLLAVA ALTFHCMMLL VAARRIAD-   93
SEQ_ID_NO_319    AVVGSGVLGL PYTFSRTGWV AGSVLLLAVA ALTFHCMMLL VACRRLAY-   95
SEQ_ID_NO_321    AVVGSGVLGL PYTFSRTGWV AGSVLLLAVA ALTFHCMMLL VACRRLAY-   95
SEQ_ID_NO_300    AVVGAGVLGL PYAFKRTGWL MGVLLLVSVS VLTHHCMMLL MYTRRKLDSF   95
SEQ_ID_NO_302    AIVGAGVLGL PYAFKRTGWL MSLLMLFSVA GLTHYCMMLL MNTRSKLQSF   92

SEQ_ID_NO_310    ETDEPKNYTY GDFGEKCFGT IGRCLTEILI LISQAGGSVA YLVFIGENLH  137
SEQ_ID_NO_316    --ERPKIASF GDLGDAVFGA HGRFAVDVML VLSQASFCIG YLIFISNTMA  144
SEQ_ID_NO_325    --EHPKIASF GDLGDAVFGA HGRFAVDVML VLSQVSFCVG YLIFISNTMA  145
SEQ_ID_NO_312    --AHPKIASF GDLGHAIYGA PGRHAMDAML VLSQASFCVG YLIFISNTMA  141
SEQ_ID_NO_319    --DHPKIASF GDLGAAVCGP AGRHVVDAML VLSQASFCVG YLIFISNTMA  143
SEQ_ID_NO_321    --DHPKIASF GDLGAAVCGP AGRHVVDAML VLSQASFCVG YLIFISNTMA  143
SEQ_ID_NO_300    NAGISKIGSF GDLGFAVCGS LGRIVVDLFI ILSQAGFCVG YLIFISTTLA  145
SEQ_ID_NO_302    SGGFSKITSF GDVGFTVCGS IGRFVVDVML VLSQAGFCIG YLIFIANTLA  142

SEQ_ID_NO_310    SVFS------ ---------- -----QSMS PAGFIFAVLL PVQIALSFL   165
SEQ_ID_NO_316    HLYP---IF APSSS----- ------ALLS PKALFIWAML PFQLGLNSIK  179
SEQ_ID_NO_325    HLYP---IT APSSS----- ------ALLS PKALVIWAML PFQLGLNSIK  180
SEQ_ID_NO_312    HLYPAIGAQ SPAS------ ------PLLT AKALFIWAML PFQLGLNSIR  179
SEQ_ID_NO_319    HLYP-VGDS SPSS------ ------PLLT AKAIFIWVML PFQLGLNSIK  179
SEQ_ID_NO_321    HLYP-VGDS SPSS------ ------PLLI AKAIFIWVML PFQLGLNSIK  179
SEQ_ID_NO_300    NLSD----PE SPTSLRHQFT RLGSEFLGVS SKSLYIWGCF PFQLGLNSIK  191
SEQ_ID_NO_302    NLFN----SP SPNGLASQIL A-----LSMS AKSMYMWGCF PFQLGLNSIA  183
```

Figure 12 (continued)

| | | | | | | |
|---|---|---|---|---|---|---|
| SEQ_ID_NO_310 | SLSSLSPESI | FADVCNVLAA | AVVIRKDLQL | IDHPFANRSA | FNSVLAPFA | 215 |
| SEQ_ID_NO_316 | TLTLLAPLSI | FADVVDLGAM | GVVLGQDVAA | M.AMPPPVNA | FGGPAALLYG | 229 |
| SEQ_ID_NO_325 | TLTLLAPLSI | FADVVDLGAM | GVVLGQDVAA | WAKPVPVAA | FGGPAALLYG | 230 |
| SEQ_ID_NO_312 | TLTLLAPLSI | FADVVDLGAM | GVVLGQDASV | MLADRPPVFA | FAGPAQLLYG | 229 |
| SEQ_ID_NO_319 | TLTLLAPLSI | FADVVDLGAM | GVVLGQDVST | MLANKPPVFA | SAGPTELLYG | 229 |
| SEQ_ID_NO_321 | TLTLLAPLSI | FADVVDLGAM | GVVLGQDVST | MLANKPPVFA | SAGPTELLYG | 229 |
| SEQ_ID_NO_300 | TLTHLAPLSI | FADIVDLGAM | AVVIVEDSM | LKQRPDVVA | FGGMSLFLYG | 241 |
| SEQ_ID_NO_302 | TLTHLAPLSI | FADVVDLAAM | GVVIVKDVFL | MMENRAEVRA | EGGLSVFFYG | 233 |

| | | | | | | |
|---|---|---|---|---|---|---|
| SEQ_ID_NO_310 | FGVAVFCFEG | FSMTLALESS | MAERRKFRWV | LSDAVVGLLV | VYACFGVCGY | 265 |
| SEQ_ID_NO_316 | LGVSVYAFEG | VGMVLPLEAE | AANKRKFGVT | LGLSMAFIAV | MYGLFGVMGY | 279 |
| SEQ_ID_NO_325 | LGVSVYAFEG | VGMVLPLEAE | AANKKKGVI | LGLSMAFIAV | MYGLFGVMGY | 280 |
| SEQ_ID_NO_312 | LGVAVYAFEG | GMVLPLEAE | AADKRKFGAT | LALSMAFIAV | MYGLFGAMGY | 279 |
| SEQ_ID_NO_319 | LGVAVYAFEG | GMVLPLEAE | AADKRKFGGT | LALSMAFIAV | MYGLFGAMGY | 279 |
| SEQ_ID_NO_321 | LGVAVYAFEG | GMVLPLEAE | AADKRKFGGT | LALSMAFIAV | MYGLFGAMGY | 279 |
| SEQ_ID_NO_300 | MGVAVYSFEG | VGMVLPLESE | MKDKDKFGKV | LALGNSFISL | IYLAFGILGY | 291 |
| SEQ_ID_NO_302 | MGVAVYAFEG | GMVLPIESE | MREREKFGRI | LGLSMGLLSV | IYGAFGVLGY | 283 |

| | | | | | | |
|---|---|---|---|---|---|---|
| SEQ_ID_NO_310 | LAYGEATKDI | TLNLPNSMS | SAAVKVGLCI | ALAFTEPVMM | HPIHEIVETR | 315 |
| SEQ_ID_NO_316 | VAFGDATRDI | TTNLGAGML | SAAVQLGLCI | NLFFTMPVMM | NPVYEVAERL | 329 |
| SEQ_ID_NO_325 | VAFGDATRDI | TTNLGAGML | SAAVQLGLCI | NLFFTMPVMM | NPVYEVAERL | 330 |
| SEQ_ID_NO_312 | LAFGAATRDI | TTNLGTGML | SVLVQLGLCI | NLFFTMPVMM | NPVYEVAERL | 329 |
| SEQ_ID_NO_319 | LAFGAATRDI | TTNLGTGML | SVAVQLGLCI | NLFFTMPVMM | NPVYEVAERL | 329 |
| SEQ_ID_NO_321 | LAFGAATRDI | TTNLGTGML | SVFVQLGLCI | NLFFTMPVMM | NPVYEVAERL | 329 |
| SEQ_ID_NO_300 | LAFGEDTKDI | TANLGAGLV | STVVQLGLCI | NLFFTFPLMM | NPVFEIVERR | 341 |
| SEQ_ID_NO_302 | FAFGNDTQDI | TANLGPGL | SLLVQLGLCI | NLFFTFPLMM | NPVYEILERR | 333 |

| | | | | | | |
|---|---|---|---|---|---|---|
| SEQ_ID_NO_310 | LRSSGCFQKL | SHGVPGAEML | GLHSSRLMV | TLLNMASCI | PAFGSFVSLV | 365 |
| SEQ_ID_NO_316 | L--------- | -HGKRYCWL | -----RWLLV | VVVGLAAMYV | PNFTDFLALV | 364 |
| SEQ_ID_NO_325 | L--------- | -HGKRYCWL | -----RWLLV | IVVGLAAMYV | PNFTDFLALV | 365 |
| SEQ_ID_NO_312 | L--------- | -CGKRYAWL | -----RWILV | VLVGLLAMLV | PNFADFLSLV | 364 |
| SEQ_ID_NO_319 | L--------- | -CRKRYAWL | -----RWLLV | MVVGLMAMLV | PNFADFLSLV | 364 |
| SEQ_ID_NO_321 | L--------- | -CRKRYAWL | -----RWLLV | MVVGLMAMLV | PNFADFLSLV | 364 |
| SEQ_ID_NO_300 | F--------- | -SRGMYSAWL | -----RWLV | LAVTLVALFV | PNFADFLSLV | 376 |
| SEQ_ID_NO_302 | F--------- | -WGGRYCLWL | -----RWSV | LLVTLVALMV | PNFADFMSLV | 368 |

Figure 12 (continued)

| | | | | | | | |
|---|---|---|---|---|---|---|---|
| SEQ_ID_NO_310 | GCTVCALLSF | VLPTFFHLN | VGSSMSLWRR | VLDYGFLLFG | LGFAGYGLFT | | 415 |
| SEQ_ID_NO_316 | GSSVCVLLGF | VLPASFHLKV | FGAEMAWPGV | LSDALLVVLG | LALAVFGTYT | | 414 |
| SEQ_ID_NO_325 | GSSVCVLLGF | VLPASFHLKV | FGGEMEWPGV | VSDVLLVVIG | LSLAVFGTYT | | 415 |
| SEQ_ID_NO_312 | GSSVCVVLGF | VLPAVFHLKV | FGIEIGWAGL | VADVAIIVTG | LALAVSGTWT | | 414 |
| SEQ_ID_NO_319 | GSSVCVLLGF | VLPAAFHLKV | FGAEVGWPGL | AGDVAVIVVG | TALAVSGTWT | | 414 |
| SEQ_ID_NO_321 | GSSVCVLLGF | VLPAAFHLKV | FGAEVGWPGL | AGDVAVIVVG | TALAVSGTWT | | 414 |
| SEQ_ID_NO_300 | GSSICCVLGF | VLPALFHLLM | FKEEMGWLQW | SSDTAIVVLG | VVLAVSGTWS | | 426 |
| SEQ_ID_NO_302 | GSSVCCGLGF | VLPALFHLLM | FKEEMSWKGW | SIDVGIVALG | LVLAVSGTWY | | 418 |

| | | |
|---|---|---|
| SEQ_ID_NO_310 | ALSSH----- - | 420 |
| SEQ_ID_NO_316 | SLLQIFHSSS A | 425 |
| SEQ_ID_NO_325 | SLLQIFHSSS A | 426 |
| SEQ_ID_NO_312 | SLVQIFSSSD L | 425 |
| SEQ_ID_NO_319 | SLAQIFSSSD V | 425 |
| SEQ_ID_NO_321 | SLAQIFSSSD V | 425 |
| SEQ_ID_NO_300 | SLSEIFSVKV - | 436 |
| SEQ_ID_NO_302 | ALMEIFAVKV - | 428 |

| | | | | | | |
|---|---|---|---|---|---|---|
| SEQ_ID_NO_366 | SSSLVEECFT | KYD--IVLANR | PDLHLDLRSL | GASTISVIGA | PYGDHWRNLR | 133 |
| SEQ_ID_NO_348 | SSSLVEECFT | KYD--IVLANR | PCASVDRRSL | GFSTTSVIGA | PYGDHWRNLR | 133 |
| SEQ_ID_NO_365 | SSSLVEECFT | KYD--IVLNFSNR | PQPSVDRRSL | GFSTTSVIGA | PYGDHWRNLR | 133 |
| SEQ_ID_NO_346 | TPDAAKAFLK | TLD--LNFSNR | PPNAGATH-L | AYGAQDWFA | HYGPRMKLLR | 129 |
| SEQ_ID_NO_2546 | NGAIAKEVFK | TND--INFANR | PEFGSSEY-Q | IYNDIMFSIM | DYNKLWIFLK | 139 |
| SEQ_ID_NO_332 | | | | | | 0 |
| SEQ_ID_NO_338 | SPSIAYEIFR | TQD--VNVSSR | DFPTNEGS-L | LFGSFGFGTA | PYGEYWKFMK | 136 |
| SEQ_ID_NO_341 | SAAVATDVFK | THD--LAFSSR | PAFAFAER-L | PFGTSGFVTA | PYGPYWRFMK | 126 |
| SEQ_ID_NO_2549 | SAAMAAEIFK | TND--LAFASR | PRLAFADK-L | PYGTSSFITA | EYGDYWRFMK | 138 |
| SEQ_ID_NO_2544 | TPELFKLFLQ | THE--AASFNTR | FQTSAIKR-L | TYDNS-VAMV | PFGPYWKFIR | 132 |
| SEQ_ID_NO_2541 | TPELFKLFLQ | THE--ATSFNTR | FQTSAIRR-L | TYDSS-VAMV | PFGPYWKFVR | 132 |
| SEQ_ID_NO_358 | TPELFKLFLQ | THE--ATSFNTR | FQTSAIRR-L | TYDSS-VAMV | PIGPYWKFVR | 132 |
| SEQ_ID_NO_360 | TPELFKLFLQ | THE--AVSFNTR | FQTSAIRR-L | TYDNS-VAMV | PFGPYWKFVR | 132 |
| SEQ_ID_NO_339 | TPDLFKLFLQ | THEA-SSFNTR | FQTSAIRR-L | TYDNS-VAMV | PFAPYWKFIR | 133 |
| SEQ_ID_NO_2550 | TPELFKLFLQ | TCE--ESFTNR | PIMIASEN-L | TYGAADYFFI | PYGNYWRFLK | 132 |
| SEQ_ID_NO_2543 | TAESAKQILK | TYE--ESFCNR | PIMIASEN-L | TYGAADYFFI | PYGTYWRFLK | 130 |
| SEQ_ID_NO_2551 | SAEMAKQILK | THE--AAFLDR | AMPTAVHR-L | MYGGQDFIFS | AYGPYWRFMK | 130 |
| SEQ_ID_NO_2548 | SPDAAREVLK | THE--AAFLDR | PKPAAVHR-L | TYGGQDFSFS | AYGPYWRFMK | 139 |
| SEQ_ID_NO_353 | SPDAAREVLK | THE--AAFLDR | PKPAAVHR-L | TYGGQDFSFS | AYGPYWRFMK | 136 |
| SEQ_ID_NO_354 | TPETAKEFLK | THE--NGFCDR | PKSTAVDF-L | TYGSADFSFA | PYGPYWRFMK | 137 |
| SEQ_ID_NO_334 | TPHFJAKCLQ | THE--LAFNCR | IESTAVKK-V | TYESS-LAFA | PYGDYWRFIK | 130 |
| SEQ_ID_NO_356 | TPDLARDFLK | TNE--LAFSSR | KHSLAIDH-V | TYGVS-FAFA | PYGTYWKFIK | 128 |
| SEQ_ID_NO_349 | TPDLAKDFLK | TNE--LAFSSR | KHSLAIDH-I | TYGVA-FAFA | PYGPYWKFIK | 133 |
| SEQ_ID_NO_351 | TPDLARDFLK | TNE--LAFSSR | KHSLAIDH-I | TYGVA-FAFA | PYGPYWKFIK | 128 |
| SEQ_ID_NO_2553 | SPELAKECLK | THE--LVFSSR | KHSTAIDI-V | TYDSS-FAFA | PYGPYWKFIK | 132 |
| SEQ_ID_NO_364 | TPELAREFLK | THE--LDFSSR | KHSTAIDI-V | TYDSS-FAFA | PYGPYWKFIK | 123 |
| SEQ_ID_NO_347 | TPELAREFLK | TNE--LAFSSR | KHSTAIDI-V | TYDSS-FAFS | PYGPYWKFIK | 123 |
| SEQ_ID_NO_359 | | | | | PYGPYWKYIK | 125 |

| SEQ_ID | | | | | | |
|---|---|---|---|---|---|---|
| SEQ_ID_NO_366 | LTFNNLMRML | AGKIYYGEEA | EDEEEAKRFR | DMTKEALELM | NTFNLAEIFP | 233 |
| SEQ_ID_NO_348 | LTFNNIMRMV | AAKRYYGEEA | EDDEEAKRFR | DLTKEALELT | SASNPGEIFP | 233 |
| SEQ_ID_NO_365 | LTFNNLMRMV | AGKRYYGEEA | EDDEEAKRFR | DLTKEALELT | SASNPGEIFP | 233 |
| SEQ_ID_NO_346 | AMANMIGQVI | LSKRVFVN-- | KGV-EVNEFK | DMVVELVTTA | GYFNIGDFIP | 225 |
| SEQ_ID_NO_2546 | MTNNLICRLI | MSTRTSTN-- | VN--ESAEIR | EIAKGIVLLA | GQLGLGEIFG | 234 |
| SEQ_ID_NO_332 | LVNNTVCQMI | MGRSCSEE-- | NG--EAERVR | GLVTKTDALT | KKFILAGILR | 48 |
| SEQ_ID_NO_338 | LVNNTVCQMI | MGRSCSEE-- | NG--EAERVR | GLVTKTDALT | KKFILAGILR | 227 |
| SEQ_ID_NO_341 | FTNNVTCRTA | MSTSCAEK-- | CE--DAERIR | KLVKEGFELA | AKLCFGDVLG | 221 |
| SEQ_ID_NO_2549 | LTNHSTCRVI | LSARCSED-- | ND--EAERLI | EMVTEWVELA | VKMSFGDVFG | 233 |
| SEQ_ID_NO_2544 | WTNNTISMLM | LG-------- | ---EAEEVR | DLARETVKIF | GEYSLTDFIW | 219 |
| SEQ_ID_NO_2541 | WTNSTISMMM | LG-------- | ---EAEEIR | DIAREVLKIF | GEYSLTDFIW | 219 |
| SEQ_ID_NO_358 | WTNSTISMMM | LG-------- | ---EAEEIR | DIAREVLKIF | GEYSLTDFIW | 219 |
| SEQ_ID_NO_360 | WTNSTISMMM | LG-------- | ---EAEEIR | DIAREVLKIF | GEYSLTDFIW | 219 |
| SEQ_ID_NO_339 | WTNNTISRMM | LG-------- | ---EAEEVR | DIAREVLKIF | GEYSLTDFIW | 220 |
| SEQ_ID_NO_2550 | WTNNTISRMM | LG-------- | ---EAEEVR | DIAREVLKIF | GEYSLTDFIW | 219 |
| SEQ_ID_NO_2543 | HTNNIISRMT | MGKKSSGM-- | ND--EVGQLR | KVVREIGELL | GAFNLGDIIG | 225 |
| SEQ_ID_NO_2551 | HTNNIISRMT | MGKKSNGT-- | ND--EVGQVR | KLVREIGELL | GAFNLGDIIG | 225 |
| SEQ_ID_NO_2548 | VTGDIVSRMV | MSRRWTGD-- | DSATDTEEMR | GVIAETAMLT | GTFNLQDYIG | 237 |
| SEQ_ID_NO_353 | LTGDIVSRMV | MGRRWTGD-- | DN--DAEEMR | SVVAETAELT | GTFNLQDYIG | 231 |
| SEQ_ID_NO_354 | LTGDIVSRMV | MGRRWTGD-- | DN--DAEEMR | SVVAETAELT | GTFNLQDYIG | 232 |
| SEQ_ID_NO_334 | LTNNVISRMA | MSQRCSDN-- | DD--EADEVR | NLVHEVADLT | GKFNLSDFIW | 225 |
| SEQ_ID_NO_356 | LTNNVISIMM | VG-------- | ---EAEEAR | DVVRDVTEIF | GEFNVSDFIW | 215 |
| SEQ_ID_NO_349 | LTNVICQMM | MSIRCSGT-- | NN--EADEAK | NLVREVTKIF | GEFNISDFIC | 228 |
| SEQ_ID_NO_351 | LTNNVISQMM | MSIRCSGT-- | NS--EADEAK | NLVREVTKIF | GQFNVSDFIW | 223 |
| SEQ_ID_NO_2553 | LTNNVICQMM | MSIRCSGT-- | NS--EADEAK | NLVREVTTIF | GQFNVSDFIW | 227 |
| SEQ_ID_NO_364 | LTSNVISHMM | LSIRCSET-- | ES--EAEAAR | TVIREVTQIF | GEFDVSDFIW | 218 |
| SEQ_ID_NO_347 | LTSNVISNMM | LGIRCSGT-- | EG--EAEVAR | TVIREVTQIF | GEFDVSEIVW | 218 |
| SEQ_ID_NO_359 | LTSNVISHMM | LSIRCSED-- | EG--DAEAAR | TVIREVTQIF | GEFDVTDIIW | 220 |

FIG. 13 (continued)

| SEQ_ID_NO | | | | | | |
|---|---|---|---|---|---|---|
| SEQ_ID_NO_366 | -ILRWIGCNG | FEKQLPVHSR | KTDEIMQGLL | DEHR- | --- | --- | 266 |
| SEQ_ID_NO_348 | -ILRWLGCNG | LEKKLAVHSR | KTDEFMQGLL | DEHR- | --- | --- | 266 |
| SEQ_ID_NO_365 | -ILRWLGFNG | LEKKLAVHAR | KTDEFMQGLL | DEHR- | --- | --- | 266 |
| SEQ_ID_NO_346 | -CLAWMDLQG | IEKGMKRLHK | KFDALLTKMF | DEHK- | --- | AtSY | 282 |
| SEQ_ID_NO_2546 | -PLKKYDLLG | AGRKAKALLL | KFDKLMDGII | KKHE- | DER- | --V | 272 |
| SEQ_ID_NO_332 | KPLQKIGISL | FKKELMDASC | KFNEVLEKIL | VEYK- | --- | EKVE | 86 |
| SEQ_ID_NO_338 | KPLQKIGISL | FKKELMDASC | KFNEVLEKIL | VEYK- | --- | EKVE | 265 |
| SEQ_ID_NO_341 | -PFKELGFWV | YGKKAIDMST | RYDELLEEVL | KEHE- | --- | SRAN | 262 |
| SEQ_ID_NO_2549 | -PLKRLGFWI | YGRKAVELTL | RYDEILEKML | KEHE- | HKR- | --- | 268 |
| SEQ_ID_NO_2544 | -PLKKLKFGK | YEKRIDEIFN | KFDPVIEKVI | KKRQE | IVRRR | KN- | GEVV | 264 |
| SEQ_ID_NO_2541 | -PLKHLKVGK | YEKRIDDILN | KFDPVVERVI | KKRRE | IVRRR | KN- | GEVV | 264 |
| SEQ_ID_NO_358 | -PLKHLKVGK | YEKRIDDILN | KFDPVVERVI | KKRRE | IVRRR | KN- | GEVD | 264 |
| SEQ_ID_NO_360 | -PLKKLKVGK | YEKRIDDILN | KFDPVVERVI | KKRRE | IVRRR | KN- | GEVV | 264 |
| SEQ_ID_NO_339 | -PLKKLKVGK | YEKKIEEIFN | KFDPVIEKVI | KKRQD | VRRRR | KERN- | GELE | 267 |
| SEQ_ID_NO_2550 | -PLKKLKVGQ | YEKRIDEIFN | KFDPVIEKVI | KKRQE | ITKRR | KERD- | GELE | 266 |
| SEQ_ID_NO_2543 | -FMRPLDLQG | FGKRNKDTHH | RFDTMTERII | KEHE- | EAR- | AI- | KEGA | 266 |
| SEQ_ID_NO_2551 | -FMRPFDLQG | FGKKNRDAHH | KMDVMMEKVL | KEHE- | EAR- | AKE- | KGGA | 268 |
| SEQ_ID_NO_2548 | -VFKYWDMQG | LGKRIDAVHR | NMDVMMEKVL | TARDA | CRRRR | RKEP- | ADGA | 284 |
| SEQ_ID_NO_353 | -VFKYWDVQG | LGKRIDAVHR | KFDAMMERIL | TPREA | KRKLR | RQ- | AAAD | 276 |
| SEQ_ID_NO_354 | -VFKYWDVQG | LGKRIDAVHR | KFDAMMERIL | TAREA | KRKLR | RQ- | AAAD | 277 |
| SEQ_ID_NO_334 | -FCKNLDLQG | FGKRLKEVRK | KFDAMMERIL | MEHE- | EAR- | KKK- | KETG | 268 |
| SEQ_ID_NO_356 | -LFKKMDLQG | FGKRIEDLFQ | RFDTLVERII | GKREQ | TRKDR | RRNGK | KGEQG | 264 |
| SEQ_ID_NO_349 | -LFKNIDLQG | FKKRYVDTHT | RYNALLEKMI | FIERE- | EKR- | KQ- | KKSE | 270 |
| SEQ_ID_NO_351 | -FCKNIDLQG | FKKRYEGTHR | RYDALLERII | MGRE- | --- | RR- | GK\*K | 265 |
| SEQ_ID_NO_2553 | -FCKNLDLQG | FKKRYEDTHR | RYDALLEKII | GERE- | ENR- | RK- | GGKR | 269 |
| SEQ_ID_NO_364 | -LCKNFDFQG | IRKRSEDIQR | RYDALLEKII | TDRE- | EKR- | RTH- | GGGG | 261 |
| SEQ_ID_NO_347 | -FCKNLDLQG | IRKRSEDIRR | RYDALLEKII | GDRE- | KQR- | LRG- | GGGG | 261 |
| SEQ_ID_NO_359 | -FCKKFDLQG | IKKRSEDIQR | RYDALLEKII | GDRE- | RLR- | RQNRDK | HGGG | 266 |

| SEQ_ID | Sequence | Position |
|---|---|---|
| SEQ_ID_NO_366 | EWAMSLLLNH PKVLEKARQE MDTLVGHERM VEEDDLPKLR YLHYIILETL | 363 |
| SEQ_ID_NO_348 | EWAMSLLLNH PKVLEKARKE LDTLVGHERM VDEHDLPKLR YLHCIVLETL | 363 |
| SEQ_ID_NO_365 | EWAMSLILNH PQVLEKARKE LDTLVGHERM VDEHDLPKLR YLHCIVLETL | 363 |
| SEQ_ID_NO_346 | EWALAEMMKN PALKKAQGE MDQVIGNNRR ILLESDIPNLP YLRAICKETF | 360 |
| SEQ_ID_NO_2546 | QWGAEVLNH PKALKKLQEE IDRVVGPNRL VDDSDIPNLP YLQAVVKETL | 371 |
| SEQ_ID_NO_332 | QWIMAEIINN SYILERLREE IDSVVGKTRL IQETDLPNLP CLQATVKEGL | 185 |
| SEQ_ID_NO_338 | QWIMAEIINN SYILERLREE IDSVVGKTRL IQETDLPNLP CLQATVKEGL | 364 |
| SEQ_ID_NO_341 | QWAMAELLNH PEAFQKVRKE IELVTGNVRL VDESDITNLP YLQAVVKETL | 361 |
| SEQ_ID_NO_2549 | QWTIAELINH PDVFKKVREE IDLAVGRTRL VEESDIPNLP YIRAIVKETF | 367 |
| SEQ_ID_NO_2544 | EWALAELINN PDVLQKAREE VYSVVGKDRL VDEVDTQNLP YIRAIVKETF | 363 |
| SEQ_ID_NO_2541 | EWALAELINN PKVLEKAREE VYSVVGKDRL VDEVDTPNLP YIGAIVKETF | 363 |
| SEQ_ID_NO_358 | EWALAELINN PKVLEKAREE VYSVVGKDRL VDEVDTQNLP YIRAIVKETF | 363 |
| SEQ_ID_NO_360 | EWALAELINN PKVLEKAREE VYSVVGKDRL VDEVDTQNLP YIRAVVKETF | 363 |
| SEQ_ID_NO_339 | EWALSELINN PRVMKKAREE VDSVVGKDRL VDESDIQNLP YIRAVVKETF | 366 |
| SEQ_ID_NO_2550 | QWALSELINN PRVLKKAREE VESVVGKDRL VDEADIQNLP YIRAIVKETF | 365 |
| SEQ_ID_NO_2543 | EWALAELIRN PHVFKKAREE IDSTVGKERL FKESDIPNLP YLQAVVKETL | 366 |
| SEQ_ID_NO_2551 | EWSLAELIRN PQVFKKAREE IDSVVGKERL VKESDIPNLP YLQAIAKETL | 367 |
| SEQ_ID_NO_2548 | EWALSELINN PDILRRAQAE LDAIVGASRL ADESDIPRLP YLQAIAKETL | 383 |
| SEQ_ID_NO_353 | EWALSELINN PPVLRKLQAE LDAVVGGARL ADESDIPSLP YLQAVAKETL | 375 |
| SEQ_ID_NO_354 | EWALSELINN PPVLRKLQAE LDAVVGGARL ADESDIPSLP YLQAVAKETL | 376 |
| SEQ_ID_NO_334 | EWSLAELINN PNILERAREE IDSVVGQSRL VQESDIANLP YVQAILKETL | 367 |
| SEQ_ID_NO_356 | EWALVELVKK PSVLQKVREE IDNVVGKDRL VEESDCPNLP YLQAILKETF | 363 |
| SEQ_ID_NO_349 | EWTLVELINN PKVLENARKE IAEVVGDERL VQESDIPNLP YIQAIIKETL | 368 |
| SEQ_ID_NO_351 | EWALVELINN PNALEKARQE IDQVIGDERL VQESDTPNLP YIQAIIKETL | 363 |
| SEQ_ID_NO_2553 | EWTMVELINN PKVLEKAKKE VDNVIGNSRL VQESDAPNLP YIQAIIKEAL | 368 |
| SEQ_ID_NO_364 | EWAIAEVINN PNVLKKAQEE IANIVGFDRI LQESDAPNLP YLNAIIKETF | 360 |
| SEQ_ID_NO_347 | EWAIAELISN PNVLKKAQEE MDKVIGSQRL LQESDAPNLP YLNAIIKETF | 360 |
| SEQ_ID_NO_359 | EWAIAELINN PNVLKKAQEE ISRIIGTKRI VQESDAPDLP YLQAIIKETF | 365 |

FIG. 13 (continued)

| SEQ_ID | | | | | | | |
|---|---|---|---|---|---|---|---|
| SEQ_ID_NO_366 | RLFPSVPTLV | PHEPSEDCNI | GGYNVPKGTM | IIVNAWAIHR | DPKVW-DDPM | 412 |
| SEQ_ID_NO_348 | RLFPSVPTLV | PHEPSEDCKI | GGYNVPKGTM | VLVNAWAIHR | DPKVW-DDPL | 412 |
| SEQ_ID_NO_365 | RLFPSVPTLV | PHEPSEDCKI | GGYNVPKGTM | ILVNAWAIHR | DPKVW-DDPL | 412 |
| SEQ_ID_NO_346 | RKHPSTPLNL | PRISNEPCIV | DGYYIPKNTR | LSVNIWAIGR | DPEVW-ENPL | 409 |
| SEQ_ID_NO_2546 | RVHPSLP-LI | FRKCREDCVV | NGYTIPKNSR | LVLNIYAINR | DPNEW-RDAD | 419 |
| SEQ_ID_NO_332 | RLHPPVP-IV | LRTFKEGCTI | GGFYVPEKTT | LVVHGYAMMR | DPEYW-EDPQ | 233 |
| SEQ_ID_NO_338 | RLHPPVP-LV | LRTFKEGCTI | GGFYVPEKTT | LVVNGYAMMR | DPEYW-EDPQ | 412 |
| SEQ_ID_NO_341 | RLYPPAP-IT | TRECRQHCKI | NSFDVPPKTA | VAINLYAIMR | DPDSW-DNPN | 409 |
| SEQ_ID_NO_2549 | RLHPPAP-VA | TRECRKNCKI | GGFNIPEKTA | VAINLYAIMR | DPEIW-DDPT | 415 |
| SEQ_ID_NO_2544 | RMHPPLP-VV | KRKCVEECEI | EGCVIPEGAL | ILFNVWAVGR | DPKVW-DRPS | 411 |
| SEQ_ID_NO_2541 | RMHPPLP-VV | KRKCTEECEI | NGYVIPEGAL | ILFNVWQVGR | DPKYW-DRPS | 411 |
| SEQ_ID_NO_358 | RMHPPLP-VV | KRKCTEECEI | NGYVIPEGAL | ILFNVWQVGR | DPKYW-DRPS | 411 |
| SEQ_ID_NO_360 | RMHPPLP-VV | KRKCTEECEI | NGYVIPEGAL | VLFNVWAVGR | DPKYW-DRPL | 414 |
| SEQ_ID_NO_339 | RMHPPLP-VV | KRKCVQECEL | NGYVIPEGAL | ILFNVWAVGR | DPKVW-EGPS | 413 |
| SEQ_ID_NO_2550 | RMHPPTP-IF | AREATRSCQV | DGYDVPAFSK | IFINAWAIGR | DPNYW-DNPL | 414 |
| SEQ_ID_NO_2543 | RMHPPTP-IF | AREAIRGCQV | DGYDIPANSK | IFINAWAIGR | DPKYW-DNPQ | 415 |
| SEQ_ID_NO_2551 | RLHPAFP-LV | VRRSTEPCKV | SGYDVPAGST | VFVNVWAIGR | DPACWAPDPL | 432 |
| SEQ_ID_NO_2548 | RLHPTGP-LV | VRRSLERATV | AGYDVPAGAT | VFVNVWAIGR | DAAWM--PEPT | 423 |
| SEQ_ID_NO_353 | RLHPTGP-LV | VRRSLERATV | AGYDVPAGAT | VFVNVWAIGR | DAAWW--PEPT | 424 |
| SEQ_ID_NO_354 | RLHPTGP-II | LRESSESCTI | NGYEIPARTR | LFVNVWAINR | DPNYW-ENPL | 415 |
| SEQ_ID_NO_334 | RMHPPVP-MV | TRRCVAECTV | ENYVIPEDSL | LFVNVWSIGR | NPKFW-DNPL | 411 |
| SEQ_ID_NO_356 | RMHPPIP-MV | IRKSIDNVTV | QGYDIRAGTM | LFVNIWSIGR | NPLYW-ESPL | 416 |
| SEQ_ID_NO_349 | RLHPPIP-ML | IRKSTENVIV | QGYDIPAGTL | LFVNIWSIGR | NPQCW-ETPL | 411 |
| SEQ_ID_NO_351 | RLHPPIP-ML | IRKSIEKVTV | QGYEIPAGTM | LFVNIWSIGR | NAQYW-ESPL | 416 |
| SEQ_ID_NO_2553 | RLHPPIP-ML | ARKSISDCVI | DGYMIPANTL | LFVNLWSMGR | NPKIW-DYPT | 408 |
| SEQ_ID_NO_364 | RLHPPIP-ML | TRKSISDVVV | NGYTIPAKTL | LFVNLWSMGR | NPNYW-ENPM | 408 |
| SEQ_ID_NO_347 | RLHPPIP-ML | SRKSTSDCTV | NGYKIQAKSL | LFVNIWSIGR | NPNYW-ESPM | 413 |
| SEQ_ID_NO_359 | | | | | | |

| SEQ_ID | Sequence | | | | Pos |
|---|---|---|---|---|---|
| SEQ_ID_NO_366 | LAKKFVGLAL | ASLIQCFDWE | R-ISA--EKI | --- | EGAGRITLPK 483 |
| SEQ_ID_NO_348 | LAQKFVGLAL | GSLIQCFDWE | R-TSP--EKI | --- | EGSG--TLPK 482 |
| SEQ_ID_NO_365 | LAQKFVGLAL | GSLIQCFEWE | R-MSA--EKI | --- | EGSG--TLPK 482 |
| SEQ_ID_NO_346 | MGIVMVEYIL | GTLVHSFDWK | L-PSEV-EL- | --- | EAFG-LALQK 487 |
| SEQ_ID_NO_2546 | LAAAVLHRTL | GVLIQCFDWK | I--KGA--EKL | --- | QGVG-FSSAM 508 |
| SEQ_ID_NO_332 | LAYISVGTAI | GVMVQCFDWE | I---KGDKI | --- | EAPGKITLTM 312 |
| SEQ_ID_NO_338 | LAYISVGTAI | GVMVQCFDWE | I---KGDKI | --- | EAPGKITLTM 491 |
| SEQ_ID_NO_341 | LAFSLMNTAV | AAMVQCFDWK | IGKDGKGEKV | --- | SGSG-MSLSM 492 |
| SEQ_ID_NO_2549 | LAFAMMNTTV | AAIVQCFDWK | LGGDGDGGKV | --- | SGPG-LTLSM 498 |
| SEQ_ID_NO_2544 | LSTSGMATLL | ASVIQCFDLQ | VILDPQGHVL | KGDDAKVSME | ERAG-LTVPR 501 |
| SEQ_ID_NO_2541 | LATSGMATLL | ASLIQCFDLQ | VILGPQGQIL | KGGDAKVSME | ERAG-LTVPR 501 |
| SEQ_ID_NO_358 | LATSGMATLL | ASLIQCFDLQ | VILGPQGQIL | KGGDAKVSME | ERAG-LTVPR 501 |
| SEQ_ID_NO_360 | LATSGMATLL | SSVLQCFELQ | V--AGPNGQIL | KGADAKVSMD | ERAG-LTVPR 501 |
| SEQ_ID_NO_339 | LATSGMATLL | ASVIQCFDLQ | V--VGCKGKLL | KGSDAKVSME | ESPG-LTVPR 504 |
| SEQ_ID_NO_2550 | LALLVIQATL | ASLVQCFDWV | V--NDGKSHDI | --- | EVGR-VTVFL 501 |
| SEQ_ID_NO_2551 | LALLVIQATL | ASLVQCFDWV | V--NDGKNSEI | --- | EEGR-VTVFL 496 |
| SEQ_ID_NO_2548 | LAMLVVQAAL | AAMLQCFEWA | P--IVGG--ATV | --- | EGPG-LTLPR 497 |
| SEQ_ID_NO_353 | LAMLVVQAAL | AAMVQCFEWS | P--IVGG--APV | --- | EGPG-LTLPR 514 |
| SEQ_ID_NO_354 | LAMLVVQAAL | AAMVQCFEWS | P--IVGG--APV | --- | EGPG-LTLPR 503 |
| SEQ_ID_NO_334 | LALQMVQTGL | AAMIQCFDWK | V--NGTVI--- | --- | EGTG-LTLPR 504 |
| SEQ_ID_NO_356 | LAMQEVPALL | GAIIQCFDFH | V--VGPKGEIL | KGDDIVINVD | ERPG-LTAPR 493 |
| SEQ_ID_NO_349 | LAMRELPVVI | AGLIQCFEWN | A--NDK--EVL | SMD | ERAG-LTAPR 500 |
| SEQ_ID_NO_351 | LAMRELSVVI | ANLIQCFDWD | V--VGE--RLL | NTD | ERAG-LTAPR 493 |
| SEQ_ID_NO_2553 | LAMRELPVVI | AGLIQCFEWD | V--NNK--EAL | ITD | ERAG-LTAPR 490 |
| SEQ_ID_NO_364 | LAIQEVVIII | GTMIQCFDWK | L--PDGSGHV- | DMA | ERPG-LTAPR 495 |
| SEQ_ID_NO_347 | LGMQELFSII | GAMVQCFDWK | L--PDGV-KGV | DMT | ERPG-LTAPR 486 |
| SEQ_ID_NO_359 | LAIQEVVSII | GTMVQCFDWK | L--ADGSGNNV | DMT | ERSG-LTAPR 492 |

FIG. 13 (continued)

| | | | | |
|---|---|---|---|---|
| SEQ_ID_NO_366 | ATTLEAMCKP | RHVMEKVLRQ | VSNV | - | 507 |
| SEQ_ID_NO_348 | AKTLEAMCKP | RHVMEKVLRQ | VSNV | - | 506 |
| SEQ_ID_NO_365 | AKTLEAMCKP | RHIMERVLRQ | VSNV | - | 506 |
| SEQ_ID_NO_346 | AVPLEAMVTP | RLPIDVYAPL | A | - | 508 |
| SEQ_ID_NO_2546 | VHPLICYPVV | R---VNPL | EIAN | - | 527 |
| SEQ_ID_NO_332 | AHPLNCTLVP | RTLIPVTSTV | QIPSS | - | 337 |
| SEQ_ID_NO_338 | AHPLNCTLVP | RTLIPVTSTV | QIPSS | - | 516 |
| SEQ_ID_NO_341 | VHPLICVPVV | H---FIPY | DI | - | 509 |
| SEQ_ID_NO_2549 | LHPLKCHPIV | H---FNPF | EG | - | 515 |
| SEQ_ID_NO_2544 | KHNLVCLPLA | K---TTLAAKL | LSP | - | 522 |
| SEQ_ID_NO_2541 | AHSLVCVPLA | R---IGVASKL | LS | - | 521 |
| SEQ_ID_NO_358 | AHSLVCVPLA | R---IGVASKL | LS | - | 521 |
| SEQ_ID_NO_360 | AHSLVCVPLA | R---IGVASKL | LS | - | 521 |
| SEQ_ID_NO_339 | AHNLVCVPLA | R---PGAAAKL | LSS | - | 525 |
| SEQ_ID_NO_2550 | AHNLMCVPLA | R---TNVTSEL | LSS | - | 522 |
| SEQ_ID_NO_2543 | AKPLKCKPVP | H---FVPF | ISSA | - | 514 |
| SEQ_ID_NO_2551 | AKPLKCKPVP | R---FVPF | SA | - | 514 |
| SEQ_ID_NO_2548 | KRPLVCTVKA | R---LHPV | PVPTAAAADN | GVDGTLHCA | 548 |
| SEQ_ID_NO_353 | KRPLVCTVSP | R---IHPL | PAAASASLT | - | 527 |
| SEQ_ID_NO_354 | KRPLVCTVSP | R---IHPL | PAAASASLT | - | 528 |
| SEQ_ID_NO_334 | AHPLICVPVA | R---LNPF | PSF | - | 511 |
| SEQ_ID_NO_356 | AHNLVCVPVD | RTSGGPLKI | IEC | - | 523 |
| SEQ_ID_NO_349 | AVDLEFVPLM | R---CNCPNIF | VSA | - | 514 |
| SEQ_ID_NO_351 | AVDFVCVPLE | R---GNTLKI | LGSN | - | 511 |
| SEQ_ID_NO_2553 | AVDFVCVPSM | R---ENCPKVF | - | - | 513 |
| SEQ_ID_NO_364 | ETDLFCRVVP | R---VDPL | VVSTQ | - | 506 |
| SEQ_ID_NO_347 | ANDLVCGLVP | R---IDPV | VVSGP | - | 506 |
| SEQ_ID_NO_359 | AFDLVCRLYP | R---VDPA | TISGA | - | 512 |

| | | | | | | |
|---|---|---|---|---|---|---|
| SEQ_ID_NO_475 | ·········· | ··MSS· | ···· ·············· | ·······R· | ······YVGN | 9 |
| SEQ_ID_NO_436 | MAFCNKLGNL | LRQGATQS·· | ······SHAP VSSMLNYLRH | MSSSKLFIGG | 42 |
| SEQ_ID_NO_420 | MAFLSKVGKI | FRQTGAHVTA | SNSMLQSI·· ········RC | MSSSKIFVGG | 40 |
| SEQ_ID_NO_473 | ·········· | ··MAASDV· | ······EF· ········RC | ······FVGG | 14 |
| SEQ_ID_NO_369 | ·········· | ··MAGGEL·· | ······EF· ········RC | ······FVGG | 13 |
| SEQ_ID_NO_371 | ·········· | ··MASADV· | ······EF· ········RC | ······FVGG | 14 |
| SEQ_ID_NO_372 | ·········· | ··MASADV· | ······EF· ········RC | ······FVGG | 14 |
| SEQ_ID_NO_373 | ·········· | ····MAEV· | ······EY· ········RC | ······FVGG | 12 |
| SEQ_ID_NO_458 | ·········· | ····MADV· | ······EY· ········RC | ······FVGG | 12 |
| SEQ_ID_NO_597 | ·········· | ····MADV· | ······EY· ········RC | ······FVGG | 12 |
| SEQ_ID_NO_455 | ·········· | ··MAAADV· | ······EY· ········RC | ······FVGG | 14 |
| SEQ_ID_NO_477 | ·········· | ··MAAADV· | ······EY· ········RC | ······FVGG | 14 |
| SEQ_ID_NO_465 | ·········· | ··MAASDV· | ······EY· ········RC | ······FVGG | 14 |
| SEQ_ID_NO_488 | ·········· | ··MAAPDV· | ······EY· ········RC | ······FVGG | 14 |
| SEQ_ID_NO_494 | ·········· | ··MAAPDV· | ······EY· ········RC | ······FVGG | 14 |
| SEQ_ID_NO_374 | ·········· | ···MDAEV· | ······EY· ········RC | ······FVGG | 13 |
| SEQ_ID_NO_441 | ·········· | ····MAEV· | ······EY· ········RC | ······FVGG | 12 |
| SEQ_ID_NO_444 | ·········· | ··MASADV· | ······EY· ········RC | ······FVGG | 14 |
| SEQ_ID_NO_451 | ·········· | ····MGUV· | ······EY· ········RC | ······FVGG | 12 |
| SEQ_ID_NO_595 | ·········· | ····MAEV· | ······EY· ········RC | ······FVGG | 12 |
| SEQ_ID_NO_474 | ·········· | ····MAEV· | ······EY· ········RC | ······FVGG | 12 |
| SEQ_ID_NO_447 | ·········· | ····MAEV· | ······EY· ········SC | ······FVGG | 12 |
| SEQ_ID_NO_450 | ·········· | ···MAAEV· | ······EY· ········SC | ······FVGG | 13 |
| SEQ_ID_NO_434 | ·········· | ··MGSSDV· | ······EY· ········RC | ······FVGG | 14 |
| SEQ_ID_NO_437 | ·········· | ··MAAADI· | ······EY· ········RC | ······FVGG | 14 |
| SEQ_ID_NO_438 | ·········· | ···MSADI· | ······EY· ········RC | ······FVGG | 13 |
| SEQ_ID_NO_454 | ·········· | ····MAE·· | ······EY· ········RC | ······FVGG | 11 |
| SEQ_ID_NO_392 | ·········· | ···MSAEV· | ······EY· ········RC | ······FVGG | 13 |
| SEQ_ID_NO_425 | ·········· | ··MASAEV· | ······EF· ········RC | ······FVGG | 14 |
| SEQ_ID_NO_504 | ·········· | ··MASAEI· | ······EF· ········RC | ······FVGG | 14 |
| SEQ_ID_NO_368 | ·········· | ··MASDDV· | ······EY· ········RC | ······FVGG | 14 |
| SEQ_ID_NO_422 | ·········· | ··MASPDV· | ······EY· ········RC | ······FVGG | 14 |
| SEQ_ID_NO_596 | ·········· | ··MASADV· | ······EF· ········RC | ······FVGG | 14 |
| SEQ_ID_NO_433 | ·········· | ···M·ADV· | ······FD· ········RC | ······FVGG | 12 |
| SEQ_ID_NO_376 | ·········· | ··MASADV· | ······EY· ········RC | ······FVGG | 14 |
| SEQ_ID_NO_440 | ·········· | ··MASADV· | ······EY· ········RC | ······FVGG | 14 |

Figure 14 (continued)

| | | | | | | | |
|---|---|---|---|---|---|---|---|
| SEQ_ID_NO_475 | LSWNAKEEDL | RTYFGKFGEV | EEASIALDRE | SGRSRGFGFV | TLPADVA-KD | 58 |
| SEQ_ID_NO_436 | LSYGVDDQSL | KDAFASYGEV | VEARVITDRD | TGRSRGFGFV | NFTSDESATS | 92 |
| SEQ_ID_NO_420 | ISYSTDEFGL | REAFSKYGEV | VDAKIIVDRE | TGRSRGFAFV | TFTSTEEASN | 90 |
| SEQ_ID_NO_473 | LAWATDDABL | ERAFSTYGDI | VESKIINDRE | TGRSRGFGFV | TFRDEQSMRD | 64 |
| SEQ_ID_NO_369 | LAWATTDGRL | EGAFRPFGEV | VQSKVISDRE | TGRSRGFGFV | TFADENSMNA | 63 |
| SEQ_ID_NO_371 | LAWSTDDRSL | QEAFSPYGEV | VESKIISDRE | TGRSRGFGFV | TFNDEQSMRD | 64 |
| SEQ_ID_NO_372 | LSWSTDDRSL | KDAFTAFGEV | MDSKVVSDRE | TGRSRGFGFV | TFMDEQSMRD | 64 |
| SEQ_ID_NO_373 | LSWGTDDRSL | AEAFNKFGEV | TDSKIINDRE | TGRSRGFGFV | TFANEQSMRD | 62 |
| SEQ_ID_NO_458 | LAWATDDQSL | DNAFSKYGDV | IDSKIITDRE | TGRSRGFGFV | TFASDEAMRD | 62 |
| SEQ_ID_NO_507 | LRWATDDQSL | DNAFSKYGDV | IDSKIITDRE | TGRSRGFGFV | TFASDEAMRD | 62 |
| SEQ_ID_NO_455 | LAWATNNETL | EQAFANFGQV | IDSKVITDRE | TGRSRGFGFV | TFSSEQSMLD | 64 |
| SEQ_ID_NO_477 | LAWATDNASL | DQAFASYGDV | LDSKVITDRE | TGRSRGFGFV | TFSSEQSMLD | 64 |
| SEQ_ID_NO_465 | LAWATDDHSL | HNAFSTYGEV | LESKIILDRE | TDRSRGFGFV | TFSTEEAMRN | 64 |
| SEQ_ID_NO_488 | LAWATDDRSL | EAAFSTYGEI | LDSKIINDRE | TGRSRGFGFV | TFSSEQSMRD | 64 |
| SEQ_ID_NO_494 | LAWATDDRSL | EAAFSTYGEI | LDSKIINDRE | TGRSRGFGFV | TFSSEQSMRD | 64 |
| SEQ_ID_NO_374 | LAWATDDQSL | ERAFSNYGQV | LESKIINDRE | TGRSRGFGFV | TFSSEQAMRD | 63 |
| SEQ_ID_NO_441 | LAWATNDESL | EQAFSQFGDI | TDSKIINDRE | TGRSRGFGFV | TFKDEKSMRD | 62 |
| SEQ_ID_NO_444 | LAWATTDQSL | SEAFSQYGEI | LESKIINDRE | TGRSRGFGFV | TFKDEQSMRD | 64 |
| SEQ_ID_NO_451 | LAWATTDNTL | SEAFSQYGEV | VESKIINDRE | TGRSRGFGFV | TFKDEQAMRD | 62 |
| SEQ_ID_NO_505 | LAWATTDQTL | GDAFSQFGEI | LDSKIINDRE | TGRSRGFGFV | TFKDEKAMRD | 62 |
| SEQ_ID_NO_474 | LAWATTDQIL | GDAFSQYGEI | LDSKIINDRE | TGRSRGFGFV | TFKDEQAMRD | 62 |
| SEQ_ID_NO_447 | LAWATTDRTL | ADAFGTYGEV | LDSKIINDRE | TGRSRGFGFV | TFKDEKCMRD | 62 |
| SEQ_ID_NO_450 | LAWATTDRTL | SDAFGTYGEV | VDSKIINDRE | TGRSRGFGFV | TFKDEKSMKE | 63 |
| SEQ_ID_NO_434 | LAWATDSQAL | EQAFSKFGEI | TDSKVINDRE | TGRSRGFGFV | TFAEEKSMRD | 64 |
| SEQ_ID_NO_437 | LAWATSDKAL | EEAFSAYGEV | LESKIINDRE | TGRSRGFGFV | TFNNEKSMRD | 64 |
| SEQ_ID_NO_438 | LAWATTDQSL | DEAFSPYGEI | LDSKIINDRE | TGRSRGFGFV | TFNNEKSMRD | 63 |
| SEQ_ID_NO_454 | LAWATNDQSL | EQAFSQFGEI | TDCKIINDRE | TGRSRGFGFV | TFSSSESMKN | 61 |
| SEQ_ID_NO_392 | LAWATTDQVL | DEAFSQYGEI | IDSKIINDRE | TGRSRGFGFV | TFGNEKAMRD | 63 |
| SEQ_ID_NO_425 | LAWATDHDAL | EKAFSQFGEI | VESKVINDRE | TGRSRGFGFV | TFATEQAMRD | 64 |
| SEQ_ID_NO_504 | LAWATDNDAL | ERAFSPFGEI | IESKIINDRE | TGRSRGFGFV | TFSNEKAMRD | 64 |
| SEQ_ID_NO_368 | LAWATDDRAL | ETAFAQYGDV | IDSKIINDRE | TGRSRGFGFV | TFKDEKAMKD | 64 |
| SEQ_ID_NO_422 | LAWATDDRAL | ETAFSQYGEI | LDSKIINDRE | TGRSRGFGFV | TFKDEKSMKD | 64 |
| SEQ_ID_NO_506 | LAWATTDSSL | HEAFSAYGDI | LESKIINDRE | TGRSRGFGFV | TFRDEKSMRD | 64 |
| SEQ_ID_NO_433 | LAWATDNDAL | EKAFSQYGEI | VDSKIINDRE | TCRSRGFGFV | TFANEKSMND | 62 |
| SEQ_ID_NO_376 | LAWATDDRAL | EEAFSVYGEI | VESKIINDRE | SGRSRGFGFV | TFRDEKSMRD | 64 |
| SEQ_ID_NO_440 | LAWATDDHAL | EQAFSQYGEV | VESKIINDRE | TGRSRGFGFV | TFSNEKSMND | 64 |

Figure 14 (continued)

| | | | | | | | | |
|---|---|---|---|---|---|---|---|---|
| SEQ_ID_NO_475 | AI EKTNGAEF | MGRNI KVNEA | SPPGER·PPR | TNN······Y | GGGYGDFN·· | | | 99 |
| SEQ_ID_NO_436 | ALSAMDGQDL | NGRNI RVSYA | NDRPBA···· | ·········· | ····P···· | | | 119 |
| SEQ_ID_NO_420 | AMQLLDGQDL | HGRRI RVNYA | TERGSGFGGR | G········F | GGP······ | | | 124 |
| SEQ_ID_NO_473 | AI KGMNGQTL | DGRNI TVNEA | ENFANA·VAA | ·········G | TAAAAEVAVT | | | 104 |
| SEQ_ID_NO_369 | AI KEMNGQEL | DGRNI TVNQA | QSRGGG·GGG | GG·······G | GGGYGR···· | | | 101 |
| SEQ_ID_NO_371 | AI DAMNGKML | DGRSI TVNPA | QSRGNG·GGG | GGG······G | SRGYR····· | | | 102 |
| SEQ_ID_NO_372 | AI EGMNGRDL | DGRNI TVNRA | QARGGG·GGG | GG·······G | GGGYRG···· | | | 102 |
| SEQ_ID_NO_373 | AI DEMNGKEL | DGRSI TVNEA | QSRGSG·GGG | ·········G | GGGYRS···· | | | 98 |
| SEQ_ID_NO_458 | AI EAMNGQDL | DGRNI TVNEA | HSRRBG·GGG | GGFSGG···G | GGGYGGQRRE | | | 108 |
| SEQ_ID_NO_507 | AI EAMNGQDL | DGRNI TVNEA | QSRRBD·GGG | GFGG·····G | GGGYGGQRRE | | | 106 |
| SEQ_ID_NO_455 | AI ENMNGKEL | DGRNI TVNQA | QSRGGG·GGG | GGYGG····G | GGGY······ | | | 103 |
| SEQ_ID_NO_477 | AI EAMNGKDL | DGRNI TVNQA | QSRGGG···· | ·········G | GGGY······ | | | 95 |
| SEQ_ID_NO_465 | AI EGMNGKEL | DGRNI TVNEA | QSRGGR·GG· | ·········G | GGGYG····· | | | 98 |
| SEQ_ID_NO_488 | AI EGMNGKEL | DGRNI TVNEA | QSRRBG·GGG | ·········G | GGGY······ | | | 98 |
| SEQ_ID_NO_494 | AI EGMNGKEL | DGRNI TVNEA | QSRRBG·GGG | GGYGG····G | GGGY······ | | | 103 |
| SEQ_ID_NO_374 | AI EGMNGQDL | DGRNI TVNEA | QSRGSG·GGG | GGYRGG···G | GGGY······ | | | 103 |
| SEQ_ID_NO_441 | AI EGMNGQEL | DGRNI TVNEA | QSRGSG·GGG | GRREG····G | GGGY······ | | | 101 |
| SEQ_ID_NO_444 | AI EGMNGQTL | DGRNI TVNEA | QSRGSG·GN· | ·········G | GGGFRGPRRD | | | 103 |
| SEQ_ID_NO_451 | AI EGMNGQDL | DGRNI TVNEA | QSRGGG·GGG | GGR······G | GGGYGGGRRE | | | 105 |
| SEQ_ID_NO_505 | AI EGMKGQDL | DGRNI TVNEA | QSRGSG·GGG | ·········G | GGGYR····· | | | 97 |
| SEQ_ID_NO_474 | AI EGMNGQDL | DGRNI TVNEA | QSRGSG·GGG | GG·······Y | RGG·-R···· | | | 98 |
| SEQ_ID_NO_447 | AI EGMNGQEL | DGRSI TVNEA | QARGSG·GGG | GG·······Y | GGGRRE···· | | | 100 |
| SEQ_ID_NO_450 | AI SGMNGSEL | DGRNI TVNEA | QARGSG·GGG | G········G | GGGFGGGRRR | | | 104 |
| SEQ_ID_NO_434 | AI EEMNGQDI | DGRNI TVNEA | QSRGSG·GGG | RGGGGGGYGG | GGGYGG···· | | | 109 |
| SEQ_ID_NO_437 | AI EGMNGQNL | DGRNI TVNEA | QSRGGG·GG· | ·········G | GGGYR····· | | | 98 |
| SEQ_ID_NO_438 | AI QGMNSQEL | DGRNI TVNEA | QSRGSG·GGG | ·········G | GGGYSR···· | | | 99 |
| SEQ_ID_NO_454 | AI EGMNGQDL | DGRNI TVNEA | QSRSGG···· | ·········G | GGGY······ | | | 92 |
| SEQ_ID_NO_392 | AI DGMNGQDL | DGRNI TVNEA | QSRGSG·GGG | G········G | GGGYNR···· | | | 100 |
| SEQ_ID_NO_425 | AI EGMNGQNL | DGRNI TVNEA | QSRGKGGGGG | GGGYGG···G | GGGY······ | | | 105 |
| SEQ_ID_NO_504 | AI EGMNGQNL | DGRNI TVNEA | QSRGSG·GGG | GG·······N | GGGYSR···· | | | 102 |
| SEQ_ID_NO_368 | AI EGMNGQDL | DGRSI TVNEA | QSRGSG·GGG | GHRGG····G | GGGY-R···· | | | 104 |
| SEQ_ID_NO_422 | AI EGMNGQDL | DGRSI TVNEA | QSRGSG·GGG | GGRG·····G | GGGYR····· | | | 103 |
| SEQ_ID_NO_506 | AI EGMNGQNL | DGRNI TVNEA | QSRGSG·GGG | GGGYGSR··G | GGGY······ | | | 105 |
| SEQ_ID_NO_433 | VI EAMNGQDL | DGRNI TVNQA | QSRGSG·GGG | GGR······G | GGGY······ | | | 99 |
| SEQ_ID_NO_376 | AI EGMNGQNL | DGRNI TVNEA | QSRBG·GGG | GEGYGG···G | SGGYKR···· | | | 106 |
| SEQ_ID_NO_440 | AI EGMNGQNL | DGRNI TVNEA | QSRGSG·GGG | GRREGG···G | GGGYGR···· | | | 106 |

Figure 14 (continued)

| SEQ_ID | Seq1 | Seq2 | Seq3 | Seq4 | Seq5 | Seq6 | Seq7 | # |
|---|---|---|---|---|---|---|---|---|
| SEQ_ID_NO_475 | GNGGGRDYG | - | RGGYGR- | NGGY | GGRNAG | YGG | | 128 |
| SEQ_ID_NO_436 | RGGG GGY- | - | GGGY- | - | - | G- DGF | | 134 |
| SEQ_ID_NO_420 | GGGNAGGYGA | P- | SGGYGGG- | GGY | - | G- GGA | | 149 |
| SEQ_ID_NO_473 | EVVG- | - | -TAATAGTA- | - | - | V- DRR | | 120 |
| SEQ_ID_NO_369 | REQGGGGY- | - | GGGYGGSR- | GGG | - | D- REG | | 124 |
| SEQ_ID_NO_371 | GGGG- | - | GGGYGGSRD | RG- DRGY | - | G- GGG | | 125 |
| SEQ_ID_NO_372 | GGGG- | - | SGGYGGG- | SGGY | ESRRSG | GGG | | 127 |
| SEQ_ID_NO_373 | GGGG- | - | GGGYGGG- | GGGY | GGRREG | GGG | | 122 |
| SEQ_ID_NO_458 | GGGGGGGY- | - | GGGRSGG- | GGGY | GS- R- EGG | | | 133 |
| SEQ_ID_NO_507 | GGGG- GYGG | G- | GGGYGGGR- | - | - | S- GGG | | 127 |
| SEQ_ID_NO_455 | GGREGGGYGG | G- | GGGYGGRRE | G- GGGY | GGGGYG | GGG | | 137 |
| SEQ_ID_NO_477 | GGGRQGGYGG | G- | GGGYGGGGG | GGGY | GG- G- RRE | | | 125 |
| SEQ_ID_NO_465 | GGRGGGYGG | GGRRDG- | GGGYGGG- | GGGY | - | GGG | | 128 |
| SEQ_ID_NO_468 | GGGG GGYGG | GRG- | GGGYGGGG- | GGGY | GRREGGYGGG | | | 132 |
| SEQ_ID_NO_484 | GGGGGGGYGR | R- | EGGYGGG- | - | - | G- GYG | | 125 |
| SEQ_ID_NO_374 | GGRREGGYNR | GG- | GGGYGGG- | GGGY | - | G- GGG | | 130 |
| SEQ_ID_NO_441 | -GGG GGYGG | RREGGG- | GGGYGGR- | - | - | E- GGG | | 127 |
| SEQ_ID_NO_444 | GGGG GGYGG | GRR- | DGGYGGN- | GGY | GG- G- RRE | | | 131 |
| SEQ_ID_NO_451 | GGGG- GYGG | - | GGGYGGGRR | E- | - | G- GGG | | 127 |
| SEQ_ID_NO_505 | GGGG GGYGG | GGRR- | EGGYGGG- | GGY | GG- G- RRE | | | 126 |
| SEQ_ID_NO_474 | GGGG GGYGG | GGRR- | EGGYGGG- | GGGY | GG- G- RRE | | | 128 |
| SEQ_ID_NO_447 | GGGG- GYGG | G- | GGGYGGGRR | - | - | E- GGG | | 122 |
| SEQ_ID_NO_450 | EGGG GGYGG | - | GGGYRGG- | GGGY | - | GGG | | 128 |
| SEQ_ID_NO_434 | GGGGYGGGGG | RRDGGYSRSG | GGGGYGGGG- | DRGY | G- G- GGG | | | 147 |
| SEQ_ID_NO_437 | NGGG GGYGG | GRR- | EGGYGGG- | GGY | - S- RGG | | | 124 |
| SEQ_ID_NO_438 | GGGG GGYGG | GGRR- | EGGYGGG- | GGGY | NSRS- S- GGG | | | 131 |
| SEQ_ID_NO_454 | SRGG- | - | - | - | - | - | | 96 |
| SEQ_ID_NO_392 | NSGG GGYGG | GGRREG- | GGGYSRG- | GGGY | GG- G- GGG | | | 132 |
| SEQ_ID_NO_425 | GGGG- GYSR | G- | GGGYGGGGG | RR- EGGY | NR- N- GGG | | | 135 |
| SEQ_ID_NO_504 | GGGG GGYGG | - | GGGYGGGGR | R- EGG | GGYSRG GGG | | | 134 |
| SEQ_ID_NO_368 | SGGG GGYSG | - G- | GGGYGGG- | - | - | - | | 122 |
| SEQ_ID_NO_422 | SGGG GGYGG | G- | GGGYGGGGR | EGGY | - S- GGG | | | 130 |
| SEQ_ID_NO_506 | GGGGRRESGG | - | GGGYGGSR- | GY | - G- GGG | | | 129 |
| SEQ_ID_NO_433 | GGGG- | - | - | - | - | - | | 103 |
| SEQ_ID_NO_376 | SGGG GGYGR | - R- | EGGYGGGRR | EGVFWNGGGY | DG- G- GGG | | | 141 |
| SEQ_ID_NO_440 | REGG GGYSR | GGG- | GGGYGGG- | GGGY | G- G- GNG | | | 134 |

Figure 14 (continued)

| SEQ_ID_NO | Sequence | # |
|---|---|---|
| SEQ_ID_NO_475 | RGNFG - GQG - - - - - - GYGD NRFGNDNFGG SYGGREGYRG - PRGPSAEEN | 169 |
| SEQ_ID_NO_436 | SNRGG - GGG - - - - - - - - - - - - - - - - - - - - - - - - - - - - - | 142 |
| SEQ_ID_NO_420 | GGYGA - PGG - - - - - - GYGK - - - WWWL - RR RCWWLRC - - - - - - - - - - - | 174 |
| SEQ_ID_NO_473 | MGTGG - - - - - - - - - - - - - - - - - - - - AK AVVRLPR - - - - - - - - - - - | 134 |
| SEQ_ID_NO_369 | SGYGG - SRG G - - - - GYG - - - - - - - - GG GGGGYGG - R - GG - - - - - - - | 148 |
| SEQ_ID_NO_371 | GGYGG - GGG - - - - - - GYG - - - - - - - - GG GGSRYGG - - - GG - - - - - - - | 147 |
| SEQ_ID_NO_372 | SGGGGYSGGG RERSERGYGG GSRN - - - - GG GYGGYSG - GG - GGGSRYGGG | 171 |
| SEQ_ID_NO_373 | GGYGG - GSG G - - - - GYGG - - - RRE - - GG GGGGYGG - G - GGGGYRG - - | 155 |
| SEQ_ID_NO_458 | GGYGG - GGG - - - - - - GYGG SRGGS - - - GG GGGGYGGSRG - G - - - - - - - - | 163 |
| SEQ_ID_NO_507 | GGYGSRDGGG G - - - - - GYL - - - - - - - - - GG GGGGYGG - S RGG - - - - - - - | 153 |
| SEQ_ID_NO_455 | GGYGGREGGG - - - - - - GYGG - - - - - - - - GG GYGGNRG - - - - - - - - - - - | 160 |
| SEQ_ID_NO_477 | GGYGG - GGG GGRREGGYG - - - - - - - - GG GYGSRG - - - - - - - - - - - | 150 |
| SEQ_ID_NO_465 | GGYGG - GGG - - - - - - GYGG - - - - - - - - GN RGGGYGN - - - - - - - - - - - | 149 |
| SEQ_ID_NO_468 | GGYGGGRGGG G - - - - - GYG - - - - - - - - GG RGGGYGG - - - - - - - - - - - | 155 |
| SEQ_ID_NO_494 | GGRGG - GGG - - - - - - GYG - - - - - - - - GG RGGGYGG - - - - - - - - - - - | 145 |
| SEQ_ID_NO_374 | GGYGG - GGG - - - - - - GYGG - - - - - - - - GR REGYGG - G - GGDRYARG - | 160 |
| SEQ_ID_NO_441 | GGYGG - GGG - - - - - - GYGG RR - - - - - EG GDGGYGG - - - - - - - - - - - | 150 |
| SEQ_ID_NO_444 | GGYGG - GDR - - - - - - GYG - - - - - - - - GG GGGGSRYSRG - GG - - - - - - - | 156 |
| SEQ_ID_NO_451 | GGYSG - GGG - - - - - - GYGG GRREGGY - GG GGGGYGGGDR YSDRSSRGGG | 168 |
| SEQ_ID_NO_505 | GGYGG - GGG G - - - - - GYGG - - - - - - - GR REGGYGG - - - - - - - - - - - | 148 |
| SEQ_ID_NO_474 | GGYGG - GGG - - - - - - YGG - - - - - - - - GR REGGYGG - - - - - - - - - - - | 148 |
| SEQ_ID_NO_447 | GGYGG - GRR - - - - - - - - - - - - - - - - EG GGGGYGG - - - - - - - - - - - | 139 |
| SEQ_ID_NO_450 | RREGG - GGG - - - - - - GYGG GRRE - - - - GG GGGGYGG - - - - - - - - - - - | 153 |
| SEQ_ID_NO_434 | GGYGG - GRD R - - - - - GYGG - - - - - - - - GG GDRGYGG - GG - GGDRYSRGG | 180 |
| SEQ_ID_NO_437 | GGYGG - GGG - - - - - - GYG - - - - - - - - GG RDRGYGGGGD - GGSRYSRGG | 156 |
| SEQ_ID_NO_438 | GGYGG - GRD Q - - - - - GYGG - - - - - - - - GG GGSRYSR - - G - GG - - - - - - | 156 |
| SEQ_ID_NO_454 | - - - - - - - GGG - - - - - - - - - - - - - - - - - - - - - - - - - - - - - - | 99 |
| SEQ_ID_NO_392 | YGSGG - GGG - - - - - - GYG - - - - - - - - GG RDRGYGD - - - - GGSRYSSR | 160 |
| SEQ_ID_NO_425 | GGYGG - GGG GYGGGGGYGG - - - - - - - - GG RDRGYGG - D - GGSRYSRGG | 172 |
| SEQ_ID_NO_504 | GGYGS - GGG - - - - - - GYGG G - - - - - - GR REGGYGGGEG - GGARYSRGS | 168 |
| SEQ_ID_NO_368 | - GRRE - GGG - - - - - - GYG - - - - - - - - GG EGGGYGG - S - GG - - - - - - - | 144 |
| SEQ_ID_NO_422 | GGYSSRGGGG G - - - - - GYGG GGRRD - - - GG EGGGYGG - S - GG - - - - - - - | 162 |
| SEQ_ID_NO_506 | GGYGGRREGG YSRDG - GYG - - - - - - - - GD GGSRYSR - - S - GA - - - - - - - | 159 |
| SEQ_ID_NO_433 | - - - - - - - - - - - - - - - - - - - - - - - - - - - - - - - - - - - - - - - | 103 |
| SEQ_ID_NO_376 | GGYGG - GGG - - - - - - GYG - - - - - - - - GG GGGGY - - - - - - - - - - - - | 159 |
| SEQ_ID_NO_440 | GGYGG - GRE QR - - - - GYGD - - - - - - - - SG GGSRYSR - - - - - - - - - - - | 157 |

Figure 14 (continued)

| SEQ_ID | Sequence | # |
|---|---|---|
| SEQ_ID_NO_475 | NSNNYGGY- | 177 |
| SEQ_ID_NO_436 | ----GGGW- | 146 |
| SEQ_ID_NO_420 | --SSWWLWRR WLQCSRWWLR RWLILWWKCC WWRLWR | 208 |
| SEQ_ID_NO_473 | ----SEGWAS | 140 |
| SEQ_ID_NO_369 | --PSSGNWRN DRQPEY---- | 162 |
| SEQ_ID_NO_371 | --SEGGSWRR | 155 |
| SEQ_ID_NO_372 | GVSDDGGWRS | 181 |
| SEQ_ID_NO_373 | --NSDGNWRN | 163 |
| SEQ_ID_NO_456 | --SGGNWRE | 171 |
| SEQ_ID_NO_507 | --SGGGNWRE | 161 |
| SEQ_ID_NO_455 | --DSGGNWRN | 168 |
| SEQ_ID_NO_477 | --DSGGNWRN | 158 |
| SEQ_ID_NO_465 | ---SDGNWRN | 156 |
| SEQ_ID_NO_488 | --DSGGNWRN | 163 |
| SEQ_ID_NO_494 | --DSGGNWRN | 153 |
| SEQ_ID_NO_374 | --NSDSDWRN | 168 |
| SEQ_ID_NO_441 | ----GGGGSR W- | 157 |
| SEQ_ID_NO_444 | --ASDGNWRN | 164 |
| SEQ_ID_NO_451 | GGSSDGNWRN | 178 |
| SEQ_ID_NO_505 | --GSEG--- | 152 |
| SEQ_ID_NO_474 | --GSEGNWRN | 156 |
| SEQ_ID_NO_447 | --GGYGGGGR Y- | 148 |
| SEQ_ID_NO_450 | --GGYGGGDR Y- | 162 |
| SEQ_ID_NO_434 | GADSGGNWRD | 190 |
| SEQ_ID_NO_437 | G-ASEGNWRS | 165 |
| SEQ_ID_NO_438 | --ESDGNWKN | 164 |
| SEQ_ID_NO_454 | --DSGGNWRN | 107 |
| SEQ_ID_NO_392 | GESEGGSWRS | 170 |
| SEQ_ID_NO_425 | GCSDGGSWRN | 162 |
| SEQ_ID_NO_504 | GCSEGGSWRS | 178 |
| SEQ_ID_NO_368 | ----GGGW- | 148 |
| SEQ_ID_NO_422 | ----GGGW- | 166 |
| SEQ_ID_NO_506 | --SDGGSWRN | 167 |
| SEQ_ID_NO_433 | ----GG--- | 105 |
| SEQ_ID_NO_376 | ----GG--- | 161 |
| SEQ_ID_NO_440 | -DSDGGNWRS | 166 |

Figure 15

| | | | | | | | |
|---|---|---|---|---|---|---|---|
| SEQ_ID_NO_527 | ---MAGI SVI | VVVVAFLHI | LAFVLAI GAE | MRRST----- | ---------- | | 32 |
| SEQ_ID_NO_529 | MGDVGRSSI L | VHI LVI ALCL | AAFGFAI AAE | RRRST----- | ---------- | | 35 |
| SEQ_ID_NO_530 | MGDTERSSI L | VHI LVI ALCL | TAFGFAI AAE | RRRSTVKSTY | LRYI LNFVFE | | 50 |
| SEQ_ID_NO_531 | MGDTERSSI L | VHI LVI ALCL | TAFGFAI AAE | RRRST----- | ---------- | | 35 |
| SEQ_ID_NO_510 | MGEFGKASTL | VFI LVVALSL | VAFGFSI AAE | RRRSI----- | ---------- | | 34 |
| SEQ_ID_NO_525 | MGEFGKGSTL | VFI LVI ALCL | VAFGFSI AAE | RRRSI----- | ---------- | | 34 |
| SEQ_ID_NO_521 | MAEFGRGSTL | VHLLVVVLCL | VAFGFAI AAE | RRRSV----- | ---------- | | 34 |
| SEQ_ID_NO_513 | MGEFGKGSTL | VHLLVVVLSL | VAFGFAI AAE | RRRSV----- | ---------- | | 34 |
| SEQ_ID_NO_517 | MFEFGKGSTL | VHLLVVVLSL | VAFGFAI AAE | RRRS------ | ---------- | | 33 |
| SEQ_ID_NO_511 | ----MASKL | LLI AVFVLDL | AFGLAVAAE | QRRST----- | ---------- | | 30 |
| SEQ_ID_NO_523 | ----MASI L | VQVSALLLNL | AFGLAVAAE | QRRSK----- | ---------- | | 30 |

| | | | | | | |
|---|---|---|---|---|---|---|
| SEQ_ID_NO_527 | ---------- | ---CKVVPDE | YDERTFCAYD | SDASTAYGLS | AFGLLLLSQA | 69 |
| SEQ_ID_NO_529 | ---------- | ---GSI VTDS | S-NTTFCVYD | SDI ATGYGVG | AFLFLLSGHS | 71 |
| SEQ_ID_NO_530 | FMDGVFFTI Y | I VQGSI VTDS | F-NSTFCVYD | SDI ATGYGVG | AFLFLLSGDS | 99 |
| SEQ_ID_NO_531 | ---------- | ---GSI VTDS | F-NSTFCVYD | SDI ATGYGVG | AFLFLLSGDS | 71 |
| SEQ_ID_NO_510 | ---------- | ---GKSI QDP | I TNTTFCVYD | SDVATGYGVG | AFLFLLSSES | 71 |
| SEQ_ID_NO_525 | ---------- | ---GKSI QDP | I TNATYCVYS | SDVATGYGVG | AFLFLLSSES | 71 |
| SEQ_ID_NO_521 | ---------- | ---GTMHKI E | GTNETFCSYS | SDVATGYGVG | AFLFLLSXES | 71 |
| SEQ_ID_NO_513 | ---------- | ---GTVVKDD | I TNSTYCVYN | SDVATGYGVG | AFLFLLSGES | 71 |
| SEQ_ID_NO_517 | ---------- | ---------- | ---------- | ------YGVG | AFLFLLSSES | 47 |
| SEQ_ID_NO_511 | ---------- | ---AKI VQDS | EVNYNYCVYD | SYI STGYGVG | AFLFLMVSQA | 67 |
| SEQ_ID_NO_523 | ---------- | ---ATVFPDL | AKEYDYCVYD | SDVATGYGVG | ALLLLVAAQA | 67 |

| | | | | | | |
|---|---|---|---|---|---|---|
| SEQ_ID_NO_527 | VMSAATRCLC | FGRGLSAGGP | RTCAI ASFVV | SWI SFLVAEV | CLLAGSARNA | 119 |
| SEQ_ID_NO_529 | LLMGLTKCMC | FGAPLAPGGS | RAWSI I YFAS | SWVTFAI AEA | CLI AGATKNA | 121 |
| SEQ_ID_NO_530 | LLMVVTKCMC | FGKPLAPGGS | RAWSI I YFAS | SWVTFMI AES | CLI AGATKNA | 149 |
| SEQ_ID_NO_531 | LLMVVTKCMC | FGKPLAPGGS | RAWSI I YFAS | SWVTFMI AES | CLI AGATKNA | 121 |
| SEQ_ID_NO_510 | LLMSVTKCMC | FGRPLAPGSD | RAWSI I YFI S | SWMTFLVAEA | CVI AGATKNA | 121 |
| SEQ_ID_NO_525 | LLMGVTKCMC | FGRPLSPGSD | RAWSI I YFI S | SWMTFLVAEA | CLI AGATKNA | 121 |
| SEQ_ID_NO_521 | LXMGVTKCMC | FGRPLTPGVN | RAXSI XYFLS | SWVTFXVAEA | CLI AGATKNA | 121 |
| SEQ_ID_NO_513 | LLMGVTKCMC | FGRPLAPGSD | RAWSI I YFVS | SWLTFLVAFA | CLI AGATRNA | 121 |
| SEQ_ID_NO_517 | LLMGI TKCMC | FGRSLAPGGD | RAWAI I YFVS | SWATFLVAEG | CLI AGAKKNA | 97 |
| SEQ_ID_NO_511 | LI MAASKCFC | CGKGLNPSGS | RAWAVI LFI V | CMLFFLI AEI | CLLAGSVRNA | 117 |
| SEQ_ID_NO_523 | VVMLASRCFC | CGRGLKPGGS | RACALMLFLF | SWLTFLVAAA | CLLAGSVRNA | 117 |

Figure 15 (continued)

| | | | | | | | |
|---|---|---|---|---|---|---|---|
| SEQ_ID_NO_527 | YHTKYVGYYA | KKDLSSCTAL | RKGVFAAGAT | FVLLSMISSL | LYYWSYSKA- | 168 |
| SEQ_ID_NO_529 | YHTKYRDMVY | AGNW-TCQSL | RKGVFIAGAV | FVVFTMILDV | YFYMYYAKA- | 169 |
| SEQ_ID_NO_530 | YHTKYRHMVY | VGSW-TCESL | RKGVFIAGAV | FVVFTMILNV | YFYMYYTKS- | 197 |
| SEQ_ID_NO_531 | YHTKYRHMVY | VGSW-TCESL | RKGVFIAGAV | FVVFTMILNV | YFYMYYTKS- | 169 |
| SEQ_ID_NO_510 | YHTKY---LS | SQTF-SCASL | RKGIFIAGAV | FLVATMVLNV | YYYMYFTKSV | 167 |
| SEQ_ID_NO_525 | YHTKY---LS | AQAF-SCESL | RKGIFIAGAV | FTVATMILNV | YYYFHFTKFV | 167 |
| SEQ_ID_NO_521 | YHTKYRGMIY | AHNF-SCEAL | RKGXFIAGAV | FVVATMILNV | YYYMYFTKAM | 170 |
| SEQ_ID_NO_513 | YHTKYRGMIY | AQNF-SCETL | RKGVFIAGAV | FVVATMILNV | YYYMYFAKAT | 170 |
| SEQ_ID_NO_517 | YHTKYRGMIY | AQNF-TCETL | RKGVFIAGAV | FVVATMILNV | YYYMYFSKAT | 146 |
| SEQ_ID_NO_511 | YHTKYRTIFS | EDPP-SCETV | RKGVFGAGAA | FIFLNAIVNK | FYYICYSSA- | 165 |
| SEQ_ID_NO_523 | YHTRYRGIFN | GDPL-SCETL | RKGVFAAGAA | FTFFTALSE | FYYISYSKS- | 165 |

| | | | | | |
|---|---|---|---|---|---|
| SEQ_ID_NO_527 | -DMGGWKHQ | NEGGVGMAEF | GPEKRGLGNT NG | 199 |
| SEQ_ID_NO_529 | TSQAAKKISK | TTPSVGMTGY | A--------- -- | 190 |
| SEQ_ID_NO_530 | TSQAAKKLNK | TTPNVGMTGY | A--------- -- | 218 |
| SEQ_ID_NO_531 | TSQAAKKLNK | TTPNVGMTGY | A--------- -- | 190 |
| SEQ_ID_NO_510 | SSPPAHKANR | SSSNIGMAGY | A--------- -- | 188 |
| SEQ_ID_NO_525 | FFPPTHKANR | SSSNIGMAGY | A--------- -- | 188 |
| SEQ_ID_NO_521 | TXPVXHKANR | VSSTVGMAGY | A--------- -- | 191 |
| SEQ_ID_NO_513 | TTMPAHKANR | TNSTVGMTGY | A--------- -- | 191 |
| SEQ_ID_NO_517 | ASKAAHKTNR | TSS-VGMTGN | P--------- -- | 168 |
| SEQ_ID_NO_511 | -RDKSFQAYG | GETGVGMGTY | K--------- -- | 185 |
| SEQ_ID_NO_523 | -RDAAGGAPY | GGSSIGMGFY | T--------- -- | 185 |

Figure 16

```
SEQ_ID_NO_546     ----MSSSLE RKKGKTVI-- ---------M LRSCSQCGSN GHN------    28
SEQ_ID_NO_542     ---------- ---------- ---------M GRKCSHCGNI GHN------    14
SEQ_ID_NO_547     ---------- ---------- ---------M TRRCSHCSTN GHN------    14
SEQ_ID_NO_533     ----MESVVA I--------- ---------W SREEEKAFEN AIALHCV---   25
SEQ_ID_NO_539     ----MSSGGT I--------- ---------W SYDEEKAFEN AIAMHM---    25
SEQ_ID_NO_535     ----MAGSVS ---------- ---------W SREEEKAFEN AIAMHM---    24
SEQ_ID_NO_538     ----MASVGT ---------- ---------W TRDEEKTFEN AIAMHM---    24
SEQ_ID_NO_553     ----MTSQAA TTTTTAAAAA A--------W TREDDKAFEN ALAACAAPPP   38
SEQ_ID_NO_550     ----MAAEEA SSSGGGEEGS GAGAGG---W TREQEKAFEN ALATV-----   38
SEQ_ID_NO_552     ----MAVNEA SSSGGGEEGC GS-------W TREQEKAFEN AVATMGG---   36
SEQ_ID_NO_536     ----METLYP SSHLSSSGAWF VLDNPS-TKW TKEENKMFES ALAIY-----   40
SEQ_ID_NO_543     MDRGIEILSP ASYLQNSNWL FPETRA-TKW TPEENKQFEN ALALY-----   44
SEQ_ID_NO_548     ----MEILAP SSYFSSSSWF LEESRSTTRW TAAENKAFEN ALAVF-----   41

SEQ_ID_NO_546     --SRTCGESS SAAGNGAGDG EFMLFGVRVK VDPMRKSVSM NDLSD-YELP   75
SEQ_ID_NO_542     ---------- SR-TCNSLRG SGBFVGVRLF GVQLDLSSSC VSMKKSFSMD   53
SEQ_ID_NO_547     --SRTCPNRG VKLFGVRLT -DGLRKSAS MGNLTHFASG SGCGS-TPLN   59
SEQ_ID_NO_533     -EEEITEDQW NKIMSSMVPS -KALEEVKKH YQLLEDVKA IENGQ-VPLP   71
SEQ_ID_NO_539     -EESSKEQW EK-IASAVPS -KSMEEVKQH YQVLVEDVSA IEAGH-ISFP   70
SEQ_ID_NO_535     -DKEECEEQW EK-IASTVPI -KSLEELKLH YELLVEDVTA IEAGH-VPLP   70
SEQ_ID_NO_538     --DEDSNEQW EK-IASMVPS -KSLEELKLH YKILVEDVCA IEAGN-VPIP   69
SEQ_ID_NO_553     ADGGAPDDDW FAALAASVPG ARSAEEVRRH YEALVEDVAA IDAGR-VPLP   87
SEQ_ID_NO_550     -DEEEGEAMW DK-IADAVES -KTPEEVRRH YELLVEDVDG IEAGR-VPLL   84
SEQ_ID_NO_552     --EEDGDARW EK-LAEAVES -KTPEEVRRH YELLVEDVDG IESGR-VPLP   81
SEQ_ID_NO_536     --DKETPDRW FK-VAALIPG -KTVSDVIKQ YKELEEDVCE IEAGR-FPVP   85
SEQ_ID_NO_543     --DKDEPDRW DK-IVAAVPG -KTVGDVIKQ YRELEEDVSD IEAGL-IPIP   89
SEQ_ID_NO_548     --DENTPNRW ER-VAERVPG -KTVGDVMRQ YKELEDDVSS IEAGF-VPVP   86
```

Figure 16 (continued)

| | | | | | | | |
|---|---|---|---|---|---|---|---|
| SEQ_ID_NO_546 | SNVN----- | QNGVDNSKWS | NDSDKVVADD | VVTAGAGYV- | ---------S | | 109 |
| SEQ_ID_NO_542 | SFPT----- | ---SSSSPTS | SFSSSRLTID | DRASIGYLSD | GL-------- | | 86 |
| SEQ_ID_NO_547 | GVVH----- | DSPGDTPDHP | A-VGGGSADS | YASEDFVAG- | ---------- | | 91 |
| SEQ_ID_NO_533 | RYHHRKGLIV | DEAAAAATSP | ANRDBHSSGS | SEKKPNPGTS | GIS------S | | 115 |
| SEQ_ID_NO_539 | NYAS----- | DETTSSNKD- | FHGSSKATSS | DKRSNCNYGS | GFSGLGLDST | | 113 |
| SEQ_ID_NO_535 | CYKG----- | EEPSSSAKDY | FHGPSMAPNS | DRRSNSGYGN | GFSGLTLDST | | 114 |
| SEQ_ID_NO_538 | NYEG----- | EEAASSTKD- | LHGLSGTMTT | VKKLNCGYGS | GFVGLGHESS | | 112 |
| SEQ_ID_NO_553 | RYAG----- | EESAAPPDGA | GAAAAASKDG | GHRRDERKCG | G--------G | | 123 |
| SEQ_ID_NO_550 | VYAG----- | DGDEGGSGGG | AGGSGGGGGG | GGKKSGGGG- | ---------G | | 118 |
| SEQ_ID_NO_552 | AYAA----- | ---------- | -DGAAEEGGG | GGKKGSGGG- | ---------G | | 104 |
| SEQ_ID_NO_536 | GYDL----- | ----ASSFSF | EFVDDRNFDV | YRRKSSVG-- | ---------- | | 113 |
| SEQ_ID_NO_543 | GYSS----- | ---SDAFTLE | WFNNNQGYDG | FRHYYTPGG- | ---------- | | 119 |
| SEQ_ID_NO_548 | GYST----- | ----SSPFTL | EWGSGHGFDG | FKQSYGTGG- | ---------- | | 115 |

| | | | | | | | |
|---|---|---|---|---|---|---|---|
| SEQ_ID_NO_546 | ADDAVDHQ-- | STGGRERKRG | IPWTEEEHKL | FLLGLDKVGK | GDWRGISRNF | | 157 |
| SEQ_ID_NO_542 | ---------- | IVRTQERKKG | VPWTEEEHRK | FLVGLEKLGK | GDWRGISRNY | | 126 |
| SEQ_ID_NO_547 | ---------- | SSSSRERKKG | VPWTEEEHRM | FLLGLDKLGK | GDWRGIARNY | | 131 |
| SEQ_ID_NO_533 | SNGGRSGG-- | SRAEQERRKG | IPWTEEEHRL | FLLGLDKFGK | GDWRSISRNF | | 163 |
| SEQ_ID_NO_539 | THSSGKGGLS | RSSEQERRKG | IPWTEEEHRL | FLLGLDKFGK | GDWRSISRNF | | 163 |
| SEQ_ID_NO_535 | GHGCKQS--- | SRSDQERRKG | IPWTEEEHRL | FLLGLDKFGK | GDWRSISRNF | | 161 |
| SEQ_ID_NO_538 | GHGGKGA--- | SRSEQERRKG | IPWTEEEHRL | FLLGLDKFGK | GDWRSISRNF | | 159 |
| SEQ_ID_NO_553 | GYDGGKSC-- | SKAEQERRKG | IPWTEEEHRL | FLLGLDKFGK | GDWRSISRNF | | 171 |
| SEQ_ID_NO_550 | GHGEKGSS-- | KSAEQERRKG | IAWTEDEHRL | FLLGLEKYGK | GDWRSISRNF | | 166 |
| SEQ_ID_NO_552 | THGDKRSA-- | KSAEQERRKG | IAWTEDEHRL | FLLGLEKYGK | GDWRSISRNF | | 152 |
| SEQ_ID_NO_536 | ---------- | RGSEHERKKG | VPWTEEEHKQ | FLRGLLKYGK | GDWRNISRNF | | 153 |
| SEQ_ID_NO_543 | ----KRTTAA | RSSEQERKKG | VPWTEEEHRQ | FLMGLQKYGK | GDWRNISRNF | | 165 |
| SEQ_ID_NO_548 | ----RKSSSG | RPSEQERKKG | VPWTEEEHKL | FLMGLKKYGK | GDWRNISRNF | | 161 |

Figure 16 (continued)

| | | | | | | |
|---|---|---|---|---|---|---|
| SEQ_ID_NO_546 | VKTRTPTQVA | SHAQKYYLRK | NNLNRRRRRS | SLFDITTDSV | PGGLPMDDVK | 207 |
| SEQ_ID_NO_542 | VTTRTPTQVA | SHAQKYFIRL | ATLNKKKRRS | SLFDMVGSGK | TN-KTVD--- | 172 |
| SEQ_ID_NO_547 | VISRTPTQVA | SHAQKYFIRD | SNMSRRKRRS | SLFDIVADES | GDTPMVSR-- | 179 |
| SEQ_ID_NO_533 | VISRTPTQVA | SHAQKYFIRL | NSMNRDRRRS | SIHDITTVNN | QA-------- | 205 |
| SEQ_ID_NO_539 | VISRTPTQVA | SHAQKYFIRL | NSMNRDRRRS | SIHDITSVNN | GD-------- | 205 |
| SEQ_ID_NO_535 | VISRTPTQVA | SHAQKYFIRL | NSMNRDRRRS | SIHDITSVNN | GD-------- | 203 |
| SEQ_ID_NO_538 | VISRTPTQVA | SHAQKYFIRL | NSMNRDRRRS | SIHDITSLNN | GD-------- | 201 |
| SEQ_ID_NO_553 | VISRTPTQVA | SHAQKYFIRL | NSMNRDRRRS | SIHDITSVTA | GDQV------ | 215 |
| SEQ_ID_NO_550 | VISRTPTQVA | SHAQKYFIRL | NSMNRERRRS | SIHDITSVNL | GE-------- | 207 |
| SEQ_ID_NO_552 | VISRTPTQVA | SHAQKYFIRL | NSMNRERRRS | SIHDITSVNN | GD-------- | 194 |
| SEQ_ID_NO_536 | VNSKTPTQVA | SHAQKYFMRQ | LSGGKDKRRP | SIHDITTVNL | TE-------- | 195 |
| SEQ_ID_NO_543 | VTTRTPTQVA | SHAQKYFIRD | STGGKDERRS | SIHDITTVNL | PDTKS----- | 210 |
| SEQ_ID_NO_548 | VITRTPTQVA | SHAQKYFIRD | LSGGKDKRRA | SIHDITTVNL | SDNQTPS--- | 208 |

| | | | | | | |
|---|---|---|---|---|---|---|
| SEQ_ID_NO_546 | NHQDKSVPKV | LQHSQVPHAE | KPNMNGYTIA | PFPLAVGPIL | LFVQVHNPME | 257 |
| SEQ_ID_NO_542 | ---------- | ------PNNS | SKSKSGDSVC | RHDHEVEKDA | TLSL---LIN | 203 |
| SEQ_ID_NO_547 | ---------- | ------DFLA | DDPAQAEMQS | ----NNLLPP | TPAVDEECES | 209 |
| SEQ_ID_NO_533 | ---------- | ------PAMT | GGGQQPQVVK | ----HRPAQP | QPQP---Q-- | 230 |
| SEQ_ID_NO_539 | ---------- | ------VASS | QAPITGLHSS | -----TISSN | TMGV------ | 228 |
| SEQ_ID_NO_535 | ---------- | ------TSH | QAPITGQQAN | -------TN | SPGA---AVM | 225 |
| SEQ_ID_NO_538 | ---------- | ------VSSH | QAPITGQQAN | ----TSPAGP | APAM------ | 225 |
| SEQ_ID_NO_553 | ---------- | ------AAQQ | GAPITGHQAT | ----GNPAAA | ALGP---PGM | 242 |
| SEQ_ID_NO_550 | ---------- | ------ASAA | QGPITG---- | ----TNGQAA | VPGK---S-- | 228 |
| SEQ_ID_NO_552 | ---------- | ------PSTA | QGPITGQ--- | ----TNGQAA | NPGK---P-- | 216 |
| SEQ_ID_NO_536 | ---------- | ------PTAS | ENEKLSSMDQ | ---FSKLPSL | QKSP---CYQ | 223 |
| SEQ_ID_NO_543 | ---------- | ------PSPD | EKKSSPDHSI | TSLQSQPQQK | MVGM---A-- | 239 |
| SEQ_ID_NO_548 | ---------- | ------PDNK | KPFSSPDHSM | ----AQQQTS | STSI---H-- | 233 |

Figure 16 (continued)

| SEQ_ID_NO_546 | NKAFHWGDHQ L-QNGPGMLL RTVPFIPVAN S---------- ------SSAR | 292 |
|---|---|---|
| SEQ_ID_NO_542 | SLQQQTKSDD Y-DMQKIEDD SEEAEHKDVP D---------- ------WLHPL | 238 |
| SEQ_ID_NO_547 | MGSAASANSI DGEHALPLPE SSCYQHPLVY PAYVAPFYPM PYPCWPGYTA | 259 |
| SEQ_ID_NO_533 | PQPQQHHPPT --MAGLGMYG GAPVGQPIIA P---------- ------PDHMG | 264 |
| SEQ_ID_NO_539 | GQSLKHRVQG HIPPGLGMYG TLPVGHPVAA P---------- ------PGHMA | 263 |
| SEQ_ID_NO_535 | GQSVKHRAQP H-LPGLGMYG ALPVGRPIAN A---------- ------PGHIG | 259 |
| SEQ_ID_NO_538 | GPPVKHRTQA H-MPGLAMYG P-PLGHPVAP P---------- ------PGHMA | 259 |
| SEQ_ID_NO_553 | KHHHHHHPGG A-PPPMPNYS AAPMGHPVA- ---------- ------GHMV | 274 |
| SEQ_ID_NO_550 | PKQSPHQPGN L-PPGVDAFG TLTLGQPVGG P---------- ------LV--- | 259 |
| SEQ_ID_NO_552 | SKQSP-QPAN T-PPGVDAYG TLTLGQPVGG P---------- ------LV--- | 246 |
| SEQ_ID_NO_536 | KLLFDWNRSB --NGGLLGLG BLNYGDRLMS F---------- ------PSGLA | 256 |
| SEQ_ID_NO_543 | KGLIDWKPQN EGGGAAGVFS Q-ANGNLLMA P---------- ------LCGL- | 273 |
| SEQ_ID_NO_548 | KLPFQWDQTS N-ETIMGFAS SGHHGNMFQS N---------- ------PFGM- | 267 |

| SEQ_ID_NO_546 | DLNLN-QRML ----EGEPSS P--------- --------LS LKLSLSSSDN | 319 |
|---|---|---|
| SEQ_ID_NO_542 | TKSLN-MTLV LPNSSNVAP P--------- --------DL ELTLAGSKSN | 269 |
| SEQ_ID_NO_547 | EPAIAETHEM LKPIAVHSKS PINVDELVGM SKLSLGESIG DAAKPPSLSL | 309 |
| SEQ_ID_NO_533 | -SAVGLTPVM LPPPMGTHHH H--------- --------HH HHLGVAPYAV | 295 |
| SEQ_ID_NO_539 | -SAVGLTPVM LPPGFHPHPH P--------- --------HH HAHPHPPYVL | 294 |
| SEQ_ID_NO_535 | -SAVGLTPVM LPPAHHPHS P--------- --------- -----PPYIV | 282 |
| SEQ_ID_NO_538 | -SAVGLTPVM LPPPGHHPH- ---------- --------- -----PPYVV | 281 |
| SEQ_ID_NO_553 | PAAVGLTPVV F-PPGH---- ---------- --------- -----APYVV | 293 |
| SEQ_ID_NO_550 | -SAVGLTPVT LPVAAPPHM G--------- --------YA MHAPVPGTVV | 289 |
| SEQ_ID_NO_552 | -SAVGLTPVT LPVSAPPHL A--------- --------YG MRAPVPGAVV | 276 |
| SEQ_ID_NO_536 | ANGLK-N--- --EQDCELNS A--------- --------YY GTYSKPHKS | 283 |
| SEQ_ID_NO_543 | -SSYGLQRL- --QEQNLLRG T--------- --------LP GYQFAPYNL | 301 |
| SEQ_ID_NO_548 | -NSYGLFKM- --QGQQMQRG G--------- --------FC DTYLGSQNMA | 295 |

Figure 16 (continued)

| | | | |
|---|---|---|---|
| SEQ_ID_NO_546 | SQSSSTRHST GFQAMAATSF SKGGDSIISV A-- | 350 |
| SEQ_ID_NO_542 | NMEQDKTSSS SFLIGPISVT ---------- --- | 289 |
| SEQ_ID_NO_547 | KLVEGSSRQS AFHANPSSGS SGMNSSHNPI HAV | 342 |
| SEQ_ID_NO_533 | PA------- -YPVPPLPQQ HPAPSTMH-- --- | 314 |
| SEQ_ID_NO_539 | PLA------ -YPMAPPTMH Q--------- --- | 307 |
| SEQ_ID_NO_535 | PVA------ -YPMAPPPMH Q--------- --- | 295 |
| SEQ_ID_NO_538 | PVA------ -YPTAPPKTA ---------- --- | 293 |
| SEQ_ID_NO_553 | PVG------ -YPAPPAKMH Q--------- --- | 306 |
| SEQ_ID_NO_550 | PRAPM---- -YPMPPPPSR ---------- --- | 303 |
| SEQ_ID_NO_552 | PGAPVNIAPM PYPMPPPPSH G--------- --- | 297 |
| SEQ_ID_NO_536 | ---------- -FQFEPSRYQ IYG------- --- | 295 |
| SEQ_ID_NO_543 | ---------- -FQMQPMQRQ ---------- --- | 310 |
| SEQ_ID_NO_548 | ---------- -FQMQSGLHF PNA------- --- | 307 |

| | | | | | | | |
|---|---|---|---|---|---|---|---|
| SEQ_ID_NO_559 | PSA I LPGSK | EELSNTI RC | RKGSWT RLR | SGGHSYEGLS | YTS----DTP | 116 |
| SEQ_ID_NO_586 | PSM I LPQSK | EELAASVVCS | NRGLWT RLR | SGGHSYEGLS | YVA----DTP | 112 |
| SEQ_ID_NO_591 | PRV I LPESM | DQLANVI SCC | TRGSWT RLR | SGGHSYEGLS | HI A----DNP | 113 |
| SEQ_ID_NO_581 | PLG I AATEH | AHADT TVRCG | RRHGVRVRVR | SGGHDYEGLS | YASVHLHNRN | 130 |
| SEQ_ID_NO_588 | PLA YAATEP | AHADAAVRCG | RRHGVRVRTR | SGGHDYEGLS | YASL---DPR | 125 |
| SEQ_ID_NO_589 | PLY VTPTDV | KHI QVAVSCG | RRHNVRI RVR | SGGHDYEGLS | YRS----EI P | 124 |
| SEQ_ID_NO_590 | PLY VTPTDV | KHI QVAVSCG | RRHNVRI RVR | SGGHDYEGLS | YRS----EI P | 129 |
| SEQ_ID_NO_584 | PLY I TPTNV | SHI QSAVVCG | RRHSVRI RVR | SGGHDYEGLS | YRS----LCP | 123 |
| SEQ_ID_NO_583 | PVY I TPTEA | AHI QATVACG | RXHGLRVRVR | SGGHDYEGLS | YRS----AKP | 128 |
| SEQ_ID_NO_585 | PLY I TPTNA | SHI QAAVVCG | RRHGMRI RVR | SGGHDYEGLS | YRS----EKP | 125 |
| SEQ_ID_NO_560 | PLV VTPBNV | SHI QASI LCS | KKVGLQI RTR | SGGHDAEGLS | YI S----QVP | 126 |
| SEQ_ID_NO_577 | PLV VTPQVV | SHI QATI KCS | QRHGLQI RTR | SGGHDYEGLS | YVA----RVP | 121 |
| SEQ_ID_NO_569 | PLI I TPLDE | SHVSAAV CS | QKI GFDLKI R | SGGHDYEGLS | YVF----DNP | 124 |
| SEQ_ID_NO_575 | PLL VTPLSE | NCVQATYVCA | KSI GLQLKI R | SGGHDFEGVS | YI S----QVP | 128 |
| SEQ_ID_NO_576 | PLA I TAKDD | SHI QETI KCA | KSNN QI RI R | SGGHDYEGFS | YVS----DVP | 119 |
| SEQ_ID_NO_578 | PFL I TAEHV | SHI QAAVVCG | KQNRLLKTR | SGGHDYEGLS | YLT----NTN | 129 |
| SEQ_ID_NO_579 | PI L I IALHP | SHI QAAVVCA | KTHRLLMKTR | SGGHDYEGLS | YVT----NSN | 128 |
| SEQ_ID_NO_558 | PVA VAAADV | THI QATI TCA | KKLGLQLRI R | SGGHDYDGMS | YLS----TI D | 126 |
| SEQ_ID_NO_571 | PLA I AAKHE | SHVQATI CS | KKLQLQI RI R | SGGHDYDGLS | YVS----DVA | 119 |

| | | | | | | | |
|---|---|---|---|---|---|---|---|
| SEQ_ID_NO_559 | --F LI DLMN | LNRVSI DLES | ETAWWESGST | LGELYYA IE | SSSKL-GFTA | 163 |
| SEQ_ID_NO_586 | --F VI DLMN | LNRI SI DLES | KTAWESGAT | LGEI YCAI SE | ASDTL-GFSG | 159 |
| SEQ_ID_NO_591 | --FVI DLMN | LNG SI DLDT | QTAWESGAT | LGEI YHAI CK | SSGTM-AFSA | 160 |
| SEQ_ID_NO_581 | EPFAVLDLAA | LRAI HVDAAR | AEAWWESGAT | VGELYYANGA | ASRSL-GFPA | 179 |
| SEQ_ID_NO_588 | ESFAVLDLAA | FRENRVDAAR | AEAWGSGAT | LGEVYYANGA | ASRAL-AFPA | 174 |
| SEQ_ID_NO_589 | EPFAI VDLVN | MRNVTVDGKA | RTAWESGAD | GELYYGI SK | ASPTL-AFPA | 173 |
| SEQ_ID_NO_590 | EPFAI VDLVN | MRNVTVDGKA | RTAWESGAD | GELYYGI SK | ASPTL-AFPA | 178 |
| SEQ_ID_NO_584 | ETFAVVDLNK | MHAVVVDGKA | RTAWDSGAD | LGELYYAI YK | ASPTL-AFPA | 172 |
| SEQ_ID_NO_583 | ETFAVVDLSM | MRQVR DGKA | ATAWDSGAD | LGELYYAVAK | MTPSL-GFPA | 177 |
| SEQ_ID_NO_585 | EPFAVVDMNK | MRAVSI DGKA | ATAWDSGAD | LGDLYYG AK | ASPKL-GFPA | 174 |
| SEQ_ID_NO_560 | --FAI VDLRN | MHTVKVDI HS | QTAWEAGAT | LCEVYYW NE | MNENF-SFPG | 173 |
| SEQ_ID_NO_577 | --FVI LDLLN | FREI KVDVEN | RTAWQVGAT | LGELYYT SQ | ASKTL-GFPA | 168 |
| SEQ_ID_NO_569 | --FFVLDMFN | LRSI TVNMAD | ETAWGAGAT | LGELYYN WK | NSKVH-GFPA | 171 |
| SEQ_ID_NO_575 | --F I LDMFN | FQDVTVDVQN | EI AV QAGAS | LGQVYYRI WE | KSKVH-GFPS | 175 |
| SEQ_ID_NO_576 | --F I LDMFH | LNSVDI NLCE | STAWESGAT | LGKI YYN AN | KSNKL-AFPS | 166 |
| SEQ_ID_NO_578 | QPFF VDMFN | LRSI NVDI EQ | ETAWQAGAT | LGEVYYRI AE | KSNKH-GFPA | 178 |
| SEQ_ID_NO_579 | QPFFVVDMFN | LRSI NVSI ED | ETAWQAGAT | LGEVYYRI AF | KSNSH-AFPA | 177 |
| SEQ_ID_NO_558 | --FVVLDMFN | LRSI NI DPKL | QTAWQSGAT | LGEI YYGVAN | KSNDLRGFPA | 174 |
| SEQ_ID_NO_571 | --F I LDMFN | LRSI NI DI ED | ESAWVQAGAT | LGEVYYRI AE | KSNVH-GFPA | 166 |

Figure 17 (continued)

| | | | | | | | |
|---|---|---|---|---|---|---|---|
| SEQ_ID_NO_559 | GWCPTVGTGG | HISGGGFGMM | SRKYGLAADN | VVDALIDAN | GALDRQAMG | 213 |
| SEQ_ID_NO_586 | GYCPTVGSGG | HISGGGFGMM | SRKYGLAADN | VIDALIVDAN | GAVLDRSSMG | 209 |
| SEQ_ID_NO_591 | GYCPTGSSGG | HIAPGGFGMM | SRKYGLAADN | VVDALLVDAN | GVVLDRESMG | 210 |
| SEQ_ID_NO_581 | GSCPTMGVGG | HLSGGGFGSL | ARKYGLSADN | VLDAVVVDAD | GRLVNRSTMG | 229 |
| SEQ_ID_NO_588 | GVCPTVGVGG | HLGGGFGTL | MRRYGLAADN | VLDAVLVDAD | GRLLNRTTMG | 224 |
| SEQ_ID_NO_589 | GVCPTIGVGG | HFSGGGFGML | LRKFGLASDN | VLDVKVVDAN | GKVQDRKSMG | 223 |
| SEQ_ID_NO_590 | GVCPTIGVGG | HFSGGGFGML | LRKFGLASDN | VLDVKVVDAN | GKVQDRKSMG | 228 |
| SEQ_ID_NO_584 | GVCPTIGVGG | NFAGGGFGML | LRKYGIAAEN | VIDVKLYDAN | GKLHDKKSMG | 222 |
| SEQ_ID_NO_583 | GVCATIGVGG | HFSGGGFGML | LRKYGTAGDN | VIDAKVVDAN | GTLLDRKSMG | 227 |
| SEQ_ID_NO_585 | GVCITIGVGG | HFSGGGFGML | LRKYGTAADN | VIDAKVVDAQ | GRLLDRKAMG | 224 |
| SEQ_ID_NO_560 | GYCPTVGVGG | HFSGGGYGAL | MRNYGLAADN | IDAHLVNVD | GKVLDRKSMG | 223 |
| SEQ_ID_NO_577 | GVCYSVGAGG | HSGGGYGFL | MRKYGLAADN | VIDAHIIDVN | GNLLDRKAMG | 218 |
| SEQ_ID_NO_569 | GVCPTVGVGG | HLSGAGYGTL | RKYGLSVDH | VVDAKLVDVN | GKILDRKTMG | 221 |
| SEQ_ID_NO_575 | GACPTVGVGG | HLSGGGYGNM | RKYGLSVDH | VVDAKIVDVK | GRILDKESMG | 225 |
| SEQ_ID_NO_576 | GVCFTLGAGG | HFSGGGYGNL | MRKFGLSVDN | IDAKMVDVK | GNLLDRKSMG | 216 |
| SEQ_ID_NO_578 | GVCPTVGVGG | HFSGGGYGNL | MRKYGLSVDN | VDAQIIDVN | GKLLDRKSMG | 228 |
| SEQ_ID_NO_579 | GVCPTVGVGG | HFSGGGYGNL | MGKYGLSVDN | VDAQLIDVN | GKLLNRKSMG | 227 |
| SEQ_ID_NO_558 | GICPGLGAGG | HFSGGGYGNM | MRKYGLSIDN | IDAKIVDAK | GKVLDRSSMG | 224 |
| SEQ_ID_NO_571 | GVCPTLGVGG | HFSGGGYGNM | MRKYGLSVDN | VDAQIIDVR | GRILDRKSMG | 216 |

| | | | | | | | |
|---|---|---|---|---|---|---|---|
| SEQ_ID_NO_559 | EDVFWAIRGG | GGGVNGAIYA | WKIKLLPVPE | KVTVFRVTKN | VAIDE--ATS | 261 |
| SEQ_ID_NO_586 | EDVFWAIRGG | GGGVNGAIYA | WKLQLLPVPK | QVTVFKLVKN | FDNIE-EASK | 258 |
| SEQ_ID_NO_591 | EDVFWAIRGG | GGGVNGAVYA | WKLQLVPVFK | NVTIFRLVKH | SEVED--ASK | 259 |
| SEQ_ID_NO_581 | EDHFWALCGG | GGESFGVVLS | WKVRLVPVFE | TVTVFSIVRS | RSDS---AVE | 276 |
| SEQ_ID_NO_588 | EDLFWAIRGG | GGESFGVVLS | WKLRLVPVFE | TVTVFTVRRS | RNQS---ASE | 271 |
| SEQ_ID_NO_589 | EDYLWAVRGG | GGSSFGIVVS | WKLRLLPVPA | TVTVIQMPKM | VNEG---AVD | 270 |
| SEQ_ID_NO_590 | EDYLWAVRGG | GGSSFGIVVS | WKLRLLPVPA | TVTVIQMPKM | VNEG---AVD | 275 |
| SEQ_ID_NO_584 | DDNFWAVRGG | GGESFGIVVA | WQVKLLPVPP | TVTIFKISKT | VSEG---AVD | 269 |
| SEQ_ID_NO_583 | EDYFWAIRGG | GGESFGIMVS | WQVQLVPVPP | KVTVFQIHRG | VKDG---AID | 274 |
| SEQ_ID_NO_585 | EDHFWAIRGG | GGESFGIVAS | WQVKLLPVPP | KVTVFQVHKG | IKES---AID | 271 |
| SEQ_ID_NO_560 | EDLFWAIRGG | GGENFGIIAA | WKILVVPS | KATIFSVKKN | MEHG--LVK | 271 |
| SEQ_ID_NO_577 | EDLFWAIRGG | GGASFGVIVS | WKIKLVPVPS | TVTVFNVERF | LEEN---ATE | 265 |
| SEQ_ID_NO_569 | EDLFWAIRGG | GAASFGVVLS | YKIKLVPVPE | TVTVFRIERL | LTEN---ATD | 268 |
| SEQ_ID_NO_575 | EDLFWAIRGG | GGASFGVILS | YIVKLVPVPE | NVTVFQIDKT | LEEN---ATD | 272 |
| SEQ_ID_NO_576 | EDLFWAIRGG | GGASFGVILS | WKLQLVPVTP | QVLVFDVKRN | VSEG---ATD | 263 |
| SEQ_ID_NO_578 | EDLFWAITGG | GGVSFGVVLA | YKIKLVRVPE | VVTVFTIERR | EEQN---LST | 275 |
| SEQ_ID_NO_579 | EDLFWAITGG | GGVSFGVVVA | YKIKLVRVPT | TVTVFNVQRT | SEQN---LST | 274 |
| SEQ_ID_NO_558 | EDLFWALRGG | GAASFCVVLA | WKIKLVPVPA | KVTVFNIETF | GNTGSVNTTE | 274 |
| SEQ_ID_NO_571 | EDLFWAIRGG | GAASFGVILS | WKIKLVPVPE | IVTVFSVDRT | LEEG---VSD | 263 |

Figure 17 (continued)

| SEQ_ID_NO_559 | LLHKWQFM-A | EELEEDFTLG | VLGGADEK-- | -------- QVW | LTMLGFHFGL | 301 |
|---|---|---|---|---|---|---|
| SEQ_ID_NO_586 | MLHKWQVV-A | PALEDDFTLS | VLAGADTN-- | -------- G W | FSFLGLYLGP | 298 |
| SEQ_ID_NO_591 | LLHKWQLV-A | PKLEDDFSLA | VLAGTNKDS-- | -------- SIW | LTFLGLYLGP | 299 |
| SEQ_ID_NO_581 | LITKWQEM-A | PASPQELYLR | VLVL------ | -------- NDQ | ANFQALFLGR | 312 |
| SEQ_ID_NO_588 | LITKWQEI-A | PALPRDLLLR | VVVQ------ | -------- GRH | AQFEALFLGR | 307 |
| SEQ_ID_NO_589 | LLTKWQSL-A | PTFPEDLMR | VMAQ------ | -------- ADK | AVFEGLYLGT | 306 |
| SEQ_ID_NO_590 | LLTKWQSL-A | PTFPEDLMR | VMAQ------ | -------- ADK | AVFEGLYLGT | 311 |
| SEQ_ID_NO_564 | IINKWQVM-A | PQLPADLMR | IAQ------- | -------- GPK | ATFEAMYLGT | 305 |
| SEQ_ID_NO_583 | LINKWQQV-A | PSLPDDLMR | MAM------- | -------- EQD | AMFEALYLGT | 310 |
| SEQ_ID_NO_585 | LVTKWQTV-A | PALPDDLMR | MAM------- | -------- GQG | AMFEALYLGT | 307 |
| SEQ_ID_NO_560 | LFNKWQNI-A | YKYDKDLMLT | THFRTRNITD | NHGKNKTTVH | GYFSSIFLGG | 320 |
| SEQ_ID_NO_577 | IIEKWQLV-A | NKLDERFLR | MDLARANSS- | QHGKL--ALQ | ANFVAMFQGG | 311 |
| SEQ_ID_NO_569 | ITFKWQT-A | PTTDENLFMR | MLLQPVTRN- | --KKK--TAR | ISVIALYLGD | 312 |
| SEQ_ID_NO_575 | LVWQWQKV-A | PHTDDRLYLR | LVLQPYSSNF | VKGKK--TIR | ASVEALFLGE | 319 |
| SEQ_ID_NO_576 | FVYKWQL-A | PKLHKDLFIR | AQPNVVQIG- | QEGKK--VVQ | ISFIGQFLGK | 309 |
| SEQ_ID_NO_578 | IAERWVQM-A | DKLDRDLFLR | MTFSVINDT- | NGG-K--TVR | AIFPTLYLGN | 320 |
| SEQ_ID_NO_579 | IAHRWIQM-A | DKLDNDLFLR | MTFNVINNT- | NGE-K--TIR | GLFPTLYLGN | 319 |
| SEQ_ID_NO_558 | LVAKWQE-A | DKIONDLFIR | LTLGSSNK-- | -------- TVK | ASFMGMYLGN | 314 |
| SEQ_ID_NO_571 | LAWKWQQIAA | DKLDNDLFIR | LMLQPVNGT- | QEGKK--TIQ | ASFVAMFLGR | 310 |

| SEQ_ID_NO_559 | KTYAKSTFDL | LFPELGLVEF | DYLEMSWGES | FAYLAGLE-- | ------TVSQL | 344 |
|---|---|---|---|---|---|---|
| SEQ_ID_NO_586 | KELASSVDQ | NFPELNLVME | DCKEMSWVES | FAHLAGLN-- | ------SVEEM | 341 |
| SEQ_ID_NO_591 | KELASSSMHK | KFPELNLLLE | DCNEMSWVEA | TAELAGLK-- | ------SVSEL | 342 |
| SEQ_ID_NO_561 | CGGLHRLMQD | RFPELGMTEQ | DCEEVSWVQS | TAFFGFSTTS | V----PPEQL | 358 |
| SEQ_ID_NO_588 | CSRVLEHMRA | HFPELGVARA | DCEEISWIQS | TVYFAFYSSS | K----PPELL | 353 |
| SEQ_ID_NO_589 | CDALLPLVTS | RFPELGVNRS | HCNEMSWYQS | AFIHLGKNA T | ----VKDI | 351 |
| SEQ_ID_NO_590 | CDALLPLVTS | RFPELGVNRS | HCNEMSWYQS | AFIHLGKNA T | ----VKDI | 356 |
| SEQ_ID_NO_564 | CKTLTPLMSS | KFPELGMNPG | HCNEMSWIQS | PFVHLGHRD A | ----LEDDL | 351 |
| SEQ_ID_NO_583 | CKDLLPLMAS | RFPELGVKQE | DCNEMPIMQS | VAFIPMGKSA T | ------VMDL | 355 |
| SEQ_ID_NO_585 | CKDLVLLMTA | RFPELGMNAF | HCKEMTWIES | VPYLPMGPKG T | ------VRDL | 352 |
| SEQ_ID_NO_560 | VDSLYDLMNK | SFPELGIKKT | DCKELSWIDT | TIFYSGVVNY | NTANFKKEIL | 370 |
| SEQ_ID_NO_577 | VEELIPLMQK | NFPELGLKRK | DCTETSWIBS | ANFITNGALIG | SSGHEAPEVL | 361 |
| SEQ_ID_NO_569 | SDSLVSLLQK | DFPELSIGKS | NCNETTWIDS | VLWWANFNLG T | ----PPTAL | 358 |
| SEQ_ID_NO_575 | ADELVKLLGD | EFPLLGLKKE | LCHEMRWIDS | VVWWANYNDG S | ------SVNAL | 365 |
| SEQ_ID_NO_576 | IERLLTLMNK | EFPELGLNKS | DCFSMPMNS | TLFWYGEPIG T | ------PLEVL | 355 |
| SEQ_ID_NO_578 | SRNLVTLLNK | DFPELGLQES | DCTEMSWVES | VLYYTGFPSG T | ------PTTAL | 366 |
| SEQ_ID_NO_579 | STALVALLNK | DFPELGVEIS | DCIEMSWIES | VLFYTNFPIG T | ------PTTAL | 365 |
| SEQ_ID_NO_558 | SSNLLEIMNA | KFPELGLIKR | ECIEMKWIES | VLFWLGIPPG TA | ---PTTSM | 361 |
| SEQ_ID_NO_571 | AERLLSVMNE | SFPELGLQAK | DCAEMRWIES | VLSAVGMPKG T | ------PLEVL | 356 |

Figure 17 (continued)

| | | | | | | | |
|---|---|---|---|---|---|---|---|
| SEQ_ID_NO_559 | NNRFLKFDER | AFKTKVDLTK | EPLPGKAFYG | LL-ERLGK-- | EPNGFIALNG | | 391 |
| SEQ_ID_NO_586 | NNRFLKYDDR | AFKTKVDFVK | EPIPLEGIKG | AL-TMLTK-- | ELRGFMAFNG | | 388 |
| SEQ_ID_NO_591 | KDRFLRYDDR | AFKTKVDFPK | FAPLEGIDG | AL-ELKK-- | EQRGFMVMNG | | 389 |
| SEQ_ID_NO_581 | LNR-SSNPSY | YLKAKSDHVQ | EPIPRDVMES | LWTTWLEK-- | PEAALLMLDP | | 405 |
| SEQ_ID_NO_588 | LDR-IGETGR | YVKAKSDYYQ | EPIPRHAMES | TMSWLEK-- | PEAGLLILDP | | 399 |
| SEQ_ID_NO_589 | LNR-TSSIRA | FGKYKSDYVT | QPLSKATMDT | YKDMFSK-- | PGSGIMIMDP | | 398 |
| SEQ_ID_NO_590 | LNR-TSSIRA | FGKYKSDYVT | QPLSKATMDI | YKDMFSK-- | PGSGIMIMDP | | 403 |
| SEQ_ID_NO_584 | LNR-NNSFKP | FAEYKSDYVY | QPFPKTVMEQ | LNTVLVK-- | PGAGIMIFDP | | 398 |
| SEQ_ID_NO_583 | LNR-TSNIKA | FGKYKSDYVK | DPIPRDVMEK | YL-TWLAK-- | PGAGVMIMDP | | 401 |
| SEQ_ID_NO_585 | LNR-TSNIKA | FGKYKSDYVL | EPIPKSDMEK | FL-TWLVK-- | PGAGVMIMDP | | 398 |
| SEQ_ID_NO_560 | LDR-SAGKKT | AFSIKLDYVK | KEJPETAMVK | L-EKLYEEE | VGYGMYMLYP | | 418 |
| SEQ_ID_NO_577 | LNR-TQIRSG | KYKGKSDYVR | KPIPVDGLRG | LW-RWLNDDK | VQYSQLQFAP | | 409 |
| SEQ_ID_NO_569 | LDR-DLNDAG | FLKRKSDYYQ | TPIPKSGLES | LW-QKME-- | LGKVGMVFNA | | 404 |
| SEQ_ID_NO_575 | LDR-NHYSVH | SNKRKSDYYQ | TPISKQGFTW | W-KKME-- | LGKYSIVFNP | | 411 |
| SEQ_ID_NO_576 | LDEPKDPQPL | YQKNKSDYVK | KPIPREALES | W-KLME-- | GENFLMQMNP | | 402 |
| SEQ_ID_NO_578 | LSR-TPQRLN | PFKIKSDYYQ | NPISKRQFEF | F-ERMKE-- | LENQMLAFNP | | 412 |
| SEQ_ID_NO_579 | LSR-TPQRLN | PFKIKSDYYK | NTISKQGFES | F-ERMKE-- | LENQMLAFNP | | 411 |
| SEQ_ID_NO_558 | RNR-IPQKQI | YLKRKSDYVQ | KPISRTGLES | F-KIMTE-- | NENVTMAFNP | | 407 |
| SEQ_ID_NO_571 | LDR-IPKGVS | YLKRKSDYVK | EPISKEGLES | W-KVMTE-- | VGEYAMLMNP | | 402 |

| | | | | | | | |
|---|---|---|---|---|---|---|---|
| SEQ_ID_NO_559 | FGGQMSKISS | DFTPFPHRSG | TRLMVEYIVA | ANQSEQKKKT | EFLDWLEKVY | | 441 |
| SEQ_ID_NO_586 | QGGLMSRISS | DSTPFPHRKP | TLMMMEYIVA | ADRDEDAKSY | EFIGMLHGFY | | 438 |
| SEQ_ID_NO_591 | QGGMMDRIST | DASPFPHRSG | TLSMVEYIVA | DKHEDLHSN | EFIHWLHQLF | | 439 |
| SEQ_ID_NO_581 | YGGLMSSIPP | SETPFPHRGG | NLYQLQYYSF | WYENGTAAAE | KRMSWVRGLY | | 455 |
| SEQ_ID_NO_588 | YGGRMASISP | SATPFPHRKG | NLYNLQYYSF | WFENGTAAME | KRMNWVRGLY | | 449 |
| SEQ_ID_NO_589 | YGATISKPGE | ADTPFPHRKG | MLYNIQYITF | WFGEGAPAEA | -PIKMIRDFY | | 447 |
| SEQ_ID_NO_590 | YGATISKPGE | ADTPFPHRKG | MLYNIQYITF | WFGEGAPAEA | -PIKMIRDFY | | 452 |
| SEQ_ID_NO_584 | YGATISATPE | SATPFPHRKG | VLFNIQYVNY | WFAPGAAAA- | -PLSWSKDIY | | 446 |
| SEQ_ID_NO_583 | YGARISSIPQ | DATPFPHRQG | VLFNIQYVSY | WFGEGDGAA- | -PTQWSRDMY | | 449 |
| SEQ_ID_NO_585 | YGGIASVPE | SATPFPRRSG | VLFNIQYVVY | WFGEGAAAL- | -PTQWTRDIY | | 446 |
| SEQ_ID_NO_560 | YGGLMDEISE | SAIPFPHRAG | IMYELMYTAT | MEKQEDNEK- | -HINWVRSVY | | 466 |
| SEQ_ID_NO_577 | YGGKMDNISF | SFIPFAHRSG | YIFHIHYVVY | MQEEGDEATQ | RHVNMIRRLY | | 459 |
| SEQ_ID_NO_569 | YGGRMDQIKP | DETPFPHRAG | NLYKIQYSVN | MDQPGSEADK | NFTTQAKLLH | | 454 |
| SEQ_ID_NO_575 | YGGKMNEVPS | DATPFPHRAG | NLYKIQYTVS | MQEPGAAVEK | SFLSDIRVLH | | 461 |
| SEQ_ID_NO_576 | YGGRMEEILP | SETPFSHRAG | NLFLIQYLNI | ASNESSEVSE | RHVNFSRSFF | | 452 |
| SEQ_ID_NO_578 | YGGRMSEISE | FAKPFPHRSG | NIAKIQYEVN | MEDLSDEAEN | RYLNFTRLMY | | 462 |
| SEQ_ID_NO_579 | YGGRMSEISE | FAKPFPHRSG | NIAKIQYEVN | MDELGNEAAN | RYLNFTRVMY | | 461 |
| SEQ_ID_NO_558 | YGGRMSEIPS | TETAFPHRAG | NMFKIQYAAN | WFVPGEAVAK | DCLSQTERLF | | 457 |
| SEQ_ID_NO_571 | YGGKMSEISE | TETAFPHRAG | NIFKIQYSVN | MQEGIDTIN | HYVNLTRTLF | | 452 |

Figure 17 (continued)

| | | | | | |
|---|---|---|---|---|---|
| SEQ_ID_NO_559 | EFMKPFVSKN | PRLGYVNHID | LDLGGIDW-- | -GNKTVVNN- | AIEISRS-WG | 486 |
| SEQ_ID_NO_586 | NYMGQFLPSD | PRIAYVNHVD | LDLGRLDW-- | -TNSTIASN- | AIEIART-WG | 483 |
| SEQ_ID_NO_591 | DYMGKFVSNN | PRVGYVNHVD | LDLGRIDW-- | -VNKTISSGR | AIEIART-WG | 485 |
| SEQ_ID_NO_581 | KEMEPYVSKN | PRAVYVNYRD | LDLGTNELD- | -GDYT---- | SYEKARVS-WG | 498 |
| SEQ_ID_NO_588 | REMEPYVSKN | PRTGYVNYRD | LDLGTNELE- | -GNVT---- | SYAKARI-WG | 491 |
| SEQ_ID_NO_589 | AFMEPYVTKN | PRQAYVNYRD | LDLGVNAVEA | GANVS---- | CYQVGKV-WG | 491 |
| SEQ_ID_NO_590 | AFMEPYVTKN | PRQAYVNYRD | LDLGVNAVEA | GANVS---- | CYQVGKV-WG | 496 |
| SEQ_ID_NO_584 | NYMEPYVSKN | PRQAYANYRD | IDLGRNEVV- | -NDVR---- | TYASGKV-WG | 488 |
| SEQ_ID_NO_583 | AFMEPYVSKN | PRQAYANYRD | LDLGVNEVV- | -GDVS---- | TYDSGRV-WG | 491 |
| SEQ_ID_NO_585 | DFMTPYVSKN | PRQAYVNYRD | LDLGVNQVV- | -GNVS---- | TYASGKV-WG | 488 |
| SEQ_ID_NO_560 | NFTTPYVSQN | PRLAYLNYRD | LDLGKTNP-- | -ESPN---- | NYTQARI-WG | 507 |
| SEQ_ID_NO_577 | KYMEPYVSNS | PRAAYVNYRD | LDIGVNN--- | -NGYT---- | SYHQAS-WG | 499 |
| SEQ_ID_NO_569 | DFMTPFVSKN | PRSAYFNYRD | DVG-S---- | -TKKW---- | SYEEGKV-YG | 492 |
| SEQ_ID_NO_575 | NYMTPFVSKN | PRSAYFNYRD | LDIGNS--- | -HGKD---- | NFEDGKV-YG | 501 |
| SEQ_ID_NO_576 | EFMTPYVSTS | PREAFLNYRD | ADIGANHP-- | -SNVT---- | RFDIAKT-YG | 493 |
| SEQ_ID_NO_578 | DYMTPFVSKN | PREAFLNYRD | LDIGINS--- | -HGRN---- | AYTEGMV-YG | 502 |
| SEQ_ID_NO_579 | DYMTPFVSKN | PREAFLNYRD | LDIGVNS--- | -HGKN---- | AYGEGMV-YG | 501 |
| SEQ_ID_NO_558 | ERMSPYVSKN | PREAFLNYRD | VDIGK---- | -SLNS---- | TYEEGKV-YG | 495 |
| SEQ_ID_NO_571 | EAMTPYVSKN | PREAFLNYRD | IDIGSIGS-- | -HGNG---- | TFQERSM-YG | 493 |

| | | | | | |
|---|---|---|---|---|---|
| SEQ_ID_NO_559 | ESYFLS-NYE | RLIRAKTLID | PNNVFNHPQS | PPMANFDYL | EKTLGSDGGE | 535 |
| SEQ_ID_NO_586 | EKYFLS-NYE | RLVRAKTLID | PKNVFHHPQS | PPMPQDDLR | PNGIWRTEEM | 532 |
| SEQ_ID_NO_591 | EKYFMS-NYD | RLVRAKTMID | PKNVFNHPQS | PPLLEIMLD | NVKENDVIYK | 534 |
| SEQ_ID_NO_581 | DKYFKG-NFK | RLAAVKTMVD | PHDFFRNEQS | PPLPTAKMM | IDSI------ | 541 |
| SEQ_ID_NO_588 | EKYFRG-NFE | RLAAVKAMVD | PDDFFRNEQS | PPLPAAKGW | SSI------- | 533 |
| SEQ_ID_NO_589 | EKYFKG-NFE | RLARTKAKVD | PTDFFRNEQS | PPLLA---- | ---------- | 526 |
| SEQ_ID_NO_590 | EKYFKG-NFE | RLARTKAKVD | PTDFFRNEQS | PPLLA---- | ---------- | 531 |
| SEQ_ID_NO_584 | QKYFKG-NFE | RLAITKGKVD | PTDYFRNEQS | PPLIKKY-- | ---------- | 525 |
| SEQ_ID_NO_583 | EKYYNG-NFE | RLARTKAKVD | PCDYFRNEQS | PPLLK---- | ---------- | 526 |
| SEQ_ID_NO_585 | EKYFKG-NFE | RLARTKGKID | PEDYFRNEQS | PPLL----- | ---------- | 522 |
| SEQ_ID_NO_560 | EKYFGK-NFN | RLVKVKTKAD | PNNFFRNEQS | PPLPPHHH- | ---------- | 545 |
| SEQ_ID_NO_577 | LKYFSN-NFK | RLATVKTKVD | PHNFFRNEQS | PTLSKE--- | ---------- | 535 |
| SEQ_ID_NO_569 | ESYFNG-NYE | RLVDVKTAVD | ANNFFRNEQS | PPRSSKI-- | ---------- | 529 |
| SEQ_ID_NO_575 | IKYFNK-NFE | RLVKVKSAID | PENFFANEQS | PTYPRSNA- | ---------- | 539 |
| SEQ_ID_NO_576 | SKFFKG-NFE | RLVSVKTKVD | PQNFFRYEQS | PTRSL---- | ---------- | 528 |
| SEQ_ID_NO_578 | HKYFKETNYK | RLVSVKTKVD | PDNFFRNEQS | PTLSS---- | ---------- | 538 |
| SEQ_ID_NO_579 | HKYFKETNYK | RLTMVKTRVD | PSNFFRNEQS | PTLSSWK-- | ---------- | 540 |
| SEQ_ID_NO_558 | FKYFKD-NFE | KLVKIKSRVD | PDNFFRYEQS | PVLSSH--- | ---------- | 531 |
| SEQ_ID_NO_571 | HKYFKD-NFD | RLVQIKTRVD | PDNFFGYEQS | PTQSSSYRP | DLCAWQQPRK | 542 |

Figure 17 (continued)

| SEQ_ID_NO_559 | VVI- - - - - - - - - - - - - - - - - - - - - - - - - - - - - - - - - - - - - - - - - - - - - - - - - - | 536 |
|---|---|---|
| SEQ_ID_NO_586 | FFLE- - - - - - - - - - - - - - - - - - - - - - - - - - - - - - - - - - - - - - - - - - - - - - - - | 536 |
| SEQ_ID_NO_591 | L- - - - - - - - - - - - - - - - - - - - - - - - - - - - - - - - - - - - - - - - - - - - - - - - - - | 535 |
| SEQ_ID_NO_581 | | 541 |
| SEQ_ID_NO_588 | | 533 |
| SEQ_ID_NO_589 | | 526 |
| SEQ_ID_NO_590 | | 531 |
| SEQ_ID_NO_584 | | 525 |
| SEQ_ID_NO_583 | | 526 |
| SEQ_ID_NO_585 | | 522 |
| SEQ_ID_NO_560 | | 545 |
| SEQ_ID_NO_577 | | 535 |
| SEQ_ID_NO_569 | | 529 |
| SEQ_ID_NO_575 | | 539 |
| SEQ_ID_NO_576 | | 528 |
| SEQ_ID_NO_578 | | 538 |
| SEQ_ID_NO_579 | | 540 |
| SEQ_ID_NO_558 | | 531 |
| SEQ_ID_NO_571 | RTLGARTSER AWQQHQAADT WRRAVMPYGL GKLARLAKHP KRRFTGPPAW | 592 |

| SEQ_ID_NO_559 | | 536 |
|---|---|---|
| SEQ_ID_NO_586 | | 536 |
| SEQ_ID_NO_591 | | 535 |
| SEQ_ID_NO_581 | | 541 |
| SEQ_ID_NO_588 | | 533 |
| SEQ_ID_NO_589 | | 526 |
| SEQ_ID_NO_590 | | 531 |
| SEQ_ID_NO_584 | | 525 |
| SEQ_ID_NO_583 | | 526 |
| SEQ_ID_NO_585 | | 522 |
| SEQ_ID_NO_560 | | 545 |
| SEQ_ID_NO_577 | | 535 |
| SEQ_ID_NO_569 | | 529 |
| SEQ_ID_NO_575 | | 539 |
| SEQ_ID_NO_576 | | 528 |
| SEQ_ID_NO_578 | | 538 |
| SEQ_ID_NO_579 | | 540 |
| SEQ_ID_NO_558 | | 531 |
| SEQ_ID_NO_571 | VCRHVLWQT PTSGSAATRA WGMCPALLTL QTWALGADSH ARVNCDPHLS | 642 |

Figure 17 (continued)

| SEQ_ID_NO_559 | | 538 |
|---|---|---|
| SEQ_ID_NO_586 | | 536 |
| SEQ_ID_NO_591 | | 535 |
| SEQ_ID_NO_581 | | 541 |
| SEQ_ID_NO_588 | | 533 |
| SEQ_ID_NO_589 | | 526 |
| SEQ_ID_NO_590 | | 531 |
| SEQ_ID_NO_584 | | 525 |
| SEQ_ID_NO_583 | | 526 |
| SEQ_ID_NO_585 | | 522 |
| SEQ_ID_NO_560 | | 545 |
| SEQ_ID_NO_577 | | 535 |
| SEQ_ID_NO_569 | | 529 |
| SEQ_ID_NO_575 | | 539 |
| SEQ_ID_NO_576 | | 528 |
| SEQ_ID_NO_578 | | 538 |
| SEQ_ID_NO_579 | | 540 |
| SEQ_ID_NO_558 | | 531 |
| SEQ_ID_NO_571 | RTQEEYI KLG PAQQDPFKLG SALEGPKI AR LDPLALALVA LMGPVLSKTH | 692 |

| SEQ_ID_NO_559 | | 538 |
|---|---|---|
| SEQ_ID_NO_586 | | 536 |
| SEQ_ID_NO_591 | | 535 |
| SEQ_ID_NO_581 | | 541 |
| SEQ_ID_NO_588 | | 533 |
| SEQ_ID_NO_589 | | 526 |
| SEQ_ID_NO_590 | | 531 |
| SEQ_ID_NO_584 | | 525 |
| SEQ_ID_NO_583 | | 526 |
| SEQ_ID_NO_585 | | 522 |
| SEQ_ID_NO_560 | | 545 |
| SEQ_ID_NO_577 | | 535 |
| SEQ_ID_NO_569 | | 529 |
| SEQ_ID_NO_575 | | 539 |
| SEQ_ID_NO_576 | | 528 |
| SEQ_ID_NO_578 | | 538 |
| SEQ_ID_NO_579 | | 540 |
| SEQ_ID_NO_558 | | 531 |
| SEQ_ID_NO_571 | QRSLKKKI SL M | 703 |

Figure 18

| | | | | | | | |
|---|---|---|---|---|---|---|---|
| SEQ_ID_NO_603 | MAAAT-SSS | AVAVSTPQGV | AERRGI PAAS | FVEDVETYLR | QAGLEVNSAL | | 48 |
| SEQ_ID_NO_605 | MAAAA---- | --SASTPQGV | AERRGI PAAA | FVEDVEAYLR | QAGLDVNSAL | | 43 |
| SEQ_ID_NO_610 | MAAAAASSSS | SSAAATPQGV | TERRGI PAAS | FVEDVETYLR | QAGLDVNSSL | | 50 |
| SEQ_ID_NO_593 | MSSSS----- | --PSGSGSDL | TERRGI PAAK | FIQDVETYLS | QSGLDPNSAL | | 43 |
| SEQ_ID_NO_595 | MASSS----S | TAVATATETT | TERRGI PGAQ | FVEDVETYLN | QSGLDVNSAL | | 46 |
| SEQ_ID_NO_599 | MASSS----- | ------SESAM | SERRGI PGAQ | FVEDVQTYLT | QSGLDVSSAL | | 40 |

| | | | | | | | |
|---|---|---|---|---|---|---|---|
| SEQ_ID_NO_603 | AFLQERLQQY | KMVEMKLLAQ | QRELQAKI PD | EKCLDI VAT | LKAKKALGEA | | 98 |
| SEQ_ID_NO_605 | AFLQERLQQY | KIVEMKLLAQ | QRDLQAKI PD | EKCLDI VST | LQAKKDLGEA | | 93 |
| SEQ_ID_NO_610 | AFLQERLQQY | KIVEMKLLAQ | QRDLQAKI PD | EKCLDI VAT | LQAKKALGEA | | 100 |
| SEQ_ID_NO_593 | AFHQERLQQY | KVVEMKLLAQ | QRDLQAKI PD | IEKCLEVVAT | LEAKKGTGEA | | 93 |
| SEQ_ID_NO_595 | SFLQERLQQY | KLVEMKLLAQ | QRDLQAKI PD | EKCLDVVAT | LQAKKGTGEP | | 96 |
| SEQ_ID_NO_599 | AFLQERLQQY | KVVEMKLLAQ | QRDLQAKI PD | EKCLDVVAT | LKAKKGTGEE | | 90 |

| | | | | | | | |
|---|---|---|---|---|---|---|---|
| SEQ_ID_NO_603 | LIADFELSEG | IYSRAKI EDS | DSVCLVLGAN | VMLEYSCDEA | NELLKSNLEN | | 148 |
| SEQ_ID_NO_605 | LIADFELSEG | IYSCAKI EDT | DSVCLVLGAN | VMLEYSCDEA | NALLKKNLEN | | 143 |
| SEQ_ID_NO_610 | LTADFELSEG | IYSRAKI EDT | DSVCLVLGAN | VMLEYSCDEA | NALLKKNLEN | | 150 |
| SEQ_ID_NO_593 | LLADFEVSEG | IYSRACI EDT | DSVCLVLGAN | VMLEYSCEEA | SALLKNNLEN | | 143 |
| SEQ_ID_NO_595 | LIADFEVSEG | IYSQARI EDA | ESVCLVLGAN | VMLEYSCEEA | NDLLQKNLDN | | 146 |
| SEQ_ID_NO_599 | LIADFEVSEG | IYSRARI EET | NSVCLVLGAN | VMLEYSLEEA | TGLLQKNLDN | | 140 |

| | | | | | | | |
|---|---|---|---|---|---|---|---|
| SEQ_ID_NO_603 | ARASLEVLVS | DLHFLRDQQT | TQVTI ARI F | NWDVHQ-RRS | KQ-----SVM | | 192 |
| SEQ_ID_NO_605 | AKASLEVLVA | DLQFLRDQQT | TQVTI ARVF | NWDVHH-RRS | KQ------AV | | 186 |
| SEQ_ID_NO_610 | AKASLEVLVA | DLQFLRDQQT | TQVTI ARVF | NWDVHQ-RRS | KQ------AI | | 193 |
| SEQ_ID_NO_593 | AKASLEVLVA | DLQFLRDQVT | VTQVTI ARVY | NWDVHQ-RRV | KQVTPTALAV | | 192 |
| SEQ_ID_NO_595 | AKASLEVLVA | DLKFLRDQVT | TQVTI ARVY | NWDVHQKRRM | RE---AVTAE | | 193 |
| SEQ_ID_NO_599 | ARASLEVLIA | DLQFLRDQVT | TQVTI ARVY | NWDVHQ-RRV | QQ---AVATT | | 186 |

| | | |
|---|---|---|
| SEQ_ID_NO_603 | KET | 195 |
| SEQ_ID_NO_605 | KEP | 189 |
| SEQ_ID_NO_610 | KET | 196 |
| SEQ_ID_NO_593 | ADS | 195 |
| SEQ_ID_NO_595 | KDS | 196 |
| SEQ_ID_NO_599 | AQD | 189 |

Figure 19

```
SEQ_ID_NO_622    ----MAFSNA  LRSAAKLVAS  SESSLSNSVS  RGFHSTGMKR  M-GGGHGHDE  45
SEQ_ID_NO_613    ----MALSTS  RSVSKIISS   SEASVSRSVT  RSFHSTGVKK  MSGGGHGSYD  46
SEQ_ID_NO_620    ----MALNTG  IRSISKIIAF  SEASVSRSVS  RSFHSTGAKK  M-SGGHGHDE  45
SEQ_ID_NO_626    ----MALNTG  RSVSRLIAS   SESSVSRSVS  RSFHSTGAKK  M-SGGHGHDE  45
SEQ_ID_NO_643    ----MAAAAA  --------AA  GEEE--GEAS  RGFHATGVKR  M--GGHGHDE  34
SEQ_ID_NO_644    MATATALNRG  LRSGIRLLAT  GAEAISKTDS  RGFHATGVKR  M--GGHGHDE  47
SEQ_ID_NO_624    --MATALNRG  LRSGIRLLAT  GAEAISKPAS  RGFHATGVKR  M--SGHGHDE  45
SEQ_ID_NO_638    --MATALNRG  LRSGIRLLAA  GAEAISKPAS  RGFHATGVKR  M--GGHGHDE  45
SEQ_ID_NO_634    ----MALSRG  IRSGLKLLSH  SEAALPRSVT  HEFHATSMKR  M--GGHGHDE  44
SEQ_ID_NO_615    ----MAMIRG  GSGIKLLTS   SEAALFRSVT  REFHATGMKR  M--GGHGHDE  44

SEQ_ID_NO_622    PYYLHAKHMY  NLDRMKHQGL  KMSLAVFTAF  SIGVAVPVYA  VIFQQKKTAS  95
SEQ_ID_NO_613    EYYLHAKHMY  NLDRMKYQAL  KMSLGVFTAF  SIGVGVPIFA  VVFQQRKTQS  96
SEQ_ID_NO_620    PYYLHAKHMY  NLDRMKYQGL  KMSLGVFTAF  SIGVGVPIFA  VVFQQRKTAS  95
SEQ_ID_NO_626    PYYLHAKHMY  NLDRMKFDGL  KMSLAVFTAF  SIGVGVPIFA  VVFQQRKTAS  95
SEQ_ID_NO_643    PYYLHAKHMY  NLHRMKHQKP  KVYLSVLGAV  GIGIAVPVYA  VVFQQKKTAS  84
SEQ_ID_NO_644    PYYLHAKHMY  NLHRMKHQKP  KVYLSVLGAV  GIOIAVPVYA  VVFQQKKTAS  97
SEQ_ID_NO_624    PYYLHAKHMY  NLHRMKHQKL  TAWTSVLGAV  SIGIGVPVFA  VVFQQKKTSS  95
SEQ_ID_NO_638    PYYLHAKHMY  NLHRMKHQGL  KVTLSVLGAV  SIGVGVPVYA  VIFQQKKTAS  95
SEQ_ID_NO_634    PFYIHAKHMY  NLDRMKHQKL  KVTLGVLSAF  SIGVMVPIYA  VIFQQKKAAS  94
SEQ_ID_NO_615    PYYLHAKHMY  NLDQMKHQKL  KVALSVWSAF  GIGMAVPVYA  VMFQQKKAAS  94

SEQ_ID_NO_622    S  96
SEQ_ID_NO_613    G  97
SEQ_ID_NO_620    G  96
SEQ_ID_NO_626    G  96
SEQ_ID_NO_643    G  85
SEQ_ID_NO_644    G  98
SEQ_ID_NO_624    G  96
SEQ_ID_NO_638    G  96
SEQ_ID_NO_634    G  95
SEQ_ID_NO_615    A  95
```

Figure 20

| | | | | | | | |
|---|---|---|---|---|---|---|---|
| SEQ_ID_NO_685 | MGFISFVGRV | LFASLFLLSA | YQEFLEFGND | GGPAAKTLKP | KFNLFVKLVS | | 50 |
| SEQ_ID_NO_679 | MGFVSFAGRV | LFASVFLLSA | YQEFSEFGAD | GGPAAKALRP | KYNVFTKNIS | | 50 |
| SEQ_ID_NO_681 | MGFVSFAGRV | LFASVFLLSA | YQEFSEFGAD | GGPAAKALRP | KYNVFTKNIS | | 50 |
| SEQ_ID_NO_668 | MGFVSFVGRV | LFVAAFLLSA | YQEFNEFGAD | GGPAAKALRP | KFNVFVKNVS | | 50 |
| SEQ_ID_NO_676 | MGFVSFVGRV | LFVAAFLLSA | YQEFNEFGTD | GGPAAKALQP | KFNVFVKNIS | | 50 |
| SEQ_ID_NO_646 | MELASFLGRA | LFVSVFLLSA | WQEFNDFGED | GGRSAKSLKP | KFNAFVNHVT | | 50 |
| SEQ_ID_NO_648 | MALVSFYGRV | LFASVFILSA | WQEFNEFGVD | GGPAAKALKP | KFNVFSKTVT | | 50 |
| SEQ_ID_NO_656 | MAFTSFLGRV | LFASVFILSA | YQEFNEFGVD | GGPAAKALKP | KFGVFTSHVQ | | 50 |
| SEQ_ID_NO_660 | MAFASFLGRV | LFASVFILSA | YQEFNEFGVD | GGPAAKALRP | KFDAFTHRVH | | 50 |

| | | | | | | | |
|---|---|---|---|---|---|---|---|
| SEQ_ID_NO_685 | KNTGLGVPHI | DIKTVIAATM | FLKGFGGLLF | FSSSFGAFL | LLIYLAFMTP | | 100 |
| SEQ_ID_NO_679 | AHLGVAVPHV | ELKHIVAATI | GLKGLGGLLF | LSSSFGAYL | LLIYLAFITP | | 100 |
| SEQ_ID_NO_681 | AHLGVAVPHV | ELKHIVAATI | GLKGLGGLLF | LSSSFGAYL | LLIYLAFITP | | 100 |
| SEQ_ID_NO_668 | AHLGVAVPHI | ELKHVIAATI | GLKGLGSLLF | LSSSLGAYL | LLLYLALITP | | 100 |
| SEQ_ID_NO_676 | SHLGVAVPHI | ELKHVIAATI | ALKGLGGLLF | LSCSLGAYL | LLLYLAIVTP | | 100 |
| SEQ_ID_NO_646 | THTSQQLPPV | DMKILVAAAI | ALKGIGGLLF | VFGSSLGAYL | LLHQAVATP | | 100 |
| SEQ_ID_NO_648 | AHTGVEVPEF | DIKVLVAAAV | AFKGVGGILF | FGSTIGAYL | LAQQVVTT | | 100 |
| SEQ_ID_NO_656 | SHAGIQVPEI | EIKHLVSAAI | FLKGIGGILF | IGSSLGAYL | LIHDLATP | | 100 |
| SEQ_ID_NO_660 | SDVGFQLPEI | DLKFLIAGA | ALKGLGGVLF | FGSSFGAFL | LLHDLATP | | 100 |

| | | | | | | | |
|---|---|---|---|---|---|---|---|
| SEQ_ID_NO_685 | IVYDFYNYEM | ESEQFVQLFF | KFTQNLAFIG | ALLFFLGMKN | SIPRRRSK | | 148 |
| SEQ_ID_NO_679 | VVYDFYNYNM | EKSEFVQLFM | KFTQNLALFG | ALLFFLGMKN | SIPKROAK | | 148 |
| SEQ_ID_NO_681 | VVYDFYNYDM | EKSEFVQLFM | KFTQNLALFG | ALLFFLGMKN | SIPKROAK | | 148 |
| SEQ_ID_NO_668 | IIHDFYNYDM | EKAEFAGLFA | KFTQDLALIG | ALLFFLGMKN | SIPKROGK | | 149 |
| SEQ_ID_NO_676 | IVHDFYNYDM | EKAEFAQIFG | KFTQDLALIG | ALLFFLGMKN | SIPKROSK | | 148 |
| SEQ_ID_NO_646 | ILYDFYNYDV | DRKEFGQLFS | KFTQSLALLG | GLLFFIGMKN | SRKHGROLR | | 149 |
| SEQ_ID_NO_648 | ILYDFYNYDT | EKKEFGLLFS | KFSQNLALLG | ALLFFIGMKN | SIPSROLK | | 148 |
| SEQ_ID_NO_656 | ILYDFYNYDS | EEKEFNQLFI | KFTQNMALYG | ALLFFIGMKN | SFPRROHK | | 148 |
| SEQ_ID_NO_660 | IHYDFYNYDS | EDKEFTQLFI | KFTQNMALFG | ALLFFIGMKN | SIPRR-VP | | 147 |

| | | |
|---|---|---|
| SEQ_ID_NO_685 | GRTTKTKTN | 157 |
| SEQ_ID_NO_679 | KKAPKSKTN | 157 |
| SEQ_ID_NO_681 | KKAPKSKTN | 157 |
| SEQ_ID_NO_668 | KKAPKAKTN | 158 |
| SEQ_ID_NO_676 | KKAPKAKTN | 157 |
| SEQ_ID_NO_646 | KKAPKAKAN | 158 |
| SEQ_ID_NO_648 | KKAPKTKTV | 157 |
| SEQ_ID_NO_656 | KKVPKTKTG | 157 |
| SEQ_ID_NO_660 | KKAPKTKTY | 156 |

| | | | | |
|---|---|---|---|---|
| SEQ_ID_NO_708 | KSRSREAYEV | VRGAI TVDEF | 170 |
| SEQ_ID_NO_728 | KTRSREAYQV | LRDGVLVDKF | 170 |
| SEQ_ID_NO_718 | KTRSRDAYQV | LRAGI TVDKF | 170 |
| SEQ_ID_NO_687 | KSRSRDAYEV | QRNGLRVDKF | 170 |
| SEQ_ID_NO_699 | KSRNRDAYEV | LRDGVRADKF | 170 |
| SEQ_ID_NO_689 | ---------- | ---------- | 107 |
| SEQ_ID_NO_691 | KTRDRGAYEV | LRDGVGI DKF | 170 |
| SEQ_ID_NO_703 | KTRSREAYEV | TRXGVCI DKF | 170 |
| SEQ_ID_NO_706 | KTRSREAYDV | TRDGVPVDKF | 170 |
| SEQ_ID_NO_721 | KARNRDAYEV | VRDGVGI DKF | 170 |
| SEQ_ID_NO_712 | KTRSRDAYEV | VRDGI I DKF | 170 |
| SEQ_ID_NO_724 | KTRSRDAYEV | VRDGI PI DKF | 170 |

Figure 22

| | | |
|---|---|---|
| SEQ_ID_NO_737 | ··MDEL GGGG G····KKGKA WPWWL GASAA QITGALVWFR RGKGGSDMTM | 44 |
| SEQ_ID_NO_738 | ···MEEGGGG E·····EAER WPWWAGASAA QVAAGVAWFR RGRGGAAFAM | 42 |
| SEQ_ID_NO_742 | ··MDDRGGGG G····GEAER WPWWAAASAA QAAAGVAWFR RGRGGTAVAM | 44 |
| SEQ_ID_NO_735 | MKMEEAAGSG N····SDGGN KWWWGVASAA QMGLGI RTFA KGHGGDSRLM | 46 |
| SEQ_ID_NO_730 | MEEQNAGTGA GESSLLDGSG HWWWALGSGA QIMWGI RLIR RGYAGDVRLM | 50 |
| SEQ_ID_NO_732 | ···MENGCGG G····IETQW WWWWAMASMA KFGWGI SAYK RGFAGDSRLM | 43 |

| | | |
|---|---|---|
| SEQ_ID_NO_737 | PFRAFAVASL FVGAGATTVT AGVSAAGVGS VEEMKGLGAR RKWSRVPPR | 94 |
| SEQ_ID_NO_738 | PFKAFAIATL FVGAGATAVT AGVLAAGVGS VDEMKGVGAS RRWMGAPPR | 92 |
| SEQ_ID_NO_742 | PFKAFAIASL FVGAGATAVS AGVLAAGVGS VEEMKGVGAS RRWMGAPPR | 94 |
| SEQ_ID_NO_735 | PFKAFVVASL FVSSAASASV LLLQANGI HR VEDLMKAGAN RAKL GLRPR | 96 |
| SEQ_ID_NO_730 | PLKAFGVASL FVGSLATSSV ALVRAIGI HT VQDAI DLGAN RTNL GVTPQ | 100 |
| SEQ_ID_NO_732 | PLKAFAVASL FVGSAASASI ASLQASGI HK VQDLI ELGAN RTGLGVPPR | 93 |

| | | |
|---|---|---|
| SEQ_ID_NO_737 | RVEGGE····· | 100 |
| SEQ_ID_NO_738 | RRVEGGGDP·· | 101 |
| SEQ_ID_NO_742 | RAGGSD····· | 100 |
| SEQ_ID_NO_735 | TQNKNMDDS·· | 105 |
| SEQ_ID_NO_730 | IPDKQITERD G | 111 |
| SEQ_ID_NO_732 | VAKE······ | 97 |

Figure 23

| | | | | | | |
|---|---|---|---|---|---|---|
| SEQ_ID_NO_765 | MSPMSNPSFD | HSY---E--L | PLRRNLLLL | DLLGRLRFIA | EVLLDRLGVA | 45 |
| SEQ_ID_NO_763 | MMLSSAYSTP | AADELGGPPP | LPPPPGADVS | VIVGALTGVL | LGLFLFL-- | 47 |
| SEQ_ID_NO_758 | ------MGFP | VGY--PE--V | SVPNFLYTL | SLLSFLRSLT | ISFLBLLHLS | 40 |
| SEQ_ID_NO_761 | ------MGFP | VGY--SE--L | LLPRLLLQVL | LLLGHLHRFL | LAAFHAVGLG | 40 |
| SEQ_ID_NO_762 | ------MGFP | VGY--SE--L | LLPRLLLQVL | LLLGHLHRFL | LAAFHAVGLG | 40 |
| SEQ_ID_NO_755 | ------MGFY | AEDPLSG--L | TIGQAI YEVA | LMIAVLRWVL | CLFRVL-- | 39 |
| SEQ_ID_NO_748 | ------MGFF | VEE--SG--L | VTHLLYKAA | LVLAVLRWAL | AAALRFK-- | 37 |
| SEQ_ID_NO_746 | ------MTFF | IED--TS--L | IBHVLYKTA | LIITVLRWIF | AMLRYR-- | 37 |
| SEQ_ID_NO_751 | ------MTFF | IED--TS--L | IBHVLYKTA | LIITVLRWIF | AMLRYR-- | 37 |
| SEQ_ID_NO_753 | ------MSFF | IQD--SG--L | VTQLLYQMA | VFLTLLRWIF | SMLRYR-- | 37 |
| SEQ_ID_NO_760 | ------MSFF | LED--SG--L | VTQLLYQMA | VLITLLRWIF | TMLRYR-- | 37 |

| | | | | | | |
|---|---|---|---|---|---|---|
| SEQ_ID_NO_765 | SW------QG | CVHLPGQLWG | WGGEHASDAT | LEHFLEARLW | ETGTRSPLTT | 89 |
| SEQ_ID_NO_763 | ---------- | --IYAKHCRQ | RGRGGARGAA | GGLGLGFRAS | STCDRCRSGV | 85 |
| SEQ_ID_NO_758 | DL-------- | ---------- | ---------L | DTDFSTTLP | QSHIHRPTLS | 63 |
| SEQ_ID_NO_761 | DLIDNPPGLA | ATEQDMMLQG | RGGGMAEGWA | SSSALQHRRP | EFRAIPPM- | 88 |
| SEQ_ID_NO_762 | DLIDNPPGLA | ATEQDLMLQG | RGGGMAEGWA | SSSALQHRRP | EFRAIPPM- | 88 |
| SEQ_ID_NO_755 | ---------- | ---------- | ---------N | NDRRTQSDE | TPTPEPCSQM | 59 |
| SEQ_ID_NO_748 | ---------- | ---------- | ---------N | RTHLASPSND | SLRRSHPVPS | 58 |
| SEQ_ID_NO_746 | ---------- | ---------- | ---------- | SRSSSSSSS | SQSSSSPSIS | 57 |
| SEQ_ID_NO_751 | ---------- | ---------- | ---------- | --SRSSSSSS | SQSSSSPSIS | 55 |
| SEQ_ID_NO_753 | ---------- | ---------- | ---------- | -------SKS | RTSSAPPVLS | 49 |
| SEQ_ID_NO_760 | ---------- | ---------- | ---------- | ----SRSTSS | SSSTPPLLS | 52 |

| | | | | | | |
|---|---|---|---|---|---|---|
| SEQ_ID_NO_765 | TRYRRRRVAL | AQPADGKLAA | EGDAEGAA-- | AVCAICVAGL | ESGDLEIVVE | 137 |
| SEQ_ID_NO_763 | SLSVVDALPV | VRFGD---MG | GAAAAQP-- | -ECAVCLGTF | DPAADELLRV | 129 |
| SEQ_ID_NO_758 | ALLRQFLPI | ITFND---LA | EGDSBPPY-- | -GCAVCLNEF | --AGEEEIRC | 105 |
| SEQ_ID_NO_761 | --AIEEALPV | VRFDE---LV | ASAPAAVCGG | GDCAVCLSGI | --CGRDEVRR | 131 |
| SEQ_ID_NO_762 | --AIEEALPV | VRFDE---LV | ASAPAAVCGG | GDCAVCLSGI | --CGRDEVRR | 131 |
| SEQ_ID_NO_755 | TRQKDSILLL | TITFGE---K | ERLPETE--- | ETCAVCLSQL | --SVEDEVRE | 101 |
| SEQ_ID_NO_748 | SQQIRDGLIL | TITFGD---VT | ERMPLGVC-- | DTCAVCLSQL | --RDQDEVRE | 100 |
| SEQ_ID_NO_746 | SQTIKESLAV | FAFRD---AV | ERSPAAIN-- | DMCAVCLGDL | --EDEDEIRE | 100 |
| SEQ_ID_NO_751 | SQTIKESLAV | SAFRD---AV | ERSPAAIN-- | DMCAVCLGDL | --EDEDEIRE | 98 |
| SEQ_ID_NO_753 | SQAIKESLSV | TTFHD---AL | ERKPELLS-- | DTCAVCLGDL | --EDGDEVRE | 92 |
| SEQ_ID_NO_760 | SQTIKESLAV | TTFRD---AA | DRSPELLS-- | DTCAVCLGDL | --EDGDEVRE | 95 |

Figure 23 (continued)

| | | | | | | |
|---|---|---|---|---|---|---|
| SEQ_ID_NO_765 | LCSCSHAFHD | ACIDAWRSG | D--------- | -DDAATCPLC | RAPCCPRRG- | 176 |
| SEQ_ID_NO_763 | LPKCRHAFHA | DCVDTMLEA- | ---------- | ---HSTCPVC | RRRVGKEDA- | 164 |
| SEQ_ID_NO_758 | MANCRHMFHR | TCVDRWIDHD | ---------- | ---QKTCPLC | RTHFVPYHK- | 141 |
| SEQ_ID_NO_761 | LSNCRHVFHR | GCLDRWMAHE | ---------- | ---QRTCPLC | RAPLIPDELL | 168 |
| SEQ_ID_NO_762 | LSNCRHVFHR | GCLDRWMAHE | ---------- | ---QRTCPLC | RAPLIPDELL | 168 |
| SEQ_ID_NO_755 | LMNCYHVFHR | ECIDRWLEHE | HE-------- | -NHSATCPIC | RAPLLSSSC- | 141 |
| SEQ_ID_NO_748 | LRNCCHVFHR | DCIDRWVDHD | HEHD------ | -ENHNTCPLC | RAPLLTTSQ- | 142 |
| SEQ_ID_NO_746 | LRNCTHVFHR | DCIDRWLDYE | CCGGDD---- | -DNHRTCPLC | RTPLLPSFT- | 144 |
| SEQ_ID_NO_751 | LRNCTHVFHR | DCIDRWLDYE | CCGGDD---- | -DNHRTCPLC | RTPLLPSFT- | 142 |
| SEQ_ID_NO_753 | LRNCSHVFHR | ECIDRWLDYE | CCGGDGNEGE | EDNHRTCPLC | RTPLLAADT- | 141 |
| SEQ_ID_NO_760 | LRNCSHVFHR | ECIDRWLDYE | CCGGDDNDGE | EDNHRTCPLC | RTPLLAANT- | 144 |

| | | | | | | |
|---|---|---|---|---|---|---|
| SEQ_ID_NO_765 | ---------- | ---------- | TTTGGEQSLS | R----VLKSV | CVSVP | 197 |
| SEQ_ID_NO_763 | ---------- | -----FAVLP | ELEAADADIY | PAREAEMQIV | VRRPA | 194 |
| SEQ_ID_NO_758 | -----MEDYN | ORLWNDAASE | DDIDDDVSLF | SHRHDYYYIA | NASL- | 180 |
| SEQ_ID_NO_761 | PAASGLPDPS | DYDLSYYPSP | LPLAPTPTLL | RPHELLLNGL | GGFQ- | 212 |
| SEQ_ID_NO_762 | PAASGLPDPS | DYDLSYYPSP | LPLAPTPTLL | RPHELLLNGL | GGFQ- | 212 |
| SEQ_ID_NO_755 | ---------- | ----HHSSAT | CLPPPQPSWA | VERLLYLFGD | DLLPC | 172 |
| SEQ_ID_NO_748 | ---------- | --------SL | ARTRAEPSWA | VERILYLFGD | DLVM- | 168 |
| SEQ_ID_NO_746 | ---------- | ---------D | YSTVTQTSWA | VERLLYLFGD | DLLP- | 169 |
| SEQ_ID_NO_751 | ---------- | ---------D | YSTVTQTSWA | VERLLYLFGD | DLLP- | 167 |
| SEQ_ID_NO_753 | ---------- | -----SSCGD | WPVKTEPSWA | VERLLYLFGD | DLLV- | 170 |
| SEQ_ID_NO_760 | ---------- | -----SSCAD | WPVKNEPSWA | VERLLYLFGD | DLLV- | 173 |

Figure 24

| | | |
|---|---|---|
| SEQ_ID_NO_779 | MVLESIL SS S--KSPSF------RRQF AKHELGSWST LKRHRFLLF | 39 |
| SEQ_ID_NO_783 | MVLDSILSSS PCLKSPSF------SRQF ARHELGSWST VKRHCFLLS | 42 |
| SEQ_ID_NO_769 | MVLDGLV SS PSRRQCL------KKQW--DELGSWST LIQRHQYLLT | 39 |
| SEQ_ID_NO_777 | MVLDGFV SS PLRRHQS------KKQW--EDLGSCST VVNRHRYLLT | 39 |
| SEQ_ID_NO_773 | MVLDSMI TS PHRRSPSF------RKPF PRDELGSWST LLRRHRFLLT | 41 |
| SEQ_ID_NO_771 | MVLDGLV SS PLRRSAST------RRQS SRDEFGSWST LVERHRFLLT | 41 |
| SEQ_ID_NO_789 | MVLDSL--SS PHRRSQNTVF LASPSKKQQS GFNEPGSWST IYERHRFLLT | 48 |
| SEQ_ID_NO_795 | MVLDSL--SS PHRRSQNTFF VSSA-KKPQS SRDD--SWSA LVERHRFLLT | 45 |
| SEQ_ID_NO_790 | MVLDSL--SS PHRRSQNTFF LSSP-KKLQS SKDDVGSWSA LVERHRFLLT | 47 |
| | | |
| SEQ_ID_NO_779 | ALALLTVLCT YLYFAVTFA AN--DSCSGL NGPLKDSCHM EHVKASVAKS | 87 |
| SEQ_ID_NO_783 | ALALLTVLCT YLYFAVTFA AN--DSCSGL SGSLRDSCHM EHVMDSEAKS | 90 |
| SEQ_ID_NO_769 | ALALLAFLCT VYLYFAVTLG ARH-SSCYGL TGKDKAMCQL -QLVQALSKG | 87 |
| SEQ_ID_NO_777 | ALLLGFLCT VYLYFAVTLD ARHNSGCYGL AGKEKAMC-------QAISKG | 83 |
| SEQ_ID_NO_773 | AFALLAFLCT YLYFAVTLG AT--ESCSGL TGTKKTLCRL ELAKDSVGNG | 89 |
| SEQ_ID_NO_771 | ALSLLAFLCT YLYFAVTLG AT--DTCSGL KGTEKATCNL QHVSSTLSHG | 89 |
| SEQ_ID_NO_789 | MLALLAFLCT YLYFAVTLG AT--GSCSGM SGAEKALC--QAKSSLHKG | 93 |
| SEQ_ID_NO_795 | TLLVLAFLCT VYLYFAVTLG AS--DACTGL TGAERIEC--QARSVLQHG | 90 |
| SEQ_ID_NO_790 | TLVKLVFLCT YLYFAVTLG AP--DACSGL AGTEKAVC--RAKSALRHG | 92 |
| | | |
| SEQ_ID_NO_779 | KLKGLRHF | 95 |
| SEQ_ID_NO_783 | KLKGLRHL | 98 |
| SEQ_ID_NO_769 | KLK---FF | 92 |
| SEQ_ID_NO_777 | KLK---LF | 88 |
| SEQ_ID_NO_773 | KLK---FF | 94 |
| SEQ_ID_NO_771 | KLK---FL | 94 |
| SEQ_ID_NO_789 | KLK---FF | 98 |
| SEQ_ID_NO_795 | KLK---FR | 95 |
| SEQ_ID_NO_790 | KLK---FF | 97 |

Figure 25

| | | | | | | |
|---|---|---|---|---|---|---|
| SEQ_ID_NO_799 | --MIAE--SM LL NPTSH ST | A-DSL DDPSP | A--------- | ---------- | | 26 |
| SEQ_ID_NO_819 | MMMMGE------GVSSVPP | M----SHLPV | SGVDVLGGGG | G-------GG | | 32 |
| SEQ_ID_NO_821 | MMMMGE------GVSSVPP | M----SHLPV | SGVDVLGGGG | G-------GG | | 32 |
| SEQ_ID_NO_810 | MMMMGE-------RAMAPP | M----QHSPA | A------SGV | T-------DA | | 25 |
| SEQ_ID_NO_816 | MMMMGE-------GAHAPP | WQQQQQQPAA | S------AGM | V-------DG | | 29 |
| SEQ_ID_NO_801 | -MMI GE SHH RSNPTVQ PD | WDPYEEQTTT | SPSLSPI PTS | P--------F | | 41 |
| SEQ_ID_NO_792 | -MMI GE-SHR GFNPTVHI PP | W-PLSEDL EV | SDI YGSPDGG | S--------- | | 38 |
| SEQ_ID_NO_794 | -MML GE-THR P-NPTVHVPP | W-PDLDDDQT | DVVYSPI HYN | ATDNNLSSNG | | 46 |
| SEQ_ID_NO_808 | -MML GEPPHR T-NPTVHVPP | W-PTLNNPTA | E-FSPLTSN | D-------DY | | 39 |
| SEQ_ID_NO_805 | -MML GE-THR P-NPTVHVPP | W--------A | FEL FSPYTGN | A-------DY | | 32 |
| | | | | | | |
| SEQ_ID_NO_799 | -----I SSYF STAHVSPLDS | PTAALMDFDS | SL WEDPDLPA | PVDAYSCDDF | | 71 |
| SEQ_ID_NO_819 | DEMTPY-VI A ALRDYLPAND | VGVGA-DEEE | EAAAMAA--- | AVDAYACDEF | | 77 |
| SEQ_ID_NO_821 | DEMTPV-VI A ALRDYLPAND | VGVGA-DEEE | EAAAMAA--- | AVDAYACDEF | | 77 |
| SEQ_ID_NO_810 | DDASPYALLA ALQHYLPSNE | V--AAFDEDD | EEAALAAATA | AVDAYACDEF | | 73 |
| SEQ_ID_NO_816 | DDASPYSLLV ALRHFLPSNE | AAAAAYDEDD | E-----EALA | AVDAYACDEF | | 74 |
| SEQ_ID_NO_801 | TNFNALDSLT SLHRYLPSNE | PDP---TFED | ELDL------ | PVDAFSCDHF | | 82 |
| SEQ_ID_NO_792 | ---SMMEALA EL QRYLPSNE | PDP---DSDP | DL SGPDS--- | PI DAYTCDHF | | 79 |
| SEQ_ID_NO_794 | NPFYLHEALS ALQRYLPSNG | PDV---ELDS | EFPGLDDPDS | PVDAYSCDHF | | 93 |
| SEQ_ID_NO_808 | SQFYMQEALS AFQHYVNENN | DS----DSDS | EI FPTHE--- | SVDSYSNDHF | | 82 |
| SEQ_ID_NO_805 | SPYSMQEALS ALQHYESTDA | ------ESDS | EVPSREP-EV | PVDAYSCDHF | | 75 |
| | | | | | | |
| SEQ_ID_NO_799 | RMYEFKVRSC | ARGRSHDWTK | CPYAHT GEKA | RRRDPRKFNY | SGAECPDLRH | 121 |
| SEQ_ID_NO_819 | RMYEFKVRRC | ARGRSHDWTE | CPFAHPGEKA | RRRDPRKYHY | SGTACPDFRK | 127 |
| SEQ_ID_NO_821 | RMYEFKVRRC | ARGRSHDWTE | CPFAHPGEKA | RRRDPRKYHY | SGTACPDFRK | 127 |
| SEQ_ID_NO_810 | RMYEFKVRRC | SRGRNHDWTA | CPYAHPGEKA | RRRDPRRYHY | SGAACPDFRK | 123 |
| SEQ_ID_NO_816 | RMYEFKVRRC | SRGRSHDWTD | CPYAHPGEKA | RRRDPRRYHY | SGTACPDYRK | 124 |
| SEQ_ID_NO_801 | RMYEFKVKRC | ARGRSHDWTE | CPYAHPGEKA | RRRDPRRYHY | SGTACPEFRK | 132 |
| SEQ_ID_NO_792 | RMYEFKVRRC | ARGRSHDWTE | CPYAHPGEKA | RRRDPRKFHY | SGTACPEFRK | 129 |
| SEQ_ID_NO_794 | RMYEFKI RRC | ARGRSHDWTE | CPYAHPGEKA | RRRDPRKYHY | SGTACPDFRK | 143 |
| SEQ_ID_NO_808 | RMFEFKI RRC | ARGRSHDWTE | CPFSHPGEKA | RRRDPRKYNY | SGTSCPDFRK | 132 |
| SEQ_ID_NO_805 | RMFEFKVRRC | ARCRSHDWTD | CPYAHPGEKA | RRRDPRKYHY | SGTACPDFRK | 125 |

Figure 25 (continued)

| | | | | | | |
|---|---|---|---|---|---|---|
| SEQ_ID_NO_799 | GCCKKGDACE | YAHGTFELML | HPDRYRTQPC | RDGTCCRRRV | CFFAHTSEQL | 171 |
| SEQ_ID_NO_819 | GGCKRGDACE | YAHGVFECWL | HPARYRTQPC | KDGTACRRRV | CFFAHTPDQL | 177 |
| SEQ_ID_NO_821 | GGCKRGDACE | YAHGVFECWL | HPARYRTQPC | KDGTACRRRV | CFFAHTPDQL | 177 |
| SEQ_ID_NO_810 | GGCKRGDACE | LAHGVFECWL | HPSRYRTQPC | KDGTSCRRRV | CFFAHTPDQL | 173 |
| SEQ_ID_NO_816 | GGCKRGDACE | FAHGVFECWL | HPSRYRTQPC | KDGTACRRRV | CFFAHTPDXL | 174 |
| SEQ_ID_NO_801 | GGCKKGDACE | FAHGVFECWL | HPARYRTQPC | KDGPACRRRV | CFFAHTPEQL | 182 |
| SEQ_ID_NO_792 | GCCKRGDACE | FSHGVFECWL | HPARYRTQPC | KDGGNCRRRV | CFFAHSPDQI | 179 |
| SEQ_ID_NO_794 | GNCRKGDSCE | FAHGVFECWL | HPARYRTQPC | KDGSGCRRRV | CFFAHTPDQL | 193 |
| SEQ_ID_NO_808 | GSCKKGDSCE | FAHGVFECWL | HPSRYRTQPC | KDGTSCRRPM | CFFAHTTEQL | 182 |
| SEQ_ID_NO_805 | GSCKKGDACE | YAHGVFECWL | HPARYRTQPC | KDGTSCRRRV | CFFAHTPDQL | 175 |

| | | | | | | |
|---|---|---|---|---|---|---|
| SEQ_ID_NO_799 | RILPGKQSVR | SPRAREM--- | ---------- | ---------A | IPAVSS | 194 |
| SEQ_ID_NO_819 | RVLPAQQS-- | SPRSVAS--S | PLAESYD-GS | PLRRQAFESY | LTKTI-MSSS | 221 |
| SEQ_ID_NO_821 | RVLPAQQS-- | SPRSVAS--S | PLAESYD-GS | PLRRQAFESY | LTKTI-MSSS | 221 |
| SEQ_ID_NO_810 | RVPPPRQS-- | SPRGAAAA-S | PLAESYD-GS | PLRRQAFESY | LTKSGIVSSP | 219 |
| SEQ_ID_NO_816 | RVLPPQQSSA | SPRGACAAPS | PLAESYD-GS | PLRRQAFESY | LTKTGIMSSS | 223 |
| SEQ_ID_NO_801 | RLLPQQ---- | SPKGNGSGSG | LGGGEYDFGS | PVLIHPFDSY | MTKAGIFVSS | 227 |
| SEQ_ID_NO_792 | RVLPNQ---- | SPDR------ | --VDSFDVLS | PTIRRAFQ-- | ------FSLS | 209 |
| SEQ_ID_NO_794 | RLVSS----- | ---------- | --TDTYD-GS | PL-------- | CGKTLTFMSS | 216 |
| SEQ_ID_NO_808 | RAPTQQ---- | SPRSVPS--- | --VDSYD-GS | PL-RLAFESS | CVKTLQFMSS | 221 |
| SEQ_ID_NO_805 | RVLPQQ---- | SPRS------ | --ADSYD-GS | PL-RHAFESS | CAKSHPFVAS | 211 |

| | | | | | | |
|---|---|---|---|---|---|---|
| SEQ_ID_NO_799 | PTSLLSPSS | ------DSP | PLSPSP--V | SGG------ | ESLSRLVALM | 229 |
| SEQ_ID_NO_819 | PTSTLMSPPK | SPPS---ESP | PLSPDGAA-A | RRGSMPGVG | SPVNDYLASF | 267 |
| SEQ_ID_NO_821 | PTSTLMSPPK | SPPS---ESP | PLSPDGAA-A | RRGSMPGVG | SPVNDYLASF | 267 |
| SEQ_ID_NO_810 | PTSTLVSPPR | SPPS---ESP | PMSPDAAA-A | LRRGSMPGVG | SPVNEVLASM | 265 |
| SEQ_ID_NO_816 | PTSTLVSPPR | SPPS---ESP | PMSPDAAAGA | LRRGSMPGVG | SPVNEVVASL | 270 |
| SEQ_ID_NO_801 | PTSLLISPPV | SPPS---DSP | PMSPGSF--Q | VIGGSGPGSL | NSMSALLASM | 272 |
| SEQ_ID_NO_792 | PSSN--SPPV | SPRG------ | --DSDSSCSL | SRSLGSNLG | ---NDVVASL | 246 |
| SEQ_ID_NO_794 | PGSS--SPPV | SPRAESCSSP | PVSPMAQ--S | LSRSLGSASI | NEML--VTBL | 259 |
| SEQ_ID_NO_808 | PGSV--SPPV | -------ESP | PMSPMTR--S | LGRSVGS--- | SSVNEMVASL | 257 |
| SEQ_ID_NO_805 | PGSA--SSPV | -------ESP | PMSPMT---- | ---------- | VSVNEMVASL | 238 |

Figure 25 (continued)

| | | | | | |
|---|---|---|---|---|---|
| SEQ_ID_NO_799 | HSLRLDELK- | ---------- | ---------- | ---------- | TNPGVSSF-- | 246 |
| SEQ_ID_NO_819 | RQLRLNKVK- | -SSPSGGWSY | PSSS------ | AVYGSPKAA- | --TGLYSLPT | 306 |
| SEQ_ID_NO_821 | RQLRLNKVK- | -SSPSGGWSY | PSSS------ | AVYGSPKAA- | --TGLYSLPT | 306 |
| SEQ_ID_NO_810 | RQLRLGGGS- | PRSAPSGGSF | LGGG------ | YPFGSPKSP- | ---AGLYSLPS | 305 |
| SEQ_ID_NO_816 | RQLRLGGGGS | PRSAPSGGSF | LVG------- | YPFGSPKSP- | ---AALYSLPS | 310 |
| SEQ_ID_NO_801 | RGLQVGKAK- | MGSPVGSWGV | QSG------- | FRFGSPRGSS | LRPGFCSLPS | 314 |
| SEQ_ID_NO_792 | RNLQLNKVK- | -SSLSESYNN | QTGGYG---- | SGFGSPRGSV | LGPGFRSLPT | 280 |
| SEQ_ID_NO_794 | RNLQLGKGK- | ------SWKT | QVGCCSPSSP | SSFGSPRAAM | IRPGFCSLPS | 302 |
| SEQ_ID_NO_808 | RNLQLGTMK- | --SLPSSWNV | QMGS------ | PRFGSPRGPV | IRPGFCSLPS | 298 |
| SEQ_ID_NO_805 | RNLQLGKVK- | --SLPSSWNV | -MGS------ | SGFGSPRGPM | RPGFFSLPT | 278 |

| | | | | | |
|---|---|---|---|---|---|
| SEQ_ID_NO_799 | SPNL------ | -RRSSGAAF- | -DLMDRG-N | EEEPAMERVE | SGRNLRAQMY | 285 |
| SEQ_ID_NO_819 | TPLASTATVT | TASSFMPNL- | -EPLDLGLIG | DEEPVLDRVE | SGRALREKVF | 353 |
| SEQ_ID_NO_821 | TPLASTATVT | TASSFMPNL- | -EPLDLGLIG | DEEPVLDRVE | SGRALREKVF | 353 |
| SEQ_ID_NO_810 | TPTRPSPVTV | TTASGATVLT | VERLNLGLIG | DEEPVMERVE | SGRALREKVF | 355 |
| SEQ_ID_NO_816 | TPTRPAAVTV | TTPSGATVMT | VERLNLGLIG | DEEPVMERVE | SGRALREMVF | 360 |
| SEQ_ID_NO_801 | TPTR---TM | ASRSGLSQL- | -DI MGDGVTC | EEEPAMERVE | SGRDLRAKIY | 358 |
| SEQ_ID_NO_792 | TPTRP----- | ------GFM | -NI MENGF-L | EEEPAMERVE | SGRELRAQLF | 325 |
| SEQ_ID_NO_794 | TPTR---NL | -TRPGISYP- | -DGMDKA--C | EEEPVMERVE | SGRDLRAKMF | 343 |
| SEQ_ID_NO_808 | TPTQ----V | PSRGRVNHF- | -DLMDQS--C | EEEPVMERVE | SGRDIRVKMF | 339 |
| SEQ_ID_NO_805 | TPTQ----A | PTRGGVNYF- | -DDMDQS-CC | EEEPVMERVE | SGRSLRARMF | 320 |

| | | | | | |
|---|---|---|---|---|---|
| SEQ_ID_NO_799 | AKLMRENSVD | RVRPMISA- | ---------- | GSLN------ | ---------- | 307 |
| SEQ_ID_NO_819 | ERLSRDGAIY | GDATAFATAG | -----VGLDV | DWVSDLIN- | ---------- | 386 |
| SEQ_ID_NO_821 | ERLSRDGAIS | GDATAFATAG | -----VGLDV | DWVSDLIN- | ---------- | 386 |
| SEQ_ID_NO_810 | ERLSKEATYP | SDTAABANVE | GAA--PAPDV | GWVSDLIN- | ---------- | 391 |
| SEQ_ID_NO_816 | ERLSKEATYP | NDAAASANAE | GAAPAAAPDV | GWVSDLIN- | ---------- | 398 |
| SEQ_ID_NO_801 | AKLSKENSVD | RDRGDSGVSG | -------PDV | GWVSELVK-- | ---------- | 389 |
| SEQ_ID_NO_792 | EKLSKENCMG | RIEPDPDQGA | G----OTPDV | GWVSDLVM-- | ---------- | 359 |
| SEQ_ID_NO_794 | EKLSKENSLE | RVNPDQSSGG | -------PDL | NWVSDLGKQA | MGIIVMVDIV | 386 |
| SEQ_ID_NO_808 | EKLSKENSFN | GSGMGSGSGL | GEVV-EDPDV | GWVSELVSPF | LGD------- | 381 |
| SEQ_ID_NO_805 | EKLSKENHLD | GSCSGSSQIG | ------VPDV | GWVSELVSR- | ---------- | 353 |

Figure 25 (continued)

| | | |
|---|---|---|
| SEQ_ID_NO_799 | ‐ ‐ ‐ ‐ ‐ ‐ | 307 |
| SEQ_ID_NO_819 | ‐ ‐ ‐ ‐ ‐ ‐ | 386 |
| SEQ_ID_NO_821 | ‐ ‐ ‐ ‐ ‐ ‐ | 386 |
| SEQ_ID_NO_810 | ‐ ‐ ‐ ‐ ‐ ‐ | 391 |
| SEQ_ID_NO_816 | ‐ ‐ ‐ ‐ ‐ ‐ | 398 |
| SEQ_ID_NO_801 | ‐ ‐ ‐ ‐ ‐ ‐ | 389 |
| SEQ_ID_NO_792 | ‐ ‐ ‐ ‐ ‐ ‐ | 359 |
| SEQ_ID_NO_794 | L F I K Y F | 392 |
| SEQ_ID_NO_808 | ‐ ‐ ‐ ‐ ‐ ‐ | 381 |
| SEQ_ID_NO_805 | ‐ ‐ ‐ ‐ ‐ ‐ | 353 |

| | | | | |
|---|---|---|---|---|
| SEQ_ID_NO_1706 | MA- -PPLSSWP | WASLG- YKYF | LLGPLVWKVA | QEWAE- -QGG | AP- -LGSRWL 45 |
| SEQ_ID_NO_828 | MA- -APLSSWP | MTSLGQYKYA | LLGPLAWKVV | QEWREQGQGA | LP- VLGSWWL 49 |
| SEQ_ID_NO_1713 | MA- -PPLSSWP | WASLGQYKYV | LFGALVWKVV | QEWRE- -QGG | LP- -LGSWWL 45 |
| SEQ_ID_NO_824 | MAPPLSSWP | WASLGQYKYV | LLGPLVWKVL | QEWRE- -QAG | LP- -LGSWWL 46 |

| | | | | |
|---|---|---|---|---|
| SEQ_ID_NO_1708 | HLLLLFSARG | LTYQFWFSYS | NMLFLTRRRR | VVPDGVDFRC | VDHEWDW- - - 92 |
| SEQ_ID_NO_826 | HLLLLFVRG | LTYQFWFTYG | NMLFFTRRRR | VVADGVDFRC | DAEWDW- - - 96 |
| SEQ_ID_NO_1713 | HLLVLFAVRG | LTYQFWFTYG | NMLFFTRRRR | VVADGVDFRC | DAEWDW- - - 92 |
| SEQ_ID_NO_824 | HLLLLFAARG | LTYQFWFSYG | NMLFFTRRRR | VVADGVDFRC | DAEWDWKKI 96 |

| | | | | |
|---|---|---|---|---|
| SEQ_ID_NO_1708 | - - - - - - - - - - | - - - - - - - - - - | - - - - - - - - - - | - - - - - - - - - - | 92 |
| SEQ_ID_NO_828 | - - - - - - - - - - | - - - - - - - - - - | - - - - - - - - - - | - - - - - - - - - - | 96 |
| SEQ_ID_NO_1713 | - - - - - - - - - - | - - - - - - - - - - | - - - - - - - - - - | - - - - - - - - - - | 92 |
| SEQ_ID_NO_824 | LWIPPPNNQP | WSPSDTGNAQ | AHLAGIGRLF | FLRLVPAFG- | 135 |

```
SEQ_ID_NO_828       ---MGRKP-- DAVAKSYHSG GGGAAASS-- ---------- --PRAARKAS   31
SEQ_ID_NO_845       ---MGRKP-- DPSKPHY--- GGGAS----- ---------- --PRAARRTQ   25
SEQ_ID_NO_847       ---MGRKP-- DPSKPHY--- GGGAS----- ---------- --PRAARRTQ   25
SEQ_ID_NO_832       -MLSLLSE-- KPNLALYNQS NGKHYQYHQN IYNDWRWWRS SATQQHRRKV   47
SEQ_ID_NO_837       --MGVVAEVW RSSVRLLTNS PQLNGGSHKS ALWKWRFF-- ---SAQPKRIV  44
SEQ_ID_NO_840       --MKRRKQ-- RSHEKLFLYL QIILHTLIF- ---------- --KRRRIHH    33
SEQ_ID_NO_842       ---MVLPR-- RRGGHNHH-- ---------- ---------- --PCPRRAVL   21
SEQ_ID_NO_844       ---MGSRR-- RRHHHHHG-- ---------- ---------- --PMLVPAVA   21
SEQ_ID_NO_839       MFMAPRRGLL DGGEDRYGLM SFGTKDI--- ---------- --FTMRRKIR   35
SEQ_ID_NO_850       ---MSEAEKF IYHRKLAEYK GISVGESKAE KLRSY----- --LVSRSRMK   40

SEQ_ID_NO_828       PSP------- MFLGTALFVL GFVSLFTGHV VTDADW---- AKIRSRWRPK   70
SEQ_ID_NO_845       PSP------- MFLGTALFVL GFVSLFTGHI VTDADW---- SRIRSRWRSK   64
SEQ_ID_NO_847       PSP------- MFLGTALFVL GFVSLFTGHI VTDADW---- SRIRSRWRSK   64
SEQ_ID_NO_832       PWS------- LVCGLMLFGL GLVSLFTGHV ASDLEW---- YSQRLVKRSL   86
SEQ_ID_NO_837       MWT------- WVCGFMLFSL GMISLFTGHV VSHLEW---- YSQQLSKRSL   83
SEQ_ID_NO_840       LLP------- LKAALTGGIL FFFVLFSPPI TSQHH----- HLINPIWFNN   71
SEQ_ID_NO_842       PAA------- ALLLL--FLL AAVTLLYVSP PPLSDHPALA YSRRRSPHAL   62
SEQ_ID_NO_844       PAA------- AAFAAAGLLL VVWAFHCFLS PPLGDGGGGA RVVRRPNPPF   64
SEQ_ID_NO_839       YWQKQFKQRH LFGGLMVLLL MCVITKFILM NMFSDQ---- LDLDTAIPSN   81
SEQ_ID_NO_850       LWM------- IRAVTILLLW SCVV----HL MALGEFWG-- PRLLKGWPSC   77

SEQ_ID_NO_828       -----QHRNY EP-------- ---------D IWESKYSSMY YGCSERSASF   99
SEQ_ID_NO_845       -----QVRNN EP-------- ---------N IWKSRYSNLY YGCSRRSVNF   93
SEQ_ID_NO_847       -----QVRNN EP-------- ---------N IWKSRYSNLY YGCSRRSVNF   93
SEQ_ID_NO_832       FYSRLEGRRR EA-------- ---------D IWKSKYSNLF YGCSERGRNF  120
SEQ_ID_NO_837       ----LDMSRR EP-------- ---------D VWKSKYSKFF YGCSERGRNF  113
SEQ_ID_NO_840       GTELQMNLQK EH----VFRV PMGGGSLSGD IWTSKQSLLY HGCSNSSYKF  117
SEQ_ID_NO_842       LNSSGGGSLV EPGRREISRV PKGGWSATDG LWGSKLASKF YGCSNSSSKF  112
SEQ_ID_NO_844       LLKKPAEVAR SVIGAVDFTV PSGGSKHGQE LWESKATGNF FGCSNATKHF  114
SEQ_ID_NO_839       VVQDEPSPNN WP-------- --------TLC IWKHPNSDNY FNCMGRAK--  114
SEQ_ID_NO_850       ---------- ---------- --------FN HHDLPVAAET ASLPMKIA--   97
```

Figure 27 (continued)

```
SEQ_ID_NO_828   RSAVPENSST GYLLIATSGG LNQQRIGITD AVVVAW LNA TLVVPELDHH   149
SEQ_ID_NO_845   RSAVPENSST GYLLIGTSGG LNQQRIGITD AVVVARILNA TLVVPELDHH   143
SEQ_ID_NO_847   RSAVPENSST GYLLIGTSGG LNQQRIGITD AVVVARILNA TLVVPELDHH   143
SEQ_ID_NO_832   PPAVRERASN GYLLIAASGG LNQQRTGITD AVVVARILNA TLVVPELDHH   170
SEQ_ID_NO_837   LPAVQEQSSN GYLLIAASGG LNQQRTGITD AVVVARILNA TLVVPELDHH   163
SEQ_ID_NO_840   PSADVNTHPN RYLMIATSGG LNQQRTGIVD AVVAAHILNA VLVVPKLDQK   167
SEQ_ID_NO_842   LDSGVMTHPD RYLMIVTSGG LNQQRTGILD AVVAARILNA TLVVPKLDQT   162
SEQ_ID_NO_844   ADAKAVTKLD RYLMIATSGG LNQQRTGILD AVVAARILNA TLVIPKLDEE   164
SEQ_ID_NO_839   KDIRQGNNTN GYLLVHANGG LNQMKTGISD MVAIAKIMNA TLVFPTLDHN   164
SEQ_ID_NO_850   LPPKRVYKNN GYLMVSCNGG LNQMRAAFCD MVTLARYMNV TLIVPELDKT   147

SEQ_ID_NO_828   SFWKDDSDFS DIFDVEWFIS HLSKDVTIVK RIPYEVMLSM DKLPWTMRAP   199
SEQ_ID_NO_845   SFWKDDSDFS DIFDVDWFIS YLSKDVTIVK RIPYEVMMSM DKLPWTMRAP   193
SEQ_ID_NO_847   SFWKDDSDFS DIFDVDWFIS YLSKDVTIVK RIPYEVMMSM DKLPWTMRAP   193
SEQ_ID_NO_832   SYWKDDSDFV NIFDVDWFIS YLAKDVTIVK RVPDKVMRSM EKPPYTMRVP   220
SEQ_ID_NO_837   SYWKDDSDFS DIFDVNWFIS SLAKDVTIVK RVPDRMMRAM EKPPYTTRVP   213
SEQ_ID_NO_840   SYWKDSSNFS EIFDVDRFIS HLSKDVKIIR DIPR--IGDK VITPYTTRVP   215
SEQ_ID_NO_842   SFWKDASDFA EIFNADWFIS FLSKDVRIVK CLPK--IGGK LWAPHRMRVP   210
SEQ_ID_NO_844   SFWNDASDFA QIFDVDSFIY SLSNDVKVIR QLPD--MNGK KLSPYKMRIP   212
SEQ_ID_NO_839   SFWTDPSDFK EIFNMKNFVE VLNEDVCVVE SLPPELAAIK P----ALKAP   210
SEQ_ID_NO_850   SFWSDPSEFD DIFDVDHFIT SLRDEVRILK ELPPRLKRRF ELGMYYSFPP   197

SEQ_ID_NO_828   RK-SVPEFYI DEVLPILMRR RALQLTKFDY RLTSD-LDED LQKLRCRVNF   247
SEQ_ID_NO_845   RK-SMPDFYI DEVLPILMRR RALQLTKFDY RLTNE-LDEE LQKLRCRVNF   241
SEQ_ID_NO_847   RK-SMPDFYI DEVLPILMRR RALQLTKFDY RLTNE-LDEE LQKLRCRVNF   241
SEQ_ID_NO_832   RK-SPPEYYL DQVLPILLRR RVVQLTKFDY RLASN-LDEE LQKLRCRANY   268
SEQ_ID_NO_837   RK-STLEYYL DQVLPILTRR HVLQLTKFDY RLAND-LDED MQKLRCRVNY   261
SEQ_ID_NO_840   RK-CNAKCYQ TRILPILKKK HAVQLTKFDY RLSNR-LDID MQKLRCRVNF   263
SEQ_ID_NO_842   RK-CTQRCYL NRVLPALVKK HVVRITKFDY RLANR-LDSD LQKLRCRVNY   258
SEQ_ID_NO_844   RK-CTPKCYE NRVLPALLKK HVVQLTKFDY RVSNR-LETD LQKLRCRVNY   260
SEQ_ID_NO_839   VSWSKASNYR TDMLQLLKKH KVIKFTHTDS RLVNNGLASS IQRVRCRAMY   260
SEQ_ID_NO_850   ISWSDISYYS NQILPLVKKY KVVHLNKTDT RLANNGLSLD LQKLRCRVNF   247
```

Figure 27 (continued)

| | | | | | | |
|---|---|---|---|---|---|---|
| SEQ_ID_NO_828 | HALKFTSSI H | AMGQKLVQKL | RLMNTRYVAI | HLRFEPDMLA | FSGCYYGGGE | 297 |
| SEQ_ID_NO_845 | HALRFTNSI Q | TLGEKLVRKL | RSMSSRYVAV | HLRFEPDMLA | FSGCYYGGGD | 291 |
| SEQ_ID_NO_847 | HALRFTNSI Q | TLGEKLVRKL | RSMSSRYVAV | HLRFEPDMLA | FSGCYYGGGD | 291 |
| SEQ_ID_NO_832 | HALRFTKPI Q | EIGERLVTKM | RKMAKRYIAI | HLRFEPDMLA | FSGCYFGGGE | 318 |
| SEQ_ID_NO_837 | HALRFTKRI Q | SVGMKVVKRM | RKMAKRFIAV | HLRFEPDMLA | FSGCDFGGGE | 311 |
| SEQ_ID_NO_840 | HALKFTDPI I | EMGRKLVERI | RMKSKHFVAL | HLRFEPDMLA | FSGCYYGGGD | 313 |
| SEQ_ID_NO_842 | HALRFTDPI Q | EMGEKIIQRV | RERSTMFIAL | HLRFEPDMLA | FSGCYYGGGE | 308 |
| SEQ_ID_NO_844 | HALQFTDPI L | RMGELLVQRM | KEKSGRFIAL | HLRFEPDMLA | FSGCYYGGGD | 310 |
| SEQ_ID_NO_839 | EALRFAVPI E | ELGKKLVNRL | RENNTPYIAL | HLRYEKDMLA | FTGCSHNLTK | 310 |
| SEQ_ID_NO_850 | NALRFTPQI E | ELGRRVYRIL | REK-GPFLVL | HLRYEMDMLA | FSGCSHGCNP | 296 |

| | | | | | | |
|---|---|---|---|---|---|---|
| SEQ_ID_NO_828 | KERKELGEI R | ---KRWDILP | ELSAEDERSR | GKCPLTPHEV | GLMLRALGFG | 344 |
| SEQ_ID_NO_845 | KERRELGEI R | ---KRWDILP | ELSAEDERSR | GKCPLTPQEI | GLMLRALGFS | 338 |
| SEQ_ID_NO_847 | KERRFIGFI R | ---KRWDIIP | ELSAEDERSR | GKCPLTPQEI | GLMLRALGFS | 338 |
| SEQ_ID_NO_832 | KERFELGEI R | ---KRWAILP | DLSPDGERER | GKCPLTPHEV | GLMLRALGFA | 365 |
| SEQ_ID_NO_837 | KERAELAEI R | ---KRWDFLP | DLDPLEERKR | GKCPLTPHEV | GLMLRALGFT | 358 |
| SEQ_ID_NO_840 | KETKELGKI R | ---KRWKTLH | ATNPDKERRH | GKCPLTPEEI | GLMLRALGFG | 360 |
| SEQ_ID_NO_842 | KEKRELGVI R | ---KRWKTLH | ASNPEKERRH | GRCPLTPEEV | GLMLRALGYR | 355 |
| SEQ_ID_NO_844 | TERRELGEI R | ---KRWKTLH | ASNPDRERRH | GKCPLTPEEV | GLMLRALGFG | 357 |
| SEQ_ID_NO_839 | EEITQELKKMR | YSVKHMKE-K | EIDSKSKRLKI | GSCPMTPREV | AVFLEALGYP | 359 |
| SEQ_ID_NO_850 | DEEEELTRMR | YAYPWAKE-K | VLNSELKRKD | GLCPLTPEET | ALALNALGID | 345 |

| | | | | | | |
|---|---|---|---|---|---|---|
| SEQ_ID_NO_828 | NDTLLYVASG | EIYGGDSTLQ | PLRGLFPNFY | TKEKLAG-DD | LNPFLPFSSR | 393 |
| SEQ_ID_NO_845 | NDTYLYVASG | EIYGGEETLQ | PLRDLFPNYY | TKEMLAG-ND | LKLFLPFSSR | 387 |
| SEQ_ID_NO_847 | NDTYLYVASG | EIYGGEETLQ | PLRDLFPNYY | TKEMLAG-ND | LKPFLPFSSR | 387 |
| SEQ_ID_NO_832 | NDTYLYVASG | EIYGGEETLR | PLRELFPNFY | TKEMLAL-EE | LKSFFPFSSR | 414 |
| SEQ_ID_NO_837 | NDTYIYVASG | EIYGGEKTLK | PLRELFPNFY | TKEMLAN-DE | LKPLLPYSSR | 407 |
| SEQ_ID_NO_840 | NDVHIYVASG | EIYGGEETLA | PLKALFPNFY | SKETIASKEE | LAPFSSFSSR | 410 |
| SEQ_ID_NO_842 | KNVHIYVASG | DIYGGAKTLA | PLKALFPNLH | TKETVTSKDE | LAPFSKYSSR | 405 |
| SEQ_ID_NO_844 | KDVHLYVASG | DVYGGEETLA | PLKALFPNFH | SKETLASKEE | LAPFLPYSSR | 407 |
| SEQ_ID_NO_839 | VDTKIYVAAG | VIYGSEG-MK | PLQKKFPNLL | WHSSLATKEE | LQPFEGHLNQ | 408 |
| SEQ_ID_NO_850 | RNVQIYIAAG | EIYGGERRMK | ALAEAFPNVV | RKETLLEPSD | LKFFONHSSQ | 395 |

Figure 27 (continued)

| | | | | | | | |
|---|---|---|---|---|---|---|---|
| SEQ_ID_NO_828 | LAAIDFIVCD | ESDVFVTNNN | GNMAKVLAGR | RRYMGHKRTI | RPNAKKLNVL | | 443 |
| SEQ_ID_NO_845 | LAAIDFIVCD | GSDVFVTNNN | GNMAKVLAGR | RRYMGHKRTI | RPNAKKLNLL | | 437 |
| SEQ_ID_NO_847 | LAAIDFIVCD | GSDVFVTNNN | GNMAKVLAGR | RRYMGHKRTI | RPNAKKLNLL | | 437 |
| SEQ_ID_NO_832 | MAAIDYIVCD | ESDVFVTNNN | GNMAKILAGR | RRYAGHKRTI | RPNAKKLSAL | | 464 |
| SEQ_ID_NO_837 | LAAIDYIVSD | ESDVFITNNN | GNMAKILAGR | RRYMGHKRTI | RPNAKKLSAL | | 457 |
| SEQ_ID_NO_840 | MAALDFMVCD | ESDVFVSNNN | GNMARMLAGR | RRYFGHKPTI | RPNAKKLYKL | | 460 |
| SEQ_ID_NO_842 | MAALDFIVCD | GSDAFVTNNN | GNMAKILAGR | RRYLGHKRTI | RPNARKLYSL | | 455 |
| SEQ_ID_NO_844 | MAALDFIVCD | RSDVFVTNNN | GNMARMLAGR | RRYFGHRRTI | RPNAKKLYSL | | 457 |
| SEQ_ID_NO_839 | LAALDYYTV | ESDVFVSYD | GNMAKAARGH | RKFDGFKKTI | SPDKQRFVRL | | 458 |
| SEQ_ID_NO_850 | MAALDYLVSL | ESDIFVPTYD | GNMAKVVEGH | RRFLGFKKTI | LLDRKLLVNL | | 445 |

| | | | | | | | |
|---|---|---|---|---|---|---|---|
| SEQ_ID_NO_828 | FQTRNQ--LS | WDTFSRKVQR | VQRGLMGEPD | DI----RPK | QDD-FHEFP | | 484 |
| SEQ_ID_NO_845 | FKRRKQ-MS | WDIFSQKVKK | VQRGLMGEPD | DI----RPG | RDD-FNEFP | | 478 |
| SEQ_ID_NO_847 | FKRRKQ-MS | WDIFSQKVKK | VQRGLMGEPD | DI----RPG | RDD-FNEFP | | 478 |
| SEQ_ID_NO_832 | FKARDR-MD | WDTFAKKYKA | SQRGFMGEPD | EV----RPG | RGD-FHEYP | | 505 |
| SEQ_ID_NO_837 | FMDREK-ME | NCTFAKKVKS | CQRGFMGDPD | EF----KPG | RGE-FHEYP | | 498 |
| SEQ_ID_NO_840 | FLSRNN--MT | WEEFASQVRT | SQLGFMGEPM | EV----KPG | RGE-FHENP | | 501 |
| SEQ_ID_NO_842 | FLSRGN-MS | WDAFSSKVHM | AQKGFMGEPK | EL----RPG | RGE-FHENP | | 496 |
| SEQ_ID_NO_844 | FLNRTS--MS | WDTFASKVLT | FQKGFMGEPN | EI----KPG | RGE-FHEHP | | 498 |
| SEQ_ID_NO_839 | IDQLDNGLIS | ANDFSTKVKS | HAKKKGAPQ | AR-KIHRHPK | FEETFYANPF | | 507 |
| SEQ_ID_NO_850 | IDQYTEGLLS | WDEFSSTVKE | VHEDRMGSPK | KRLVIPDKPK | EEDYFYANP | | 494 |

| | | | | | | |
|---|---|---|---|---|---|---|
| SEQ_ID_NO_828 | SSCICSRK-- | ---------- | ---------- | ---------- | ---------- | 492 |
| SEQ_ID_NO_845 | SSCICQR-- | ---------- | ---------- | ---------- | ---------- | 486 |
| SEQ_ID_NO_847 | SSCICQR-- | ---------- | ---------- | ---------- | ---------- | 486 |
| SEQ_ID_NO_832 | -SCICEKPFT | DDENRKGEDL | LSDRIHMNLK | ENVDSKYVGE | NQGDKSLQRL | 554 |
| SEQ_ID_NO_837 | QSCICQRP-- | ---------- | ---------- | ---------- | ------FSYD | 510 |
| SEQ_ID_NO_840 | SACICADS-- | ---------- | ---------- | ---------- | ---------- | 509 |
| SEQ_ID_NO_842 | TTCICENT-- | --------D | PKTPTKPNPR | SEQGLINGTE | GRKAITEPTV | 525 |
| SEQ_ID_NO_844 | MDCICAKA-- | ---------- | -NGKIGQSRH | HQIKRAGKGA | | 525 |
| SEQ_ID_NO_839 | PGCICQK-- | ---------- | ---------- | ---------- | ---------- | 514 |
| SEQ_ID_NO_850 | HECLQLL--- | ---------- | ---------- | ---------- | ---------- | 501 |

Figure 27 (continued)

```
SEQ_ID_NO_828    ..........  ..........  ..........  ..........  ..........   492
SEQ_ID_NO_845    ..........  ..........  ..........  ..........  ..........   486
SEQ_ID_NO_847    ..........  ..........  ..........  ..........  ..........   486
SEQ_ID_NO_832    KKRSIEEPIS  LRENKDVTVI  GSANELGLCT  GDRYVKVNGT  CLVASTKSDL   604
SEQ_ID_NO_837    KTSTDDEEED  MSFFNHNSTS  PGHVHLSS..  ..........  ..........   538
SEQ_ID_NO_840    DANDREDASL  FGTHSIISEI  DTGSSTNSAR  RDMVEVTDGQ  ASEEEQEWS-   558
SEQ_ID_NO_842    ANHTNEELVG  SSAEEDDASV  EKEDDTSAEK  EDDTSEEKEE  IADPEAEDDA   585
SEQ_ID_NO_844    ENHSSDGDLD  WRDLDYGEHT  PLGRDSSNES  ESDDIRVGGS  ..........   565
SEQ_ID_NO_839    ..........  ..........  ..........  ..........  ..........   514
SEQ_ID_NO_850    ..........  ..........  ..........  ..........  ..........   501

SEQ_ID_NO_828    ........PG  NISATT....  .             500
SEQ_ID_NO_845    ........PV  NRSVTARAEN  L             499
SEQ_ID_NO_847    ........PV  NRSVTARAEN  L             499
SEQ_ID_NO_832    LCHHVLSFST  PFLDETGSGM  L             625
SEQ_ID_NO_837    ........AD  NERDEVFPD-  -             549
SEQ_ID_NO_840    ........DT  EYMETELEI-  -             569
SEQ_ID_NO_842    LVRP....DD  PELEEVLSD-  -             600
SEQ_ID_NO_844    ........DI  PELEDMMSD-  -             576
SEQ_ID_NO_839    ........PT  HLMAETNHES  L             527
SEQ_ID_NO_850    ........DE  PLRTTRLSMF  L             514
```

Figure 28

```
SEQ_ID_NO_876    ....MGPVVL TQLATGLSML AGAALVKSVM DQN--TMMGP GSD...RF..    39
SEQ_ID_NO_855    ....MSPIVI TQLATGISVL AGAVFIKSVM DQK.....P MAG...QF..    35
SEQ_ID_NO_862    ....MGPIVL TQLATGLSVL AGAVLVKSVM DQK.....P MAG.......    33
SEQ_ID_NO_858    ....MVPIVL TQMATGLGVL AGAVFVKSVM DQK.....P MAG...PF..    35
SEQ_ID_NO_856    ....MFPAVL TQVATGLSVL AGAVLVKSVM DQK.....P MAG...PF..    35
SEQ_ID_NO_885    MVVVVAPIAV A--SAGLGML AGVAMASRSS NSSSSSGRTS SPAALLRVGA    48
SEQ_ID_NO_868    ...MVSPVVI A--SAGLGML AGVALASRGT GDG.....IP ASS...RVDA    37
SEQ_ID_NO_886    ...MVGPIVI A--SAGLGML AGVAMANRTM GGGGDGRQLP AAS...RVDA    42
SEQ_ID_NO_870    ...MVAPVVI A--SAGLGML AGVAMANRSL GNG.....LP AAS...RVDA    37
SEQ_ID_NO_878    ...MVAPVVI T--SAGLGML AGLAMANRSL GDG.....LP AAS...RVDA    37

SEQ_ID_NO_876    ....PRCSRC NGTGRVSC-L CNRWSD--GD -RGCRTCAGS GRMVCSSCGG    81
SEQ_ID_NO_855    ....PRCPTC NGTGRVTC-F CSRWSD--GD -VGCRRCSGS GRAACSNCGG    77
SEQ_ID_NO_862    ....PLCPSC NGTGRVAC-L CSRWSD--GD -AGCRACSGS GRMACSSCGG    75
SEQ_ID_NO_858    ....QRCPTC NGTGRVSC-L CSRWSD--GD -VGCRTCSGS GRRACSSCGG    77
SEQ_ID_NO_856    ....QRCPTC NGTGRITC-L DTRWSD--GD -IGCRTCAGS GRMACSSCGG    77
SEQ_ID_NO_885    PEPAPRCAAC GGTGREECRL CARWSDARGD CSGCRACAGT RRAPCRSCGG    98
SEQ_ID_NO_868    R---PRCSTC SGTGREEC-L CSRWSD--GD -VGCGTCSGS GRKRCRSCGG    80
SEQ_ID_NO_886    R---PRCATC GGSGRVDC-L CNRWSD--GD -SGCRTCAGS GRMPCRSCGG    85
SEQ_ID_NO_870    R---PRCATC GGSGRVEC-L CNRWSD--GD -SGCRTCAGS GRMPCRSCGG    80
SEQ_ID_NO_878    R---PRCATC GGSGRVEC-L CNRWSD--GD -SGCRTCAGS GRMPCRSCGG    80

SEQ_ID_NO_876    TGTGRPLPVQ SVR....... ...PPNQS.. ...Y.            101
SEQ_ID_NO_855    SGTGRPLPAQ TVQ....... ...PPNRP.. ...Y.             97
SEQ_ID_NO_862    TGTGRPIPVQ SMR....... ...SPNRP.. ...PS             96
SEQ_ID_NO_858    SGTGRPIPVQ LIVR....... ...QPTNR.. ...SF             98
SEQ_ID_NO_856    SGTGRPIPVQ SVR....... ...QPTNR.. ...NS             99
SEQ_ID_NO_885    SGTGRRAPVR VSSS....... ...APPSR.. ......           117
SEQ_ID_NO_868    SGTGRPLPAR LIVQ..... EQKLPTAPGR RGDYN           109
SEQ_ID_NO_886    SGTGRPLPAR LIARGHHHHHH NPPPSSAPGR GGDYS           120
SEQ_ID_NO_870    SGTGRPLPAR LTVQ...HQ KPPPPPPG. ...YN           107
SEQ_ID_NO_878    SGTGRPLPAR LIVQ...HH K--PPPPAG. ...YN           105
```

Figure 29

```
SEQ_ID_NO_907  ------MAV- --------D SMHVVMFPFL AFGHISPFYQ LARKLVAAG-                    33
SEQ_ID_NO_912  ---MAAAVVE AD------DE AMHVALFPFL AFGHISPFAQ LARSLGAVG-                    40
SEQ_ID_NO_911  MGSAGAAPVA TAAGGGGGDG DLHVVMFPFL AFGHISPFAQ LARKMAGVGA                    50
SEQ_ID_NO_898  ----MPSELA MN------ND ELHVVMFPFL AFGHISPFYQ LSNKLFSH--                    38
SEQ_ID_NO_913  ------MSLK GN------DK ELHLVMFPFF AFGHITPFYQ LSNKISSLYP                    38
SEQ_ID_NO_901  ----MENEMK HS------ND ALHVVMFPFF AFGHISPFYQ LANKLSSY--                    38
SEQ_ID_NO_915  ----MENE-- --------K VLHVVMFPFF AFGHISPFAQ LANKLSSH--                    33
SEQ_ID_NO_904  ---MGSQA-- --------T THHMAMYPWF GVGHLTAFFR LANKLASK--                    34
SEQ_ID_NO_905  ---MGSQA-- --------T TYHMAMYPWF GVGHLTGFFR LANKLAGK--                    34
SEQ_ID_NO_908  ---MGSQA-- --------T TYHMAMYPWF GVGHLTGFFR LANKLAGK--                    34
SEQ_ID_NO_891  ------ME-- --------P TFHAFMFPWF AFGHMPFLH LANKLAEK--                    31
SEQ_ID_NO_893  MSDLISKR-- --------S SFRLLMFPWF AVGHLTPFLH LSNKLAEK--                    37

SEQ_ID_NO_907  GVRVTLLSAA ANVPRVEAML GPAAGAV--A VAPLRLQRVP GLPEGAESTA                    81
SEQ_ID_NO_912  GVRVTFLSAA ANVARVEAML PADGTAV--- VAALHLPRVP GLPVGAESTA                    87
SEQ_ID_NO_911  GVRVTFLSAA ANVPRVEAML GGTGGTS--T VAALELPRVP GLPEGAESTA                    98
SEQ_ID_NO_898  GVHVTFLSAA SNIPRIRSTL NLNPAIN--- VISLKFPN-- ----GTNTA                     79
SEQ_ID_NO_913  GVKITFLAAS ASVSRIETML NPSTNTK--- VIPLTLPRVD GLPEGVENTA                    85
SEQ_ID_NO_901  GVKVSFFTAS GNASRVKSML NSAPTTH--- VPLTLPHVE GLPPGAESTA                      85
SEQ_ID_NO_915  GVKVSFFTAS GNASRLRSML NSAPTTTHID LVPLTLPHVE GLPPGSESTA                    83
SEQ_ID_NO_904  GHRISFLPK  NTQSKLASLF NLHPHLV--S FVPITVPSIP GLPPGAETTS                    81
SEQ_ID_NO_905  GHRISFLPK  NTQSKLESLF NLHPHLI--S FVPIVVPSIP GLPPGAETTS                    81
SEQ_ID_NO_908  GHRISFLPK  NTQSKLESLF NLHPHLI--S FVPIVVPSIP GLPPGAETTS                    81
SEQ_ID_NO_891  GHQITFLLPK KAQKQLEH-H NLFPDSI--V FHPLTIPHVN GLPAGAETTS                    78
SEQ_ID_NO_893  GCTISFLLPN KAIKLLQH-F NLYPDHL--T FHPVKNPHVE GLPLGTETAS                    84

SEQ_ID_NO_907  EVSADGAELL KVAVDGTRPQ VAALLAELRP DALLFDFATP WVTELAAPLR                    131
SEQ_ID_NO_912  EVDADGAELL KLALDGTRPQ VEALLARLRP DVVLFDFATP WVADVARQLG                    137
SEQ_ID_NO_911  EVSADGAELL KLAVDGTRPQ VEALLARLRP DVVLFDFATP WVVDVARPLG                    148
SEQ_ID_NO_898  ELPPHLAGNL FHALDLTQDQ VKSLLLELKP HYVFFDFAQH MLPKLASEVG                    129
SEQ_ID_NO_913  DASPATIGLL YVAIDLMQPQ IKTLLANLKP DFVIFDFVHW MLPEIASELG                    135
SEQ_ID_NO_901  ELTPASAELL KVALDLMQPQ IKTLLSHLKP HFVLFDFAQE MLPKMANGLG                    135
SEQ_ID_NO_915  ELTPVTAELL KVALDLMQPQ IKTLLSHLKP HFVLFDFAQE MLPKMADELG                    133
SEQ_ID_NO_904  DVPFSSTHLL MEAMDKTQTD IEILKNLEV DVVFFDFTH  MLPGLARKIG                      130
SEQ_ID_NO_905  DVPFPSTHLL MEAMDKTQND IEILKDLKV DVVFYDFTH  MLPSLARKIG                      130
SEQ_ID_NO_908  DVPFPSTHLL MEAMDKTQND IEILKDLKV DVVFYDFTH  MLPSLARKIG                      130
SEQ_ID_NO_891  DISSMDNLL  SEALDLTRDQ VEAAVRALRP DLIFFDFAH  MPEIAKEHM                      127
SEQ_ID_NO_893  DIPIHLTHFL CVAMDRTRDQ VEKIIRDCKP DFVMYDMAY- MPEVARPLG                      133
```

Figure 29 (continued)

| | | | | | | | |
|---|---|---|---|---|---|---|---|
| SEQ_ID_NO_907 | IKALQFSVFS | AVSGAYLMNP | ARRLGAGGQL | --PTADDLTS | PPAGFPPSSS | 179 | |
| SEQ_ID_NO_912 | ARAAHFSVFT | AVTSAYLTVP | ARRLHHGAA | SCPTVDDLAT | APVGFPPSSS | 187 | |
| SEQ_ID_NO_911 | VKAALFSVFA | AVSGAYVMAP | ARRRLPGPWR | --PTVDDLAS | APEGFPPSSP | 196 | |
| SEQ_ID_NO_898 | IKSVHFSVYS | AISDAYITVP | SRFADVEGRN | --ITFEDLKK | PPPGYPQNSN | 177 | |
| SEQ_ID_NO_913 | IKTIYFSVYM | ----ANIVWP | STSKLTGNKP | --SIVEDIK- | ---ALQQSDG | 175 | |
| SEQ_ID_NO_901 | IKTVYYSVVV | ALSTAFLTCP | ARVLE-PKKY | --PSLEDMKK | PPLGFPQTSV | 182 | |
| SEQ_ID_NO_915 | IKTVFYSVFV | ALSTAFLTCP | ARVTE-PKKY | --PTLEDMKK | PPLGFPHTSI | 180 | |
| SEQ_ID_NO_904 | IKSVFYSTIS | PLMHGFALSP | ERRVA--GKQ | --LTEADMMK | APASFPDPSI | 176 | |
| SEQ_ID_NO_905 | IKSVFYSTIS | PLMHGYALSP | ERRVV-GKQ | --LTEADMMK | APASFPDPSI | 176 | |
| SEQ_ID_NO_908 | IKSVFYSTIS | PLMHGYALSP | ERRVV-GKQ | --LTEADMMK | APASFPDPSI | 176 | |
| SEQ_ID_NO_891 | IKSVSYMVS | ATTIAYTFAP | G--------- | -----GVLGV | PPPGYPSSKV | 183 | |
| SEQ_ID_NO_893 | IKTIKYSVVS | AAAIAIVLVP | ARNVV-EGKA | --ITAAELSV | PPTGYPSTSV | 180 | |

| | | | | | | | |
|---|---|---|---|---|---|---|---|
| SEQ_ID_NO_907 | ITVPAYQAA | DFSYVFTSFH | GEP-CVYDRV | LAGVQASDAL | VIKTCFEMEG | 228 | |
| SEQ_ID_NO_912 | LATVPTYQAA | DFTYVFTSFH | GMP-SAYDRV | AACDKASDVL | VFKTCAEMEG | 236 | |
| SEQ_ID_NO_911 | LATVPAYQAA | DFSYVFESFH | GMP-CVYDRV | AACHNACDAL | VIKTCAEMEG | 245 | |
| SEQ_ID_NO_898 | I-SLKAFEAM | DFMFLFTRFS | EKNLTGYERV | LQSLGECSFI | VFKTCKEIEG | 226 | |
| SEQ_ID_NO_913 | LI-PVKTFEAI | SLMNVFKSFH | -------DNM | DKCINGCNLM | LIKSCREMEG | 217 | |
| SEQ_ID_NO_901 | T-SVRTFEAR | DFLYVFKSFH | NGP-TLYDRI | QSGLRGCSAI | LAKTCSQMEG | 230 | |
| SEQ_ID_NO_915 | T-SVKTFEAQ | DFLYIFKSFN | NRP-TVYDRV | LSGLKGCSAI | LAKTCSQMEG | 228 | |
| SEQ_ID_NO_904 | K--LHAHEAR | GFTARTVMKF | GGDITFFDRI | FTAVSESDGL | AYSTCREIEG | 224 | |
| SEQ_ID_NO_905 | K--LHAHEAR | GFTARTVMKF | GGDITFFDRI | FTAVSESDGL | AYSTCREIEG | 224 | |
| SEQ_ID_NO_908 | K--LHAHEAR | GFTARTVMKF | GGDITFFDRI | FTAVSESDGL | AYSTCREIEG | 224 | |
| SEQ_ID_NO_891 | LI-YRENDAH | ALATLSIFVK | ----RLYHQI | TTGFKSCDI | ALRTCNEIEG | 207 | |
| SEQ_ID_NO_893 | VI--LRGHEVR | SLLFVSQPVG | EGT-TFYERA | CTGMKGCDAI | AIRSCYEMEE | 227 | |

| | | | | | | | |
|---|---|---|---|---|---|---|---|
| SEQ_ID_NO_907 | PYINYLTAQH | GKPVLVTGPV | VPEPPQGE-L | EERWARMLSS | FPDNAVVFAS | 277 | |
| SEQ_ID_NO_912 | PYIEYVATQY | DKPILVTGPL | VPEPPHGE-L | EERWETMLSS | FPDNAVVFAS | 285 | |
| SEQ_ID_NO_911 | PYIDYIAAEH | GKPVLVTGPI | VPEPPRGE-L | EERWATMLSS | FPDNSVVFAS | 294 | |
| SEQ_ID_NO_898 | PYLDYIETQF | RKPVLLSGPL | VPEPSTDV-L | EEKWSKMLDG | FPAKSVILCS | 275 | |
| SEQ_ID_NO_913 | SRIDDNTKQS | TRPVFLIGPV | VPEPHSGE-L | DEITWANMLNR | FPAKSVIYCS | 266 | |
| SEQ_ID_NO_901 | PYIKYVEAQF | NKPVFLIGPV | VPDPPSGK-L | EEKWATMLNK | FEGGTVIYCS | 279 | |
| SEQ_ID_NO_915 | PYIEYVKSQF | KKPVLLVGPV | VPDPPSGK-L | EEKWDAMLNK | FEAGTVIYCS | 277 | |
| SEQ_ID_NO_904 | QFCDYIETQF | KKPVLLAGPA | LPVPSKST-M | EQKWSDMGK | FKEGSVIYCA | 273 | |
| SEQ_ID_NO_905 | QFCDYIETQF | CKPVLLAGPA | LPVPSKST-M | EQKWSDMLGK | FKEGSVIYCA | 273 | |
| SEQ_ID_NO_908 | QFCDYIETQF | QKPVLLAGPA | LPVPSKST-M | EQKWSDMLGK | FKEGSVIYCA | 273 | |
| SEQ_ID_NO_891 | KFCDYISSQY | HKKVLLTGPM | LPEDDISKPL | EEQLSHFLSR | FPPRSVVFCA | 257 | |
| SEQ_ID_NO_893 | KLCDYIGRQY | GKPVFLTGPV | LPESARTP-L | EDRWADMLNR | FEAGSVVFCS | 276 | |

Figure 29 (continued)

```
SEQ_ID_NO_907   FGSETFLPAA AATELLLGLE STNRPFFVYL NFPKGTDTEA ELAKCTPPGF  327
SEQ_ID_NO_912   FGSETFLPTA AATELLLGLE ATGDPFVAVL NFPRSVDAEA EVKKCMAPGF  335
SEQ_ID_NO_911   FGSETFLLHA AATELLLGLE ATRLPFLAVL NFPKGTDAEA ELRKLTPPSL  344
SEQ_ID_NO_898   FGSETFLSDY QIKELASGLE LTGLPFILVL NFPSNLSAKA ELERALPKGY  325
SEQ_ID_NO_913   FGSETFLTDD QIRELALGLE LTGLPFFLVL NFPANVDKSA ELKRTLPDGF  316
SEQ_ID_NO_901   FGSETFLTDD QVKELALGLE QTGLPFFLVL NFPANVDVSA ELNRALPEGF  329
SEQ_ID_NO_915   FGSETFLKDD QIKELALGLE QTGLPFFLVL NFPANVDASA ELNRGLPEGF  327
SEQ_ID_NO_904   FGSECTLRKE QFQELLWGLE LTGMPFFAAL KAPFGTDS-- -IEAAIPEEL  320
SEQ_ID_NO_905   FGSECTLRKD KFQELLWGLE LTGMPFFAAL KPPFETES-- -VEAAIPEEL  320
SEQ_ID_NO_908   FGSECTLRKD KFQELLWGLE LTGMPFFAAL KPPFEAES-- -IEAAIPEEL  320
SEQ_ID_NO_891   LQSQIVLEKD QFQELQLGME LTGLPFLIAV KPPRGSST-- -VEEGLPEGF  304
SEQ_ID_NO_893   FGSQLILEKE QLQELVLGFE STGLPFLVVL KPPVGSST-- -IEEALPEGF  323

SEQ_ID_NO_907   AERTKGRGVV HTGWVQQQHI LRHRGVGCFV NHAGLSSVVE GLVAGCRLVL  377
SEQ_ID_NO_912   EERVKGRGVV HSGWVQQQHI LRHRSVGCYV NHAGFSSVVE GLVAGCRLVL  385
SEQ_ID_NO_911   EERVKGRGIL HTGWVQQQHI LRHRSVGCFV NHSGLSSVVE GLIAGCRLVL  394
SEQ_ID_NO_898   LERVKNRGVV HSGWFQQQLV LKHSSVGCYV CHGGFSSVIE AMVNECQLVL  375
SEQ_ID_NO_913   LERVKDKGIV HSGWVQQRHI LAHDSVGCYV FHAGYGSVIE GLVNDCQLVM  366
SEQ_ID_NO_901   LERVKDKGII HSGWVQQQNI LAHSSVGCYV CHAGFSSVIE ALVNDCQVVM  379
SEQ_ID_NO_915   RERVKEKGVI HSGWVQQQHI LAHTSVGCYV CHAGFSSVIE AFMNDCQVVM  377
SEQ_ID_NO_904   REKIHGKGIV HSGWVQQQLF LQHPSVGCFV SHCGWASLSE ALVNDCQIVL  370
SEQ_ID_NO_905   KEKIQGRGIV HGEWVQQQLF LQHPSVGCFV SHCGWASLSE ALVNDCQIVL  370
SEQ_ID_NO_908   KEKIQGRGIV HGEWVQQQLF LQHPSVGCFV SHCGWASLSE ALVNDCQIVL  370
SEQ_ID_NO_891   QERVKGRGVV WGGWVQQPLI LDHPSIGCFV NHCGPGTIME CLMTDCQMVL  354
SEQ_ID_NO_893   EERVKGRGVV WGGWVQQLE LDIPSIGCFV NTCGFGSMAE SLMSDCQIVL  373

SEQ_ID_NO_907   LPMKGDQYLN AALFARDLRV GAEVARRDSD GWFGRGDVSD AVDTAMAD--  425
SEQ_ID_NO_912   LPMKSDQFFN AALLARELRV GTEVARRDGD GWFGHDAVRD AVNAAMAD--  433
SEQ_ID_NO_911   LPMKGDQYLN AALFARELRV GTEVARRARD GWFGREDVRD ALAAAFAG--  442
SEQ_ID_NO_898   LPFKGDQFFN BKLIANDLKA GVEVNRSDED GFFHKEDILE ALKTVMLEDN  425
SEQ_ID_NO_913   LPMKVDQFTN BKVIALELKA GVEVNRRDED GYFGKDDVFE AVESVMMDTE  416
SEQ_ID_NO_901   LPQKGDQILN AKLVSGDMEA GVEINRRDED GYFGKEDIKE AVEKVMVDVE  429
SEQ_ID_NO_915   LPQKGDQLLN AKLVSGDMKA GVEVNRRDED GYFSKDDIEE AVEKVMVEL-  425
SEQ_ID_NO_904   LPQVGDQIIN ARIMSVSLKV GVEVEKGEED GVFSREBVCK AVKAVM-DEK  419
SEQ_ID_NO_905   LPQVGDQIIN ARIMSVSLKV GVEVEKGEED GVFSREBVCK AVKAVM-DEK  419
SEQ_ID_NO_908   LPQVGDQIIN ARIMSVSLKV GVEVEKGEED GVFSREBVCK AVKAVM-DEK  419
SEQ_ID_NO_891   LPFLGDQVLF TRLMTEEFKV SVEVSRLEKT GWFSKEBLSD AIKSVM-DKD  402
SEQ_ID_NO_893   VPHLGDQILN TRLMAEELKV AVEVERLDEK GWFTKENLSN AIKCVM-DKD  421
```

Figure 29 (continued)

| SEQ_ID_NO_907 | ...GMEGQG- ·IKWRDFLMD DAVQKRLADD FVRDFKKFVR A--- | 461 |
| --- | --- | --- |
| SEQ_ID_NO_912 | ...AGGGDDD ERKWREFLTD DAVQRRFVEE FVRELRKLVL ---- | 470 |
| SEQ_ID_NO_911 | ...GEDGGGE EKKWREFLMD DAVQRRFVRE FVAGLRRLKG ---- | 479 |
| SEQ_ID_NO_898 | KEQGKCI REN HMQWSKFLSN KEI QNKFITD LVAQLKSMA- ---- | 464 |
| SEQ_ID_NO_913 | NEPAKSI REN HRKLKEFLQN DEI QKKYIAD FVENLKAL- ---- | 454 |
| SEQ_ID_NO_901 | KDPGKLI REN QKKWKEFLLN KDI QSKYIGN LVNEMTAMAK VSTT | 473 |
| SEQ_ID_NO_915 | ----KVI REN QKKWKEFLLN KDTHSKFVED LVHDMMAMAK LSTT | 465 |
| SEQ_ID_NO_904 | SEI GREVRGN HDKLRGFLLN ADLDSKYMDS FNQKLQDLLG ---- | 459 |
| SEQ_ID_NO_905 | SEI GREVRGN HDKLRGFLMN ADLDSKYMDS FNQKLQDLLG ---- | 459 |
| SEQ_ID_NO_908 | SEI GREVRGN HDKLRGFLLN ADLDSKYMDS FNQKLQDLLG ---- | 459 |
| SEQ_ID_NO_891 | SDLGKLVRSN HAKLKETLGS HGLLTGYVDK FVEELQEYLI ---- | 442 |
| SEQ_ID_NO_893 | SEYGSMI KKN HTEWRKLLRS EGFMSSYFDK FFQNMQELVD HK-- | 463 |

Figure 30

| | | | | | | | |
|---|---|---|---|---|---|---|---|
| SEQ_ID_NO_935 | MAY--DRRRS | -SLFDAFTLS | PLPYPVLLIL | LMVFLLLSLS | WFFDHESFME | | 47 |
| SEQ_ID_NO_917 | MSYYGDRRAE | SSIVEAFTLS | PLPYPVILVL | LMVTLLLGAS | WFFTYDDFIE | | 50 |
| SEQ_ID_NO_925 | MSYY-DRRGE | SSVLEAFTLS | PLPYPVILIL | MMVTLLLGAS | WFFSYEDFME | | 49 |
| SEQ_ID_NO_940 | MAY--QRGET | SSVVEAFTLS | PLPYPVILIL | LMVMLLGVS | WFFTYEDFME | | 48 |
| SEQ_ID_NO_937 | MAYYGDRRPE | SSIVEAFTLS | PLPYPVILIL | LMVSLLLGVS | WFFTYEDFIE | | 50 |
| SEQ_ID_NO_921 | MAY--EERRS | -SILDSFSLS | PLPYPVLLIL | AVASVFLLSS | WYFSLEEAAE | | 47 |
| SEQ_ID_NO_919 | MHY--YRRRS | DSIFDAFTLN | PLPYPVLLIL | AVLSIFLGMS | WFFSYEDMVE | | 48 |
| SEQ_ID_NO_923 | MGY--GRSRA | SSVLDGFSLN | PVPYPVLLIL | SLILFLGIS | WYLSYEEVVE | | 48 |

| | | | | | | | |
|---|---|---|---|---|---|---|---|
| SEQ_ID_NO_935 | ETEEQMSWL | LTLPVVLILV | RWLSSIERL | DDTLMGLFRY | DRRRPSVYGY | | 97 |
| SEQ_ID_NO_917 | EASQQLSWAL | LGVPIALVLL | RWISSVDSF | EGYLGFYPR | ESRWKGRYE- | | 98 |
| SEQ_ID_NO_925 | EASEQFSWFL | LGVPIALVLL | RWISSVDTF | EGYFGFYPT | ESRWRG-YP- | | 96 |
| SEQ_ID_NO_940 | EAAEQLSWAL | LLVPVALVLL | RWISSVDTF | DGYFSFYPT | ERRWNRMDP- | | 96 |
| SEQ_ID_NO_937 | EAAEQFSWAL | LVVPIALVLL | RWISSVDSF | DGYFFGFYPS | ERRWRPGYG- | | 99 |
| SEQ_ID_NO_921 | SAEEQINFAL | LLIPLFLIVL | VRWLSSMENP | DAL-LGMFSS | SRRTTYVSPG | | 96 |
| SEQ_ID_NO_919 | TTEEQMGML | LVVPLVLIVI | VRWLSSMENP | DMI-FVMSPW | DKRRRTHHR- | | 96 |
| SEQ_ID_NO_923 | AAEEQLGAML | LATPVLILV | VRWLSSVDTS | EMFFFNSSPW | ERRRRTHHF- | | 97 |

| | | | | | | | |
|---|---|---|---|---|---|---|---|
| SEQ_ID_NO_935 | SQPQEGSSPW | GIAAVLVLLL | VMVYF---- | ---------- | ---------- | | 122 |
| SEQ_ID_NO_917 | RGPAEGSSPW | GVALLVLLLL | VLARAGCGKV | VYGNPGRLGR | KRRGGDKVKE | | 148 |
| SEQ_ID_NO_925 | AAPSEGSSPW | GVAMVVVLLL | LLASF---- | ---------- | ---------- | | 121 |
| SEQ_ID_NO_940 | -GPAEGSSPW | GVAMVVLLLL | VLASF---- | ---------- | ---------- | | 120 |
| SEQ_ID_NO_937 | SAPAEGSSPW | GVAMLVLLLI | VLASF---- | ---------- | ---------- | | 124 |
| SEQ_ID_NO_921 | AGGDGGSSPW | GVAALIVELL | VLLQY---- | ---------- | ---------- | | 121 |
| SEQ_ID_NO_919 | --PSEGSSPW | GVAAFIVLLL | VLVKF---- | ---------- | ---------- | | 119 |
| SEQ_ID_NO_923 | --PSEGSSPW | GVAALILLVL | VLLHY---- | ---------- | ---------- | | 120 |

| | | | | | | | |
|---|---|---|---|---|---|---|---|
| SEQ_ID_NO_935 | ---HSSQDM | NGP------ | ---------- | ---------- | ---------- | | 132 |
| SEQ_ID_NO_917 | QAGDEAAKFP | NSGMRLATEK | RRRVRRSPSK | KGIVLKQKSR | KVSLQHRSKK | | 198 |
| SEQ_ID_NO_925 | ---HSTFQDM | MKP------ | ---------- | ---------- | ---------- | | 131 |
| SEQ_ID_NO_940 | ---HSTFQDM | MKP------ | ---------- | ---------- | ---------- | | 130 |
| SEQ_ID_NO_937 | ---HETTRDM | NRP------ | ---------- | ---------- | ---------- | | 134 |
| SEQ_ID_NO_921 | ---QSSFLEM | NSG------ | ---------- | ---------- | ---------- | | 131 |
| SEQ_ID_NO_919 | ---QSTFLDS | NLV------ | ---------- | ---------- | ---------- | | 129 |
| SEQ_ID_NO_923 | ---HSTFLDA | NFV------ | ---------- | ---------- | ---------- | | 130 |

Figure 30 (continued)

| | | |
|---|---|---|
| SEQ_ID_NO_935 | - - - | 132 |
| SEQ_ID_NO_917 | L K A | 201 |
| SEQ_ID_NO_925 | - - - | 131 |
| SEQ_ID_NO_940 | - - - | 130 |
| SEQ_ID_NO_937 | - - - | 134 |
| SEQ_ID_NO_921 | - - - | 131 |
| SEQ_ID_NO_919 | - - - | 129 |
| SEQ_ID_NO_923 | - - - | 130 |

Figure 31

| | | |
|---|---|---|
| SEQ_ID_NO_947 | MGI KFSQGPS NTTI HNRS-- -HQDGEDQRN ETATK NHDK PQNQSS--SF | 45 |
| SEQ_ID_NO_972 | MGSL-GPSTI SSMNMAKAAS VVGGKTGVVA VADQQKEVPP KTMNCSSYAF | 49 |
| SEQ_ID_NO_967 | MGSL-GPAVV VSASAAKM-- ---AGGGQDP STERKETSSA FGGGCCGGGF | 44 |
| SEQ_ID_NO_964 | MGSLLGPTVT VNVSMTKPDA AAAGGGQQPP --ERKEGGGR CGVLGC--GF | 46 |
| SEQ_ID_NO_944 | MGSL-GPTVS LSI-MARP-- ----GGQQPA EMERKKDSGV FFGGGC--GF | 40 |
| SEQ_ID_NO_946 | ---MSGVSCP SSVSSAMP-- -----KDLRP NGYNQHQASK RGTCSC---F | 37 |
| SEQ_ID_NO_962 | MGSI SOPVAN LSLAASAQ-- ---------- --AKQQQRDL H----C---F | 29 |
| SEQ_ID_NO_950 | MESVTTRPSP NVVGVANS-- ---------- --------K HGVEWCG-HF | 28 |

| | | |
|---|---|---|
| SEQ_ID_NO_947 | QI PLHYPKYT KSDYEKMPEW QLDRLLREYG LPVLGDSYEK RKFAI GAFLW | 95 |
| SEQ_ID_NO_972 | QMPLHYPRYK KADYESMPEW RVDCLLREYG LPADGDLDSK RKFAMGAFLW | 99 |
| SEQ_ID_NO_967 | QMPLHYPRYK KADYEAMPEW RVDCLLREYG LPVDGGVEEK RRFAMGAFLW | 94 |
| SEQ_ID_NO_964 | RMPLHYPRYK KEDYESMPEW RVDSLLREYG LPADGDLDSK RRFAMGAFLW | 96 |
| SEQ_ID_NO_944 | RMPLHYPRYK KADYESMPEW RVDCLLREYG LPADGDVDSK RRFAMGAFLW | 90 |
| SEQ_ID_NO_946 | QMPLHYPRYK KSDYETMPEW RLDCLLKEYG LPAI GDANDK RKFAMGAFLW | 87 |
| SEQ_ID_NO_962 | RMPLHYPRYT RADYESMPEW KLDCLLREYG LPVTGDVDHK RSFAMGAFLW | 79 |
| SEQ_ID_NO_950 | QMPLHYPRYT QADYEAMPEW RLDCLLKEYG LPI FGDVESK RKFAMGAFLW | 78 |

| | | |
|---|---|---|
| SEQ_ID_NO_947 | SSENEH | 101 |
| SEQ_ID_NO_972 | PDQY- | 103 |
| SEQ_ID_NO_967 | PDQY- | 98 |
| SEQ_ID_NO_964 | PDQY- | 100 |
| SEQ_ID_NO_944 | PDQY- | 94 |
| SEQ_ID_NO_946 | PSENE- | 92 |
| SEQ_ID_NO_962 | PAH--- | 82 |
| SEQ_ID_NO_950 | I K---- | 80 |

Figure 32

```
SEQ_ID_NO_976    ------MALH LNTVIDLTVD NYWLFRIPPI TIDFLNKLPQ QSEAPTPASA    44
SEQ_ID_NO_980    MAPSTIYQYH MRQDFSTNVD SN---NSTAP TTDAIIHLQ FSHVLELCYP      47
SEQ_ID_NO_978    ---------- ---------- ---------- MARLLFRLLQ ETNSPTPATP     20

SEQ_ID_NO_976    VTAQLTRRFT CSTGDFL-VL YRQPQRVEEM VTAAGLPLEC APSVAEFISL    92
SEQ_ID_NO_980    ETIQIPLNTT NESHLFPRCL FSSHVNRESI VKEILSSMGC SSDFIESAAP    97
SEQ_ID_NO_978    SP-------- --------AL YSDLVF--VV IAALLCALIC VLGLLAVSF-    49

SEQ_ID_NO_976    SVRSNSYRK- ---------- --PVVMTVEV GAPVDEDEDE DEEL------   123
SEQ_ID_NO_980    DISSFALDMV TNPCNASSSE VLTMVLAIHV TTPYDEREEI DRALSESLMQ   147
SEQ_ID_NO_978    --RCVWLRRI ANR------- ---------- SATNSDQPPA NKGLKKKVLK    80

SEQ_ID_NO_976    ---------- ---------- -PPGAVFEEC AICVKEYLVG GATSVKLACS   152
SEQ_ID_NO_980    EASRFKPASK SCIDGLKRMS LEGSCSMKEC MVCLEEFLMG SEVLVCLPCG   196
SEQ_ID_NO_978    SLPKLTYSPD S--------- -PPAEKFAEC AICLNEFAAG DELRVLSQCG   120

SEQ_ID_NO_976    ITFHRKCLDR ATAVNRTCPY CRAPVPVEQD YWDDEDACDN GESESDDIPS   202
SEQ_ID_NO_980    HLFHGDCIVR WLETSHLCPL CRFAMPL--- ---------- ---------   222
SEQ_ID_NO_978    HGFHVSCIDT WLGSHSSCPS CRQILV---- ---------- SIARCQKCGG   156

SEQ_ID_NO_976    EEGDDEESEY DDIPSEGGDD EETEHDDI PS EEGDDWESEY EDVPNEEDDG   252
SEQ_ID_NO_980    ---------- ---------- ---------- ---------- ----------   222
SEQ_ID_NO_978    LPGSSSSGPE PDTRIKQDDP NSNNNDNXSX LN-------- ----------   188

SEQ_ID_NO_976    SSPAPDGSSQ EITAASPEFV SSVRDLSLSC LRLD    286
SEQ_ID_NO_980    ---------- ---------- ---------- ----    222
SEQ_ID_NO_978    ---------- ---------- ---------- ----    188
```

Figure 33

| SEQ_ID | Block 1 | | | | | Length |
|---|---|---|---|---|---|---|
| SEQ_ID_NO_991  | -MAMGMLEVH | LISGKGLRAH | DPLN------ | ------KPID | PYVENYKGQ | 37 |
| SEQ_ID_NO_1032 | -MAMGMLEVH | LISGKGLQAH | DPLN------ | ------KPID | PYVENYKGQ | 37 |
| SEQ_ID_NO_985  | -MGMGMLEVH | LISGKGLQAH | DPLN------ | ------KPID | PYVDNYKGQ | 37 |
| SEQ_ID_NO_992  | -MAMGMLEVH | LISGKGLQAH | DPLN------ | ------KPID | PYVENYKGQ | 37 |
| SEQ_ID_NO_1008 | MAGSGVLEVH | LVDAKGLTGN | DFL------- | -------GKID | PYVVVQYRSQ | 37 |
| SEQ_ID_NO_1001 | -MPRGTLEVV | LISAKGLEDN | DFL------- | -------SSID | PYVILSYRAQ | 36 |
| SEQ_ID_NO_1003 | -MAQGTLEVL | LVGAKGLENT | DYL------- | -------CNMD | PYAVLKCTSQ | 36 |
| SEQ_ID_NO_1028 | -MVQGTLEVL | LVGAKGLENT | DYL------- | -------CNMD | PYAVLKCRSQ | 36 |
| SEQ_ID_NO_984  | -MPQGKLQVV | LVSAKGLENT | DFL------- | -------CNMD | PYVLLTCRTQ | 36 |
| SEQ_ID_NO_995  | -MPEGTIQVV | LVGAKGLENT | DFFNYRVPCN | DVKTYPSNID | PYVLLTCRSQ | 49 |
| SEQ_ID_NO_982  | -MPHGTLEVV | LVSAKGLEDS | DFL------- | -------NSMD | PYVLLTCRTQ | 36 |
| SEQ_ID_NO_996  | -MPHGTLEVV | LVSAKGLEDA | DFL------- | -------NNMD | PYVQLTCRTQ | 36 |
| SEQ_ID_NO_1011 | -MVRGKLEVL | LVSAKGLDDS | DFF------- | -------NSMD | PYVILTCRSH | 36 |
| SEQ_ID_NO_1023 | -MVHGKLEVL | LVSAKGLEDT | DFL------- | -------NNMD | PYVILTCRTQ | 36 |
| SEQ_ID_NO_1026 | ---------- | ---------- | ---------- | --------MD | PYVILTCRTQ | 12 |

| SEQ_ID | Block 2 | | | | | Length |
|---|---|---|---|---|---|---|
| SEQ_ID_NO_991  | ERMSKVAKNA | GPDPVWNEKF | KFLAEYPGSG | GDFLLFKVM  | DHDVIDGDDY | 87 |
| SEQ_ID_NO_1032 | ERMSKVAKNA | GPDPVWNEKF | KFLAEYPGSG | GDFLLFKVM  | DHDVIDGDDY | 87 |
| SEQ_ID_NO_985  | ERMSGVAKNG | GPNPLWDEKF | KFLAEYPGSG | GDFHLFKVM  | DHDADGDDY  | 87 |
| SEQ_ID_NO_992  | ERMSKVAKNA | GPDPLWDEKF | KFLAEYPGSG | GDFHVLFKVM | DHDAIDGDDY | 87 |
| SEQ_ID_NO_1008 | ERKSSVARDQ | GKNPSWNEVF | KFQINSTAAT | GDHKLFLRLM | DHDTFSRDDF | 87 |
| SEQ_ID_NO_1001 | EHKSTVQEGA | GSNPQWNETF | LFTV---SD  | SASELNLRIM | EKDNFNNDDN | 82 |
| SEQ_ID_NO_1003 | EQKSTVASGK | GSDPEWNETF | VFTV---SE  | NATELVKLL  | DSDGGTDDDS | 82 |
| SEQ_ID_NO_1028 | EQKSSVASGK | GSDPEWNETF | MFSV---TH  | NATELIKLM  | DSDSGTDDDF | 82 |
| SEQ_ID_NO_984  | EQKSSVASGK | GSEPEWNEDF | FNI----SE  | GASELAKIM  | DSDAGSQDDF | 82 |
| SEQ_ID_NO_995  | EQRSSVASGQ | GSEPEWNETF | VFTI---SE  | GTSELVLKIV | DHDTLTDDDY | 95 |
| SEQ_ID_NO_982  | DQKSNVASGQ | GTTPEWNETF | IFNV---SE  | GTTELKAKIF | DTDVGTEDDP | 82 |
| SEQ_ID_NO_996  | DQKSNVAEGM | GTTPEWNETF | FTV----SE  | GTTELKAKIF | DKDVGTEDDA | 82 |
| SEQ_ID_NO_1011 | EQKSTVASGA | GSEPEWNETF | FFAV---BG  | DSPELRVKIM | DSDALSADDL | 82 |
| SEQ_ID_NO_1023 | EQKSSVANGE | GSEPEWNETF | FTV----SD  | DIPQLNLKIM | DSDLVTNDDF | 81 |
| SEQ_ID_NO_1026 | EQKSSVAKGA | GSEPEWNETF | VFTV---SD  | DVPQLNVKIM | DSDAFSADDF | 58 |

Figure 33 (continued)

| | | | | | | |
|---|---|---|---|---|---|---|
| SEQ_ID_NO_991  | IGDVSIDVKD | LLVEGVRKGW | SELPPRMYQV | AHKLYFKGE | EVGVSFKRQ | 137 |
| SEQ_ID_NO_1032 | IGDVSIDVKD | LLVEGVRKGW | SELPPRMYQV | AHKLYFKGE | EVGVSFKRQ | 137 |
| SEQ_ID_NO_985  | IGDVKIDVKD | LLAEGVRKGW | SEIPPRMYHV | AHKIHFKGE | EVGVSFKLQ | 137 |
| SEQ_ID_NO_992  | IGDVKIDVKD | LLAEGVRKGW | SEIRPRMYHV | AHKIHFKGE | EVGVSFKLQ | 137 |
| SEQ_ID_NO_1008 | LGEATINVTD | LLSLGMEHGT | WEMSESKHRV | LADKIYHGE | RVSLTFTAS | 137 |
| SEQ_ID_NO_1001 | LGEAIPLEA | VFEEG----  | -SLAENAYKL | MKEQEYCGE | KVALTFTPE | 125 |
| SEQ_ID_NO_1003 | VGEATIPLDG | VYTEG----  | -SIPPTVYNV | MKDEEYRGE | KIGLTFTPE | 125 |
| SEQ_ID_NO_1028 | VGEATISLEA | IYTEG----  | -SIPPTVYNV | MKEEEYRGH | KVGLTFTPE | 125 |
| SEQ_ID_NO_984  | VEEVAIPLEP | VFIER----  | -NIPLTPYTV | MKDGEYRGE | KFSLTFTPE | 125 |
| SEQ_ID_NO_995  | LGKASIPLEP | LFIEG----  | -NLPITAYNV | MKDEEYRGE | RVGLSFTPE | 138 |
| SEQ_ID_NO_982  | LGEATIPLEA | VFLEG----  | -DPPAAYNV  | MKDEEFKGE | IWALSFKPS | 125 |
| SEQ ID NO_996  | VGEATIPLEP | VFMEG----  | -SIPPTAYNV | MKDEEYKGE | IWALSFKPS | 125 |
| SEQ_ID_NO_1011 | VGEACIPLEA | VLCFG----  | -SLPPAVHRV | MKDEEYRGE | KIALTFTPA | 125 |
| SEQ_ID_NO_1023 | VGEASIPLEA | VFQEG----  | -SLPPTVHPV | MKEEKYCGE | KLALTFTPA | 124 |
| SEQ_ID_NO_1026 | VGEANLPLEP | VFLEG----  | -SLPPAVHRV | MKEEKYCGE | KVALTFTPA | 101 |

| | | | | | | |
|---|---|---|---|---|---|---|
| SEQ_ID_NO_991  | ---------- | ---------- | ---------- | ---------- | ---------- | 137 |
| SEQ_ID_NO_1032 | ---------- | ---------- | ---------- | ---------- | ---------- | 137 |
| SEQ_ID_NO_985  | ---------- | ---------- | ---------- | ---------- | --GGGGCGGC | 145 |
| SEQ_ID_NO_992  | ---------- | ---------- | ---------- | ---------- | --GGGGCAGC | 145 |
| SEQ_ID_NO_1008 | ---------- | ---------- | ---------- | ---------- | AKAQDHAEQV | 147 |
| SEQ_ID_NO_1001 | ---------- | ---------- | ---------- | ---------- | --RNDEEETC | 133 |
| SEQ_ID_NO_1003 | --E------- | ---------- | ---------- | ---------A | RDEDQPHHNY | 137 |
| SEQ_ID_NO_1028 | --D------- | ---------- | ---------- | ---------D | RDRGLSEEDI | 137 |
| SEQ_ID_NO_984  | ERE------- | ---------- | ---------- | ---------S | RDFEV-EESF | 138 |
| SEQ_ID_NO_995  | RRT------- | ---------- | ---------- | ---------S | RTFDAGEESY | 152 |
| SEQ_ID_NO_982  | --E------- | ---------- | ---------- | ---------N | RSRGFEEESY | 137 |
| SEQ_ID_NO_996  | --E------- | ---------- | ---------- | ---------N | RSRGMDEESY | 137 |
| SEQ_ID_NO_1011 | ---------- | ---------- | ---------- | ---------- | -EENEEEESY | 134 |
| SEQ_ID_NO_1023 | -VE------- | ---------- | ---------- | ---------T | RRPDNEEGTY | 137 |
| SEQ_ID_NO_1026 | AVKTLTSVSC | NIDGVVAIVS | EHLVGVCDAN | VLDTRISSGN | SPSSQPRERG | 151 |

Figure 33 (continued)

| SEQ_ID_NO_991 | . G . . . . . . . . . | 138 |
| SEQ_ID_NO_1032 | . G . . . . . . . . . | 138 |
| SEQ_ID_NO_985 | N P W E N . . . . . . | 150 |
| SEQ_ID_NO_992 | Y P W E N . . . . . . | 150 |
| SEQ_ID_NO_1008 | G G W A H S F R Q . . | 156 |
| SEQ_ID_NO_1001 | G G W K E S T R D F . | 143 |
| SEQ_ID_NO_1003 | G G W N Q S S . . . . | 144 |
| SEQ_ID_NO_1028 | G G W K Q S S . . . . | 144 |
| SEQ_ID_NO_984 | G G W K Q S S Y T D . | 148 |
| SEQ_ID_NO_995 | G G W K E S A Y T D . | 162 |
| SEQ_ID_NO_982 | G G W K N S E A S Y . | 147 |
| SEQ_ID_NO_996 | G G W K N S E A S Y . | 147 |
| SEQ_ID_NO_1011 | G G W N Q S T . . . . | 141 |
| SEQ_ID_NO_1023 | S S W N . . . . . . . | 141 |
| SEQ_ID_NO_1026 | G G L Q Q L E L I A C Y | 163 |

Figure 34

```
SEQ_ID_NO_1058   MHRFASGLAS ---------- ------KARL ARKGANQIAS RSSASRN---      31
SEQ_ID_NO_1077   ---MASTFAG MSSAGPLAAP STSSNKLSSY ANISSTSFGS KRNVALRKSR      47
SEQ_ID_NO_1078   ---MASTFAG MSSAGPLAAP SISSNKLSSY ANISSISFGS KRNVALRKSR      47
SEQ_ID_NO_1075   ---MNTQIHP --HTSLLFFP PN----RFNF ISSFSSF--- -----RRRNP      33
SEQ_ID_NO_1095   ---MTTARGL ---------- ------SART TRGA------ -----SNRRV      20
SEQ_ID_NO_1055   ---MAQSQLA ---------- ------KGSR QTTGRPFQNK P----ARAAR      27
SEQ_ID_NO_1080   ---MATIPTT --GSASLLRG SA---ALQRD GRSTRPSSAA RPLPGRRARS      42
SEQ_ID_NO_1086   ---MATMPST CASSSSLFLL IR----KDRR SSRSASL--- -----PGPAR      35
SEQ_ID_NO_1085   ---MATIPTT --DSALLLGS SA---LHRA RRASAARLPG A----NRRRP      37
SEQ_ID_NO_1097   ---MATIPTT --DSGLLLCS ------SALL RRIRRAASSA RLPAAARRRP      39
SEQ_ID_NO_1054   ---MASANAI --STASPFRP LS----QGRL ---------- ----ATRSQ      25
SEQ_ID_NO_1088   ---MASANAI --STASLLRS FS----SQGRV RRAK------ -----NGRAQ      31
SEQ_ID_NO_1068   ---MASANAL --SSASVLCS SR----QSKL G-GGNQQQGQ RVSYNKRIIR      40
SEQ_ID_NO_1072   ---MATANAL --SSPSVLCS SR----QCKL SL-GGSQQKGQ RVSY-RKANR    39
SEQ_ID_NO_1057   ---MASANAL --SSASILCS PN----KGSL RRKGNQRQNQ RVNY-RQGNN      40
SEQ_ID_NO_1061   ---MATSNAL --STASILCS PK----QGGL RRRGNQONNS RLNY-GLSSR      40
SEQ_ID_NO_1076   ---MASTNAL --SSTGILRS PTN---QADT SLSKKVKQHG RVNF-RQKPN      41
SEQ_ID_NO_1092   ---MASTNAL --SSTGILRS PTNN--QADT SLSKKAKOHG RVNY-RQNPN      42
SEQ_ID_NO_1074   ---MASTNAL --SSASILRS PN----RQSL TRRANH--NG RVNY-RKPNN      38
SEQ_ID_NO_1083   ---MASTNAL --SSASILRS PN----HQSL SRRANQ--NG RVNY-RQPNH      38

SEQ_ID_NO_1058   ------YAAK DVKFGVEARG --LMLKGVED LADAVKVTMG PKGRNVVIEQ      73
SEQ_ID_NO_1077   RLTIL-AAAK ELFFNKDGSA IKKLQNGVNK LADLVGVTLG PKGRNVVLES      96
SEQ_ID_NO_1078   RPTIL-AAAK ELFFNKDGSA IKKLQNGVNK LADLVGVTLG PKGRNVVLES      96
SEQ_ID_NO_1075   QFAVR-ASPK KISFGKECRE --NLQVGIDK LADAVSLTVG PKGRNVILSE      80
SEQ_ID_NO_1095   QVQVR-AEAK KLIFDMARRR --KIQAGIDK LADAVGVTLG PRGRNVLEE       67
SEQ_ID_NO_1055   RLVIRAADAK EIVFDQESRR --RLQAGINK VADAVGVTLG PRGRNVVLEQ      75
SEQ_ID_NO_1080   LSVVR-ASAK DIAFDQASRS --ALQAGVEK LAAAVGVTLG PRGRNVVLDE      89
SEQ_ID_NO_1086   RLGIVRASAK EIAFDQGSRS --SLQAGVEK LAAAVAVTLG PRGRNVVLDE      83
SEQ_ID_NO_1085   CALVR-ASAK EIAFDQGARA --SLQAGVEK LAAAVGVTLG PRGRNVVLDE      84
SEQ_ID_NO_1097   CLLVR-ASAK EIAFDQGSRA --SLQAGVEK LAAAVGVTLG PRGRNVVLDE      86
SEQ_ID_NO_1054   RFVVR-ANAK DIAFDQKSRA --ALQAGVEK LANAVGVTLG PRGRNVVLDE      72
SEQ_ID_NO_1088   RLVVR-ADAK DIAFDQKSRA --ALQAGVEK LANAVGVTLG PRGRNVVLDE      78
SEQ_ID_NO_1068   RFSVR-ANYK EIAFDQHSRA --ALQAGIDK LADCVGLTLG PRGRNVVLDE      87
SEQ_ID_NO_1072   RFSLR-ANYK EIAFDQSSRA --ALQAGIDK LADAVGLTLG PRGRNVVLDE      86
SEQ_ID_NO_1057   RFGVK-ACAK EIAFDQSSRA --AMQAGIDK LADAVGLTLG PRGRNVVLDE      87
SEQ_ID_NO_1061   RFSVR-ANAK DIAFDQKSRA --ALQSGIDK LADAVGLTLG PRGRNVVLDE      87
SEQ_ID_NO_1076   RFVVK-AAAK DIAFDQHSRS --AMQAGIDK LADAVGLTLG PRGRNVVLDE      88
SEQ_ID_NO_1092   RFWVK-AAAK DIAFDQHSRR --AMQAGIDK LADAVGLTLG PRGRNVVLDE      89
SEQ_ID_NO_1074   RFSVK-ASAK EIAFDQHSRS --AMQAGIDK LADAVGLTLG PRGRNVVLDE      85
SEQ_ID_NO_1083   RFAVK-ASAK EIAFDQSSRA --AIQAGIDK LADAVGLTLG PRGRNVVLDE      85
```

Figure 34 (continued)

| SEQ_ID_NO_1058 | SYGAPKVTKD | GVTVAKSIEF | KDKVKNVGAS | LVKQVANKTN | DVAGDGTTCA | 123 |
|---|---|---|---|---|---|---|
| SEQ_ID_NO_1077 | KYGAPKIVND | GVTVAREVEL | EDPVKNIGAK | LVRQAAKTN | DLAGDGTTTS | 146 |
| SEQ_ID_NO_1078 | KYGAPKIVND | GVTVAREVEL | EDPVENIGAK | LVRQAAKTN | DLAGDGTTTS | 146 |
| SEQ_ID_NO_1075 | -SGKLKVIND | GVTIARSIEL | SDAIENAGAM | LIQEVASKMN | DLAGDGTSTA | 129 |
| SEQ_ID_NO_1095 | KFGMPQVIND | GVTIARAIEL | PDPVENAGAM | LIKEVAGRTN | DSAGDGTTTA | 117 |
| SEQ_ID_NO_1055 | KFGVPQVIND | GVSIRRAIEL | KDPVENAGAQ | LIKEVAGRTN | DAAGDGTTTA | 125 |
| SEQ_ID_NO_1080 | -FGSPKVVND | GVTIARAIEL | ADPMENAGAA | LIREVASKTN | DSAGDGTTTA | 138 |
| SEQ_ID_NO_1086 | -FGSPKVVND | GVTIARAIEL | ADPMENAGAA | LIREVASKTN | DSAGDGTTTA | 132 |
| SEQ_ID_NO_1085 | -FGTPKVVND | GVTIARAIEL | ADPMENAGAS | LIREVASKTN | DSAGDGTTTA | 133 |
| SEQ_ID_NO_1097 | -FGTPKVVND | GVTIARAIEL | ADPMENAGAA | LIREVASKTN | DSAGDGTTTA | 135 |
| SEQ_ID_NO_1054 | -YGNPKVVND | GVTIARAIEL | YDPMENAGAA | LIREVASKTN | DSAGDGTTTA | 121 |
| SEQ_ID_NO_1088 | -YGSPKVVND | GVTIARAIEL | YDPMENAGAA | LIREVASKTN | DSAGDGTTTA | 127 |
| SEQ_ID_NO_1068 | -FGSPKVVND | GVTIARAIEL | PNAMENAGAA | LIREVASKTN | DSAGDGTTTA | 136 |
| SEQ_ID_NO_1072 | -FGSPKVVND | GVTIARAIEL | PDAMENAGAA | LIREVASKTN | DSAGDGTTTA | 135 |
| SEQ_ID_NO_1057 | -FGSPKVVND | GVTIARAIEL | PNAMENAGAA | LIREVASKTN | DSAGDGTTTA | 136 |
| SEQ_ID_NO_1061 | -FGSPKVVND | GVTIARAIEL | PDPMENAGAA | LIREVASKTN | DSAGDGTTTA | 136 |
| SEQ_ID_NO_1076 | -FGSPKVVND | GVTIARAIEL | PDPMENAGAA | LIREVASKTN | DSAGDGTTTA | 137 |
| SEQ_ID_NO_1092 | -FGSPKVVND | GVTIARAIEL | PDPMENAGAA | LIREVASKTN | DSAGDGTTTA | 138 |
| SEQ_ID_NO_1074 | -FGSPKVVND | GVTIARAIEL | PDPMENAGAA | LIREVASKTN | DSAGDGTTTA | 134 |
| SEQ_ID_NO_1083 | -FGSPKVVND | GVTIARAIEL | PDAMENAGAA | LIREVASKTN | DSAGDGTTTA | 134 |

| SEQ_ID_NO_1058 | EILTRAIFTE | GCKSVAAGMN | AMDLRRGISM | AVDSVVTNLK | SRARMSTSE | 173 |
|---|---|---|---|---|---|---|
| SEQ_ID_NO_1077 | VVLAQGLIAE | GVKVMAAGAN | PVLITRGIEK | TAKAVAELK | NMSKEVEDS- | 195 |
| SEQ_ID_NO_1078 | VVLAQGLIAE | GVKVMAAGAN | PVLITRGIEK | TAKAVAELK | NMSKEVEDS- | 195 |
| SEQ_ID_NO_1075 | IILARAMIKS | GLSAVAFGAN | PISLKKGMEK | TVKDLVKFLK | KRSIPVEGRD | 179 |
| SEQ_ID_NO_1095 | SVLAREMIKY | GLQSVAAGAN | PVTVKRGMDK | TSEFCRKKLD | ELTIPVRNAA | 167 |
| SEQ_ID_NO_1055 | SVLAREMIHY | GLQSVTAGAN | PIAVKRGLDK | TAEYLVAKLK | EHAKPVKGRD | 175 |
| SEQ_ID_NO_1080 | SVLAREIIKL | GLLSVTGAN | PVSIKKGIDK | TVQSLVEELE | KKSRPVKGSG | 188 |
| SEQ_ID_NO_1086 | SVLAREIIKL | GLLSVTGAN | PVSIKKGIDK | TVHSLVEELE | KKSRPVKGSG | 182 |
| SEQ_ID_NO_1085 | SVLAREIIKL | GMLSVTGAN | PVSIKKGIDK | TVQKLVEELE | KKSRPVKGGG | 183 |
| SEQ_ID_NO_1097 | SVLAREIIKL | GMLSITGAN | PVSVKKGIDK | TVQKLVEELE | KKSRPVKGGG | 185 |
| SEQ_ID_NO_1054 | CVLAREIIKL | GLLSVTGAN | PVSLKKGIDK | TVQGLIQELE | NKSRPIKGGG | 171 |
| SEQ_ID_NO_1088 | SVLAREIIKL | GLLSVTGAN | PVSLKKGIDK | TVHGLIEELE | KKARPVKGSG | 177 |
| SEQ_ID_NO_1068 | SILAREIIKH | GLLSVISGAN | PVSLKRGIDK | TVQGLIEELQ | KKARPVKGRD | 186 |
| SEQ_ID_NO_1072 | SVLAREIIKH | GLLSVTSGAN | PVSLKRGIDK | TVQALIEELE | KRSRPVKGGR | 185 |
| SEQ_ID_NO_1057 | SVLAREIIKL | GLLTVTSGAN | PVSVKRGIDK | TVQSLIEELE | KKARPVKGRD | 186 |
| SEQ_ID_NO_1061 | SVLAREIIKL | GLLSVTSGAN | PVSIKRGIDK | TVQGLVEELE | KKARPVKGRD | 186 |
| SEQ_ID_NO_1076 | SILAREIIKL | GLLNVTSGAN | PVSIKKGIDK | TVAALVEELE | KLARPVKGGD | 187 |
| SEQ_ID_NO_1092 | SILAREIIKL | GLLSVTSGAN | PVSIKKGIDK | TVAGLIEELE | KLARPVKGGD | 188 |
| SEQ_ID_NO_1074 | SVLAREIIKL | GLLSVTSGAN | PVSLKRGIDK | TVQGLVEELE | KKARPVKGGD | 184 |
| SEQ_ID_NO_1083 | SVLAREIIKL | GLLSVTSGAN | PVSLKRGIDK | TVQGLVEELE | KRARPVKGGD | 184 |

Figure 34 (continued)

| SEQ_ID_NO | | | | | | |
|---|---|---|---|---|---|---|
| SEQ_ID_NO_1058 | EIAQVGTISA | NGEREGELI | AKAMEKVGKE | GVITISDGKT | LFNELEVVEG | 223 |
| SEQ_ID_NO_1077 | ELPDVAAVSA | GNNLEVGSMI | AEPMSTVGRK | GVVTLEEGKS | AENSLRVVEG | 245 |
| SEQ_ID_NO_1078 | ELADVAAVSA | GNNLEVGSMI | AEAMSKVGRK | GVVTLEEGKS | AENSLRVVEG | 245 |
| SEQ_ID_NO_1075 | HIKAVASISA | GNDEYVGNLI | AEAIEKIGFD | GVITIESSRS | SETSVVIEEG | 229 |
| SEQ_ID_NO_1095 | DIRAVASISA | GNNEEIGNMI | AEAIEKVGPD | GVLSIETSSG | LETVVEVEEG | 217 |
| SEQ_ID_NO_1055 | DIKNVASISA | GNDNAIGEMI | ADALDKVGSN | GVLSIETSNS | TETVVEVQEG | 225 |
| SEQ_ID_NO_1080 | DIKAIAAISA | GNDDFIGTMI | AEAINKVGPD | GVLSIESSSS | FETTVEVEEG | 238 |
| SEQ_ID_NO_1086 | DIKAVAAISA | GNDDFVGTMI | AEAIDKVGPD | GVLSIESSSS | FETTVEVEEG | 232 |
| SEQ_ID_NO_1085 | DIKAVAAISA | GNDEFVGTMI | AEAIDKVGPD | GVLSIESSSS | FETTVEVEEG | 233 |
| SEQ_ID_NO_1097 | DIKAVAAISA | GNDEFVGTMI | AEAIDKVGPD | GVLSIESSSS | FETTVEVEEG | 235 |
| SEQ_ID_NO_1054 | DIKAVASISA | GNDEFIGSMI | AEAIDKVGPD | GVLSIESSSS | FETTVEVEEG | 221 |
| SEQ_ID_NO_1088 | DIKAVASISA | GNDELIGSMI | ADAIDKVGPD | GVLSIESSSS | FETTVDVEEG | 227 |
| SEQ_ID_NO_1068 | DIRAVASISA | GNDDLIGSMI | ADAIDKVGPD | GVLSIESSSS | FETTVEVEEG | 236 |
| SEQ_ID_NO_1072 | DIKAVATISA | GNDELIGAMI | ADAIDKVGPD | GVSPIESSSS | FETTVEVEEG | 235 |
| SEQ_ID_NO_1057 | DIKAVASISA | GNDDLIGTMV | ADAIDKVGPD | GVLSIESSSS | FETTVDVEEG | 236 |
| SEQ_ID_NO_1061 | DIKAVASISA | GNDELIGTMI | ADAIDKVGPD | GVLSIESSSS | FETVVEVEEG | 236 |
| SEQ_ID_NO_1076 | DIKAVATISA | GNDELIGKMI | AEAIDKVGPD | GVLSIESSNS | FETTVEVEEG | 237 |
| SEQ_ID_NO_1092 | DIKAVASISA | GNDELIGKMI | AEAIDKVGPD | GVLSIESSSS | FETTVEVEEG | 238 |
| SEQ_ID_NO_1074 | DIKAVASISA | GNDELIGDMI | AEAIDKVGPD | GVLSIESSSS | FETTVEVEEG | 234 |
| SEQ_ID_NO_1083 | DIKAVASISA | GNDELIGKMI | AEAIDKVGPD | GVLSIESSSS | FETTVEVEEG | 234 |

| SEQ_ID_NO | | | | | | |
|---|---|---|---|---|---|---|
| SEQ_ID_NO_1058 | MKLDRGYISP | YFITNQKNQK | CELDDPLILI | HEKKISSINS | VVKVLELALK | 273 |
| SEQ_ID_NO_1077 | MQFDRGYFAP | YFVTDSEKMS | VEYDNCKLLL | VDKKITNAKD | LVNVLKDAIR | 295 |
| SEQ_ID_NO_1078 | MQFDRGYVSP | YFVTDSEKMS | VEYENCKLLL | VDKKITNARD | LVNVLEDAIR | 295 |
| SEQ_ID_NO_1075 | MKIDRGYMSP | HFITNQEKSI | VEFDNAKVLV | TDQKISSVRE | IVPLLEKAMQ | 279 |
| SEQ_ID_NO_1095 | MEIDRGYISP | QFVNDNERLM | VEYEGCRILI | TDEKIEQVQM | LVPLLEEVSQ | 267 |
| SEQ_ID_NO_1055 | MEIDRGYISP | QFVTNQERLL | VEYDNCRVLV | TDQKIDAIRD | IIPILEQVTR | 275 |
| SEQ_ID_NO_1080 | MEIDRGYISP | QFVTNSEKSV | VEFENARVLV | TDQKISSIKE | ILPLLEQTTQ | 288 |
| SEQ_ID_NO_1086 | MEIDRGYISP | QFVTNPEKSL | VEFENARILV | TDQKISSIKE | IIPLLEQTTQ | 282 |
| SEQ_ID_NO_1085 | MELDRGYISP | QFVTNPEKST | VEFENARILV | TDQKISSIKE | ILPLLEQTTQ | 283 |
| SEQ_ID_NO_1097 | MELDRGYISP | QFVTNPEKST | VEFENARILV | TDQKISSIKE | IIPLLEQTTQ | 285 |
| SEQ_ID_NO_1054 | MEIDRGYISP | QFVTNLEKSI | VEFENCKYLI | TDQKITSIKE | ILPILEKTTQ | 271 |
| SEQ_ID_NO_1088 | MEIDRGYISP | QFVTNLEKSI | VEFENAKVLI | TDQKITSIKE | ILPILEKTTQ | 277 |
| SEQ_ID_NO_1068 | MEIDRGYISP | QFVTNPEKLL | AEFENARVLI | TDQKITAIKD | IIPILEKTTQ | 286 |
| SEQ_ID_NO_1072 | MEIDRGYISP | QFVTNPEKLL | VEFENARVLI | TDQKITAIKD | IIPILEKTTQ | 285 |
| SEQ_ID_NO_1057 | MEIDRGYISP | QFVTNPEKLL | CEFENARVLV | TDQKITAIKD | IIPLLEKTTQ | 286 |
| SEQ_ID_NO_1061 | MEIDRGYISP | QFVTNPEKLL | CEFENARVLI | TDQKITAIKD | IIPLLEKTTQ | 286 |
| SEQ_ID_NO_1076 | MEIDRGYISP | QFVTNPEKSI | VEFENARVLI | TDQKISAIKD | IIPLLEKTTQ | 287 |
| SEQ_ID_NO_1092 | MEIDRGYISP | QFVTNLEKSI | VEFENARVLI | TDQKISAIKD | IIPLLEKTTQ | 288 |
| SEQ_ID_NO_1074 | MEIDRGYISP | QFVTNPEKLI | VEFENARVLI | TDQKISAIKD | IIPLLEKTTQ | 284 |
| SEQ_ID_NO_1083 | IEIDRGYISP | -FVTNLEKSI | VEFENARVLV | TDQKISAIKD | IIPLLEKTTQ | 283 |

Figure 34 (continued)

| SEQ_ID_NO | | | | | | |
|---|---|---|---|---|---|---|
| SEQ_ID_NO_1058 | RQ- RPLLIVS | EDVESDALAT | LILNKLRAG | KVCAIKAPGF | GENRKASLHD | 322 |
| SEQ_ID_NO_1077 | NG- SPILIIA | ENIDQEALAT | LVVNKLRGAL | KNAALKAPGF | GERKSQYLDD | 344 |
| SEQ_ID_NO_1078 | NG- YPILIIA | EDIEQEALAT | LVVNKLRGAL | KVAALKAPGF | GERKSQYLDD | 344 |
| SEQ_ID_NO_1075 | LS- APLLIIA | EDVTAQVLET | LIVNKMQGLL | RVAAVKCPGL | GDSKKALLQD | 328 |
| SEQ_ID_NO_1095 | AGSPPLLIIA | EDITGEALAT | LVVNKMRGVL | KVAAIKAPGF | GERRKALLQD | 317 |
| SEQ_ID_NO_1055 | LN- APLLIIA | EDVSGEALAT | LVVNKLRGVL | NVCAIKAPGF | GERRKSLLQD | 324 |
| SEQ_ID_NO_1080 | LR- APLLIIA | EDVSGEALAT | LVVNKLRGIL | NVAAIKAPGF | GERRKALLQD | 337 |
| SEQ_ID_NO_1086 | LR- APLLIIA | EDVAGEALAT | LVVNKLRGIL | NVAAIKAPGF | GERRKALLQD | 331 |
| SEQ_ID_NO_1085 | LR- APLLIIA | EDVSGEALAT | LVVNKLRGIL | NVAAIKAPGF | GERRKALLQD | 332 |
| SEQ_ID_NO_1097 | LR- APLLIIA | EDVSGEALAT | LVVNKLRGIL | NVAAIKAPGF | GERRKALLQD | 334 |
| SEQ_ID_NO_1054 | LR- APLFIIA | EDITGEALAT | LVVNKLRGIL | NVAAIKAPSF | GERRKAVLQD | 320 |
| SEQ_ID_NO_1088 | LR- APLFIIA | EDITGEALAT | LVVNKLRGIL | NVAAIKAPSF | GERRKAVLQD | 326 |
| SEQ_ID_NO_1068 | LR- APLLIIA | EDVTGEALAT | LVVNKLRGVL | NVVAVKAPGF | GERRKAMLQD | 335 |
| SEQ_ID_NO_1072 | LR- APLLIIA | EDVTGEALAT | LVVNKLRGVL | NVVAVKAPGF | GERRKAMLQD | 334 |
| SEQ_ID_NO_1057 | LR- APLLIIA | EDVTGEALAT | LVVNKLRGIL | NVAAIKAPSF | GERRKAVLQD | 335 |
| SEQ_ID_NO_1061 | LR- APLLIIA | EDVTGEALAT | LVVNKLRGVL | NVAAIKAPGF | GERRKAMLQD | 335 |
| SEQ_ID_NO_1076 | LR- APLLIIS | EDITGEALAT | LVVNKLRGIL | NVAAIKAPGF | GERRKALLQD | 336 |
| SEQ_ID_NO_1092 | LR- APLFIIA | EDITGEALAT | LVVNKLRGIL | NVAAIKAPGF | GERRKALLQD | 337 |
| SEQ_ID_NO_1074 | LR- APLLIIA | EDVTGEALAT | LVVNKLRGIL | NVAAIKAPGF | GERRKALLQD | 333 |
| SEQ_ID_NO_1083 | LR- APLIIIA | EDVTGEALAT | LVVNKLRGIL | NVAAIKAPSF | GERRKAVLQD | 332 |

| SEQ_ID_NO | | | | | | |
|---|---|---|---|---|---|---|
| SEQ_ID_NO_1058 | LAVLTGGQLI | TEELGMNLEK | VDLDMEGSCK | KITISKDDIV | LDGAGDKKS | 372 |
| SEQ_ID_NO_1077 | AILTGGTVI | REELGLTLDK | ADKEVLGHAA | KVVLTKDATT | VGDGSTQEA | 394 |
| SEQ_ID_NO_1078 | AILTGGTVI | REELGLTLDK | ADKEVLGHAA | KVVLTKDATT | VGDGSTQEA | 394 |
| SEQ_ID_NO_1075 | ALMTGADFL | CGDLGLTLEG | TTSDQLGSAL | KVKITSNATT | FADPNTKAE | 378 |
| SEQ_ID_NO_1095 | AIVTGAQYI | AKDLGLSVQR | AIMDSLGYAR | KVSIAQTTTT | LIADGASKED | 367 |
| SEQ_ID_NO_1055 | AIVTGAEFI | AKDLGMKVEQ | AVVEQLGVAR | KVTYANNTTT | LIADAASKDE | 374 |
| SEQ_ID_NO_1080 | AIVTGAEFQ | AKDLGQLIEQ | TTVEQLGIAR | KVTISGSSTT | IADVATKDE | 387 |
| SEQ_ID_NO_1086 | AIVTGAEFQ | AKDLGLLVES | TTVEQLGIAR | KVTISQBSTT | IADVATKDE | 381 |
| SEQ_ID_NO_1085 | AIVTGAEYQ | SKDLGLLVEK | TTVEQLGIAR | KVTISSSSTT | IADAASKDD | 392 |
| SEQ_ID_NO_1097 | AIVTGAEYQ | SKDLGLLVEN | TTVEQLGIAR | KVTISSSSTT | IADAASKDD | 394 |
| SEQ_ID_NO_1054 | AIVTGAEFL | AKDLGLLVEN | ATEEQLGTAR | KVTIHQITTT | LIADAASKDE | 370 |
| SEQ_ID_NO_1088 | AIVTGAEFL | AKDLGLLVEN | ATEEQLGTAR | KVTIHQITTT | LIADAASKDE | 376 |
| SEQ_ID_NO_1068 | AILTGAEYL | AMDMSLLVEN | ATIDQLGIAR | KVTISKDSTT | LIADAASKDE | 385 |
| SEQ_ID_NO_1072 | AILTEPS- T | ALDMGLLVEN | TTIDQLGIAR | KVTISKDSTT | LIADAASKAE | 383 |
| SEQ_ID_NO_1057 | AILTGAEFQ | ANDLGLLIEN | TSVEQLGIAR | KVI TKDSTD | IADAASKDE | 385 |
| SEQ_ID_NO_1061 | AILTGAEFQ | ASDLGLSIEN | TSIEQLGLAR | KVTISKDSTT | IADAASKDE | 385 |
| SEQ_ID_NO_1076 | AILTGAEFQ | ASDLGLLVEN | TTIEQLGLAR | KVTISKDSTT | IADAASKDE | 386 |
| SEQ_ID_NO_1092 | AILTGAEYQ | ASDLGLLVEN | TSIEQLGLAR | KVTISKDSTT | IADAASKDE | 387 |
| SEQ_ID_NO_1074 | AILTGAEFQ | ASDLGLLVEN | TSVEQLGLAR | KITISKDSTT | VIADAATKDE | 383 |
| SEQ_ID_NO_1083 | AILTGAEFQ | ASDLGLLVEN | TSIEQLGLAR | KVTISKDSTT | IADAASKDE | 382 |

Figure 34 (continued)

| | | | | | | |
|---|---|---|---|---|---|---|
| SEQ_ID_NO_1058 | EERCEQI RS | A ELSTSDYD | KEKLDERLAK | LSGGVAYLKI | GASEAEVGE | 422 |
| SEQ_ID_NO_1077 | VNKRVAQI KN | LI EAADQDYE | KEKLNERI AK | LSGGVAVI QV | GAQTETELKE | 444 |
| SEQ_ID_NO_1078 | VNKRVAQI KN | LI EAADQDYE | KEKLNERI AK | LSGGVAVI QV | GAQTETELKE | 444 |
| SEQ_ID_NO_1075 | QARI QI KK | DLI ETDNANH | SRKLSERI AK | LTGGI AVI KV | GAHTELELED | 428 |
| SEQ_ID_NO_1095 | DMRVAQLKQ | ELAETDSVYD | TEKLSERI AK | LAGGVAVI KV | GAATETEMEE | 417 |
| SEQ_ID_NO_1055 | EMRI AQLKK | ELAETDSVYD | TEKLSERI AK | LSGGVAVI KV | GAATEAELED | 424 |
| SEQ_ID_NO_1080 | QARI AQLKR | ELSQTDSTYD | SEKLAERI AK | LSGGVAVI KV | GAATETELED | 437 |
| SEQ_ID_NO_1086 | QARI AQLKR | ELSQTDSAYD | SEKLAERI AK | LSGGVAVI KV | GAATETELED | 431 |
| SEQ_ID_NO_1085 | QARI AQLKR | ELSQTDSTYD | SEKLAERI AK | LSGGVAVI KV | GASTEAELED | 432 |
| SEQ_ID_NO_1097 | QARI AQLKR | ELSQTDSAYD | SEKLAERI AK | LSGGVAVI KV | GASTEAELED | 434 |
| SEQ_ID_NO_1054 | QARI AQLKK | ELAETDSVYD | TEKLAERI AK | LAGGVAVI KV | GAATETELED | 420 |
| SEQ_ID_NO_1088 | QARVAQLKK | ELSETDSI YD | TEKLAERI AK | LSGGVAVI KV | GAATETELED | 426 |
| SEQ_ID_NO_1068 | QARI AQLKK | ELFETDSVYD | SEKLAERI AK | LSGGVAVI KV | GAATETELED | 435 |
| SEQ_ID_NO_1072 | QARI SQLKK | ESFETDSVYD | SEKLAERI AK | LSGGVAVI KV | GAATETELED | 433 |
| SEQ_ID_NO_1057 | QARVQQLKK | ELAETDSVYD | TEKLAERI AK | LSGGVAVI KV | GAATETELED | 435 |
| SEQ_ID_NO_1061 | QARI AQLKK | ELSETDSVYD | SEKLAERI AK | LSGGVAVI KV | GAATETELED | 435 |
| SEQ_ID_NO_1076 | QSRVAQLKK | ELSETDSI YD | SEKLAERI AK | LSGGVAVI KV | GAATETELED | 436 |
| SEQ_ID_NO_1092 | QSRVAQLKK | ELSETDSVYD | SEKLAERI AK | LSGGVAVI KV | GAATETELED | 437 |
| SEQ_ID_NO_1074 | QARVAQLKK | ELSQTDSVYD | TEKLAERI AK | LSGGVAVI KV | GAATETELED | 433 |
| SEQ_ID_NO_1083 | QARVAQLKK | ELAETDAVYD | SVKLAERI TK | LSGGVAVI KV | GAATETELED | 432 |

| | | | | | | |
|---|---|---|---|---|---|---|
| SEQ_ID_NO_1058 | KKDRVTDALN | ATKAAVEEGI | VPGGGVALLY | ASKELDKL - | STANFDQKI G | 470 |
| SEQ_ID_NO_1077 | KKLRVEDALN | ATKAAVERGI | VVGGGCTLLR | LAAKVDAI KG | TLANDEEKVG | 494 |
| SEQ_ID_NO_1078 | KKLRVEDALN | ATKAAVEEGI | VVGGGCTLLR | LAAKVDAI KG | TLANDEEKVG | 494 |
| SEQ_ID_NO_1075 | RKLRI EDAKN | ATFAAI NEGL | VPGGGATYVH | LLDLI PAI KN | SMEDLDEQI G | 478 |
| SEQ_ID_NO_1095 | RKLRI EDAKN | ATFAAVEEGI | VPGGGAALVH | LSKMIDEFI P | TLTSAEERLG | 467 |
| SEQ_ID_NO_1055 | RKLRI EDAKN | ATFAAVEEGI | VPGGGAALLH | LSELVPAFKE | TLTDAEEKLG | 474 |
| SEQ_ID_NO_1080 | RKLRI EDAKN | ATFAAI EEGI | VPGGGAAYVH | LSTFVPAI KE | KLDDPEERLG | 487 |
| SEQ_ID_NO_1086 | RKLRI EDAKN | ATFAAI EEGI | VPGGGAAYVH | LSKFVPAI KE | KLDDPEERLG | 481 |
| SEQ_ID_NO_1085 | RKLRI ENAKN | ATFAAI EEGI | VPGGGAAYVH | LSTFVPAI KE | KLDDPEERLG | 482 |
| SEQ_ID_NO_1097 | RKLRI EDAKN | ATFAAI EEGI | VPGGGAAYVH | LSTFVPAI KE | TLDDPEERLG | 484 |
| SEQ_ID_NO_1054 | RQLRI EDAKN | ATFAAI EEGI | VPGGGAAYVH | LSTVVPKI KE | AI EDPDERLG | 470 |
| SEQ_ID_NO_1088 | RQLRI EDAKN | ATFAAI EEGI | VPGGGTAYVH | LSTTVPAI KE | TI EDHDERLG | 476 |
| SEQ_ID_NO_1068 | RKLRI EDAKN | ATFAAI EEGI | VPGGGAALVH | LSTVI PAI KE | TFEDADERLG | 485 |
| SEQ_ID_NO_1072 | RKLRI EDAKN | ATFAAI EEGI | VPGGGATLVH | LSTVI PAI KE | TFEDADVRLG | 483 |
| SEQ_ID_NO_1057 | RKLRI EDAKN | ATFAAI EEGI | VPGGGAALVH | LSTCVPAI KD | KLEDPEERI G | 485 |
| SEQ_ID_NO_1061 | RKLRI EDAKN | ATFAAI EEGI | VPGGGAALVH | LSTCVPAI KD | KI EDADERLG | 485 |
| SEQ_ID_NO_1076 | RKLRI EDAKN | ATFAAI EEGI | VPGGGTALVH | LSGYVPAI KE | KLEDADERLG | 486 |
| SEQ_ID_NO_1092 | RKLRI EDAKN | ATFAAI EEGI | VPGGGTALVH | LSAYVPAI KE | KLEDADERLG | 487 |
| SEQ_ID_NO_1074 | RKLRI EDAKN | ATFAAI EEGI | VPGGGTALVH | LSTHVPAI KD | KLEDADERLG | 483 |
| SEQ_ID_NO_1083 | RKLRI EDAKN | ATFLAI EVGI | VL - VDTALLH | LSTHVPAI KD | KLEDADERLG | 480 |

Figure 34 (continued)

| SEQ_ID | Col1 | Col2 | Col3 | Col4 | Col5 | Col6 | End |
|---|---|---|---|---|---|---|---|
| SEQ_ID_NO_1058 | VQI TQNALKT | PVHTI ASNAG | VEGAVVVGKL | LEDDNPDLGY | DAAKGEYVDM | | 520 |
| SEQ_ID_NO_1077 | ADI VQRALSY | PLKLI AKNAG | VNGSVVSEKV | LSSDDPKFGY | NAATGNYEDL | | 544 |
| SEQ_ID_NO_1078 | ADI VKRALSY | PLKLI AKNAG | VNGSVVSEKV | LSSDDPKFGY | NAATGNYEDL | | 544 |
| SEQ_ID_NO_1075 | ADI VAKALVE | PAKSI AANAG | VDGDVVVEKT | RIFID-VRI GY | NAMTGTYEDL | | 527 |
| SEQ_ID_NO_1095 | AEI VQKALLA | PCRLI GNNAG | VEGDVI VQHV | MEGD-FNYGY | DAMVGEYGDL | | 516 |
| SEQ_ID_NO_1055 | ADI VMKSLRA | PCRLI ADNAG | VEGEVI VQRL | LGKP-FEVGY | NAMI DKVENL | | 523 |
| SEQ_ID_NO_1080 | ADI I QKALVA | PASLI AHNAG | VEGEVI VEKI | KDSE-VEFGY | NAMTDKHENL | | 536 |
| SEQ_ID_NO_1086 | ADI I QKALVA | PAALI AHNAG | VEGEVI VEKI | KESE-VEVGY | NAMADRHENL | | 530 |
| SEQ_ID_NO_1085 | ADI I QKALVA | PAALI AHNAG | VEGEVI VDKI | KESE-VEYGY | NAMADKHENL | | 531 |
| SEQ_ID_NO_1097 | ADI I QKALVA | PAALI AHNAG | VEGEVI VDKI | RESE-VEFGY | NAMADKHENL | | 533 |
| SEQ_ID_NO_1054 | ADI I QKALVA | PASLI AHNAG | VEGVVVEKI | KDSD-VEVGY | NAMTDKYENL | | 519 |
| SEQ_ID_NO_1088 | ADI I QKALVA | PASLI AHNAG | VEGVVVEKI | KDGE-VEVGY | NAMNDKYENL | | 525 |
| SEQ_ID_NO_1068 | ADI VQKALLS | PAALI AQNAG | VEGEVVVEKI | MFSD-VENGY | NAMTDTYENL | | 534 |
| SEQ_ID_NO_1072 | ADI VQKALVA | Q-SLI AQNAG | I EGEVVVEKI | MFSE-VELGY | NAMTDTYENL | | 531 |
| SEQ_ID_NO_1057 | ADI VQKALVA | PASLI AQNAG | MEGEVVVEKV | KNSE-VEI GY | NAMTDTYENL | | 534 |
| SEQ_ID_NO_1061 | ADI VQKALYS | PASLI AQNAG | I EGEVVVEKL | KASE-VEI GY | NAMTDKYENL | | 534 |
| SEQ_ID_NO_1076 | ADI VQKALVA | PAALI AQNAG | I EGEVVVEKI | KNGE-VEVGY | NAMTDTYENL | | 535 |
| SEQ_ID_NO_1092 | ADI VQKALVA | PASLI AQNAG | I EGEVVVEKI | RNGE-VEVGY | NAMTDTYENL | | 536 |
| SEQ_ID_NO_1074 | ADI VQKALI A | PAALI AQNAG | I EGEVVVEKI | KSGE-VEVGY | NAMADRYENL | | 532 |
| SEQ_ID_NO_1083 | ADI VQKALI A | PASLI AQNAG | I EGEVVVEKV | KNGE-VEVGY | NAMTDRYENL | | 529 |

| SEQ_ID | Col1 | Col2 | Col3 | Col4 | Col5 | End |
|---|---|---|---|---|---|---|
| SEQ_ID_NO_1058 | -I KAGI I DPL | KVI RTALVDA | ASVSSLMITT | EAI VVELPKD | E----KEVPA | 565 |
| SEQ_ID_NO_1077 | I MAAGI I DPT | KVVRCCLEHA | ASVAKTFLMS | DCVVVEI KEP | E----AAVAG | 590 |
| SEQ_ID_NO_1078 | -MAAGI I DPT | KVVRCCLEHA | ASVAKTFLMS | DCVVVEI KEP | E----AAYAG | 589 |
| SEQ_ID_NO_1075 | -LNAGVADPS | RVARCALQSA | VSI AGVVLTT | QAI LVDKYL- | -----GSN-K | 569 |
| SEQ_ID_NO_1095 | -I EKGVI DPK | KVTRSGVQNS | CSI AGMVLTT | QAVI TELPKK | KRAI GANAGP | 565 |
| SEQ_ID_NO_1055 | -LDAGVI DPA | KVTRNGLLNS | VSI AGI MLTT | QAVMVEKHKP | SEI PGGMT-A | 571 |
| SEQ_ID_NO_1080 | -VEAGVI DPA | KVTRCALQNA | ASVAGMVLTT | QAI VVEKPSK | K----APA-P | 580 |
| SEQ_ID_NO_1086 | -VQAGVI DPA | KVTRCALQNA | ASVAGMVLTT | QAI VVEKPKK | K----ASA-A | 574 |
| SEQ_ID_NO_1085 | -VEAGVI DPA | KVTRCALQNA | ASVAGMVLTT | QAI VVEKPKK | K----APA-A | 575 |
| SEQ_ID_NO_1097 | -VEAGVI DPA | KVTRCALQNA | ASVAGMVLTT | QAI VVEKPCK | -----APA-A | 576 |
| SEQ_ID_NO_1054 | -MEAGVI DPA | KVTRCALQNA | ASVAGMVLTT | QAI VVEKPKP | K----PQV-A | 563 |
| SEQ_ID_NO_1088 | -I EAGVI DPA | KVTRCALQNA | ASVAGMVLTT | QAI VVEKPKP | K----APV-A | 569 |
| SEQ_ID_NO_1068 | -FEAGVI DPA | KVTRCALQNA | ASVAGMVLTT | QAI VVDKPKP | K----APA-A | 578 |
| SEQ_ID_NO_1072 | -LEAGVI DPA | KVTRCALQNA | ASVAGMVLTT | QAI VVDKPKP | K----APA-A | 575 |
| SEQ_ID_NO_1057 | -LAAGVI DPA | KVTRCALQNA | ASVAGMVLTT | QAI VVEKAKP | K----APA-A | 578 |
| SEQ_ID_NO_1061 | -MEAGVI DPA | KVTRCALQNS | ASVAGMVLTT | QAI VVEKPKP | K----TPA-A | 578 |
| SEQ_ID_NO_1076 | -VESGVI DPA | KVTRCALQNA | ASVAGMVLTT | QAI VVEKPKP | K----AAV-A | 579 |
| SEQ_ID_NO_1092 | -I ESGVI DPA | KVTRCALQNA | ASVAGMVLTT | QAI VVEKPKP | R----APV-P | 580 |
| SEQ_ID_NO_1074 | -VEAGVI DPA | KVTRCALQNA | ASVAGMVLTT | QAI VVEKPKP | K----APV-A | 576 |
| SEQ_ID_NO_1083 | -VEAGVI DPA | KVTRCALQNA | ASVAGMVLTT | QAI VVEKPKP | K----APT-A | 573 |

Figure 34 (continued)

| | | | |
|---|---|---|---|
| SEQ_ID_NO_1058 | MGGGMGGMDY | | 575 |
| SEQ_ID_NO_1077 | NPMDNSGYGY | | 600 |
| SEQ_ID_NO_1078 | NPMDNSGYGY | | 599 |
| SEQ_ID_NO_1075 | NALTNGKVTV | AVSYSWGMMK PMYYKA | 595 |
| SEQ_ID_NO_1095 | MADEEGNFSL | | 575 |
| SEQ_ID_NO_1055 | SGMPSG-MTI | | 580 |
| SEQ_ID_NO_1080 | AGMPQGMM- | | 588 |
| SEQ_ID_NO_1086 | SGAPEGSLAM | | 584 |
| SEQ_ID_NO_1085 | AGAPEGSFAM | | 585 |
| SEQ_ID_NO_1097 | AAAP- | | 580 |
| SEQ_ID_NO_1054 | -EPPEGALTV | | 572 |
| SEQ_ID_NO_1088 | -EPAEGTLTV | | 578 |
| SEQ_ID_NO_1068 | -AAPEG-LMV | | 586 |
| SEQ_ID_NO_1072 | -AAPEG-LMV | | 583 |
| SEQ_ID_NO_1057 | -AAPEG-LTI | | 586 |
| SEQ_ID_NO_1061 | -AATQGQYAV | | 587 |
| SEQ_ID_NO_1076 | -AAPQG-LTI | | 587 |
| SEQ_ID_NO_1092 | -GAPQG-LTV | | 588 |
| SEQ_ID_NO_1074 | -GAPQG-LTV | | 584 |
| SEQ_ID_NO_1083 | -AAPQG-LTI | | 581 |

Figure 35

```
SEQ_ID_NO_1106    MAELNVAPSP PPSTILTLED MLRKLPLPSD ETIRSPATTK MCKIVSHRSS    50
SEQ_ID_NO_1105    .......... .......... .......... .......... .........M    1
SEQ_ID_NO_1108    .......... .......... .......... .......... ......MREY    4
SEQ_ID_NO_1109    --MAAVAPIA MPARVHHHHH HHRRALAASP AALAAAGNGL SATRRVRRSP   48
SEQ_ID_NO_1101    .......... ......MPFA SSSSLIKRRP LL........ ......RHAN   20
SEQ_ID_NO_1099    .......... .......... MTRHVILTSE E......... ......RNSP   15
SEQ_ID_NO_1103    .......... .......... MTRHVILKSP LLVSSEESTM ......RNSP   24

SEQ_ID_NO_1106    PRHPTTKANK G......FQC AEVAGGTTAG CAALVCC.PC GIVGLLVLAT    93
SEQ_ID_NO_1105    TRQNQLQNRR R......SV GEVAGNALAE CAAICCCVPC AVVDMVALAT    44
SEQ_ID_NO_1108    GRGHEEEEGE E--HEPQPGC GEGAGQAAAN CAAVCCCCPL ALLDVLLLVT    52
SEQ_ID_NO_1109    AVEMRRERER RRAREQQPRC GEVAGGTAAE CAAVFCCFPE AVVELVVLAA    98
SEQ_ID_NO_1101    SSGSSCCSGR F......... GEIAGGTTAE CAAICCCCPC GLVNLLVLTI    61
SEQ_ID_NO_1099    PTTMIKHAER R......KV GEVAGGAAAE CAAVCCCPC AVVNLVVLAV    58
SEQ_ID_NO_1103    PSTTSLSKER R......KV GEVAGGAAAE CAAVCCCPC AVVNLMVLAV    67

SEQ_ID_NO_1106    VKLPAGLCRR ALSQKRRKRV KKR....... ......STTL RSRAMSFVSD   130
SEQ_ID_NO_1105    YKVPASLMKK AAINNRKKRL LKQ....... .......... MKKDMKNFLE    77
SEQ_ID_NO_1108    VKLPAGVMRR VRRRRRRHRD RVS....RK KRSAAAAAVE PABPSGSSGK    97
SEQ_ID_NO_1109    VRAPAALCRR AVRGGRRRRV RST....KP KETGAMDIAS PRSLAAAAAK   143
SEQ_ID_NO_1101    YKIPAGICRR ALKRKQRKKL IKKGLFPPRG RGYGCGSCDD PELHIHPMAR   111
SEQ_ID_NO_1099    YRVPAAVCKK AMRQTKRQRF MRR....RH GLLASAAA.. .ESTVHARLK   100
SEQ_ID_NO_1103    YKVPAAVCKK AMRRSKRRRF TRK....RH GLLASATAEG SESTVHARLN   112

SEQ_ID_NO_1106    DEDFGVPSFV PRTPETWPSK SPSVEVAEK- EEEMWAEFY SAGFWRSPSQ   178
SEQ_ID_NO_1105    HEKPGGP--G PETVVVGPTM EELLAQEELP EEDLWARFS VNGFWRSSSS   124
SEQ_ID_NO_1108    AMIGAAP--S PLEAEEEEAR GEAAAAAEL EREIMSSRFY GAGFWRSVSS   144
SEQ_ID_NO_1109    ARKVDAD--F PAT----PKA EHLVDM--- EKEVWASFY GGGFWRSPSQ   182
SEQ_ID_NO_1101    VEDSLRE--F DGEHE AVKK EEL-AMLRL EKEMWETFY GTGFWRSPSQ   153
SEQ_ID_NO_1099    EEDPTAE--I VFEHE NVVN VELNDVVVL EDEMFERFY GAGFWRSPSQ   144
SEQ_ID_NO_1103    EEDLTAE--I VFEHECHVSG GELNDVVRL ENEML-DRFY GAGFWRSPSQ   157
```

Figure 35 (continued)

| SEQ_ID_NO_1106 | ---------- KESN- ---- ---------- ---------- --- | 182 |
|---|---|---|
| SEQ_ID_NO_1105 | ----- QKHEP DELQTGEN-- ---------- ---------- -NR | 139 |
| SEQ_ID_NO_1108 | ---------- GCGSSASMRY Q--------- ---------- --- | 155 |
| SEQ_ID_NO_1109 | REDRRCI AAG DGAAAAALFF FSFTTVVGFL AFLLPFLGKR EDR | 225 |
| SEQ_ID_NO_1101 | RELPAKRSSP RETPNARL-- ---------- ---------- --- | 171 |
| SEQ_ID_NO_1099 | ---------- RDTSSGSI-- ---------- ---------- --- | 152 |
| SEQ_ID_NO_1103 | ---------- KDTSSGSL-- ---------- ---------- --- | 165 |

Figure 36

| | | | | | | | | |
|---|---|---|---|---|---|---|---|---|
| SEQ_ID_NO_1112 | MAQNKMVMV | LLSTFLVMA | RSLWPEEPS | NADD-IRGAC | IEECTKE-NK | | | 48 |
| SEQ_ID_NO_1113 | MAQNKTIAVA | LLLATLVAV- | ----MGKEPE | TLEETLRAGC | KEECSEQKKK | | | 45 |
| SEQ_ID_NO_1114 | MAQNKTIAVA | LLLATLVAV- | ----MGKEPE | TLEEAVRAGC | KEECSEQKKK | | | 45 |

| | | | | | | | |
|---|---|---|---|---|---|---|---|
| SEQ_ID_NO_1112 | APSDKKTCEV | LC------- | ---------- | ---------- | --------T | 61 |
| SEQ_ID_NO_1113 | API DEKQCED | FCFIKTKSIF | EAHKGVKDLK | ADRFIDFCNN | ECNAVYKEDP | 95 |
| SEQ_ID_NO_1114 | API DEKQCED | FCFIKTKSIF | EAHKGVKDLK | ADRFIDFCNN | ECNAVYKEDP | 95 |

| | | | | | | |
|---|---|---|---|---|---|---|
| SEQ_ID_NO_1112 | KLTKKPSEEG | KHD------ | ---------- | ---- | 74 |
| SEQ_ID_NO_1113 | ATSKKCAESC | EADAKEAEVF | LDKVVAYMQT | MKQA | 129 |
| SEQ_ID_NO_1114 | ATSKKCAESC | EADAKEAEVF | LDKVVAYIQT | TKQA | 129 |

Figure 37

| | | | | | | |
|---|---|---|---|---|---|---|
| SEQ_ID_NO_1138 | M- - -KRSREA | EEEEEQAA- - | - -GAELLLLL | SLSRGDKPA- | - - - - - - - - - - | 32 |
| SEQ_ID_NO_1141 | M- - - - - -TKH | PRDGEVIS- - | - -LSLSLTLG | AAADSGERK- | - - - - - - - - - - | 29 |
| SEQ_ID_NO_1143 | -MAMKR-MRS | EDIVGDKDSL | DDMAKCLMLL | S- -HGSGLT- | - - - - - - - - - - | 35 |
| SEQ_ID_NO_1120 | MLLSKYGQAD | HEILTNYR- - | - -SAAAAAAA | A- -TAGA- - - | - - - - - - - - - - | 31 |
| SEQ_ID_NO_1147 | MAKRERAAWE | VEAGAAAD- - | - -TARLLMLL | A- -QAQQHL | LQQHAHHHHH | 44 |
| SEQ_ID_NO_1132 | - - - - -MAMKR | QRSNEGID- - | - -YANCLMLL | S- -CPQQ- - | - - - - - - - - - - | 26 |
| SEQ_ID_NO_1134 | MSAMKR-SRE | DRQVEAAA- - | - -MANCLMLL | S- -KLNDKS- | - - - - - - - - - - | 32 |
| SEQ_ID_NO_1136 | - - - - - - - - - - | - - - - - - - - - - | - -MARILLLF | SGHHQHHAH- | - - - - - - - - - - | 17 |
| SEQ_ID_NO_1145 | - - - - - - - - - - | - - - - - - - - - - | - -MPMPMPVA | A- -RGHR- - - | - - - - - - - - - - | 13 |
| SEQ_ID_NO_1144 | MVAI- - -SE | KSTVETTA- - | - -AANCLMLL | S- -RMGQEN- | - - - - - - - - - - | 30 |
| SEQ_ID_NO_1116 | MVAI- - -SE | NPTVEAT- - - | - -AANCLMLL | S- -RMGQK- - | - - - - - - - - - - | 28 |
| SEQ_ID_NO_1123 | MVAI- - -SE | KSTVDVT- - - | - -AANCLMLL | S- -RMGQEN- | - - - - - - - - - - | 29 |
| SEQ_ID_NO_1140 | -MTIKRSWED | DREVENLA- - | - -MANCLMLL | S- -RVGCS- - | - - - - - - - - - - | 31 |
| SEQ_ID_NO_1133 | MVMINIPMKR | TREANDFDSI | TTMANCLMLL | SQNRSGEFI- | - - - - - - - - - - | 39 |
| SEQ_ID_NO_1118 | - - - - - - -MKR | GRDLDAMD- - | - -MADCLMLL | S- -RMGET- - | - - - - - - - - - - | 25 |
| SEQ_ID_NO_1129 | - - - - - - -MKR | GREESKLD- - | - -MANCLMLL | T- -KMGES- - | - - - - - - - - - - | 25 |

| | | | | | | |
|---|---|---|---|---|---|---|
| SEQ_ID_NO_1138 | - - - - - -TVRK | K- - -VRAAEG | - - -VFECKLC | SRQFPTFQAL | GGHRISHNRP | 70 |
| SEQ_ID_NO_1141 | - - - - - -KPRR | GSSPAASGSG | - - -DFVCKTC | SRAFPSFQAL | GGHRTSHLRG | 70 |
| SEQ_ID_NO_1143 | - - - - - -TDTK | - - - -PKTCPH | PVDVFECKTC | NRQFSSFQAL | GGHRASHKRP | 75 |
| SEQ_ID_NO_1120 | - - - - - - - - - - | - - - -GAGAGR | - - -SFSCKTC | NKNFPSFQAL | GGHRASHKKP | 64 |
| SEQ_ID_NO_1147 | HHHGVGVPPF | PAGRAAVHGR | - - -VFECKTC | SRQFPTFQAL | GGHRASHKRP | 91 |
| SEQ_ID_NO_1132 | - - - - - - - - - - | - - - -KSYENG | - - -EYECKTC | NKKFSSFQAL | GGHRASHKRM | 59 |
| SEQ_ID_NO_1134 | - - - - - -TSTT | TT- -NQDHHN | - - -DFECKTC | NKRFSSFQAL | GGHRASHKRP | 71 |
| SEQ_ID_NO_1136 | - - - - - -YG- - | - - - -PSSPER | - - -VFECKTC | NRRFPSFQAL | GGHRASHKKP | 52 |
| SEQ_ID_NO_1145 | - - - - - - - - - - | - - - - - -APER | - - -VFVCKTC | DRRFPSFQAL | GGHRASHKKP | 44 |
| SEQ_ID_NO_1144 | - - - - - -VD- - | - - - -GGSAKR | - - -VFTCKTC | LKEFHSFQAL | GGHRASHKKP | 65 |
| SEQ_ID_NO_1116 | - - - - - - - - - - | - - - -GGDQKR | - - -VFTCKTC | LKEFHSFQAL | GGHRASHKKP | 61 |
| SEQ_ID_NO_1123 | - - - - - -VD- - | - - - -GGDQKR | - - -VFTCKTC | LKQFHSFQAL | GQHRASHKKP | 64 |
| SEQ_ID_NO_1140 | - - - - - - - - - - | - - - - -GSTPDR | - - -VFHCKTC | DKEFKSFQAL | GGHRASHKRP | 64 |
| SEQ_ID_NO_1133 | - - - - - -DSTT | SNSSNLNSNR | - - -VFECKTC | NRQFPSFQAL | GGHRASHKRP | 80 |
| SEQ_ID_NO_1118 | - - - - - - - - - - | - - - -DRVAGR | - - -VFACKTC | NKKFSSFQAL | GGHRASHKKP | 58 |
| SEQ_ID_NO_1129 | - - - - -ETNY | PISKGSDIG- | - - -DFKCKTC | NRRFSSFQAL | GGHRASHKKP | 65 |

Figure 37 (continued)

| SEQ_ID_NO_1138 | RVDRS----- -----TS--- ---------- ---------- --RRSVHQCS | 85 |
| --- | --- | --- |
| SEQ_ID_NO_1141 | RHGLA----L GLAAATAKET TKKVQEKPA- ---------- --AAATHECH | 103 |
| SEQ_ID_NO_1143 | RLMGE----- -----EHKVD RTKLCSSGN- ---------- --KPKMHECS | 102 |
| SEQ_ID_NO_1120 | KLKES----- -----T---- -GNLLKLPNS PS-------- --KPKTHQCS | 89 |
| SEQ_ID_NO_1147 | RVLQQQQLQQ QQTVVADHAG QLCLGRQPLQ LPLPTTTTPQ QAKPRVHECP | 141 |
| SEQ_ID_NO_1132 | KLAEG----- ---------- -EELKEQAKS LSLWN----- --KPKMHECS | 86 |
| SEQ_ID_NO_1134 | KLLIG----- -----A---- -GEFLVQPS- ---------- --SKKMHECS | 93 |
| SEQ_ID_NO_1136 | RLADG----- ---------- --AGAEPP-- ---------- --KPKVHGCS | 71 |
| SEQ_ID_NO_1145 | RLDDG----- ---------- -GDL------ ---------- --KPKLHGCS | 60 |
| SEQ_ID_NO_1144 | NNENL----- -----S---- -GLMKKTK-- ---------- --ASSSHPCP | 86 |
| SEQ_ID_NO_1116 | NNNES----- ---------L SGLVKKAK-- ---------- --APSSHPCP | 83 |
| SEQ_ID_NO_1123 | NNDAL----- -----SS--- -GLMKKV--- ---------- --KTSSHPCP | 85 |
| SEQ_ID_NO_1140 | KTSDG----- ---------- -SEARTPP-- ---------- --KPKTHECP | 84 |
| SEQ_ID_NO_1133 | RLGGD----- ---------- -LTLSDIPVA AA-------- --KPKTHECS | 104 |
| SEQ_ID_NO_1118 | KLTVG----- -----DN--- -EGLAVSP-- ----K----- --KPKTHECS | 81 |
| SEQ_ID_NO_1129 | KLMVT----- -----DL--- -SCHQELPNP TMKQ------ --QPRMHPCP | 93 |

| SEQ_ID_NO_1138 | ICGVEFAMGC ALGGHMRRHK PMAEDSKRSD PKK------- ---------- | 118 |
| --- | --- | --- |
| SEQ_ID_NO_1141 | CSQGFEMGC ALGGHMRRHR EEAAAAAAV H--------- ---------- | 134 |
| SEQ_ID_NO_1143 | LCGDKFSMGC ALGGHMRRHR A--NEGLSSI MNPLDHA--- ------KVPM | 141 |
| SEQ_ID_NO_1120 | ICGLEFPLGC ALGGHMRRHR APNNVDTTST SSKDHELAVT QPPFLPAVPV | 139 |
| SEQ_ID_NO_1147 | VCGLEFAVGC ALGGHMRRHR AEAEAEATEA PSKVMMR--- --------PA | 180 |
| SEQ_ID_NO_1132 | CGMGFSLGC ALGGHMRKHR AVINEGVSSI NQIIEKF--- --------PV | 125 |
| SEQ_ID_NO_1134 | ICGMEFSLGC ALGGHMRRHR AAIDEKSKNA TKAMMIP--- ---------Y | 131 |
| SEQ_ID_NO_1136 | ICGLEFAVGC ALGGHMRRHR AVAAAGPGVG LGLSLGL--- --GLGPNEDG | 116 |
| SEQ_ID_NO_1145 | VCGLEFAIGC ALGGHMRRHR AMAAGGGGM MPMTPPT--- -----AAALKE | 103 |
| SEQ_ID_NO_1144 | ICGVEFPMGC ALGGHMRRHR NESG-GAGAL VTRELLP--- -----EAALMT | 128 |
| SEQ_ID_NO_1116 | ICGVEFPMGC ALGGHMRRHR NEIG-GGAAL VTRALLP--- -----EPTMTT | 125 |
| SEQ_ID_NO_1123 | ICGVEFPMGC ALGGHMRRHR NESGAAGGAL VTRALLP--- -----EPTVTT | 128 |
| SEQ_ID_NO_1140 | VCGLEFAIGC ALGGHMRRHR DVGNEK--BG RPVAARP--- ---------- | 119 |
| SEQ_ID_NO_1133 | ICGLEFAIGC ALGGHMRRHR AAMSDSASGN SASPPRDDRT VVVKKSNIV- | 153 |
| SEQ_ID_NO_1118 | ICGLEFAIGC ALGGHMRRHR AALNDG--L VTRDLLP--- ---------E | 116 |
| SEQ_ID_NO_1129 | ICGLEFAIGC ALGGHMRKHR TAINDGLLCG KPSSSLS--- -------ILKE | 134 |

Figure 37 (continued)

| | | |
|---|---|---|
| SEQ_ID_NO_1138 | ................ M DLT MADPEF- .......... G DL HR VR --- | 135 |
| SEQ_ID_NO_1141 | ................ ..... APPV- .......... .......... | 138 |
| SEQ_ID_NO_1143 | LMKRSNS--- ---TRVVCSL DLN -LTPL .......... E N -DLK LLF | 170 |
| SEQ_ID_NO_1120 | LKRSNSS--- ---KRVLC-L DLSLALPMY- .......... Q NDSELQ LEK | 171 |
| SEQ_ID_NO_1147 | HDKTCDV--- ---AGGI C-L DLN -LTPS- .......... E NCAKCRSMMV | 211 |
| SEQ_ID_NO_1132 | LKRLNS- ---KRI MG- DLN -LTPL- .......... E ND-DLM- FGL | 153 |
| SEQ_ID_NO_1134 | LKKSNSS--- ---KRI FC-L DLN -LTPR- .......... N EDVDLK LWP | 161 |
| SEQ_ID_NO_1136 | NKKAAA --- ---AAELA-L DLN -EPAL- .......... E EEPADR AML | 145 |
| SEQ_ID_NO_1145 | HGESGDDDAV VGMKRGLW-L DLN -HPPCD EYGAGSESDD ECGHVD-AAA | 149 |
| SEQ_ID_NO_1144 | LKKSSS- ---GRLAC-L DLS -LGMV- .......... E NL-NLK LEL | 156 |
| SEQ_ID_NO_1116 | LKKSSSG--- ---KRVAC-L DLS -LGMV- .......... E NL-NLK LEL | 154 |
| SEQ_ID_NO_1123 | LKKSSSG--- ---KRVAC-L DLS -LGMV- .......... D NL-NLK LEL | 157 |
| SEQ_ID_NO_1140 | ---ESVT--- ---KRGLF-M DLN -LTPL- .......... E N -DLK LNS | 144 |
| SEQ_ID_NO_1133 | --DDDND--- ---RRVWG-L DLN -LTPF- .......... E N -HLE FQL | 179 |
| SEQ_ID_NO_1118 | MNKSTGD--- ---GRDPS-L DLG -LTSW- .......... G VDLELK L | 144 |
| SEQ_ID_NO_1129 | SSKDGDQ--- ---KLNLR-L DLN -LTPL- .......... E ED-DLK LNE | 163 |

| | | |
|---|---|---|
| SEQ_ID_NO_1138 | -------RTG SHCQL QL FV | 148 |
| SEQ_ID_NO_1141 | .......... ----LL ELFV | 144 |
| SEQ_ID_NO_1143 | -------GKM APKVDL RL M | 183 |
| SEQ_ID_NO_1120 | .......... VARPML RCF I | 181 |
| SEQ_ID_NO_1147 | LGAAAGQGVH KTLAML DCSL | 231 |
| SEQ_ID_NO_1132 | -------KSP PTPI PL GLF | 165 |
| SEQ_ID_NO_1134 | -------TAP ISSPVL RI F I | 174 |
| SEQ_ID_NO_1136 | -------GLA VGFRPRGG-- | 156 |
| SEQ_ID_NO_1145 | AGYTFHQFMD TGTMAV DCV- | 168 |
| SEQ_ID_NO_1144 | -------GRP VC-------- | 161 |
| SEQ_ID_NO_1116 | -------GRT VC-------- | 159 |
| SEQ_ID_NO_1123 | -------GRT VY-------- | 162 |
| SEQ_ID_NO_1140 | -------NTV NTALAM --- | 153 |
| SEQ_ID_NO_1133 | -------GKI APT--VDCFL | 190 |
| SEQ_ID_NO_1118 | -------GKV TPTPVNHCFI | 157 |
| SEQ_ID_NO_1129 | .......... -RTPVL NCF I | 172 |

Figure 38

| | | | | | | | |
|---|---|---|---|---|---|---|---|
| SEQ_ID_NO_1162 | MATKIFALLV | LLALSASATT | AVIPQCSLA | PIAAIIPRFL | PPYSAIGFEH | | 50 |
| SEQ_ID_NO_1163 | MATKIFVLLA | LLALSVSTTT | AVIPQCSLA | PNAFIISQFL | PPLTLVGFEH | | 49 |
| SEQ_ID_NO_1161 | MAAKIFAILA | LLALSASVAT | ATIIPQCSQ- | ------QYL | SPVTAARFEY | | 42 |
| SEQ_ID_NO_1159 | MATKIFSLLM | LLALSACVAN | ATIFPQCSQA | PIASLLPPYL | PSMIASVCEN | | 50 |
| SEQ_ID_NO_1164 | MAAKIFCFLM | LLGLSASVAT | ATIFPQCSQA | PIASLLPPYL | SPAVSSMCEN | | 50 |

| | | | | | | | |
|---|---|---|---|---|---|---|---|
| SEQ_ID_NO_1162 | PAVQAYRLQQ | ALAASIL--- | ----QQPLAQ | LQQQSSAHLT | IQTIAAQQ-Q | | 92 |
| SEQ_ID_NO_1163 | PALQAYRLQQ | ALANSIL--- | ----QQPFPQ | LQQQSSAHLT | VQTIAAQQQQ | | 92 |
| SEQ_ID_NO_1161 | PTIQSYRLQE | AIAASILRSL | ALTVQQPYAL | LQQPSLMNLY | LQRIAAQQLQ | | 92 |
| SEQ_ID_NO_1159 | PALQPYRLQQ | AIAASNIPLS | PLLFQQSPAL | ----SLVQSL | VQTIRAQQLQ | | 96 |
| SEQ_ID_NO_1164 | PIVQPYRIQQ | AIATGLLPLS | PLFLQQPSAL | QQLPLVHLV | AQNIRAQQLQ | | 100 |

| | | | | | | | |
|---|---|---|---|---|---|---|---|
| SEQ_ID_NO_1162 | QQFLPSLSQL | AAANPTAYLQ | QQLLASNPLA | VANAIAYQHQ | QQLQQLLPAL | | 142 |
| SEQ_ID_NO_1163 | QQFLPALSQL | ALANPVAYLQ | QQLLASNPLA | LVNNAAYQ-Q | QQLQQVLPVI | | 141 |
| SEQ_ID_NO_1161 | QQLLPTINQV | VAANLAAYLQ | Q--------- | ---------- | ---QQFLPF-F | | 119 |
| SEQ_ID_NO_1159 | QLVLPVINQV | ALANLSPYSQ | Q--------- | ---------- | ---QQFLPF-F | | 123 |
| SEQ_ID_NO_1164 | -------QL | VLANLAAYSQ | Q--------- | ---------- | ---HQFLPF-F | | 119 |

| | | | | | | | |
|---|---|---|---|---|---|---|---|
| SEQ_ID_NO_1162 | SQLAVANPAA | YLQ-SQLFPS | NPLVIANAAA | YLQQQQLQQI | LPVLSQLAVA | | 190 |
| SEQ_ID_NO_1163 | SQVAMANPAA | YLQ-QQQLAV | NPIVAANAAA | YLQQQQLQQI | LPALSQLALV | | 190 |
| SEQ_ID_NO_1161 | NQLAGVNPAA | YLQAQQLLPF | NQLVIRSPAA | FLLQQQL--- | LPIFHLQVVA | | 164 |
| SEQ_ID_NO_1159 | NQLSTLNPAA | YLQ-QQLLPF | SQLA----TA | YSQQQQL--- | LPIFNQLAAL | | 164 |
| SEQ_ID_NO_1164 | NQLAALNSAA | YLQ-QQFLPF | SQLV---AA | YP--RQF--- | LPIFNQLAAL | | 157 |

| | | | | | | | |
|---|---|---|---|---|---|---|---|
| SEQ_ID_NO_1162 | DPNSYL-QQQ | QLLPFNQVAV | ANNAVYEQQH | QLLQVNPLA- | -----AAFLQ | | 233 |
| SEQ_ID_NO_1163 | NPAAYL-QQQ | QLLPFNQLAV | TNTAAYLQQQ | QLLRVNPVVA | ANPLAAAFLQ | | 239 |
| SEQ_ID_NO_1161 | NIAAFLQQQQ | QLLPFYPQVV | GNINAFLQQQ | QLLPFYPQDV | ANN--VAFLQ | | 212 |
| SEQ_ID_NO_1159 | NPAAYL-QQQ | ILLPFSQLAA | ANRASFLTQQ | QLLPFYQQFA | ANP--ATLLQ | | 211 |
| SEQ_ID_NO_1164 | NSAAYL-QQQ | QLLPFSQLAD | VSPAAFLTQQ | QLLPFYLHAM | PNA--GTLLQ | | 204 |

| | | | | | |
|---|---|---|---|---|---|
| SEQ_ID_NO_1162 | QQQRQLLPFN | QMSLNNPALS | WQQPIVGGVG | F- | 264 |
| SEQ_ID_NO_1163 | QQ--QLLPFN | QISLNNPAFS | WQQPIVGSAI | F- | 268 |
| SEQ_ID_NO_1161 | QQ--QLLPFN | QLALTNPTTL | LQQPTIGGAI | F- | 241 |
| SEQ_ID_NO_1159 | LQ--QLLPFV | QLALTDRAAS | YQQHIIGGAL | F- | 240 |
| SEQ_ID_NO_1164 | LQ--QLLPFN | QLALTNSTVF | YQQPIIGGAL | FQ | 234 |

Figure 39

| | | | | | | | |
|---|---|---|---|---|---|---|---|
| SEQ_ID_NO_1167 | MAK------ | -NGI NNSVAV | GI AVQSDWDN | RHFSSSLSLN | VRRLFEFLLQ | | 42 |
| SEQ_ID_NO_1182 | MGR----GG | --GMGNPVNV | GI AVQADWEN | REFI SNI SLN | VRRLFDFLLR | | 43 |
| SEQ_ID_NO_1166 | MGR----GG | --GMGNPVNV | GI AVQADWEN | REFI SNI SLN | VRRLFDFLLR | | 43 |
| SEQ_ID_NO_1183 | MAR----AG | GHGMGNPVNV | GI AVQADWEN | REFI SNI SLN | VRRLFDFLLR | | 45 |
| SEQ_ID_NO_1173 | MARAGGGGGG | GGGI TNAVNV | GI AVQADWEN | REFI SHI SLN | I RRLFDFLIQ | | 50 |
| SEQ_ID_NO_1169 | MSR----GG | GVGI TNAVNV | GI AVQADWEN | REFI SNI SIN | VRRLFDFLIN | | 45 |
| SEQ_ID_NO_1177 | MAR----AG | --GI TNAVNV | GI AVQADWEN | REFI SHI SLN | VRRLFDFLVQ | | 43 |
| SEQ_ID_NO_1180 | MAR----AG | --GI TNAVNV | GI AVQADWEN | REFI SHI SLN | VRRLFDFLVQ | | 43 |
| SEQ_ID_NO_1171 | MAR----AG | --GI TNAVNV | GI AVQADWEN | REFI SHI SLN | VRRLFEFLLQ | | 43 |
| SEQ_ID_NO_1175 | MAK----AG | --GI TNAVNV | GI AVQADWEN | REFI SHI SLN | VRRLFEFLVQ | | 43 |
| | | | | | | | |
| SEQ_ID_NO_1167 | FESSTRSKLA | TLNEKLTVLE | RQLEFLEADF | STAL INPV-- | -------- | | 79 |
| SEQ_ID_NO_1182 | FEATTKSKLA | SLNEKLDI LE | RKLEVLEVQV | SSATTNPSVF | N------ | | 84 |
| SEQ_ID_NO_1166 | FEATTKSKLA | SLNEKLDI LE | RKLEVLEVQV | GSATTNPSVF | N------ | | 84 |
| SEQ_ID_NO_1183 | FEATTKSKLA | SLNEKLDI LE | RKLEVLEVQV | SSATTNPSVF | NL------ | | 86 |
| SEQ_ID_NO_1173 | FESTTKSKLS | SLNLKLDFLE | RRLQLLELQV | STATSNPSLF | ISTTTTTA | | 98 |
| SEQ_ID_NO_1169 | FEATTKSKLA | SLNEKLDTLE | RRLELLEVQV | GTASANPSLF | T------ | | 86 |
| SEQ_ID_NO_1177 | FEATTKSKLA | SLNEKLDVLE | RRLELLEVQV | GNASANPSLF | AT----- | | 85 |
| SEQ_ID_NO_1180 | FEATTKSKLA | SLNEKLDVLE | RRLELLEVQV | GNASANPSLF | AT----- | | 85 |
| SEQ_ID_NO_1171 | FEATTKSKLA | SLNEKLDTLE | RRLELLEVQV | GTASANPSLF | ST----- | | 85 |
| SEQ_ID_NO_1175 | FESTTKSKLA | SLNEKLDLLE | RRLEMLEVQV | STATANPSLF | AT----- | | 85 |

Figure 40

| | | | | | | |
|---|---|---|---|---|---|---|
| SEQ_ID_NO_1187 | MFSWLRGCR | DECSATDQLK | Q----------------A | RDVFVAKEAV | | 32 |
| SEQ_ID_NO_1185 | MFAWLRGCR | DECSASDQLK | Q----------------A | HDVFKAKEVV | | 32 |
| SEQ_ID_NO_1189 | MFSWLRGCR | DECSASDQLK | Q----------------A | RDVFMAKEAV | | 32 |
| SEQ_ID_NO_1190 | MFAWLRGCR | DECSASDQLK | QGVVKEKNRC WFWGAFSYNA | RDVFVAKEAV | | 50 |
| SEQ_ID_NO_1191 | MFAWLRGCR | DECSASDQLK | Q----------------A | RDVFVAKEAV | | 32 |

| | | | | | | |
|---|---|---|---|---|---|---|
| SEQ_ID_NO_1187 | LQKKISQEME | RAKEFKKSGN | KQAAMQCLKR | KRYYESQMNQ | VGSVRLRIDT | 82 |
| SEQ_ID_NO_1185 | LQKKISQEVE | RAKEFTKSGN | KQAAMQCLKR | KRYYESQMNQ | VGSVQLRINT | 82 |
| SEQ_ID_NO_1189 | LQKKISQEME | RAKEFTKSGN | KQAAMQCLKR | KKYYESQMSQ | VGSVQLRINT | 82 |
| SEQ_ID_NO_1190 | LQKKISQEME | RAKEFTKSGN | KQAAMQCLKR | KKYYESQMNQ | VGSVQLRINT | 100 |
| SEQ_ID_NO_1191 | LQKKISQEME | RAKEFTKSGN | KQAAMQCLKR | KKYYESQMNQ | VGSVQLRINT | 82 |

| | | | |
|---|---|---|---|
| SEQ_ID_NO_1187 | KEKMIADNMV | N--K | 94 |
| SEQ_ID_NO_1185 | KERMIADHTG | N--K | 94 |
| SEQ_ID_NO_1189 | KEKMIADHMG | N--K | 94 |
| SEQ_ID_NO_1190 | KEKMIADHSG | NKEDK | 115 |
| SEQ_ID_NO_1191 | KEKMIADHSG | NKEDK | 97 |

Figure 41

```
SEQ_ID_NO_1204        ........MVK TRAAATPR.. ............ .....PSGGG GAGAADITAG      26
SEQ_ID_NO_1203        MGEQSLSDPK PQPLSPFPSP PASAAL---- ......PPPAS ASASASASAA       41
SEQ_ID_NO_1205        MESPNPQDVN SMGDOSPLSP NLHPLS.... ......PSPSA AAAAAA....       37
SEQ_ID_NO_1196        MGEDTPSDPQ PGVDSQPPND SSTTTQAQVQ NQSGDPSNTS TAAVSTVTTA       50
SEQ_ID_NO_1202        MGEQTLGDAQ SLIEPQPL.. ............ .....PAPSS TAVPDGATVD        33
SEQ_ID_NO_1194        ...MSLRKTL TAVNQSSL.. ............ .....PPDSL ISAGNLTVSE       30
SEQ_ID_NO_1200        MGKPVTRSHS LLLHEPSS.. ............ .....PPLS. ..........         22

SEQ_ID_NO_1204        .......... .......... ....KISFRS RKIVKSTPAK GKSVATTTTA            62
SEQ_ID_NO_1203        .......... ..........S TSRTTSAAAS RPKKKVTN-P SPDRNPAKKP            71
SEQ_ID_NO_1205        .......... ..........T PTPAAAAASS RSSRSKKFPH SSDPNQSKKP            68
SEQ_ID_NO_1196        CTAIVACGPT ELVNVPLPTS SPPSKIPSRP RKIRKLSPDL SFDPNASQDA           100
SEQ_ID_NO_1202        ..........S ELNNVPRPTT SPATKIPLRP RKIRKVSPDP STSESQVETP            74
SEQ_ID_NO_1194        .......... ..........VS GSSSRIRFRP RKIRKVSSDP SPRIITIASP            62
SEQ_ID_NO_1200        .......... ..........T TTSSKISFQS RKIRKLSTNK TTTTTTAITS            63

SEQ_ID_NO_1204        .......... .VLS...... .......... ...PP....P LSSPGELAAA            68
SEQ_ID_NO_1203        .......... .RLT...... .......... ...FSIPGRP LSAVGEVGVA            91
SEQ_ID_NO_1205        .......... .RLT...... .......... ...LTVPGRP LSADGEVAAA            88
SEQ_ID_NO_1196        TTSSSTSLTE QRKTVGRTSK TKLSQHRALA VVAPRIIARS LSEEGEVETA           150
SEQ_ID_NO_1202        .......... KPAKTGGRN TTKAAPPRAL TVVPRIVARS LSDGEVEIA              113
SEQ_ID_NO_1194        .......... .......... .......... .......P LSTKSTVDIA              73
SEQ_ID_NO_1200        .......... .TSI...... .......... ...PPL.-KP LSHKGEIELA             71

SEQ_ID_NO_1204        LSHLRTADPL LSEVTASTGA PAFISSPSRP AFHSLAHSIL HQQLAPSAAA           118
SEQ_ID_NO_1203        IRYLRAADPA LAAVIDAH-E PPVFDCPHRP -FHSLVRSIL YQQLAFKAAA           139
SEQ_ID_NO_1205        IQHLRAADPA LATVIDAH-D PPAFQCPHRP -FHSLVRSIL YQQLAFKAAA           136
SEQ_ID_NO_1196        IRHLRDADPL LASLIDLH-P PPTFDTFHAP -FLALTRSIL YQQLAFKAGT           198
SEQ_ID_NO_1202        LRYLRNADPV LSPLIDIH-Q PPTFDNFHTP -FLALTRSIL YQQLAYKAGT           161
SEQ_ID_NO_1194        LRHLQSSDEL LGALITTHND PPVFDSSNTP -FLSLARSIL YQQLATKAAK           122
SEQ_ID_NO_1200        LDHLSKSDPL LAPLLNSH-E PPALNPCTSP -FLSLTKSIL FQQLATNAAK           119
```

Figure 41 (continued)

```
SEQ_ID_NO_1204   AI YARFLAL  PAAADPDAAV  VNPAAVLALS  AADLRAJGVS  ARKAAYLHDL  168
SEQ_ID_NO_1203   SVYSRFLALL  ----G-GESD  VAPDAVLALT  PHQLRQIGVS  PRKASYLHDL  184
SEQ_ID_NO_1205   BVYSRFLSLL  ----G-GEHN  VLPEAVLALT  TQDLRQIGVS  PRKASYLHDL  181
SEQ_ID_NO_1196   SIYTRFISLD  ----G-GENG  VVPETVLSLT  SQDLRQIGVS  GRKASYLHDL  243
SEQ_ID_NO_1202   SIYTRFIALD  ----G-GENG  VVPETVLALT  PQQLRQIGVS  GRKASYLHDL  206
SEQ_ID_NO_1194   CYDRFISLF   ----NGGEAG  VFPESVISLS  AVDLRKIGVS  GRKASYLHDL  168
SEQ_ID_NO_1200   SIYTRFLTLD  ----D-GESD  VNPDTVLSLS  APKLREIGVS  GRKASYLHDL  164

SEQ_ID_NO_1204   AGRFAAGELS  ESAVAAMDEA  ALLAELTKVK  GVGLMVHMF   MIFSLHRPDV  218
SEQ_ID_NO_1203   ARKYASGILS  DAAIVNMDDR  SLAAMLTMVK  GIGSWSVHMF  MIFSLARPDV  234
SEQ_ID_NO_1205   ARKYASGILS  DAAVVNMDDR  SLAAMLTMVK  GIGAWSVHMF  MIFSLNRPDV  231
SEQ_ID_NO_1196   ARKYQTGILS  DSAIVNMDDK  SLFTMLTMVN  GIGSWSVHMF  MIFSLHRPDV  293
SEQ_ID_NO_1202   ARKYQNGILS  DSAIVNMDDK  SLLTMLTMVN  GIGSWSVHMF  MIFSLHRPDV  256
SEQ_ID_NO_1194   ADKYNNGVLS  DELILKMSDE  ELIDRLTLVK  GIGVMTVHMF  MIFSLHRPDV  218
SEQ_ID_NO_1200   AEKYRNGSLS  DSSILEMNDD  MLLNRLTEVK  GIGVWSVHMF  MLFSLHRPDV  214

SEQ_ID_NO_1204   LPSGDLGVRK  GVQELYGLPA  LPKPEEMAAL  CERWRPYRSV  GAWYMWRLME  268
SEQ_ID_NO_1203   LPSADLGVRK  GVQMLYALED  VPRPSQMDKL  CERWRPYRSV  GAWYMWRLIE  284
SEQ_ID_NO_1205   LPAADLGVRK  GVQHLYGLDA  VPRPSQMEKL  CEQWRPYRSV  GAWYMWRLIE  281
SEQ_ID_NO_1196   LPINDLGVRK  GVQLLYNLEE  LPRPSQMDQL  CEKWRPYRSV  ASWYLWRYVE  343
SEQ_ID_NO_1202   LPINDLGVRK  GVQLLYNLED  LPRPSQMDQL  CDKWRPYRSV  ASWYMWREVE  306
SEQ_ID_NO_1194   LPVGDLGVRK  GVKDLYGLKN  LPGPLQMEQL  CEKWRPYRSV  GSWYMWRLIE  268
SEQ_ID_NO_1200   LPVGDLGVRK  GVQSLYGLKD  LPQALEMEQI  CEKWKPYRSV  GSWYMWRLME  264

SEQ_ID_NO_1204   SKGAAAKKAK  SNAIAFLPS-  -------SC-  ----------  ----------  289
SEQ_ID_NO_1203   SKVPQPAPAI  PVGSLAFPS-  --------P   DGQSMLDQDE  QQQQQTVIQM  324
SEQ_ID_NO_1205   SKAPPPPPAI  PVGPPALTE-  -------HGD  ELMLQQQQHQ  QQQCQSVIQM  323
SEQ_ID_NO_1196   AKGAPSSAAA  YAAGASLPP-  ----------  ----LQQEE   PQQHQQQPPL  378
SEQ_ID_NO_1202   AKGTPSSAVA  VATGAGLQQQ  QHHQHHHQHQ  QQEQQQQQQQ  QQQHPPQPQL  356
SEQ_ID_NO_1194   SRKTK-----  ----------  ----------  ----------  ----------  273
SEQ_ID_NO_1200   AKALANKAAK  KA--------  ----------  ----------  ----------  276
```

Figure 41 (continued)

| | | |
|---|---|---|
| SEQ_ID_NO_1204 | ---------- -------- | 289 |
| SEQ_ID_NO_1203 | I DPL QML PGM G------ | 335 |
| SEQ_ID_NO_1205 | I DPL QML PGM G------ | 334 |
| SEQ_ID_NO_1196 | MDPI NSI LNL G-ACAWGQ | 395 |
| SEQ_ID_NO_1202 | LDPI NSMFNL GAACAWGQ | 374 |
| SEQ_ID_NO_1194 | ---------- -------- | 273 |
| SEQ_ID_NO_1200 | ---------- -------- | 276 |

Figure 42

| | | | | | | |
|---|---|---|---|---|---|---|
| SEQ_ID_NO_1241 | MFLVDWFYGV | LASLGLWQKD | AKILFLGLDN | AGKTTLLHML | KDERLVQHQP | 50 |
| SEQ_ID_NO_1229 | MFVDWFYGV | LASLGLWQKE | AKILFLGLDN | AGKTTLLHML | KDERLVQHQP | 50 |
| SEQ_ID_NO_1249 | MFLWDWFYGV | LASLGLWQKE | AKILFLGLDN | AGKTTLLHML | KDERLVQHQP | 50 |
| SEQ_ID_NO_1264 | ---MGIVFTR | LFSSVFGNRE | ARILVLGLDN | AGKTTILYRL | QMGEVVSTIP | 47 |
| SEQ_ID_NO_1251 | ---MGIVFTR | LFSSVFGNRE | ARILVLGLDN | AGKTTILYRL | QMGEVVSTIP | 47 |
| SEQ_ID_NO_1265 | ---MGIVFTR | LFSSVFGNRE | ARILVLGLDN | AGKTTILYRL | QMGEVVSTIP | 47 |
| SEQ_ID_NO_1253 | ---MGIVFTK | LFSSVFGNKE | ARILVLGLDN | AGKTTILYRL | QMGEVVSTIP | 47 |
| SEQ_ID_NO_1210 | ---MGILFTR | MFSSVFGNKE | ARILVLGLDN | AGKTTILYRL | QMGEVVSTIP | 47 |
| SEQ_ID_NO_1267 | ---MGILFTR | MFSSVFGNKE | ARILVLGLDN | AGKTTILYRI | QMGEVVSTIP | 47 |
| SEQ_ID_NO_1213 | ---MGILFTK | MFSNLFGNRE | ARILVLGLDN | AGKTTILYRL | QMGEVVSTIP | 47 |
| SEQ_ID_NO_1248 | ---MGILFSK | MFSSVFGNKE | ARILVLGLDN | AGKTTILYRL | QMGEVVSTIP | 47 |
| SEQ_ID_NO_1232 | ---MGLVFTK | LFSSLFGNKE | ARILVLGLDN | AGKTTILYRL | QMGEVVSTIP | 47 |
| SEQ_ID_NO_1234 | ---MGLVFTR | LFSSVFGNKE | ARILVLGLDN | AGKTTILYRL | QMGEVVSTIP | 47 |
| SEQ_ID_NO_1272 | ---MGLSFTK | LFSRLFAKKE | MRILMVGLDA | AGKTTILYKL | KLGEIVTTIP | 47 |
| SEQ_ID_NO_1268 | ---MGITFAK | LFQRLFSKKE | MRILMVGLDA | AGKTTILYKL | KLGEIVTTIP | 47 |
| SEQ_ID_NO_1211 | ---MGIRFTK | ALSRLFSKKE | MRILMVGLDA | AGKTTILYKL | KLGEIVTTIP | 47 |
| SEQ_ID_NO_1216 | ---MGLSFTK | LLGRLFSEKE | MRILMVGLDA | AGKTTILYKL | KLGEIVTTIP | 47 |
| SEQ_ID_NO_1269 | ---MGLSFTK | LLGRLFSKKE | MRILMVGLDA | AGKTTILYKL | KLGEIVTTIP | 47 |
| SEQ_ID_NO_1239 | ---MGLSFTK | LFSRLFAKKE | MRILMVGLDA | AGKTTILYQL | KLGEIVTTIP | 47 |
| SEQ_ID_NO_1259 | ---MGLTFTK | LFSRLFAKKE | MRILMVGLDA | AGKTTILYKL | KLGEIVTTIP | 47 |
| SEQ_ID_NO_1233 | ---MGLTFTK | LFSRLFAKKE | MRILMVGLDA | AGKTTILYKL | KLGEIVTTIP | 47 |
| SEQ_ID_NO_1235 | ---MGLSFTK | LFSRLFAKKE | MRILMVGLDA | AGKTTILYKL | KLGEIVTTIP | 47 |
| SEQ_ID_NO_1243 | ---MGLSFTK | LFSRLFAKKE | MRILMVGLDA | AGKTTILYKI | KLGEIVTTIP | 47 |
| SEQ_ID_NO_1270 | ---MGLSFTK | LFSRLFAKKE | MRILMVGLDA | AGKTTILYKL | KLGEIVTTIP | 47 |
| SEQ_ID_NO_1242 | ---MGLSFGK | LFSRLFAKKE | MRILMVGLDA | AGKTTILYKL | KLGEIVTTIP | 47 |
| SEQ_ID_NO_1238 | ---MGLSFTK | LFSRLFAKKE | MRILMVGLDA | AGKTTILYKL | KLGEIVTTIP | 47 |
| SEQ_ID_NO_1236 | ---MGLSFTK | LFSRLFAKKE | MRILMVGLDA | AGKTTILYKL | KLGEIVTTIP | 47 |
| SEQ_ID_NO_1240 | ---MGLSFGK | LFSRLFAKKE | MRILMVGLDA | AGKTTILYKL | KLGEIVTTIP | 47 |

Figure 42 (continued)

| | | | | |
|---|---|---|---|---|
| SEQ_ID_NO_1241 | T---------- -----QYPT SEELSIGNIK | FKAFDLGGHQ | IARRVWRDYY | 85 |
| SEQ_ID_NO_1229 | T---------- -----QHPT SEELSIGKIK | FKAFDLGGHQ | IARRVWKDYY | 85 |
| SEQ_ID_NO_1249 | T---------- -----QHPT SEELSIGKIK | FKAFDLGGHQ | IARRVWKDYY | 85 |
| SEQ_ID_NO_1264 | SGFPAPDSLI FFLPFAI GFN VETVQYNNIK | FQVWDLGGQT | SIRPYARCYF | 97 |
| SEQ_ID_NO_1251 | T---------- ------I GFN VETVQYNNIK | FQVWDLGGQT | SIRPYARCYF | 82 |
| SEQ_ID_NO_1265 | T---------- ------I GFN VETVQYNNIK | FQVWDLGGQT | SIRPYARCYF | 82 |
| SEQ_ID_NO_1253 | T---------- ------I GFN VETVQYNNIK | FQVWDLGGQT | SIRPYARCYF | 82 |
| SEQ_ID_NO_1210 | T---------- ------I GFN VETVQYNNIK | FQVWDLGGQT | SIRPYARCYF | 82 |
| SEQ_ID_NO_1267 | T---------- ------I GFN VETVQYNNIK | FQVWDLGGQT | SIRPYARCYF | 82 |
| SEQ_ID_NO_1213 | T---------- ------I GFN VETVQYNNIK | FQVWDLGGQT | SIRPYARCYF | 82 |
| SEQ_ID_NO_1218 | T---------- ------I GFN VETVQYNNIK | FQVWDLGGQT | SIRPYARCYF | 82 |
| SEQ_ID_NO_1232 | T---------- ------I GFN VETVQYNNIK | FQVWDLGGQT | SIRPYARCYF | 82 |
| SEQ_ID_NO_1234 | T---------- ------I GFN VETVQYNNIK | FQVWDLGGQT | SIRPYARCYF | 82 |
| SEQ_ID_NO_1272 | T---------- ------I GFN VETVEYKNIS | FTVWDVGGQD | KIRPLWRHYF | 82 |
| SEQ_ID_NO_1269 | T---------- ------I GFN VETVEYKNIS | FTVWDVGGQD | KIRPLWRHYF | 82 |
| SEQ_ID_NO_1211 | T---------- ------I GFN VETVEYKNIS | FTVWDVGGQD | KIRPLWRHYF | 82 |
| SEQ_ID_NO_1216 | T---------- ------I GFN VETVEYKNIS | FTVWDVGGQD | KIRPLWRHYF | 82 |
| SEQ_ID_NO_1269 | T---------- ------I GFN VETVEYKNIS | FTVWDVGGQD | KIRPLWRHYF | 82 |
| SEQ_ID_NO_1239 | T---------- ------I GFN VETVEYQYS | FTVWDVGGQD | KIRPLWRHYF | 82 |
| SEQ_ID_NO_1259 | T---------- ------I GFN VETVEYKNIS | FTVWDVGGQD | KIRPLWRHYF | 82 |
| SEQ_ID_NO_1233 | T---------- ------I GFN VETVEYKNIS | FTVWDVGGQD | KIRPLWRHYF | 82 |
| SEQ_ID_NO_1235 | T---------- ------I GFN VETVEYKNIS | FTVWDVGGQD | KIRPLWRHYF | 82 |
| SEQ_ID_NO_1243 | T---------- ------I GFN VETVEYKNIS | FTVWDVGGQD | KIRPLWRHYF | 82 |
| SEQ_ID_NO_1270 | T---------- ------I GFN VETVEYKNIS | FTVWDVGGQD | KIRPLWRHYF | 82 |
| SEQ_ID_NO_1242 | T---------- ------I GFN VETVEYKNIS | FTVWDVGGQD | KIRPLWRHYF | 82 |
| SEQ_ID_NO_1238 | T---------- ------I GFN VETVEYKNIS | FTVWDVGGQD | KIRPLWRHYF | 82 |
| SEQ_ID_NO_1236 | T---------- ------I GFN VETVEYKNIS | FTVWDVGGQD | KIRPLWRHYF | 82 |
| SEQ_ID_NO_1240 | T---------- ------I GFN VETVEYKNIS | FTVWDVGGQD | KIRPLWRHYF | 82 |

Figure 42 (continued)

| | | | | | | | |
|---|---|---|---|---|---|---|---|
| SEQ_ID_NO_1241 | AKVDAVVYLV | DANDRERFPE | AKKELDGLLS | DESLTNVPFL | ILGNKIDIPY | | 135 |
| SEQ_ID_NO_1229 | AKVDAVVYLV | DAYDKERFAE | SKKELDALLS | DESLATVPFL | ILGNKIDIPY | | 135 |
| SEQ_ID_NO_1249 | AKVDAVVYLV | DAYDKERFAE | SKKELDALLS | DDSLANVPFL | ILGNKIDIPY | | 135 |
| SEQ_ID_NO_1264 | PNTQAIIYVV | DSSDTDRLVT | AKEEFHAILE | EDELKGAVVL | VYANKQDLPG | | 147 |
| SEQ_ID_NO_1251 | PNTQAIIYVV | DSSDTDRLVT | AKEEFHSILE | EDELKGAVVL | VYANKQDLPG | | 132 |
| SEQ_ID_NO_1265 | PNTQAIIYVV | DSSDTDRLVT | AKEEFHAILE | EDELKGAVVL | VYANKQDLPG | | 132 |
| SEQ_ID_NO_1253 | PNTQAVIYVV | DSSDTDRIGV | AKEEFHAILE | EEELKGAMVL | IFANKQDLPG | | 132 |
| SEQ_ID_NO_1210 | PNTQAVIYVV | DSSDTDRIGV | AKEEFHAILE | EDELKGAVVL | IFANKQDLPG | | 132 |
| SEQ_ID_NO_1267 | PNTQAVIYVV | DSSDTDRIGV | AKEEFHAILE | EEELKGAVVL | IFANKQDLPG | | 132 |
| SEQ_ID_NO_1213 | PNTQAIYVV | DSSDTDRLV | AKEEFHAILE | EEELRGAAVL | FANKQDLPG | | 132 |
| SEQ_ID_NO_1218 | PNTQAIYVV | DSSDVDRLV | AKDEFHAILE | EEELRGAIVL | FANKQDLPG | | 132 |
| SEQ_ID_NO_1232 | PNTQAIYVV | DSSUVDRLV | AKEEFHAILE | EEELKGAVVL | FANKQDLPG | | 132 |
| SEQ_ID_NO_1234 | PNTQAIYVV | DSSDTDRLV | AREEFHAILE | EEELKGAVVL | FANKQDLPG | | 132 |
| SEQ_ID_NO_1272 | QNTQGLIFVV | DSNDRDRVVF | ARDELHRMLN | EDELRDAVLL | VFANKQDLPN | | 132 |
| SEQ_ID_NO_1268 | QNTQGLIFVV | DSNDRDRVSE | ARDELHRMLN | EDELRDAVLL | VFANKQDLPN | | 132 |
| SEQ_ID_NO_1211 | QNTQGLIFVV | DSNDRERVVE | ARDELHRMLN | EDELRDAVLL | VFANKQDLPN | | 132 |
| SEQ_ID_NO_1216 | QNTQGLIFVV | DSNDRDRVGE | AREELHRMLN | EDELRDAVLL | VFANKQDLPN | | 132 |
| SEQ_ID_NO_1269 | QNTQGLIFVV | DSNDRDRVGE | ARDELHRMLN | EDELRDAVLL | VFANKQDLPN | | 132 |
| SEQ_ID_NO_1239 | QNTQGLIFVV | DSNDRDRVVE | ARDELHRMLN | EDELRDAVLL | VFANKQDLPN | | 132 |
| SEQ_ID_NO_1259 | QNTQGLIFVV | DSNDRDRIVE | AKDELHRMLN | EDELRDAVLL | VFANKQDLPN | | 132 |
| SEQ_ID_NO_1233 | QNTQGLIFVV | DSNDRDRVVE | ARDELHRMLN | EDELRDAVLL | VFANKQDLPN | | 132 |
| SEQ_ID_NO_1235 | QNTQGLIFVV | DSNDRDRVVE | ARDELHRMLN | EDELRDAVLL | VFANKQDLPN | | 132 |
| SEQ_ID_NO_1243 | QNTQGLIFVV | DSNDRDRVVE | ARDELHRMLN | EDELREAVLL | VFANKQDLPN | | 132 |
| SEQ_ID_NO_1270 | QNTQGLIFVV | DSNDRDRVVE | ARDELHRMLN | EDELRDAVLL | VFANKQDLPN | | 132 |
| SEQ_ID_NO_1242 | QNTQGLIFVV | DSNDRDRVVE | ARDELHRMLN | EDELREAVLL | VFANKQDLPN | | 132 |
| SEQ_ID_NO_1238 | QNTQGLIFVV | DSNDRDRVVE | AKDELHRMLN | GDELRDAVLL | VFANKQDLPN | | 132 |
| SEQ_ID_NO_1236 | QNTQGLIFVV | DSNDRDRVVE | ARDELHRMLN | EDELRDAVLL | VFANKQDLPN | | 132 |
| SEQ_ID_NO_1240 | QNTQGLIFVV | DSNDRDRVVE | ARDELHRMLN | EDELRDAVLL | VFANKQDLPN | | 132 |

Figure 42 (continued)

| | | | | | | | |
|---|---|---|---|---|---|---|---|
| SEQ_ID_NO_1241 | AASEDELRYH | LGLTGMTTGK | GNI NLAGTNV | RP - - I E VF MC | SI VRK - - MGY | | 181 |
| SEQ_ID_NO_1229 | AASEDELRYH | LGLSNFTTGK | GKVDLYGSNV | RP - - LE VF MC | SI VRK - - MGY | | 181 |
| SEQ_ID_NO_1249 | AASEEELRYH | LGLSSFTTGK | GKVSLCDSNV | RP - - LE VF MC | SVVRK - - MGY | | 181 |
| SEQ_ID_NO_1264 | ALDDAAI TES | LELIIKI KS - - | - - - - - - - - - - | RQ - - WA FKT | SAI KG - EGL | | 181 |
| SEQ_ID_NO_1251 | ALDDAAI TES | LELIIKI KS - - | - - - - - - - - - - | RQ - - WA FKT | SAI KG - EGL | | 166 |
| SEQ_ID_NO_1265 | ALDDAAI TES | LEL HKI KS - - | - - - - - - - - - - | RQ - - WA FKT | SAI KG - EGL | | 166 |
| SEQ_ID_NO_1253 | ALDDAAVTEA | LEL HKI KS - - | - - - - - - - - - - | RQ - - WA FKT | CAVKG - EGL | | 166 |
| SEQ_ID_NO_1210 | ALDDAAVTEA | LEL HKI KS - - | - - - - - - - - - - | RQ - - WA FKT | CAVKG - EGL | | 166 |
| SEQ_ID_NO_1267 | ALDDAAVTEA | LEL HKI KS - - | - - - - - - - - - - | RQ - - WA FKT | CAVKG - EGL | | 166 |
| SEQ_ID_NO_1213 | ALDDAAVTES | LEL HKI KN - - | - - - - - - - - - - | RQ - - WA FKT | SAI KG - EGL | | 166 |
| SEQ_ID_NO_1218 | ALDDAAVTEA | LEL HKI KN - - | - - - - - - - - - - | RQ - - WA FKT | SAI KG - EGL | | 166 |
| SEQ_ID_NO_1232 | ALDDAAVTEA | LEL HKI KN - - | - - - - - - - - - - | RQ - - WA FKT | SAI KG - EGL | | 166 |
| SEQ_ID_NO_1234 | ALDDAAVTES | LEL HKI KN - - | - - - - - - - - - - | RQ - - WA FKT | SAI KG - EGL | | 166 |
| SEQ_ID_NO_1272 | AMNAAEI TDK | LGLHSLRQ - - | - - - - - - - - - - | RPNLWGLI NS | PKEVPLVANL | | 170 |
| SEQ_ID_NO_1268 | AMSAAEI TDK | LGLHSLRQ - - | - - - - - - - - - - | RH - - WFI QST | CATSG - - EGL | | 166 |
| SEQ_ID_NO_1211 | AMNAAEI TDK | LGLHSLRQ - - | - - - - - - - - - - | RH - - WYI QST | CATSG - - EGL | | 166 |
| SEQ_ID_NO_1216 | AMNAAEI TDK | LGLHSLRQ - - | - - - - - - - - - - | RH - - WYI QST | CATSG - - EGL | | 166 |
| SEQ_ID_NO_1269 | AMNAAEI TDK | LGLHSLRQ - - | - - - - - - - - - - | RH - - WYI QST | CATSG - - EGL | | 166 |
| SEQ_ID_NO_1239 | AMNAAEI TDK | HGLHSLRQ - - | - - - - - - - - - - | RH - - WYI QST | CATSG - - EGL | | 166 |
| SEQ_ID_NO_1259 | AMNAAEI TDK | LGLHSLRQ - - | - - - - - - - - - - | RH - - WYI QST | CATSG - - EGL | | 166 |
| SEQ_ID_NO_1233 | AMNAAEI TDK | LGLHSLRQ - - | - - - - - - - - - - | RH - - WYI QST | CATSG - - EGL | | 166 |
| SEQ_ID_NO_1235 | AMNAAEI TDK | LGLHSLRQ - - | - - - - - - - - - - | RH - - WYI QST | CATSG - - EGL | | 166 |
| SEQ_ID_NO_1243 | AMNAAEI TDK | LGLHSLRQ - - | - - - - - - - - - - | RH - - WYI QST | CATSG - - EGL | | 166 |
| SEQ_ID_NO_1270 | AMNAAEI TDK | LGLHSLRQ - - | - - - - - - - - - - | RH - - WYI QST | CATSG - - EGL | | 166 |
| SEQ_ID_NO_1242 | AMNAAEI TDK | LGLHSLRQ - - | - - - - - - - - - - | RH - - WYI QST | CATSG - - EGL | | 166 |
| SEQ_ID_NO_1238 | AMNAAEI TDK | LGLHSLRQ - - | - - - - - - - - - - | RH - - WYI QST | CATSG - - EGL | | 166 |
| SEQ_ID_NO_1236 | AMNAAEI TDK | LGLHSLRQ - - | - - - - - - - - - - | RH - - WYI QST | CATSG - - EGL | | 166 |
| SEQ_ID_NO_1240 | AMNAAEI TDK | LGLHSLRQ - - | - - - - - - - - - - | RH - - WYI QST | CATSG - - EGL | | 166 |

Figure 42 (continued)

| | | | | | |
|---|---|---|---|---|---|
| SEQ_ID_NO_1241 | GEGFK | | | WMSQY | K | 193 |
| SEQ_ID_NO_1229 | GEGFK | | | MLSQY | K | 193 |
| SEQ_ID_NO_1249 | GDGFK | | | WVSQY | N | 193 |
| SEQ_ID_NO_1264 | FEGLD | CSVLQ HIILQFLPDE CIWEYLMELT YKSLMYLHIE | KNRFVENDE | 231 |
| SEQ_ID_NO_1251 | FEGLN | | | MLSNA | LKSGGS | 182 |
| SEQ_ID_NO_1265 | FEGLD | | | MLSNA | LKSKSS | 182 |
| SEQ_ID_NO_1253 | FEGLD | | | MLSNT | LKSGTG | 182 |
| SEQ_ID_NO_1210 | FEGLD | | | MLSNT | LKSGSG | 182 |
| SEQ_ID_NO_1267 | FEGLD | | | MLSNT | LKSGSG | 182 |
| SEQ_ID_NO_1213 | FEGLD | | | MLSNT | LKSGSG | 182 |
| SEQ_ID_NO_1218 | FEGLD | | | MLSNT | LKSGGG | 182 |
| SEQ_ID_NO_1232 | FEGLD | | | MLSNT | LKSGGG | 182 |
| SEQ_ID_NO_1234 | FEGLD | | | MLSNT | LKSGGG | 182 |
| SEQ_ID_NO_1272 | FLGF | | | AKGVL | LIGGGPKNLG | 188 |
| SEQ_ID_NO_1268 | YEGLD | | | MLSSN | SQRA | 181 |
| SEQ_ID_NO_1211 | YEGLD | | | MLSNN | LANKT | 181 |
| SEQ_ID_NO_1216 | YEGLD | | | MLSNN | ASKA | 181 |
| SEQ_ID_NO_1269 | YEGLD | | | MLSNN | SSKA | 181 |
| SEQ_ID_NO_1239 | YEGLD | | | MLSNN | ANKA | 181 |
| SEQ_ID_NO_1259 | YEGLD | | | MLSNN | ASKA | 181 |
| SEQ_ID_NO_1233 | YEGLD | | | MLSNN | ASKA | 181 |
| SEQ_ID_NO_1235 | YEGLE | | | MLSNN | ASKA | 181 |
| SEQ_ID_NO_1243 | YEGLD | | | MLSNN | ASKA | 181 |
| SEQ_ID_NO_1270 | YEGLD | | | MLSNN | ASKG | 181 |
| SEQ_ID_NO_1242 | YEGLD | | | MLSNN | SNKA | 181 |
| SEQ_ID_NO_1238 | YEGLD | | | MLSNN | ANKA | 181 |
| SEQ_ID_NO_1236 | YEGLD | | | MLSNN | ANKA | 181 |
| SEQ_ID_NO_1240 | YEGLD | | | MLSNN | ANKA | 181 |

Figure 42 (continued)

| SEQ_ID_NO_1241 | . . . . . . . . . . . . . | 193 |
| --- | --- | --- |
| SEQ_ID_NO_1229 | . . . . . . . . . . . . . | 193 |
| SEQ_ID_NO_1249 | . . . . . . . . . . . . . | 193 |
| SEQ_ID_NO_1264 | QTVRTLGHWW LYP | 244 |
| SEQ_ID_NO_1251 | . . . . . . . . . . . . . | 182 |
| SEQ_ID_NO_1265 | . . . . . . . . . . . . . | 182 |
| SEQ_ID_NO_1253 | . . . . . . . . . . . . . | 182 |
| SEQ_ID_NO_1210 | . . . . . . . . . . . . . | 182 |
| SEQ_ID_NO_1267 | . . . . . . . . . . . . . | 182 |
| SEQ_ID_NO_1213 | . . . . . . . . . . . . . | 182 |
| SEQ_ID_NO_1218 | . . . . . . . . . . . . . | 182 |
| SEQ_ID_NO_1232 | . . . . . . . . . . . . . | 182 |
| SEQ_ID_NO_1234 | . . . . . . . . . . . . . | 182 |
| SEQ_ID_NO_1272 | LLSPKPK--- ... | 195 |
| SEQ_ID_NO_1268 | . . . . . . . . . . . . . | 181 |
| SEQ_ID_NO_1211 | . . . . . . . . . . . . . | 181 |
| SEQ_ID_NO_1216 | . . . . . . . . . . . . . | 181 |
| SEQ_ID_NO_1269 | . . . . . . . . . . . . . | 181 |
| SEQ_ID_NO_1239 | . . . . . . . . . . . . . | 181 |
| SEQ_ID_NO_1259 | . . . . . . . . . . . . . | 181 |
| SEQ_ID_NO_1233 | . . . . . . . . . . . . . | 181 |
| SEQ_ID_NO_1235 | . . . . . . . . . . . . . | 181 |
| SEQ_ID_NO_1243 | . . . . . . . . . . . . . | 181 |
| SEQ_ID_NO_1270 | . . . . . . . . . . . . . | 181 |
| SEQ_ID_NO_1242 | . . . . . . . . . . . . . | 181 |
| SEQ_ID_NO_1238 | . . . . . . . . . . . . . | 181 |
| SEQ_ID_NO_1236 | . . . . . . . . . . . . . | 181 |
| SEQ_ID_NO_1240 | . . . . . . . . . . . . . | 181 |

Figure 43

```
SEQ_ID_NO_1285  ..........  ..........  ....MVGNAF  VEQYYSLHR  DPDQVHRFYH   26
SEQ_ID_NO_1297  MAVSDGVQTP  TP........  ...DVVGNAF  VEQYYSLHQ  DPDQVHKFYH   39
SEQ_ID_NO_1284  MALQ-TATPP  TT........  PSAQVVGNAF  VEQYYHLHH  SPSSVYRFYQ   41
SEQ_ID_NO_1300  MAAPL-QPAAP  AP.....EAP  PSAQVVGNAF  VQQYYLVLHQ  SPDLVYRFYQ   44
SEQ_ID_NO_1294  MAAPL-Q-ASP  S.........  PSAQVVGNAF  VQQYYQLHQ  SPDLVYRFYQ   39
SEQ_ID_NO_1295  MAAPL-Q-ASP  S.........  PSAQVVGNAF  VQQYYQLHQ  SPDLVYRFYQ   39
SEQ_ID_NO_1287  MAAPL-TPPPA  AAPAAAPGPT  PPAQVVGNAF  VQQYYNILHO  SPELVFRFYQ   49
SEQ_ID_NO_1289  -MAS-QPPPP  AA-AAASGAP  PPAQVVGNAF  VHQYYNILHQ  SPELVYRFYQ   47
SEQ_ID_NO_1291  MASPL-PPPPP  AG-AAAPGSP  PPAQVVGNAF  VNQYYNILHQ  SPELVHRFYQ   48
SEQ_ID_NO_1274  MAMLGAQQVP  AA-----ACT  PL-DMVGNAF  VPQYYHILHQ  SPEHVHRFYQ   43
SEQ_ID_NO_1276  MASV-EQQVP  AG-----IAT  PTSDVVGNAF  VHQYYLLHQ  SPELVHRFYH   44
SEQ_ID_NO_1280  MAAPL-VTQLP  V.........  PTADVVGNAF  AHQYYHILQQ  SPDLVHRFYQ   40

SEQ_ID_NO_1285  DSSVMSRPL-  -EEDGTMTTV  TTAEIDKKI  QSLEYTSFRV  EVLSADAQPS   73
SEQ_ID_NO_1297  ESSVLSRPL-  -EEDGTMTTV  TTAEIDKKI  QSFDYTSYRV  EVLSADAQPS   86
SEQ_ID_NO_1284  DSSVISRPL-  -DSSGVMTSV  TTMKGINEKI  LSLNFKEFKA  EIKTADAQKS   88
SEQ_ID_NO_1300  DASRLARPAS  AAGAAGMDSV  TTMEAISEKI  MEMDVS--KA  EIRTVDSQES   92
SEQ_ID_NO_1294  DASRLGRPLP  ADRYGDMVSV  TTMEAINEKI  MAMDMS--RA  EIKTVDSQES   86
SEQ_ID_NO_1295  DASRLGRPLP  ADRYGDMVSV  TTMEAINEKI  MAMDMS--RA  EIKTVDSQES   86
SEQ_ID_NO_1287  EASRIGRPAT  TGADL-MDTV  TTMEAINEKI  MSMDLA--RA  EIRGVDAQES   95
SEQ_ID_NO_1289  EASQLGRPAG  TGADQ-MDTV  TTMDAINDKI  VSMGID--RA  KIKAVDAQES   94
SEQ_ID_NO_1291  DASRLGRPAG  AGADQ-MDTV  TTMDAISDKI  VSMGIT--RA  EIKAVDAQES   95
SEQ_ID_NO_1274  ELSKLGRPL-  -EENGLMSIT  STLQAIDKKI  MALGYGVISA  EISTVDTQES   90
SEQ_ID_NO_1276  DSSKLGRPL-  -EENGGMSIT  TTMQAINEKI  LSLGYGEFTA  EITTVDAQDS   91
SEQ_ID_NO_1280  DGSKFGRPL-  -GEDGVMSTT  TTMNAINEKI  LSLGYGQVRA  EIVTVDSQES   87

SEQ_ID_NO_1285  YNNGVMVVVT  GQLTGTDNIK  RKFAQSFFLA  PQDKGFYYLN  DVFRYVDAY-  122
SEQ_ID_NO_1297  YNSGVVVVVT  GQLTGTDNVK  RKFAQSFFLA  PQDKGFYYLN  DVFRYVDAY-  135
SEQ_ID_NO_1284  YKEGVTVLVT  GQLTGKDNLR  RKFAQSFFLA  PQDNGYFVLN  DVFRYVEDH-  137
SEQ_ID_NO_1300  LGGGVTVLVT  GHLTGRDSVR  REFSQSFFLA  PQEKGYFVLN  DIFRFVGDL-  141
SEQ_ID_NO_1294  LGGGVTVLVT  GHLTVRDGVC  REFSQSFFLA  PQEKGYFVLN  DMFRYVGDG-  135
SEQ_ID_NO_1295  LGGGVTVLVT  GHLTVRDGVC  REFSQSFFLA  PQEKGYFVLN  DMFRYVGDG-  135
SEQ_ID_NO_1287  LCGGVTVLVT  GHLTGKDDVC  REFAQSFFLA  PQEKGYFVLN  DILRYVGQG-  144
SEQ_ID_NO_1289  LCGGVSVLVM  GHLTGRNSVS  RQFVDSFFLA  PQEKGYFVLN  DILRYVGEG-  143
SEQ_ID_NO_1291  LGGGVTVLVM  GHLTGRTSVG  REFVDSFFLA  PQEKGYFVLN  DILRYVGDGX  145
SEQ_ID_NO_1274  HGSGYIVLVT  GYLTGKDSVR  RTFSQTFFLA  PQEIGYFVLM  DMFRFIDEG-  139
SEQ_ID_NO_1276  HNGGVLVLVT  GYLTGKDKVK  RKFTDSFFLA  PQDKGYFVLM  DVFRFVDDT-  140
SEQ_ID_NO_1280  YKGGVLVLVT  GYLNGNDNLR  QKFTDSFFLA  PQDKGFYFVLN  DVFRYVDDS-  136
```

Figure 43 (continued)

| SEQ_ID_NO_1285 | · · · · · · · · KS | IDIESVPAND | ADESAPSER | ITPEPEPVHV | PEVIPPTQTV | 164 |
| SEQ_ID_NO_1297 | · · · · · · · · · K | SVDIETVPAN | DADESAPSEA | FTPDPEPIHV | A· · · · · · · ED | 169 |
| SEQ_ID_NO_1284 | · · · · · · · · EP | SELPPVTGDG | DSAAVTVTPE | LEPSHVAD- - | · · · · · · · SC | 169 |
| SEQ_ID_NO_1300 | · · · · · · · · PA | PTAVEAQPCA | DAVVPPVAAP | LANGTATPAV | EPAIPDDHDA | 183 |
| SEQ_ID_NO_1294 | · · · · · · · PTP | AAAAAAAVEV | QPEADAVAPP | LANGTATAPL | QPAAPDY-DG | 177 |
| SEQ_ID_NO_1295 | · · · · · · · · P | TPAAAAAAEV | QPEADAVAPP | LANGTATAPL | QPAAPDY-DA | 175 |
| SEQ_ID_NO_1287 | · ·EADPSLPP | PQQQPPAPEL | DAVVAP-AAA | LANGTVAP- - | VETVPREQEA | 189 |
| SEQ_ID_NO_1289 | · · · ·GGDEGA | EKQPAPEVAA | DAEKTTSAPI | LANGTVGGDA | TTVPQ- - -DA | 186 |
| SEQ_ID_NO_1291 | GEEGAGHPPP | PPQQPVQETV | TGAEAVPAPI | LANGTVGG- D | NETLPCEQDA | 194 |
| SEQ_ID_NO_1274 | · · · · · · · · · · | · · · ·TVVHGN | QIPVNNVQAP | VNTYQDTAAA | KEIPDDFVQE | 175 |
| SEQ_ID_NO_1276 | · · · · · · · · · · | · · · ·KHQPGG | QDPVNGFERS | LTHEQGHS- - | · · · · · · · · · · | 164 |
| SEQ_ID_NO_1280 | · · · · · · · · · · | · · · ·THQNGN | QEPASNFEAP | VAPDQDTP- - | · · · · · · · · · · | 160 |

| SEQ_ID_NO_1285 | IPTAQTVPP | TQTVIADTET | IISKEVSLPL | ENGKLSVT- - | · · · · · · · · · · | 202 |
| SEQ_ID_NO_1297 | IPTIQPVLAD | TDTNISK- - | - - - -EVSLPL | ENGKLSVT- - | · · · · · · · · · · | 200 |
| SEQ_ID_NO_1284 | APEPTNSHVN | KGQTVAEL- - | - - - -NAVELS | NNHERQIPV- | · · · · · · · · · · | 201 |
| SEQ_ID_NO_1300 | VPQQENHVVD | RSPPQPEEED | EA- -EVYNPP | PEEVV- · · · | · · · · · · · · · · | 216 |
| SEQ_ID_NO_1294 | MPQEEPDVVE | HAAVPPEEEE | · · · -EVYNPP | LEEVEGGAV- | · · · · · · · · · · | 212 |
| SEQ_ID_NO_1295 | MPHEEPDVVE | NVAVPPEEEE | · · · -EVYNPP | LEEVEGGAV- | · · · · · · · · · · | 210 |
| SEQ_ID_NO_1287 | SPQPELDLSE | SVPHTNEEED | PKE-EVYNPP | NDVEVPV- - | · · · · · · · · · · | 225 |
| SEQ_ID_NO_1289 | SPQPECQVAE | PALNPKEEVL | NG- -EVCNBL | SDVEKPV- - | · · · · · · · · · · | 221 |
| SEQ_ID_NO_1291 | SPQPEQPAAE | SAPPTPEEED | LYGEEVYNPP | NDMEKPV- - | · · · · · · · · · · | 231 |
| SEQ_ID_NO_1274 | KYVQENHAVK | QTEVLSKSTN | EPE-KVFTPS | EDEQVSA- - - | · · · · · · · · · · | 211 |
| SEQ_ID_NO_1276 | -PVPENHIEQ | PAA-LPEECN | GP- -EVYNBS | ENGDCSIE- - | · · · · · · · · · · | 198 |
| SEQ_ID_NO_1280 | -HTQETHLSE | PTAALSEEVI | GG- -EVYNPS | ESGDVSVEVE | EEESGDVSFE | 207 |

| SEQ_ID_NO_1285 | ENVIPVNHVK | ESSHHVKEPE | QPTSIEKVAS | NTQEDIPKKS | FASIVNALKD | 252 |
| SEQ_ID_NO_1297 | ENVIPVNHVK | ESSHQEQMAS | IEKV- · · ·PS | NTQEDIPKKS | FASIVSAYKD | 246 |
| SEQ_ID_NO_1284 | ENEGNVESHF | QSNGNDDSQA | TELA- - - - -S | SAQDDAPKKS | YASIVKVQKG | 246 |
| SEQ_ID_NO_1300 | DEEQPVPEVI | NEVPNNVAPV | AATT- - -VAP | VLQEEAPKKS | YASIVKVMKE | 263 |
| SEQ_ID_NO_1294 | EEEQSVPEVI | NEVPNNVVPV | VAPA- - -AAP | VSHEEAPKKS | YASIVKVMKE | 259 |
| SEQ_ID_NO_1295 | EEEQSVPEVI | NEVPNNVVPV | VAPA- - -DAP | VSHEEAPKKS | YASIVKVMKE | 257 |
| SEQ_ID_NO_1287 | VEETLVPEVI | DEVPNNVAAS | IPVS- - -APP | VPHEEAPKKS | YASIVKVMKA | 272 |
| SEQ_ID_NO_1289 | AEETPVPDVI | NEVPNNVAVA | PPIS- - -SPP | VPLKEAPKKS | YASIVKVMKE | 268 |
| SEQ_ID_NO_1291 | VDETPVAEVI | NEVPNNVAVA | APSS- - -SPS | IPIEEAPKKS | YASIVKVMKE | 278 |
| SEQ_ID_NO_1274 | AEEVLVTEIV | NEAPIEVQKV | GESD- · · · · | SRTGEIPKRS | YASIVKVMKE | 255 |
| SEQ_ID_NO_1276 | EEESPVAEVV | DEIPDDSKMV | SDSK- · · · · | FEMEELPKKS | YASILKVLKE | 242 |
| SEQ_ID_NO_1280 | EEEEPMPEVV | DEIPPDSQLV | ADSQVVVESS | AKIEDTPKKS | YASVVKVQKE | 257 |

Figure 43 (continued)

| SEQ_ID_NO_1285 | NSAPFHL--- -RASPAKPAV HPP--RVHSV PAPEAPTPNM DIPLEKNN-- | 294 |
|---|---|---|
| SEQ_ID_NO_1297 | NSAPFLS--- -RTSPAKPAV QPP--RVHSV PAPEAPAPNM DIPSEKNN-- | 288 |
| SEQ_ID_NO_1284 | SSVPTKVYV- -PTNTLKSGP NKT-ESKVV ES-VESTEVP EAALESMSNP | 291 |
| SEQ_ID_NO_1300 | VPLPA----- -PAPPTRPAP PKP--EKQS- -P-PAPTPVT DVPPFSSN-P | 301 |
| SEQ_ID_NO_1294 | APVPAPIPAT RPAPAARPAP PKP--EKQSP AP-PAPAPVA DATPFSSN-A | 305 |
| SEQ_ID_NO_1295 | APVPAPIPAT RPAPAARPAP PKP--EKQSP AP-PAPAPVA DATPFSSN-A | 303 |
| SEQ_ID_NO_1287 | VLPPN----- -STVPYRPAP PKP--EKQA- -PAPAQSVAV DAPTFSPN-P | 311 |
| SEQ_ID_NO_1289 | HRPLA----- -PAVPSRPAP PIT--EKQA- -S-PAPTPVT EAPAFSPN-P | 306 |
| SEQ_ID_NO_1291 | YPPPA----- -PAVPSRPAP PKP--EKQA- -P-PAPSLVA DAPAFSPN-T | 316 |
| SEQ_ID_NO_1274 | NAAPMSA--- -SRTPTKVEP KKQ--EDQA HI-PLPTPLS EKSDSGANVA | 298 |
| SEQ_ID_NO_1276 | NAVPVSAP-- -TQSPVKSAV KSQGHPRIAA PP-SAPMPAS DAQVSSNNVT | 288 |
| SEQ_ID_NO_1280 | YTAPFSSP-- -TPSPLRSAP KIQ--EQVTA AV-SQP-PAA ESHVSSSNTF | 300 |

| SEQ_ID_NO_1285 | ENAGR----- --AHAIFVAN LPMSATVEQL DRAFKKFGP KRDGIQVRSN | 337 |
|---|---|---|
| SEQ_ID_NO_1297 | ENGGR----- --AHAIFVAN LPMTATVEQL DRVFKKFGTI KRDGIQVRSN | 331 |
| SEQ_ID_NO_1284 | ESSDAHE-EV E-GHSIYIRN LPLNVTVADL ELEFKKFGP KPGGIQVRNN | 339 |
| SEQ_ID_NO_1300 | DNSNQEPEV D-AHAIYVRN LPLNATETQL EDEFKKFGTI KQNGIQVRSN | 350 |
| SEQ_ID_NO_1294 | ESSNTHEPEV D-AHAIYVRS LPLNATTTQL EDEFKKFGTI KPDGIQVRSH | 354 |
| SEQ_ID_NO_1295 | ESSNTHEPEV D-AHAIYVRS LPLNATTTQL EDEFKKFGTI KPDGIQVRSH | 352 |
| SEQ_ID_NO_1287 | ESSNQDQEV D-ALAVYVKN LPLHATPSQL EEEFKRFGTI KHDGIQVRSH | 360 |
| SEQ_ID_NO_1289 | QSGGFQDPEV D-AHAIYVRS LPLNATPQDL EEEFKRFGTI KHEGIQVRSN | 355 |
| SEQ_ID_NO_1291 | QGGSFQDPEV D-AHAIYVRN LPLNATPQDL EEEFKRFGTI KHEGIQVRSN | 365 |
| SEQ_ID_NO_1274 | VNENNQENER ALGPSIYLKG LPLDATPALL ENEFQKFGL RTNGIQVRSQ | 348 |
| SEQ_ID_NO_1276 | ENGNNQDAEA E-GPSIYVKG LPLNATPSML EVEFKKFGP KSGGIQVRSQ | 337 |
| SEQ_ID_NO_1280 | ENGNADESE- E-GPSIYVKG LPLDATFILL ENEFKKFGP RNGGVQVRFQ | 348 |

| SEQ_ID_NO_1285 | K--CSCFGFV EFESAASMQS ALEASPPVML DNRRLSIEER RGR------ | 378 |
|---|---|---|
| SEQ_ID_NO_1297 | K--CSCFGFV EFESAASLQS ALEASPPVML DNRRLSIEER RGR------ | 372 |
| SEQ_ID_NO_1284 | KQGYCFGFV EFLSLNSMNS AIQAS-PYP GGRQKVVE-K RTTTRVGSGI | 388 |
| SEQ_ID_NO_1300 | KIQGFCYGFV EFEDSTSVQS AIEAS-PVI GGRQCYVEEK RTP---GSR- | 395 |
| SEQ_ID_NO_1294 | KIQGFCYGFV EFEEATAVQS AIEAS-PVMI GGRQCFVEEK RTP---GSR- | 399 |
| SEQ_ID_NO_1295 | KIQGFCYGFV EFEEATAVQS AIEAS-PVMI GGRQCFVEEK RTP---GSR- | 397 |
| SEQ_ID_NO_1287 | KIQGFCYGFI EFEDASSVQS ALAAS-PVTI DDRPCHVEEK RTP---GS-- | 404 |
| SEQ_ID_NO_1289 | KIQGFCYGFV EFEDASAVQA AIEAS-PVI GERQCFVEEK RTT---GSRG | 401 |
| SEQ_ID_NO_1291 | KIQGFCYGFV EFEDANAVQT AIEAS-PVMI SERQCYVEEK RTT---GSR- | 410 |
| SEQ_ID_NO_1274 | K--GFCFGFV EFESASSMQS AIEAS-PVML NGKVVVEEK RST---A--- | 389 |
| SEQ_ID_NO_1276 | K--GFCFGFV EFEMASSVQS AIEAS-PIN GGRKAVVEEK RST---S--- | 378 |
| SEQ_ID_NO_1280 | K--GFCFGFV EFEVASAVQS ALEL IYLFLF T--------- --------- | 377 |

Figure 43 (continued)

| SEQ_ID | col1 | col2 | col3 | col4 | col5 | col6 | col7 | col8 | pos |
|---|---|---|---|---|---|---|---|---|---|
| SEQ_ID_NO_1285 | SGYR- | ----- | ----NDRND | NFRGRGNFGG | GRGGGFNGRN | DF- | ERRGGEF | | 416 |
| SEQ_ID_NO_1297 | GGYR- | ----- | ----NDRND | NFRGRGNFGG | GRGGGFNGRN | DF- | DRRG-EF | | 409 |
| SEQ_ID_NO_1284 | NGTGRPR | PS | GRG--GLRND | SFRGRGNYVG | GR-G--YGRN | DY- | VSRG-GF | | 431 |
| SEQ_ID_NO_1300 | GSSRGGRFAP | GRGN- | NFRSE | GTRGRGNYGG | GR-G--YGRG | EF- | SYRS-DY | | 439 |
| SEQ_ID_NO_1294 | GSSRGGRFAP | GRGNNNFRAD | GMRGRGNYGG | GR-S--YGRG | DF- | SYRS-DY | | | 444 |
| SEQ_ID_NO_1295 | GSSRGGRFAP | GRGNNNFRAD | GMRGRGNYGG | GR-S--YGRG | DF- | SYRS-DY | | | 442 |
| SEQ_ID_NO_1287 | RGSSRGRFPP | GRGG- | NFRGE | GMRGRGSYTG | GR-G--YGRG | EYNNYRS-DF | | | 449 |
| SEQ_ID_NO_1289 | GGSRGGRFPP | GRGG- | NFRGE | GIRGRGTYNG | GR-G--YGRG | EF- | SYRS-DY | | 445 |
| SEQ_ID_NO_1291 | GSNRGGRFAP | GRGG- | NFRGE | GLRGRGTYNG | GR-G--YGRG | EF- | SYRS-DY | | 454 |
| SEQ_ID_NO_1274 | RGNYRGRSTF | GVNT- | GYRNE | GGRGRGSFGG | GRGG--YGRT | DFNGYSN--- | | | 433 |
| SEQ_ID_NO_1276 | RGN-KGKSSS | VSGA- | GYRNE | GARGRGNYGG | GR-G--YSRG | EF------- | | | 415 |
| SEQ_ID_NO_1280 | TGNNRGRFPS | GSGA- | GYKSE | GMRGRGNL-G | GK-V--YGR | EF-GIRT-EF | | | 420 |

| SEQ_ID | col1 | col2 | col3 | col4 | col5 | col6 | pos |
|---|---|---|---|---|---|---|---|
| SEQ_ID_NO_1285 | SGRSRGG-QN | AGR- | ----- | ----- | ----- | -------S | 429 |
| SEQ_ID_NO_1297 | SGRPRGG-NN | TGR- | ----- | ----- | ----- | -------S | 422 |
| SEQ_ID_NO_1284 | SGRGRGH--- | ----- | ----- | ----- | ----- | -------- | 438 |
| SEQ_ID_NO_1300 | GGRSGGR-GG | PAR- | ----- | ----- | ----- | -------G | 452 |
| SEQ_ID_NO_1294 | GGRGGGR-GG | SAR- | ----- | ----- | ----- | -------G | 457 |
| SEQ_ID_NO_1295 | GGRGGGR-GG | SAR- | ----- | ----- | ----- | -------G | 455 |
| SEQ_ID_NO_1287 | GGRGGGR-GG | SGR- | ----- | ----- | ----- | -------G | 462 |
| SEQ_ID_NO_1289 | GGRGGGR-GG | SLH- | ----- | ----- | ----- | -------G | 458 |
| SEQ_ID_NO_1291 | GGRGGGR-GG | SSR- | ----- | ----- | ----- | -------G | 467 |
| SEQ_ID_NO_1274 | -NRGNNR-GG | YANRAN--- | ----- | ----- | ----- | -------G | 448 |
| SEQ_ID_NO_1276 | GNRSSNR-GG | YSS- | ----- | ----- | ----- | -------R | 428 |
| SEQ_ID_NO_1280 | GNRGGSRGGG | YSNRGGDGYS | NRGGGGGGGG | DGYSNRGGGG | GGDGYSNRGG | | 470 |

| SEQ_ID | col1 | col2 | col3 | col4 | col5 | pos |
|---|---|---|---|---|---|---|
| SEQ_ID_NO_1285 | NGDAVPRSYQ | NG--GGKVAA | RQPPVKVQ-- | --------- | ---- | 455 |
| SEQ_ID_NO_1297 | NGDAAPRSYQ | NG--GGKV-A | RQPPVKAQ-- | --------- | ---- | 447 |
| SEQ_ID_NO_1284 | -GEGYHQG-- | ----RGRG-G | RSSGQKQNAV | SN-------- | ---- | 462 |
| SEQ_ID_NO_1300 | ADVGYQRVDH | ASYAGGRG-G | RTAAAGAPAK | ---------- | ---- | 481 |
| SEQ_ID_NO_1294 | PDVGYQRVD- | ----GGRG-G | RTSAGPGAPA | K--------- | ---- | 482 |
| SEQ_ID_NO_1295 | PDVGYQRVD- | ----GGRG-G | RTSAGPGAPA | K--------- | ---- | 480 |
| SEQ_ID_NO_1287 | GDVGYQRVDH | SGT-GGRGGA | RAAAK----- | ---------- | ---- | 486 |
| SEQ_ID_NO_1289 | GDVGYQRVDY | SGTSSGRG-A | RAPSAAAAMA | K--------- | ---- | 488 |
| SEQ_ID_NO_1291 | -EVGYQRVDH | SGTAGGRG-T | RPASAATAAK | ---------- | ---- | 495 |
| SEQ_ID_NO_1274 | DGGGFPRANG | NL--NGRV-R | RGGGIDANRA | TKPVDDAPHV | SVTA | 488 |
| SEQ_ID_NO_1276 | GGDGYQRGEH | MGGNGGRV-S | RSGEATFNAS | TKNV--APRV | SAPA | 469 |
| SEQ_ID_NO_1280 | GGDGYRRADK | MGNNGGRA-N | RSGGLGLNGT | AKTT--APRV | SATA | 511 |

Figure 44

| SEQ_ID_NO_1327 | MVYTVAATG- | PDTAETLHST | TFASRYVRDQ | LPRYRMPENS | PKEAAYQII | 49 |
| --- | --- | --- | --- | --- | --- | --- |
| SEQ_ID_NO_1333 | MVVSVAATGA | GTDAEPVTST | FFASRYVRDP | LRRYRMPERS | PREAAYQII | 50 |
| SEQ_ID_NO_1336 | MVVSVAATDS | DTAQPVQVST | FFASRYVRDP | LPRFRMPEDS | PREAAYQII | 50 |
| SEQ_ID_NO_1319 | MVLTTTS--- | RDSEESLHCF | -FASRYVQEP | LPKFKMPKKS | MPKEAAYQIV | 47 |
| SEQ_ID_NO_1302 | MVLATN---- | SDSDEHLHST | -FASRYVRAV | VPRFKMPDHC | MPKDAAYQVI | 45 |
| SEQ_ID_NO_1311 | MVISTAA--- | TDSDENLYST | -FASRYVRTA | LPRFKMPENS | MPKDAAYQVI | 46 |
| SEQ_ID_NO_1317 | MVLTSTATHP | DEQDQSLNYT | -FASRYVREP | IPKFKMPEKS | PKDAAYQII | 49 |
| SEQ_ID_NO_1305 | MLAAT----- | NPTEEHVHST | -FASRYVRAP | VPRFKMPEKS | PKDAAYQVI | 44 |
| SEQ_ID_NO_1339 | MALSSA---- | TDSDGSIHST | -FASRYVQFS | LPRFQIPSRS | PKDAAYQII | 45 |
| SEQ_ID_NO_1318 | MVLSETA--- | THMDASVHST | -FASRYVRTS | LPRFKMGENS | PKEAAYQII | 46 |
| SEQ_ID_NO_1331 | MVLSNTASSG | SESDLSIHST | -FASRYVRTS | LPRFKMPQES | PKEAAYQII | 49 |
| SEQ_ID_NO_1313 | MVLSKTA--- | SESDVSIHST | -FASRYVRTS | LPRFEMPENS | PKEAAYQII | 46 |
| SEQ_ID_NO_1303 | MVLSKTF--- | SESDESIHST | -FASRYVRNS | LPRFTMPENS | PKEAAYQII | 46 |
| SEQ_ID_NO_1340 | MVLSKTA--- | SESDVSVHST | -FASRYVRAS | LPRFKMPENS | PKEAAFQII | 46 |
| SEQ_ID_NO_1320 | MVLSKTA--- | SESDVSIHST | -FASRYVRTS | LPRFKMPENS | PKEAAYQII | 46 |
| SEQ_ID_NO_1326 | MVLSKIV--- | SQSDVSIHST | -FASRYVRTS | LPRFKMPDNS | PKEAAYQII | 46 |
| SEQ_ID_NO_1334 | MVLSKAV--- | SESDMSVHST | -FASRYVRAS | LPRYRMPENS | PKEAAYQII | 46 |
| SEQ_ID_NO_1330 | MVLSHGV--- | GGSDESVHST | -FASRYVRTS | LPRYRMPEDS | PKEAAYQII | 46 |

| SEQ_ID_NO_1327 | SDELMLDGNP | RLNLASFVTT | MMEPECCKLI | NDSVNKNYVD | MDEYPVTTEL | 99 |
| --- | --- | --- | --- | --- | --- | --- |
| SEQ_ID_NO_1333 | NDELMLDGNP | RLNLASFVTT | MMEPECDKLI | MSSINKNYVD | MDEYPVTTEL | 100 |
| SEQ_ID_NO_1336 | NDELMLDGNP | RLNLASFVTT | MMEPECDKLI | NDSVNKNYVD | MDEYPVTTEL | 100 |
| SEQ_ID_NO_1319 | NDELMLDGNP | RLNLASFVST | MMEPECDKLI | MSSINKNYVD | MDEYPVTTEL | 97 |
| SEQ_ID_NO_1302 | NDELMLDGNP | RLNLASFVTT | MMEPECDKLI | NDSVNKNYVD | MDEYPVTTEL | 95 |
| SEQ_ID_NO_1311 | NDELMLDGNP | RLNLASFVTT | MMEPECNDLI | MASINKNYVD | MDEYPVTTEL | 96 |
| SEQ_ID_NO_1317 | NDELMLDGAP | RLNLASFVTT | MMEPECDKLI | MASLNKNYVD | MDEYPVTTEL | 99 |
| SEQ_ID_NO_1305 | HDELMLDGNP | RLNLASFVTT | MMEPECDKLM | MAAINKNYVD | MDEYPVTTEL | 94 |
| SEQ_ID_NO_1339 | SDELMLDGNP | RLNLASFVTT | MMEPECDKLI | MQAINKNYVD | MDEYPVTTEL | 95 |
| SEQ_ID_NO_1318 | NDELMLDGNP | RLNLASFVTT | MMEPECDKLI | MASINKNYVD | MDEYPVTTEL | 96 |
| SEQ_ID_NO_1331 | NDELMLDGNP | RLNLASFVTT | MMEPECDKLI | MASINKNYVD | MDEYPVTTEL | 99 |
| SEQ_ID_NO_1313 | NDELMLDGNP | RLNLASFVTT | MMEPECDKLM | MESINKNYVD | MDEYPVTTEL | 96 |
| SEQ_ID_NO_1303 | NDELMLDGNP | RLNLASFVTT | MMEPECDKLM | MAAINKNYVD | MDEYPVTTEL | 96 |
| SEQ_ID_NO_1340 | NDELMLDGNP | RLNLASFVTT | MMEPECDKLI | ASINKNYVD | MDEYPVTTEL | 96 |
| SEQ_ID_NO_1320 | NDELMLDGNP | RLNLASFVTT | MMEPECNKLM | MDSINKNYVD | MDEYPVTTEL | 96 |
| SEQ_ID_NO_1326 | NDELMLDGNP | RLNLASFVTT | MMEPECDKLM | MDSINKNYVD | MDEYPVTTEL | 96 |
| SEQ_ID_NO_1334 | NDELMLDGNP | RLNLASFVTT | MMEPECDKLI | MAAINKNYVD | MDEYPVTTEL | 96 |
| SEQ_ID_NO_1330 | NDELMLDGNP | RLNLASFVTT | MMEPECDKLI | GASVNKNYVD | MDEYPVTTEL | 96 |

Figure 44 (continued)

| | | | | | | |
|---|---|---|---|---|---|---|
| SEQ_ID_NO_1327 | QDRCVNMIAH | LFNAPIGEDE | TAIGVSTVGS | SEAIMLAGLA | FKRKWANKMK | 149 |
| SEQ_ID_NO_1333 | QNRCVNMIAH | LFNAPIKEDE | TAVGVGTVGS | SEAIMLAGLA | FKRKWQNKRK | 150 |
| SEQ_ID_NO_1336 | QNRCVNMIAH | LFNAPIKFDE | TAIGVGTVGS | SEAIMLAGLA | FKRKWQNKRK | 150 |
| SEQ_ID_NO_1319 | QNRCVNMLAH | LFHAPVGDDE | TAVGVGTVGS | SEAIMLAGLA | FKRKWQSKRK | 147 |
| SEQ_ID_NO_1302 | QNRCVNMIAN | FFHAPVGEDE | AAIGLGTVGS | SEAIMLAGLA | FKRKWQHRRK | 145 |
| SEQ_ID_NO_1311 | QNRCVNIIAH | LFNAPVGEKF | TAVGVGTVGS | SEAIMLAGLA | FKRKWQNKRK | 146 |
| SEQ_ID_NO_1317 | QNRCVNIIAN | LFHAPISDDE | TAVGVGTVGS | SEAIMLAGLA | FKRKWQTKRK | 149 |
| SEQ_ID_NO_1305 | QNRCVNMIAN | LFHAPVGEEE | TAVGVGTVGS | SEAIMLAGLA | FKRRWQHKRK | 144 |
| SEQ_ID_NO_1339 | QNRCVNIIAN | LFNAPLGDGE | EAVGVGTVGS | SEAIMLAGLA | FKRKWQNKRK | 145 |
| SEQ_ID_NO_1318 | QNRCVNMIAH | LFNAPLEDSE | PAVGVGTVGS | SEAIMLAGLA | FKRKWQNRRK | 146 |
| SEQ_ID_NO_1331 | QNRCVNMIAH | LFNAPLGDSD | F--VGTVGS | SEAIMLAGLA | FKRTWQNRRK | 146 |
| SEQ_ID_NO_1313 | QNRCVNMIAR | LFNAPLGDGE | AAVGVGTVGS | SEAIMLAGLA | FKRQWQNKRK | 146 |
| SEQ_ID_NO_1303 | QNRCVNIIAR | LFNAPLEDSE | TAVGVGTVGS | SEAIMLAGLA | FKRKWQNKRK | 146 |
| SEQ_ID_NO_1340 | QNRCVNMIAH | LFNAPLGUSE | TAVGVGTVGS | SEAIMLAGLA | FKRKWQNKRK | 146 |
| SEQ_ID_NO_1320 | QNRCVNMIAH | LFNAPLGDGE | TAVGVGTVGS | SEAIMLAGLA | FKRKWQNKMK | 146 |
| SEQ_ID_NO_1326 | QNRCVNMIAH | LFNAPLEDGE | TAVGVGTVGS | SEAIMLAGLA | FKRKWQNKMK | 146 |
| SEQ_ID_NO_1334 | QNRCVNMIAH | LFHAPLGEDE | TAVGVGTVGS | SEAIMLAGLA | FKRRWQNKRK | 146 |
| SEQ_ID_NO_1330 | QNRCVNMIAH | LFNAPLGDAE | TAVGVGTVGS | SEAIMLAGLA | FKRRWQNKMK | 146 |

| | | | | | | |
|---|---|---|---|---|---|---|
| SEQ_ID_NO_1327 | EQGKPCDKPN | VTGANVQYC | MEKFARYFEV | ELKEVKLTEG | YYVMDPKKAV | 199 |
| SEQ_ID_NO_1333 | EQGKPYDKPN | VTGANVQYC | MEKFARYFEV | ELKEVKLSEG | YYVMDPVKAV | 200 |
| SEQ_ID_NO_1336 | EQGKPCDKPN | VTGANVQYC | MEKFARYFEV | ELKEVKLSEG | YYVMDPVKAV | 200 |
| SEQ_ID_NO_1319 | AEGKPFDKPN | VTGANVQYC | MEKFARYFEV | ELKEVKLKEG | YYVMDPAKAV | 197 |
| SEQ_ID_NO_1302 | AQGLPIDKPN | VTGANVQYC | MEKFARYFEV | ELKEVKLSED | YYVMDPAKAV | 195 |
| SEQ_ID_NO_1311 | AEGKPYDKPN | VTGANVQYC | MEKFARYFEV | ELKEVKLTEG | YYVMDPVKAV | 196 |
| SEQ_ID_NO_1317 | AEGKPYDKPN | VTGANVQYC | MEKFARYFEV | ELKEVKLKEG | YYVMDPAKAV | 199 |
| SEQ_ID_NO_1305 | TEGKPTDNPN | VTGANVQYC | MEKFARYFEV | GLKEVKLKEG | YYVMDPEQAV | 194 |
| SEQ_ID_NO_1339 | AEGKPYDKPN | VTGANVQYC | MEKFARYFEV | ELKEVKLKKD | YYIMDPVKAV | 195 |
| SEQ_ID_NO_1318 | SEGKSGENPN | VTGANVQYC | MEKFARYFEV | ELKEVKLRDG | YYVMDPEKAA | 196 |
| SEQ_ID_NO_1331 | AEGKPHDKPN | VTGANVQYC | MEKFARYFEV | ELKEVKLSEG | YYVMDPQKAV | 196 |
| SEQ_ID_NO_1313 | AQGLPYDKPN | VTGANVQYC | MEKFARYFEV | ELKEVKLREG | YYVMDPEKAV | 196 |
| SEQ_ID_NO_1303 | AEGKPFDKPN | VTGANVQYC | MEKFARYFEV | ELKEVKLSEG | YYVMDPAKAV | 196 |
| SEQ_ID_NO_1340 | AEGKPYDKPN | VTGANVQYC | MEKFARYFEV | ELKEVKLSDG | YYVMDPEKAV | 196 |
| SEQ_ID_NO_1320 | AQGKPCDKPN | VTGANVQYC | MEKFARYFEV | ELKEVKLSDG | YYVMDPEKAV | 196 |
| SEQ_ID_NO_1326 | AQGKPCDKPN | VTGANVQYC | MEKFARYFEV | ELKEVKLSEG | YYVMDPEKAV | 196 |
| SEQ_ID_NO_1334 | AEGKPFDKPN | ITGANVQYC | MEKFARYFEV | ELKEVKLRDG | YYVMDPEKAV | 196 |
| SEQ_ID_NO_1330 | AAGKPCDKPN | VTGANVQYC | MEKFARYFEV | ELKEVKLSDG | YYVMDPQKAV | 196 |

Figure 44 (continued)

| SEQ_ID | Col1 | Col2 | Col3 | Col4 | Col5 | Pos |
|---|---|---|---|---|---|---|
| SEQ_ID_NO_1327 | EMVDENTICV | AAILGSTLTG | EYEDVKLLND | LLVEKNKETG | WNVPIHVDAA | 249 |
| SEQ_ID_NO_1333 | DMVDENTICV | AAILGSTLTG | EFEDVKQLND | LLTEKNKETG | WDVPIHVDAA | 250 |
| SEQ_ID_NO_1336 | FMVDENTICV | AAILGSTLTG | EFEDVKLLNN | LLTEKNKETG | WDVPIHVDAA | 250 |
| SEQ_ID_NO_1319 | EIVDENTICV | AAILGSTLTG | EFEDVKLLNE | LLTKKNKETG | WETPIHVDAA | 247 |
| SEQ_ID_NO_1302 | EMVDENTICV | AAILGSTLTG | EFEDVKQLND | LLAEKNAETG | WETPIHVDAA | 245 |
| SEQ_ID_NO_1311 | EMVDENTICV | AAILGSTLTG | EFEDVKLLND | LLSKKNKETG | WNTPIHVDAA | 246 |
| SEQ_ID_NO_1317 | EMVDENTICV | AAILGSTMTG | EFEDVKLLDE | LLTKKNNETG | WDTPIHVDAA | 249 |
| SEQ_ID_NO_1305 | ELVDENTICV | AAILGSTLTG | EFEDVKTLND | LLMKKNEETG | WGTPIHVDAA | 244 |
| SEQ_ID_NO_1339 | EMVDENTICV | AAILGSTYNG | EFEDVKLVND | LLIQKNKETG | WDTPIHVDAA | 245 |
| SEQ_ID_NO_1318 | EMVDENTICV | AAILGSTLNG | EFEDVKRLND | LLVEKNAETG | WDTPIHVDAA | 246 |
| SEQ_ID_NO_1331 | DLVDENTICV | AAILGSTLNG | EFEDVKRLND | LLIEKNKETG | WDTPIHVDAA | 246 |
| SEQ_ID_NO_1313 | EMVDENTICV | AAILGSTLTG | EFEDVKLLND | LLVEKNKQTG | WDTGHVDAA | 246 |
| SEQ_ID_NO_1303 | EMVDENTICV | AAILGSTLNG | EFEDVKLLND | LLTEKNKETG | WDTPIHVDAA | 246 |
| SEQ_ID_NO_1340 | QMVDENTICV | AAILGSTLNG | EFEDVKLLND | LLVEKNKSTG | WDTPIHVDAA | 246 |
| SEQ_ID_NO_1320 | EMVDENTICV | AAILGSTLNG | EFEDVKRLND | LLIEKNKETG | WDTPIHVDAA | 246 |
| SEQ_ID_NO_1326 | EMVDENTICV | AAILGSTLNG | EFEDVKRLND | LLVEKNKETG | WDTPIHVDAA | 246 |
| SEQ_ID_NO_1334 | DMVDENTICV | AAILGSTLNG | EFEDVKLLND | LLDKKNKETG | WETPIHVDAA | 246 |
| SEQ_ID_NO_1330 | DMVDENTICV | AAILGSTLNG | EFEDVKLLND | LLTKKNAETG | WDTPIHVDAA | 246 |

| SEQ_ID | Col1 | Col2 | Col3 | Col4 | Col5 | Pos |
|---|---|---|---|---|---|---|
| SEQ_ID_NO_1327 | SGGFIAPFLD | PELEWDFRLP | LVKSINVSGH | KYGLVYPGVG | WIWRSKDDL | 299 |
| SEQ_ID_NO_1333 | SGGFIAPFLY | PELEWDFRLP | LVKSINVSGH | KYGLVYAGVG | WIWRSKKDL | 300 |
| SEQ_ID_NO_1336 | SGGFIAPFLY | PELEWDFRLP | LVKSINVSGH | KYGLVYPGVG | WIWRSKEDL | 300 |
| SEQ_ID_NO_1319 | SGGFIAPFLW | PDLEWDFRLP | LVKSINVSGH | KYGLVYAGVG | WIWRSKEDL | 297 |
| SEQ_ID_NO_1302 | SGGFIAPFLY | PDLEWDFRLP | WKSINVSGH | KYGLVYAGVG | WVWRTKDDL | 295 |
| SEQ_ID_NO_1311 | SGGFIAPFIW | PDLEWDFRLP | LVKSINVSGH | KYGLVYAGVG | WVWRTKEDL | 296 |
| SEQ_ID_NO_1317 | SGGFIAPFLY | PDLEWDFRLP | LVKSINYSCH | KYGLVYPGVG | WVWRSKDDL | 299 |
| SEQ_ID_NO_1305 | SGGFIAPFLY | PDLEWDFRLP | LVKSINVSGH | KYGLVYAGVG | WVWRNKEDL | 294 |
| SEQ_ID_NO_1339 | SGGFIAPFLY | PELEWDFRLP | LVKSINVSGH | KYGLVYAGIG | WIWRAKQDL | 295 |
| SEQ_ID_NO_1318 | SGGFIAPFLY | PELVWDFRLS | LVKSINVSGH | KYGLVYAGIG | MIWRSKEDL | 296 |
| SEQ_ID_NO_1331 | SGGFIAPFIY | PELEWDFRLP | LVKSINVSGH | KYGLVYAGIG | WIWRNKEDL | 296 |
| SEQ_ID_NO_1313 | SGGFIAPFLY | PELEWDFRLP | LVKSINVSGH | KYGLVYAGIG | WVWRTKSDL | 296 |
| SEQ_ID_NO_1303 | SGGFIAPFLY | PELEWDFRLP | LVKSINVSGH | KYGLVYAGIG | WVWRNKEDL | 296 |
| SEQ_ID_NO_1340 | SGGFIAPFIY | PELEWDFRLP | LVKSINVSGH | KYGLVYAGIG | WIWRNKEDL | 296 |
| SEQ_ID_NO_1320 | SGGFIAPFLY | PELEWDFRLP | LVKSINVSGH | KYGLVYAGIG | WAWRNKEDL | 296 |
| SEQ_ID_NO_1326 | SGGFIAPFIY | PELEWDFRLP | LVKSINVSGH | KYGLVYAGIG | WVWRNKDDL | 296 |
| SEQ_ID_NO_1334 | SGGFIAPFLY | PELEWDFRLP | WKSINVSGH | KYGLVYAGIG | WCWRNKEDL | 296 |
| SEQ_ID_NO_1330 | SGGFIAPFLY | PELEWDFRLP | LVKSINVSGH | KYGLVYAGIG | WCWRTKVDL | 296 |

Figure 44 (continued)

| | | | | | | | |
|---|---|---|---|---|---|---|---|
| SEQ_ID_NO_1327 | PEELIFHINY | LGADQPTFTL | NFSKGQ-QII | AQYYQLIRLG | FEGYKHIMEN | 348 |
| SEQ_ID_NO_1333 | PEELIFHINY | LGTDQPTFTL | NFSKGSSQII | AQYYQLIRLG | FQGYKNIMEN | 350 |
| SEQ_ID_NO_1336 | PEELIFHINY | LGIDQPTFTL | NFSKGSSQII | AQYYQLIRLG | FEGYKNIMQN | 350 |
| SEQ_ID_NO_1319 | PDELVFHINY | LGSDQPTFTL | NFSKGSYQII | AQYYQLIRLG | FEGYKNVMKN | 347 |
| SEQ_ID_NO_1302 | PEELVFHINY | LGADQPTFTL | NFSKGSSQII | AQYYQFRLG | FEGYKNIMEN | 345 |
| SEQ_ID_NO_1311 | PDELIFHINY | LGSDQPTFTL | NFSKGSGQII | AQYYQFRLG | FEGYKRIMEN | 346 |
| SEQ_ID_NO_1317 | PDELVFHINY | LGSDQPTFTL | NFSKGSSQII | AQYYQLIRLG | FEGYKNIMEN | 349 |
| SEQ_ID_NO_1305 | PDDLVFHINY | LGSDQPTFTL | NFSKGSSQII | AQYYQFRLG | FEGYKNIIEN | 344 |
| SEQ_ID_NO_1339 | PEELIFHINY | LGADQPTFTL | NFSKGASQII | AQYYQLIRLG | FEGYRNIMGN | 345 |
| SEQ_ID_NO_1318 | PEELIFHINY | LGADQPTFTL | NFSKGSSQVI | AQYYQLIRLG | YEGYRNVMEN | 346 |
| SEQ_ID_NO_1331 | PEELIFHINY | LGADQPTFTL | NFSKGSSQII | AQYYQLIRLG | YEGYKHVMEN | 346 |
| SEQ_ID_NO_1313 | PDELIFHINY | LGADQPTFTL | NFSKGSSQVI | AQYYQLIRLG | FEGYRNVMDN | 346 |
| SEQ_ID_NO_1303 | PEELIFHINY | LGADQPTFTL | NFSKGSSQVI | AQYYQLIRLG | FEGYRNVMEN | 346 |
| SEQ_ID_NO_1340 | PEELIFHINY | LGADQPTFTL | NFSKGSSQVI | AQYYQLIRLG | YEGYKNVMEN | 346 |
| SEQ_ID_NO_1320 | PDELIFHINY | LGADQPTFTL | NFSKGSSQVI | AQYYQLIRLG | FEGYKNVMEN | 346 |
| SEQ_ID_NO_1326 | PDELIFHINY | LGADQPTFTL | NFSKGSSQVI | AQYYQLIRLG | YEGYKNVMEN | 346 |
| SEQ_ID_NO_1334 | PEELIFHINY | LGADQPTFTL | NFSKGSSQVI | AQYYQLIRHG | FEGYRNIMEN | 346 |
| SEQ_ID_NO_1330 | PEELIFHINY | LGADQPTFTL | NFSKGSSQVI | AQYYQLIRLG | FEGYKNIMEN | 346 |

| | | | | | | | |
|---|---|---|---|---|---|---|---|
| SEQ_ID_NO_1327 | CKLNAAVLKE | GIDATGRFDV | LSKADGVPLV | ALRLKDSTNF | SVFDISENLR | 398 |
| SEQ_ID_NO_1333 | CMENAAILRE | GIAATGRFDI | LSKDAGVPLV | AFSLKDSSRF | SVFDISENLR | 400 |
| SEQ_ID_NO_1336 | CMENTALRE | GIEATGRFE | LSKEAGVPLV | AFSLKDSGRY | TVFDISEHLR | 400 |
| SEQ_ID_NO_1319 | CLSNAKVLTE | GITKMGRFDI | VSKDVGVPYV | AFSLRDSSKY | TVFEVSEHLR | 397 |
| SEQ_ID_NO_1302 | CMDNARRLRE | GIEMTGKFNI | VSKDIGVPLV | AFSLKDSSKH | TVFEIAESLR | 395 |
| SEQ_ID_NO_1311 | CLENARVLRE | GLEKTGRFDI | VSKDKGVPLV | AFSLKDSSKH | TVFEIAESLR | 396 |
| SEQ_ID_NO_1317 | CMENARVLKE | GIERTGRFNI | SKDIGVPLV | AFSLQDSSQH | TVFEIADHLR | 399 |
| SEQ_ID_NO_1305 | CMENMKVLKQ | GIENTGRFNI | LSKDIGVPLV | AFSLKDSSKH | TVFEIAENLR | 394 |
| SEQ_ID_NO_1339 | CAANAKALSD | GLVRTGRFNI | LSKEIGVPLV | ATSLKDSSRH | DEYEISDHLR | 395 |
| SEQ_ID_NO_1318 | CRDNMVYLKD | GLEKTERFE | VSKDEGVPLV | AFTLKDHNNF | NEFQISDMLK | 396 |
| SEQ_ID_NO_1331 | CRDNMLVLKE | GLQKTGRFE | VSKDNGVPLV | AFTLKDHTHY | NEFQISDSL | 395 |
| SEQ_ID_NO_1313 | CRENMMVLRE | GLEKTGRFNI | VSKENGVPLV | AFSLKDSSRH | DEFEVAETLR | 396 |
| SEQ_ID_NO_1303 | CHENAMVLKE | GLEKTGRFNI | VSKDEGVPLV | AFSLKDNKRH | DEFEVAELLR | 396 |
| SEQ_ID_NO_1340 | CRDNMLVLKQ | GLEKTGKFNI | VSKDKGVPLV | AFSLKDNSLH | NEFEVSDMLR | 396 |
| SEQ_ID_NO_1320 | CQENARVLRE | GLEKSGRFNI | ISKEIGVPLV | AFSLKDNSQH | NEFEISETLR | 396 |
| SEQ_ID_NO_1326 | CQENASVLRE | GLEKTGRFNI | SKEIGVPLV | AFSLKDNRQH | NEFEISETLR | 396 |
| SEQ_ID_NO_1334 | CHENAMVLKE | GLVKTGRFDI | VSKDEGVPLV | AFSLKDRSRH | DEFEISDMLR | 396 |
| SEQ_ID_NO_1330 | CQENATVLKQ | GLEKTGKFNI | VSKDNGVPLV | AFSLKDSSRH | SEFEISDFLR | 396 |

Figure 44 (continued)

| | | | | | | |
|---|---|---|---|---|---|---|
| SEQ_ID_NO_1327 | RFGW VPAYT | MPADAEHVAV | LRI VI REDFN | RSLAORLLAD | NKI I GELDA | 448 |
| SEQ_ID_NO_1333 | RFGW VPAYT | MPADAEHVAV | LRVVI REDFS | RTLLERLVGD | VLKI LRELDA | 450 |
| SEQ_ID_NO_1336 | RFGW VPAYT | MPANAEHVAV | LRVVI REDFS | RSLAERLVSD | VKI LHELDA | 450 |
| SEQ_ID_NO_1319 | RFGW VPAYT | MPPDAEHI AV | LRVVI REDFS | HSLAERLVSD | EKI LSELDT | 447 |
| SEQ_ID_NO_1302 | KFGW I PAYT | MPADAQHI AV | LRVVI REDFS | RGLADRLI TH | DVLKEI EG | 445 |
| SEQ_ID_NO_1311 | RFGW I PAYT | MPANAQHI AV | LRVVVREDFN | RSLAERLVSH | DQVMKETDS | 446 |
| SEQ_ID_NO_1317 | KFGW VPAYT | MPPDAQHI AV | LRVVI REDFS | RGLAERLAAD | EKVVKLLDT | 449 |
| SEQ_ID_NO_1305 | RFGW LPAYT | MPANAQHVAV | LRAVI REDFS | HGLAKRLVAH | EQVLKEMDG | 444 |
| SEQ_ID_NO_1339 | RFGW VPAYT | MAPDAQEVKL | LRVVVREDFN | RSLAERLVHD | EKVLHELDT | 445 |
| SEQ_ID_NO_1318 | RHGW I PAYT | MPPDAEHVTV | LRVVI REDFS | RTFAERLV D | TRVI HELDL | 446 |
| SEQ_ID_NO_1331 | ---------- | ---------A | LRV------- | ---------- | --------DS | 401 |
| SEQ_ID_NO_1313 | RFGW VPAYT | MPADAQHVTM | LRVVI REDFS | RTLAERLVAD | FEKVLHELDT | 446 |
| SEQ_ID_NO_1303 | RFGW VPAYT | MPADAQHI TV | LRVVI REDFS | RTLAERLVLD | TKVLHELDS | 446 |
| SEQ_ID_NO_1340 | RFGW VPAYT | MPPDAQHVTV | LRVVI REDFS | RTLAERLV D | GKVLHELET | 446 |
| SEQ_ID_NO_1320 | RFGW I PAYT | MPPNAQHVTV | LRVVI REDFS | RTLAERLV D | EKVLHELDT | 446 |
| SEQ_ID_NO_1326 | RFGW VPAYT | MPPNAQHI TV | LRVVI REDFS | RTLAERLVRD | EKVLHELDT | 446 |
| SEQ_ID_NO_1334 | RFGW VPAYT | MPPDAQHVTV | LRVVI REEFS | RTLAERLVLD | EKVMYQLDA | 446 |
| SEQ_ID_NO_1330 | RFGW VPAYT | MPPDAQHVTV | LRVVI REDFS | RTLAERLVLD | EKVLHELDA | 446 |

| | | | | | | |
|---|---|---|---|---|---|---|
| SEQ_ID_NO_1327 | HAVHAI KLST | AAAGGDG--- | ---------- | ---------A | SKSAVDAATE | 476 |
| SEQ_ID_NO_1333 | CATHAVRVAT | ATAAVQSGDG | GGVVARK--- | ---------S | I LELEREVAS | 488 |
| SEQ_ID_NO_1336 | HSAQVLKI SS | AI AKQQSGDD | GVVTKK---- | ---------S | VLETEREI FA | 487 |
| SEQ_ID_NO_1319 | QPPRLPTKAV | RVTAEEYRDD | KGDGLHHFHM | --------Q | TVETQKDI K | 498 |
| SEQ_ID_NO_1302 | LPSRI AHLAA | AAAVSGDDEE | VKVK------ | ---------T | AKMSLEDI TK | 480 |
| SEQ_ID_NO_1311 | LPSRVAVDAS | RI VTVDETQD | NMDGKKTVKK | ---------S | SRELQEFVTL | 487 |
| SEQ_ID_NO_1317 | LPSPLTTKAV | HI TAI TSETG | EKI KK---- | ---------A | ALETQKEI AF | 485 |
| SEQ_ID_NO_1305 | LPSGLQHKK- | ---------- | ---------- | ---------A | ERETQEEVFR | 464 |
| SEQ_ID_NO_1339 | LPSKI AREVV | ASLVDGHPEL | KEVKDLGI DV | TQFKSSAVFN | EI VNSQKAVK | 495 |
| SEQ_ID_NO_1318 | VPSRVVSTNT | I TVTGGEEDA | DNDGTVTI AN | Q-------S | VLETQRKI TT | 488 |
| SEQ_ID_NO_1331 | AGI QHAPKYS | A--------- | ---------- | ---------- | ---------- | 412 |
| SEQ_ID_NO_1313 | LPARVQAKMA | NGNANGVKK- | ---------- | ---------T | EEETTREYTA | 476 |
| SEQ_ID_NO_1303 | LPSKVLVPAS | EQNGRNGKK- | ---------- | ---------T | ELETQREVTT | 476 |
| SEQ_ID_NO_1340 | LPSRI SAKI V | LANEEKDAVA | AGKEKK---- | --------D | VQNETREI T | 483 |
| SEQ_ID_NO_1320 | LPARVNAKLA | VAEANGSGVH | KK-------- | ---------T | DREVQLEI TT | 479 |
| SEQ_ID_NO_1326 | LPARVNAKLA | VAEEQAAANG | SEVHKK---- | ---------T | DSFVQLEM T | 483 |
| SEQ_ID_NO_1334 | LPSRLMPPVP | PAPLLVVAKK | ---------- | ---------S | ELETQRSVTE | 477 |
| SEQ_ID_NO_1330 | LPARVPSGDL | AALAAAESSE | ---------- | ---------R | EMEKQRQVS | 477 |

Figure 44 (continued)

| SEQ_ID_NO_1327 | AFKDLAGK- --KKAGVC-- | 490 |
| SEQ_ID_NO_1333 | RWRDAVSK- --KKTGPC-- | 502 |
| SEQ_ID_NO_1336 | YWRDQVKK- --KDTGIC-- | 501 |
| SEQ_ID_NO_1319 | HWRKIAGK- --KTSGVC-- | 502 |
| SEQ_ID_NO_1302 | YWKRLVEH- --KRNIVC-- | 494 |
| SEQ_ID_NO_1311 | YWRRLASE- --KRTGAC-- | 501 |
| SEQ_ID_NO_1317 | YWKRLVDG- --KRLGAC-- | 499 |
| SEQ_ID_NO_1305 | CWKRLVDR- --KIAGVC-- | 478 |
| SEQ_ID_NO_1339 | AWKKFVAQ- --KANRVC-- | 509 |
| SEQ_ID_NO_1318 | AWKKFVMNRK --KTNGVC-- | 504 |
| SEQ_ID_NO_1331 | ---------- --RDRGPCSH | 420 |
| SEQ_ID_NO_1313 | YWKKFVEAKK -SNKNRIC-- | 493 |
| SEQ_ID_NO_1303 | YWRKFVSERK ANNKNKIC-- | 494 |
| SEQ_ID_NO_1340 | AWRKLVVQRK --KLNGVC-- | 499 |
| SEQ_ID_NO_1320 | AWKKFVADKK K-KTNGVC-- | 496 |
| SEQ_ID_NO_1326 | AWKKFVEEKK K-KTNRVC-- | 500 |
| SEQ_ID_NO_1334 | AWKKFVLAK- --RTNGVC-- | 492 |
| SEQ_ID_NO_1330 | LWKRAVLAKK --KTNGVC-- | 493 |

Figure 45

| SEQ_ID_NO_1363 | | | | | MSKTTNQ NRRPSFTSST | 17 |
|---|---|---|---|---|---|---|
| SEQ_ID_NO_1373 | | | | | MVD | 3 |
| SEQ_ID_NO_1342 | | | | | | 0 |
| SEQ_ID_NO_1381 | | | | | | 0 |
| SEQ_ID_NO_1362 | | | | | | 0 |
| SEQ_ID_NO_1371 | | | | | | 0 |
| SEQ_ID_NO_1366 | | | | | M | 1 |
| SEQ_ID_NO_1370 | | | | | | 0 |
| SEQ_ID_NO_1346 | | | | | | 0 |
| SEQ_ID_NO_1372 | | | | | | 0 |
| SEQ_ID_NO_1374 | | | | | MKKQEKEA | 8 |
| SEQ_ID_NO_1355 | | | | | | 0 |
| SEQ_ID_NO_1364 | | | | | | 0 |
| SEQ_ID_NO_1378 | MGSRHQVVQQ | QNRGDVVPGA | IKQKSMAVEK | KNRRALGDIG | NVV-TVRGVE | 49 |
| SEQ_ID_NO_1377 | ---MNTNRAV | LVPHRGEVGG | KQKNGQADGR | NNRRVLGDIG | NLVTGAPVIE | 47 |
| SEQ_ID_NO_1379 | MGSRAVVVPD | QQPRGR--GG | KQKNGQAEGR | -NRRVLRDIG | NLV-PVPTVE | 46 |
| SEQ_ID_NO_1360 | | | | MAGADEN | HGAVKLANFR | 17 |
| SEQ_ID_NO_1383 | | | | | | 0 |

| SEQ_ID_NO_1363 | ESSMRKRHGP | SSSSSAVK-- | PISNTAVMVA | KKRAPLGNIT | | 55 |
|---|---|---|---|---|---|---|
| SEQ_ID_NO_1373 | EENKVPATAA | ASRGSNKR-- | AFDSIAITNE | NDPLQISERP | | 41 |
| SEQ_ID_NO_1342 | | | | | | 0 |
| SEQ_ID_NO_1381 | -MADKENSTP | ASAARLTRSS | AAAGAQAKRS | AAAGVADGGA | | 39 |
| SEQ_ID_NO_1382 | -MADKENSTP | ASAARLTRSS | AAAGAQAKRS | AAAGVADGGA | | 39 |
| SEQ_ID_NO_1371 | | | -APSMTTPE- | | | 8 |
| SEQ_ID_NO_1366 | ATSENNSSAR | PQREAKKR-- | AAAISQIHG N | | | 30 |
| SEQ_ID_NO_1370 | MADQDNSTRR | PQREAKKR-- | AVAALCE--- | | | 25 |
| SEQ_ID_NO_1346 | -MAEQENCTR | VTFRAAKKR-- | AAALASTEDQ | | | 27 |
| SEQ_ID_NO_1372 | -MADKENCIR | VTRLAKKR-- | AVEAMAASEQ Q------ | | | 28 |
| SEQ_ID_NO_1374 | IMADLENCGR | VTRLAKKR-- | AAEAMASHQQ Q------ | | | 37 |
| SEQ_ID_NO_1355 | MADEKENCVR | MTRAATKRKA | SMEAAIDKE- | | | 29 |
| SEQ_ID_NO_1364 | -MAENQNSTR | MTRAAAKR-- | KASVTDEN-- | | | 25 |
| SEQ_ID_NO_1378 | GKALPQYSRP | ITRGFCAQLI | ANAEAAAAEN | NKNSLAVNAK | GADGALPIKR | 99 |
| SEQ_ID_NO_1377 | GKPKAQISRP | ATRSFCAQLL | ANAQAEKNKV | KPLAEVVNKV | | 87 |
| SEQ_ID_NO_1379 | EKPQNQISRP | VTRSLCVQ-- | PAAAAEKKNK | KPLAEVVNGG | GEVKAAAAAH | 94 |
| SEQ_ID_NO_1360 | ETTNRRALKD | IKNFVGAP-- | SFPCAANKRQ | LKEVVCGNND | | 55 |
| SEQ_ID_NO_1383 | -MITGAQGVR | QTRSKTTY-- | EVPQQQQQQS | FEW------ | | 30 |

Figure 45 (continued)

```
SEQ_ID_NO_1363    -----NQRKD SRIFPNSSSA DSAHCPNKSA KLKLAAPTQP VCYNACETKS    100
SEQ_ID_NO_1373    -----YPANK KRVVLGELNN LSNV------ --IVSTQNSD LTETHESKRK    78
SEQ_ID_NO_1342    ------MGYL RRVRLSSFAA GAAT------ --ASAAGFFL LYKDHLLARA    38
SEQ_ID_NO_1361    -----PPAKR KRVALSDLPT LSNA------ --VVVAPRQP HHPVVIKPSS    76
SEQ_ID_NO_1362    -----PPAKR KRVALSDLPT LSNA------ --VVVAPRQP HHPVVIKPSS    76
SEQ_ID_NO_1371    ------PASK RRVVLGEISN NSSA------ --VSGNEDLL CREFEVPKCV    44
SEQ_ID_NO_1366    ------AAKK KRVVLGDVTN VSSS------ ---------- -----DVAVS    53
SEQ_ID_NO_1370    ------QRKR KRVALGDITN DVVS------ --ETEKLVSD SHSHTQKKKK    61
SEQ_ID_NO_1346    ------PLNK KRVVLGELPN LSNA------ --IVSS---- -NEPQKDKAK    58
SEQ_ID_NO_1372    ------RPSK KRVVLGELKN LSSN------ ---ISS QTY DFSSGPDKDQ    63
SEQ_ID_NO_1374    ------HPSK KRVVLGEICN FSNL------ --GVSQI KGL NTEPKKDPKS    73
SEQ_ID_NO_1355    -------RINK KRVVLGELPN LSNI------ ---------- ---KKSRKA    53
SEQ_ID_NO_1364    ------PVSK KRVVLGELPN NGNV------ ---PAPLIP LQERETQKPK    59
SEQ_ID_NO_1378    AVAR--VPVD KKTVKSKPQE IEISPDTEK KKAPVLEKEI TGEKSLKKKA    147
SEQ_ID_NO_1377    ------PAKK KASDKPAVQE AVIVISPDEE VKKKTIEKSP ISKRKAKKTG    131
SEQ_ID_NO_1379    KKHYDPPKPE TVIVISSDEE LESE------ --EKKKPVAV IARKSRVGSS    136
SEQ_ID_NO_1380    -----SVIPR RPLTRQFAST LASK------ --SQQSHGET SNKHGQITGN    92
SEQ_ID_NO_1383    ------GRTS QRTSHGKPRR GSVM------ ------GGT MTTAGADVDM    61

SEQ_ID_NO_1363    TCEEYVVPIE RKAFSNLCIT PSSDTTTNVM SETENKEEKF MNLDNKDDAD    150
SEQ_ID_NO_1373    IKLRKTRNVV KEIVELKTSA NSSPK----- ---------- --------DN    105
SEQ_ID_NO_1342    ADAESNSASY SPPLATADTA FSAPP----- ---------- RAVAP---AD    68
SEQ_ID_NO_1361    KQPEPAAEAA APSGGGGGSP VSSAST---- ---------- STASPSSGVD    112
SEQ_ID_NO_1362    KQPEPAAEAA APSGGGGGSP VSSAST---- ---------- STASPSSGVD    112
SEQ_ID_NO_1371    AQKKRKRGVK EDVGVDFGEK F--------- ---------- --------DD    67
SEQ_ID_NO_1366    VSKKPVQTHK NVKLEKPAAP VATPE----- ---------- ---KVEERHD    65
SEQ_ID_NO_1370    RNIAKSPVPE KL-------- ---------- ---------- --------ED    75
SEQ_ID_NO_1346    AKPKARKGAS TKKEGVLKED VDGNP----- ---------- --------ED    85
SEQ_ID_NO_1372    KNKNKRKAKE SLGFEVKEKK VEEAG----- ---------- IDVFSQS-DD    97
SEQ_ID_NO_1374    KQQQSKRKLK RAVTSKIDKE ELNVD----- ---------- -NVDANY-DD    106
SEQ_ID_NO_1355    TTKQKKKSVS IPTIETLNSD IDTRS----- ---------- --------DD    80
SEQ_ID_NO_1364    STLFAAKKQT KTPPIPQTVD FESGS----- ---------- --------SD    86
SEQ_ID_NO_1378    PILTSTLTAR SKAASVVRTK PKEQI----- ---------- VDIDAADYNN    182
SEQ_ID_NO_1377    KTLTSTLTAR SKAACGLSNR PKNEI----- ---------- DDIDAADAAN    166
SEQ_ID_NO_1379    RIMTSILTAR SKALCGPTIK PKVPI----- ---------- ADIDAADVDN    171
SEQ_ID_NO_1380    EKHNPIIIDE DVPMVEESEE MEECELVEEI TMEDIVIDSA QDIDIGDVGN    142
SEQ_ID_NO_1383    RESYSIYLER SSAADVMTDA L--------- ---------- PDIDLYDHDN    92
```

Figure 45 (continued)

| | | | | | | | |
|---|---|---|---|---|---|---|---|
| SEQ_ID_NO_1363 | PQLYATFACD | YNHLRAAE- | -AKKQPAVDY | METVQKDVNS | TMRGILVDWL | 198 |
| SEQ_ID_NO_1373 | LDKCS-YGPL | YQHLHSLEV | EERRRPLSNY | MEKVQNNVFP | SMRTVLVDWL | 154 |
| SEQ_ID_NO_1342 | LQLSGSYASD | YTYLRSLEV | DPQRRSRSDY | EAVQADVTA | HMRSILVDWL | 118 |
| SEQ_ID_NO_1381 | PQ---YASD | YTYLRSMEV | EARRQSAADY | EBVQVDVTA | NMRAILVDWL | 158 |
| SEQ_ID_NO_1382 | PQ---YASD | YTYLRSMEV | EARRQSAADY | EAVQVDVTA | NMRAILVDWL | 158 |
| SEQ_ID_NO_1371 | PQMCSAYVSD | VYEYLKQMEM | ETKRRPIMNY | EQVQKDVTS | NMRGVLVDWL | 117 |
| SEQ_ID_NO_1366 | PQLCGPYVSD | YEYLRGMEV | DPSKRPLMDY | VQKIQRDVNA | NMRGVLVDWL | 135 |
| SEQ_ID_NO_1370 | PQLCEPYVSD | HDYLRNLEV | DPSKRPLPDY | QKVQRDINA | NMRGVLVDWL | 125 |
| SEQ_ID_NO_1346 | PQMCAPYASD | YEYIHKMEV | DPKRRPLPDY | EKVQKDVSP | NMRGILVDWL | 135 |
| SEQ_ID_NO_1372 | PQMCGAYVSD | YEYLHKMEM | ETKRRPLPDY | LDKVQKDVTA | NMRGVLIDWL | 147 |
| SEQ_ID_NO_1374 | PQMCSAYVSD | YDYLRKMEI | EEKRRPLPDY | LEKVQKDLSP | NMRGVLVDWL | 156 |
| SEQ_ID_NO_1355 | PQMCGPYVTS | FEYLRQLE- | -VKSRPLVDY | EKIQKDVTS | NMRGVLVDWL | 128 |
| SEQ_ID_NO_1364 | PQMCGPFVAD | CAYLREMEG | KLKQRPLHDY | EKVQSDLTP | SMRGVLMDWL | 136 |
| SEQ_ID_NO_1378 | DLAVVEYVED | MYKFYKSAE- | -NDSRPH-DY | MDFSQPEINE | KMRAILIDWL | 228 |
| SEQ_ID_NO_1377 | HLAVVEYVED | YNFYKLTE- | -DESRVN-NY | MEFFQPELNH | KMRAILVDWL | 212 |
| SEQ_ID_NO_1379 | ELAVVEYVED | YKFYKLTE- | -GESRVH-DY | MDFSQPEINS | KMRSILIDWL | 217 |
| SEQ_ID_NO_1380 | PLAVVDYVDD | YNYYRRVE- | -ASSCVHPDY | MS-NQFDIND | KMRAILIDWL | 189 |
| SEQ_ID_NO_1383 | PLAVTQYVND | YGYNYKVE- | -PDTRVSETY | M-LQGDINY | KMRAILIDWL | 139 |

| | | | | | | | |
|---|---|---|---|---|---|---|---|
| SEQ_ID_NO_1363 | VEVSEEYRLV | PETLYLTVNY | DRYLSGNVI | SRQKLQLLGV | ACMMIAA-KY | 247 |
| SEQ_ID_NO_1373 | VEVTEEYKLV | SDTLYLAVSY | DRFLSSHVL | AMEKLQLLGV | SCMLVAS-KY | 203 |
| SEQ_ID_NO_1342 | VEVAEEYKLV | ADTLYLTISY | VDRFLSVNAL | GRDKLQLLGV | ASMLIAA-KF | 167 |
| SEQ_ID_NO_1381 | VEVADEYKLV | ADTLYLAVSY | LDRYLSAHPL | RRNRLQLLGV | GAMLIAA-KY | 207 |
| SEQ_ID_NO_1382 | VEVADEYKLV | ADTLYLAVSY | LDRYLSAHPL | RRNRLQLLGV | GAMLIAA-KY | 207 |
| SEQ_ID_NO_1371 | VEVSLEYKLL | PETLYLAISY | VDRYLSVNVL | NRQKLQLLGV | SSFLIAS-KY | 166 |
| SEQ_ID_NO_1366 | VEVAEEYKLV | SDTLYFSVAY | DRFLSLNIL | SRQRLQLLGV | ASMLIAS-KY | 184 |
| SEQ_ID_NO_1370 | VFVAFEYKLV | ADTLYFSVSY | DRFLSLNDL | SRQKLQLLGV | SSMLIAS-KY | 174 |
| SEQ_ID_NO_1346 | VEVAEEYKLV | SETLYLTVSY | VDRFLSFNVL | SRQRLQLLGV | SSMLLAS-KY | 184 |
| SEQ_ID_NO_1372 | VEVAEEYKLL | PDTLYLTVSY | DRFLSMNAL | SRQKLQLLGV | SSMLIAS-KY | 196 |
| SEQ_ID_NO_1374 | VEVAEEYKLL | SDTLYLAVSY | DRFLSTNVI | TRQKLQLLGV | SSMLISA-KY | 205 |
| SEQ_ID_NO_1355 | VEVAEEYKLL | SDTLYLAVSY | DRFLSLKTV | NKQRLQLLGV | TSMLIAS-KY | 177 |
| SEQ_ID_NO_1364 | VEVAEEYKLV | SDTLYLTVSY | VDRFLSAKPL | NRQRLQLVGV | GAMLIASRKY | 186 |
| SEQ_ID_NO_1378 | VQVHYKFELS | PETLYLTIN | VDRYLASKTT | SRRELQLLGM | SSMLIAS-KY | 277 |
| SEQ_ID_NO_1377 | LEVHRKFELM | PESLYLTIN | LDRFLSMKTV | PRKELQLVGI | SAMLIAC-KY | 261 |
| SEQ_ID_NO_1379 | TEVHRKFELM | PETLYLTIN | VDRYLSMNAV | PRRELQLVGI | SSMLIAC-KY | 266 |
| SEQ_ID_NO_1380 | VEVHYKFELM | EETLYLTVN | DRFLSRQAV | VRKKLQLVGV | TAMLLAC-KY | 238 |
| SEQ_ID_NO_1383 | VEVHLKFKLM | PETLFLTTNL | DRFLELKIV | RRNLQLVGV | TAMLVAS-KY | 188 |

Figure 45 (continued)

| SEQ_ID_NO_1363 | EEVCAPQVEE FCYITDNTYL KDEVLDMESA VLNYLKFEMS APTVKCFLRR | 297 |
|---|---|---|
| SEQ_ID_NO_1373 | EEISPPHVED FCYITDNTYT REEVVNMERD LLSFLNFEIS SPTTITFLRI | 253 |
| SEQ_ID_NO_1342 | EEISPPHPED FCYITDNTYT KEELLKMESD LKLLKFELG NPTIKTFLRR | 217 |
| SEQ_ID_NO_1361 | EEISPPHVED FCYITDNTYT RQEVVKMESD LKLLEFEMG NPTIKTFLRR | 257 |
| SEQ_ID_NO_1362 | EEISPPHVED FCYITDNTYT RQEVVKMESD LKLLEFEMG NPTIKTFLRR | 257 |
| SEQ_ID_NO_1371 | EEIKPKNVAD FVDITONTYS QQEVVKMEAD LLKTLKFEMG SPTVKTFL-G | 215 |
| SEQ_ID_NO_1366 | EEIKPPEVED FCYITDNTYS KEEVVNMEAE LKALKFELG GPTVKTFLRR | 234 |
| SEQ_ID_NO_1370 | EEIKPPEVED FCYITDNTYS KEEVLSMEAE LKTLKFELG GPTIKTFLRR | 224 |
| SEQ_ID_NO_1346 | EEINPPHVED FCYITDNTYT KEEVVKMEAD LKSLKFEMG NPTIKTFLRR | 234 |
| SEQ_ID_NO_1372 | EEISPPHVED FCYITDNTYK KEEVVKMEAD VLKFLKFEMG NPTIKTFLRR | 246 |
| SEQ_ID_NO_1374 | EEISPPHVED FCYITDNTYT KEEVVKMEAD VLKTLNFEMG NPTVKTFLRR | 255 |
| SEQ_ID_NO_1355 | EEITPPNVDD FCYITDNTYT KQEIVKMEAD LLALQFELG NPTSNTFLRR | 227 |
| SEQ_ID_NO_1364 | EEISPPKVED FVYITDNTFT RQDVVSMEAD LLALQFELG CPTIKTFLRR | 236 |
| SEQ_ID_NO_1378 | EEIWAPEVND LVCISDGSYS NEQVLRMEKK LGALEWYLT VPTPYVFLVR | 327 |
| SEQ_ID_NO_1377 | EEIWAPEVND FMHISDNVYT RDLILQMEKA LGKLEWYLT VPTPYVFLVR | 311 |
| SEQ_ID_NO_1379 | EEIWAPEVSD FIVISDNAYV REQILIMEKA LGKLEWYLT VPTPYVFLVR | 316 |
| SEQ_ID_NO_1380 | EEVSVPVVDD LVTISDRAYT RKEVLDMEKS VKTLQFNTS VPTPFVFLRR | 288 |
| SEQ_ID_NO_1363 | EEIWAPEVRD FVYISDRAYT RQQILEMEKQ MLNTLGFHLT VPTPYCFLNR | 238 |

| SEQ_ID_NO_1363 | LF-SGCPRVH EAPCHQLECM ASYIAELSLL EY-TMLSHPP SLVAASAIFL | 345 |
|---|---|---|
| SEQ_ID_NO_1373 | FL-KAAQDNL SFLTLQFEFL SCYLAELSLL DY-SCVRFLP SMTAASAIFL | 301 |
| SEQ_ID_NO_1342 | FI-RSAHEDK KGSILLMEFL GSYLAELSLL DY-GCLRFLP SVVAASVMFV | 265 |
| SEQ_ID_NO_1361 | FT-RSCQEDK KRSSLLLEFM GSYLAELSLL DY-SCLRFLP SVVAASVVFV | 305 |
| SEQ_ID_NO_1362 | FT-RSCQEDK KRSSLLLEFM GSYLAELSLL DY-GCLRFLP SVVAASVVFV | 305 |
| SEQ_ID_NO_1371 | FI-RAVQENP DVPKLKFEFL ANYLAELSLL DY-GCLEFVP SLIAASVTFL | 263 |
| SEQ_ID_NO_1366 | FS-RVGQEGV DITSDLQFEFL SCYLAELSLL DY-NCIKFLP SLVAASVVFL | 282 |
| SEQ_ID_NO_1370 | FITKVGQEGV DASELQFEFL CCYLAELSLL DY-NCVKFLP SMVAASVYFL | 273 |
| SEQ_ID_NO_1346 | FT-RVALEDY KTSNLQLEFL GFYLAELSLL DY-NCVKFLP SLVAASVIFL | 262 |
| SEQ_ID_NO_1372 | LT-RVVQDGD KNPNLQFEFL GYYLAELSLL DY-GCVKFLP SLIASSVIFL | 294 |
| SEQ_ID_NO_1374 | FT-GVAQEDY KTPNLQLEFL GYYLAELSIL DY-SCVKYVP SLLAAAVVFL | 303 |
| SEQ_ID_NO_1355 | FT-RVAQEDF EMSHLQMEFL CSYLSELSML DY-QSVKFLP STVAASAVFL | 275 |
| SEQ_ID_NO_1364 | FT-RVAQEDF NESLLQIECL CCYLSELSLL DY-SCVKFLP SMLAASAVFL | 284 |
| SEQ_ID_NO_1378 | FI-KASLPDS D----VEKNM VYFLAELGMM NYATI MYCP SMIAAAAVYA | 372 |
| SEQ_ID_NO_1377 | YI-KAAMPSD DQ---EIQNM AFFFAELGLM NYTTI SYCP SMLAASAVYA | 357 |
| SEQ_ID_NO_1379 | FI-KASVPSN DHRE-EMENM VFFLAELGLM HYPTI LYCP SMIAASAVYA | 364 |
| SEQ_ID_NO_1360 | FL-KAAGSEK K-----LELL SSFIIELSLV EY-QMLKFQP SLLAAAIYT | 331 |
| SEQ_ID_NO_1363 | FF-KAAGGDR Q-----FQLY ASYAVECALP EY-GMLKYSG STLAAAGVYI | 281 |

Figure 45 (continued)

| | | | | | | | | |
|---|---|---|---|---|---|---|---|---|
| SEQ_ID_NO_1363 | AKYTLDPTRR | PWNSTLRHYT | QYEAMELRGC | VMDLQRLCSN | AHV--- | STLP | 392 |
| SEQ_ID_NO_1373 | SRFTVLPEVC | PWTLALQQCT | GYKPSELKDC | VLVIHELQSS | LME--- | ATGR | 348 |
| SEQ_ID_NO_1342 | ARLTIDPNTN | PWNTKLQKMT | GYKVBELKDC | IVAIHDLQLN | RKC--- | PSLT | 312 |
| SEQ_ID_NO_1381 | AKLNIDPYTN | PWSKKMQKLT | GYKVSELKDC | ILAIHDLQLR | KKC--- | SNLT | 352 |
| SEQ_ID_NO_1382 | AKLNIDPYTN | PWSKKMQKLT | GYKVBELKDC | ILAIHDLQLR | KKC--- | SNLT | 352 |
| SEQ_ID_NO_1371 | ARFTIRPNVN | PWSIALQKCS | GYKSKDLKEC | VLLLHDLQMG | RRG--- | GSLS | 310 |
| SEQ_ID_NO_1366 | ARFMESTKTH | PWNSALHQLT | RYKPADLKEC | VLNLHDLYLS | RRG--- | ASLQ | 329 |
| SEQ_ID_NO_1370 | ARFMLNPKSR | PWNSAICQFT | SYKPADLKEC | VLNMHDLYLS | RKG--- | ATLQ | 320 |
| SEQ_ID_NO_1346 | TRFLMRPKTN | PWSSTLQQYT | GYKAADLREC | VLIIHDLYLS | RRG--- | GGLQ | 329 |
| SEQ_ID_NO_1372 | SRFTLQPKVH | PWNSLLQHNS | GYKPADLKEC | VLIIHDLQLS | KRG--- | SSLV | 341 |
| SEQ_ID_NO_1374 | SRFTLQPNTH | PWSLALQQYS | GYKAADLKEC | ILIHDLQLS | RRG--- | GSLA | 350 |
| SEQ_ID_NO_1355 | ARFIIRPKQH | PWNVMLEEYT | RYKAGDLKEC | VAMIHDLYLS | RKC--- | GALE | 322 |
| SEQ_ID_NO_1364 | ARFIIRPKQR | PWNQMLEEYT | KYKASDLGQP | VGIIHDLYLS | RRG--- | NSLE | 331 |
| SEQ_ID_NO_1378 | ARCTLNKMPI | -MNETLRMHT | GFSEVQLMDC | AKLLIDFHGG | STD--- | QKLQ | 418 |
| SEQ_ID_NO_1377 | ARGTLNKGPL | -MTPTLQHHT | GYSEEQLMEC | TKQLVSYHKG | AAE--- | SKLK | 403 |
| SEQ_ID_NO_1379 | ARCTLNSNPL | -MTETLKHHT | GYSEDOLGDC | AKMLARFHSD | GGGVEK | SKLK | 413 |
| SEQ_ID_NO_1380 | AQCSLKGFKF | -MTRTCEQYT | MYTEDQLLEC | SKMMVGFHRN | AGS--- | GKLT | 377 |
| SEQ_ID_NO_1383 | AIRGLQTGS- | -MNHTMEAHT | RLSESEVYPC | ACDMAELMRK | APT--- | ATLT | 326 |

| | | | | | | |
|---|---|---|---|---|---|---|
| SEQ_ID_NO_1363 | AVRDKYSQHK | YKFVAKKFCP | SIPPDFFK- | ---NSLY- | 425 |
| SEQ_ID_NO_1373 | ALREKYMNHK | YKCVAALHPP | -DIPSCFFD- | ---DA--- | 378 |
| SEQ_ID_NO_1342 | AIRDKYKQHK | FKCVSLLVP | VVPTSYFE- | ---DLAE- | 345 |
| SEQ_ID_NO_1381 | AIRDKYKQHK | FKCVSTLLPP | VDIPASYLD- | ---DLTE- | 385 |
| SEQ_ID_NO_1382 | AIRDKYKQHK | FKCVSTLLPP | VDIPASYLD- | ---DLTE- | 385 |
| SEQ_ID_NO_1371 | AVRDKYKKHK | FKCVSTLSPA | PEIPLSIFN- | ---DV--- | 341 |
| SEQ_ID_NO_1366 | AVREKYKQHK | FKCVATTPSP | PEIPLSFFEF | EGQILRQL | 367 |
| SEQ_ID_NO_1370 | AVRDKYKQHK | FKCVATTPSP | PEISLSFFEF | RGADP--- | 355 |
| SEQ_ID_NO_1346 | AVREKYKQHK | FKCVANMPSP | PELPALYFE- | ---EV--- | 360 |
| SEQ_ID_NO_1372 | AVRDKYKQHK | FKCVSTLTAP | PSPDEFFE- | ---DI--- | 372 |
| SEQ_ID_NO_1374 | AVRDKYKQHK | FKCVSSLISP | VEIPASFFE- | ---DMRQL | 384 |
| SEQ_ID_NO_1355 | AIREKYKQHK | FKCVATMPVS | PELPLTNFE- | ---DVNI- | 355 |
| SEQ_ID_NO_1364 | AVRNKYKQHK | FKCVATMPVS | PELPDAFFE- | ---DVTIR | 365 |
| SEQ_ID_NO_1378 | GIYRKYSRLE | KGAVALPQP | LLA------ | -------- | 441 |
| SEQ_ID_NO_1377 | AIYRKFSSPD | RGAVALFPPA | RNLLPTTTT- | ---TTTSS | 437 |
| SEQ_ID_NO_1379 | AVYKKFSSSD | RSSVALFPPA | RSLLLVL--- | -------- | 440 |
| SEQ_ID_NO_1380 | GVHRKYSTSK | FGFAGKSYPA | LFLLDMRL-- | -------- | 405 |
| SEQ_ID_NO_1383 | AVYKKYSSEK | FMKIATLPVP | HDLRL----- | -------- | 351 |

Figure 46

| | | | | | | | |
|---|---|---|---|---|---|---|---|
| SEQ_ID_NO_1404 | -MA------ | ---SEWSKEE | NKLFEQAIAY | YGEGAPDLWH | KVSRAMGGK | | 39 |
| SEQ_ID_NO_1401 | -MSGSRSSSP | NSKSEWSRKF | NKMFEEALAY | YGEDTPNRWD | KVASAMGGK | | 49 |
| SEQ_ID_NO_1400 | -MAGSDSSSP | NSNSTWSLKE | NKMFEEALAY | YGEGTPNLWD | KVSSAIGGK | | 49 |
| SEQ_ID_NO_1385 | -MSASRSSSP | NSISQWSQKE | NKMFEEALAY | YGEGTSNRWD | KVSRAMGGK | | 49 |
| SEQ_ID_NO_1407 | -MSASRSSSP | NSMSKMSPKE | NKMFEQALAY | YGEGTPNRWD | KVSSAMGGK | | 49 |
| SEQ_ID_NO_1387 | -MSSSHQTPR | NSSSSWTPRE | NKLFEKALAL | FDKDTPDRWQ | NIAKAVGGVK | | 49 |
| SEQ_ID_NO_1393 | MASSSLSKQK | ASDSSWTPKQ | NKLFEKALAK | YDKDTPDRWQ | NVAKAYGG-K | | 49 |
| SEQ_ID_NO_1390 | MASSSMSSQ- | -SSGSWTAKQ | NKAFEQALAT | YDQDTPNRWQ | NVAKVYGG-K | | 47 |
| SEQ_ID_NO_1395 | --MSSMSSQH | GSSGSWTAKQ | NKAFEKALAV | YDKETRDRWS | NVAKAVGG-K | | 47 |
| SEQ_ID_NO_1398 | MASGSMS--- | ---SSWTAKE | NKMFEKALAV | YDRDTPDRWH | KIARAIGG-K | | 43 |
| SEQ_ID_NO_1396 | -MASTRGSG- | ---RPWSAKE | NKAFERALAV | YDKDTPDRWA | NVARAVEG-R | | 44 |
| SEQ_ID_NO_1394 | MASSSMSAS- | ---GSWSVKE | NKAFERALAV | YDKDTPDRWY | NVAHAYGG-K | | 45 |

| | | | | | | | |
|---|---|---|---|---|---|---|---|
| SEQ_ID_NO_1404 | TADEVRLHFE | LVDDIKLIE | ARRVPFPKYN | TQGAN---- | ---------- | | 75 |
| SEQ_ID_NO_1401 | SAEEIRCHYE | DLTDDVKTIE | SGRVDFPKYK | TQGYWT---- | ---------- | | 85 |
| SEQ_ID_NO_1400 | SAEEVRCHYE | DLVDDVKMIE | SGRVIYPKYK | TQGFWTRG-- | ---------- | | 87 |
| SEQ_ID_NO_1385 | SAEEVRCHYE | DLDYDVKMIE | SGHVPYPKYK | THGFWT---- | ---------- | | 85 |
| SEQ_ID_NO_1407 | SAEEVRCHYE | DLDYDVKMIE | SGHVPYPQYK | TQGFWTRGSL | MPTNYYGSNP | | 99 |
| SEQ_ID_NO_1387 | SAEEMKRHYE | LIEDLKHIE | SGRVPIPNYK | SSRSYSNTNE | EER------- | | 92 |
| SEQ_ID_NO_1393 | SADEVKRHYE | LLEDLRHIE | SGHVPLPKYK | STGSSTNVEE | EERLLKYLKL | | 99 |
| SEQ_ID_NO_1390 | TIEEVKRHYE | LLVQDINSIE | NGHVPFPNYR | TSGGCINGRL | SQEEKRYVLS | | 97 |
| SEQ_ID_NO_1395 | TAEEVKRHYE | LLRDVFFID | NGMVPFPKYK | TTGGSHNSTS | Q--------- | | 88 |
| SEQ_ID_NO_1398 | TADEVKRYYD | LVEDVRRIE | AGQMPYANYR | SSNGRG---- | ---------- | | 79 |
| SEQ_ID_NO_1396 | TPEEVKKHYE | LVEDIKYIE | SGKVPFPNYR | TTGGNMKTDE | KRFRNLKIR- | | 93 |
| SEQ_ID_NO_1394 | TPEEVKKHYE | LLVEDIKHIE | SGKVPFPNYK | KISYSHEEKR | MRNMSLH--- | | 92 |

| | | |
|---|---|---|
| SEQ_ID_NO_1404 | ---------- | 75 |
| SEQ_ID_NO_1401 | ---------- | 85 |
| SEQ_ID_NO_1400 | ---------- | 87 |
| SEQ_ID_NO_1385 | ---------- | 85 |
| SEQ_ID_NO_1407 | SIMTKISYFQ | 109 |
| SEQ_ID_NO_1387 | ---------- | 92 |
| SEQ_ID_NO_1393 | N--------- | 100 |
| SEQ_ID_NO_1390 | ---------- | 97 |
| SEQ_ID_NO_1395 | ---------- | 88 |
| SEQ_ID_NO_1398 | ---------- | 79 |
| SEQ_ID_NO_1396 | ---------- | 93 |
| SEQ_ID_NO_1394 | ---------- | 92 |

Figure 47

```
SEQ_ID_NO_1419  ..........  .....MSFYL F.........  ..........  ..FLFITMPL   14
SEQ_ID_NO_1421  ..........  .....MAC.. F.........  ..........  ..RSRSRAAA   12
SEQ_ID_NO_1409  ..........  .....MGQRR F.........  ..........  ..EDERAALA   14
SEQ_ID_NO_1425  ..........  .....MADC. ..........  ..........  ...TTMRLAS   11
SEQ_ID_NO_1424  MEPWRWQICL  VTPRSFLFQA FVRTGFRAMR VSSASSTPPP  PAFAAAAWAV   50
SEQ_ID_NO_1413  ..........  .....MNRRF L.........  ..........  ..FVLSSLSF   14
SEQ_ID_NO_1418  ..........  .....MRMEH I.........  ..........  ..YKFQHWLF   14
SEQ_ID_NO_1415  MEGELKMRGG  DLIRPGRFCI L.........  ..........  ...SVATISS   29

SEQ_ID_NO_1419  IVFCDF....  ..........  ..ENPSGSST QFHSFHE..  ..........   36
SEQ_ID_NO_1421  VVVVTM....  ..........  ..LLLQCSEV SASSSPQF.  ....RKM..    38
SEQ_ID_NO_1409  TVASLL....  ..........  ..LILTTAQAA AAAASGRH.  ....LSLPT.   42
SEQ_ID_NO_1425  SVTLIL....  ..........  ..LLLVASDAL VVSGESSS.  ....SAM..    37
SEQ_ID_NO_1424  VLLAWL....  .......RSD VALAAASSN DDTGLSPLMP PPPPLAAPVP   89
SEQ_ID_NO_1413  AVLFLF....  ..........  LVALFSGQGK NINGSFGL.  ....KLLR.    42
SEQ_ID_NO_1418  FIGLGV....  .........L LSLSLSVKAN DFEGSNDR.  ....RSIALK   45
SEQ_ID_NO_1415  LLAVFFEDIY  HSSMHASSLV SLLNPVDTQ SLTELFHL.  ....KAVSEI   73

SEQ_ID_NO_1419  .......DKN  GSLTVSEKVE HAH.......  ..........  ......YTPR   56
SEQ_ID_NO_1421  ..........  .LVSYNASSM SSS.......  ..........  .GG-GGHSAE   56
SEQ_ID_NO_1409  ..QKAAAARM  NDTSSSDMQV ITP.......  ..........  .APLAISTAA   72
SEQ_ID_NO_1425  ..QSKTLNMN  KLLNISED.. HSP.......  ..........  .NG-GRHWMQ   64
SEQ_ID_NO_1424  AAVSPAPATP  PAVLSPRKLL RPPGADVVGV GFVSGSGGGG  GGGGGGDGVR  139
SEQ_ID_NO_1413  ..LRINQGNH  TLLTPHRKLL RTA.......  ..........  ......LAEPN   68
SEQ_ID_NO_1418  A-RSFVSINE  NRTALSRKLL LSP.......  ..........  .DI--GDGTN   74
SEQ_ID_NO_1415  GSKKPYFYKE  NNTNFARKLL QLP.......  ..........  .DA---GSTN  102

SEQ_ID_NO_1419  KFWFHGSCTK  -RDISISQSK GST--SGIPQ YLVQIVNTCV  SG.......    95
SEQ_ID_NO_1421  PLE-LEECSK  -DLLEVFCNN APSMAGGMPT YSVEITNTCI  -D.......    97
SEQ_ID_NO_1409  RMG-PDGCSG  -EDVAVYQSS ANPLPSGIPA YTVRINVCS   GG.......   112
SEQ_ID_NO_1425  RMQ-PDSCSE  -QNVWVYQNN AEILPSGIPT YSVEIINVCT  -A.......   103
SEQ_ID_NO_1424  TRRVDDGCAG  ADDIAIYQGR ATPLPSGVPA YTVDVMNRCA  GGGGGGGDEE  189
SEQ_ID_NO_1413  RIW-GEKCSK  -ADIVLNQGP TAPLPSGIPT YTVEILNVCV  SG.......   108
SEQ_ID_NO_1418  RIG--QDCSK  -DDIVLFQGS TNPLPSGVPS YTVEIFNSCV  SD.......   113
SEQ_ID_NO_1415  RIG--AACSK  -DGIDIVQGS TAPLPNGIPS YTVQILNVCV  SG.......   141
```

Figure 47 (continued)

| | | | | | | | |
|---|---|---|---|---|---|---|---|
| SEQ_ID_NO_1419 | CAPYDIHLHD | GWFASARIIN | PKLFKRLSND | DCLVHGGKPL | TSNQIRFTY | | 145 |
| SEQ_ID_NO_1421 | CAVCDVHIAC | GDFASNDVID | PDKFRRLGFN | DCLVNGGGS | EPSFPVSFQY | | 147 |
| SEQ_ID_NO_1409 | CTVYDVHVSC | GDFASTELVD | PAKFQRVGFN | DCVVKGGGAL | EPSETVSFQY | | 162 |
| SEQ_ID_NO_1425 | CTVYDVHISC | GEFASAELVD | PSQFQRIGFN | DCLVKGGGRL | GPSEAVSFQY | | 153 |
| SEQ_ID_NO_1424 | CAIAGIHVRC | GWFSSVSLVD | PRVFRRLGHD | DCLLNDGRPL | LAGETVSFEY | | 239 |
| SEQ_ID_NO_1413 | CDISGIHLTC | GWFSSARLIN | PKIFKRLRYN | DCLVNDGKPL | INGGTLSFQY | | 158 |
| SEQ_ID_NO_1418 | CNIAEIHVSC | GWFSSNRLVN | PRVFRRLDYD | DCLVNDGQPL | GPGQSLSFQY | | 163 |
| SEQ_ID_NO_1415 | CSISNIHVSC | GWFSSAKLIN | PSVFRRIYYD | DCLVNDGEPL | GPGETLSFQY | | 191 |

| | | | | | | | |
|---|---|---|---|---|---|---|---|
| SEQ_ID_NO_1419 | SNSFMYPLAE | KSARFC---- | ---------- | ---------- | ---------- | | 161 |
| SEQ_ID_NO_1421 | GNSFPYPMTV | ASASCDCN-- | ---------- | ---------- | ---------- | | 165 |
| SEQ_ID_NO_1409 | SNSFSYHLSV | ASVACR---- | ---------- | ---------- | ---------- | | 178 |
| SEQ_ID_NO_1425 | SNSFAYPLAV | ANVACFHYSI | VWASMIPCLP | EHACHTASSV | KGLGPRPHA | | 202 |
| SEQ_ID_NO_1424 | TNSFPYKLSV | SVATCVVDPA | AP-------- | ---------- | ---------- | | 261 |
| SEQ_ID_NO_1413 | ANTFLYPLSV | SRVVCS---- | ---------- | ---------- | ---------- | | 174 |
| SEQ_ID_NO_1418 | ANSFSYPLSV | ASVSC----- | ---------- | ---------- | ---------- | | 179 |
| SEQ_ID_NO_1415 | ANSFLYPLSV | SSVACC---- | ---------- | ---------- | ---------- | | 207 |

Figure 48

| | | | | | | | |
|---|---|---|---|---|---|---|---|
| SEQ_ID_NO_1436 | · · · · · · · · · · | · · MTRPARFL | ETAATPPQPS | EQ· · · · · · · · | · · · · · · · MLA | 23 |
| SEQ_ID_NO_1444 | · · · · · · · · · M | GVHARAMSWY | TSPPGSPAPG | SAAEA·QHAL | SSSPRGGDTS | 40 |
| SEQ_ID_NO_1452 | · · · · · · · · · M | GVHGRSMGWY | LSPPGSPAPG | SAVAEAQHAL | SSSPGGGDAS | 41 |
| SEQ_ID_NO_1428 | · · · · · · · · · · | · · MHRL· · LL | ESHGGGNETS | GSGGG· · · · | · · DGYTRDMN | 29 |
| SEQ_ID_NO_1430 | MMQAKTAMVT | TLYHRPHRLL | LDTQPNASPS | LPNGS· · · ·R | TRNAFANEAN | 46 |
| SEQ_ID_NO_1432 | · · · · · · · · · · | · · MHRS· RML | DTVPLDVAPA | NGNL· · · · ·R | THDSYINETN | 30 |
| SEQ_ID_NO_1439 | · · · · · · · · · · | · · · · · · · MPP | SVGGG· · · N | TSDTFISDAN | 19 |
| SEQ_ID_NO_1442 | · · · · · · · · · · | · ·MRRLSDAG | EATPLVTPA | AAAAAGGTLA | SPAAAGSNAN | 37 |
| SEQ_ID_NO_1453 | · · · · · · · · · · | · ·MRRLGDVV | EAPALVLTPA | SMQQA· · · · | · ·GQRGSSGA | 31 |
| SEQ_ID_NO_1457 | · · · · · · · · · · | · ·MRRLVDVV | EAPALVLTPA | WAATA· · · S | MQQAGGSSGA | 34 |

| | | | | | | |
|---|---|---|---|---|---|---|
| SEQ_ID_NO_1436 | AESDMVVILS | ALLCALICVA | GLNAVVRCA· | ·MLRRFTTGE | NSPSANK· · | 68 |
| SEQ_ID_NO_1444 | FDTNMVVVLA | ALLFALLFAL | GINSLARCLI | RWARRAPAAE | GGGG· · · · · | 84 |
| SEQ_ID_NO_1452 | FDTNMVIILA | ALLFALLFAL | GLNQLARCLI | RWARRASEGE | AGARGG· · · · | 87 |
| SEQ_ID_NO_1428 | FDANMVIILA | ALLCALILAL | GLNSILRCAM | RCGFGLSSSA | AAGTVADRA· | 78 |
| SEQ_ID_NO_1430 | FDTNMVIILA | ALLCALICAL | GLNSIMRCTF | RCGRRFGLDA | TEETAARLAA | 96 |
| SEQ_ID_NO_1432 | FDTNMVIILA | ALLCALIGAL | GLNSIVRCLL | RCSSRFALET | TEEAAARLAA | 80 |
| SEQ_ID_NO_1439 | FDTNMVIILA | ALLCALICAL | GLNSIARCAL | RCGRPFGNET | AEDAAARLAG | 69 |
| SEQ_ID_NO_1442 | FDANMVIILA | ALLCVLIFAL | GLNSVIRCVL | HCGRRLAPSS | SLAASATTAR | 87 |
| SEQ_ID_NO_1453 | LDASMVVILA | ALLCVVICAL | GLTSLIRCAL | HCARGLSPTI | ATPTPSVSTA | 81 |
| SEQ_ID_NO_1457 | LDANMVIVLA | ALLCVVICSL | GLSSLIRCAL | HCARGLSPSP | AMATPAAATT | 84 |

| | | | | | | | |
|---|---|---|---|---|---|---|---|
| SEQ_ID_NO_1436 | · · · · · · · · ·G | LKKKALQSLP | RSTFTAAEST | SGTAAEDG· | · · ·GDSTECAI | 105 |
| SEQ_ID_NO_1444 | · · · · · · · · ·G | FFKAVLRSMP | VEVY· · · · · | ·GAAAVL· · · | · · ·TVADVCAI | 112 |
| SEQ_ID_NO_1452 | · · · · · · · · ·G | LKRRALRSIP | VEVY· · · · · | ·GACGADGAA | A·VAADVCAI | 120 |
| SEQ_ID_NO_1428 | · · · · · · · · ·G | LKKRELKKFP | VAEY· · · · · | ·GSGEVK· · · | · ·AATECAI | 107 |
| SEQ_ID_NO_1430 | AT· · · · · ·G | KKSALRRLP | VAVY· · · · · | ·GSGMD· · · · | · ·MKATECPI | 126 |
| SEQ_ID_NO_1432 | T· · · · · · ·G | LKKRDLRQIP | VAIY· · · · · | ·GAGGS· · · · | · ·SATECPI | 109 |
| SEQ_ID_NO_1439 | T· · · · · · ·G | LKRRELSRIP | VAVY· · · · · | ·GAAGENT· · | · ·PATECPI | 100 |
| SEQ_ID_NO_1442 | TTTSVHVQAG | LKRKALRKIP | VEVY· · · · · | ·GGAKSSGGA | LPATATECAX | 130 |
| SEQ_ID_NO_1453 | AT· · · · ·AG | LKKTELRRIP | VEVY· · · · · | ·GAKQAG· · · | · · ·VPDGECAI | 113 |
| SEQ_ID_NO_1457 | TG· · · · · · ·G | LKKKELRRIT | VEVY· · · · · | ·GAKQAG· · · | · · ·VPDAECAI | 115 |

Figure 48 (continued)

| | | | | | | |
|---|---|---|---|---|---|---|
| SEQ_ID_NO_1436 | CLSDFADGEE | RVLPLCGHS | FHVECIDKML | VSRSSCPXCR | XLRPV---X | 152 |
| SEQ_ID_NO_1444 | CLGEFADGEK | VRVLPRCTHG | FHVRCVDTWL | LSHDSCPTCR | ASVLDG---- | 158 |
| SEQ_ID_NO_1452 | CLGEFADGEK | VRVLPRCAHG | FHVRCVDTWL | LSHDSCPTCR | GTVLEAAAPG | 170 |
| SEQ_ID_NO_1428 | CLGEFADGER | VRVLPPCNHS | FHMSCIDTWL | VSHSSCPNCR | HSLIEV---- | 153 |
| SEQ_ID_NO_1430 | CLGEFMGGEK | VRVLPKCNHG | FHVRCIDTWL | LSHSSCPTCR | QSLLDQA--T | 174 |
| SEQ_ID_NO_1432 | CLGEFVDGEK | VRVLPKCNHG | FHVRCIDTWL | LSHSSCPNCR | HSLLEH---T | 156 |
| SEQ_ID_NO_1439 | CLGEFEKGDR | VRMLPKCNHG | FHVRCIDTWL | LSHSSCPNCR | HSLLEK---- | 146 |
| SEQ_ID_NO_1442 | CLGEFADGEK | VRVLPRCHHG | FHVRCIDMML | ATHTSCPNCR | ASLAED---- | 176 |
| SEQ_ID_NO_1453 | CLGDFADGDK | VRVLPRCHHG | FHVRCIDTWL | AAHTSCPTCR | DSILSV---- | 159 |
| SEQ_ID_NO_1457 | CLGDFADGDK | VRVLPRCHHG | FHVGCIDTWL | AAHTSCPTCR | DSILSV---- | 161 |

| | | | | | | |
|---|---|---|---|---|---|---|
| SEQ_ID_NO_1436 | CDRCGHASXA | GSQMKDHQHX | QHXSDLTSXX | XTFXP | | 187 |
| SEQ_ID_NO_1444 | --AKAATPAG | GGSRMQGSEA | AAIAVVIR-- | ----- | | 184 |
| SEQ_ID_NO_1452 | KDKAAASAPA | GGSRRQGSEA | AAIAVVIG-- | ----- | | 196 |
| SEQ_ID_NO_1428 | -------HVA | GSE------- | ---------- | ----- | | 159 |
| SEQ_ID_NO_1430 | SSSDGAVEIE | NGIRPHGNSS | GQQADVPVP | ADEVG | | 209 |
| SEQ_ID_NO_1432 | TDSGAAQEVT | GAARPGENDP | GRQARGWP- | -EHGG | | 188 |
| SEQ_ID_NO_1439 | ---PAAAPES | GSGRRSEVVV | VVEQAS---- | ----- | | 169 |
| SEQ_ID_NO_1442 | ----GAAAAN | GGGR------ | ---------- | ----- | | 166 |
| SEQ_ID_NO_1453 | -----HSVVA | GGQT------ | ---------- | ----- | | 168 |
| SEQ_ID_NO_1457 | -----HAGVT | GGQT------ | ---------- | ----- | | 170 |

Figure 49

```
SEQ_ID_NO_1473    ----------  ---MKLVWCP  ETASQAFTAS  VSALSDAEHG  PAGSAS-VAE   36
SEQ_ID_NO_1474    ----------  -----MASKAYIDG  VRALAS--HD  LAGAAADVAE              27
SEQ_ID_NO_1476    MAPPPPPAAQ  VVRMKLVWCP  EMASKAYIDG  VRALAS--HD  LAGAAADVAE   48
SEQ_ID_NO_1471    ----------  ---MKLAWSP  ERASKAYIDT  VQSCQV--FR  ESG---VAE    31
SEQ_ID_NO_1463    ----------  ---MKLVWSP  ETASDAYIDT  VKSCKS--DK  ESG---VAE    31
SEQ_ID_NO_1465    ----------  ---MKLVWTP  DTALKAYVCI  VKTCED--FK  ESS---VAE    31

SEQ_ID_NO_1473    LVSAMVGGWN  AQLVVEAPEV  SAPDSATMSL  ALAAAAGRTG  GRYARVLPDE   86
SEQ_ID_NO_1474    LVSAMAGGWN  ARLVVEAPDS  AAPAAAATSL  ALAAVARRTG  GRYALVLPDR   77
SEQ_ID_NO_1476    LVSAMAGGWN  ARLIVEAPDS  AAPAAAATSL  ALAAAARRTG  GRYALVLPDR   98
SEQ_ID_NO_1471    FISAMAGWN   SQLIVETWSQ  GGL--TATSV  GLALARSHTC  GRHVCVVPDE   79
SEQ_ID_NO_1463    FLSATAAGWN  ARLIVETWSR  GDPI--TTSV  GLAVAATHTG  GRHVCIVPDE   79
SEQ_ID_NO_1465    LLSAMAAGWN  AKLIVESWSK  AGPI-LATSI  GLAVAAKHTC  GRHVCVVPDE   79

SEQ_ID_NO_1473    DA--------  ----------  -----DRAMA  ELESVDFLVV  DARRRDGAAV   113
SEQ_ID_NO_1474    DAAASAAET   ------AEV   VVGEADEAMA  GLHSVDLLVV  DARRRDAAAV   120
SEQ_ID_NO_1476    DAAASAAET   ------AEV   VVGEADEAMA  GLHSVDLLVV  DARRRDAAAV   141
SEQ_ID_NO_1471    RARSEYAERM  GEAGYT-AEI  VVGEPEEVME  GLVGVDFLVV  DSRRKDFTRV   128
SEQ_ID_NO_1463    QSKLEYVLAM  RGFVTTEVVV  VGESVENTME  EFPGVDFLVV  DSKRREFVRT   129
SEQ_ID_NO_1465    GSRSEYVKAM  HGAGMRETEV  LVGEAEEVMA  GLVGVDFLVA  DCRRRDFVRV   129

SEQ_ID_NO_1473    LAAARPGPRG  MVVV-RHGDE  RRPGIKALEA  SMAAGT-RV   VRSVYLPVDK   160
SEQ_ID_NO_1474    LRAARPGARG  MVVV-RHGDG  RQRGAKDLAA  SMAAGT-RV   VRSVYLPIGK   167
SEQ_ID_NO_1476    LRAARPGARG  MVVV-RHGDG  RQRGAKDLAA  SMAAGT-RV   VRSVYLPIGK   188
SEQ_ID_NO_1471    LREAKLSNKG  AVLLCKNANS  NSKG-FIARS  LVAKGSBRRV  VRSAFLPVGK   177
SEQ_ID_NO_1463    LRFAKLSNKG  AVLVCKNAMH  RAISGFKMHD  VLKRGT-RV   VRSVFLPVGS   177
SEQ_ID_NO_1465    LRFAKLSHKG  AVLACKNAFQ  QSVSGFKIHG  VLERGT-RV   VKTAYLPVGQ   177

SEQ_ID_NO_1473    GVEVLHVGV   GKGPSLQCRR  SRSASSRWR   HVDHKTGEEH  LFRRP        204
SEQ_ID_NO_1474    GVEVLHVGV   GKGPSLQNHR  DRRSTSRWR   HVDHDTGEEH  VFRRQ        211
SEQ_ID_NO_1476    GVEVLHVGV   GKGPSLQNHR  DRRSTSRWR   HVDHDTGEEH  VFRRQ        232
SEQ_ID_NO_1471    GLDMAHVSAS  GLG---N-    -NSSGHRWK   HVDCHSGDVH  FIRR         213
SEQ_ID_NO_1463    GLDIVHVGAT  GRG-----D   SRNLRSRWR   HVDHLSGEEH  LFRR         215
SEQ_ID_NO_1465    GLDMAHIGSN  GLG---DKR   SRGGPSRWK   HIDRKSGEEH  VFRE-        216
```

Figure 50

| | | |
|---|---|---|
| SEQ_ID_NO_1493 | MTFLMPSPEV ---STAFAKI FSNPT-PRHK FLKSCAISKN DDEKVWSKTN | 46 |
| SEQ_ID_NO_1503 | MAFLLPKLTT ---PSCKLPP S--PL-LKPQ LAQPVHGGGK IQGSVFGSVA | 44 |
| SEQ_ID_NO_1508 | MAFLLPKLTT PSGPSCKLPP S--PL-LKPQ LAQPGHSGGK IQGSVSGAGA | 47 |
| SEQ_ID_NO_1501 | MAFLLPKLTT ---PPCRSPP P--SP-LKPQ LGLPSHGGGR ----LHGAGS | 40 |
| SEQ_ID_NO_1504 | MAFLLPKLTT ---PSCKSPP S--P--LKSQ LGLPGGGKLQ ---------P | 34 |
| SEQ_ID_NO_1505 | MAFLLPKLTT ---PSCKSPP S--P--LKSQ LGLPGGGKLQ ---------P | 34 |
| SEQ_ID_NO_1495 | MAFLLPNLSL ---PSLLLNS KSFKDREKPV LYQTQTLPSH ---------- | 36 |
| SEQ_ID_NO_1499 | MAFLLPNLSL ---PSFLLQT GKSLK-EKPI STHSLSISSS -----SSSSN | 40 |
| SEQ_ID_NO_1491 | MAFLLSNLSS ---PSIHLQT GKYPN-LKPI FSQSLSSSSS ---------V | 37 |

| | | |
|---|---|---|
| SEQ_ID_NO_1493 | ARVGVKDVGS IVSGLSQNLR LYVQFSAPVK ------RGS KSSKEEEEKQ | 89 |
| SEQ_ID_NO_1503 | AQVAAPGHLS LLLLLSASQQ AAAPL-AAKST ATKNR----- GKGGGDPQRS | 89 |
| SEQ_ID_NO_1508 | AQVAAPGHLS LLLLLSAPQQ AADPL-ASKSI ATKNR----- GKGGGDPQRS | 91 |
| SEQ_ID_NO_1501 | AQAAAPTHLN LPLLLSASQQ EAAPL-TAKSA ETRNRAASGG GGGGGDPRRS | 88 |
| SEQ_ID_NO_1504 | AQAVAPSHLN LLLLLGASQQ EAAAVPTPKS RSKNGGGRSG GGGGEDPRRS | 84 |
| SEQ_ID_NO_1505 | AQAVAPSHLN LLLLLGASQQ EAAAVPTPKS RSKNGGGRSG GGGGEDPRRS | 84 |
| SEQ_ID_NO_1495 | -YQTTTTTTS TTTKKPTNTN SSMPPPLQVK T------PPG AQDKEQHQRD | 79 |
| SEQ_ID_NO_1499 | SYEFEEGSLS LLSLPVQAP- -----PAPGA QVKTM--PSE QDKHQQHGKD | 62 |
| SEQ_ID_NO_1491 | SYEFVEENLS TLSLLSIQS- ---PLPLKDI QVQTR--HSS QDKHNNHDRD | 60 |

| | | |
|---|---|---|
| SEQ_ID_NO_1493 | DYYVNMGYAI RTLRKELPDI FVRELSFDIY RDDIVFKDPL NTFLGIDNYK | 139 |
| SEQ_ID_NO_1503 | DFYLNLGTAV RTLRDDLPDV FVREPNYDIY REDITFVDPL NTFHGIDNYK | 138 |
| SEQ_ID_NO_1508 | DFYLNLGTAV RTLRDDLPDV FDREPNYDIY REDITFVDPL NTFHGIDNYK | 141 |
| SEQ_ID_NO_1501 | DFYLNLGAAV RALRDDLPAM FLREPNYDIY REDITFVDPL NTFHGIDNYK | 138 |
| SEQ_ID_NO_1504 | DYYLNLGTAV RTLRDDLPAM FVREPNYDIY REDITFVDPL NTFHGIDNYK | 134 |
| SEQ_ID_NO_1505 | DYYLNLGTAV RTLRDDLPAM FVREPNYDIY REDITFVDPL NTFHGIDNYK | 134 |
| SEQ_ID_NO_1495 | EFYVNLGLAV RTLREDLPVL FTEDLNYDIY RDDITFIDPL NTFTGIDNYK | 129 |
| SEQ_ID_NO_1499 | EFYINLGLAI RTLREDLPLL FSKDLNYDIY RDDITLVDPA NTFSGIENYK | 132 |
| SEQ_ID_NO_1491 | EFYINLGVAV RTLREDLPLL FTRDLNYDIY RDDITFVDPM NTFTGMDNYK | 130 |

| | | |
|---|---|---|
| SEQ_ID_NO_1493 | SFFSAPRFHG RIFFKALNLD VSVWQPMEN VMVRWLHG IPRVPWESHG | 189 |
| SEQ_ID_NO_1503 | TIFWALRFHG RLLFREIGLD VSRIWQLTEN SIVVRWELWG TPRVPWFSYG | 186 |
| SEQ_ID_NO_1508 | TIFWALRFHG RLLFREIGLD VSRIWQLTET SIVVRWELWG TPRVPWESYG | 191 |
| SEQ_ID_NO_1501 | TIFWALRFHG RLLFSEIGLD VSRIWQLTET SIVVRWELWG TPRVPWESYG | 188 |
| SEQ_ID_NO_1504 | TIFWALRFHG RLLFREIGLD ISRIWQLTEN SIVVRWELWG TPRVPWESYG | 184 |
| SEQ_ID_NO_1505 | TIFWALRFHG RLLFREIGLD ISRIWQLTEN SIVVRWELWG TPRVPWESYG | 184 |
| SEQ_ID_NO_1495 | LIFWALRFHG KMLFREISLE MYRIWQPSEN VLLIRWNLKG VPRVPWEAKG | 179 |
| SEQ_ID_NO_1499 | LIFWALRFHG KILFRDXXXE XYRVWQPSEN MLIRWNXKG VPRVPWEAKG | 182 |
| SEQ_ID_NO_1491 | ISFWALRFHG KILFRDISLE IFRVWQPSEN MLIRWNLKG VPRVPWEAKG | 180 |

Figure 50 (continued)

| | | | | | | | | |
|---|---|---|---|---|---|---|---|---|
| SEQ_ID_NO_1493 | RFUGTSEYKL | DKKGKI YEHR | VDNTALNSPP | KF-HVLAVFD | LIRSVGCPST | | | 238 |
| SEQ_ID_NO_1503 | CFSGTSRYKV | DRNGKI YEHK | VDNLALDFPR | SVAKVGSIAD | MV-VATP--S | | | 235 |
| SEQ_ID_NO_1508 | CFSGTSRYKV | DRNGKI YEHK | VDNLALDFPR | SVAKVGSIAD | MV-VATP--S | | | 238 |
| SEQ_ID_NO_1501 | CFSGTSRYKV | DRNGKI YEHK | VDNLALDFPR | PAVKVSSITN | LV-VAAYPPS | | | 237 |
| SEQ_ID_NO_1504 | CFSGTSRYKV | DRNGKI YEHK | VDNLALDFPR | PAAKVGBIAD | IV-VATCPPS | | | 233 |
| SEQ_ID_NO_1505 | CFSGTSRYKV | DRNGKI YEHK | VDNLALDFPR | PAAKVGBIAD | IV-VASCPPS | | | 233 |
| SEQ_ID_NO_1495 | EFQGTSRYKL | DRNGKI YEHK | VDNLAFNFPQ | QLKPAASVLD | LV-AACPAS | | | 227 |
| SEQ_ID_NO_1499 | EFQGTSRYKL | DRNGKI YEHK | VDNLAFNFPH | QLKPATSVLD | LV-TACPAS | | | 230 |
| SEQ_ID_NO_1491 | EFQGTSRYKL | DRNGKI YEHK | VDNLAFNFPQ | QLKPAASVLD | LV TASPASS | | | 229 |

| | | | | | | | |
|---|---|---|---|---|---|---|---|
| SEQ_ID_NO_1493 | PRPTY---- | ---------- | --------F | ESSASPPEK | NI----IKP | 259 |
| SEQ_ID_NO_1503 | PNLTF-MNVV | G-TGDGCSWT | KLYEAVLEKV | EREEHSSTGI | GVGAL GPVGC | 283 |
| SEQ_ID_NO_1508 | PNLTF-MNVV | G-PGDGCSWT | KLYEAVVEKV | EREEHGSTGI | GVGGL-PVPC | 285 |
| SEQ_ID_NO_1501 | PNPTF-MDVV | G-TGDGCSWT | KLYRAVLETV | EREGDI PAGI | CMEGL--LTC | 283 |
| SEQ_ID_NO_1504 | PNLTF-MDMV | GSTGDGCSWA | NLYQAVVETV | EQEGNDPAGI | AIEGL--LTC | 280 |
| SEQ_ID_NO_1505 | PNLTF-MDMV | GSTGDGCSWA | NLYQAVVETV | EREGNDPAGI | AIFGL--LTC | 280 |
| SEQ_ID_NO_1495 | PNPTF-AGPA | D--VYSSSWV | EFYRAVRETL | DKEN---STN | CFCKM-ATC | 270 |
| SEQ_ID_NO_1499 | PNPTFMFGS- | ---SYSSSWV | EFYQAVQRTL | DKQQDQI--M | MQDRF--VLC | 272 |
| SEQ_ID_NO_1491 | PNPTFFFSPV | D--SYSSSWV | KFYQAVRGIL | ETEDMFVTTD | CL----VTC | 272 |

| | | |
|---|---|---|
| SEQ_ID_NO_1493 | P--------- | 260 |
| SEQ_ID_NO_1503 | G----CGCSF | 289 |
| SEQ_ID_NO_1508 | SFGCGCGSSF | 295 |
| SEQ_ID_NO_1501 | S--------- | 284 |
| SEQ_ID_NO_1504 | S--------- | 281 |
| SEQ_ID_NO_1505 | S--------- | 281 |
| SEQ_ID_NO_1495 | S--------- | 271 |
| SEQ_ID_NO_1499 | L--------- | 273 |
| SEQ_ID_NO_1491 | S--------- | 273 |

Figure 51

```
SEQ_ID_NO_1520    MDSLPKLR-- ---------- -HPSPFPTPL SSSLSFRSLP PPHFPSSSFR                    37
SEQ_ID_NO_1510    MESLGKLQLH HQPFHLSFTH TSSSTFPKNL -----FKSSI QFISS---LK                    42
SEQ_ID_NO_1512    MESLTKLHCR LQPLHLSFNH CRPSIFAKPI SSSVSFRTSL ---SSSSPFK                    45
SEQ_ID_NO_1516    MESVAKLHCR HQPFNLSLNP HRPSIFPKPI -TSLSFKTPP PSSSSPFKLS                    46

SEQ_ID_NO_1520    LPSIRASSSP SQNDPAFRTP RNTPSLPPLL QTLTSFLSPL LETTCIMLA                     86
SEQ_ID_NO_1510    SASIKASSSK FQNS---ITP LPK------ ST---PFRL FKSTCITLTT                      78
SEQ_ID_NO_1512    LTSIRALSSS SSS---SVP LHCTPKPSLL QT---LAPL LKTTCITITA                      87
SEQ_ID_NO_1516    STSIRASSSS SSR---ITP LN------- KN----LCTI IKITSITLTA                      82

SEQ_ID_NO_1520    AAAFFFMRFH HT-PAVIAAP LTSPAAETDT -----AFTQE EAERLLEERL                    130
SEQ_ID_NO_1510    AAALLLANLH LKSPAIAAP APPPSVESKE -----NVTLE EEERALDEHL                     123
SEQ_ID_NO_1512    GAALLFMRFH QK-PALAATP TVTPTVEPAQ TDSL-NVSLE DQEKTIEEHL                    134
SEQ_ID_NO_1516    AAALFFTRLN IK-PAIASPL TASSTVDPTE ESSKENVSIE EQERALQDYL                    131

SEQ_ID_NO_1520    STNPRDTEAL HALMEVKIKA RKMDEAFEVL NRLIELEPEE QEWPLLKANM                    180
SEQ_ID_NO_1510    ITHPSDVDAL RSLMEVKIKS RKLTEAVEVI DRLIKLEPEE KEWPVLKANI                    173
SEQ_ID_NO_1512    TQYPNDVEAL QSLMEVRIKS RKLPQAIEVI DRLIQLEPED TEWPMLRAQI                    184
SEQ_ID_NO_1516    SQNPNDIEAL RSLMEVRIKS KKLVEAIEVV DRLIELEPNE DEWPLLKSQI                    181

SEQ_ID_NO_1520    HLYNDDHASA RKLFEEILKK DPLRVEAFHG LVMATAOSNE PLKSLLKRVE                    230
SEQ_ID_NO_1510    FTYSGDLDLA KTGFEEILAK DPLRVEAYHG LLMAYSDAGL DLKEVESRIE                     223
SEQ_ID_NO_1512    HSYSGDFALA KNEFEEILAK DPVRVEAFHG LVMASSESGQ KLKELEKRIE                    234
SEQ_ID_NO_1516    YTYSGDFESA KDGFEAILKK DPLRVEAYHG LVMANSESGG SLEVVLKRIE                    231

SEQ_ID_NO_1520    EAIEVCKKQK KDSDVRDFRL LIAQIKVMEG DYTEALKAYQ ELVKEEPRDF                     280
SEQ_ID_NO_1510    EAMLKCKKEN NQNDFRDFKL LVAQIRVIEG KHSEALKLYQ ELVKEEPRDF                     273
SEQ_ID_NO_1512    GAMEKCKKEK KNKDFRDFKL LIAQIRVIEG DHLEALKVYE GLVKEEPRDF                     284
SEQ_ID_NO_1516    SAMDKCKKEK KTSDLRDFKL LVAQVRVMEE KYLDALKVYE ELVKEEPRDF                     281

SEQ_ID_NO_1520    RPYLCQGIIY TLLRKKDEAD KQFNKFRRLV PKDHPYKDYF EDNMFATKFF                      330
SEQ_ID_NO_1510    RPYLCQGIIY TLLKKKDKAE EQFDNFRKLV PKNHPYREYF MDNMIATKLF                      323
SEQ_ID_NO_1512    RPYLCMSIIY SLMKKKDEAE KHFEKNRKLV PRNHPYREYF VDNMVATKLF                      334
SEQ_ID_NO_1516    RPYLCQGIIY TLLRKKDEAE KKFEQFKKLV PKNHPYREYL VDNMFATKFF                      331
```

Figure 51 (continued)

| | | | |
|---|---|---|---|
| SEQ_ID_NO_1520 | SQKLEREGA | ···GARG | 343 |
| SEQ_ID_NO_1510 | SEKAQREMAE | EMAGSTS | 340 |
| SEQ_ID_NO_1512 | SERAEREGA | ------- | 343 |
| SEQ_ID_NO_1516 | SDKVERERS | ------- | 340 |

Figure 52

```
SEQ_ID_NO_1525           ---------  MAFPQRKRTP  SFSSSYLDSV  YRSIDESDG-  LQSDLKGS-N   39
SEQ_ID_NO_1535           ---------  MALPQRQRTD  SFSSSYLDSI  YRSIDESDG-  LQSDLRGT-N   39
SEQ_ID_NO_1527           MYKKERSSRE  STFHPRRRTP  SFSSTLLDSI  YRSIDESNG-  -EEQHVLGIK   48
SEQ_ID_NO_1534           MHERSMKEAA  GTCPQRRRTP  SFSSSLLDAI  YRSIDESKSN  LHDDQQLGLH   50

SEQ_ID_NO_1525  EN----VSS  SSSSPSPNKK  DDKLTTLRRA  MDEEHVLYA  RSS-------   77
SEQ_ID_NO_1535  SNNNENVSSS  SSSSPSPNKK  DDKLTTLRRA  MDEEHVLYG  RSS----TTT   85
SEQ_ID_NO_1527  KQSCNSVSTI  RRDTSFLEEE  KEVSTTLRRA  VR-TESVMEK  KST--RGSMQ   95
SEQ_ID_NO_1534  HHD----QTT  HSFTSEKGGK  KERM-NLRRA  VM-LEDVMEK  HGSHSLNAQL   94

SEQ_ID_NO_1525  -TTTTNSSDS  SS--------  --FSSSEAES  ----YRTKR  RLRKLAEQGK   111
SEQ_ID_NO_1535  TTTTTNSSDS  SA--------  --FSSSEAES  ----FRTKR  RLRKLAEQGN   120
SEQ_ID_NO_1527  YNSTSSSSDS  SSAGGGGSGS  GVFSSSENES  -------SVR  GNSSSCQQRT   138
SEQ_ID_NO_1534  LNSSSSSSED  SSA-----G  GIFSSSETDT  TTTLTLKKQR  PARLTSEKKK   138

SEQ_ID_NO_1525  RSGDERQRTK  RTVMDNDSRL  FSKSDDDKKP  KAVKILEEL-  KRSKQPVSPG   160
SEQ_ID_NO_1535  RLGEERQRT-  ----------  --KSDDDIKV  KAVKMFEEL-  KRSKQPVSPG   156
SEQ_ID_NO_1527  KPLSDKPHQK  PKCEG-----  --GGFHKTKL  RALKIYGEL-  KKVKQPISPG   180
SEQ_ID_NO_1534  KKQDRIMSSE  KQNKE-----  --SGFTRTKL  RALKIYGELN  QRVKQPISPG   181

SEQ_ID_NO_1525  ARLTSFLNSI  FQSN--AKKV  KLCSYGKTTD  VK--------  -------SSS   193
SEQ_ID_NO_1535  ARLTSFLNSI  FQSN--AKKV  KFCSYGKTTD  VK--------  ------SSSS   190
SEQ_ID_NO_1527  GRIASFLNSI  FNSASAAKKV  KMCSIGAMDD  VSFERKSKSA  CSSA-TSFS   228
SEQ_ID_NO_1534  SRIASFLSSI  FNSQN-VKKA  KMCYAGAVED  VSFEHKSNSP  CFSSIPSSFS   230

SEQ_ID_NO_1525  SKSCFSRTRN  KTDNNNNNC-  --KKLERSIR  FYPVRVTIDG  DCRDYADKH-   239
SEQ_ID_NO_1535  SRSCFSRTRN  KTNNNNNNAN  NFKKLERSIR  FYPVRVTIDG  DCRDYAHKN-   239
SEQ_ID_NO_1527  -RSCLSKTPP  PRGKPSNG--  ----TKRSVR  FYPVGVIVDE  DSRPCGHKS-   270
SEQ_ID_NO_1534  RRSCMSKTPS  SAKKSNNNE-  ----VKRSVR  FYPVSVILGE  DSEPQSSYHK   275

SEQ_ID_NO_1525  ---TRVRK-  --PIPEFTAK  -KSVKE----  EIKTNDHTE  FTCITRNI--   276
SEQ_ID_NO_1535  ---TR-----  --PIPTKVHD  TELMKE----  EIKTKVHDTE  LTCITRK---   274
SEQ_ID_NO_1527  ---YEDDPG  LMPTPRKVVK  SSSVKELEVA  KGAAADYLRS  YH-QRKNV--   314
SEQ_ID_NO_1534  CNILYE----  --SEPNLGVR  SSSIKELKKN  TARGNENGAE  EAAARGFVKG   319
```

Figure 52 (continued)

| | | | | | | | |
|---|---|---|---|---|---|---|---|
| SEQ_ID_NO_1525 | ------GLKD | FVRSNKY-EG | KEEEGDAMSH | SSSDLFELDS | YRI GMGRYLK | | 319 |
| SEQ_ID_NO_1535 | ------GLKD | YVRSSNI DEG | KEEEDDVWSY | SSSDLFELDH | YRI GMGRYLK | | 318 |
| SEQ_ID_NO_1527 | ------SFFD | FRGFHNYVAD | DSDSDDEF SC | TSSDLFELDH | LF GI GRYRE | | 356 |
| SEQ_ID_NO_1534 | YRNSGQSEFD | FRGF--YDDD | DEDDDDDVSC | SSSDLFELDH | LF GAARYQE | | 366 |

| | | | | |
|---|---|---|---|---|
| SEQ_ID_NO_1525 | ELPYYETTDF | KTNQAI ARSL | LL | 341 |
| SEQ_ID_NO_1535 | ELPYYETTDF | KI NQAI ARGL | LL | 340 |
| SEQ_ID_NO_1527 | ELPYYETTNF | KTNQAI ANGF | FP | 378 |
| SEQ_ID_NO_1534 | ELPYYETTNL | ETNKAI ASGL | CL | 388 |

Figure 53

```
SEQ_ID_NO_1550    MDMNESSEKG ME----GNGS SGPGGGI PVE AQSQFS---G GGFS-A---     38
SEQ_ID_NO_1552    MYSGQQSDQC PS----ANS- ---------- --------G REFSEA---      22
SEQ_ID_NO_1537    MIEGLVSQES ISLNS-MDMS VLER----LK WQQQQDQLQ QVVSHS---      41
SEQ_ID_NO_1543    MLESLVSLES MSLSS-MDVS VLER----LK WLQQQ----Q QQVLST---      37
SEQ_ID_NO_1545    MLGYANPSGN LAVD--GDMT VLERQRARMK WQEEQEYFSG NSFNGV----     44
SEQ_ID_NO_1539    MLHC------ ------TDIT VLERQRACLK WQQEQQDQQQ VQLQQQEISY     38
SEQ_ID_NO_1548    MLHCLNTSGN LVGGIISDMT VLERQRARKK EQHEHEDQ-Q QFFMVG----     45

SEQ_ID_NO_1550    HQHQQHPHMM DSFGSGMWS- --------AA SQHGAGFLAP VPGFLPPPGL     79
SEQ_ID_NO_1552    NRNTVTMHQK MGYNSG--- ---------- ---------- ------PYGF     42
SEQ_ID_NO_1537    SNNSPELLQI LQFHGSN--- --------ND ELLESSFSQF Q---MLGSGF     77
SEQ_ID_NO_1543    TNASPELLQF HGTN----- --------ND ELLQNTFSHF Q---MLRSGF     70
SEQ_ID_NO_1545    FSSSSSLHVP DSIMVAADS- --------G CALAEVVAQA QPRSNKPSA     84
SEQ_ID_NO_1539    FTELTGVFQQ AGFHESGLSE VVTRSVKPDP GLVDNGANND H---VVGLGV     85
SEQ_ID_NO_1548    CDSALGEVVA NSMKPG--- ---------- ---------- ----------     61

SEQ_ID_NO_1550    GGHFPVDSG- -FIE----RA ARSSCFVGPG AGGGMVGAGA FGGAGDQQMG    123
SEQ_ID_NO_1552    GP---YNMG- -LEE----RP GLYQSSSGTF SQNIQM--- ---------S     70
SEQ_ID_NO_1537    GPNYNMGFGP PHES----IS RTSSCHMEPV DTMEVL--- ------LKTG    113
SEQ_ID_NO_1543    GPNYSMGFGP SHEAMDGCIS ITNSCQMDQA DTVGVM--- ------LKNS    110
SEQ_ID_NO_1545    AP-----G- -LHANSSSIS RTFSCPPALV DPEPKPT--- ---------D    114
SEQ_ID_NO_1539    GPLYDNGSG- -FELNYGAIS RISSCPPAAV AAVAAATVKG SESVVSDKS    133
SEQ_ID_NO_1548    ------DLG- -FEN------ ---------- ---------- ----------     87

SEQ_ID_NO_1550    SAFGEGYLDH RRKEGGDKAE PELAGSGGVP SSEAAGGDCS SKGSDSKKRR    173
SEQ_ID_NO_1552    DEHSGGVKKR KGMD------ ---------- ------DCV AMLQNAGDQQ     97
SEQ_ID_NO_1537    EETRAVALKN KRKP------ ---------- ------EVK TREEQKTEKK    140
SEQ_ID_NO_1543    EENITISLKN KRKS------ ---------- ------EVK TREEEKTEKK    137
SEQ_ID_NO_1545    SSIGKDSFKK RKTD------ ---------- --KPHN-PKV VAENENKDKR    145
SEQ_ID_NO_1539    SGVGRESSKK RKVD------ ---------- --NKQNNSKV DAEEDTRDKR    165
SEQ_ID_NO_1548    ---VEETVKK RKAD------ ---------- -------H KVDMKSKDKR     89
```

Figure 53 (continued)

| | | | | | | | |
|---|---|---|---|---|---|---|---|
| SEQ_ID_NO_1550 | RPSEVMGGDQ | VQSSNVAADS | ANESAQSKDK | GEESSPATGT | TTGGKSKGKG | | 223 |
| SEQ_ID_NO_1552 | ---TEGSSQ | PE-------- | ----RNSLEG | NRKISPKMQS | ---KEDSSDG | | 128 |
| SEQ_ID_NO_1537 | ----IKVEAE | TESSMK---- | ----GKSNMG | NTEASSDTSK | ---ETSKGAS | | 175 |
| SEQ_ID_NO_1543 | ----IKVEAE | TELNMK---- | ----VKSNLS | NTEASSETSK | ---QKSKAAS | | 172 |
| SEQ_ID_NO_1545 | ----IKVGAD | DGESKITKCN | T---INTNTN | NKETCTDTSN | ---SKONSKA | | 185 |
| SEQ_ID_NO_1539 | ----IKGCAE | EGESKITEKN | NNKNSRNNNT | NKNNNSNKES | SA-GNSKDNS | | 210 |
| SEQ_ID_NO_1548 | ----IKVSVE | EGESKITEQI | KGN-KNTKLK | NRENCDDVGS | ----KENSKG | | 130 |

| | | | | | | |
|---|---|---|---|---|---|---|
| SEQ_ID_NO_1550 | AKESSEKEDY | IHVRARRGQA | TNSHSLAERL | RREKISERMK | LLQDLVPGCS | 273 |
| SEQ_ID_NO_1552 | DG---TKEDY | VHVRAKQGQA | TNSHSLAERL | RKKKISERMK | LLQDLVPGCS | 175 |
| SEQ_ID_NO_1537 | EN---QKLDY | IHVRARRGQA | TDRHSLAERA | RREKISKKMK | YLQDIVPGCN | 222 |
| SEQ_ID_NO_1543 | EN---QKLDY | IHVRARRGQA | TDRHSLAERA | RREKISKKMK | YLQDLVPGCN | 219 |
| SEQ_ID_NO_1545 | S----EKPDY | IHVRARRGQA | TDSHSLAERV | RREKISERMK | YLQDLVPGCN | 231 |
| SEQ_ID_NO_1539 | KVTEVQKPDY | IHVRARRGQA | TDSHSLAERV | RREKISERMK | YLQDLVPGCN | 260 |
| SEQ_ID_NO_1548 | SEIQNHKPDY | IHVRARRGQA | TDSHSLAERV | RREKISERMK | YLQDLVPGCN | 180 |

| | | | | | | |
|---|---|---|---|---|---|---|
| SEQ_ID_NO_1550 | KVTGKAVMLD | EIINYVQSLQ | RQVEFLSMKL | ATVNPRLDLN | IEGLLSKDLL | 323 |
| SEQ_ID_NO_1552 | KITGKAVMLD | EIINYVQSLQ | RQVEFLSMKL | ATVNPELGFD | IEDISKQMM | 225 |
| SEQ_ID_NO_1537 | KVTGKAGMLD | EIINYVQCLQ | RQVEFLSMKL | AVLNPELELA | VEDVSVKQAY | 272 |
| SEQ_ID_NO_1543 | KVTGRAGMLD | EIINYVQSLQ | RQVEFLSMKL | AVLNPELELA | MEDLSVKQLF | 268 |
| SEQ_ID_NO_1545 | KVTGKAGMLD | EIINYVQSLQ | RQVEFLSMKL | AAVNPRLDFS | MDDLFDKDVF | 281 |
| SEQ_ID_NO_1539 | KITGKAGMLD | EIINYVQSLQ | RQVEFLSMKL | AAVNPRLDFN | FDNLFAREAF | 310 |
| SEQ_ID_NO_1548 | KIAGKAGMLD | EIINYVQSLQ | RQVEFLSMKL | AAVNPRLDFN | IDELFAKEVF | 230 |

| | | | | | | |
|---|---|---|---|---|---|---|
| SEQ_ID_NO_1550 | RF-------- | ---PGVSSSS | MGFSPEMMHP | QLQLSQPGLM | QGGAAAMANS | 362 |
| SEQ_ID_NO_1552 | LSQDRHFAFY | GVDPGSSSLA | SQFSDGIMQP | QM-------- | --MCNISNPA | 265 |
| SEQ_ID_NO_1537 | FTNV------ | --------VA | SKCSIMVDVP | LFPLDQQGSL | --DLSAINPN | 306 |
| SEQ_ID_NO_1543 | QAYFTNLPVV | --------VA | SKPSLMVDAP | LFPLDQQGSL | --DLSVINPN | 308 |
| SEQ_ID_NO_1545 | PTCAANFPNI | GMSSTSSDIT | NPAYLPFNSP | QQIFOYDG-- | ---DTGINPSD | 328 |
| SEQ_ID_NO_1539 | PACSVNFPTI | GM---SSDMI | NPAYLDFNPA | QQQLVTCCGL | --DMGTDPPD | 355 |
| SEQ_ID_NO_1548 | TQNFQMM--- | -----QSEMS | NPAYLDFNSA | QQQVSCCGGL | INNMGILPPE | 272 |

Figure 53 (continued)

| | | | | | | | |
|---|---|---|---|---|---|---|---|
| SEQ_ID_NO_1550 | DVFRRIMDAD | ---------- | GAKDGSHSQM | AHALNGPFSD | HVAQMAYPSM | 403 |
| SEQ_ID_NO_1552 | DVLQGTIHDV | ---------- ---- | STMNQI | PAMAEGLQN | -LPQMNFNPG | 299 |
| SEQ_ID_NO_1537 | QY-------- ---------- | ---- | TSIEAP | SGSWETQSQS | -LYN------ | 327 |
| SEQ_ID_NO_1543 | QA-------- ---------- | ---- | TTIEAP | SASWETQSQS | -LYN------ | 329 |
| SEQ_ID_NO_1545 | YGLRRTISAP | VS--MPETYL | QSSCFTQMLP | SSTWEGDFQN | -LQNFDVDQA | 375 |
| SEQ_ID_NO_1539 | MGLKRTTSSP | ES--IPETFL | DSSCFTQAHP | PPAWQADLQN | -LYNVAFDQG | 402 |
| SEQ_ID_NO_1548 | IGVRRNINAP | ASASLPEIFL | DPSCFTHILP | SSTWEGDFQN | -LHSVDFDQG | 321 |

| | | | |
|---|---|---|---|
| SEQ_ID_NO_1550 | GSSHSHSQDL | S------- RPSQDAYQN | 424 |
| SEQ_ID_NO_1552 | VAADSSANN- | ---------- -SGSMKIEQ | 316 |
| SEQ_ID_NO_1537 | ---------- | ---------- -TSSLGFHY | 335 |
| SEQ_ID_NO_1543 | ---------- | ---------- -TSSLGFDY | 337 |
| SEQ_ID_NO_1545 | RATSFPSQLL | SGL------Y EASNLKMEM | 396 |
| SEQ_ID_NO_1539 | RQTSFPTQPF | TGKIKLSCS EASNLKMEM | 431 |
| SEQ_ID_NO_1548 | RSTSFPSQPF | TGM------ EASNLKMEM | 344 |

Figure 54

```
SEQ_ID_NO_1571   MAVEAVS-- ------GNGG EAVAPAPA-- ---------- ----------                              19
SEQ_ID_NO_1567   MAEEPQ--- ------PQAA AAPAAAAT- ---------- -EVVVAEKAP                              27
SEQ_ID_NO_1572   MAEEPQ--- ------PEAA PAAVAATT- ---------- -EVAVAEKAP                              27
SEQ_ID_NO_1574   MAEEPQ--- ------PEAA PAAVAATT- ---------- -EVAVAEKAP                              27
SEQ_ID_NO_1555   MAEETQK--- ------PAAA EAPTSTQP- ---------- YPEEPAVVPP                             29
SEQ_ID_NO_1563   MSQEQDVVVV TDV---PQAE KTAPVPPT- ---------- MPVVVEKEPP                             35
SEQ_ID_NO_1575   MAEEPQK--- ------PTEQ VATTPATS- ---------- -ETTIEKTPP                             28
SEQ_ID_NO_1554   MAEEPTTTTL VTPEKLPSPS LTPSEVSEST QDALPTETET LEKVTETNPP                             50
SEQ_ID_NO_1565   MAQNDSN--- ------PTPP PEPHVAAE-- ---------- ---------P                             20

SEQ_ID_NO_1571   --------- --------PV KEVSAK--- ---------- ----VEAKEA                              33
SEQ_ID_NO_1567   --AEVEKKAE EL-----PA AEAEAE--- ---------- -ETAAVADDG                              53
SEQ_ID_NO_1572   VEAEKEKKVE EET----PA VEAEAK--- --EEKKDEAA ---AAGGDEA                              63
SEQ_ID_NO_1574   VEAEKEKKVE EET----PA VEAEAK--- --EEKKDEAA AAAAAGGDEA                              66
SEQ_ID_NO_1555   PVPAAEIQLP DSAPAPPQPE ASPAKP---- --DSVAEVAE DEKPKASEEF                             73
SEQ_ID_NO_1563   V--------- --------PV PETEEEPMKP KQVEEGAVET QVLKPSGGDD                             68
SEQ_ID_NO_1575   PQAEEVVAAA DADAVVVPPV VAEETE---- --KPAEDVKP ADETAAATDK                             72
SEQ_ID_NO_1554   ETADTTTKPE EETAAEHHPP TVTETETAST EKQEVKDEAS QKEVAEEKKS                             100
SEQ_ID_NO_1565   ITEDLVQDKE EEDDSSKIVI PVPESE---- ---------- ----------                             46

SEQ_ID_NO_1571   AAVTKNASFR EESNFLDDLK ESERKALAEL RDKVEAATLE GKLFDDGKPE                              83
SEQ_ID_NO_1567   GAVEATGSFK EESNLVADLP DPEKKALDEF KELIVAALAA GEFNLPPPPP                             103
SEQ_ID_NO_1572   GAIEGTGSFK EESNLVADLP DPEKKALDEF KQLIAAALAA CEFNLPPPPP                             113
SEQ_ID_NO_1574   GAIEGTGSFK EESNLVADLP DPEKKALDEF KQLIAAALAA CEFNLPPPPP                             116
SEQ_ID_NO_1555   EKISQSVSFK EESNVVGELP ESQRKALADL KVLIQEALNK HEFTAPPAPL                             123
SEQ_ID_NO_1563   EKVPQLVSFK EESTKVADLL DSEKKALQEF KQLVQEALN- ----------                             107
SEQ_ID_NO_1575   KILQ-SVSFK EETNVVSELP ESQKKALDEL KQLIQEALNK HEFTAPPPPP                             121
SEQ_ID_NO_1554   MIPQNLGSFK EESSKLSDLS NSEKKSLDEL KHLVREALQN HQFTN-----                             145
SEQ_ID_NO_1565   ----SLSLK EDSNRVSDF- -SEKNAIDEL KKLLKEELED ----------                              70

SEQ_ID_NO_1571   ---------- ---------- VKEKREAKKK AEKAPEEKKE EEEGKKEPE                              113
SEQ_ID_NO_1567   PPKAKTEAAA EETKTEAPAK EEAKTEEPAK AEEPAKEEPK AEEPAKAEAA                             153
SEQ_ID_NO_1572   PPKAKVEAAV EETKA----- EESKAEEEPK AEEPAKEEEP KAEVAAAAAA                             158
SEQ_ID_NO_1574   PPKAKVEAAV EETKA----- EETKAEEEPK AEEPAKEEEP KAEVAAAAAA                             161
SEQ_ID_NO_1555   PPK-----E EEKPA----- EEKKEDTEKP AEQPQIDE-P AKEPVIEEPP                             161
SEQ_ID_NO_1563   ---------- ---------- ---------- ---------- ----------                             107
SEQ_ID_NO_1575   PTKAVAEVAE EKKPE----- EEKKKTEEVV AEEKKVEEVV AEEKKVEEAV                             166
SEQ_ID_NO_1554   ---------- ---------- ---------- ---------- ----------                             145
SEQ_ID_NO_1565   ---------- ---------- ---------- ---------- ----------                             70
```

Figure 54 (continued)

| SEQ_ID | Sequence | Pos |
|---|---|---|
| SEQ_ID_NO_1571 | AVEKKGEEDD KKEAEVEGKE EEEESKKEAE KEMEQEF--- ---------- | 150 |
| SEQ_ID_NO_1567 | AAEPAAEEPK AVVA------ ----AEAAAE EPAKEEPK-- ---AEEAKPA | 188 |
| SEQ_ID_NO_1572 | PPEAGTEEPK AEASSEEAKT EEPKAEAAAD EPAKQESKAE AAPAEEAKPA | 208 |
| SEQ_ID_NO_1574 | PPEAGTEEPK AEASSEEAKT EEPKAEAAAD EPAKEESKAE AAPAEEAKPA | 211 |
| SEQ_ID_NO_1555 | KTEAEPEPVT ETVTVKVEET ITPHPAPETS LAPEADEKAA EPSTVVEKVA | 211 |
| SEQ_ID_NO_1563 | ---------- ---------- ---------- ---------- ---------- | 107 |
| SEQ_ID_NO_1575 | AEEKKVEEVE KKEEEKGSSS EEPKTEAKIE AEPEAKKEET VLEVVEKIAT | 216 |
| SEQ_ID_NO_1554 | ---------- ---------- ---------- ---------- ---------- | 145 |
| SEQ_ID_NO_1565 | ---------- ---------- ---------- ---------- ---------- | 78 |

| SEQ_ID | Sequence | Pos |
|---|---|---|
| SEQ_ID_NO_1571 | ---------- ---------- ---------- --AGEAEKVA AAAEEKPAET | 168 |
| SEQ_ID_NO_1567 | EPKKEEEAVV VAEE--GTKT ------AEPV EEAAAAATTT EQAAAPEPEA | 230 |
| SEQ_ID_NO_1572 | EPEPEEKTVV VTEEEAATKT VEAIEETVVP AAAAPAAAAT EEAAAPEPEV | 258 |
| SEQ_ID_NO_1574 | EPEPGGED-- ---------- ------RRGH RGRGGHODGG SDRGNRRARC | 243 |
| SEQ_ID_NO_1555 | VIDEDGAKTV EAIEESVVAV ------STPP PEESAPSKEE AEVEVEAAEA | 255 |
| SEQ_ID_NO_1563 | ---------- ---------- ---------- ---------- ---------- | 107 |
| SEQ_ID_NO_1575 | STEEDGAKTV EAIQESIVSV ------TVTD GEOPVTETVG EAVAVAEVE- | 259 |
| SEQ_ID_NO_1554 | ---------- ---------- ---------- ---------- ---------- | 145 |
| SEQ_ID_NO_1565 | ---------- ---------- ---------- ---------- ---------- | 78 |

| SEQ_ID | Sequence | Pos |
|---|---|---|
| SEQ_ID_NO_1571 | AAVVVDKDIA LWGVPLLPSK GDE-ATDVVL LKFLRARDFK AGAAFEMLRR | 217 |
| SEQ_ID_NO_1567 | E-AAAPEPVF IWGVPLV--- GDDERTDAVL LKFLRAREFK VKEAMAMLRS | 276 |
| SEQ_ID_NO_1572 | QAAAAPEPVL IWGVPLV--- GDDERTDFVL LKFLRAREFK VKEAMAMLRS | 305 |
| SEQ_ID_NO_1574 | CCACCRRHGG SRGAGTG--- GDDERTDFVL LKFLRAREFK VKEAMAMLRS | 290 |
| SEQ_ID_NO_1555 | VPPPPPEEVF IWGIPLL--- GDE-RSDVIL LKFLRARDFK VKDAFTMIKN | 301 |
| SEQ_ID_NO_1563 | ---------- ---------- ----KSDVIL LKFLRARDFK VKDAFTMLKS | 133 |
| SEQ_ID_NO_1575 | VTPTTPEEVE IWGIPLL--- ADE-RSDVIL LKFLRARDFK VKEAYTMIKD | 305 |
| SEQ_ID_NO_1554 | ----TPEEVK IWGIPLL--- EDD-RSDVVL LKFLRAREFK VKDSFAMLKN | 187 |
| SEQ_ID_NO_1565 | ------EEVS IWGVPLF--- KDD-RTDVIL LKFLRARELK VKDALVMFDN | 118 |

| SEQ_ID | Sequence | Pos |
|---|---|---|
| SEQ_ID_NO_1571 | TLRWRRDWPG FDADADADLP -EELAGACVL DGADREGHPV CYNALRVFAD | 266 |
| SEQ_ID_NO_1567 | AVLWRKRF-G IESLLEADLA FPELEKVVFY RGADREGHPV CYNVYGEFQD | 325 |
| SEQ_ID_NO_1572 | AVLWRKRF-G IESLLDADLA LPFLDSVVFY RGADREGHPV CYNVYGEFQD | 354 |
| SEQ_ID_NO_1574 | AVLWRKRF-G IESLLDADLA LPELDSVVFY RGADREGHPV CYNVYGEFQD | 339 |
| SEQ_ID_NO_1555 | TVRWRKQF-D IEALLDEDLG -NQMDKVVFS HGVDREGHPV CYNVFGEFEN | 349 |
| SEQ_ID_NO_1563 | TIRWKEF-G IDELLEQDLG FDDLEKVVFM HGLDKEGHPV CYNVYGEFON | 182 |
| SEQ_ID_NO_1575 | TYIWRKEF-G IEALLQEDLG -TDMDKVVFT DGYDKEGHPV YYNVFGEFEN | 353 |
| SEQ_ID_NO_1554 | TIKWRKEF-K IDEL VEEDLV -DDLDKVVFM HGHDREGHPV CYNVFGEFON | 235 |
| SEQ_ID_NO_1565 | TLRWRKDF-N IDALLDEDLG -DRLEKVVFM HGHGREGHPV CYNVYGEFON | 160 |

Figure 54 (continued)

| | | | | | | | |
|---|---|---|---|---|---|---|---|
| SEQ_ID_NO_1571 | DAVYKKAL GT | EEGKARFLRW | RVRAMERHV- | AELDLKP- GG | AASLLQVTDL | | 314 |
| SEQ_ID_NO_1567 | KEVYEKAFGD | EEKRERFLKW | RI QLERG L | SQLDFAP- SG | ICSMVQVTDL | | 374 |
| SEQ_ID_NO_1572 | KDLYEKAFGD | EEKRERFLKW | RI QLERG L | SQLDFSP- SG | ICSMVQVTDL | | 403 |
| SEQ_ID_NO_1574 | KDLYEKAFGD | EEKRERFLKW | RI QLERG L | SQLDFSP- SG | ICSMVQVTDL | | 388 |
| SEQ_ID_NO_1555 | KDLYQI TFSD | DEKSLKFLRW | RVQFLEKSI - | RKLDFSP- NG | I STI VQVNDL | | 397 |
| SEQ_ID_NO_1563 | KELYKNSFSD | EEKRQRFLRW | RI QFLEKSI - | RTLDFSP- GG | I STI VQVNDL | | 230 |
| SEQ_ID_NO_1575 | KELYQNTFSD | DEKRTKFI RW | RI QSLEKSI - | RKLDFTP- SG | I STI VQVNDL | | 401 |
| SEQ_ID_NO_1554 | KELYNKTFSD | EEKRKHFLRT | RI QFLERSI - | RKLDFSS- GG | VSTI FQVNDM | | 283 |
| SEQ_ID_NO_1565 | KDLYHKAFSS | QDNRNKFLRW | RI QLLERSI - | RHLDFTPSSG | I NTI FQVNDL | | 215 |
| | | | | | | | |
| SEQ_ID_NO_1571 | KNSPGPAKKD | FRVAVKQVLD | LFQDNYPELV | ARNI LI NVPF | WYNAFSTLFY | | 364 |
| SEQ_ID_NO_1567 | KNSPPVLGKH | - RAVTRQAVA | LLQDNYPEFI | AKKVFI NVPW | WYLAANKMMS | | 423 |
| SEQ_ID_NO_1572 | KNSPPVLGKH | - RAVTRQAVA | LLQDNYPEFI | AKKVFI NVPW | WYLAANKMMS | | 452 |
| SEQ_ID_NO_1574 | KNSPPVLGKH | - RAVTRQAVA | LLQDNYPEFI | AKKVFI NVPW | WYLAANKMMS | | 437 |
| SEQ_ID_NO_1555 | KNSPGLTKME | LRNATKRALQ | LFQDNYPEFA | AKQVFI NVPW | WYLANNRMI S | | 447 |
| SEQ_ID_NO_1563 | KNSPGPAKRE | LRQATRQALQ | LLQDNYPEFV | AKQI FI NVPW | WYLTVNRMI S | | 280 |
| SEQ_ID_NO_1575 | KNSPGLGKKE | LRQATNKALQ | LLQDNYPEFV | AKQVFI NVPW | WYLAFSRFLS | | 451 |
| SEQ_ID_NO_1554 | KNSPGLGKKE | LRSATKQAVE | LLQDNYPEFV | FKQAFI NVPW | WYLVFYTVI G | | 333 |
| SEQ_ID_NO_1565 | KNSPGPAKRE | LRLATKQALQ | LLQDNYPEFV | AKQVFI NVPW | WYLAFYTMI N | | 265 |
| | | | | | | | |
| SEQ_ID_NO_1571 | PFLTQRTKSK | FVLARPSKVT | ETLLKYI PI E | AFPVKYGGLK | RDD- - - DI EF | | 411 |
| SEQ_ID_NO_1567 | PFLTQRTKSK | FVFASQAKSP | ETLFRYI APE | QVPVQFGGLF | KED- - - DPDF | | 470 |
| SEQ_ID_NO_1572 | PFLTQRTKSK | FI FASPAKSA | ETLFRYI APE | QVPVQFGGLF | KED- - - DPEF | | 499 |
| SEQ_ID_NO_1574 | PFLTQRTKSK | FI FASPAKSA | ETLFRYI APE | QVPVQFGGLF | KED- - - DPEF | | 484 |
| SEQ_ID_NO_1555 | PFFTQRTKSK | FVFAGPSKTA | ETLFKYVTPE | QVPVQYGGLS | REG- - - EQEF | | 494 |
| SEQ_ID_NO_1563 | PFLTQRTRSK | FVFVGPSKSA | ETLI RYI ANE | QI PVKYGGLS | KDG- - - - - EF | | 325 |
| SEQ_ID_NO_1575 | AFLTQRTKSK | FVFAGPSKSA | DTLFKYI APE | QVPVQYGGLS | REG- - - EQEF | | 498 |
| SEQ_ID_NO_1554 | PFMTPRSKSK | LVFAGPSRSA | ETLFKYI SPE | QVPVQYGGLS | VDPCDCNPDF | | 383 |
| SEQ_ID_NO_1565 | PFLTSRTKSK | FVFAGPSKSP | DTLFKYI FPE | QVPVQYGGLS | VDFCDCNPDF | | 315 |
| | | | | | | | |
| SEQ_ID_NO_1571 | SSADDGEVAE | LTVKGSSTET | EI EAAEADA | TLTMDLI VLG | WEVNYKEEFV | | 461 |
| SEQ_ID_NO_1567 | TTSD- - SVTE | LTI KASSKET | EI PVTE- NS | TI VWELRVLG | WEVSHGAEFT | | 517 |
| SEQ_ID_NO_1572 | TTSD- - AVTE | LTI KPSSKET | VEI PVTE- NS | TI GWELRVLG | WEVSYGAEFT | | 546 |
| SEQ_ID_NO_1574 | TTSD- - AVTE | LTI KPSSKET | VEI PVTE- NS | TI GWELRVLG | WEVSYGAEFI | | 531 |
| SEQ_ID_NO_1555 | SI DD- - PVTE | VAI KAATKHT | VEFPI SE- PS | LLVWELRVVG | WDVSYGAEFL | | 541 |
| SEQ_ID_NO_1563 | GSAD- - AVTE | I TVKPAAKHT | VEFPVTE- TC | LLTMEVRVAG | WDVSYSAEFV | | 372 |
| SEQ_ID_NO_1575 | TTAD- - PATE | VTI KPATKHA | VEFPI SE- KS | TLVWEVRVVD | WSVNYGAEFV | | 545 |
| SEQ_ID_NO_1554 | SLED- - SASE | I TVKPGTKQT | VEI I YE KC | ELVWEI RVTG | WEVSYKAEFV | | 430 |
| SEQ_ID_NO_1565 | TMSD- - PVTE | I PI KPTTKQT | VEI A YE KC | I LVWELRVVG | WEVSYNAEFK | | 362 |

Figure 54 (continued)

| | | | | | | | | |
|---|---|---|---|---|---|---|---|---|
| SEQ_ID_NO_1571 | PADEGSYTII | VRKGKKMGAG | EEAVLRNSFR | AGEPGKVVLT | VENTSH-KKK | | | 509 |
| SEQ_ID_NO_1567 | PDAEGAYTVI | VQKTRKVPAN | EEPIMKGSFK | AGEAGKIVLT | VSNAASLKKK | | | 566 |
| SEQ_ID_NO_1572 | PDAEGGYTVI | VQKTRKVPAN | EEPIMKGSFK | VGEPGKIVLT | INNPASLKKK | | | 595 |
| SEQ_ID_NO_1574 | PDAEGGYTVI | VQKTRKVPAN | EEPIMKGSFK | VGEPGKIVLT | INNPASLKKK | | | 580 |
| SEQ_ID_NO_1555 | PSAEGGYTVI | VQKTAKLGPA | DEPVISNSYR | VGEAGKIVLT | IDNLSSKKKK | | | 591 |
| SEQ_ID_NO_1563 | PSAEDSYTVI | IQKARKVAAT | EEPVVCNSFK | IGEPGKVVLT | IDNSTSKKKK | | | 422 |
| SEQ_ID_NO_1575 | PSAEDGYTVI | IQKNRKVAPA | DETIISNTFK | IGEPGKVILT | IDNQSSLKKK | | | 594 |
| SEQ_ID_NO_1554 | PEEKDAYTVV | IQKPRKMRPS | DEPVLTHSFK | VNELGKVLLT | VDNPTSLKKK | | | 479 |
| SEQ_ID_NO_1565 | PDVEDAYTVI | IQKATKMSPT | DEPVVSNSFK | VVELGKLLLT | IDNPTL-KKK | | | 411 |

| | | | | |
|---|---|---|---|---|
| SEQ_ID_NO_1571 | KVLFRHKSKS | AFAKKC---- | - | 525 |
| SEQ_ID_NO_1567 | KLLYRSKVKC | STGESVEADI | P | 587 |
| SEQ_ID_NO_1572 | KLLYRSKVKS | TSESV----- | - | 610 |
| SEQ_ID_NO_1574 | KLLYRSKVKS | TSESV----- | - | 595 |
| SEQ_ID_NO_1555 | ILLYRSKTKP | ISD------- | - | 604 |
| SEQ_ID_NO_1563 | KLLYRLKTKP | ASSD------ | - | 436 |
| SEQ_ID_NO_1575 | KLLYRSKTIP | ISE------- | - | 607 |
| SEQ_ID_NO_1554 | KLVYRFNVKP | L--------- | - | 490 |
| SEQ_ID_NO_1565 | RLLYRFKIKP | YSD------- | - | 424 |

Figure 55

| | | | | | | |
|---|---|---|---|---|---|---|
| SEQ_ID_NO_1578 | ........ | ........ | ........ | ........ | -MSFYRGTAS | 9 |
| SEQ_ID_NO_1607 | MADNKDGVTP | KSSAAFPLR- | ........N | PNVTLNERNF | AAFTNRSAAA | 40 |
| SEQ_ID_NO_1440 | MDEEMNAVAE | MNAVASKVKE | EY......R | RAPKLNQRII | SSMSRRSVAA | 43 |
| SEQ_ID_NO_1648 | ....MSEEAA | TETGSSSVK- | ........R | TTPKLNERIL | SSLSRRSVAA | 36 |
| SEQ_ID_NO_1651 | ...MSQENGA | TNGHLAEEQQ | DVVMEVEPKR | RAPRLNERIL | SSLSRRSVAA | 47 |
| SEQ_ID_NO_1487 | MSSENGENGH | GAADEVVEPV | QQTP....R | PGPKLNERIL | SSLSRRSVAA | 45 |
| SEQ_ID_NO_1040 | --MSQEDSTS | AAAAQQPTS- | ........R | PAPKLNERIL | SSLSRRGGGA | 38 |
| SEQ_ID_NO_1485 | ---MSEEDTN | AAAGQP.... | ........R | RAPKLNERIL | SSLSRRSVAA | 34 |
| SEQ_ID_NO_1580 | ....MSEEDK | NEAKVLETP- | ........R | KPPRLNERIL | SSMSRRSVAA | 36 |
| SEQ_ID_NO_1623 | ........MS | NENDDLSPQ- | ........R | RAPRLNERII | SSISRRSVAA | 32 |
| SEQ_ID_NO_1622 | MSEHDDEVQE | VQENVQEIH- | ........R | PVPRLNERIL | SSLSRRSVAA | 40 |
| SEQ_ID_NO_1041 | ....MSDVTK | TQENEVETK- | ........H | QAPRLNERIL | SSLSRRTVAA | 36 |
| SEQ_ID_NO_1590 | ...MSDETKT | QENEVVEAK- | ........R | QAPRLNERIL | SSLSRRTVAA | 37 |
| SEQ_ID_NO_1577 | ...MNGEEVK | TSDPQKKLQ- | ........N | PTPRLNERIL | SSLSKRSVAA | 37 |
| SEQ_ID_NO_1611 | ...MSEEVKE | NQSDKLQ--- | ........R | TAPRLNERIL | SSLSRKSVAA | 35 |
| SEQ_ID_NO_1637 | ...MSEEVKE | NQSGKLQ--- | ........K | PTPRLNERIL | SSLGKRSVAA | 35 |
| SEQ_ID_NO_1627 | -MAPSQEVAA | ATKEPSTNGN | GTQAAAAPKT | KTPALNERIL | SSITRRSVAA | 49 |
| SEQ_ID_NO_1608 | MAPPLETVQK | VQPPPNAJEP | HVTYPHDH-S | SHPPLNERIL | SSMRRSIAA | 49 |
| SEQ_ID_NO_1609 | ---MSPPFES | PAKVAITQH- | ........S | KPPLNERII | SSMRRSVAA | 37 |
| | | | | | | |
| SEQ_ID_NO_1578 | HPWHDLHPGN | DAPNFVSCVI | EIPRGSKVKY | ELDKDTGLCF | VDRILYSSVV | 59 |
| SEQ_ID_NO_1607 | HPWHDLEIGP | EAPAVFNCVV | EISKGGKVKY | ELDKNSGLIK | VDRVLYSSIV | 90 |
| SEQ_ID_NO_1440 | HPWHDLEIGP | NAPEFCNCVV | EIPKGSKVKY | ELDKKTGLIM | VDRLYSSVV | 93 |
| SEQ_ID_NO_1648 | HPWHDLEIGP | GAPSVVNAVV | EITKGSKVKY | ELDKKTGMIK | VDRVLYSSVV | 86 |
| SEQ_ID_NO_1651 | HPWHDLEIGP | EAPAVFNVVV | EITKGSKVKY | ELDKKTGLIK | VDRVLYSSVV | 97 |
| SEQ_ID_NO_1487 | HPWHDLEIGP | DAPAVFNVVV | EITKGSKVKY | ELDKKTGLIK | VDRILYSSVV | 95 |
| SEQ_ID_NO_1040 | HPWHDLEIGP | GAPAVFNVYV | EITKGSKVKY | ELDKKTGLIK | VDRVLYSSVV | 88 |
| SEQ_ID_NO_1485 | HPWHDLEIGP | GAPAVFNVVV | EITKGSKVKY | ELDKKTGLIK | VDRVLYSSVV | 84 |
| SEQ_ID_NO_1580 | HPWHDLEIGP | GAPAIFNCVV | EIPKGSKVKY | ELDKKTGLIK | VDRVLYSSVV | 86 |
| SEQ_ID_NO_1623 | HPWHDLEIGP | EAPSVFNVVI | EISKGSKVKY | ELDKKTGLIK | VDRILYSSVV | 82 |
| SEQ_ID_NO_1622 | HPWHDLEIGP | GAPHIFNCVV | EITKGSKVKY | ELDKKTGLIK | VDRILYSSVV | 90 |
| SEQ_ID_NO_1041 | HPWHDLEIGP | GAPHIFNVVV | EITKGSKVKY | ELDKKTGLIK | VDRILYSSVV | 86 |
| SEQ_ID_NO_1590 | HPWHDLEIGP | GAPHIFNVVV | EITKGSKVKY | ELDKKTGLIK | VDRILYSSVV | 87 |
| SEQ_ID_NO_1577 | HPWHDLEIGP | GAPVIFNVVI | EISKGSKVKY | ELDKKTGLIK | VDRILYSSVV | 87 |
| SEQ_ID_NO_1611 | HPWHDLEIGP | GAPSIFNVVI | EISKGSKVKY | ELDKKTGLIK | VDRILYSSVV | 85 |
| SEQ_ID_NO_1637 | HPWHDLEIGP | GAPVIFNVVV | EISKGSKVKY | ELDKKTGLIK | VDRILYSSVV | 85 |
| SEQ_ID_NO_1627 | HPWHDLEIGP | DAPTIFNCYI | EIPKGSKVKY | ELDKKTGLIK | VDRVLYSSVV | 99 |
| SEQ_ID_NO_1608 | HPWHDLEIGP | GAPKIFNCYI | EIPKGSKVKY | ELDKKTGLIK | GDRILDSSVV | 99 |
| SEQ_ID_NO_1609 | HPWHDLEIGP | EAPKIFNCVV | EIGKGSKVKY | ELDKKTGLIK | VDRVLYSSVV | 87 |

Figure 55 (continued)

| SEQ_ID_NO | | | | | | |
|---|---|---|---|---|---|---|
| SEQ_ID_NO_1578 | YPHNYGFVPK | TLCEDGDPLD | VLVLMQEPVV | PMCFLRAKPI | GVMQMLDQGE | 109 |
| SEQ_ID_NO_1607 | YPHNYGFIPR | TICEDSDPID | VLVLMQEPVL | TGSFLRARAI | GLMPMIDQGE | 140 |
| SEQ_ID_NO_1440 | YPHNYGFIPR | TLCEDGDPMD | VLVLMQEPVV | PGRFLRARAI | GLMPMIDQGE | 143 |
| SEQ_ID_NO_1648 | YPHNYGFIPR | TLCEDNDPLD | VLILMQEPVL | PGCFLRIRAI | GLMPMIDQGE | 136 |
| SEQ_ID_NO_1651 | YPHNYGFIPR | SLCEDNDPMD | VLVLMQEPVL | PGAFLRARAI | GLMPMIDQGE | 147 |
| SEQ_ID_NO_1467 | YPHNYGFIPR | TLCEDNDPMD | VLVLMQEPVL | PGSFLRARAI | GLMPMIDQGE | 145 |
| SEQ_ID_NO_1040 | YPHNYGFIPR | TLCEDNDPMD | VLVLMQEPVI | PGSFLRARAI | GLMPMIDQGE | 138 |
| SEQ_ID_NO_1485 | YPHNYGFIPR | TLCEDNDPMD | VLVLMQEPVI | PGSFLRARAI | GLMPMIDQGE | 134 |
| SEQ_ID_NO_1550 | YPHNYGFIPR | TLCEDNDPLD | CLVIMQEPVL | PGCFLRARAL | GLMPMIDQGE | 136 |
| SEQ_ID_NO_1623 | YPQNYGFIPR | TLCEDNDPMD | VLVLMQEPVL | PGCFLRARAI | GLMPMIDQGE | 132 |
| SEQ_ID_NO_1622 | YPHNYGFIPR | TLCEDNDPID | VLVLMQEPVL | PGCFLRARAI | GLMPMIDQGE | 140 |
| SEQ_ID_NO_1041 | YPHNYGFIPR | TLCEDNDPLD | VLVLMQFPVI | PGCFLRARAI | GLMPMIDQGE | 136 |
| SEQ_ID_NO_1590 | YPHNYGFIPR | TLCEDNDPLD | VLVLMQEPVL | PGCFLRARAI | GLMPMIDQGE | 137 |
| SEQ_ID_NO_1577 | YPHNYGFVPR | TLCEDNDPID | VLVIMQEPVL | PGCFLRARAI | GLMPMIDQGE | 137 |
| SEQ_ID_NO_1611 | YPHNYGFIPR | TLCEDNDPLD | VLVIMQEPVL | PGCFLRARAI | GLMPMIDQGE | 135 |
| SEQ_ID_NO_1637 | YPHNYGFIPR | TLCEDNDPLD | VLVIMQEPVL | PGCFLRARAI | GLMPMIDQGE | 135 |
| SEQ_ID_NO_1627 | YPHNYGFIPR | TLCDDSDPID | VLVIMQEPVV | PGCFLRAKAI | GLMPMIDQGE | 149 |
| SEQ_ID_NO_1608 | YPHNYGFIPR | TLCEDNDPLS | CLDIMQEPVV | PGCFLRAKAI | GLMPMIDQGE | 149 |
| SEQ_ID_NO_1609 | YPHNYGFIPR | TICEDSDPMD | VLVIMQEPVL | PGCFLRAKAI | GLMPMIDQGE | 137 |

| SEQ_ID_NO | | | | | | |
|---|---|---|---|---|---|---|
| SEQ_ID_NO_1578 | KDDKLIAVHA | DDPEYKGFTD | ISQLPPHRLA | EIKRFFEDYK | KNEHKEVVVD | 159 |
| SEQ_ID_NO_1607 | KDDKIIAVCA | DDPEFRHYRD | IKELPPHRLA | EIRRFFEDYK | KNENKKVAVE | 190 |
| SEQ_ID_NO_1440 | KDDKIIAVCA | DDPEVRHYTD | INQLPPHRLA | EIRRFFEDYK | KNENKEVAVN | 193 |
| SEQ_ID_NO_1648 | KDDKIIAVCA | DDPEYRHYTD | IKQLAPHRLA | EIRRFFEDYK | KNENKEVAVN | 185 |
| SEQ_ID_NO_1651 | KDDKIIAVCA | DDPEYRHYND | ISELSPHRLQ | EIRRFFEDYK | KNENKEVAVN | 197 |
| SEQ_ID_NO_1467 | KDDKIAVCA | DDPEYRHFNN | LSELSPHRLQ | EIRRFFEDYK | KNENKEVAVN | 195 |
| SEQ_ID_NO_1040 | KDDKIAVCA | DDPEYRHYSI | SVSLLPFRLQ | EIKRFLEDYK | KNENKEVAVD | 186 |
| SEQ_ID_NO_1485 | KDDKIAVCA | DDPEYRHYND | N--------- | ---------K | KNENKEVAVD | 167 |
| SEQ_ID_NO_1580 | KDDKIAVCV | DDPEYKHYTD | KDLPPHRLT | EIRRFFEDYK | KNENKEVAVD | 186 |
| SEQ_ID_NO_1623 | KDDKIIAVCA | DDPEYRHYTD | KQLPPHRLA | EIRRFFEDYK | KNENKDVAVD | 182 |
| SEQ_ID_NO_1622 | KDDKIIAVCA | DDPEYKHFTD | YKELAPHRIM | EIRRFFEDYK | KNENKEVAVN | 190 |
| SEQ_ID_NO_1041 | KDDKIIAVCA | DDPEYKHYTD | IKELAPHRLS | EIRRFFEDYK | KNENKEVAVN | 186 |
| SEQ_ID_NO_1590 | KDDKIIAVCA | DDPEYKHYTD | RELAPHRLS | EIRRFFEDYK | KNENKEVAVN | 187 |
| SEQ_ID_NO_1577 | KDDKIIAVCV | DDPEYKHITN | NELPPHRLS | EIRRFFEDYK | KNENKEVAVN | 187 |
| SEQ_ID_NO_1611 | KDDKIAVCV | DDPEYKHYTD | KELPPHRLS | EIRRFFEDYK | KNENKEVAVN | 185 |
| SEQ_ID_NO_1637 | KDDKIAVCV | DDPEYKHYTD | KELPPHRLT | EIRRFFEDYK | KNENKEVAVN | 185 |
| SEQ_ID_NO_1627 | ADDKIAVCA | DDPEYRHFND | KELPPHRLA | EIRRFFEDYK | KNENKEVAVN | 199 |
| SEQ_ID_NO_1608 | KDDQIIAVCA | DDPEYRHYND | KELPPHRLA | EIRRFFEDYK | KNENKEVAVD | 199 |
| SEQ_ID_NO_1609 | KDDKIIAVCA | DDPEYRHYND | KELPPHRLA | EIRRFFEDYK | KNENKEVEVH | 187 |

Figure 55 (continued)

| | | | | | |
|---|---|---|---|---|---|
| SEQ_ID_NO_1578 | DFLGAEEAKK | VVKDSLNMYQ | EHYVPRKLRN | VYE | 192 |
| SEQ_ID_NO_1607 | GFLPAQAAID | AIKDSMDLYA | A-YIKAGLQR | --- | 219 |
| SEQ_ID_NO_1440 | EFLPAQIAHD | AIQHSMDLYA | E-YILQTLRR | --- | 222 |
| SEQ_ID_NO_1648 | DFLPSATAHE | AIQYSMDLYA | E-YIMMSLRR | --- | 215 |
| SEQ_ID_NO_1651 | EFLPAEAARE | AIQYSMDLYG | Q-YIMQTLRR | --- | 226 |
| SEQ_ID_NO_1487 | DFLPAPTARE | AIQYSMDLYA | Q-YILQSLKR | --- | 224 |
| SEQ_ID_NO_1040 | AFLPATTARE | AIQYSMDLYA | Q-YILQSLRQ | --- | 215 |
| SEQ_ID_NO_1485 | AFLPANTARD | AIQYSMDLYA | Q-YILQSLRQ | --- | 196 |
| SEQ_ID_NO_1580 | KFLPATAAVE | AVQYSMDLYA | E-YIMQTLRR | --- | 215 |
| SEQ_ID_NO_1623 | DFLPPNSAVN | AIQYSMDLYA | E-YILHSLRK | --- | 211 |
| SEQ_ID_NO_1622 | DFLPPSTAVE | AIQYSMDLYA | E-YILHTLRR | --- | 219 |
| SEQ_ID_NO_1041 | DFLPSNTAVE | AIQYSMDLYA | E-YILHTLRR | --- | 215 |
| SEQ_ID_NO_1590 | DFLPSNSAVE | AIQYSMDLYA | E-YILHTLRR | --- | 216 |
| SEQ_ID_NO_1577 | DFLQPGPAIE | AIQYSMDLYA | E-YILHTLRR | --- | 216 |
| SEQ_ID_NO_1611 | DFLPNGPAVE | AIQYSMDLYA | E-YILHTLRR | --- | 214 |
| SEQ_ID_NO_1637 | DFLPNGPAVE | AIQYSMDLYA | E-YILHTLRR | --- | 214 |
| SEQ_ID_NO_1627 | DFLPSEDAYE | AIQHSMDLYA | T-YICEGLRR | --- | 228 |
| SEQ_ID_NO_1608 | DFLPASTAFD | AIQHSMNLYA | D-YIVESLRR | --- | 228 |
| SEQ_ID_NO_1609 | DFLLATTAMR | AIKHSMTLYA | D-YIVESLRR | --- | 216 |

Figure 56

| | | | | | | | | |
|---|---|---|---|---|---|---|---|---|
| SEQ_ID_NO_361 | --MNGGI GDA | LMQP- -QHVQ | V-MSS- | ---- | -------- | S | LPMVASTEVA | 31 |
| SEQ_ID_NO_443 | MDDPGASADP | AARHHLSPQQ | LGGQP- | ---- | -------- | P | VPRSPTPLDL | 36 |
| SEQ_ID_NO_212 | -MDDPGAADP | GARP- -HHLS | PGQPP- | ---- | -------- | V | VPRSPTPLDL | 33 |
| SEQ_ID_NO_421 | ---------- | ---------- | ------ | ---- | -------- | - | ---------- | 0 |
| SEQ_ID_NO_1437 | MGGGSDTTDT | NMMQRVNSSS | GTSSS- | ---- | -------- | S | PKHNLHLNP | 36 |
| SEQ_ID_NO_740 | -MGDTEEANS | EMI QRLQSSF | GTTQSSSTTM | AKQPFSLI NQ | IDVSQLSLNP | 49 |
| SEQ_ID_NO_173 | -MEDTEAASS | FKMN- -NIIME | QLTI P- | ---- | -------- | Q | FNASSQSQMR | 33 |
| SEQ_ID_NO_1461 | -MEDTEAASS | FKMN- -NHME | QLTI P- | ---- | -------- | Q | FNASSQSQMR | 33 |

| | | | | | | | | |
|---|---|---|---|---|---|---|---|---|
| SEQ_ID_NO_361 | EPAAAAAA- | ---------- | ---------- | -ANKP- RAAG | ----LPPTP- | 52 |
| SEQ_ID_NO_443 | ASAAAASG- | -YRRLSPS- | ---LRPPAHP | QARLP- SPYG | ----QI PSP- | 72 |
| SEQ_ID_NO_212 | SSAAAAAAAA | SYRRLSPS- | ---LRPPAHP | QARLP- SPYP | ----QI PSSS | 73 |
| SEQ_ID_NO_421 | ---------- | ---------- | ----MADS | NSKPPMSSQN | ---------- | 14 |
| SEQ_ID_NO_1437 | ALI RSHHH- | -----FRH- | ---PFTGAPP | PPI PPI SPYS | ----QI PATL | 69 |
| SEQ_ID_NO_740 | TQMRARHFTN | FSQNFSGDSN | KRVGFPPSHP | NQI PPI SPYS | ----QI PVSR | 95 |
| SEQ_ID_NO_173 | TVTRNHHH- | ---NQRGG- | ---GI PPSHP | HQI PPI SPYS | HMNNQI PVSR | 73 |
| SEQ_ID_NO_1461 | TVTRNHHH- | ---NQRGG- | ---GI PPSHP | HQI PPI SPYS | HMNNQI PVSR | 73 |

| | | | | | | | | |
|---|---|---|---|---|---|---|---|---|
| SEQ_ID_NO_361 | ---------- | ---------- | ----P- QVFA | AQRAAAAA- | ---------- | 65 |
| SEQ_ID_NO_443 | ---------- | -GAGA- HHAR | SLSQP- LFFS | LDSLPPPP- | ---------- | 97 |
| SEQ_ID_NO_212 | S------ AAA | AGSSG- HHAR | SLSQP- LFFS | LDSLPPLP- | ---------- | 103 |
| SEQ_ID_NO_421 | ---------- | FGVGAVSHNR | SLSQS- SLFS | NSCLPPLSPF | PPSEPGMVSG | 53 |
| SEQ_ID_NO_1437 | ---------- | --LQP- RHSR | SMSQPSSFFS | FDSLPPLNPS | APL------- | 98 |
| SEQ_ID_NO_740 | PVNQQMGPQS | FSLGP- THSR | SLSQPSSFFS | LDSLPPLSPA | PFRDSSSPSV | 144 |
| SEQ_ID_NO_173 | PL---QMPSHS | TSPTP- SHTR | SLSQP- SFFS | LDSLPPLSPC | TFRESSSTSD | 118 |
| SEQ_ID_NO_1461 | PL---QMPSHS | TSPTP- SHTR | SLSQP- SFFS | LDSLPPLSPC | TFRESSSTSD | 118 |

| | | | | | | | | |
|---|---|---|---|---|---|---|---|---|
| SEQ_ID_NO_361 | ----GGDVCM | EESAQGGGG- | ---------- | ---------- | --GLPPRKA- | 87 |
| SEQ_ID_NO_443 | ----YADL- | ------GAAP | AVPPSPPP- | --STSDPPPL | --GLPPRRAG | 129 |
| SEQ_ID_NO_212 | ----YADL- | ------AAPP | AI PPSPPS- | --SSSDPPPP | --GLPPRKGG | 135 |
| SEQ_ID_NO_421 | RSS-1KDI SM | EEADVNSQGV | GVVSS----- | --FTRD---- | --GLPPRKG- | 88 |
| SEQ_ID_NO_1437 | ----SVSVSV | EEKTGAGFSP | SLPPSPFIMC | HSSSSRNAGD | GENLPPRKS- | 143 |
| SEQ_ID_NO_740 | SDPISTDVFM | EEKDGGSHSL | -LPPSPF- | --NRGNAPRN | VESLPPRKA- | 187 |
| SEQ_ID_NO_173 | ----HADVSM | EDRDVTSHSP | -LPP----- | --FAARNP- | --SLPPRKS- | 150 |
| SEQ_ID_NO_1461 | ----HADVSM | EDRDVTSHSP | -LPP----- | --FAARNP- | --SLPPRKS- | 150 |

Figure 56 (continued)

```
SEQ_ID_NO_361     HRRSSSDVPF GYL-----A GQHQLLPP- ---------- ----------   109
SEQ_ID_NO_443     HRRSQSDIPF GFA-----Q LSPPLPPP- ---------- ----------   151
SEQ_ID_NO_212     HRRSQSDIPF GFS-----H LSPPLPPP- ---------- ----------   157
SEQ_ID_NO_421     HRRSNSDVPL GFSAMI--Q SSPQLMPI- ---------- ---------S   114
SEQ_ID_NO_1437    HRRSNSDVTF GFSSMMSQNQ KSPPLSSLER SISGEDT--- --------SD   182
SEQ_ID_NO_740     HRRSNSDIPF GLANVL--Q CSPPLIPS-R GSSGLERSMS GRENLGMAKP   233
SEQ_ID_NO_173     HRRSNSDIPF GFSTVL--Q SSPPLIPL-R GREGV----- --------KP   183
SEQ_ID_NO_1461    HRRSNSDIPF GFSTVL--Q SSPPLIPL-R GREGV----- --------KP   183

SEQ_ID_NO_361     -----KNEAG A-----GHL GAGA----GG AAAADDLFNA YLNLDGLDGL   144
SEQ_ID_NO_443     --APVKREVT A-----AAD GCRSDGGGGD DAALYDLVNA YMDLDGLDPL   193
SEQ_ID_NO_212     --APVKREAA T-----AAE GCRSD---GD DFALYDLVNS YMDLDGMEAL   196
SEQ_ID_NO_421     GDKVLGRAVS LG----DSN GKIDERKPKG ELVTDELLFS YMNLENIETL   158
SEQ_ID_NO_1437    VSNLVKKE- - -------PRE GFYKGRKPEV EAAMDDYFTA YMNLDNIDVL   223
SEQ_ID_NO_740     AQSVKK- - -E MERGGDSNAE GMGERKS-EG ELVVDDLFSA YMNLDNIDVL   278
SEQ_ID_NO_173     NSSVVKRETN MEHG---NVE CSCEKKSPEG ELVVDDLFSA YMNLDSFDTL   229
SEQ_ID_NO_1461    NSSVVKRETN MEHG---NVE EKIKSLSPEG ELVVDDLFSA YMNLDNIDAI   228

SEQ_ID_NO_361     NSSDDRH-DE GD------ SRGSSI-KTN GADSSENESE ECADDTRGGI   184
SEQ_ID_NO_443     NSSEDRH-DD RD------ SRASGTRAGS AAESSENEAE S--------   225
SEQ_ID_NO_212     NSSEERH-ED RD------ SRASGTRTGS VADSSENEAE S--------   228
SEQ_ID_NO_421     NGSGTKD-RD KD------ SIVSGT-KVT GSESSNNEAE SVMKGNNVS-   197
SEQ_ID_NO_1437    NSFGGEDGKN GNENVEEMES SRGSGIKKTN GGDSSDSEGD SSASGNVK--   271
SEQ_ID_NO_740     NSSGTDD-KN GNENREDLD- SRASGT-KTN GGDSSDNEAE SSVNESGGNL   325
SEQ_ID_NO_173     NSSGTDD-KN GDENRDDLD- SRADGT-KTN GGDSSDNEAE SSVNESG--- 274
SEQ_ID_NO_1461    NDDKNAATDD ---------- SRASGT-KTN GGDSSDNEAE SSVNESG---  264

SEQ_ID_NO_361     RLWS-ADGGE RREGVKRNAA GEPATAPLAR IARSLSMDS- LIGKFNFTAG   232
SEQ_ID_NO_443     ---------- QSTSADRKDG GK-----BR HCRSLSIDS- FMGKLSFAAG   258
SEQ_ID_NO_212     ---------- HSTPVERKDG GG----KSR HCRSLSVDS- FIEKLNF---   259
SEQ_ID_NO_421     -----IQPIN LREGIKRSAD AN--IAPAAR HFRSLSMDS- AIGNFHY--G   237
SEQ_ID_NO_1437    -----VALSS SSSGVKRRAG GD--IAPTGR HYRSVSMDSC FMGKLNF--G   312
SEQ_ID_NO_740     PRAGLSSSTE KREGIKRSAG GD--IAPTTR HYRSVSMDS- FMGKLNF--G   370
SEQ_ID_NO_173     ------GGSE KREGMKRSAG GE--IAPTTR HYRSVSMDS- FIGKLNF--G   313
SEQ_ID_NO_1461    ------DSMD RREGNKRSAG GD--IAPTTR HYRSVSMDS- FIGKLNF--N   303
```

Figure 56 (continued)

| SEQ_ID_NO_361 | TA------- | AAAGNGVALG | PN------- | RFSLEFGSGE | FTPSEMKKIM | 266 |
| SEQ_ID_NO_443 | EESP-KLPLP | SPGGSLTRSG | SGSLEGGAVA | LFNMEFINGE | FTDSEKKKIM | 307 |
| SEQ_ID_NO_212 | DESP-KLPLP | SPSGGLSRSG | SGSLDGGAAS | LFGAEFANGE | FTEAEKKKIM | 308 |
| SEQ_ID_NO_421 | DESP-NLP-T | SLMMRSGQLS | PSNSGNESSS | KHNLDFGNSE | FSEAEMKKIM | 285 |
| SEQ_ID_NO_1437 | DESSLKLP-P | SSSA---KVS | PTNSGEGNSS | AYSVEFGNSE | FTAAEMKKIA | 358 |
| SEQ_ID_NO_740 | NESP-KLP-P | SPGTRPGQLS | PTDSIDGN-- | AFSLDFGNGE | FSGAELKKIM | 416 |
| SEQ_ID_NO_173 | DESP-KLP-P | SPGQRGRLMS | PAGGDGNSA | AFSLEFGSGE | FSGPELKKIM | 361 |
| SEQ_ID_NO_1461 | DESL-KMP-P | SPGG---LMS | PGNSGDGNNA | AFSLEFGNGE | FSGPELKKIM | 348 |

| SEQ_ID_NO_361 | ADEKLAEMAL | ADPKRVKRVL | ANRQSAARSK | ERKMRYIAEL | EQKVQLLQSE | 316 |
| SEQ_ID_NO_443 | ANERLAEIAL | TDPKRVKRIL | ANRQSAARSK | ERKMRYIQEL | EHKVQVLQTE | 357 |
| SEQ_ID_NO_212 | ANERLAEIAL | TDPKRVKRIL | ANRQSAARSK | ERKMRYIQEL | EHKVQVLQTE | 358 |
| SEQ_ID_NO_421 | ADERLAEIAV | LDPKRAKRIL | ANRLSAARSK | ERKTRYISEL | EHKVQKLQTE | 335 |
| SEQ_ID_NO_1437 | ADEKLAEIVM | ADPKRVKRIL | ANRVSAARSK | ERKTRYMAEL | EHKVQTLQTE | 408 |
| SEQ_ID_NO_740 | ANEKLAEIAL | ADPKRAKRIL | ANRQSAARSK | ERKMRYISEL | EHKVQTLQTE | 466 |
| SEQ_ID_NO_173 | ANEKLAEIAL | TDPKRAKRIL | ANRQSAARSK | ERKMRYISEL | EHKVQTLQTE | 411 |
| SEQ_ID_NO_1461 | ANEKLAEIAM | ADPKRAKRIL | ANRQSAARSK | ERKMRYISEL | EHKVQTLQTE | 398 |

| SEQ_ID_NO_361 | ATNLSAQLTM | MQRDSAGLAT | QNNELKFRLH | AMEQQAQLRD | ALNEALTIFV | 366 |
| SEQ_ID_NO_443 | ATTLSAQLTM | LQRDSAGLAT | QNNELKIRLQ | AMEQQAQLRD | ALNEALTAEV | 407 |
| SEQ_ID_NO_212 | ATTLSAQLTM | LQRDSTGLAT | QNNELKIRLQ | AMEQQAQLRD | ALNEALTAEV | 408 |
| SEQ_ID_NO_421 | TTTLSTQVTI | LQKNFVE SS | LNSELKFRIQ | AMEQQAQLRD | ALHEALTAEV | 385 |
| SEQ_ID_NO_1437 | ATTLSAQLTH | LQRDSMGLTN | QNSELKFRLQ | AMEQQAQLRD | ALSEKLNEEV | 458 |
| SEQ_ID_NO_740 | ATTLSAQLTL | LQRDSVGLTN | QNNELKFRIQ | AMEQQAQLRD | ALNEALTAEV | 516 |
| SEQ_ID_NO_173 | ATTLSAQLTL | LQRDSAGLTN | QNSELKFRLQ | SMEQQAKLRD | ALNEALTAEV | 461 |
| SEQ_ID_NO_1461 | ATTLSAQLTL | LQRDSVGLTN | QNSELKFRLQ | SMEQQAKLRD | ALNEALTAEV | 448 |

| SEQ_ID_NO_361 | QRLKLATAEL | GDSCSSSSLA | QCLQLNAQNQ | MFQL----- | -------QQD | 403 |
| SEQ_ID_NO_443 | QRLKLATGEV | T-DGRMPKGL | QCQM---NSQ | MLQL----- | -------QQL | 440 |
| SEQ_ID_NO_212 | QRLKLATGEI | T-DGRMSKGL | QCQM---NSQ | LLQL----- | ---------- | 438 |
| SEQ_ID_NO_421 | QRLKLAAGEH | REEGRLPNNM | TQQT-PMKHN | FQM------ | ---------- | 418 |
| SEQ_ID_NO_1437 | QRLKLVLGEP | NRRQSGSSSS | ESKMSLNPE | MFQQ----- | ---------L | 492 |
| SEQ_ID_NO_740 | RRLKIATAEQ | GGDSDPSKSM | VQQQLSINPQ | MYLQQPRPSQ | LGMHQLQQQS | 566 |
| SEQ_ID_NO_173 | QRLKIATAEL | SSDSHGSSCL | PQH-SVNPL | MFQQ----- | -------QPP | 497 |
| SEQ_ID_NO_1461 | QRLKIVTAEL | NGESLPSNCM | PQH-SVNPM | MFQQ----- | ---------- | 481 |

Figure 56 (continued)

| | | | | | | |
|---|---|---|---|---|---|---|
| SEQ_ID_NO_381 | QATQLPFYQL | QQSQ | ---------- | Q | NGAAKNNESK | E | 429 |
| SEQ_ID_NO_443 | QVQQQAPQAQ | QQGQ | ---------- | - | RQQQQQPQKS | A | 465 |
| SEQ_ID_NO_212 | --QQLQIQQQ | QSSQ | ---------- | - | ----TTQQDR | L | 457 |
| SEQ_ID_NO_421 | --QRQQPSQM | QQLS | ---------- | VGK | ASAASATPAS | A | 444 |
| SEQ_ID_NO_1437 | SLSQLQHQQM | QHSN | ---------- | -QC | STMKAKHTSN | D | 519 |
| SEQ_ID_NO_740 | SASQENMHQR | QRQQQQQQQQ | QSSQPQPQQN | GNTTPKPDSN | Q | 607 |
| SEQ_ID_NO_173 | SASQQNIHLQ | QQQH | ---------- | RQN | GNANSNSDLK | Q | 525 |
| SEQ_ID_NO_1461 | ---QHQHQQH | QQQQ | ---------- | QQN | GNANSKNELK | Q | 506 |

```
SEQ_D_NO_97    ----MGMKSP  NIAAFMLPLL  LILFTLSSQL  KVVESTGRKL  -AWGFGGTPI  45
SEQ_D_NO_2018  MKKKMGSKSP  NIGAFVLPLL  LILFTLSSQA  RLIESTGRKL  AAWGFGGAPI  50
SEQ_D_NO_2015  ----MGSKSP  NIAALVLPLL  LILFSLSSQA  RLVESSGRKL  AAWGFGGAPI  46

SEQ_D_NO_97    VYTPPSRSCG  TSPAVFTSKW  RRPRPCRLPP  GSY PASQQS  P   86
SEQ_D_NO_2013  WTPPSNSCG   ASPAVWYPKP  TKRGPCRGPP  GIGIPTSYQS  P   91
SEQ_D_NO_2015  GTPSSNSCG   ASPAVWYPKP  TKPRPCRRTP  GIGIPTSHQS  P   87
```

FIG. 57

```
Lead-CeresClone37288   MGRGKIEIKK    IENINSRQVT    FSKRRNGLIK    KAKELSILCD    AEVALIFSS     50
CeresClone:523628      MGRGKIEIKK    IENLNSRQVT    FSKRRNGLLK    KAKELSVLCD    AEVAVIIFSS    50
gi|38326712            MGRGKIEIKR    IDNASSRQVT    FSKRRTGLFK    KAQELSILCD    AEVAVIVFSN    50
gi|34452081            MGRGKIDIKL    IENVNNRQVT    FSKRRAGLLK    KANELSVLCD    AEVAVIIFSS    50
gi|52789958            MGRGKIEIKR    IENANSRQVT    FSKRRAGLLK    KAKELAILCD    AEVAVIIFSN    50

Consensus              MGRGKIEIK-    IEN-NSRQVT    FSKRR-GLLK    KAKELSILCD    AEVAVIIFSN    50

Lead-CeresClone37288   TGKIYDFSSV    CMEQILSRYG    YTTASTEHKQ    QREHQLL---    ---ICASHGN    94
CeresClone:523628      TGKLYEFSNT    SMEHTLSRYS    K---GAESDS    A-EQPID---    -----VPPTDV   89
gi|38326712            TGKLFEFSSS    GMKRYLSRYN    KCLGSTDAAV    A-EIKTQ---    ---------    86
gi|34452081            TGKLFEFSST    SMKQTLSRYN    RCLASTETSA    I-EKKLEDNE    QPQPLQTYVP    99
gi|52789958            TGKLFEFSSS    GMNKTISRYK    SAQGSPETAQ    V-EHKAE---    ---------    86

Consensus              TGKLFEFSS-    -M-QTLSRYN    K---STE-A-    --E-KLE---    ----------    100

Lead-CeresClone37288   EAVLRNDDSM    KVELERLQLA    IERLKGKELE    GMSFPDLISF    ENQLNESLHS    144
CeresClone:523628      MAVEPIDTNLL   MEEITKLRSA    YLRMMGKELD    GLSLKELQQL    ENQLSEGMQS    139
gi|38326712            KEDSKMVEIL    REEIAKLETK    QLQLVGKDLT    GLGLKELQNL    EQQLNEGLLS    136
gi|34452081            KQEQKEMDIL    KDELSKLKMD    QLRLLGKDLS    GMGLNELRLL    EHQLNEGLLA    149
gi|52789958            KQDSKEADHL    KDEIAKLQMK    QLQLLGKNLT    SMSLKELQLL    EQQLNEGLLS    136

Consensus              KQD-K--DIL    K-EI-KLQM-    QLRLMGK-LT    GMSLKELQ-L    ENQLNEGLLS    150

Lead-CeresClone37288   VKDQKTQILL    NQIEQSRIQE    KKALEENQIL    RKQVEMLG--    ---RGSGPK     188
CeresClone:523628      VKDKKEQVLV    EQLRKSRIQE    QKAMLENEVL    RKQVEEIQ--    ---NKTKSQ     183
gi|38326712            VKARK-----    --LEQSRVQE    QRVMLENETL    RRQIEELRCL    FPQSESMVP-    178
gi|34452081            IKDRKEELLI    QQLEQSRRQE    ERAALESETL    RRQLEELRGL    FPLSISLPPP    199
gi|52789958            VKEKKEQLLM    QQLEQSRLQE    QRAMLENETL    RRQVEELRGF    FPTTDHPIQP    186

Consensus              VKD-KEQIL-    QQLEQSRIQE    QRAMLENETL    RRQ-EELR--    FP-S----P-    200
```

FIG. 58

```
Lead-CeresClone37288  V-NERPQDSS     PEADPESSSS     EEDEN----D    NEEHH-SDTS   LQLGLSSIGY   233
CeresClone:523628     FLEFSSLDR-     -TFSKNGSKS     ---LFNC---A   SEEND-SDTS   LQLGLSTDYG   226
gi|38326712           -FQYQHTEGK     NTFVDTGARY     LNLANNC--G    NEKGS-SDTS   FHLGLPAGV-   223
gi|34452081           YLEYHPLEQK     YPILKEGEES     LDSDTACEDG    VDDED-SNTT   LQLGLPIVGR   248
gi|52789958           YLECYPVERK     NSLMSHSIPS     PDLTCNC---T   VEKGD-SDTT   LYLGLPSDYH   233

Consensus             YLEY-PLERK     -T----GS-S     -D----NC---   NE--D-SDTS   LQLGLPS---   250

Lead-CeresClone37288  CTKRKKPKI-E    LVCDNSGSQV     ASD  256
CeresClone:523628     --RQRKALKM     EPCNDSGSQV     ASH  247
gi|38326712           --QEEGPQER     NLFK------     ---  235
gi|34452081           --KRKKPEQD     SPSSNSENQV     GSK  269
gi|52789958           --KRKKPE-E     SHSNESESQL     GLL  254

Consensus             --KRKKPE-E     S--N-S-SQV     -S-  273
```

FIG. 58 (continued)

NUCLEOTIDE SEQUENCES AND CORRESPONDING POLYPEPTIDES CONFERRING MODIFIED PHENOTYPE CHARACTERISTICS IN PLANTS

CROSS REFERENCE TO RELATED APPLICATIONS

This application in a Continuation-in-Part of application Ser. No. 13/644,359 filed on Oct. 4, 2012 (pending), which is a Continuation-in-Part of application Ser. No. 13/465,846 filed on May 7, 2012 (pending), and for which priority is claimed under 35 U.S.C. § 120. Application Ser. No. 13/465,846 is a Division of application Ser. No. 10/572,827 filed on Mar. 7, 2007 (now U.S. Pat. No. 8,193,409). Application Ser. No. 10/572,827 is a national phase under 35 U.S.C. § 371 of PCT International Application No. PCT/US2003/025997 which has the International filing date of Aug. 18, 2003, which designated the United States of America. The entire contents of each of the above-identified applications are hereby incorporated by reference, including their sequence listings.

This application in a Continuation-in-Part of application Ser. No. 14/175,856 filed on Feb. 7, 2014 (pending), which is a Reissue of application Ser. No. 12/281,616 filed on Dec. 5, 2008 (now U.S. Pat. No. 8,110,724). Application Ser. No. 12/281,616 is a national phase under 35 U.S.C. § 371 of PCT International Application No. PCT/US2007/06651 which has the International filing date of Mar. 14, 2007, which designated the United States of America, and which claims priority under 35 U.S.C. § 119(e) of U.S. Provisional Application No. 60/821,639 filed on Aug. 7, 2006, and U.S. Provisional Application No. 60/782,428 filed on Mar. 14, 2006. The entire contents of each of the above-identified applications are hereby incorporated by reference, including their sequence listings.

Application Ser. No. 13/644,359 filed on Oct. 4, 2012 (pending) is a Continuation-in-Part of application Ser. No. 11/779,266 filed on Jul. 17, 2007 (pending) and for which priority is claimed under 35 U.S.C. § 120. Application Ser. No. 11/779,266 is a Continuation-in-Part of application Ser. No. 11/778,060 filed Jul. 15, 2007 (abandoned). Application Ser. No. 11/778,060 is a Continuation-in-Part of application Ser. No. 11/248,547 filed Oct. 12, 2005 (now U.S. Pat. No. 7,244,879). The entire contents of each of which are hereby incorporated by reference, including their sequence listings.

Application Ser. No. 13/644,359 filed on Oct. 4, 2012 (pending) is a Continuation-in-Part of application Ser. No. 12/514,991 filed on Jan. 8, 2010 (abandoned), and for which priority is claimed under 35 U.S.C. § 120. Application Ser. No. 12/514,991 is a national phase under 35 U.S.C. § 371 of PCT International Application No. PCT/US2007/085007 which has the International filing date of Nov. 16, 2007, which designated the United States of America, and which claims priority under 35 U.S.C. § 119(e) of U.S. Provisional Application No. 60/859,467 filed Nov. 16, 2006. The entire contents of each of which are hereby incorporated by reference, including their sequence listings.

Application Ser. No. 13/644,359 filed on Oct. 4, 2012 (pending) is a Continuation-in-Part of application Ser. No. 12/445,005 filed on Jul. 13, 2011 (abandoned), and for which priority is claimed under 35 U.S.C. § 120. Application Ser. No. 12/445,005 is a national phase under 35 U.S.C. § 371 of PCT International Application No. PCT/US2007/081301 which has the International filing date of Oct. 12, 2007, which designated the United States of America, and which claims priority under 35 U.S.C. § 119(e) of U.S. Provisional Application No. 60/851,585 filed Oct. 12, 2006. The entire contents of each of which are hereby incorporated by reference, including their sequence listings.

Application Ser. No. 13/644,359 filed on Oct. 4, 2012 (pending) is a Continuation-in-Part of application Ser. No. 12/515,707 filed on Dec. 16, 2009 (abandoned) and for which priority is claimed under 35 U.S.C. § 120. Application Ser. No. 12/515,707 is a national phase under 35 U.S.C. § 371 of PCT International Application No. PCT/US2007/085439 which has the International filing date of Nov. 21, 2007, which designated the United States of America, and which claims priority under 35 U.S.C. § 119(e) of U.S. Provisional Application No. 60/860,296 filed Nov. 21, 2006. The entire contents of each of which are hereby incorporated by reference, including their sequence listings.

Application Ser. No. 13/644,359 filed on Oct. 4, 2012 (pending) is a Continuation-in-Part of application Ser. No. 12/615,920 filed on Nov. 10, 2009 (now U.S. Pat. No. 8,471,099), and for which priority is claimed under 35 U.S.C. § 120. Application Ser. No. 12/615,920 is a Continuation of application Ser. No. 11/114,963 filed on Apr. 25, 2005 (now U.S. Pat. No. 7,696,409). Application Ser. No. 11/114,963 claims priority under 35 U.S.C. § 119(e) of U.S. Provisional Application No. 60/564,659 filed Apr. 23, 2004. The entire contents of each of which are hereby incorporated by reference, including their sequence listings.

Application Ser. No. 13/644,359 filed on Oct. 4, 2012 (pending) is a Continuation-in-Part of application Ser. No. 12/605,261 filed on Oct. 23, 2009 (abandoned), and for which priority is claimed under 35 U.S.C. § 120. Application Ser. No. 12/605,261 is a Division of application Ser. No. 11/298,391 filed on Dec. 8, 2005 (now U.S. Pat. No. 7,663,027). Application Ser. No. 11/298,391 claims priority under 35 U.S.C. § 119(e) of U.S. Provisional Application Nos. 60/635,115, filed Dec. 8, 2004 and 60/635,140 filed on Dec. 8, 2004. The entire contents of each of which are hereby incorporated by reference, including their sequence listings.

Application Ser. No. 13/644,359 filed on Oct. 4, 2012 (pending) is a Continuation-in-Part of application Ser. No. 12/377,106 filed on Aug. 13, 2010 (abandoned) and for which priority is claimed under 35 U.S.C. § 120. Application Ser. No. 12/377,106 is a national phase under 35 U.S.C. § 371 of PCT International Application No. PCT/US2007/075747 which has the International filing date of Aug. 10, 2007, which designated the United States of America, and which claims priority under 35 U.S.C. § 119(e) of U.S. Provisional Application No. 60/837,434 filed Aug. 11, 2006. The entire contents of each of which are hereby incorporated by reference, including their sequence listings.

Application Ser. No. 13/644,359 filed on Oct. 4, 2012 (pending) is a Continuation-in-Part of application Ser. No. 12/541,607 filed on Aug. 14, 2009 (abandoned), and for which priority is claimed under 35 U.S.C. § 120. Application Ser. No. 12/541,607 is a Continuation of application Ser. No. 11/140,347 filed on May 27, 2005 (now U.S. Pat. No. 7,576,260). Application Ser. No. 11/140,347 claims priority under 35 U.S.C. § 119(e) of U.S. Provisional Application No. 60/575,309 filed May 27, 2004. The entire contents of each of which are hereby incorporated by reference, including their sequence listings.

Application Ser. No. 13/644,359 filed on Oct. 4, 2012 (pending) is a Continuation-in-Part of application Ser. No. 13/184,361 filed on Jul. 15, 2011 (pending), and for which priority is claimed under 35 U.S.C. § 120. Application Ser. No. 13/184,361 is a Division of application Ser. No. 11/140,450 filed on May 27, 2005 (now U.S. Pat. No. 8,022,273).

Application Ser. No. 11/140,450 claims priority under 35 U.S.C. § 119(e) of U.S. Provisional Application No. 60/575,253 filed May 27, 2004. The entire contents of each of which are hereby incorporated by reference, including their sequence listings.

Application Ser. No. 13/644,359 filed on Oct. 4, 2012 (pending) is a Continuation-in-Part of application Ser. No. 11/654,357 filed on Jan. 16, 2007 (abandoned), and for which priority is claimed under 35 U.S.C. § 120. Application Ser. No. 11/654,357 is a Non-Provisional which claims priority under 35 U.S.C. § 119(e) of U.S. Provisional Application Nos. 60/778,568 filed Mar. 1, 2006 and 60/758,831 filed on Jan. 13, 2006. The entire contents of each of which are hereby incorporated by reference, including their sequence listings.

Application Ser. No. 13/644,359 filed on Oct. 4, 2012 (pending) is a Continuation-in-Part of application Ser. No. 13/465,841 filed on May 7, 2012 (pending) and for which priority is claimed under 35 U.S.C. § 120. Application Ser. No. 13/465,841 is a Division of application Ser. No. 11/858,117 filed on Sep. 19, 2007 (abandoned). Application Ser. No. 11/858,117 is a Continuation-in-Part of Application No. PCT/US2007/06544 which has the International filing date of Mar. 14, 2007, and which claims priority under 35 U.S.C. § 119(e) of U.S. Provisional Application No. 60/782,735 filed Mar. 14, 2006. The entire contents of each of which are hereby incorporated by reference, including their sequence listings.

Application Ser. No. 13/644,359 filed on Oct. 4, 2012 (pending) is a Continuation-in-Part of application Ser. No. 12/918,609 filed on Nov. 22, 2010 (abandoned) and for which priority is claimed under 35 U.S.C. § 120. Application Ser. No. 12/918,309 is a national phase under 35 U.S.C. § 371 of PCT International Application No. PCT/US2009/034638 which has the International filing date of Feb. 20, 2009, which designated the United States of America, and which claims priority under 35 U.S.C. § 119(e) of U.S. Provisional Application No. 61/030,152, filed Feb. 20, 2008. The entire contents of each of which are hereby incorporated by reference, including their sequence listings.

Application Ser. No. 13/644,359 filed on Oct. 4, 2012 (pending) is a Continuation-in-Part of application Ser. No. 12/922,143 filed on Feb. 1, 2011 (abandoned), and for which priority is claimed under 35 U.S.C. § 120. Application Ser. No. 12/922,143 is a national phase under 35 U.S.C. § 371 of PCT International Application No. PCT/US2009/037025 which has the International filing date of Mar. 12, 2009, which designated the United States of America, and which claims priority under 35 U.S.C. § 119(e) of U.S. Provisional Application No. 61/036,396, filed Mar. 13, 2008. The entire contents of each of which are hereby incorporated by reference, including their sequence listings.

Application Ser. No. 13/644,359 filed on Oct. 4, 2012 (pending) is a Continuation-in-Part of application Ser. No. 11/241,685 filed on Sep. 30, 2005 (now U.S. Pat. No. 8,481,814), and for which priority is claimed under 35 U.S.C. § 120. Application Ser. No. 11/241,685 is a non-provisional which claims priority under 35 U.S.C. § 119(e) of U.S. Provisional Application No. 60/615,080, filed on Sep. 30, 2004. The entire contents of each of which are hereby incorporated by reference, including their sequence listings.

Application Ser. No. 13/644,359 filed on Oct. 4, 2012 (pending) is a Continuation-in-Part of application Ser. No. 12/863,773 filed on Nov. 23, 2010 (abandoned), and for which priority is claimed under 35 U.S.C. § 120. Application Ser. No. 12/863,773 is a national phase under 35 U.S.C. § 371 of PCT International Application No. PCT/US2009/031609 which has the International filing date of Jan. 21, 2009, which designated the United States of America, and which claims priority under 35 U.S.C. § 119(e) of U.S. Provisional Application No. 61/022,786 filed Jan. 22, 2008. The entire contents of each of which are hereby incorporated by reference, including their sequence listings.

Application Ser. No. 13/644,359 filed on Oct. 4, 2012 (pending) is a Continuation-in-Part of application Ser. No. 12/282,342 filed on Nov. 17, 2008 (now U.S. Pat. No. 8,324,454), and for which priority is claimed under 35 U.S.C. § 120. Application Ser. No. 12/282,342 is a national phase under 35 U.S.C. § 371 of PCT International Application No. PCT/US2007/06544 which has the International filing date of Mar. 14, 2007, which designated the United States of America, and which claims priority under 35 U.S.C. § 119(e) of U.S. Provisional Application No. 60/782,735, filed Mar. 14, 2006. The entire contents of each of which are hereby incorporated by reference, including their sequence listings.

Application Ser. No. 13/644,359 filed on Oct. 4, 2012 (pending) is a Continuation-in-Part of application Ser. No. 12/776,319 filed on May 7, 2010 (abandoned), and for which priority is claimed under 35 U.S.C. § 120. Application Ser. No. 12/776,319 is a Division of application Ser. No. 11/324,093 filed on Dec. 29, 2005 (now U.S. Pat. No. 7,803,983). Application Ser. No. 11/324,093 is a Continuation-in-Part of application Ser. No. 11/172,740 filed on Jun. 30, 2005 (now U.S. Pat. No. 7,396,979). Application Ser. No. 11/172,740 claims priority under 35 U.S.C. § 119(e) of U.S. Provisional Application Nos. 60/584,829, 60/583,621, and 60/584,800, all filed on Jun. 30, 2004. The entire contents of each of which are hereby incorporated by reference, including their sequence listings.

Application Ser. No. 13/644,359 filed on Oct. 4, 2012 (pending) is a Continuation-in-Part of application Ser. No. 12/911,698 filed on Oct. 25, 2010 (pending), and for which priority is claimed under 35 U.S.C. § 120. Application Ser. No. 12/911,698 is a Division of application Ser. No. 11/324,098 filed on Dec. 29, 2005 (now U.S. Pat. No. 7,884,261). Application Ser. No. 11/324,098 is a Continuation-in-Part of application Ser. No. 11/172,740 filed on Jun. 30, 2005 (now U.S. Pat. No. 7,396,979). Application Ser. No. 11/172,740 claims priority under 35 U.S.C. § 119(e) of U.S. Provisional Application Nos. 60/584,829, 60/583,621, and 60/584,800, all filed on Jun. 30, 2004. The entire contents of each of which are hereby incorporated by reference, including their sequence listings.

Application Ser. No. 13/644,359 filed on Oct. 4, 2012 (pending) is a Continuation-in-Part of application Ser. No. 13/609,176 filed on Sep. 10, 2012 (abandoned) and for which priority is claimed under 35 U.S.C. § 120. Application Ser. No. 13/609,176 is a Division of application Ser. No. 12/139,269 filed on Jun. 13, 2008 (abandoned). Application Ser. No. 12/139,269 is a Division of application Ser. No. 11/172,740 filed on Jun. 30, 2005 (now U.S. Pat. No. 7,396,979). Application Ser. No. 11/172,740 claims priority under 35 U.S.C. § 119(e) of U.S. Provisional Application Nos. 60/584,829, 60/583,621, and 60/584,800, all filed on Jun. 30, 2004. The entire contents of each of which are hereby incorporated by reference, including their sequence listings.

REFERENCE TO SEQUENCE LISTING SUBMITTED VIA EFS-WEB

This application is being filed electronically via EFS-Web and includes an electronically submitted sequence listing in .txt format. The .txt file contains a sequence listing entitled "2015-05-29 2750_2197PUS2_Sequence_Listing.txt" created on May 29, 2015, and is 21,939,971 bytes in size. The sequence listing contained in this .txt file is part of the specification and is hereby incorporated by reference herein in its entirety.

TECHNICAL FIELD

The present invention relates to methods and materials involved in tolerance of a plant to limiting exogenous nitrogen sources. For example, this document provides plants having increased low-nitrogen tolerance levels as well as materials and methods for making plants and plant products having increased low-nitrogen tolerance levels.

BACKGROUND

Nitrogen is often the rate-limiting element in plant growth, and all field crops have a fundamental dependence on exogenous nitrogen sources.

According to a recent study published in Field Crops Research (Volume 100, Issues 2-3, 1 Feb. 2007, Pages 210-217), Nitrogenous fertilizer, which is usually supplied as ammonium nitrate, potassium nitrate, or urea, typically accounts for 40% of the costs associated with crops, such as corn and wheat in intensive agriculture.

Improving nitrogen use efficiency of crop plants is an important goal towards reducing input costs and reducing the environmental consequences of intensive nitrogen fertilization on the environment. Increased efficiency of nitrogen use by plants should enable the production of higher yields with existing fertilizer inputs and/or enable existing yields of crops to be obtained with lower fertilizer input, or better yields on soils of poorer quality. Also, higher amounts of proteins in the crops could also be produced more cost-effectively.

Plants have a number of means to cope with nutrient deficiencies, such as poor nitrogen availability. One important mechanism senses nitrogen availability in the soil and respond accordingly by modulating gene expression while a second mechanism is to sequester or store nitrogen in times of abundance to be used later. The nitrogen sensing mechanism relies on regulated gene expression and enables rapid physiological and metabolic responses to changes in the supply of inorganic nitrogen in the soil by adjusting nitrogen uptake, reduction, partitioning, remobilization and transport in response to changing environmental conditions. Nitrate acts as a signal to initiate a number of responses that serve to reprogram plant metabolism, physiology and development (Redinbaugh et al. (1991) *Physiol. Plant.* 82, 640-650.; Forde (2002) *Annual Review of Plant Biology* 53, 203-224). Nitrogen-inducible gene expression has been characterized for a number of genes in some detail. These include nitrate reductase, nitrite reductase, 6-phosphoglucante dehydrogenase, and nitrate and ammonium transporters (Redinbaugh et al. (1991) *Physiol. Plant.* 82, 640-650; Huber et al. (1994) Plant Physiol 106, 1667-1674; Hwang et al. (1997) *Plant Physiol.* 113, 853-862; Redinbaugh et al. (1998) *Plant Science* 134, 129-140; Gazzarrini et al. (1999) *Plant Cell* 11, 937-948; Glass et al. (2002) *J. Exp. Bot.* 53, 855-864; Okamoto et al. (2003) *Plant Cell Physiol.* 44, 304-317).

In the fields of agriculture and forestry, efforts are constantly being made to produce plants with an increased growth potential in order to feed the ever-increasing world population and to guarantee the supply of reproducible raw materials. There is a need for methods of increasing nitrogen use efficiency in plants, which leads to better growth potential and more biomass. This is done conventionally through plant breeding. The breeding process is, however, both time-consuming and labor-intensive. Furthermore, appropriate breeding programs must be performed for each relevant plant species. In addition, although great progresses that have been made about nitrogen utilization and the components involved in nitrogen use efficiency, such as nitrogen uptake, nitrogen assimilation and nitrogen partitioning or remobilization, much is still unknown about many of these complex interactions. Therefore, there is a continuing need for generally applicable processes that improve forest or agricultural plant growth to suit particular needs depending on specific environmental conditions. For example, genes that confer tolerance to growth on low nitrogen supply are valuable product prototypes for manipulating nitrogen use efficiency in plants (Good et al., 2004). One strategy to achieve such desirable traits involves genetic manipulation of plant characteristics through the introduction of exogenous nucleic acids conferring increased efficiency of nitrogen use by plants, which in turn should enable the production of higher yields with existing fertilizer inputs and/or enable existing yields of crops to be obtained with lower fertilizer input, or better yields on soils of poorer quality. Such approaches have the advantage of not usually being limited to one plant species, but instead being transferable among plant species. The present invention relates to a method for increasing growth potential, and/or increasing levels of nitrogen use efficiency in plants, characterized by expression of recombinant DNA molecules stably integrated into the plant genome

SUMMARY

The present invention provides methods and materials related to plants having modulated levels of low-nitrogen tolerance. For example, the present invention provides transgenic plants and plant cells having increased levels of low-nitrogen tolerance, nucleic acids (i.e. isolated polynucleotides), polypeptides encoded thereby used to generate transgenic plants and plant cells having increased levels of low-nitrogen tolerance, and methods for making plants and plant cells having increased levels of low-nitrogen tolerance. Such plants and plant cells can be grown under limiting exogenous nitrogen without stunted growth and diminished yields. Plants having increased low-nitrogen tolerance levels may be useful to produce biomass which may be converted to a liquid fuel or other chemicals and/or to produce food and feed on land that is currently marginally productive, resulting in an overall expansion of arable land.

Methods of producing a plant tissue are provided herein. In one aspect, a method comprises growing a plant cell comprising an exogenous nucleic acid. The exogenous nucleic acid comprises a regulatory region operably linked to a nucleotide sequence encoding a polypeptide. The Hidden Markov Model (HMM) bit score of the amino acid sequence of the polypeptide is greater than about 20, using an HMM generated from the amino acid sequences depicted in one of FIGS. 1-57. The tissue has a difference in the level of low-nitrogen tolerance as compared to the corresponding level in tissue of a control plant that does not comprise the exogenous nucleic acid.

In another aspect, a method comprises growing a plant cell comprising an exogenous nucleic acid. The exogenous nucleic acid comprises a regulatory region operably linked to a nucleotide sequence encoding a polypeptide having 80 percent or greater sequence identity to an amino acid sequence set forth in SEQ ID NO:3, SEQ ID NO:49, SEQ ID NO:77, SEQ ID NO:97, SEQ ID NO:100, SEQ ID NO:152, SEQ ID NO:166, SEQ ID NO:186, SEQ ID NO:208, SEQ ID NO:218, SEQ ID NO:234, SEQ ID NO:246, SEQ ID NO:300, SEQ ID NO:332, SEQ ID NO:368, SEQ ID NO:510, SEQ ID NO:533, SEQ ID NO:556, SEQ ID NO:558, SEQ ID NO:593, SEQ ID NO:613, SEQ ID NO:646, SEQ ID NO:687, SEQ ID NO:730, SEQ ID NO:746, SEQ ID NO:769, SEQ ID NO:792, SEQ ID NO:824, SEQ ID NO:828, SEQ ID NO:853, SEQ ID NO:855, SEQ ID NO:891, SEQ ID NO:917, SEQ ID NO:944, SEQ ID NO:976, SEQ ID NO:982, SEQ ID NO:1054, SEQ ID NO:1099, SEQ ID NO:1112, SEQ ID NO:1116, SEQ ID NO:1157, SEQ ID NO:1159, SEQ ID NO:1166, SEQ ID NO:1185, SEQ ID NO:1194, SEQ ID NO:1210, SEQ ID NO:1274, SEQ ID NO:1302, SEQ ID NO:1342, SEQ ID NO:1385, SEQ ID NO:1409, SEQ ID NO:1428, SEQ ID NO:1437, SEQ ID NO:1463, SEQ ID NO:1491, SEQ ID NO:1510, SEQ ID NO:1525, SEQ ID NO:1537, SEQ ID NO:1554, or SEQ ID NO:1577. A plant and/or plant tissues produced from the plant cell has a difference in the level of low-nitrogen tolerance as compared to the corresponding level of low-nitrogen tolerance of a control plant that does not comprise the exogenous nucleic acid.

In another aspect, a method comprises growing a plant cell comprising an exogenous nucleic acid. The exogenous nucleic acid comprises a regulatory region operably linked to a nucleotide sequence having 80 percent or greater sequence identity to a nucleotide sequence, or a fragment thereof, set forth in SEQ ID NO:1, SEQ ID NO:48, SEQ ID NO:76, SEQ ID NO:96, SEQ ID NO:99, SEQ ID NO:151, SEQ ID NO:165, SEQ ID NO:175, SEQ ID NO:185, SEQ ID NO:207, SEQ ID NO:217, SEQ ID NO:233, SEQ ID NO:245, SEQ ID NO:299, SEQ ID NO:331, SEQ ID NO:367, SEQ ID NO:509, SEQ ID NO:532, SEQ ID NO:555, SEQ ID NO:557, SEQ ID NO:592, SEQ ID NO:612, SEQ ID NO:645, SEQ ID NO:686, SEQ ID NO:729, SEQ ID NO:745, SEQ ID NO:768, SEQ ID NO:791, SEQ ID NO:823, SEQ ID NO:827, SEQ ID NO:852, SEQ ID NO:854, SEQ ID NO:890, SEQ ID NO:916, SEQ ID NO:943, SEQ ID NO:975, SEQ ID NO:981, SEQ ID NO:1053, SEQ ID NO:1098, SEQ ID NO:1111, SEQ ID NO:1115, SEQ ID NO:1156, SEQ ID NO:1158, SEQ ID NO:1165, SEQ ID NO:1184, SEQ ID NO:1193, SEQ ID NO:1209, SEQ ID NO:1273, SEQ ID NO:1301, SEQ ID NO:1341, SEQ ID NO:1384, SEQ ID NO:1408, SEQ ID NO:1427, SEQ ID NO:1462, SEQ ID NO:1490, SEQ ID NO:1509, SEQ ID NO:1524, SEQ ID NO:1536, SEQ ID NO:1553, or SEQ ID NO:1576. A plant and/or plant tissues produced from the plant cell has a difference in the level of low-nitrogen tolerance as compared to the corresponding level low-nitrogen tolerance of a control plant that does not comprise the exogenous nucleic acid.

In another aspect, the invention provides a method of producing a plant, the method comprising growing a plant cell comprising an exogenous nucleic acid that is effective for downregulating an endogenous nucleic acid in the plant cell, wherein the endogenous nucleic acid encodes a polypeptide, and wherein the HMM bit score of the amino acid sequence of the polypeptide is greater than about 20, said HMM based on the amino acid sequences depicted in one of FIGS. 1-57

Methods of modulating the level of low-nitrogen tolerance in a plant are provided herein. In one aspect, a method comprises introducing into a plant cell an exogenous nucleic acid, that comprises a regulatory region operably linked to a nucleotide sequence encoding a polypeptide. The HMM bit score of the amino acid sequence of the polypeptide is greater than about 20, using an HMM generated from the amino acid sequences depicted in one of FIGS. 1-57. A plant and/or plant tissue produced from the plant cell has a difference in the level of low-nitrogen tolerance as compared to the corresponding level of low-nitrogen tolerance of a control plant that does not comprise the exogenous nucleic acid.

In certain embodiments, the HMM bit score of the amino acid sequence of the polypeptide is greater than about 40, using an HMM generated from the amino acid sequences depicted in one of FIGS. 1-57, wherein the polypeptide comprises a Pfam domain having 70 percent or greater sequence identity to a Pfam domain of any one of the polypeptides in the sequence listing.

In another aspect, a method comprises modulating the level of low-nitrogen tolerance in a plant by introducing into a plant cell an exogenous nucleic acid that comprises a regulatory region operably linked to a nucleotide sequence encoding a polypeptide having 80 percent or greater sequence identity to an amino acid sequence set forth in SEQ ID NO:3, SEQ ID NO:49, SEQ ID NO:77, SEQ ID NO:97, SEQ ID NO:100, SEQ ID NO:152, SEQ ID NO:166, SEQ ID NO:186, SEQ ID NO:208, SEQ ID NO:218, SEQ ID NO:234, SEQ ID NO:246, SEQ ID NO:300, SEQ ID NO:332, SEQ ID NO:368, SEQ ID NO:510, SEQ ID NO:533, SEQ ID NO:556, SEQ ID NO:558, SEQ ID NO:593, SEQ ID NO:613, SEQ ID NO:646, SEQ ID NO:687, SEQ ID NO:730, SEQ ID NO:746, SEQ ID NO:769, SEQ ID NO:792, SEQ ID NO:824, SEQ ID NO:828, SEQ ID NO:853, SEQ ID NO:855, SEQ ID NO:891, SEQ ID NO:917, SEQ ID NO:944, SEQ ID NO:976, SEQ ID NO:982, SEQ ID NO:1054, SEQ ID NO:1099, SEQ ID NO:1112, SEQ ID NO:1116, SEQ ID NO:1157, SEQ ID NO:1159, SEQ ID NO:1166, SEQ ID NO:1185, SEQ ID NO:1194, SEQ ID NO:1210, SEQ ID NO:1274, SEQ ID NO:1302, SEQ ID NO:1342, SEQ ID NO:1385, SEQ ID NO:1409, SEQ ID NO:1428, SEQ ID NO:1437, SEQ ID NO:1463, SEQ ID NO:1491, SEQ ID NO:1510, SEQ ID NO:1525, SEQ ID NO:1537, SEQ ID NO:1554, or SEQ ID NO:1577, or a fragment thereof. A plant and/or plant tissue produced from the plant cell has a difference in the level of low-nitrogen tolerance as compared to the corresponding level of low-nitrogen tolerance of a control plant that does not comprise the exogenous nucleic acid.

In another aspect, a method comprises modulating the level of low-nitrogen tolerance in a plant by introducing into a plant cell an exogenous nucleic acid, that comprises a regulatory region operably linked to a nucleotide sequence having 80 percent or greater sequence identity to a nucleotide sequence set forth in SEQ ID NO:1, SEQ ID NO:48, SEQ ID NO:76, SEQ ID NO:96, SEQ ID NO:99, SEQ ID NO:151, SEQ ID NO:165, SEQ ID NO:175, SEQ ID NO:185, SEQ ID NO:207, SEQ ID NO:217, SEQ ID NO:233, SEQ ID NO:245, SEQ ID NO:299, SEQ ID NO:331, SEQ ID NO:367, SEQ ID NO:509, SEQ ID NO:532, SEQ ID NO:555, SEQ ID NO:557, SEQ ID NO:592, SEQ ID NO:612, SEQ ID NO:645, SEQ ID NO:686, SEQ ID NO:729, SEQ ID NO:745, SEQ ID NO:768, SEQ ID NO:791, SEQ ID NO:823, SEQ ID NO:827, SEQ ID NO:852, SEQ ID NO:854, SEQ ID NO:890, SEQ ID NO:916, SEQ ID NO:943, SEQ ID NO:975, SEQ ID NO:981, SEQ ID NO:1053, SEQ ID NO:1098, SEQ ID NO:1111, SEQ ID NO:1115, SEQ ID NO:1156, SEQ ID NO:1158, SEQ ID NO:1165, SEQ ID NO:1184, SEQ ID NO:1193, SEQ ID NO:1209, SEQ ID NO:1273, SEQ ID NO:1301, SEQ ID NO:1341, SEQ ID NO:1384, SEQ ID NO:1408, SEQ ID NO:1427, SEQ ID NO:1462, SEQ ID NO:1490, SEQ ID NO:1509, SEQ ID NO:1524, SEQ ID NO:1536, SEQ ID NO:1553, or SEQ ID NO:1576, or a fragment thereof. A plant and/or plant tissue produced from the plant cell has a difference in the level of low-nitrogen tolerance as compared to the corresponding level of low-nitrogen tolerance of a control plant that does not comprise the exogenous nucleic acid.

Plant cells comprising an exogenous nucleic acid are provided herein. In one aspect, the exogenous nucleic acid comprises a regulatory region operably linked to a nucleotide sequence encoding a polypeptide. The HMM bit score of the amino acid sequence of the polypeptide is greater than about 20, using an HMM based on the amino acid sequences depicted in one of FIGS. 1-57. The plant has a difference in the level of low-nitrogen tolerance as compared to the corresponding level of low-nitrogen tolerance of a control plant that does not comprise the exogenous nucleic acid. In another aspect, the exogenous nucleic acid comprises a regulatory region operably linked to a nucleotide sequence encoding a polypeptide having 80 percent or greater sequence identity to an amino acid sequence selected from the group consisting of SEQ ID NO:3, SEQ ID NO:49, SEQ ID NO:77, SEQ ID NO:97, SEQ ID NO:100, SEQ ID NO:152, SEQ ID NO:166, SEQ ID NO:186, SEQ ID NO:208, SEQ ID NO:218, SEQ ID NO:234, SEQ ID NO:246, SEQ ID NO:300, SEQ ID NO:332, SEQ ID NO:368, SEQ ID NO:510, SEQ ID NO:533, SEQ ID NO:556, SEQ ID NO:558, SEQ ID NO:593, SEQ ID NO:613, SEQ ID NO:646, SEQ ID NO:687, SEQ ID NO:730, SEQ ID NO:746, SEQ ID NO:769, SEQ ID NO:792, SEQ ID NO:824, SEQ ID NO:828, SEQ ID NO:853, SEQ ID NO:855, SEQ ID NO:891, SEQ ID NO:917, SEQ ID NO:944, SEQ ID NO:976, SEQ ID NO:982, SEQ ID NO:1054, SEQ ID NO:1099, SEQ ID NO:1112, SEQ ID NO:1116, SEQ ID NO:1157, SEQ ID NO:1159, SEQ ID NO:1166, SEQ ID NO:1185, SEQ ID NO:1194, SEQ ID NO:1210, SEQ ID NO:1274, SEQ ID NO:1302, SEQ ID NO:1342, SEQ ID NO:1385, SEQ ID NO:1409, SEQ ID NO:1428, SEQ ID NO:1437, SEQ ID NO:1463, SEQ ID NO:1491, SEQ ID NO:1510, SEQ ID NO:1525, SEQ ID NO:1537, SEQ ID NO:1554, and SEQ ID NO:1577. A plant and/or plant tissue produced from the plant cell has a difference in the level of low-nitrogen tolerance as compared to the corresponding level of low-nitrogen tolerance of a control plant that does not comprise the exogenous nucleic acid. In another aspect, the exogenous nucleic acid comprises a regulatory region operably linked to a nucleotide sequence having 80 percent or greater sequence identity to a nucleotide sequence selected from the group consisting of SEQ ID NO:1, SEQ ID NO:48, SEQ ID NO:76, SEQ ID NO:96, SEQ ID NO:99, SEQ ID NO:151, SEQ ID NO:165, SEQ ID NO:175, SEQ ID NO:185, SEQ ID NO:207, SEQ ID NO:217, SEQ ID NO:233, SEQ ID NO:245, SEQ ID NO:299, SEQ ID NO:331, SEQ ID NO:367, SEQ ID NO:509, SEQ ID NO:532, SEQ ID NO:555, SEQ ID NO:557, SEQ ID NO:592, SEQ ID NO:612, SEQ ID NO:645, SEQ ID NO:686, SEQ ID NO:729, SEQ ID NO:745, SEQ ID NO:768, SEQ ID NO:791, SEQ ID NO:823, SEQ ID NO:827, SEQ ID NO:852, SEQ ID NO:854, SEQ ID NO:890, SEQ ID NO:916, SEQ ID NO:943, SEQ ID NO:975, SEQ ID NO:981, SEQ ID NO:1053, SEQ ID NO:1098, SEQ ID NO:1111, SEQ ID NO:1115, SEQ ID NO:1156, SEQ ID NO:1158, SEQ ID NO:1165, SEQ ID NO:1184, SEQ ID NO:1193, SEQ ID NO:1209, SEQ ID NO:1273, SEQ ID NO:1301, SEQ ID NO:1341, SEQ ID NO:1384, SEQ ID NO:1408, SEQ ID NO:1427, SEQ ID NO:1462, SEQ ID NO:1490, SEQ ID NO:1509, SEQ ID NO:1524, SEQ ID NO:1536, SEQ ID NO:1553, and SEQ ID NO:1576, or a fragment thereof. A plant and/or plant tissue of a plant produced from the plant cell has a difference in the level of low-nitrogen tolerance as compared to the corresponding level of low-nitrogen tolerance of a control plant that does not comprise the exogenous nucleic acid. A transgenic plant comprising such a plant cell is also provided.

Isolated nucleic acids are also provided. In one aspect, an isolated nucleic acid comprises a nucleotide sequence having 80% or greater sequence identity to the nucleotide sequence set forth in SEQ ID NO:1, SEQ ID NO:48, SEQ ID NO:76, SEQ ID NO:96, SEQ ID NO:99, SEQ ID NO:151, SEQ ID NO:165, SEQ ID NO:175, SEQ ID NO:185, SEQ ID NO:207, SEQ ID NO:217, SEQ ID NO:233, SEQ ID NO:245, SEQ ID NO:299, SEQ ID NO:331, SEQ ID NO:367, SEQ ID NO:509, SEQ ID NO:532, SEQ ID NO:555, SEQ ID NO:557, SEQ ID NO:592, SEQ ID NO:612, SEQ ID NO:645, SEQ ID NO:686, SEQ ID NO:729, SEQ ID NO:745, SEQ ID NO:768, SEQ ID NO:791, SEQ ID NO:823, SEQ ID NO:827, SEQ ID NO:852, SEQ ID NO:854, SEQ ID NO:890, SEQ ID NO:916, SEQ ID NO:943, SEQ ID NO:975, SEQ ID NO:981, SEQ ID NO:1053, SEQ ID NO:1098, SEQ ID NO:1111, SEQ ID NO:1115, SEQ ID NO:1156, SEQ ID NO:1158, SEQ ID NO:1165, SEQ ID NO:1184, SEQ ID NO:1193, SEQ ID NO:1209, SEQ ID NO:1273, SEQ ID NO:1301, SEQ ID NO:1341, SEQ ID NO:1384, SEQ ID NO:1408, SEQ ID NO:1427, SEQ ID NO:1462, SEQ ID NO:1490, SEQ ID NO:1509, SEQ ID NO:1524, SEQ ID NO:1536, SEQ ID NO:1553, or SEQ ID NO:1576. In another aspect, an isolated nucleic acid comprises a nucleotide sequence encoding a polypeptide having 80% or greater sequence identity to the amino acid sequence set forth in SEQ ID NO:3, SEQ ID NO:49, SEQ ID NO:77, SEQ ID NO:97, SEQ ID NO:100, SEQ ID NO:152, SEQ ID NO:166, SEQ ID NO:186, SEQ ID NO:208, SEQ ID NO:218, SEQ ID NO:234, SEQ ID NO:246, SEQ ID NO:300, SEQ ID NO:332, SEQ ID NO:368, SEQ ID NO:510, SEQ ID NO:533, SEQ ID NO:556, SEQ ID NO:558, SEQ ID NO:593, SEQ ID NO:613, SEQ ID NO:646, SEQ ID NO:687, SEQ ID NO:730, SEQ ID NO:746, SEQ ID NO:769, SEQ ID NO:792, SEQ ID NO:824, SEQ ID NO:828, SEQ ID NO:853, SEQ ID NO:855, SEQ ID NO:891, SEQ ID NO:917, SEQ ID NO:944, SEQ ID NO:976, SEQ ID NO:982, SEQ ID NO:1054, SEQ ID NO:1099, SEQ ID NO:1112, SEQ ID NO:1116, SEQ ID NO:1157, SEQ ID NO:1159, SEQ ID NO:1166, SEQ ID NO:1185, SEQ ID NO:1194, SEQ ID NO:1210, SEQ ID NO:1274, SEQ ID NO:1302, SEQ ID NO:1342, SEQ ID NO:1385, SEQ ID NO:1409, SEQ ID NO:1428, SEQ ID NO:1437, SEQ ID NO:1463, SEQ ID NO:1491, SEQ ID NO:1510, SEQ ID NO:1525, SEQ ID NO:1537, SEQ ID NO:1554, or SEQ ID NO:1577.

In another aspect, methods of identifying a genetic polymorphism associated with variation in the level of low-nitrogen tolerance are provided. The methods include providing a population of plants, and determining whether one or more genetic polymorphisms in the population are genetically linked to the locus for a polypeptide selected from the group consisting of the polypeptides depicted in FIGS. 1-57, SEQ ID NO:556, SEQ ID NO:853, SEQ ID NO:1157, and functional homologs thereof, such as those in the Sequence Listing. The correlation between variation in the level of low-nitrogen tolerance in a tissue in plants of the population and the presence of the one or more genetic polymorphisms in plants of the population is measured, thereby permitting identification of whether or not the one or more genetic polymorphisms are associated with such variation.

In another aspect, the invention provides a method of making a plant line, said method comprising:
  a) determining whether one or more genetic polymorphisms in a population of plants is associated with the locus for a polypeptide selected from the group consisting of the polypeptides depicted in FIGS. 1-57, SEQ ID NO: 556, SEQ ID NO: 853, and SEQ ID NO: 1157 and functional homologs thereof;
  b) identifying one or more plants in said population in which the presence of at least one allele at said one or more genetic polymorphisms is associated with variation in a trait;
  c) crossing each said one or more identified plants with itself or a different plant to produce seed;
  d) crossing at least one progeny plant grown from said seed with itself or a different plant; and
  e) repeating steps c) and d) for an additional 0-5 generations to make said plant line, wherein said at least one allele is present in said plant line.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DESCRIPTION OF THE DRAWINGS

FIG. 1 is an alignment of Ceres SEEDLINE No. ME00919 (SEQ ID NO:3) with homologous and/or orthologous amino acid sequences GI No.5921925 (SEQ ID NO:4), CeresClone:1929222 (SEQ ID NO:6), CeresAnnot:1471370 (SEQ ID NO:10), GI No.84380741 (SEQ ID NO:21), GI No.5921926 (SEQ ID NO:22), GI No.84514161 (SEQ ID NO:25), CeresClone:779234 (SEQ ID NO:27), CeresClone:1600726 (SEQ ID NO:29), GI No.78183420 (SEQ ID NO:36), CeresClone:1877346 (SEQ ID NO:38), GI No.125562440 (SEQ ID NO:39), GI No.115477665 (SEQ ID NO:40), GI No.1173624 (SEQ ID NO:46), and GI No.84468276 (SEQ ID NO:47). In all the alignment figures shown herein, a dash in an aligned sequence represents a gap, i.e., a lack of an amino acid at that position. Identical amino acids or conserved amino acid substitutions among aligned sequences are identified by boxes. FIG. 1 and the other alignment figures provided herein were generated using the program MUSCLE version 3.52.

FIG. 2 is an alignment of ME01312 (SEQ ID NO:49) with homologous and/or orthologous amino acid sequences CeresClone:1869410 (SEQ ID NO:51), CeresAnnot:1540549 (SEQ ID NO:53), CeresClone:978708 (SEQ ID NO:58), CeresClone:1623097 (SEQ ID NO:60), GI No.92873064 (SEQ ID NO:63), GI No.37051131 (SEQ ID NO:64), GI No.3341468 (SEQ ID NO:65), CeresClone:937560 (SEQ ID NO:67), CeresClone:456844 (SEQ ID NO:69), GI No.125564100 (SEQ ID NO:70), GI No.52077334 (SEQ ID NO:71), GI No.113205234 (SEQ ID NO:73), and CeresAnnot:6100272 (SEQ ID NO:75).

FIG. 3 is an alignment of ME01463 (SEQ ID NO:77) with homologous and/or orthologous amino acid sequences GI No.2811029 (SEQ ID NO:78), CeresClone:1853284 (SEQ ID NO:80), CeresAnnot:1476446 (SEQ ID NO:82), CeresClone:527024 (SEQ ID NO:87), GI No.27527063 (SEQ ID NO:88), CeresClone:913632 (SEQ ID NO:90), CeresClone:1386710 (SEQ ID NO:92), GI No.115461885 (SEQ ID NO:93), and CeresAnnot:6054519 (SEQ ID NO:95)

FIG. 4 is an alignment of ME01910 (SEQ ID NO:100) with homologous and/or orthologous amino acid sequences GI No.585238 (SEQ ID NO:101), GI No.90704789 (SEQ ID NO:102), CeresClone:1895729 (SEQ ID NO:104), CeresAnnot:1442808 (SEQ ID NO:108), CeresClone:1104700 (SEQ ID NO:113), GI No.32966575 (SEQ ID NO:116), GI No.4996567 (SEQ ID NO:117), GI No.62286644 (SEQ ID NO:118), GI No.2623960 (SEQ ID NO:119), GI No.585241 (SEQ ID NO:120), GI No.790929 (SEQ ID NO:122), CeresClone:579112 (SEQ ID NO:125), CeresClone:244199 (SEQ ID NO:137), CeresClone:1725848 (SEQ ID NO:144), GI No.6474950 (SEQ ID NO:145), GI No.125546057 (SEQ ID NO:146), GI No.115455945 (SEQ ID NO:147), GI No.2641211 (SEQ ID NO:149), and GI No.30024108 (SEQ ID NO:150).

FIG. 5 is an alignment of ME02538 (SEQ ID NO:152) with homologous and/or orthologous amino acid sequences CeresClone:1843642 (SEQ ID NO:154), CeresAnnot:1459112 (SEQ ID NO:158), CeresClone:953633 (SEQ ID NO:162), and CeresClone:587957 (SEQ ID NO:164).

FIG. 6 is an alignment of ME02603 (SEQ ID NO:166) with homologous and/or orthologous amino acid sequences CeresClone:1857256 (SEQ ID NO:168), CeresAnnot:1442042 (SEQ ID NO:170), GI No.89257469 (SEQ ID NO:174), CeresClone:389818 (SEQ ID NO:177), CeresClone:2019147 (SEQ ID NO:181), GI No.125537720 (SEQ ID NO:182), GI No.115443697 (SEQ ID NO:183), and GI No.20340241 (SEQ ID NO:184).

FIG. 7 is an alignment of ME02613 (SEQ ID NO:186) with homologous and/or orthologous amino acid sequences CeresAnnot:1490274 (SEQ ID NO:188), CeresClone:873093 (SEQ ID NO:193), GI No.6635384 (SEQ ID NO:194), CeresClone:663726 (SEQ ID NO:196), GI No.92881411 (SEQ ID NO:197), CeresClone:686525 (SEQ ID NO:199), CeresClone:1524364 (SEQ ID NO:201), CeresClone:1742159 (SEQ ID NO:203), and GI No.125543535 (SEQ ID NO:204).

FIG. 8 is an alignment of ME02801 (SEQ ID NO:208) with homologous and/or orthologous amino acid sequences CeresClone:981621 (SEQ ID NO:214) and CeresClone:564714 (SEQ ID NO:216).

FIG. 9 is an alignment of ME03123 (SEQ ID NO:218) with homologous and/or orthologous amino acid sequences CeresClone:1899168 (SEQ ID NO:220), CeresAnnot:1494669 (SEQ ID NO:222), CeresClone:1017441 (SEQ ID NO:225), CeresClone:1065937 (SEQ ID NO:227), CeresClone:1822919 (SEQ ID NO:229), GI No.125553329 (SEQ ID NO:230), GI No.115439053 (SEQ ID NO:231), and CeresAnnot:6040744 (SEQ ID NO:1052).

FIG. 10 is an alignment of ME04204 (SEQ ID NO:234) with homologous and/or orthologous amino acid sequences CeresAnnot:1519952 (SEQ ID NO:236), CeresClone:

234768 (SEQ ID NO:241), GI No.108707052 (SEQ ID NO:242), and GI No.55978030 (SEQ ID NO:244).

FIG. 11 is an alignment of ME04477 (SEQ ID NO:246) with homologous and/or orthologous amino acid sequences CeresClone:1620215 (SEQ ID NO:248), GI No.38016527 (SEQ ID NO:249), CeresClone:1798756 (SEQ ID NO:251), CeresAnnot:1460527 (SEQ ID NO:255), GI No.119720772 (SEQ ID NO:260), CeresClone:708446 (SEQ ID NO:262), GI No.92896423 (SEQ ID NO:265), GI No.113196593 (SEQ ID NO:267), GI No.75133829 (SEQ ID NO:268), CeresClone:1030374 (SEQ ID NO:270), CeresClone:1387149 (SEQ ID NO:274), GI No.5031281 (SEQ ID NO:277), CeresClone:1775820 (SEQ ID NO:279), GI No.35187687 (SEQ ID NO:286), GI No.115468934 (SEQ ID NO:290), GI No.118424243 (SEQ ID NO:296), and CeresAnnot:6063957 (SEQ ID NO:298).

FIG. 12 is an alignment of ME04507 (SEQ ID NO:300) with homologous and/or orthologous amino acid sequences CeresAnnot:1513514 (SEQ ID NO:302), CeresClone:923483 (SEQ ID NO:310), CeresClone:304357 (SEQ ID NO:312), CeresClone:1902716 (SEQ ID NO:316), GI No.116309713 (SEQ ID NO:319), GI No.38345408 (SEQ ID NO:321), and CeresAnnot:6017635 (SEQ ID NO:325).

Figure 13:
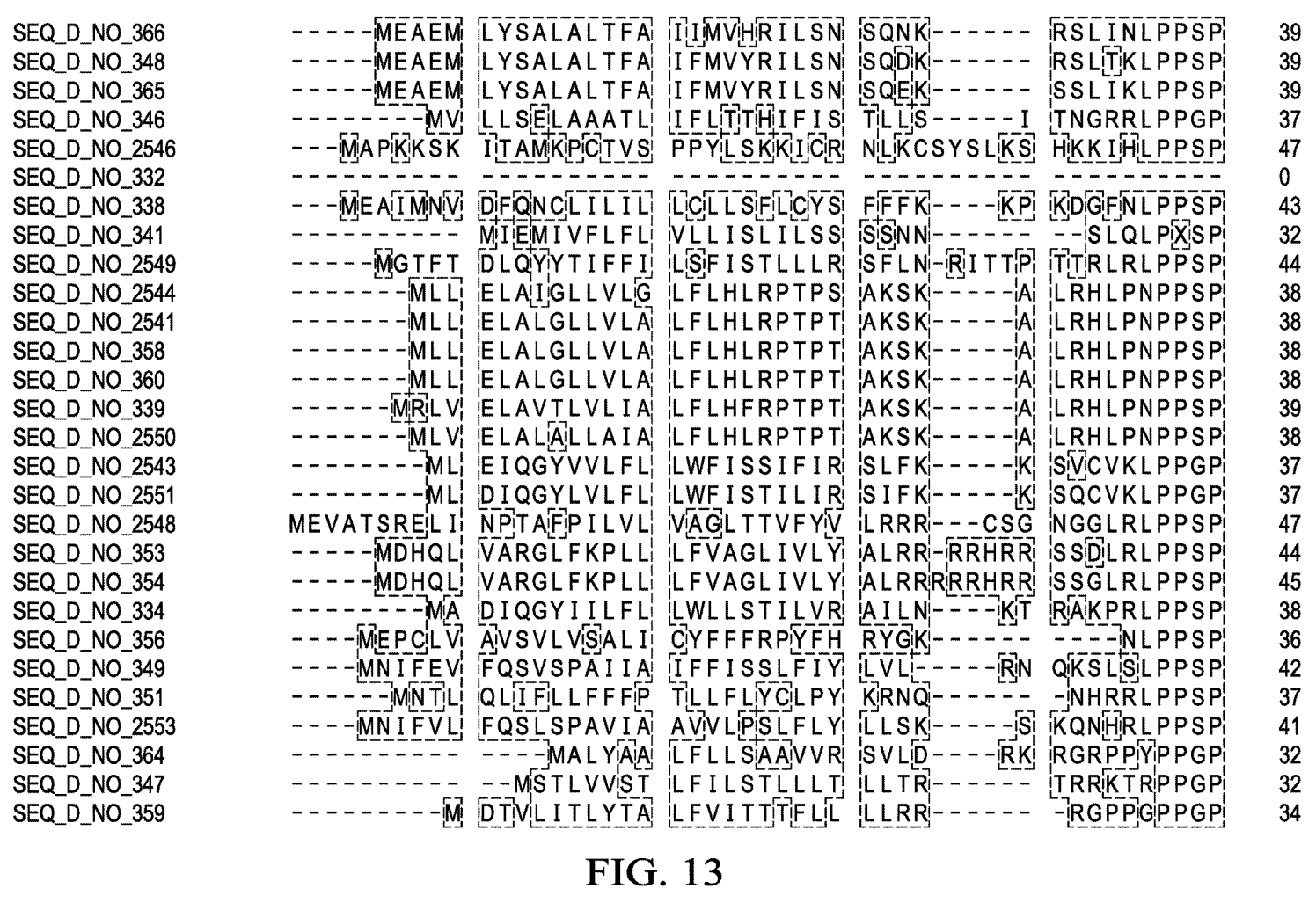
Figure 13:
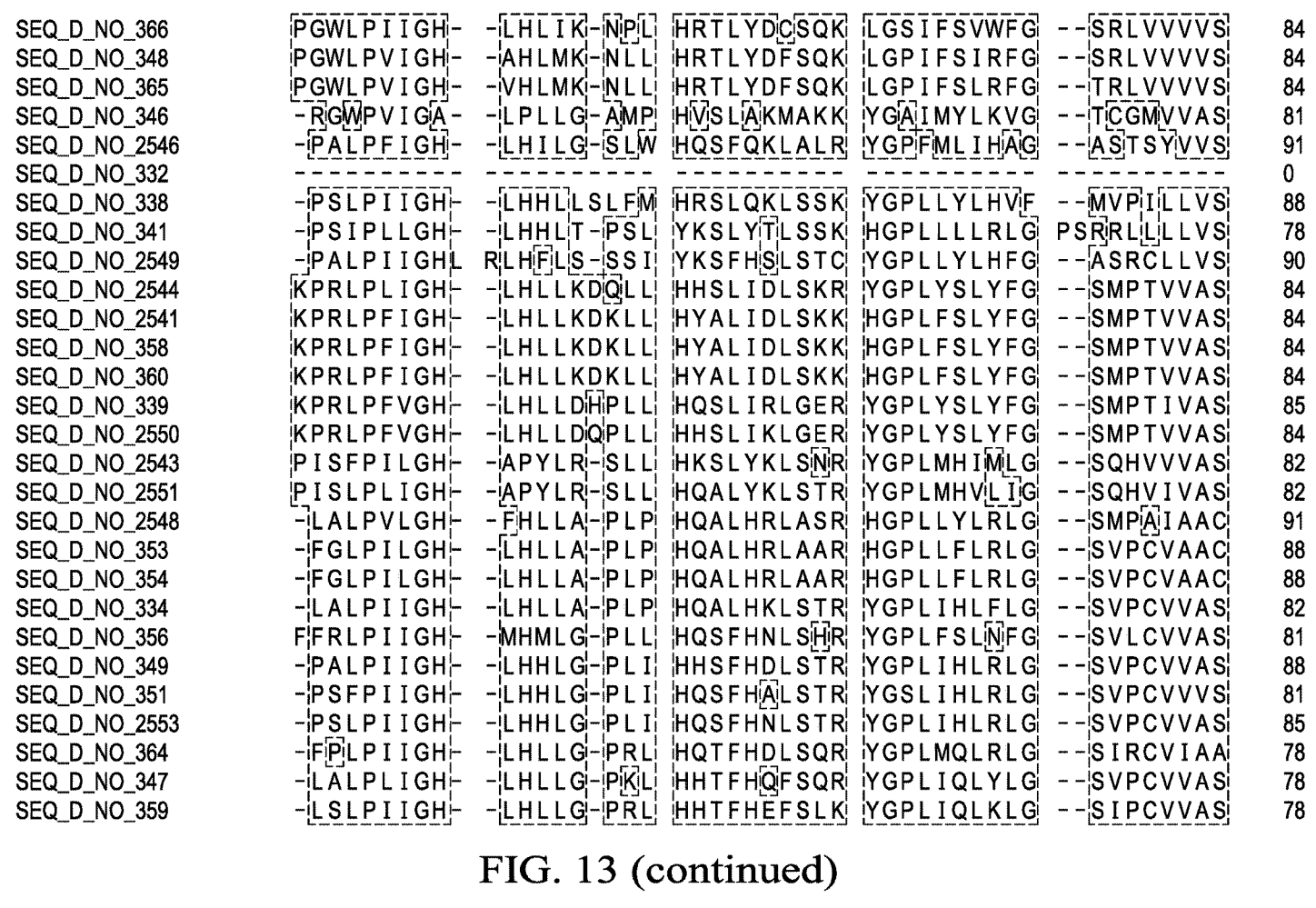
Figure 13:
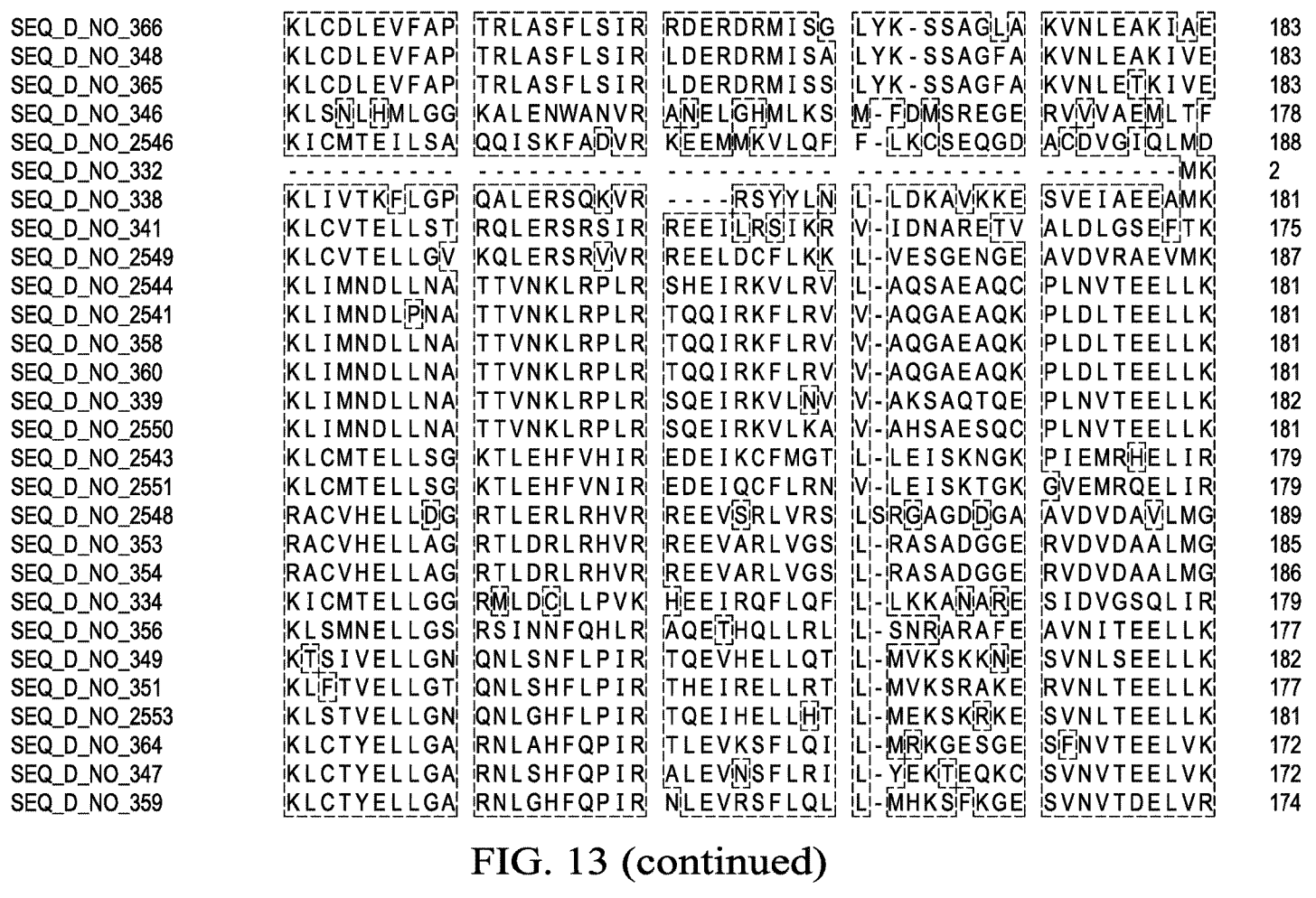
Figure 13:
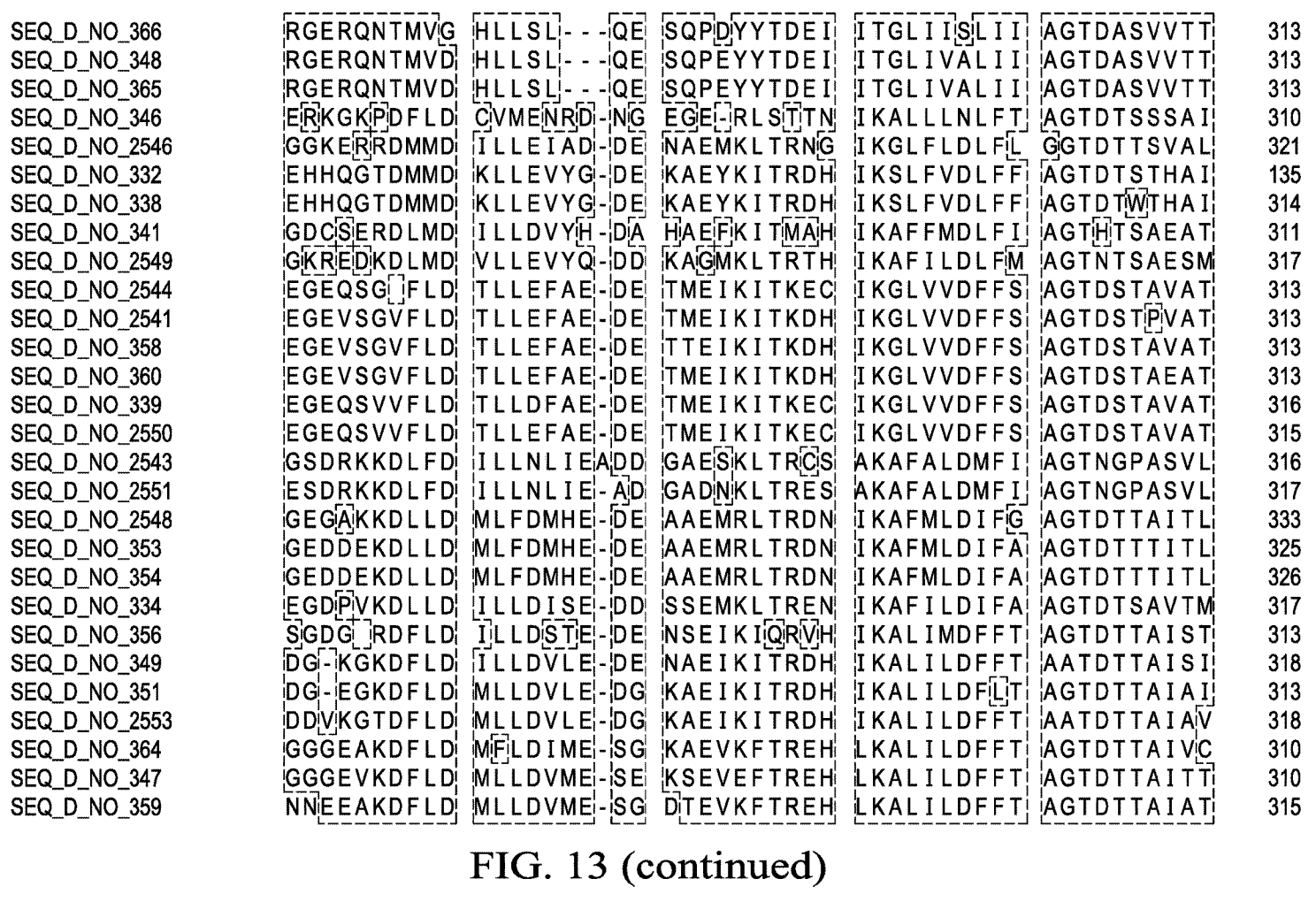
Figure 13:
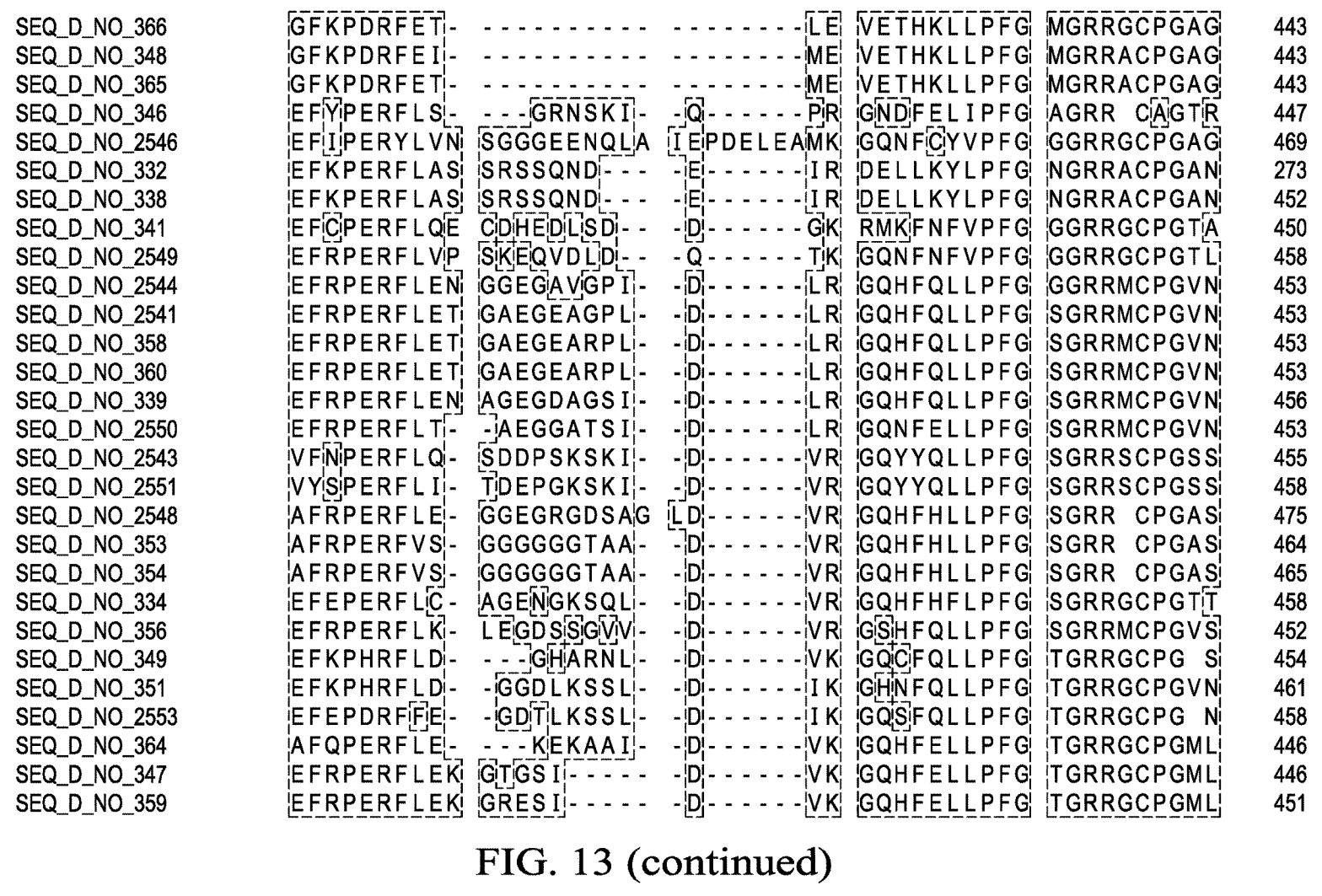

FIG. 13 is an alignment of ME04587 (SEQ ID NO:332) with homologous and/or orthologous amino acid sequences Ceres ANNOT ID no.1474882 (SEQ ID NO:334), Ceres ANNOT ID no.553243 (SEQ ID NO:338), Public GI ID no.5514645 (SEQ ID NO:339), Ceres CLONE ID no.464376 (SEQ ID NO:341), Public GI ID no.1345643 (SEQ ID NO:346), Public GI ID no.5832707 (SEQ ID NO:347), Public GI ID no.81157968 (SEQ ID NO:348), Public GI ID no.6118407 (SEQ ID NO:349), Public GI ID no.5081817 (SEQ ID NO:351), Public GI ID no.125556057 (SEQ ID NO:353), Public GI ID no.115468946 (SEQ ID NO:354), Public GI ID no.5915860 (SEQ ID NO:356), Public GI ID no.6979544 (SEQ ID NO:358), Public GI ID no.5832709 (SEQ ID NO:359), Public GI ID no.6979542 (SEQ ID NO:360), Public GI ID no.14278923 (SEQ ID NO:364), Public GI ID no.81157970 (SEQ ID NO:365), Public GI ID no.81157972 (SEQ ID NO:366), Public GI ID no.169793907 (SEQ ID NO:2541), Public GI ID no.84514153 (SEQ ID NO:2543), Public GI ID no.184202209 (SEQ ID NO:2544), Ceres ANNOT ID no.8459850 (SEQ ID NO:2546), Ceres ANNOT ID no.8743452 (SEQ ID NO:2548), Public GI ID no.157327290 (SEQ ID NO:2549), Public GI ID no.148839039 (SEQ ID NO:2550), Public GI ID no.197209782 (SEQ ID NO:2551), Public GI ID no.171906244 (SEQ ID NO:2553).

FIG. 14 is an alignment of ME04753 (SEQ ID NO:368) with homologous and/or orthologous amino acid sequences GI No.21388658 (SEQ ID NO:369), GI No.4704605 (SEQ ID NO:371), GI No.90704785 (SEQ ID NO:372), GI No.115529229 (SEQ ID NO:373), GI No.20152613 (SEQ ID NO:374), CeresClone:1916226 (SEQ ID NO:376), CeresAnnot:1460836 (SEQ ID NO:392), GI No.83032218 (SEQ ID NO:420), GI No.1346180 (SEQ ID NO:422), CeresClone:621487 (SEQ ID NO:425), GI No.6273331 (SEQ ID NO:433), GI No.92874469 (SEQ ID NO:434), GI No.1778374 (SEQ ID NO:436), GI No.18076086 (SEQ ID NO:437), GI No.2674201 (SEQ ID NO:438), GI No.2267567 (SEQ ID NO:440), GI No.544426 (SEQ ID NO:441), GI No.6911144 (SEQ ID NO:444), GI No.469071 (SEQ ID NO:447), GI No.1934994 (SEQ ID NO:450), GI No.82623423 (SEQ ID NO:451), GI No.90265701 (SEQ ID NO:454), GI No.544423 (SEQ ID NO:455), CeresClone:1320097 (SEQ ID NO:458), CeresClone:1469740 (SEQ ID NO:465), CeresClone:1740834 (SEQ ID NO:473), GI No.2226370 (SEQ ID NO:474), GI No.27527723 (SEQ ID NO:475), CeresClone:1762613 (SEQ ID NO:477), GI No.125545195 (SEQ ID NO:488), GI No.108710322 (SEQ ID NO:494), GI No.34851124 (SEQ ID NO:504), GI No.111162637 (SEQ ID NO:505), GI No.7024451 (SEQ ID NO:506), and GI No.1229138 (SEQ ID NO:507).

FIG. 15 is an alignment of ME04772 (SEQ ID NO:510) with homologous and/or orthologous amino acid sequences GI No.38016521 (SEQ ID NO:511), CeresClone:1895044 (SEQ ID NO:513), CeresAnnot:1512198 (SEQ ID NO:517), CeresClone:682503 (SEQ ID NO:521), CeresClone:685324 (SEQ ID NO:523), CeresClone:1384414 (SEQ ID NO:525), CeresClone:1739919 (SEQ ID NO:527), CeresClone:2002832 (SEQ ID NO:529), GI No.125531563 (SEQ ID NO:530), and GI No.115478344 (SEQ ID NO:531).

FIG. 16 is an alignment of ME04909 (SEQ ID NO:533) with homologous and/or orthologous amino acid sequences CeresClone:1839156 (SEQ ID NO:535), GI No.56605378 (SEQ ID NO:536), CeresAnnot:1467946 (SEQ ID NO:538), GI No.110931704 (SEQ ID NO:539), GI No.92869601 (SEQ ID NO:542), GI No.12005328 (SEQ ID NO:543), GI No.119331596 (SEQ ID NO:546), GI No.7705206 (SEQ ID NO:547), GI No.18874263 (SEQ ID NO:548), CeresClone:753605 (SEQ ID NO:550), CeresClone:291733 (SEQ ID NO:552), and GI No.21902114 (SEQ ID NO:553).

Figure 17:
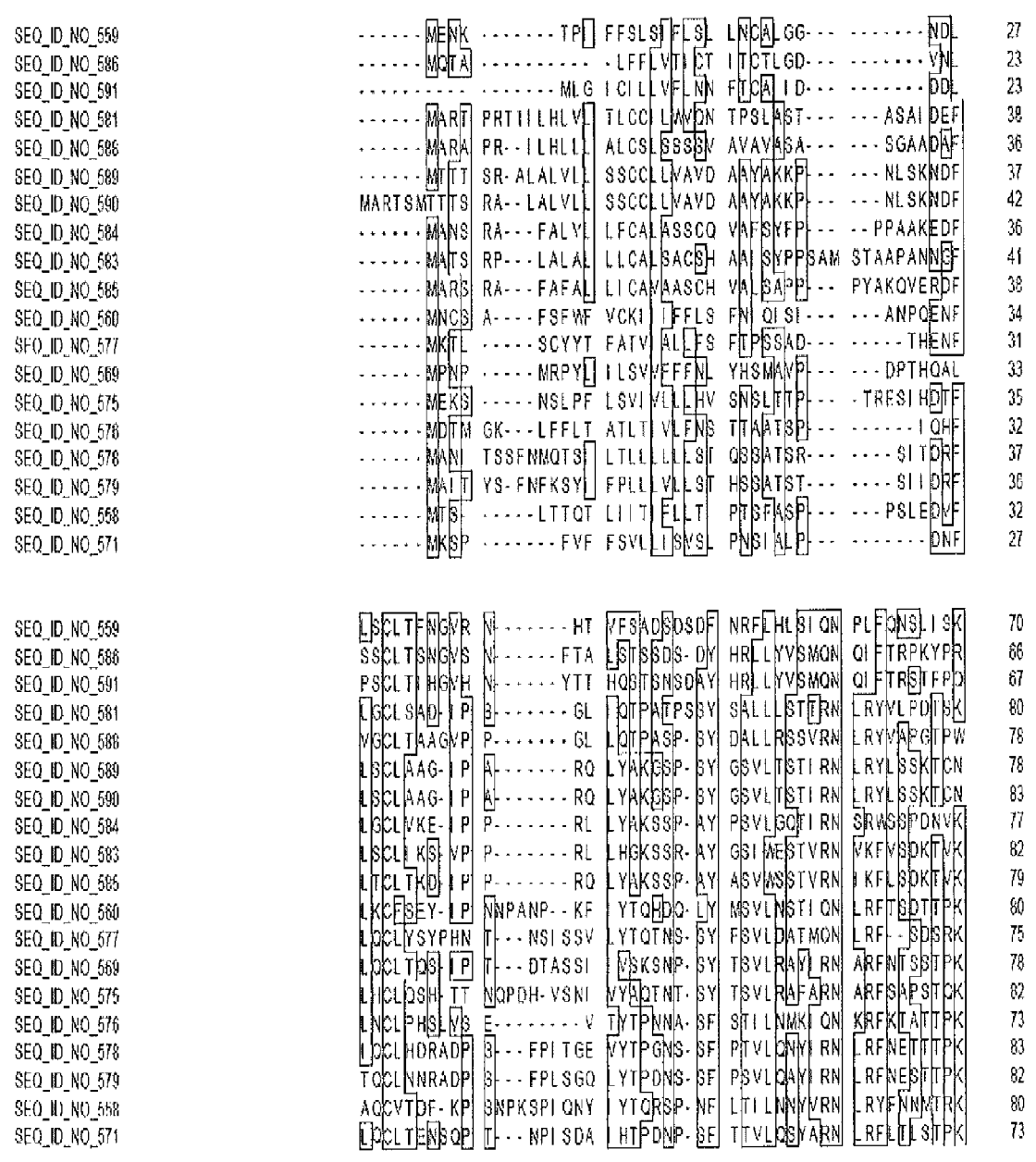

FIG. 17 is an alignment of ME05194 (SEQ ID NO:558) with homologous and/or orthologous amino acid sequences GI No.400972 (SEQ ID NO:559), GI No.81158002 (SEQ ID NO:560), CeresClone:1834135 (SEQ ID NO:569), CeresAnnot:1467218 (SEQ ID NO:571), CeresClone:1104143 (SEQ ID NO:575), GI No.87240745 (SEQ ID NO:576), GI No.13161397 (SEQ ID NO:577), GI No.18652400 (SEQ ID NO:578), GI No.18652398 (SEQ ID NO:579), CeresClone:778892 (SEQ ID NO:581), CeresClone:222523 (SEQ ID NO:583), GI No.82492267 (SEQ ID NO:584), GI No.41393750 (SEQ ID NO:585), GI No.4335857 (SEQ ID NO:586), CeresClone:1776394 (SEQ ID NO:588), GI No.125555681 (SEQ ID NO:589), GI No.115468460 (SEQ ID NO:590), and GI No.51980210 (SEQ ID NO:591).

FIG. 18 is an alignment of ME05267 (SEQ ID NO:593) with homologous and/or orthologous amino acid sequences CeresAnnot:1511954 (SEQ ID NO:595), CeresClone:560687 (SEQ ID NO:599), CeresClone:579724 (SEQ ID NO:603), CeresClone:286197 (SEQ ID NO:605), and GI No.115489090 (SEQ ID NO:610).

FIG. 19 is an alignment of ME05300 (SEQ ID NO:613) with homologous and/or orthologous amino acid sequences CeresAnnot:6431448 (SEQ ID NO:615), CeresClone:969084 (SEQ ID NO:620), CeresClone:471052 (SEQ ID NO:622), CeresClone:733048 (SEQ ID NO:624), CeresClone:1062332 (SEQ ID NO:626), CeresClone:1743166 (SEQ ID NO:634), CeresClone:1778589 (SEQ ID NO:638), GI No.125548354 (SEQ ID NO:643), and GI No.115458464 (SEQ ID NO:644).

FIG. 20 is an alignment of ME05341 (SEQ ID NO:646) with homologous and/or orthologous amino acid sequences CeresClone:1808421 (SEQ ID NO:648), CeresAnnot:1452653 (SEQ ID NO:656), CeresClone:1660955 (SEQ ID NO:660), CeresClone:1287179 (SEQ ID NO:668), CeresClone:1770929 (SEQ ID NO:676), GI No.125542421 (SEQ ID NO:679), GI No.115450741 (SEQ ID NO:681), and CeresAnnot:6063505 (SEQ ID NO:685).

Figure 21:
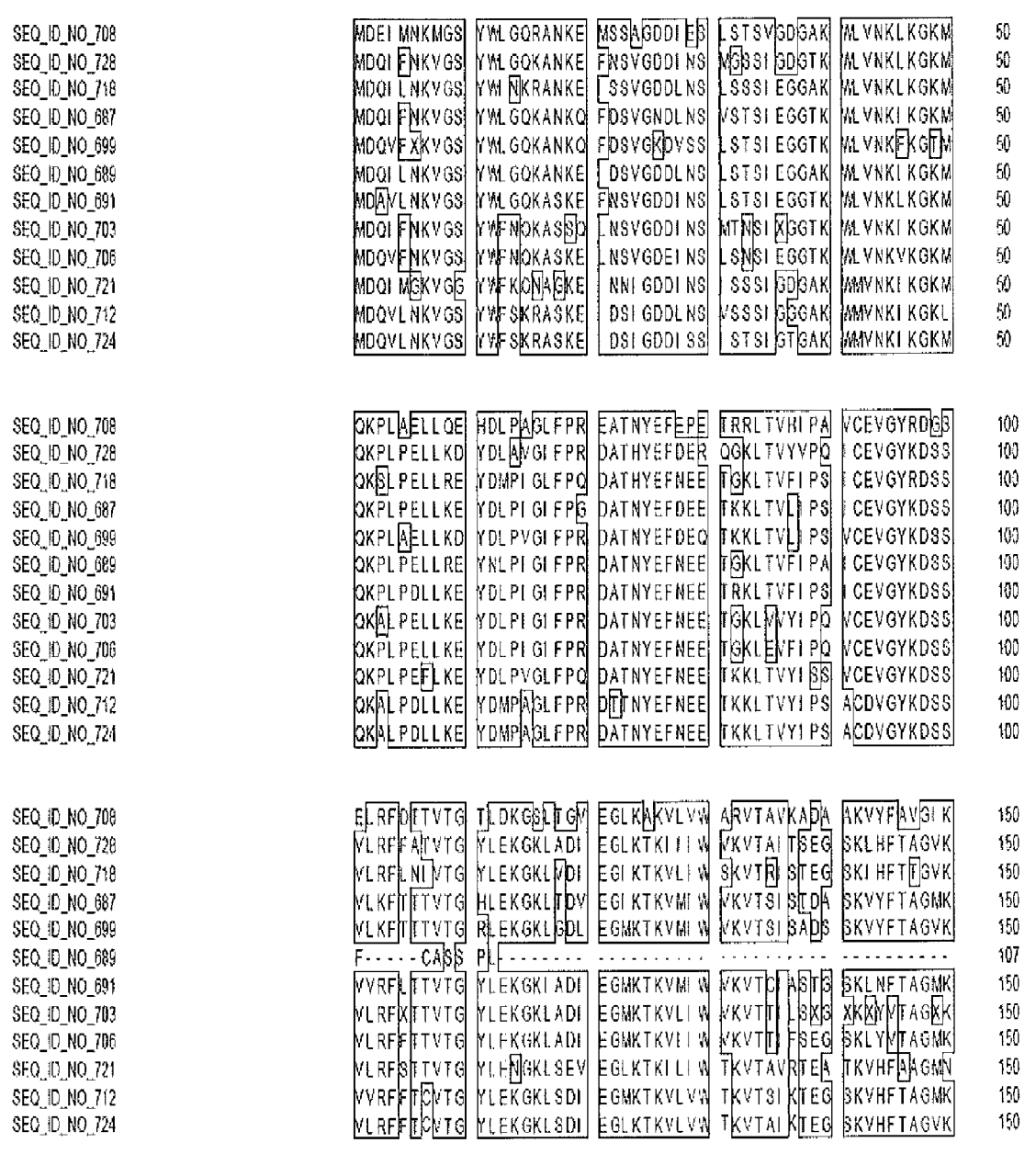

FIG. 21 is an alignment of ME05392 (SEQ ID NO:687) with homologous and/or orthologous amino acid sequences CeresClone:1841531 (SEQ ID NO:689), CeresAnnot:1507382 (SEQ ID NO:691), CeresClone:978410 (SEQ ID NO:699), CeresClone:527314 (SEQ ID NO:703), GI No.92893019 (SEQ ID NO:706), CeresClone:638935 (SEQ ID NO:708), CeresClone:1437744 (SEQ ID NO:712), CeresClone:1728293 (SEQ ID NO:718), GI No.125526460 (SEQ ID NO:721), GI No.115463325 (SEQ ID NO:724), and GI No.40642817 (SEQ ID NO:728).

FIG. 22 is an alignment of ME05429 (SEQ ID NO:730) with homologous and/or orthologous amino acid sequences CeresAnnot:1539629 (SEQ ID NO:732), CeresClone: 682471 (SEQ ID NO:735), CeresClone:729869 (SEQ ID NO:737), GI No.115459766 (SEQ ID NO:738), and CeresAnnot:6026765 (SEQ ID NO:742).

FIG. 23 is an alignment of ME05493 (SEQ ID NO:746) with homologous and/or orthologous amino acid sequences CeresAnnot:1455092 (SEQ ID NO:748), GI No.15229284 (SEQ ID NO:751), CeresClone:961796 (SEQ ID NO:753), CeresClone:706956 (SEQ ID NO:755), GI No.87162911 (SEQ ID NO:758), CeresClone:1061446 (SEQ ID NO:760), GI No.125540686 (SEQ ID NO:761), GI No.115447931 (SEQ ID NO:762), GI No.20152976 (SEQ ID NO:763), and CeresAnnot:6007280 (SEQ ID NO:765).

FIG. 24 is an alignment of ME05885 (SEQ ID NO:769) with homologous and/or orthologous amino acid sequences CeresClone:1808741 (SEQ ID NO:771), CeresAnnot: 1437729 (SEQ ID NO:773), CeresClone:952789 (SEQ ID NO:777), CeresClone:724313 (SEQ ID NO:779), CeresClone:791239 (SEQ ID NO:783), CeresClone:208975 (SEQ ID NO:785), CeresClone:1727075 (SEQ ID NO:789), and GI No.115475611 (SEQ ID NO:790).

FIG. 25 is an alignment of ME07344 (SEQ ID NO:792) with homologous and/or orthologous amino acid sequences CeresClone:1843695 (SEQ ID NO:794), GI No.56605376 (SEQ ID NO:799), CeresAnnot:1508502 (SEQ ID NO:801), CeresClone:1239229 (SEQ ID NO:805), GI No.92893962 (SEQ ID NO:808), CeresClone:327364 (SEQ ID NO:810), CeresClone:1820378 (SEQ ID NO:816), GI No.125524748 (SEQ ID NO:819), and GI No.115435036 (SEQ ID NO:821).

FIG. 26 is an alignment of ME07859 (SEQ ID NO:824) with homologous amino acid sequence Fragment_of_Ceres ANNOT ID no.6007357 (SEQ ID NO:826), Fragment_of_Ceres CLONE ID no.771707 (SEQ ID NO:1708), and Fragment_of_Ceres CLONE ID no.1790436 (SEQ ID NO:1713).

FIG. 27 is an alignment of ME08464 (SEQ ID NO:828) with homologous and/or orthologous amino acid sequences CeresAnnot:1499777 (SEQ ID NO:832), GI No.22328730 (SEQ ID NO:837), GI No.92886131 (SEQ ID NO:839), GI No.559921 (SEQ ID NO:840), CeresClone:910787 (SEQ ID NO:842), CeresClone:1797432 (SEQ ID NO:844), GI No.116310135 (SEQ ID NO:845), GI No.38345464 (SEQ ID NO:847), and GI No.90657544 (SEQ ID NO:850).

FIG. 28 is an alignment of ME11735 (SEQ ID NO:855) with homologous and/or orthologous amino acid sequences GI No.35187445 (SEQ ID NO:856), CeresClone:1798230 (SEQ ID NO:858), CeresAnnot:1500963 (SEQ ID NO:862), CeresClone:567542 (SEQ ID NO:868), CeresClone:702251 (SEQ ID NO:870), CeresClone:1606777 (SEQ ID NO:876), CeresClone:1789146 (SEQ ID NO:878), GI No.116309500 (SEQ ID NO:885), and GI No.115446281 (SEQ ID NO:886).

FIG. 29 is an alignment of ME12910 (SEQ ID NO:891) with homologous and/or orthologous amino acid sequences CeresAnnot:1466353 (SEQ ID NO:893), CeresClone: 519143 (SEQ ID NO:898), GI No.2501497 (SEQ ID NO:901), GI No.119394507 (SEQ ID NO:904), GI No.62857206 (SEQ ID NO:905), CeresClone:766529 (SEQ ID NO:907), GI No.62857204 (SEQ ID NO:908), GI No.125534279 (SEQ ID NO:911), GI No.115485437 (SEQ ID NO:912), GI No.23955910 (SEQ ID NO:913), and GI No.22759895 (SEQ ID NO:915).

FIG. 30 is an alignment of ME12927 (SEQ ID NO:917) with homologous and/or orthologous amino acid sequences CeresAnnot:1503548 (SEQ ID NO:919), CeresClone:37778 (SEQ ID NO:921), CeresClone:681297 (SEQ ID NO:923), CeresClone:575835 (SEQ ID NO:925), CeresClone: 1714750 (SEQ ID NO:935), CeresClone:1721907 (SEQ ID NO:937), and GI No.115451923 (SEQ ID NO:940).

FIG. 31 is an alignment of ME12929 (SEQ ID NO:944) with homologous and/or orthologous amino acid sequences CeresAnnot:1447562 (SEQ ID NO:946), GI No.98962139 (SEQ ID NO:947), CeresClone:641607 (SEQ ID NO:950), CeresClone:1715150 (SEQ ID NO:962), CeresClone: 1873767 (SEQ ID NO:964), GI No.115468306 (SEQ ID NO:967), and CeresAnnot:6059980 (SEQ ID NO:972).

FIG. 32 is an alignment of ME12954 (SEQ ID NO:976) with homologous and/or orthologous amino acid sequences CeresClone:957229 (SEQ ID NO:978) and CeresAnnot: 1496202 (SEQ ID NO:980).

FIG. 33 is an alignment of ME12970 (SEQ ID NO:982) with homologous and/or orthologous amino acid sequences CeresClone:1935438 (SEQ ID NO:984), GI No.117573664 (SEQ ID NO:985), GI No.68349002 (SEQ ID NO:991), GI No.68348998 (SEQ ID NO:992), CeresAnnot:1497170 (SEQ ID NO:995), GI No.15221718 (SEQ ID NO:996), GI No.3860331 (SEQ ID NO:1001), CeresClone:1075911 (SEQ ID NO:1003), GI No.2920839 (SEQ ID NO:1008), CeresClone:698452 (SEQ ID NO:1011), CeresClone: 2019456 (SEQ ID NO:1023), GI No.90399071 (SEQ ID NO:1026), GI No.115459588 (SEQ ID NO:1028), and GI No.68349016 (SEQ ID NO:1032).

FIG. 34 is an alignment of ME13021 (SEQ ID NO:1054) with homologous and/or orthologous amino acid sequences GI No.2493647 (SEQ ID NO:1055), CeresClone:1924252 (SEQ ID NO:1057), GI No.461736 (SEQ ID NO:1058), CeresAnnot:1542060 (SEQ ID NO:1061), GI No.15226314 (SEQ ID NO:1068), GI No.464727 (SEQ ID NO:1072), CeresClone:480644 (SEQ ID NO:1074), GI No.124301264 (SEQ ID NO:1075), GI No.1710807 (SEQ ID NO:1076), GI No.110349923 (SEQ ID NO:1077), GI No.1762130 (SEQ ID NO:1078), CeresClone:706098 (SEQ ID NO:1080), GI No.3790441 (SEQ ID NO:1083), CeresClone:1795282 (SEQ ID NO:1085), GI No.125546535 (SEQ ID NO:1086), GI No.115488160 (SEQ ID NO:1088), GI No.84468456 (SEQ ID NO:1092), GI No.116060917 (SEQ ID NO:1095), and CeresAnnot:6039555 (SEQ ID NO:1097).

FIG. 35 is an alignment of ME13064 (SEQ ID NO:1099) with homologous and/or orthologous amino acid sequences CeresAnnot:1528508 (SEQ ID NO:1101), CeresClone:9248 (SEQ ID NO:1103), GI No.87240560 (SEQ ID NO:1105), GI No.19453 (SEQ ID NO:1106), CeresClone:1795329 (SEQ ID NO:1108), and GI No.108862979 (SEQ ID NO:1109).

FIG. 36 is an alignment of ME13071 (SEQ ID NO:1112) with homologous and/or orthologous amino acid sequences GI No.125541485 (SEQ ID NO:1113), and GI No.115449245 (SEQ ID NO:1114).

FIG. 37 is an alignment of ME13087 (SEQ ID NO:1116) with homologous and/or orthologous amino acid sequences CeresClone:100062822 (SEQ ID NO:1118), CeresAnnot: 1440025 (SEQ ID NO:1120), GI No.15238538 (SEQ ID NO:1123), GI No.69111473 (SEQ ID NO:1129), GI No.92873711 (SEQ ID NO:1132), GI No.55734106 (SEQ ID NO:1133), GI No.2346974 (SEQ ID NO:1134), Ceres- Clone:569852 (SEQ ID NO:1136), CeresClone:1715326 (SEQ ID NO:1138), CeresClone:1608104 (SEQ ID NO:1140), GI No.115456237 (SEQ ID NO:1141), GI No.68655289 (SEQ ID NO:1143), GI No.81022807 (SEQ ID NO:1144), GI No.75706704 (SEQ ID NO:1145), and CeresAnnot:6016055 (SEQ ID NO:1147).

FIG. 38 is an alignment of ME13107 (SEQ ID NO:1159) with homologous and/or orthologous amino acid sequences CeresClone:1371824 (SEQ ID NO:1161), GI No.22585 (SEQ ID NO:1162), GI No.22208482 (SEQ ID NO:1163), and GI No.16073 (SEQ ID NO:1164).

FIG. 39 is an alignment of ME13108 (SEQ ID NO:1166) with homologous and/or orthologous amino acid sequences GI No.99109436 (SEQ ID NO:1167), CeresClone:1627939 (SEQ ID NO:1169), CeresClone:1840433 (SEQ ID NO:1171), CeresAnnot:1524198 (SEQ ID NO:1173), CeresClone:1650 (SEQ ID NO:1175), CeresClone:691979 (SEQ ID NO:1177), GI No.92876897 (SEQ ID NO:1180), CeresClone:1774130 (SEQ ID NO:1182), and GI No.115450018 (SEQ ID NO:1183).

FIG. 40 is an alignment of ME13110 (SEQ ID NO:1185) with homologous and/or orthologous amino acid sequences CeresClone:737317 (SEQ ID NO:1187), CeresClone:1880853 (SEQ ID NO:1189), GI No.125558381 (SEQ ID NO:1190), and GI No.115472157 (SEQ ID NO:1191).

FIG. 41 is an alignment of ME13125 (SEQ ID NO:1194) with homologous and/or orthologous amino acid sequences CeresClone:1938817 (SEQ ID NO:1196), CeresAnnot:1457245 (SEQ ID NO:1200), CeresClone:577910 (SEQ ID NO:1202), Public PUBLICCLONE ID no.100736184 (SEQ ID NO:1203), GI No.125553355 (SEQ ID NO:1204), and GI No.5091600 (SEQ ID NO:1205).

FIG. 42 is an alignment of ME13149 (SEQ ID NO:1210) with homologous and/or orthologous amino acid sequences GI No.1703374 (SEQ ID NO:1211), CeresClone:1846330 (SEQ ID NO:1213), GI No.29124979 (SEQ ID NO:1216), CeresAnnot:1531725 (SEQ ID NO:1218), GI No.3334321 (SEQ ID NO:1229), CeresClone:571410 (SEQ ID NO:1232), GI No.39653273 (SEQ ID NO:1233), GI No.92875403 (SEQ ID NO:1234), GI No.11131026 (SEQ ID NO:1235), GI No.77812440 (SEQ ID NO:1236), GI No.89475524 (SEQ ID NO:1238), GI No.3182919 (SEQ ID NO:1239), GI No.7643794 (SEQ ID NO:1240), GI No.1710851 (SEQ ID NO:1241), GI No.115501471 (SEQ ID NO:1242), GI No.77999251 (SEQ ID NO:1243), GI No.3450893 (SEQ ID NO:1249), CeresClone:704589 (SEQ ID NO:1251), CeresClone:1384151 (SEQ ID NO:1253), CeresClone:1713894 (SEQ ID NO:1259), GI No.125560752 (SEQ ID NO:1264), GI No.115475543 (SEQ ID NO:1265), GI No.3182922 (SEQ ID NO:1267), GI No.145353078 (SEQ ID NO:1268), GI No.11131023 (SEQ ID NO:1269), GI No.47026845 (SEQ ID NO:1270), and GI No.38353642 (SEQ ID NO:1272).

FIG. 43 is an alignment of ME13151 (SEQ ID NO:1274) with homologous and/or orthologous amino acid sequences CeresClone:1884601 (SEQ ID NO:1276), CeresAnnot:1445717 (SEQ ID NO:1280), CeresClone:527903 (SEQ ID NO:1284), GI No.92891722 (SEQ ID NO:1285), CeresClone:790881 (SEQ ID NO:1287), CeresClone:299417 (SEQ ID NO:1289), CeresClone:1993894 (SEQ ID NO:1291), GI No.125539547 (SEQ ID NO:1294), GI No.48716424 (SEQ ID NO:1295), GI No.84468278 (SEQ ID NO:1297), and CeresAnnot:6036303 (SEQ ID NO:1300).

FIG. 44 is an alignment of ME13153 (SEQ ID NO:1302) with homologous and/or orthologous amino acid sequences GI No.70609690 (SEQ ID NO:1303), CeresClone:1927524 (SEQ ID NO:1305), CeresAnnot:1467310 (SEQ ID NO:1311), GI No.45935270 (SEQ ID NO:1313), CeresClone:718446 (SEQ ID NO:1317), GI No.92875133 (SEQ ID NO:1318), GI No.1706318 (SEQ ID NO:1319), GI No.3252856 (SEQ ID NO:1320), GI No.1169238 (SEQ ID NO:1326), GI No.31296711 (SEQ ID NO:1327), CeresClone:1468893 (SEQ ID NO:1330), GI No.51587340 (SEQ ID NO:1331), CeresClone:1796201 (SEQ ID NO:1333), GI No.125543034 (SEQ ID NO:1334), GI No.115476804 (SEQ ID NO:1336), GI No.75268060 (SEQ ID NO:1339), and GI No.75268007 (SEQ ID NO:1340).

FIG. 45 is an alignment of ME13177 (SEQ ID NO:1342) with homologous and/or orthologous amino acid sequences CeresAnnot:1443786 (SEQ ID NO:1346), GI No.15239172 (SEQ ID NO:1355), GI No.562190 (SEQ ID NO:1363), GI No.83032266 (SEQ ID NO:1364), CeresClone:602910 (SEQ ID NO:1366), GI No.7242793 (SEQ ID NO:1370), GI No.116167 (SEQ ID NO:1371), GI No.2190259 (SEQ ID NO:1372), GI No.5420278 (SEQ ID NO:1373), GI No.1064931 (SEQ ID NO:1374), GI No.6093215 (SEQ ID NO:1377), GI No.461726 (SEQ ID NO:1378), GI No.89111295 (SEQ ID NO:1379), GI No.82949283 (SEQ ID NO:1380), GI No.125537180 (SEQ ID NO:1381), GI No.115489300 (SEQ ID NO:1382), and GI No.55978000 (SEQ ID NO:1383).

FIG. 46 is an alignment of ME13200 (SEQ ID NO:1385) with homologous and/or orthologous amino acid sequences CeresAnnot:1503394 (SEQ ID NO:1387), GI No.4914437 (SEQ ID NO:1390), CeresClone:638126 (SEQ ID NO:1393), GI No.124360540 (SEQ ID NO:1394), GI No.7981380 (SEQ ID NO:1395), GI No.118137433 (SEQ ID NO:1396), CeresClone:1723374 (SEQ ID NO:1398), CeresClone:1785379 (SEQ ID NO:1400), GI No.125553354 (SEQ ID NO:1401), GI No.115471859 (SEQ ID NO:1404), and CeresAnnot:6040771 (SEQ ID NO:1407).

FIG. 47 is an alignment of ME13204 (SEQ ID NO:1409) with homologous and/or orthologous amino acid sequences CeresClone:1939206 (SEQ ID NO:1413), CeresAnnot:1453316 (SEQ ID NO:1415), GI No.79319075 (SEQ ID NO:1418), GI No.124359953 (SEQ ID NO:1419), CeresClone:891431 (SEQ ID NO:1421), GI No.125536578 (SEQ ID NO:1424), and GI No.20270065 (SEQ ID NO:1425).

FIG. 48 is an alignment of ME14649 (SEQ ID NO:1428) with homologous and/or orthologous amino acid sequences CeresClone:1978733 (SEQ ID NO:1430), CeresAnnot:1476165 (SEQ ID NO:1432), CeresClone:871529 (SEQ ID NO:1436), CeresClone:1043344 (SEQ ID NO:1439), CeresClone:786542 (SEQ ID NO:1442), CeresClone:346115 (SEQ ID NO:1444), CeresClone:1821683 (SEQ ID NO:1452), GI No.125533171 (SEQ ID NO:1453), and GI No.77553492 (SEQ ID NO:1457)

FIG. 49 is an alignment of ME16546 (SEQ ID NO:1463) with homologous and/or orthologous amino acid sequences CeresAnnot:1444102 (SEQ ID NO:1465), CeresClone:582439 (SEQ ID NO:1471), CeresClone:579953 (SEQ ID NO:1473), GI No.125539335 (SEQ ID NO:1474), and GI No.115445987 (SEQ ID NO:1476).

FIG. 50 is an alignment of ME17567 (SEQ ID NO:1491) with homologous and/or orthologous amino acid sequences CeresClone:1895876 (SEQ ID NO:1493), CeresAnnot:1464522 (SEQ ID NO:1495), CeresClone:968434 (SEQ ID NO:1499), CeresClone:686479 (SEQ ID NO:1501), CeresClone:1564962 (SEQ ID NO:1503), GI No.125549699 (SEQ ID NO:1504), GI No.125591612 (SEQ ID NO:1505), and CeresAnnot:6006969 (SEQ ID NO:1508).

FIG. 51 is an alignment of ME17932 (SEQ ID NO:1510) with homologous and/or orthologous amino acid sequences CeresClone:1842178 (SEQ ID NO:1512), CeresAnnot: 1475265 (SEQ ID NO:1516) and CeresClone:1044646 (SEQ ID NO:1520).

FIG. 52 is an alignment of ME17936 (SEQ ID NO:1525) with homologous and/or orthologous amino acid sequences CeresAnnot:1454324 (SEQ ID NO:1527), CeresClone: 1652842 (SEQ ID NO:1534), and GI No.75214620 (SEQ ID NO:1535).

FIG. 53 is an alignment of ME18275 (SEQ ID NO:1537) with homologous and/or orthologous amino acid sequences CeresAnnot:1514086 (SEQ ID NO:1539), CeresClone: 1087909 (SEQ ID NO:1543), CeresClone:1359070 (SEQ ID NO:1545), GI No.92880913 (SEQ ID NO:1548), CeresClone:932449 (SEQ ID NO:1550), and CeresClone: 1788695 (SEQ ID NO:1552).

FIG. 54 is an alignment of ME18924 (SEQ ID NO:1554) with homologous and/or orthologous amino acid sequences GI No.82469976 (SEQ ID NO:1555), CeresAnnot:1533704 (SEQ ID NO:1563), CeresClone:524404 (SEQ ID NO:1565), CeresClone:846541 (SEQ ID NO:1567), CeresClone:1769321 (SEQ ID NO:1571), GI No.125528559 (SEQ ID NO:1572), GI No.125572823 (SEQ ID NO:1574), and GI No.84453208 (SEQ ID NO:1575).

FIG. 55 is an alignment of ME19182 (SEQ ID NO:1577) with homologous and/or orthologous amino acid sequences GI No.4033417 (SEQ ID NO:1040), GI No.5669924 (SEQ ID NO:1041), GI No.40642617 (SEQ ID NO:1440), GI No.90399018 (SEQ ID NO:1485), GI No.115464117 (SEQ ID NO:1487), GI No.75164812 (SEQ ID NO:1578), CeresClone:1794223 (SEQ ID NO:1580), CeresAnnot:1471422 (SEQ ID NO:1590), CeresClone:968096 (SEQ ID NO:1607), GI No.6752884 (SEQ ID NO:1608), GI No.47775656 (SEQ ID NO:1609), CeresClone:1020799 (SEQ ID NO:1611), GI No.87240865 (SEQ ID NO:1622), GI No.2500047 (SEQ ID NO:1623), CeresClone:705340 (SEQ ID NO:1627), CeresClone:1430456 (SEQ ID NO:1637), GI No.84619270 (SEQ ID NO:1648), and CeresClone:1821143 (SEQ ID NO:1651).

FIG. 56 is an alignment of ME20628 (SEQ ID NO:1437) with homologous and/or orthologous amino acid sequences GI No.113367236 (SEQ ID NO:173), GI No.115477615 (SEQ ID NO:212), GI No.125542223 (SEQ ID NO:361), GI No.1838976 (SEQ ID NO:421), CeresClone:1547185 (SEQ ID NO:443), CeresAnnot:1450452 (SEQ ID NO:740), and GI No.92870675 (SEQ ID NO:1461).

FIG. 58 is an alignment of CeresClone 37288 (SEQ ID NO:5752) with homologous and/or orthologous amino acid sequences CeresClone 523628 (SEQ ID NO:2898), Public GI ID no. 38326712 (SEQ ID NO:5755), Public GI ID no. 34452081 (SEQ ID NO:5756), and Public GI ID no. 52789958 (SEQ ID NO:5753).

FIG. 57 is an alignment of ME01821 (SEQ ID NO:97) with homologous and/or orthologous amino acid sequences Public GI ID no.167480754 (SEQ ID NO:2013) and Public GI ID no.83830869 (SEQ ID NO:2015).

DETAILED DESCRIPTION

The invention provides methods and materials related to modulating low-nitrogen tolerance levels in plants. In some embodiments, the plants may also have modulated levels of low-nitrogen tolerance. The methods can include transforming a plant cell with a nucleic acid encoding a low nitrogen tolerance-modulating polypeptide, wherein expression of the polypeptide results in a modulated level of low-nitrogen tolerance. Plant cells produced using such methods can be grown to produce plants having an increased tolerance to conditions with limiting exogenous nitrogen sources. Such plants can be used for the production of higher yields and biomasses with existing fertilizer inputs, and/or enable existing yields and biomass of crops to be obtained with lower fertilizer input, or better yields and biomasses on soils of poorer quality.

Definitions:

"Amino acid" refers to one of the twenty biologically occurring amino acids and to synthetic amino acids, including D/L optical isomers.

"Cell type-preferential promoter" or "tissue-preferential promoter" refers to a promoter that drives expression preferentially in a target cell type or tissue, respectively, but may also lead to some transcription in other cell types or tissues as well.

"Control plant" refers to a plant that does not contain the exogenous nucleic acid present in a transgenic plant of interest, but otherwise has the same or similar genetic background as such a transgenic plant. A suitable control plant can be a non-transgenic wild type plant, a non-transgenic segregant from a transformation experiment, or a transgenic plant that contains an exogenous nucleic acid other than the exogenous nucleic acid of interest.

"Domains" are groups of substantially contiguous amino acids in a polypeptide that can be used to characterize protein families and/or parts of proteins. Such domains have a "fingerprint" or "signature" that can comprise conserved primary sequence, secondary structure, and/or three-dimensional conformation. Generally, domains are correlated with specific in vitro and/or in vivo activities. A domain can have a length of from 10 amino acids to 400 amino acids, e.g., 10 to 50 amino acids, or 25 to 100 amino acids, or 35 to 65 amino acids, or 35 to 55 amino acids, or 45 to 60 amino acids, or 200 to 300 amino acids, or 300 to 400 amino acids.

"Down-regulation" refers to regulation that decreases production of expression products (mRNA, polypeptide, or both) relative to basal or native states.

"Exogenous" with respect to a nucleic acid indicates that the nucleic acid is part of a recombinant nucleic acid construct, or is not in its natural environment. For example, an exogenous nucleic acid can be a sequence from one species introduced into another species, i.e., a heterologous nucleic acid. Typically, such an exogenous nucleic acid is introduced into the other species via a recombinant nucleic acid construct. An exogenous nucleic acid can also be a sequence that is native to an organism and that has been reintroduced into cells of that organism. An exogenous nucleic acid that includes a native sequence can often be distinguished from the naturally occurring sequence by the presence of non-natural sequences linked to the exogenous nucleic acid, e.g., non-native regulatory sequences flanking a native sequence in a recombinant nucleic acid construct. In addition, stably transformed exogenous nucleic acids typically are integrated at positions other than the position where the native sequence is found. It will be appreciated that an exogenous nucleic acid may have been introduced into a progenitor and not into the cell under consideration. For example, a transgenic plant containing an exogenous nucleic acid can be the progeny of a cross between a stably transformed plant and a non-transgenic plant. Such progeny are considered to contain the exogenous nucleic acid.

"Expression" refers to the process of converting genetic information of a polynucleotide into RNA through transcription, which is catalyzed by an enzyme, RNA polymerase, and into protein, through translation of mRNA on ribosomes.

"Heterologous polypeptide" as used herein refers to a polypeptide that is not a naturally occurring polypeptide in a plant cell, e.g., a transgenic *Panicum virgatum* plant transformed with and expressing the coding sequence for a nitrogen transporter polypeptide from a *Zea mays* plant.

"Isolated nucleic acid" as used herein includes a naturally-occurring nucleic acid, provided one or both of the sequences immediately flanking that nucleic acid in its naturally-occurring genome is removed or absent. Thus, an isolated nucleic acid includes, without limitation, a nucleic acid that exists as a purified molecule or a nucleic acid molecule that is incorporated into a vector or a virus. A nucleic acid existing among hundreds to millions of other nucleic acids within, for example, cDNA libraries, genomic libraries, or gel slices containing a genomic DNA restriction digest, is not to be considered an isolated nucleic acid.

"Low Nitrogen Conditions" as used herein refers to nitrogen concentrations which lead to nitrogen deficiency symptoms such as pale green leaf color, chlorosis and reduced growth and vigor. Typically, low nitrogen conditions lead to a reduction of at least 20%, 25%, 30%, 35%, 40%, 45%, 50%, 60%, 70%, 80% or 90% in growth and/or vigor.

"Modulation" of the level of low-nitrogen tolerance refers to the change in the level of tolerance of a plant to limiting exogenous nitrogen sources that is observed as a result of expression of, or transcription from, an exogenous nucleic acid in a plant cell. The change in low-nitrogen tolerance level is measured by changes in plant size and greenness as well as greater photosynthesis efficiency, relative to the corresponding level in control plants in an environment with limiting nitrogen supply.

"Nucleic acid" and "polynucleotide" are used interchangeably herein, and refer to both RNA and DNA, including cDNA, genomic DNA, synthetic DNA, and DNA or RNA containing nucleic acid analogs. Polynucleotides can have any three-dimensional structure. A nucleic acid can be double-stranded or single-stranded (i.e., a sense strand or an antisense strand). Non-limiting examples of polynucleotides include genes, gene fragments, exons, introns, messenger RNA (mRNA), transfer RNA, ribosomal RNA, siRNA, micro-RNA, ribozymes, cDNA, recombinant polynucleotides, branched polynucleotides, nucleic acid probes and nucleic acid primers. A polynucleotide may contain unconventional or modified nucleotides.

"Operably linked" refers to the positioning of a regulatory region and a sequence to be transcribed in a nucleic acid so that the regulatory region is effective for regulating transcription or translation of the sequence. For example, to operably link a coding sequence and a regulatory region, the translation initiation site of the translational reading frame of the coding sequence is typically positioned between one and about fifty nucleotides downstream of the regulatory region. A regulatory region can, however, be positioned as much as about 5,000 nucleotides upstream of the translation initiation site, or about 2,000 nucleotides upstream of the transcription start site.

"Polypeptide" as used herein refers to a compound of two or more subunit amino acids, amino acid analogs, or other peptidomimetics, regardless of post-translational modification, e.g., phosphorylation or glycosylation. The subunits may be linked by peptide bonds or other bonds such as, for example, ester or ether bonds. Full-length polypeptides, truncated polypeptides, point mutants, insertion mutants, splice variants, chimeric proteins, and fragments thereof are encompassed by this definition.

"Progeny" includes descendants of a particular plant or plant line. Progeny of an instant plant include seeds formed on $F_1$, $F_2$, $F_3$, $F_4$, $F_5$, $F_6$ and subsequent generation plants, or seeds formed on $BC_1$, $BC_2$, $BC_3$, and subsequent generation plants, or seeds formed on $F_1BC_1$, $F_1BC_2$, $F_1BC_3$, and subsequent generation plants. The designation $F_1$ refers to the progeny of a cross between two parents that are genetically distinct. The designations $F_2$, $F_3$, $F_4$, $F_5$ and $F_6$ refer to subsequent generations of self- or sib-pollinated progeny of an $F_1$ plant.

"Regulatory region" refers to a nucleic acid having nucleotide sequences that influence transcription or translation initiation and rate, and stability and/or mobility of a transcription or translation product. Regulatory regions include, without limitation, promoter sequences, enhancer sequences, response elements, protein recognition sites, inducible elements, protein binding sequences, 5' and 3' untranslated regions (UTRs), transcriptional start sites, termination sequences, polyadenylation sequences, introns, and combinations thereof. A regulatory region typically comprises at least a core (basal) promoter. A regulatory region also may include at least one control element, such as an enhancer sequence, an upstream element or an upstream activation region (UAR). For example, a suitable enhancer is a cis-regulatory element (−212 to −154) from the upstream region of the octopine synthase (ocs) gene. Fromm et al. (1989) *The Plant Cell*, 1:977-984.

"Up-regulation" refers to regulation that increases the level of an expression product (mRNA, polypeptide, or both) relative to basal or native states.

"Vector" refers to a replicon, such as a plasmid, phage, or cosmid, into which another DNA segment may be inserted so as to bring about the replication of the inserted segment. Generally, a vector is capable of replication when associated with the proper control elements. The term "vector" includes cloning and expression vectors, as well as viral vectors and integrating vectors. An "expression vector" is a vector that includes a regulatory region.

Polypeptides

Polypeptides described herein include low nitrogen tolerance-modulating polypeptides. Low nitrogen tolerance-modulating polypeptides can be effective to modulate low-nitrogen tolerance levels when expressed in a plant or plant cell. Such polypeptides typically contain at least one domain indicative of low nitrogen tolerance-modulating polypeptides, as described in more detail herein. Low nitrogen tolerance-modulating polypeptides typically have an HMM bit score that is greater than 20, as described in more detail herein. In some embodiments, low nitrogen tolerance-modulating polypeptides have greater than 80% identity to SEQ ID NO:3, SEQ ID NO:49, SEQ ID NO:77, SEQ ID NO:97, SEQ ID NO:100, SEQ ID NO:152, SEQ ID NO:166, SEQ ID NO:186, SEQ ID NO:208, SEQ ID NO:218, SEQ ID NO:234, SEQ ID NO:246, SEQ ID NO:300, SEQ ID NO:332, SEQ ID NO:368, SEQ ID NO:510, SEQ ID NO:533, SEQ ID NO:556, SEQ ID NO:558, SEQ ID NO:593, SEQ ID NO:613, SEQ ID NO:646, SEQ ID NO:687, SEQ ID NO:730, SEQ ID NO:746, SEQ ID NO:769, SEQ ID NO:792, SEQ ID NO:824, SEQ ID NO:828, SEQ ID NO:853, SEQ ID NO:855, SEQ ID NO:891, SEQ ID NO:917, SEQ ID NO:944, SEQ ID NO:976, SEQ ID NO:982, SEQ ID NO:1054, SEQ ID NO:1099, SEQ ID NO:1112, SEQ ID NO:1116, SEQ ID NO:1157, SEQ ID NO:1159, SEQ ID NO:1166, SEQ ID NO:1185, SEQ ID NO:1194, SEQ ID NO:1210, SEQ ID NO:1274, SEQ ID NO:1302, SEQ ID NO:1342, SEQ ID NO:1385, SEQ ID NO:1409, SEQ ID NO:1428, SEQ ID NO:1437, SEQ ID NO:1463, SEQ ID NO:1491, SEQ ID NO:1510, SEQ ID NO:1525, SEQ ID NO:1537, SEQ ID NO:1554, or SEQ ID NO:1577, as described in more detail herein.

Domains Indicative of Low Nitrogen Tolerance-Modulating Polypeptides

A low nitrogen tolerance-modulating polypeptide can contain a P450 domain, which is characteristic of polypeptides belonging to the Cytochrome P450 superfamily. Cytochrome P450s are haem-thiolate proteins involved in the oxidative degradation of various compounds. They are particularly well known for their role in the degradation of environmental toxins and mutagens. In plants, these proteins are important for the biosynthesis of several compounds such as hormones, defensive compounds and fatty acids. Sequence conservation is relatively low within the family—there are only 3 absolutely conserved residues—but their general topography and structural fold are highly conserved. The conserved core is composed of a coil termed the 'meander', a four-helix bundle, helices J and K, and two sets of beta-sheets. These constitute the haem-binding loop, the proton-transfer groove and the conserved EXXR motif in helix K. While prokaryotic P450s are soluble proteins, most eukaryotic P450s are associated with microsomal membranes. Their general enzymatic function is to catalyse regiospecific and stereospecific oxidation of non-activated hydrocarbons at physiological temperatures. SEQ ID NO:3 and SEQ ID NO:332 set forth the amino acid sequence of Arabidopsis clones, identified herein as ME00919 (SEQ ID NO:3) and ME04587 (SEQ ID NO:332) respectively, that are predicted to encode polypeptides containing a Cytochrome P450 domain.

A low nitrogen tolerance-modulating polypeptide can contain a zf-Dof domain, which is conserved in several DNA-binding proteins of higher plants. Dof domain is a zinc finger DNA-binding domain that shows resemblance to the Cys2 zinc finger, although it has a longer putative loop where an extra Cys residue is typically conserved. The motif is also present in SEQ ID NO:49, which sets forth the amino acid sequence of an Arabidopsis clone, identified herein as Ceres ME01312 (SEQ ID NO:49), that is predicted to encode a polypeptide containing a zf-Dof domain.

A low nitrogen tolerance-modulating polypeptide can contain an Aminotran_3 domain characteristic of polypeptides belonging to the aminotransferase Class-III family. Aminotransferases share certain mechanistic features with other pyridoxalphosphate-dependent enzymes, such as the covalent binding of the pyridoxalphosphate group to a lysine residue. Class-III aminotransferases include acetylornithine aminotransferase, which catalyzes the transfer of an amino group from acetylornithine to alpha-ketoglutarate, yielding N-acetyl-glutamic-5-semi-aldehyde and glutamic acid; ornithine aminotransferase, which catalyzes the transfer of an amino group from ornithine to alpha-ketoglutarate, yielding glutamic-5-semi-aldehyde and glutamic acid; omega-amino acid—pyruvate aminotransferase, which catalyzes transamination between a variety of omega-amino acids, mono- and diamines, and pyruvate; 4-aminobutyrate aminotransferase; GABA transaminase, which catalyzes the transfer of an amino group from GABA to alpha-ketoglutarate, yielding succinate semialdehyde and glutamic acid; DAPA aminotransferase, a bacterial enzyme (bioA), which catalyzes an intermediate step in the biosynthesis of biotin, the transamination of 7-keto-8-aminopelargonic acid to form 7,8-diaminopelargonic acid; 2,2-dialkylglycine decarboxylase, a Burkholderia cepacia (Pseudomonas cepacia) enzyme (dgdA) that catalyzes the decarboxylating amino transfer of 2,2-dialkylglycine and pyruvate to dialkyl ketone, alanine and carbon dioxide; glutamate-1-semialdehyde aminotransferase (GSA); Bacillus subtilis aminotransferases yhxA and yodT; Haemophilus influenzae aminotransferase HI0949; and Caenorhabditis elegans aminotransferase. On the basis of sequence similarity, these various enzymes can be grouped into subfamilies. The aminotran_3 domain is also present in SEQ ID NO:77, which set forth the amino acid sequences of Arabidopsis clone, identified herein as Ceres ME01463 (SEQ ID NO:77), that is predicted to encode polypeptides containing an aminotran_3 domain.

A low nitrogen tolerance-modulating polypeptide can contain a linker histone domain characteristic of polypeptides belonging to the linker histone H1 and H5 family. Linker histone H1 is an essential component of chromatin structure. H1 links nucleosomes into higher order structures. Histone H5 performs the same function as histone H1, and replaces H1 in certain cells. The structure of GH5, the globular domain of the linker histone H5 fold is similar to the DNA-binding domain of the catabolite gene activator protein, CAP, thus providing a possible model for the binding of GH5 to DNA. The domain is also present in SEQ ID NO:100, which sets forth the amino acid sequence of an Arabidopsis clone, identified herein as Ceres ME01910 (SEQ ID NO:100), that is predicted to encode a polypeptide containing a linker histone domain.

A low nitrogen tolerance-modulating polypeptide can contain a zf-C3HC4 domain, which is predicted to be characteristic of proteins belonging to the C3HC4 type zinc-finger (RING finger) protein family. The C3HC4 type zinc-finger (RING finger) is a cysteine-rich domain of approximately 40 to 60 residues that coordinates two zinc ions, and is probably involved in mediating protein-protein interactions. Members of the C3HC4 type zinc-finger (RING finger) protein family contain the loosely conserved sequence: C-X2-C-X(9-39)-C-X(1-3)-H-X(2-3)-C-X2-C-X(4-48)-C-X2-C where X is any amino acid. The domain is also present in SEQ ID NOs:166, 746, 976, 1428, which set forth the amino acid sequences of Arabidopsis clones, identified herein as Ceres ME02603 (SEQ ID NO:166), ME05493 (SEQ ID NO:746), ME12954 (SEQ ID NO:976), ME14649 (SEQ ID NO:1428) respectively, that are predicted to encode polypeptides containing a zf-C3HC4 domain.

A low nitrogen tolerance-modulating polypeptide can contain a Gal_Lectin domain characteristic of a galactose binding lectin domain protein. SEQ ID NO:208 sets forth the amino acid sequence of an Arabidopsis clone, identified herein as Ceres ME02801 (SEQ ID NO:208), that is predicted to encode a polypeptide containing a galactose binding lectin domain.

A low nitrogen tolerance-modulating polypeptide can contain a TRP_1 domain characteristic of tetratricopeptide repeat (TPR) domain protein. The tetratricopeptide repeat is a structural motif present in a wide range of proteins identified in various different organisms, ranging from bacteria to humans. It mediates protein-protein interactions and the assembly of multiprotein complexes. Sequence alignment of the TPR domains reveals a consensus sequence defined by a pattern of small and large amino acids. Proteins containing TPRs are involved in a variety of biological processes, such as cell cycle regulation, transcriptional control, mitochondrial and peroxisomal protein transport, neurogenesis and protein folding. The X-ray structure of a domain containing three TPRs from protein phosphatase 5 revealed that TPR adopts a helixturnhelix arrangement, with adjacent TPR motifs packing in a parallel fashion, resulting in a spiral of repeating anti-parallel alpha-helices. The two helices are denoted helix A and helix B. The packing angle between helix A and helix B is ~24° within a single TPR and generates a right-handed superhelical shape. Helix A interacts with helix B and with helix A' of the next TPR. Two protein surfaces are generated: the inner concave surface is contributed to mainly by residue on helices A, and the other surface presents residues from both helices A and B.

A low nitrogen tolerance-modulating polypeptide can contain a TRP_2 tetratricopeptide repeat domain, which is predicted to be characteristic of scaffold-proteins in multi-protein complexes. The TPR_2 domain consists of approximately 34-amino-acid motif with a loose consensus and is present, usually as multiple tandem repeats, in proteins with many cellular functions, including mitosis, transcription, protein transport, and development. Structural analysis of the TPR-2 domain demonstrates that it forms two α-helical regions separated by a turn, such that apposed bulky and small side chains form a "knob and hole" structure. In general, the hydrophobic surface of this structure mediates protein-protein interactions between TPR- and non-TPR-containing proteins.

SEQ ID NO:234 sets forth the amino acid sequence of Arabidopsis clone, identified herein as Ceres ME04204 (SEQ ID NO:234), that is predicted to encode a polypeptide containing a TRP_1 tetratricopeptide repeat domain and a TRP_2 tetratricopeptide repeat domain. SEQ ID NO:1510 sets forth the amino acid sequence of Arabidopsis clone, identified herein as Ceres ME17932 (SEQ ID NO:1510), that is predicted to encode a polypeptide containing a TRP_2 tetratricopeptide repeat domain.

A low nitrogen tolerance-modulating polypeptide can contain a zf-AN1 domain characteristic of polypeptides belonging to the AN1-like Zinc finger domain protein family. The AN1-like Zinc finger domain was first identified as a zinc finger at the C-terminus of An1 a ubiquitin-like protein in Xenopus laevis. The following pattern describes the zinc finger: C-X2-C-X(9-12)-C-X(1-2)-C-X4-C-X2-H-X5-H-X-C, where X can be any amino acid, and numbers in brackets indicate the number of residues.

A low nitrogen tolerance-modulating polypeptide can contain a zf-A20 domain, which is characteristic of A20- (an inhibitor of cell death)-like zinc fingers. In animals, A20-like zinc fingers are believed to mediate self-association in A20. These fingers also mediate IL-1-induced NF-kappa B activation. SEQ ID NO: 246 sets forth the amino acid sequence of Arabidopsis clone, identified herein as Ceres ME04477 (SEQ ID NO:246), that is predicted to encode a polypeptide containing an AN1-like Zinc finger domain and zf-A20 domain.

A low nitrogen tolerance-modulating polypeptide can contain an Aa_trans domain, or transmembrane amino acid transporter domain, which is predicted to be characteristic of amino acid transporters and amino acid permeases. The domain is also present in SEQ ID NO:300, which sets forth the amino acid sequence of an Arabidopsis clone, identified herein as Ceres ME04507 (SEQ ID NO:300), that is predicted to encode a polypeptide containing an transmembrane amino acid transporter domain.

A low nitrogen tolerance-modulating polypeptide can contain an RNA recognition motif (as known as RRM_1, RRM, RBD, or RNP domain), which is characteristic of polypeptides belonging to the single strand RNA-binding protein superfamily. RRM proteins have a variety of RNA binding preferences and functions, and include heterogeneous nuclear ribonucleoproteins (hnRNPs), proteins implicated in regulation of alternative splicing, protein components of small nuclear ribonucleoproteins, and proteins that regulate RNA stability and translation. The RRM in heterodimeric splicing factor U2 snRNP auxiliary factor (U2AF) appears to have two RRM-like domains with specialized features for protein recognition. The motif also appears in a few single stranded DNA binding proteins. The typical RRM consists of four anti-parallel beta-strands and two alpha-helices arranged in a beta-alpha-beta-beta-alpha-beta fold with side chains that stack with RNA bases. Specificity of RNA binding is determined by multiple contacts with surrounding amino acids. A third helix is present during RNA binding in some cases. The motif is also present in SEQ ID NO:368 and SEQ ID NO:1274, which set forth the amino acid sequences of Arabidopsis clones, identified herein as Ceres ME04753 (SEQ ID NO:368) and ME13151 (SEQ ID NO:1274) respectively, that are predicted to encode polypeptides containing an RNA recognition motif.

A low nitrogen tolerance-modulating polypeptide can contain an NTF2 domain characteristic of a nuclear transport factor 2 (NTF2) polypeptide. NTF2 is a homodimer of approximately 14 kDa subunits which stimulates efficient nuclear import of a cargo protein. NTF2 binds to both RanGDP and FxFG repeat-containing nucleoporins. NTF2 binds to RanGDP sufficiently strongly for the complex to remain intact during transport through nucleopore complexes (NPCs), but the interaction between NTF2 and FxFG nucleoporins is much more transient, which would enable NTF2 to move through the NPC by hopping from one repeat to another. NTF2 folds into a cone with a deep hydrophobic cavity, the opening of which is surrounded by several negatively charged residues. RanGDP binds to NTF2 by inserting a conserved phenylalanine residue into the hydrophobic pocket of NTF2 and making electrostatic interactions with the conserved negatively charged residues that surround the cavity. A structurally similar domain appears in other nuclear import proteins. SEQ ID NO:1274, which sets forth the amino acid sequence of an Arabidopsis clone, identified herein as Ceres ME13151 (SEQ ID NO:1274), that is predicted to encode a polypeptide containing a NTF2 domain.

A low nitrogen tolerance-modulating polypeptide can contain a DUF1218 domain. SEQ ID NO:1274, which sets forth the amino acid sequence of an Arabidopsis clone, identified herein as Ceres ME04772 (SEQ ID NO:510), that is predicted to encode a polypeptide containing a DUF1218 domain.

A low nitrogen tolerance-modulating polypeptide can contain a Myb-like DNA-binding domain characteristic of polypeptides belonging to a protein family whose members contain the DNA binding domains from Myb proteins, as well as the SANT domain family. SEQ ID NO:533, which sets forth the amino acid sequence of an Arabidopsis clone, identified herein as Ceres ME04909 (SEQ ID NO:533), that is predicted to encode a polypeptide containing a Myb-like DNA-binding domain.

A low nitrogen tolerance-modulating polypeptide can contain a FAD_binding_4 domain. This domain is predicted to be characteristic of polypeptides belonging to a family of enzymes that use FAD (flavin adenine dinucleotide) as a co-factor, most of the enzymes are similar to oxygen oxidoreductase, containing a covalently bound FAD group which is attached to a histidine via an 8-alpha-(N3-histidyl)-riboflavin linkage.

A low nitrogen tolerance-modulating polypeptide can contain a BBE domain, which is predicted to be characteristic of a berberine bridge and berberine bridge-like enzyme. BBE enzymes are typically involved in the biosynthesis of numerous isoquinoline alkaloids. They catalyse the transformation of the N-methyl group of (S)-reticuline into the C-8 berberine bridge carbon of (S)-scoulerine. SEQ ID NO:558 sets forth the amino acid sequence of an *Arabidopsis* clone, identified herein as Ceres ME05194 (SEQ ID NO:558), that is predicted to encode a polypeptide containing an FAD_binding_4 domain and a BBE domain.

A low nitrogen tolerance-modulating polypeptide can contain a prefoldin (PFD) domain characteristic of polypeptides belonging to the prefoldin subunit family. Prefoldin (PFD) is a chaperone that typically interacts with type II chaperonins, hetero-oligomers lacking an obligate co-chaperonin that are found in eukaryotes (chaperonin-containing T-complex polypeptide-1 (CCT)) and archaea. Eukaryotic PFD can typically bind both actin and tubulin co-translationally. The chaperone can then delivers the target protein to CCT, interacting with the chaperonin through the tips of the coiled coils. SEQ ID NO:593 sets forth the amino acid sequence of an *Arabidopsis* clone, identified herein as Ceres ME05267 (SEQ ID NO:593), that is predicted to encode a polypeptide containing a prefoldin domain.

A low nitrogen tolerance-modulating polypeptide can contain an HR-lesion domain characteristic of polypeptides belonging to a family of plant proteins can be associated with the hypersensitive response (HR) pathway of defense against plant pathogens. The domain is also present in SEQ ID NO: 646, which sets forth the amino acid sequence of an *Arabidopsis* clone, identified herein as Ceres ME05341 (SEQ ID NO: 646), that is predicted to encode a polypeptide containing an HR-lesion domain.

A low nitrogen tolerance-modulating polypeptide can contain a DUF538 domain. SEQ ID NO:687 sets forth the amino acid sequence of an *Arabidopsis* clone, identified herein as Ceres ME05392 (SEQ ID NO:687), that is predicted to encode a polypeptide containing a DUF538 domain.

A low nitrogen tolerance-modulating polypeptide can contain a zinc finger C-x8-C-x5-C-x3-H type domain (zf-CCCH), which is characteristic of polypeptides belonging to the zinc finger protein superfamily. Members of zinc finger domains proteins are thought to be involved in DNA-binding, and exist as different types. Proteins containing zinc finger domains of the C-x8-C-x5-C-x3-H type include zinc finger proteins from eukaryotes involved in cell cycle or growth phase-related regulation. It has been shown that different CCCH zinc finger proteins interact with the 3' untranslated region of various mRNA. SEQ ID NO:792 sets forth the amino acid sequence of an *Arabidopsis* clone, identified herein as Ceres ME07344 (SEQ ID NO:792), that is predicted to encode a polypeptide containing a zf-CCCH domain.

A low nitrogen tolerance-modulating polypeptide can contain a DUF246 domain. SEQ ID NO:828 sets forth the amino acid sequence of an *Arabidopsis* clone, identified herein as Ceres ME08464 (SEQ ID NO:828), that is predicted to encode a polypeptide containing a DUF246 domain.

A low nitrogen tolerance-modulating polypeptide can contain a C2 domain. The C2 domain is a Ca2+-dependent membrane-targeting module found in many cellular proteins involved in signal transduction or membrane trafficking C2 domains are unique among membrane targeting domains in that they typically show wide range of lipid selectivity for the major components of cell membranes, including phosphatidylserine and phosphatidylcholine. SEQ ID NO:982 sets forth the amino acid sequence of an *Arabidopsis* clone, identified herein as Ceres ME12970 (SEQ ID NO:982), that is predicted to encode a polypeptide containing an C2 domain.

A low nitrogen tolerance-modulating polypeptide can contain a Cpn60_TCP1 domain characteristic of polypeptides belonging to the TCP-1/cpn60 chaperonin family. This family includes members from the HSP60 chaperone family and the TCP-1 (T-complex protein) family. Chaperonins, a subfamily of molecular chaperones, are typically essential for the correct folding and assembly of polypeptides into oligomeric structures. Chaperonins are typically found in abundance in prokaryotes, chloroplasts and mitochondria. They are typically required for normal cell growth, and are stress-induced, acting to stabilize or protect disassembled polypeptides under heat-shock conditions. SEQ ID NO: 1054 sets forth the amino acid sequence of an *Arabidopsis* clone, identified herein as Ceres ME13021 (SEQ ID NO: 1054), that is predicted to encode a polypeptide containing a Cpn60_TCP1 domain.

A low nitrogen tolerance-modulating polypeptide can contain a zf-C2H2 domain characteristic of a C2H2 zinc finger domain polypeptide. Zinc finger domains are nucleic acid-binding protein structures composed of 25 to 30 amino-acid residues including 2 conserved Cys and 2 conserved His residues in a C-2-C-12-H-3-H type motif. The 12 residues separating the second Cys and the first His are mainly polar and basic, implicating this region in particular in nucleic acid binding. They have the ability to bind to both RNA and DNA, and it has been suggested that the zinc finger may thus represent the original nucleic acid binding protein. It has also been suggested that a Zn-centered domain could be used in a protein interaction, e.g. in protein kinase C. Many classes of zinc fingers are characterized according to the number and positions of the histidine and cysteine residues involved in the zinc atom coordination. In C2H2 zinc finger class, the first pair of zinc coordinating residues are cysteines, while the second pair are histidines. The motif is also present in SEQ ID NO:1116, which sets forth the amino acid sequence of an *Arabidopsis* clone, identified herein as Ceres ME13087 (SEQ ID NO:1116), that is predicted to encode a polypeptide containing a zf-C2H2 domain.

A low nitrogen tolerance-modulating polypeptide can contain a zein domain characteristic of polypeptides belonging to the zein family of seed storage proteins. SEQ ID NO:1159, which sets forth the amino acid sequence of an *Arabidopsis* clone, identified herein as Ceres ME13107 (SEQ ID NO: 1159), that is predicted to encode a polypeptide containing a zein domain.

A low nitrogen tolerance-modulating polypeptide can contain a snf7 domain characteristic of polypeptides belonging to a family of eukaryotic proteins related to yeast SNF7. SEQ ID NO:1185 sets forth the amino acid sequence of an *Arabidopsis* clone, identified herein as Ceres ME13110 (SEQ ID NO:1185), that is predicted to encode a polypeptide containing a snf7 domain.

A low nitrogen tolerance-modulating polypeptide can contain an HhH-GPD domain characteristic of polypeptides belonging to the HhH-GPD base excision DNA repair protein superfamily. Members of the HhH-GPD base excision DNA repair protein superfamily contain helix-hairpin-helix and Gly/Pro rich loop followed by a conserved aspartate. This domain is found in a diverse range of structurally related DNA repair proteins. The domain is also present in SEQ ID NO:1194 sets forth the amino acid sequence of an *Arabidopsis* clone, identified herein as Ceres ME13125

(SEQ ID NO:1194), that is predicted to encode a polypeptide containing an HhH-GPD domain.

A low nitrogen tolerance-modulating polypeptide can contain an Arf domain characteristic of polypeptides belonging to the ADP-ribosylation factor family. The small ADP ribosylation factor (Arf) GTP-binding proteins are major regulators of vesicle biogenesis in intracellular traffic. They are the founding members of a growing family that includes Arl (Arf-like), Arp (Arf-related proteins) and the remotely related Sar (Secretion-associated and Ras-related) proteins. Arf proteins cycle between inactive GDP-bound and active GTP-bound forms that bind selectively to effectors. The classical structural GDP/GTP switch is characterized by conformational changes at the so-called switch 1 and switch 2 regions, which bind tightly to the gamma-phosphate of GTP but poorly or not at all to the GDP nucleotide. Structural studies of Arf1 and Arf6 have revealed that although these proteins feature the switch 1 and 2 conformational changes, they depart from other small GTP-binding proteins in that they use an additional, unique switch to propagate structural information from one side of the protein to the other. The GDP/GTP structural cycles of human Arf1 and Arf6 feature a unique conformational change that affects the beta2beta3 strands connecting switch 1 and switch 2 (interswitch) and also the amphipathic helical N-terminus. SEQ ID NO: 1210 sets forth the amino acid sequence of an *Arabidopsis* clone, identified herein as Ceres ME13149 (SEQ ID NO:1210), that is predicted to encode a polypeptide containing an Arf domain.

A low nitrogen tolerance-modulating polypeptide can contain a Pyridoxal_deC domain characteristic of pyridoxal-dependent decarboxylase polypeptide. Pyridoxal-dependent decarboxylases typically share regions of sequence similarity, particularly in the vicinity of a conserved lysine residue, which provides the attachment site for the pyridoxal-phosphate (PLP) group. Pyridoxal phosphate is the active form of vitamin B6 (pyridoxine or pyridoxal). PLP is a versatile catalyst, acting as a coenzyme in a multitude of reactions, including decarboxylation, deamination and transamination. PLP-dependent enzymes, including pyridoxal-dependent decarboxylases, are involved in the biosynthesis of amino acids and amino acid-derived metabolites, but they are also found in the biosynthetic pathways of amino sugars and in the synthesis or catabolism of neurotransmitter. SEQ ID NO:1302 sets forth the amino acid sequence of an *Arabidopsis* clone, identified herein as Ceres ME13153 (SEQ ID NO:1302), that is predicted to encode a polypeptide containing a Pyridoxal_deC domain.

A low nitrogen tolerance-modulating polypeptide can contain a Cyclin_C domain, which is characteristic to the C-terminal domain of polypeptides belonging to the Cyclin family. Cyclins are eukaryotic proteins that play an active role in controlling nuclear cell division cycles, and regulate cyclin dependent kinases (CDKs). Cyclins, together with the p34 (cdc2) or cdk2 kinases, form the Maturation Promoting Factor (MPF). There are two main groups of cyclins, G1/S cyclins, which play a role in the control of the cell cycle at the G1/S (start) transition, and G2/M cyclins, which play a role in the control of the cell cycle at the G2/M (mitosis) transition. G2/M cyclins accumulate steadily during G2 and are abruptly destroyed as cells exit from mitosis (at the end of the M-phase). Cyclins typically contain two domains of similar all-alpha fold, of which this family corresponds with the C-terminal domain.

A low nitrogen tolerance-modulating polypeptide can contain a Cyclin_N domain, which defines the N-terminal domain of polypeptides belonging to the Cyclin family. SEQ ID NO: 1342 sets forth the amino acid sequence of an *Arabidopsis* clone, identified herein as Ceres ME13177 (SEQ ID NO: 1342), that is predicted to encode a polypeptide containing a Cyclin_C domain and a Cyclin_N domain A low nitrogen tolerance-modulating polypeptide can contain a DUF1442 domain. SEQ ID NO:1463, which sets forth the amino acid sequence of an *Arabidopsis* clone, identified herein as Ceres ME16546 (SEQ ID NO:1463), that is predicted to encode a polypeptide containing a DUF1442 domain.

A low nitrogen tolerance-modulating polypeptide can contain an HLH domain characteristic of polypeptides belonging to the Helix-loop-helix DNA-binding domain superfamily. Basic helix-loop-helix proteins (bHLH) are a group of eukaryotic transcription factors that can exert a determinative influence in a variety of developmental pathways. These transcription factors are characterized by a conserved bHLH domain that mediates specific dimerization. They can facilitate the conversion of inactive monomers to trans-activating dimers at appropriate stages of development. Members of this superfamily can be classified into discrete categories according to dimerization, DNA binding and expression characteristics. SEQ ID NO:1537 sets forth the amino acid sequence of an *Arabidopsis* clone, identified herein as Ceres ME18275 (SEQ ID NO:1537), that is predicted to encode a polypeptide containing an HLH domain.

A low nitrogen tolerance-modulating polypeptide can contain a CRAL_TRIO domain characteristic of the C-terminal of retinaldehyde/retinal-binding protein family. In animals, retinaldehyde/retinal-binding proteins may be functional components of the visual cycle. Cellular retinaldehyde-binding protein (CRALBP) may function as a substrate carrier protein that modulates interaction of these retinoids with visual cycle enzymes. The multidomain protein Trio can bind the LAR transmembrane tyrosine phosphatase, contains a protein kinase domain, and has separate rac-specific and rho-specific guanine nucleotide exchange factor domains. Trio is a multifunctional protein that can integrate and amplify signals involved in coordinating actin remodeling, which is necessary for cell migration and growth. Other members of the family are transfer proteins that include, guanine nucleotide exchange factor that may function as an effector of RAC1, phosphatidylinositol/phosphatidylcholine transfer protein that is required for the transport of secretory proteins from the Golgi complex and alpha-tocopherol transfer protein that enhances the transfer of the ligand between separate membranes.

A low nitrogen tolerance-modulating polypeptide can contain a CRAL_TRIO_N which defines the N-terminal of retinaldehyde/retinal-binding protein family.

A low nitrogen tolerance-modulating polypeptide can contain an EMP24_GP25L domain characteristic of polypeptides belonging to the emp24/gp25L/p24 family/GOLD gene family. Members of this family are implicated in bringing cargo forward from the ER and binding to coat proteins by their cytoplasmic domains. This domain corresponds closely to the beta-strand rich GOLD domain. The GOLD domain is often found combined with lipid- or membrane-association domains. p24 proteins are major membrane components of COPI- and COPII-coated vesicles and are implicated in cargo selectivity of ER to Golgi transport. Multiple members of the p24 family are found in all eukaryotes, from yeast to mammals. Members of the p24 family are type I membrane proteins with a signal peptide at the amino terminus, a lumenal coiled-coil (extracytosolic) domain, a single transmembrane domain with conserved amino acids, and a short cytoplasmic tail. They may be grouped into at least three subfamilies based on primary sequence. One subfamily comprises yeast Emp24p and mammalian p24A. Another subfamily comprises yeast Erv25p and mammalian Tmp21, and the third subfamily comprises mammalian gp25L proteins. SEQ ID NO:1554 sets forth the amino acid sequence of an *Arabidopsis* clone, identified herein as Ceres ME18924 (SEQ ID NO:1554), that is predicted to encode a polypeptide containing a CRAL_TRIO domain, a CRAL_TRIO_N domain, and a EMP24_GP25L domain.

A low nitrogen tolerance-modulating polypeptide can contain a Pyrophosphatase domain, which is predicted to be characteristic of an inorganic pyrophosphatase (PPase). PPase is the enzyme responsible for the hydrolysis of pyrophosphate (PPi) which is formed principally as the product of the many biosynthetic reactions that utilize ATP. PPases may require the presence of divalent metal cations, with magnesium conferring the highest activity. Among other residues, a lysine has been postulated to be part of or close to the active site. The sequences of PPases share some regions of similarities, among which is a region that contains three conserved aspartates that are involved in the binding of cations. SEQ ID NO:1577 sets forth the amino acid sequence of an *Arabidopsis* clone, identified herein as Ceres ME19182 (SEQ ID NO:1577), that is predicted to encode a polypeptide containing a Pyrophosphatase domain.

A low nitrogen tolerance-modulating polypeptide can contain a bZIP_1 domain characteristic of polypeptides belonging to the superfamily of basic ZIP transcription factors. Members of the eukaryotic bZIP transcription factor superfamily contain a basic region mediating sequence-specific DNA-binding followed by a leucine zipper region required for dimerization. SEQ ID NO: 1437 sets forth the amino acid sequence of an *Arabidopsis* clone, identified herein as Ceres ME20628 (SEQ ID NO: 1437), that is predicted to encode a polypeptide containing a bZIP_1 domain.

B. Functional Homologs Identified by Reciprocal BLAST

In some embodiments, one or more functional homologs of a reference low nitrogen tolerance-modulating polypeptide defined by one or more of the Pfam descriptions indicated above are suitable for use as low nitrogen tolerance-modulating polypeptides. A functional homolog is a polypeptide that has sequence similarity to a reference polypeptide, and that carries out one or more of the biochemical or physiological function(s) of the reference polypeptide. A functional homolog and the reference polypeptide may be natural occurring polypeptides, and the sequence similarity may be due to convergent or divergent evolutionary events. As such, functional homologs are sometimes designated in the literature as homologs, or orthologs, or paralogs. Variants of a naturally occurring functional homolog, such as polypeptides encoded by mutants of a wild type coding sequence, may themselves be functional homologs. Functional homologs can also be created via site-directed mutagenesis of the coding sequence for a low nitrogen tolerance-modulating polypeptide, or by combining domains from the coding sequences for different naturally-occurring low nitrogen tolerance-modulating polypeptides ("domain swapping"). The term "functional homolog" is sometimes applied to the nucleic acid that encodes a functionally homologous polypeptide.

Functional homologs can be identified by analysis of nucleotide and polypeptide sequence alignments. For example, performing a query on a database of nucleotide or polypeptide sequences can identify homologs of low nitrogen tolerance-modulating polypeptides. Sequence analysis can involve BLAST, Reciprocal BLAST, or PSI-BLAST analysis of nonredundant databases using a low nitrogen tolerance-modulating polypeptide amino acid sequence as the reference sequence. Amino acid sequence is, in some instances, deduced from the nucleotide sequence. Those polypeptides in the database that have greater than 20% sequence identity are candidates for further evaluation for suitability as a low nitrogen tolerance-modulating polypeptide. Amino acid sequence similarity allows for conservative amino acid substitutions, such as substitution of one hydrophobic residue for another or substitution of one polar residue for another. If desired, manual inspection of such candidates can be carried out in order to narrow the number of candidates to be further evaluated. Manual inspection can be performed by selecting those candidates that appear to have domains present in low nitrogen tolerance-modulating polypeptides, e.g., conserved functional domains.

Conserved regions can be identified by locating a region within the primary amino acid sequence of a low nitrogen tolerance-modulating polypeptide that is a repeated sequence, forms some secondary structure (e.g., helices and beta sheets), establishes positively or negatively charged domains, or represents a protein motif or domain. See, e.g., the Pfam web site describing consensus sequences for a variety of protein motifs and domains on the World Wide Web at sanger.ac.uk/Software/Pfam/ and pfam.janelia.org/. A description of the information included at the Pfam database is described in Sonnhammer et al. (1998) *Nucl. Acids Res.*, 26:320-322; Sonnhammer et al. (1997) *Proteins*, 28:405-420; and Bateman et al. (1999) *Nucl. Acids Res.*, 27:260-262. Conserved regions also can be determined by aligning sequences of the same or related polypeptides from closely related species. Closely related species preferably are from the same family. In some embodiments, alignment of sequences from two different species is adequate.

Typically, polypeptides that exhibit at least about 40% amino acid sequence identity are useful to identify conserved regions. Conserved regions of related polypeptides exhibit at least 20% amino acid sequence identity (e.g., at least 50%, at least 60%, at least 70%, at least 80%, or at least 90% amino acid sequence identity). In some embodiments, a conserved region exhibits at least 92%, 94%, 96%, 98%, or 99% amino acid sequence identity.

Examples of amino acid sequences of functional homologs of the polypeptide set forth in SEQ ID NO:3 are provided in FIG. 1 and in the Sequence Listing. Such functional homologs include SEQ ID NO:4, SEQ ID NO:6, SEQ ID NO:8, SEQ ID NO:10, SEQ ID NO:12, SEQ ID NO:14, SEQ ID NO:16, SEQ ID NO:17, SEQ ID NO:19, SEQ ID NO:20, SEQ ID NO:21, SEQ ID NO:22, SEQ ID NO:24, SEQ ID NO:25, SEQ ID NO:27, SEQ ID NO:29, SEQ ID NO:31, SEQ ID NO:33, SEQ ID NO:35, SEQ ID NO:36, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, and SEQ ID NO:47. In some cases, a functional homolog of SEQ ID NO:3 has an amino acid sequence with at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:3.

Examples of amino acid sequences of functional homologs of the polypeptide set forth in SEQ ID NO:49 are provided in FIG. 2 and in the Sequence Listing. Such functional homologs include SEQ ID NO:51, SEQ ID NO:53, SEQ ID NO:55, SEQ ID NO:56, SEQ ID NO:58, SEQ ID NO:60, SEQ ID NO:62, SEQ ID NO:63, SEQ ID NO:64, SEQ ID NO:65, SEQ ID NO:67, SEQ ID NO:69, SEQ ID NO:70, SEQ ID NO:71, SEQ ID NO:72, SEQ ID NO:73, and SEQ ID NO:75. In some cases, a functional homolog of SEQ ID NO:49 has an amino acid sequence with at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:49.

Examples of amino acid sequences of functional homologs of the polypeptide set forth in SEQ ID NO:77 are provided in FIG. 3 and in the Sequence Listing. Such functional homologs include SEQ ID NO:78, SEQ ID NO:80, SEQ ID NO:82, SEQ ID NO:84, SEQ ID NO:85, SEQ ID NO:87, SEQ ID NO:88, SEQ ID NO:90, SEQ ID NO:92, SEQ ID NO:93, SEQ ID NO:95, and CeresAnnot: 839064 (SEQ ID NO:1479). In some cases, a functional homolog of SEQ ID NO:77 has an amino acid sequence with at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:77.

Examples of amino acid sequences of functional homologs of the polypeptide set forth in SEQ ID NO:100 are provided in FIG. 4 and in the Sequence Listing. Such functional homologs include SEQ ID NO:101, SEQ ID NO:102, SEQ ID NO:104, SEQ ID NO:106, SEQ ID NO:108, SEQ ID NO:110, SEQ ID NO:111, SEQ ID NO:113, SEQ ID NO:115, SEQ ID NO:116, SEQ ID NO:117, SEQ ID NO:118, SEQ ID NO:119, SEQ ID NO:120, SEQ ID NO:121, SEQ ID NO:122, SEQ ID NO:123, SEQ ID NO:125, SEQ ID NO:126, SEQ ID NO:128, SEQ ID NO:129, SEQ ID NO:130, SEQ ID NO:131, SEQ ID NO:132, SEQ ID NO:133, SEQ ID NO:134, SEQ ID NO:135, SEQ ID NO:137, SEQ ID NO:139, SEQ ID NO:141, SEQ ID NO:142, SEQ ID NO:144, SEQ ID NO:145, SEQ ID NO:146, SEQ ID NO:147, SEQ ID NO:148, SEQ ID NO:149, and SEQ ID NO:150. In some cases, a functional homolog of SEQ ID NO:100 has an amino acid sequence with at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:100.

Examples of amino acid sequences of functional homologs of the polypeptide set forth in SEQ ID NO:152 are provided in FIG. 5 and in the Sequence Listing. Such functional homologs include SEQ ID NO:154, SEQ ID NO:156, SEQ ID NO:158, SEQ ID NO:160, SEQ ID NO:162, and SEQ ID NO:164. In some cases, a functional homolog of SEQ ID NO:152 has an amino acid sequence with at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:152.

Examples of amino acid sequences of functional homologs of the polypeptide set forth in SEQ ID NO:166 are provided in FIG. 6 and in the Sequence Listing. Such functional homologs include SEQ ID NO:168, SEQ ID NO:170, SEQ ID NO:172, SEQ ID NO:174, SEQ ID NO:177, SEQ ID NO:179, SEQ ID NO:181, SEQ ID NO:182, SEQ ID NO:183, and SEQ ID NO:184. In some cases, a functional homolog of SEQ ID NO:166 has an amino acid sequence with at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:166.

Examples of amino acid sequences of functional homologs of the polypeptide set forth in SEQ ID NO:186 are provided in FIG. 7 and in the Sequence Listing. Such functional homologs include SEQ ID NO:188, SEQ ID NO:190, SEQ ID NO:191, SEQ ID NO:193, SEQ ID NO:194, SEQ ID NO:196, SEQ ID NO:197, SEQ ID NO:199, SEQ ID NO:201, SEQ ID NO:203, SEQ ID NO:204, SEQ ID NO:205, and SEQ ID NO:206. In some cases, a functional homolog of SEQ ID NO:186 has an amino acid sequence with at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:186.

Examples of amino acid sequences of functional homologs of the polypeptide set forth in SEQ ID NO:208 are provided in FIG. 8 and in the Sequence Listing. Such functional homologs include SEQ ID NO:209, SEQ ID NO:210, SEQ ID NO:214, and SEQ ID NO:216. In some cases, a functional homolog of SEQ ID NO:208 has an amino acid sequence with at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:208.

Examples of amino acid sequences of functional homologs of the polypeptide set forth in SEQ ID NO:218 are provided in FIG. 9 and in the Sequence Listing. Such functional homologs include SEQ ID NO:220, SEQ ID NO:222, SEQ ID NO:223, SEQ ID NO:225, SEQ ID NO:227, SEQ ID NO:229, SEQ ID NO:230, SEQ ID NO:231, SEQ ID NO:232, SEQ ID NO:1039, SEQ ID NO:1049, and SEQ ID NO:1052. In some cases, a functional homolog of SEQ ID NO:218 has an amino acid sequence with at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:218.

Examples of amino acid sequences of functional homologs of the polypeptide set forth in SEQ ID NO:234 are provided in FIG. 10 and in the Sequence Listing. Such functional homologs include SEQ ID NO:236, SEQ ID NO:238, SEQ ID NO:239, SEQ ID NO:241, SEQ ID NO:242, SEQ ID NO:243, and SEQ ID NO:244. In some cases, a functional homolog of SEQ ID NO:234 has an amino acid sequence with at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:234.

Examples of amino acid sequences of functional homologs of the polypeptide set forth in SEQ ID NO:246 are provided in FIG. 11 and in the Sequence Listing. Such functional homologs include SEQ ID NO:248, SEQ ID NO:249, SEQ ID NO:251, SEQ ID NO:253, SEQ ID NO:255, SEQ ID NO:257, SEQ ID NO:259, SEQ ID NO:260, SEQ ID NO:262, SEQ ID NO:264, SEQ ID NO:265, SEQ ID NO:267, SEQ ID NO:268, SEQ ID NO:270, SEQ ID NO:272, SEQ ID NO:274, SEQ ID NO:276, SEQ ID NO:277, SEQ ID NO:279, SEQ ID NO:281, SEQ ID NO:283, SEQ ID NO:285, SEQ ID NO:286, SEQ ID NO:287, SEQ ID NO:288, SEQ ID NO:290, SEQ ID NO:291, SEQ ID NO:292, SEQ ID NO:293, SEQ ID NO:296, and SEQ ID NO:298. In some cases, a functional homolog of SEQ ID NO:246 has an amino acid sequence with at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:246.

Examples of amino acid sequences of functional homologs of the polypeptide set forth in SEQ ID NO:300 are provided in FIG. 12 and in the Sequence Listing. Such functional homologs include SEQ ID NO:302, SEQ ID NO:304, SEQ ID NO:306, SEQ ID NO:308, SEQ ID NO:310, SEQ ID NO:312, SEQ ID NO:314, SEQ ID NO:316, SEQ ID NO:318, SEQ ID NO:319, SEQ ID NO:320, SEQ ID NO:321, SEQ ID NO:322, SEQ ID NO:323, SEQ ID NO:325, SEQ ID NO:327, and SEQ ID NO:329. In some cases, a functional homolog of SEQ ID NO:300 has an amino acid sequence with at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:300.

Examples of amino acid sequences of functional homologs of the polypeptide set forth in SEQ ID NO:332 are provided in FIG. 13 and in the Sequence Listing. Such functional homologs include SEQ ID NO:332, SEQ ID NO:334, SEQ ID NO:335, SEQ ID NO:336, SEQ ID NO:338, SEQ ID NO:339, SEQ ID NO:341, SEQ ID NO:342, SEQ ID NO:343, SEQ ID NO:344, SEQ ID NO:345, SEQ ID NO:346, SEQ ID NO:347, SEQ ID NO:348, SEQ ID NO:349, SEQ ID NO:351, SEQ ID NO:352, SEQ ID NO:353, SEQ ID NO:354, SEQ ID NO:355, SEQ ID NO:356, SEQ ID NO:357, SEQ ID NO:358, SEQ ID NO:359, SEQ ID NO:360, SEQ ID NO:362, SEQ ID NO:363, SEQ ID NO:364, SEQ ID NO:365, SEQ ID NO:366, SEQ ID NO:2541, SEQ ID NO:2542, SEQ ID NO:2543, SEQ ID NO:2544, SEQ ID NO:2546, SEQ ID NO:2548, SEQ ID NO:2549, SEQ ID NO:2550, SEQ ID NO:2551, SEQ ID NO:2552, and SEQ ID NO:2553. In some cases, a functional homolog of SEQ ID NO:332 has an amino acid sequence with at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:332.

Examples of amino acid sequences of functional homologs of the polypeptide set forth in SEQ ID NO:368 are provided in FIG. 14 and in the Sequence Listing. Such functional homologs include SEQ ID NO:369, SEQ ID NO:370, SEQ ID NO:371, SEQ ID NO:372, SEQ ID NO:373, SEQ ID NO:374, SEQ ID NO:376, SEQ ID NO:378, SEQ ID NO:380, SEQ ID NO:382, SEQ ID NO:384, SEQ ID NO:386, SEQ ID NO:388, SEQ ID NO:390, SEQ ID NO:392, SEQ ID NO:394, SEQ ID NO:396, SEQ ID NO:398, SEQ ID NO:399, SEQ ID NO:401, SEQ ID NO:403, SEQ ID NO:404, SEQ ID NO:406, SEQ ID NO:408, SEQ ID NO:410, SEQ ID NO:412, SEQ ID NO:414, SEQ ID NO:416, SEQ ID NO:418, SEQ ID NO:419, SEQ ID NO:420, SEQ ID NO:422, SEQ ID NO:423, SEQ ID NO:425, SEQ ID NO:427, SEQ ID NO:428, SEQ ID NO:430, SEQ ID NO:432, SEQ ID NO:433, SEQ ID NO:434, SEQ ID NO:435, SEQ ID NO:436, SEQ ID NO:437, SEQ ID NO:438, SEQ ID NO:439, SEQ ID NO:440, SEQ ID NO:441, SEQ ID NO:444, SEQ ID NO:445, SEQ ID NO:446, SEQ ID NO:447, SEQ ID NO:448, SEQ ID NO:449, SEQ ID NO:450, SEQ ID NO:451, SEQ ID NO:452, SEQ ID NO:453, SEQ ID NO:454, SEQ ID NO:455, SEQ ID NO:456, SEQ ID NO:458, SEQ ID NO:459, SEQ ID NO:461, SEQ ID NO:463, SEQ ID NO:465, SEQ ID NO:467, SEQ ID NO:469, SEQ ID NO:471, SEQ ID NO:473, SEQ ID NO:474, SEQ ID NO:475, SEQ ID NO:477, SEQ ID NO:479, SEQ ID NO:481, SEQ ID NO:483, SEQ ID NO:485, SEQ ID NO:487, SEQ ID NO:488, SEQ ID NO:489, SEQ ID NO:490, SEQ ID NO:491, SEQ ID NO:492, SEQ ID NO:494, SEQ ID NO:495, SEQ ID NO:496, SEQ ID NO:497, SEQ ID NO:498, SEQ ID NO:499, SEQ ID NO:500, SEQ ID NO:501, SEQ ID NO:502, SEQ ID NO:504, SEQ ID NO:505, SEQ ID NO:506, SEQ ID NO:507, and SEQ ID NO:508. In some cases, a functional homolog of SEQ ID NO:368 has an amino acid sequence with at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:368.

Examples of amino acid sequences of functional homologs of the polypeptide set forth in SEQ ID NO:510 are provided in FIG. 15 and in the Sequence Listing. Such functional homologs include SEQ ID NO:511, SEQ ID NO:513, SEQ ID NO:515, SEQ ID NO:517, SEQ ID NO:521, SEQ ID NO:523, SEQ ID NO:525, SEQ ID NO:527, SEQ ID NO:529, SEQ ID NO:530, and SEQ ID NO:531. In some cases, a functional homolog of SEQ ID NO:510 has an amino acid sequence with at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:510.

Examples of amino acid sequences of functional homologs of the polypeptide set forth in SEQ ID NO:533 are provided in FIG. 16 and in the Sequence Listing. Such functional homologs include SEQ ID NO:535, SEQ ID NO:536, SEQ ID NO:538, SEQ ID NO:539, SEQ ID NO:541, SEQ ID NO:542, SEQ ID NO:543, SEQ ID NO:544, SEQ ID NO:545, SEQ ID NO:546, SEQ ID NO:547, SEQ ID NO:548, SEQ ID NO:550, SEQ ID NO:552, SEQ ID NO:553, and SEQ ID NO:554. In some cases, a functional homolog of SEQ ID NO:533 has an amino acid sequence with at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:533.

Examples of amino acid sequences of functional homologs of the polypeptide set forth in SEQ ID NO:558 are provided in FIG. 17 and in the Sequence Listing. Such functional homologs include SEQ ID NO:559, SEQ ID NO:560, SEQ ID NO:561, SEQ ID NO:562, SEQ ID NO:563, SEQ ID NO:564, SEQ ID NO:565, SEQ ID NO:566, SEQ ID NO:567, SEQ ID NO:569, SEQ ID NO:571, SEQ ID NO:572, SEQ ID NO:573, SEQ ID NO:575, SEQ ID NO:576, SEQ ID NO:577, SEQ ID NO:578, SEQ ID NO:579, SEQ ID NO:581, SEQ ID NO:583, SEQ ID NO:584, SEQ ID NO:585, SEQ ID NO:586, SEQ ID NO:588, SEQ ID NO:589, SEQ ID NO:590, and SEQ ID NO:591. In some cases, a functional homolog of SEQ ID NO:558 has an amino acid sequence with at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:558.

Examples of amino acid sequences of functional homologs of the polypeptide set forth in SEQ ID NO:593 are provided in FIG. 18 and in the Sequence Listing. Such functional homologs include SEQ ID NO:595, SEQ ID NO:597, SEQ ID NO:599, SEQ ID NO:601, SEQ ID NO:603, SEQ ID NO:605, SEQ ID NO:607, SEQ ID NO:609, SEQ ID NO:610, and SEQ ID NO:611. In some cases, a functional homolog of SEQ ID NO:593 has an amino acid sequence with at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:593.

Examples of amino acid sequences of functional homologs of the polypeptide set forth in SEQ ID NO:613 are provided in FIG. 19 and in the Sequence Listing. Such functional homologs include SEQ ID NO:615, SEQ ID NO:617, SEQ ID NO:618, SEQ ID NO:620, SEQ ID NO:622, SEQ ID NO:624, SEQ ID NO:626, SEQ ID NO:628, SEQ ID NO:630, SEQ ID NO:632, SEQ ID NO:634, SEQ ID NO:636, SEQ ID NO:638, SEQ ID NO:640, SEQ ID NO:642, SEQ ID NO:643, and SEQ ID NO:644. In some cases, a functional homolog of SEQ ID NO:613 has an amino acid sequence with at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:613.

Examples of amino acid sequences of functional homologs of the polypeptide set forth in SEQ ID NO:646 are provided in FIG. 20 and in the Sequence Listing. Such functional homologs include SEQ ID NO:648, SEQ ID NO:650, SEQ ID NO:652, SEQ ID NO:654, SEQ ID NO:656, SEQ ID NO:658, SEQ ID NO:660, SEQ ID NO:662, SEQ ID NO:664, SEQ ID NO:666, SEQ ID NO:668, SEQ ID NO:670, SEQ ID NO:672, SEQ ID NO:674, SEQ ID NO:676, SEQ ID NO:678, SEQ ID NO:679, SEQ ID NO:680, SEQ ID NO:681, SEQ ID NO:682, SEQ ID NO:683, and SEQ ID NO:685. In some cases, a functional homolog of SEQ ID NO:646 has an amino acid sequence with at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:646.

Examples of amino acid sequences of functional homologs of the polypeptide set forth in SEQ ID NO:687 are provided in FIG. 21 and in the Sequence Listing. Such functional homologs include SEQ ID NO:689, SEQ ID NO:691, SEQ ID NO:693, SEQ ID NO:694, SEQ ID NO:696, SEQ ID NO:697, SEQ ID NO:699, SEQ ID NO:701, SEQ ID NO:703, SEQ ID NO:705, SEQ ID NO:706, SEQ ID NO:708, SEQ ID NO:710, SEQ ID NO:712, SEQ ID NO:714, SEQ ID NO:716, SEQ ID NO:718, SEQ ID NO:720, SEQ ID NO:721, SEQ ID NO:722, SEQ ID NO:723, SEQ ID NO:724, SEQ ID NO:725, SEQ ID NO:726, SEQ ID NO:727, and SEQ ID NO:728. In some cases, a functional homolog of SEQ ID NO:687 has an amino acid sequence with at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:687.

Examples of amino acid sequences of functional homologs of the polypeptide set forth in SEQ ID NO:730 are provided in FIG. 22 and in the Sequence Listing. Such functional homologs include SEQ ID NO:732, SEQ ID NO:733, SEQ ID NO:735, SEQ ID NO:737, SEQ ID NO:738, and SEQ ID NO:742. In some cases, a functional homolog of SEQ ID NO:730 has an amino acid sequence with at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:730.

Examples of amino acid sequences of functional homologs of the polypeptide set forth in SEQ ID NO:746 are provided in FIG. 23 and in the Sequence Listing. Such functional homologs include SEQ ID NO:748, SEQ ID NO:750, SEQ ID NO:751, SEQ ID NO:753, SEQ ID NO:755, SEQ ID NO:757, SEQ ID NO:758, SEQ ID NO:760, SEQ ID NO:761, SEQ ID NO:762, SEQ ID NO:763, SEQ ID NO:765, and SEQ ID NO:767. In some cases, a functional homolog of SEQ ID NO:746 has an amino acid sequence with at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:746.

Examples of amino acid sequences of functional homologs of the polypeptide set forth in SEQ ID NO:769 are provided in FIG. 24 and in the Sequence Listing. Such functional homologs include SEQ ID NO:771, SEQ ID NO:773, SEQ ID NO:775, SEQ ID NO:777, SEQ ID NO:779, SEQ ID NO:781, SEQ ID NO:783, SEQ ID NO:785, SEQ ID NO:787, SEQ ID NO:789, and SEQ ID NO:790. In some cases, a functional homolog of SEQ ID NO:769 has an amino acid sequence with at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:769.

Examples of amino acid sequences of functional homologs of the polypeptide set forth in SEQ ID NO:792 are provided in FIG. 25 and in the Sequence Listing. Such functional homologs include SEQ ID NO:794, SEQ ID NO:796, SEQ ID NO:798, SEQ ID NO:799, SEQ ID NO:801, SEQ ID NO:803, SEQ ID NO:805, SEQ ID NO:807, SEQ ID NO:808, SEQ ID NO:810, SEQ ID NO:812, SEQ ID NO:814, SEQ ID NO:816, SEQ ID NO:818, SEQ ID NO:819, SEQ ID NO:820, SEQ ID NO:821, and SEQ ID NO:822. In some cases, a functional homolog of SEQ ID NO:792 has an amino acid sequence with at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:792.

Examples of amino acid sequences of functional homologs of the polypeptide set forth in SEQ ID NO:824 are provided in FIG. 26 and in the Sequence Listing. Such functional homologs include, but not limited to, SEQ ID NO:826, SEQ ID NO:1696, SEQ ID NO:1698, SEQ ID NO:1700, SEQ ID NO:1702, SEQ ID NO:1704, SEQ ID NO:1706, SEQ ID NO:1708, SEQ ID NO:1710, SEQ ID NO:1711, SEQ ID NO:1713, SEQ ID NO:1714, SEQ ID NO:1715, and SEQ ID NO:1716. In some cases, a functional homolog of SEQ ID NO:824 has an amino acid sequence with at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:824.

Examples of amino acid sequences of functional homologs of the polypeptide set forth in SEQ ID NO:828 are provided in FIG. 27 and in the Sequence Listing. Such functional homologs include SEQ ID NO:830, SEQ ID NO:832, SEQ ID NO:834, SEQ ID NO:836, SEQ ID NO:837, SEQ ID NO:838, SEQ ID NO:839, SEQ ID NO:840, SEQ ID NO:842, SEQ ID NO:844, SEQ ID NO:845, SEQ ID NO:846, SEQ ID NO:847, SEQ ID NO:848, SEQ ID NO:849, SEQ ID NO:850, and SEQ ID NO:851. In some cases, a functional homolog of SEQ ID NO:828 has an amino acid sequence with at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:828.

Examples of amino acid sequences of functional homologs of the polypeptide set forth in SEQ ID NO:855 are provided in FIG. 28 and in the Sequence Listing. Such functional homologs include SEQ ID NO:856, SEQ ID NO:858, SEQ ID NO:860, SEQ ID NO:862, SEQ ID NO:864, SEQ ID NO:866, SEQ ID NO:868, SEQ ID NO:870, SEQ ID NO:872, SEQ ID NO:874, SEQ ID NO:876, SEQ ID NO:878, SEQ ID NO:880, SEQ ID NO:882, SEQ ID NO:884, SEQ ID NO:885, SEQ ID NO:886, SEQ ID NO:887, SEQ ID NO:888, and SEQ ID NO:889. In some cases, a functional homolog of SEQ ID NO:855 has an amino acid sequence with at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:855.

Examples of amino acid sequences of functional homologs of the polypeptide set forth in SEQ ID NO:891 are provided in FIG. 29 and in the Sequence Listing. Such functional homologs include SEQ ID NO:893, SEQ ID NO:894, SEQ ID NO:895, SEQ ID NO:896, SEQ ID NO:898, SEQ ID NO:900, SEQ ID NO:901, SEQ ID NO:902, SEQ ID NO:903, SEQ ID NO:904, SEQ ID NO:905, SEQ ID NO:907, SEQ ID NO:908, SEQ ID NO:909, SEQ ID NO:910, SEQ ID NO:911, SEQ ID NO:912, SEQ ID NO:913, SEQ ID NO:914, and SEQ ID NO:915. In some cases, a functional homolog of SEQ ID NO:891 has an amino acid sequence with at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:891.

Examples of amino acid sequences of functional homologs of the polypeptide set forth in SEQ ID NO:917 are provided in FIG. 30 and in the Sequence Listing. Such functional homologs include SEQ ID NO:919, SEQ ID NO:921, SEQ ID NO:923, SEQ ID NO:925, SEQ ID NO:927, SEQ ID NO:929, SEQ ID NO:931, SEQ ID NO:933, SEQ ID NO:935, SEQ ID NO:937, SEQ ID NO:939, and SEQ ID NO:940. In some cases, a functional homolog of SEQ ID NO:917 has an amino acid sequence with at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:917.

Examples of amino acid sequences of functional homologs of the polypeptide set forth in SEQ ID NO:944 are provided in FIG. 31 and in the Sequence Listing. Such functional homologs include SEQ ID NO:946, SEQ ID NO:947, SEQ ID NO:948, SEQ ID NO:950, SEQ ID NO:952, SEQ ID NO:954, SEQ ID NO:956, SEQ ID NO:958, SEQ ID NO:960, SEQ ID NO:962, SEQ ID NO:964, SEQ ID NO:966, SEQ ID NO:967, SEQ ID NO:968, SEQ ID NO:969, SEQ ID NO:970, SEQ ID NO:972, and SEQ ID NO:974. In some cases, a functional homolog of SEQ ID NO:944 has an amino acid sequence with at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:944.

Examples of amino acid sequences of functional homologs of the polypeptide set forth in SEQ ID NO:976 are provided in FIG. 32 and in the Sequence Listing. Such functional homologs include, but not limited to, SEQ ID NO:978 and SEQ ID NO:980. In some cases, a functional homolog of SEQ ID NO:976 has an amino acid sequence with at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:976.

Examples of amino acid sequences of functional homologs of the polypeptide set forth in SEQ ID NO:982 are provided in FIG. 33 and in the Sequence Listing. Such functional homologs include SEQ ID NO:984, SEQ ID NO:985, SEQ ID NO:986, SEQ ID NO:987, SEQ ID NO:988, SEQ ID NO:989, SEQ ID NO:990, SEQ ID NO:991, SEQ ID NO:992, SEQ ID NO:993, SEQ ID NO:995, SEQ ID NO:996, SEQ ID NO:998, SEQ ID NO:1000, SEQ ID NO:1001, SEQ ID NO:1003, SEQ ID NO:1005, SEQ ID NO:1007, SEQ ID NO:1008, SEQ ID NO:1009, SEQ ID NO:1011, SEQ ID NO:1013, SEQ ID NO:1015, SEQ ID NO:1016, SEQ ID NO:1018, SEQ ID NO:1019, SEQ ID NO:1021, SEQ ID NO:1023, SEQ ID NO:1025, SEQ ID NO:1026, SEQ ID NO:1027, SEQ ID NO:1028, SEQ ID NO:1029, SEQ ID NO:1030, SEQ ID NO:1031, SEQ ID NO:1032, and SEQ ID NO:1033. In some cases, a functional homolog of SEQ ID NO:982 has an amino acid sequence with at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:982.

Examples of amino acid sequences of functional homologs of the polypeptide set forth in SEQ ID NO:1054 are provided in FIG. 34 and in the Sequence Listing. Such functional homologs include SEQ ID NO:1055, SEQ ID NO:1057, SEQ ID NO:1058, SEQ ID NO:1059, SEQ ID NO:1061, SEQ ID NO:1063, SEQ ID NO:1065, SEQ ID NO:1067, SEQ ID NO:1068, SEQ ID NO:1070, SEQ ID NO:1071, SEQ ID NO:1072, SEQ ID NO:1074, SEQ ID NO:1075, SEQ ID NO:1076, SEQ ID NO:1077, SEQ ID NO:1078, SEQ ID NO:1080, SEQ ID NO:1082, SEQ ID NO:1083, SEQ ID NO:1085, SEQ ID NO:1086, SEQ ID NO:1087, SEQ ID NO:1088, SEQ ID NO:1089, SEQ ID NO:1090, SEQ ID NO:1091, SEQ ID NO:1092, SEQ ID NO:1093, SEQ ID NO:1094, SEQ ID NO:1095, and SEQ ID NO:1097. In some cases, a functional homolog of SEQ ID NO:1054 has an amino acid sequence with at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:1054.

Examples of amino acid sequences of functional homologs of the polypeptide set forth in SEQ ID NO:1099 are provided in FIG. 35 and in the Sequence Listing. Such functional homologs include SEQ ID NO:1101, SEQ ID NO:1103, SEQ ID NO:1104, SEQ ID NO:1105, SEQ ID NO:1106, SEQ ID NO:1108, SEQ ID NO:1109, and SEQ ID NO:1110. In some cases, a functional homolog of SEQ ID NO:1099 has an amino acid sequence with at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:1099.

Examples of amino acid sequences of functional homologs of the polypeptide set forth in SEQ ID NO:1112 are provided in FIG. 36 and in the Sequence Listing. Such functional homologs include SEQ ID NO:1113 and SEQ ID NO:1114. In some cases, a functional homolog of SEQ ID NO:1112 has an amino acid sequence with at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:1112.

Examples of amino acid sequences of functional homologs of the polypeptide set forth in SEQ ID NO:1116 are provided in FIG. 37 and in the Sequence Listing. Such functional homologs include SEQ ID NO:1118, SEQ ID NO:1120, SEQ ID NO:1122, SEQ ID NO:1123, SEQ ID NO:1125, SEQ ID NO:1126, SEQ ID NO:1128, SEQ ID NO:1129, SEQ ID NO:1131, SEQ ID NO:1132, SEQ ID NO:1133, SEQ ID NO:1134, SEQ ID NO:1136, SEQ ID NO:1138, SEQ ID NO:1140, SEQ ID NO:1141, SEQ ID NO:1142, SEQ ID NO:1143, SEQ ID NO:1144, SEQ ID NO:1145, SEQ ID NO:1147, SEQ ID NO:1149, SEQ ID NO:1151, SEQ ID NO:1153, and SEQ ID NO:1155. In some cases, a functional homolog of SEQ ID NO:1116 has an amino acid sequence with at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:1116.

Examples of amino acid sequences of functional homologs of the polypeptide set forth in SEQ ID NO:1159 are provided in FIG. 38 and in the Sequence Listing. Such functional homologs include SEQ ID NO:1161, SEQ ID NO:1162, SEQ ID NO:1163, and SEQ ID NO:1164. In some cases, a functional homolog of SEQ ID NO:1159 has an amino acid sequence with at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:1159.

Examples of amino acid sequences of functional homologs of the polypeptide set forth in SEQ ID NO:1166 are provided in FIG. 39 and in the Sequence Listing. Such functional homologs include SEQ ID NO:1167, SEQ ID NO:1169, SEQ ID NO:1171, SEQ ID NO:1173, SEQ ID NO:1175, SEQ ID NO:1177, SEQ ID NO:1179, SEQ ID NO:1180, SEQ ID NO:1182, and SEQ ID NO:1183. In some cases, a functional homolog of SEQ ID NO:1166 has an amino acid sequence with at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:1166.

Examples of amino acid sequences of functional homologs of the polypeptide set forth in SEQ ID NO:1185 are provided in FIG. 40 and in the Sequence Listing. Such functional homologs include SEQ ID NO:1187, SEQ ID NO:1189, SEQ ID NO:1190, SEQ ID NO:1191, and SEQ ID NO:1192. In some cases, a functional homolog of SEQ ID NO:1185 has an amino acid sequence with at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:1185.

Examples of amino acid sequences of functional homologs of the polypeptide set forth in SEQ ID NO:1194 are provided in FIG. 41 and in the Sequence Listing. Such functional homologs include SEQ ID NO:1196, SEQ ID NO:1198, SEQ ID NO:1200, SEQ ID NO:1202, SEQ ID NO:1203, SEQ ID NO:1204, SEQ ID NO:1205, SEQ ID NO:1206, SEQ ID NO:1207, and SEQ ID NO:1208. In some cases, a functional homolog of SEQ ID NO:1194 has an amino acid sequence with at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:1194.

Examples of amino acid sequences of functional homologs of the polypeptide set forth in SEQ ID NO:1210 are provided in FIG. 42 and in the Sequence Listing. Such functional homologs include SEQ ID NO:1211, SEQ ID NO:1213, SEQ ID NO:1215, SEQ ID NO:1216, SEQ ID NO:1218, SEQ ID NO:1220, SEQ ID NO:1222, SEQ ID NO:1224, SEQ ID NO:1226, SEQ ID NO:1228, SEQ ID NO:1229, SEQ ID NO:1230, SEQ ID NO:1232, SEQ ID NO:1233, SEQ ID NO:1234, SEQ ID NO:1235, SEQ ID NO:1236, SEQ ID NO:1237, SEQ ID NO:1238, SEQ ID NO:1239, SEQ ID NO:1240, SEQ ID NO:1241, SEQ ID NO:1242, SEQ ID NO:1243, SEQ ID NO:1244, SEQ ID NO:1245, SEQ ID NO:1246, SEQ ID NO:1247, SEQ ID NO:1248, SEQ ID NO:1249, SEQ ID NO:1251, SEQ ID NO:1253, SEQ ID NO:1255, SEQ ID NO:1257, SEQ ID NO:1259, SEQ ID NO:1261, SEQ ID NO:1263, SEQ ID NO:1264, SEQ ID NO:1265, SEQ ID NO:1266, SEQ ID NO:1267, SEQ ID NO:1268, SEQ ID NO:1269, SEQ ID NO:1270, SEQ ID NO:1271, and SEQ ID NO:1272. In some cases, a functional homolog of SEQ ID NO:1210 has an amino acid sequence with at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:1210.

Examples of amino acid sequences of functional homologs of the polypeptide set forth in SEQ ID NO:1274 are provided in FIG. 43 and in the Sequence Listing. Such functional homologs include SEQ ID NO:1276, SEQ ID NO:1278, SEQ ID NO:1280, SEQ ID NO:1281, SEQ ID NO:1282, SEQ ID NO:1284, SEQ ID NO:1285, SEQ ID NO:1287, SEQ ID NO:1289, SEQ ID NO:1291, SEQ ID NO:1293, SEQ ID NO:1294, SEQ ID NO:1295, SEQ ID NO:1296, SEQ ID NO:1297, SEQ ID NO:1298, and SEQ ID NO:1300. In some cases, a functional homolog of SEQ ID NO:1274 has an amino acid sequence with at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:1274.

Examples of amino acid sequences of functional homologs of the polypeptide set forth in SEQ ID NO:1302 are provided in FIG. 44 and in the Sequence Listing. Such functional homologs include SEQ ID NO:1303, SEQ ID NO:1305, SEQ ID NO:1307, SEQ ID NO:1309, SEQ ID NO:1311, SEQ ID NO:1312, SEQ ID NO:1313, SEQ ID NO:1314, SEQ ID NO:1315, SEQ ID NO:1317, SEQ ID NO:1318, SEQ ID NO:1319, SEQ ID NO:1320, SEQ ID NO:1321, SEQ ID NO:1322, SEQ ID NO:1323, SEQ ID NO:1324, SEQ ID NO:1325, SEQ ID NO:1326, SEQ ID NO:1327, SEQ ID NO:1328, SEQ ID NO:1330, SEQ ID NO:1331, SEQ ID NO:1333, SEQ ID NO:1334, SEQ ID NO:1335, SEQ ID NO:1336, SEQ ID NO:1337, SEQ ID NO:1338, SEQ ID NO:1339, and SEQ ID NO:1340. In some cases, a functional homolog of SEQ ID NO:1302 has an amino acid sequence with at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:1302.

Examples of amino acid sequences of functional homologs of the polypeptide set forth in SEQ ID NO:1342 are provided in FIG. 45 and in the Sequence Listing. Such functional homologs include SEQ ID NO:1344, SEQ ID NO:1346, SEQ ID NO:1348, SEQ ID NO:1350, SEQ ID NO:1352, SEQ ID NO:1354, SEQ ID NO:1355, SEQ ID NO:1357, SEQ ID NO:1358, SEQ ID NO:1360, SEQ ID NO:1361, SEQ ID NO:1362, SEQ ID NO:1363, SEQ ID NO:1364, SEQ ID NO:1366, SEQ ID NO:1367, SEQ ID NO:1369, SEQ ID NO:1370, SEQ ID NO:1371, SEQ ID NO:1372, SEQ ID NO:1373, SEQ ID NO:1374, SEQ ID NO:1375, SEQ ID NO:1376, SEQ ID NO:1377, SEQ ID NO:1378, SEQ ID NO:1379, SEQ ID NO:1380, SEQ ID NO:1381, SEQ ID NO:1382, and SEQ ID NO:1383. In some cases, a functional homolog of SEQ ID NO:1342 has an amino acid sequence with at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:1342.

Examples of amino acid sequences of functional homologs of the polypeptide set forth in SEQ ID NO:1385 are provided in FIG. 46 and in the Sequence Listing. Such functional homologs include SEQ ID NO:1387, SEQ ID NO:1389, SEQ ID NO:1390, SEQ ID NO:1391, SEQ ID NO:1393, SEQ ID NO:1394, SEQ ID NO:1395, SEQ ID NO:1396, SEQ ID NO:1398, SEQ ID NO:1400, SEQ ID NO:1401, SEQ ID NO:1402, SEQ ID NO:1403, SEQ ID NO:1404, SEQ ID NO:1405, and SEQ ID NO:1407. In some cases, a functional homolog of SEQ ID NO:1385 has an amino acid sequence with at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:1385.

Examples of amino acid sequences of functional homologs of the polypeptide set forth in SEQ ID NO:1409 are provided in FIG. 47 and in the Sequence Listing. Such functional homologs include SEQ ID NO:1411, SEQ ID NO:1413, SEQ ID NO:1415, SEQ ID NO:1417, SEQ ID NO:1418, SEQ ID NO:1419, SEQ ID NO:1421, SEQ ID NO:1423, SEQ ID NO:1424, SEQ ID NO:1425, and SEQ ID NO:1426. In some cases, a functional homolog of SEQ ID NO:1409 has an amino acid sequence with at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:1409.

Examples of amino acid sequences of functional homologs of the polypeptide set forth in SEQ ID NO:1428 are provided in FIG. 48 and in the Sequence Listing. Such functional homologs include SEQ ID NO:1430, SEQ ID NO:1432, SEQ ID NO:1434, SEQ ID NO:1436, SEQ ID NO:1439, SEQ ID NO:1442, SEQ ID NO:1444, SEQ ID NO:1446, SEQ ID NO:1448, SEQ ID NO:1450, SEQ ID NO:1452, SEQ ID NO:1453, SEQ ID NO:1454, SEQ ID NO:1455, SEQ ID NO:1456, SEQ ID NO:1457, SEQ ID NO:1458, and SEQ ID NO:1459. In some cases, a functional homolog of SEQ ID NO:1428 has an amino acid sequence with at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:1428.

Examples of amino acid sequences of functional homologs of the polypeptide set forth in SEQ ID NO:1463 are provided in FIG. 49 and in the Sequence Listing. Such functional homologs include SEQ ID NO:1465, SEQ ID NO:1467, SEQ ID NO:1469, SEQ ID NO:1471, SEQ ID NO:1473, SEQ ID NO:1474, SEQ ID NO:1475, SEQ ID NO:1476, and SEQ ID NO:1477. In some cases, a functional homolog of SEQ ID NO:1463 has an amino acid sequence with at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:1463.

Examples of amino acid sequences of functional homologs of the polypeptide set forth in SEQ ID NO:1491 are provided in FIG. 50 and in the Sequence Listing. Such functional homologs include SEQ ID NO:1493, SEQ ID NO:1495, SEQ ID NO:1497, SEQ ID NO:1499, SEQ ID NO:1501, SEQ ID NO:1503, SEQ ID NO:1504, SEQ ID NO:1505, SEQ ID NO:1506, and SEQ ID NO:1508. In some cases, a functional homolog of SEQ ID NO:1491 has an amino acid sequence with at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:1491.

Examples of amino acid sequences of functional homologs of the polypeptide set forth in SEQ ID NO:1510 are provided in FIG. 51 and in the Sequence Listing. Such functional homologs include SEQ ID NO:1512, SEQ ID NO:1514, SEQ ID NO:1516, SEQ ID NO:1518, SEQ ID NO:1520, SEQ ID NO:1522, and SEQ ID NO:1523. In some cases, a functional homolog of SEQ ID NO:1510 has an amino acid sequence with at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:1510.

Examples of amino acid sequences of functional homologs of the polypeptide set forth in SEQ ID NO:1525 are provided in FIG. 52 and in the Sequence Listing. Such functional homologs include SEQ ID NO:1527, SEQ ID NO:1529, SEQ ID NO:1530, SEQ ID NO:1532, SEQ ID NO:1534, and SEQ ID NO:1535. In some cases, a functional homolog of SEQ ID NO:1525 has an amino acid sequence with at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:1525.

Examples of amino acid sequences of functional homologs of the polypeptide set forth in SEQ ID NO:1537 are provided in FIG. 53 and in the Sequence Listing. Such functional homologs include SEQ ID NO:1539, SEQ ID NO:1540, SEQ ID NO:1541, SEQ ID NO:1543, SEQ ID NO:1545, SEQ ID NO:1547, SEQ ID NO:1548, SEQ ID NO:1550, SEQ ID NO:1552, SEQ ID NO:2386, SEQ ID NO:2388, SEQ ID NO:2390, SEQ ID NO:2391, and SEQ ID NO:2392. In some cases, a functional homolog of SEQ ID NO:1537 has an amino acid sequence with at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:1537.

Examples of amino acid sequences of functional homologs of the polypeptide set forth in SEQ ID NO:1554 are provided in FIG. 54 and in the Sequence Listing. Such functional homologs include SEQ ID NO:1555, SEQ ID NO:1557, SEQ ID NO:1559, SEQ ID NO:1561, SEQ ID NO:1563, SEQ ID NO:1565, SEQ ID NO:1567, SEQ ID NO:1569, SEQ ID NO:1571, SEQ ID NO:1572, SEQ ID NO:1573, SEQ ID NO:1574, and SEQ ID NO:1575. In some cases, a functional homolog of SEQ ID NO:1554 has an amino acid sequence with at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:1554.

Examples of amino acid sequences of functional homologs of the polypeptide set forth in SEQ ID NO:1577 are provided in FIG. 55 and in the Sequence Listing. Such functional homologs include SEQ ID NO:1035, SEQ ID NO:1036, SEQ ID NO:1037, SEQ ID NO:1040, SEQ ID NO:1041, SEQ ID NO:1043, SEQ ID NO:1044, SEQ ID NO:1046, SEQ ID NO:1047, SEQ ID NO:1048, SEQ ID NO:1050, SEQ ID NO:1440, SEQ ID NO:1480, SEQ ID NO:1481, SEQ ID NO:1482, SEQ ID NO:1483, SEQ ID NO:1484, SEQ ID NO:1485, SEQ ID NO:1486, SEQ ID NO:1487, SEQ ID NO:1488, SEQ ID NO:1578, SEQ ID NO:1580, SEQ ID NO:1582, SEQ ID NO:1584, SEQ ID NO:1586, SEQ ID NO:1588, SEQ ID NO:1590, SEQ ID NO:1592, SEQ ID NO:1594, SEQ ID NO:1596, SEQ ID NO:1598, SEQ ID NO:1599, SEQ ID NO:1601, SEQ ID NO:1602, SEQ ID NO:1605, SEQ ID NO:1607, SEQ ID NO:1608, SEQ ID NO:1609, SEQ ID NO:1611, SEQ ID NO:1613, SEQ ID NO:1615, SEQ ID NO:1617, SEQ ID NO:1619, SEQ ID NO:1621, SEQ ID NO:1622, SEQ ID NO:1623, SEQ ID NO:1624, SEQ ID NO:1625, SEQ ID NO:1627, SEQ ID NO:1629, SEQ ID NO:1631, SEQ ID NO:1633, SEQ ID NO:1635, SEQ ID NO:1637, SEQ ID NO:1639, SEQ ID NO:1643, SEQ ID NO:1645, SEQ ID NO:1648, SEQ ID NO:1649, SEQ ID NO:1651, and SEQ ID NO:1653. In some cases, a functional homolog of SEQ ID NO:1577 has an amino acid sequence with at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:1577.

Examples of amino acid sequences of functional homologs of the polypeptide set forth in SEQ ID NO:1437 are provided in FIG. 56 and in the Sequence Listing. Such functional homologs include SEQ ID NO:173, SEQ ID NO:212, SEQ ID NO:361, SEQ ID NO:421, SEQ ID NO:443, SEQ ID NO:740, SEQ ID NO:744, SEQ ID NO:942, and SEQ ID NO:1461. In some cases, a functional homolog of SEQ ID NO:1437 has an amino acid sequence with at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:1437.

Examples of amino acid sequences of functional homologs of the polypeptide set forth in SEQ ID NO:97 are provided in FIG. 57 and in the Sequence Listing. Such functional homologs include SEQ ID NO:2010, SEQ ID NO:2011, SEQ ID NO:2013, SEQ ID NO:2015, SEQ ID NO:2017. In some cases, a functional homolog of SEQ ID NO:97 has an amino acid sequence with at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:97.

The identification of conserved regions in a low nitrogen tolerance-modulating polypeptide facilitates production of variants of low nitrogen tolerance-modulating polypeptides. Variants of low nitrogen tolerance-modulating polypeptides typically have 10 or fewer conservative amino acid substitutions within the primary amino acid sequence, e.g., 7 or fewer conservative amino acid substitutions, 5 or fewer conservative amino acid substitutions, or between 1 and 5 conservative substitutions. A useful variant polypeptide can be constructed based on one of the alignments set forth in FIG. 1-57 and/or homologs identified in the Sequence Listing. Such a polypeptide includes the conserved regions, arranged in the order depicted in the Figure from amino-terminal end to carboxy-terminal end. Such a polypeptide may also include zero, one, or more than one amino acid in positions marked by dashes. When no amino acids are present at positions marked by dashes, the length of such a polypeptide is the sum of the amino acid residues in all conserved regions. When amino acids are present at all positions marked by dashes, such a polypeptide has a length that is the sum of the amino acid residues in all conserved regions and all dashes.

C. Functional Homologs Identified by HMMER

In some embodiments, useful low nitrogen tolerance-modulating polypeptides include those that fit a Hidden Markov Model based on the polypeptides set forth in any one of FIGS. 1-57. A Hidden Markov Model (HMM) is a statistical model of a consensus sequence for a group of functional homologs. See, Durbin et al. (1998) *Biological Sequence Analysis: Probabilistic Models of Proteins and Nucleic Acids*, Cambridge University Press, Cambridge, UK. An HMM is generated by the program HMMER 2.3.2 with default program parameters, using the sequences of the group of functional homologs as input. The multiple sequence alignment is generated by ProbCons (Do et al. (2005) Genome Res., 15(2):330-40) version 1.11 using a set of default parameters: -c, —consistency REPS of 2; -ir, —iterative-refinement REPS of 100; -pre, —pre-training REPS of 0. ProbCons is a public domain software program provided by Stanford University.

The default parameters for building an HMM (hmmbuild) are as follows: the default "architecture prior" (archpri) used by MAP architecture construction is 0.85, and the default cutoff threshold (idlevel) used to determine the effective sequence number is 0.62. HMMER 2.3.2 was released Oct. 3, 2003 under a GNU general public license, and is available from various sources on the World Wide Web such as hmmer.janelia.org; hmmer.wustl.edu; and fr.com/hmmer232/. Hmmbuild outputs the model as a text file.

The HMM for a group of functional homologs can be used to determine the likelihood that a candidate low nitrogen tolerance-modulating polypeptide sequence is a better fit to that particular HMM than to a null HMM generated using a group of sequences that are not structurally or functionally related. The likelihood that a candidate polypeptide sequence is a better fit to an HMM than to a null HMM is indicated by the HMM bit score, a number generated when the candidate sequence is fitted to the HMM profile using the HMMER hmmsearch program. The following default parameters are used when running hmmsearch: the default E-value cutoff (E) is 10.0, the default bit score cutoff (T) is negative infinity, the default number of sequences in a database (Z) is the real number of sequences in the database, the default E-value cutoff for the per-domain ranked hit list (domE) is infinity, and the default bit score cutoff for the per-domain ranked hit list (domT) is negative infinity. A high HMM bit score indicates a greater likelihood that the candidate sequence carries out one or more of the biochemical or physiological function(s) of the polypeptides used to generate the HMM. A high HMM bit score is at least 20, and often is higher. Slight variations in the HMM bit score of a particular sequence can occur due to factors such as the order in which sequences are processed for alignment by multiple sequence alignment algorithms such as the ProbCons program. Nevertheless, such HMM bit score variation is minor.

The low nitrogen tolerance-modulating polypeptides discussed below fit the indicated HMM with an HMM bit score greater than 20 (e.g., greater than 30, 40, 50, 60, 70, 80, 90, 100, 200, 300, 400, or 500). In some embodiments, the HMM bit score of a low nitrogen tolerance-modulating polypeptide discussed below is about 50%, 60%, 70%, 80%, 90%, or 95% of the HMM bit score of a functional homolog provided the Sequence Listing of this application. In some embodiments, a low nitrogen tolerance-modulating polypeptide discussed below fits the indicated HMM with an HMM bit score greater than 20, and has a domain indicative of a low nitrogen tolerance-modulating polypeptide. In some embodiments, a low nitrogen tolerance-modulating polypeptide discussed below fits the indicated HMM with an HMM bit score greater than 20, and has 70% or greater sequence identity (e.g., 75%, 80%, 85%, 90%, 95%, or 100% sequence identity) to an amino acid sequence shown in any one of FIGS. 1-58.

Examples of polypeptides are shown in the sequence listing that have HMM bit scores greater than 800 when fitted to an HMM generated from the amino acid sequences set forth in FIG. 1 are identified in the Sequence Listing of this application. Such polypeptides include SEQ ID NO:3, SEQ ID NO:4, SEQ ID NO:6, SEQ ID NO:8, SEQ ID NO:10, SEQ ID NO:12, SEQ ID NO:14, SEQ ID NO:16, SEQ ID NO:17, SEQ ID NO:19, SEQ ID NO:20, SEQ ID NO:21, SEQ ID NO:22, SEQ ID NO:24, SEQ ID NO:25, SEQ ID NO:27, SEQ ID NO:29, SEQ ID NO:31, SEQ ID NO:33, SEQ ID NO:35, SEQ ID NO:36, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, and SEQ ID NO:47.

Examples of polypeptides are shown in the sequence listing that have HMM bit scores greater than 150 when fitted to an HMM generated from the amino acid sequences set forth in FIG. 2 are identified in the Sequence Listing of this application. Such polypeptides include SEQ ID NO:49, SEQ ID NO:51, SEQ ID NO:53, SEQ ID NO:55, SEQ ID NO:56, SEQ ID NO:58, SEQ ID NO:60, SEQ ID NO:62, SEQ ID NO:63, SEQ ID NO:64, SEQ ID NO:65, SEQ ID NO:67, SEQ ID NO:69, SEQ ID NO:70, SEQ ID NO:71, SEQ ID NO:72, SEQ ID NO:73, and SEQ ID NO:75.

Examples of polypeptides are shown in the sequence listing that have HMM bit scores greater than 540 when fitted to an HMM generated from the amino acid sequences set forth in FIG. 3 are identified in the Sequence Listing of this application. Such polypeptides include SEQ ID NO:77, SEQ ID NO:78, SEQ ID NO:80, SEQ ID NO:82, SEQ ID NO:84, SEQ ID NO:85, SEQ ID NO:87, SEQ ID NO:88, SEQ ID NO:90, SEQ ID NO:92, SEQ ID NO:93, SEQ ID NO:95, and SEQ ID NO:1479.

Examples of polypeptides are shown in the sequence listing that have HMM bit scores greater than 210 when fitted to an HMM generated from the amino acid sequences set forth in FIG. 4 are identified in the Sequence Listing of this application. Such polypeptides include SEQ ID NO:100, SEQ ID NO:101, SEQ ID NO:102, SEQ ID NO:104, SEQ ID NO:106, SEQ ID NO:108, SEQ ID NO:110, SEQ ID NO:111, SEQ ID NO:113, SEQ ID NO:115, SEQ ID NO:116, SEQ ID NO:117, SEQ ID NO:118, SEQ ID NO:119, SEQ ID NO:120, SEQ ID NO:121, SEQ ID NO:122, SEQ ID NO:123, SEQ ID NO:125, SEQ ID NO:126, SEQ ID NO:128, SEQ ID NO:129, SEQ ID NO:130, SEQ ID NO:131, SEQ ID NO:132, SEQ ID NO:133, SEQ ID NO:134, SEQ ID NO:135, SEQ ID NO:137, SEQ ID NO:139, SEQ ID NO:141, SEQ ID NO:142, SEQ ID NO:144, SEQ ID NO:145, SEQ ID NO:146, SEQ ID NO:147, SEQ ID NO:148, SEQ ID NO:149, and SEQ ID NO:150.

Examples of polypeptides are shown in the sequence listing that have HMM bit scores greater than 90 when fitted to an HMM generated from the amino acid sequences set forth in FIG. 5 are identified in the Sequence Listing of this application. Such polypeptides include SEQ ID NO:152, SEQ ID NO:154, SEQ ID NO:156, SEQ ID NO:158, SEQ ID NO:160, SEQ ID NO:162, and SEQ ID NO:164.

Examples of polypeptides are shown in the sequence listing that have HMM bit scores greater than 230 when fitted to an HMM generated from the amino acid sequences set forth in FIG. 6 are identified in the Sequence Listing of this application. Such polypeptides include SEQ ID NO:166, SEQ ID NO:168, SEQ ID NO:170, SEQ ID NO:172, SEQ ID NO:174, SEQ ID NO:177, SEQ ID NO:179, SEQ ID NO:181, SEQ ID NO:182, SEQ ID NO:183, and SEQ ID NO:184.

Examples of polypeptides are shown in the sequence listing that have HMM bit scores greater than 90 when fitted to an HMM generated from the amino acid sequences set forth in FIG. 7 are identified in the Sequence Listing of this application. Such polypeptides include SEQ ID NO:186, SEQ ID NO:188, SEQ ID NO:190, SEQ ID NO:191, SEQ ID NO:193, SEQ ID NO:194, SEQ ID NO:196, SEQ ID NO:197, SEQ ID NO:199, SEQ ID NO:201, SEQ ID NO:203, SEQ ID NO:204, SEQ ID NO:205, and SEQ ID NO:206.

Examples of polypeptides are shown in the sequence listing that have HMM bit scores greater than 380 when fitted to an HMM generated from the amino acid sequences set forth in FIG. 8 are identified in the Sequence Listing of this application. Such polypeptides include SEQ ID NO:208, SEQ ID NO:209, SEQ ID NO:210, SEQ ID NO:214, and SEQ ID NO:216.

Examples of polypeptides are shown in the sequence listing that have HMM bit scores greater than 110 when fitted to an HMM generated from the amino acid sequences set forth in FIG. 9 are identified in the Sequence Listing of this application. Such polypeptides include SEQ ID NO:218, SEQ ID NO:220, SEQ ID NO:222, SEQ ID NO:223, SEQ ID NO:225, SEQ ID NO:227, SEQ ID NO:229, SEQ ID NO:230, SEQ ID NO:231, SEQ ID NO:232, SEQ ID NO:1039, SEQ ID NO:1049, and SEQ ID NO:1052.

Examples of polypeptides are shown in the sequence listing that have HMM bit scores greater than 220 when fitted to an HMM generated from the amino acid sequences set forth in FIG. 10 are identified in the Sequence Listing of this application. Such polypeptides include SEQ ID NO:234, SEQ ID NO:236, SEQ ID NO:238, SEQ ID NO:239, SEQ ID NO:241, SEQ ID NO:242, SEQ ID NO:243, and SEQ ID NO:244.

Examples of polypeptides are shown in the sequence listing that have HMM bit scores greater than 150 when fitted to an HMM generated from the amino acid sequences set forth in FIG. 11 are identified in the Sequence Listing of this application. Such polypeptides include SEQ ID NO:246, SEQ ID NO:248, SEQ ID NO:249, SEQ ID NO:251, SEQ ID NO:253, SEQ ID NO:255, SEQ ID NO:257, SEQ ID NO:259, SEQ ID NO:260, SEQ ID NO:262, SEQ ID NO:264, SEQ ID NO:265, SEQ ID NO:267, SEQ ID NO:268, SEQ ID NO:270, SEQ ID NO:272, SEQ ID NO:274, SEQ ID NO:276, SEQ ID NO:277, SEQ ID NO:279, SEQ ID NO:281, SEQ ID NO:283, SEQ ID NO:285, SEQ ID NO:286, SEQ ID NO:287, SEQ ID NO:288, SEQ ID NO:290, SEQ ID NO:291, SEQ ID NO:292, SEQ ID NO:293, SEQ ID NO:296, and SEQ ID NO:298.

Examples of polypeptides are shown in the sequence listing that have HMM bit scores greater than 950 when fitted to an HMM generated from the amino acid sequences set forth in FIG. 12 are identified in the Sequence Listing of this application. Such polypeptides include SEQ ID NO:300, SEQ ID NO:302, SEQ ID NO:304, SEQ ID NO:306, SEQ ID NO:308, SEQ ID NO:310, SEQ ID NO:312, SEQ ID NO:314, SEQ ID NO:316, SEQ ID NO:318, SEQ ID NO:319, SEQ ID NO:320, SEQ ID NO:321, SEQ ID NO:322, SEQ ID NO:323, SEQ ID NO:325, SEQ ID NO:327, and SEQ ID NO:329.

Examples of polypeptides are shown in the sequence listing that have HMM bit scores greater than 460 when fitted to an HMM generated from the amino acid sequences set forth in FIG. 13 are identified in the Sequence Listing of this application. Such polypeptides include SEQ ID NO:332, SEQ ID NO:334, SEQ ID NO:335, SEQ ID NO:336, SEQ ID NO:338, SEQ ID NO:339, SEQ ID NO:341, SEQ ID NO:342, SEQ ID NO:343, SEQ ID NO:344, SEQ ID NO:345, SEQ ID NO:346, SEQ ID NO:347, SEQ ID NO:348, SEQ ID NO:349, SEQ ID NO:351, SEQ ID NO:352, SEQ ID NO:353, SEQ ID NO:354, SEQ ID NO:355, SEQ ID NO:356, SEQ ID NO:357, SEQ ID NO:358, SEQ ID NO:359, SEQ ID NO:360, SEQ ID NO:362, SEQ ID NO:363, SEQ ID NO:364, SEQ ID NO:365, SEQ ID NO:366, SEQ ID NO:2541, SEQ ID NO:2542, SEQ ID NO:2543, SEQ ID NO:2544, SEQ ID NO:2546, SEQ ID NO:2548, SEQ ID NO:2549, SEQ ID NO:2550, SEQ ID NO:2551, SEQ ID NO:2552, and SEQ ID NO:2553.

Examples of polypeptides are shown in the sequence listing that have HMM bit scores greater than 150 when fitted to an HMM generated from the amino acid sequences set forth in FIG. 14 are identified in the Sequence Listing of this application. Such polypeptides include SEQ ID NO:368, SEQ ID NO:369, SEQ ID NO:370, SEQ ID NO:371, SEQ ID NO:372, SEQ ID NO:373, SEQ ID NO:374, SEQ ID NO:376, SEQ ID NO:378, SEQ ID NO:380, SEQ ID NO:382, SEQ ID NO:384, SEQ ID NO:386, SEQ ID NO:388, SEQ ID NO:390, SEQ ID NO:392, SEQ ID NO:394, SEQ ID NO:396, SEQ ID NO:398, SEQ ID NO:399, SEQ ID NO:401, SEQ ID NO:403, SEQ ID NO:404, SEQ ID NO:406, SEQ ID NO:408, SEQ ID NO:410, SEQ ID NO:412, SEQ ID NO:414, SEQ ID NO:416, SEQ ID NO:418, SEQ ID NO:419, SEQ ID NO:420, SEQ ID NO:422, SEQ ID NO:423, SEQ ID NO:425, SEQ ID NO:427, SEQ ID NO:428, SEQ ID NO:430, SEQ ID NO:432, SEQ ID NO:433, SEQ ID NO:434, SEQ ID NO:435, SEQ ID NO:436, SEQ ID NO:437, SEQ ID NO:438, SEQ ID NO:439, SEQ ID NO:440, SEQ ID NO:441, SEQ ID NO:444, SEQ ID NO:445, SEQ ID NO:446, SEQ ID NO:447, SEQ ID NO:448, SEQ ID NO:449, SEQ ID NO:450, SEQ ID NO:451, SEQ ID NO:452, SEQ ID NO:453, SEQ ID NO:454, SEQ ID NO:455, SEQ ID NO:456, SEQ ID NO:458, SEQ ID NO:459, SEQ ID NO:461, SEQ ID NO:463, SEQ ID NO:465, SEQ ID NO:467, SEQ ID NO:469, SEQ ID NO:471, SEQ ID NO:473, SEQ ID NO:474, SEQ ID NO:475, SEQ ID NO:477, SEQ ID NO:479, SEQ ID NO:481, SEQ ID NO:483, SEQ ID NO:485, SEQ ID NO:487, SEQ ID NO:488, SEQ ID NO:489, SEQ ID NO:490, SEQ ID NO:491, SEQ ID NO:492, SEQ ID NO:494, SEQ ID NO:495, SEQ ID NO:496, SEQ ID NO:497, SEQ ID NO:498, SEQ ID NO:499, SEQ ID NO:500, SEQ ID NO:501, SEQ ID NO:502, SEQ ID NO:504, SEQ ID NO:505, SEQ ID NO:506, SEQ ID NO:507, and SEQ ID NO:508.

Examples of polypeptides are shown in the sequence listing that have HMM bit scores greater than 410 when fitted to an HMM generated from the amino acid sequences set forth in FIG. 15 are identified in the Sequence Listing of this application. Such polypeptides include SEQ ID NO:510, SEQ ID NO:511, SEQ ID NO:513, SEQ ID NO:515, SEQ ID NO:517, SEQ ID NO:521, SEQ ID NO:523, SEQ ID NO:525, SEQ ID NO:527, SEQ ID NO:529, SEQ ID NO:530, and SEQ ID NO:531.

Examples of polypeptides are shown in the sequence listing that have HMM bit scores greater than 520 when fitted to an HMM generated from the amino acid sequences set forth in FIG. 16 are identified in the Sequence Listing of this application. Such polypeptides include SEQ ID NO:533, SEQ ID NO:535, SEQ ID NO:536, SEQ ID NO:538, SEQ ID NO:539, SEQ ID NO:541, SEQ ID NO:542, SEQ ID NO:543, SEQ ID NO:544, SEQ ID NO:545, SEQ ID NO:546, SEQ ID NO:547, SEQ ID NO:548, SEQ ID NO:550, SEQ ID NO:552, SEQ ID NO:553, and SEQ ID NO:554.

Examples of polypeptides are shown in the sequence listing that have HMM bit scores greater than 1150 when fitted to an HMM generated from the amino acid sequences set forth in FIG. 17 are identified in the Sequence Listing of this application. Such polypeptides include SEQ ID NO:558, SEQ ID NO:559, SEQ ID NO:560, SEQ ID NO:561, SEQ ID NO:562, SEQ ID NO:563, SEQ ID NO:564, SEQ ID NO:565, SEQ ID NO:566, SEQ ID NO:567, SEQ ID NO:569, SEQ ID NO:571, SEQ ID NO:572, SEQ ID NO:573, SEQ ID NO:575, SEQ ID NO:576, SEQ ID NO:577, SEQ ID NO:578, SEQ ID NO:579, SEQ ID NO:581, SEQ ID NO:583, SEQ ID NO:584, SEQ ID NO:585, SEQ ID NO:586, SEQ ID NO:588, SEQ ID NO:589, SEQ ID NO:590, and SEQ ID NO:591.

Examples of polypeptides are shown in the sequence listing that have HMM bit scores greater than 340 when fitted to an HMM generated from the amino acid sequences set forth in FIG. 18 are identified in the Sequence Listing of this application. Such polypeptides include SEQ ID NO:593, SEQ ID NO:595, SEQ ID NO:597, SEQ ID NO:599, SEQ ID NO:601, SEQ ID NO:603, SEQ ID NO:605, SEQ ID NO:607, SEQ ID NO:609, SEQ ID NO:610, and SEQ ID NO:611.

Examples of polypeptides are shown in the sequence listing that have HMM bit scores greater than 140 when fitted to an HMM generated from the amino acid sequences set forth in FIG. 19 are identified in the Sequence Listing of this application. Such polypeptides include SEQ ID NO:613, SEQ ID NO:615, SEQ ID NO:617, SEQ ID NO:618, SEQ ID NO:620, SEQ ID NO:622, SEQ ID NO:624, SEQ ID NO:626, SEQ ID NO:628, SEQ ID NO:630, SEQ ID NO:632, SEQ ID NO:634, SEQ ID NO:636, SEQ ID NO:638, SEQ ID NO:640, SEQ ID NO:642, SEQ ID NO:643, and SEQ ID NO:644.

Examples of polypeptides are shown in the sequence listing that have HMM bit scores greater than 250 when fitted to an HMM generated from the amino acid sequences set forth in FIG. 20 are identified in the Sequence Listing of this application. Such polypeptides include SEQ ID NO:646, SEQ ID NO:648, SEQ ID NO:650, SEQ ID NO:652, SEQ ID NO:654, SEQ ID NO:656, SEQ ID NO:658, SEQ ID NO:660, SEQ ID NO:662, SEQ ID NO:664, SEQ ID NO:666, SEQ ID NO:668, SEQ ID NO:670, SEQ ID NO:672, SEQ ID NO:674, SEQ ID NO:676, SEQ ID NO:678, SEQ ID NO:679, SEQ ID NO:680, SEQ ID NO:681, SEQ ID NO:682, SEQ ID NO:683, and SEQ ID NO:685.

Examples of polypeptides are shown in the sequence listing that have HMM bit scores greater than 170 when fitted to an HMM generated from the amino acid sequences set forth in FIG. 21 are identified in the Sequence Listing of this application. Such polypeptides include SEQ ID NO:687, SEQ ID NO:689, SEQ ID NO:691, SEQ ID NO:693, SEQ ID NO:694, SEQ ID NO:696, SEQ ID NO:697, SEQ ID NO:699, SEQ ID NO:701, SEQ ID NO:703, SEQ ID NO:705, SEQ ID NO:706, SEQ ID NO:708, SEQ ID NO:710, SEQ ID NO:712, SEQ ID NO:714, SEQ ID NO:716, SEQ ID NO:718, SEQ ID NO:720, SEQ ID NO:721, SEQ ID NO:722, SEQ ID NO:723, SEQ ID NO:724, SEQ ID NO:725, SEQ ID NO:726, SEQ ID NO:727, and SEQ ID NO:728.

Examples of polypeptides are shown in the sequence listing that have HMM bit scores greater than 210 when fitted to an HMM generated from the amino acid sequences set forth in FIG. 22 are identified in the Sequence Listing of this application. Such polypeptides include SEQ ID NO:730, SEQ ID NO:732, SEQ ID NO:733, SEQ ID NO:735, SEQ ID NO:737, SEQ ID NO:738, and SEQ ID NO:742.

Examples of polypeptides are shown in the sequence listing that have HMM bit scores greater than 230 when fitted to an HMM generated from the amino acid sequences set forth in FIG. 23 are identified in the Sequence Listing of this application. Such polypeptides include SEQ ID NO:746, SEQ ID NO:748, SEQ ID NO:750, SEQ ID NO:751, SEQ ID NO:753, SEQ ID NO:755, SEQ ID NO:757, SEQ ID NO:758, SEQ ID NO:760, SEQ ID NO:761, SEQ ID NO:762, SEQ ID NO:763, SEQ ID NO:765, and SEQ ID NO:767.

Examples of polypeptides are shown in the sequence listing that have HMM bit scores greater than 180 when fitted to an HMM generated from the amino acid sequences set forth in FIG. 24 are identified in the Sequence Listing of this application. Such polypeptides include SEQ ID NO:769, SEQ ID NO:771, SEQ ID NO:773, SEQ ID NO:775, SEQ ID NO:777, SEQ ID NO:779, SEQ ID NO:781, SEQ ID NO:783, SEQ ID NO:785, SEQ ID NO:787, SEQ ID NO:789, and SEQ ID NO:790.

Examples of polypeptides are shown in the sequence listing that have HMM bit scores greater than 300 when fitted to an HMM generated from the amino acid sequences set forth in FIG. 25 are identified in the Sequence Listing of this application. Such polypeptides include SEQ ID NO:792, SEQ ID NO:794, SEQ ID NO:796, SEQ ID NO:798, SEQ ID NO:799, SEQ ID NO:801, SEQ ID NO:803, SEQ ID NO:805, SEQ ID NO:807, SEQ ID NO:808, SEQ ID NO:810, SEQ ID NO:812, SEQ ID NO:814, SEQ ID NO:816, SEQ ID NO:818, SEQ ID NO:819, SEQ ID NO:820, SEQ ID NO:821, and SEQ ID NO:822.

Examples of polypeptides are shown in the sequence listing that have HMM bit scores greater than 190 when fitted to an HMM generated from the amino acid sequences set forth in FIG. 26 are identified in the Sequence Listing of this application. Such polypeptides include SEQ ID NO:824, SEQ ID NO:826, SEQ ID NO:1696, SEQ ID NO:1698, SEQ ID NO:1700, SEQ ID NO:1702, SEQ ID NO:1704, SEQ ID NO:1706, SEQ ID NO:1708, SEQ ID NO:1710, SEQ ID NO:1711, SEQ ID NO:1713, SEQ ID NO:1714, SEQ ID NO:1715, and SEQ ID NO:1716.

Examples of polypeptides are shown in the sequence listing that have HMM bit scores greater than 630 when fitted to an HMM generated from the amino acid sequences set forth in FIG. 27 are identified in the Sequence Listing of this application. Such polypeptides include SEQ ID NO:828, SEQ ID NO:830, SEQ ID NO:832, SEQ ID NO:834, SEQ ID NO:836, SEQ ID NO:837, SEQ ID NO:838, SEQ ID NO:839, SEQ ID NO:840, SEQ ID NO:842, SEQ ID NO:844, SEQ ID NO:845, SEQ ID NO:846, SEQ ID NO:847, SEQ ID NO:848, SEQ ID NO:849, SEQ ID NO:850, and SEQ ID NO:851.

Examples of polypeptides are shown in the sequence listing that have HMM bit scores greater than 95 when fitted to an HMM generated from the amino acid sequences set forth in FIG. 28 are identified in the Sequence Listing of this application. Such polypeptides include SEQ ID NO:855, SEQ ID NO:856, SEQ ID NO:858, SEQ ID NO:860, SEQ ID NO:862, SEQ ID NO:864, SEQ ID NO:866, SEQ ID NO:868, SEQ ID NO:870, SEQ ID NO:872, SEQ ID NO:874, SEQ ID NO:876, SEQ ID NO:878, SEQ ID NO:880, SEQ ID NO:882, SEQ ID NO:884, SEQ ID NO:885, SEQ ID NO:886, SEQ ID NO:887, SEQ ID NO:888, and SEQ ID NO:889.

Examples of polypeptides are shown in the sequence listing that have HMM bit scores greater than 850 when fitted to an HMM generated from the amino acid sequences set forth in FIG. 29 are identified in the Sequence Listing of this application. Such polypeptides include SEQ ID NO:891, SEQ ID NO:893, SEQ ID NO:894, SEQ ID NO:895, SEQ ID NO:896, SEQ ID NO:898, SEQ ID NO:900, SEQ ID NO:901, SEQ ID NO:902, SEQ ID NO:903, SEQ ID NO:904, SEQ ID NO:905, SEQ ID NO:907, SEQ ID NO:908, SEQ ID NO:909, SEQ ID NO:910, SEQ ID NO:911, SEQ ID NO:912, SEQ ID NO:913, SEQ ID NO:914, and SEQ ID NO:915.

Examples of polypeptides are shown in the sequence listing that have HMM bit scores greater than 300 when fitted to an HMM generated from the amino acid sequences set forth in FIG. 30 are identified in the Sequence Listing of this application. Such polypeptides include SEQ ID NO:917, SEQ ID NO:919, SEQ ID NO:921, SEQ ID NO:923, SEQ ID NO:925, SEQ ID NO:927, SEQ ID NO:929, SEQ ID NO:931, SEQ ID NO:933, SEQ ID NO:935, SEQ ID NO:937, SEQ ID NO:939, and SEQ ID NO:940.

Examples of polypeptides are shown in the sequence listing that have HMM bit scores greater than 60 when fitted to an HMM generated from the amino acid sequences set forth in FIG. 31 are identified in the Sequence Listing of this application. Such polypeptides include SEQ ID NO:944, SEQ ID NO:946, SEQ ID NO:947, SEQ ID NO:948, SEQ ID NO:950, SEQ ID NO:952, SEQ ID NO:954, SEQ ID NO:956, SEQ ID NO:958, SEQ ID NO:960, SEQ ID NO:962, SEQ ID NO:964, SEQ ID NO:966, SEQ ID NO:967, SEQ ID NO:968, SEQ ID NO:969, SEQ ID NO:970, SEQ ID NO:972, and SEQ ID NO:974.

Examples of polypeptides are shown in the sequence listing that have HMM bit scores greater than 340 when fitted to an HMM generated from the amino acid sequences set forth in FIG. 32 are identified in the Sequence Listing of this application. Such polypeptides include SEQ ID NO:976, SEQ ID NO:978, and SEQ ID NO:980.

Examples of polypeptides are shown in the sequence listing that have HMM bit scores greater than 180 when fitted to an HMM generated from the amino acid sequences set forth in FIG. 33 are identified in the Sequence Listing of this application. Such polypeptides include SEQ ID NO:982, SEQ ID NO:984, SEQ ID NO:985, SEQ ID NO:986, SEQ ID NO:987, SEQ ID NO:988, SEQ ID NO:989, SEQ ID NO:990, SEQ ID NO:991, SEQ ID NO:992, SEQ ID NO:993, SEQ ID NO:995, SEQ ID NO:996, SEQ ID NO:998, SEQ ID NO:1000, SEQ ID NO:1001, SEQ ID NO:1003, SEQ ID NO:1005, SEQ ID NO:1007, SEQ ID NO:1008, SEQ ID NO:1009, SEQ ID NO:1011, SEQ ID NO:1013, SEQ ID NO:1015, SEQ ID NO:1016, SEQ ID NO:1018, SEQ ID NO:1019, SEQ ID NO:1021, SEQ ID NO:1023, SEQ ID NO:1025, SEQ ID NO:1026, SEQ ID NO:1027, SEQ ID NO:1028, SEQ ID NO:1029, SEQ ID NO:1030, SEQ ID NO:1031, SEQ ID NO:1032, and SEQ ID NO:1033.

Examples of polypeptides are shown in the sequence listing that have HMM bit scores greater than 1060 when fitted to an HMM generated from the amino acid sequences set forth in FIG. 34 are identified in the Sequence Listing of this application. Such polypeptides include SEQ ID NO:1054, SEQ ID NO:1055, SEQ ID NO:1057, SEQ ID NO:1058, SEQ ID NO:1059, SEQ ID NO:1061, SEQ ID NO:1063, SEQ ID NO:1065, SEQ ID NO:1065, SEQ ID NO:1067, SEQ ID NO:1068, SEQ ID NO:1070, SEQ ID NO:1071, SEQ ID NO:1072, SEQ ID NO:1074, SEQ ID NO:1075, SEQ ID NO:1076, SEQ ID NO:1077, SEQ ID NO:1078, SEQ ID NO:1080, SEQ ID NO:1082, SEQ ID NO:1083, SEQ ID NO:1085, SEQ ID NO:1086, SEQ ID NO:1087, SEQ ID NO:1088, SEQ ID NO:1089, SEQ ID NO:1089, SEQ ID NO:1090, SEQ ID NO:1091, SEQ ID NO:1092, SEQ ID NO:1093, SEQ ID NO:1094, SEQ ID NO:1095, and SEQ ID NO:1097.

Examples of polypeptides are shown in the sequence listing that have HMM bit scores greater than 260 when fitted to an HMM generated from the amino acid sequences set forth in FIG. 35 are identified in the Sequence Listing of this application. Such polypeptides include SEQ ID NO:1099, SEQ ID NO:1101, SEQ ID NO:1103, SEQ ID NO:1104, SEQ ID NO:1105, SEQ ID NO:1106, SEQ ID NO:1108, SEQ ID NO:1109, and SEQ ID NO:1110.

Examples of polypeptides are shown in the sequence listing that have HMM bit scores greater than 150 when fitted to an HMM generated from the amino acid sequences set forth in FIG. 36 are identified in the Sequence Listing of this application. Such polypeptides include SEQ ID NO:1112, SEQ ID NO:1113, and SEQ ID NO:1114.

Examples of polypeptides are shown in the sequence listing that have HMM bit scores greater than 40 when fitted to an HMM generated from the amino acid sequences set forth in FIG. 37 are identified in the Sequence Listing of this application. Such polypeptides include SEQ ID NO:1116, SEQ ID NO:1118, SEQ ID NO:1120, SEQ ID NO:1122, SEQ ID NO:1123, SEQ ID NO:1125, SEQ ID NO:1126, SEQ ID NO:1128, SEQ ID NO:1129, SEQ ID NO:1131, SEQ ID NO:1132, SEQ ID NO:1133, SEQ ID NO:1134, SEQ ID NO:1136, SEQ ID NO:1138, SEQ ID NO:1140, SEQ ID NO:1141, SEQ ID NO:1142, SEQ ID NO:1143, SEQ ID NO:1144, SEQ ID NO:1145, SEQ ID NO:1147, SEQ ID NO:1149, SEQ ID NO:1151, SEQ ID NO:1153, and SEQ ID NO:1155.

Examples of polypeptides are shown in the sequence listing that have HMM bit scores greater than 450 when fitted to an HMM generated from the amino acid sequences set forth in FIG. 38 are identified in the Sequence Listing of this application. Such polypeptides include SEQ ID NO:1159, SEQ ID NO:1161, SEQ ID NO:1162, SEQ ID NO:1163, and SEQ ID NO:1164.

Examples of polypeptides are shown in the sequence listing that have HMM bit scores greater than 160 when fitted to an HMM generated from the amino acid sequences set forth in FIG. 39 are identified in the Sequence Listing of this application. Such polypeptides include SEQ ID NO:1166, SEQ ID NO:1167, SEQ ID NO:1169, SEQ ID NO:1171, SEQ ID NO:1173, SEQ ID NO:1175, SEQ ID NO:1177, SEQ ID NO:1179, SEQ ID NO:1180, SEQ ID NO:1182, and SEQ ID NO:1183.

Examples of polypeptides are shown in the sequence listing that have HMM bit scores greater than 180 when fitted to an HMM generated from the amino acid sequences set forth in FIG. 40 are identified in the Sequence Listing of this application. Such polypeptides include SEQ ID NO:1185, SEQ ID NO:1187, SEQ ID NO:1189, SEQ ID NO:1190, SEQ ID NO:1191, and SEQ ID NO:1192.

Examples of polypeptides are shown in the sequence listing that have HMM bit scores greater than 670 when fitted to an HMM generated from the amino acid sequences set forth in FIG. 41 are identified in the Sequence Listing of this application. Such polypeptides include SEQ ID NO:1194, SEQ ID NO:1196, SEQ ID NO:1198, SEQ ID NO:1200, SEQ ID NO:1202, SEQ ID NO:1203, SEQ ID NO:1204, SEQ ID NO:1205, SEQ ID NO:1206, SEQ ID NO:1207, and SEQ ID NO:1208.

Examples of polypeptides are shown in the sequence listing that have HMM bit scores greater than 280 when fitted to an HMM generated from the amino acid sequences set forth in FIG. 42 are identified in the Sequence Listing of this application. Such polypeptides include SEQ ID NO:1210, SEQ ID NO:1211, SEQ ID NO:1213, SEQ ID NO:1215, SEQ ID NO:1216, SEQ ID NO:1218, SEQ ID NO:1220, SEQ ID NO:1222, SEQ ID NO:1224, SEQ ID NO:1226, SEQ ID NO:1228, SEQ ID NO:1229, SEQ ID NO:1230, SEQ ID NO:1232, SEQ ID NO:1233, SEQ ID NO:1234, SEQ ID NO:1235, SEQ ID NO:1236, SEQ ID NO:1237, SEQ ID NO:1238, SEQ ID NO:1239, SEQ ID NO:1240, SEQ ID NO:1241, SEQ ID NO:1242, SEQ ID NO:1243, SEQ ID NO:1244, SEQ ID NO:1245, SEQ ID NO:1246, SEQ ID NO:1247, SEQ ID NO:1248, SEQ ID NO:1249, SEQ ID NO:1251, SEQ ID NO:1253, SEQ ID NO:1255, SEQ ID NO:1257, SEQ ID NO:1259, SEQ ID NO:1261, SEQ ID NO:1263, SEQ ID NO:1264, SEQ ID NO:1265, SEQ ID NO:1266, SEQ ID NO:1267, SEQ ID NO:1268, SEQ ID NO:1269, SEQ ID NO:1270, SEQ ID NO:1271, and SEQ ID NO:1272.

Examples of polypeptides are shown in the sequence listing that have HMM bit scores greater than 700 when fitted to an HMM generated from the amino acid sequences set forth in FIG. 43 are identified in the Sequence Listing of this application. Such polypeptides include SEQ ID NO:1274, SEQ ID NO:1276, SEQ ID NO:1278, SEQ ID NO:1280, SEQ ID NO:1281, SEQ ID NO:1282, SEQ ID NO:1284, SEQ ID NO:1285, SEQ ID NO:1287, SEQ ID NO:1289, SEQ ID NO:1291, SEQ ID NO:1293, SEQ ID NO:1294, SEQ ID NO:1295, SEQ ID NO:1296, SEQ ID NO:1297, SEQ ID NO:1298, and SEQ ID NO:1300.

Examples of polypeptides are shown in the sequence listing that have HMM bit scores greater than 920 when fitted to an HMM generated from the amino acid sequences set forth in FIG. 44 are identified in the Sequence Listing of this application. Such polypeptides include SEQ ID NO:1302, SEQ ID NO:1303, SEQ ID NO:1305, SEQ ID NO:1307, SEQ ID NO:1309, SEQ ID NO:1311, SEQ ID NO:1312, SEQ ID NO:1313, SEQ ID NO:1314, SEQ ID NO:1315, SEQ ID NO:1317, SEQ ID NO:1318, SEQ ID NO:1319, SEQ ID NO:1320, SEQ ID NO:1321, SEQ ID NO:1322, SEQ ID NO:1323, SEQ ID NO:1324, SEQ ID NO:1325, SEQ ID NO:1326, SEQ ID NO:1327, SEQ ID NO:1328, SEQ ID NO:1330, SEQ ID NO:1331, SEQ ID NO:1333, SEQ ID NO:1334, SEQ ID NO:1335, SEQ ID NO:1336, SEQ ID NO:1337, SEQ ID NO:1338, SEQ ID NO:1339, and SEQ ID NO:1340.

Examples of polypeptides are shown in the sequence listing that have HMM bit scores greater than 510 when fitted to an HMM generated from the amino acid sequences set forth in FIG. 45 are identified in the Sequence Listing of this application. Such polypeptides include SEQ ID NO:1342, SEQ ID NO:1344, SEQ ID NO:1346, SEQ ID NO:1348, SEQ ID NO:1350, SEQ ID NO:1352, SEQ ID NO:1354, SEQ ID NO:1355, SEQ ID NO:1357, SEQ ID NO:1358, SEQ ID NO:1360, SEQ ID NO:1361, SEQ ID NO:1362, SEQ ID NO:1363, SEQ ID NO:1364, SEQ ID NO:1366, SEQ ID NO:1367, SEQ ID NO:1369, SEQ ID NO:1370, SEQ ID NO:1371, SEQ ID NO:1372, SEQ ID NO:1373, SEQ ID NO:1374, SEQ ID NO:1375, SEQ ID NO:1376, SEQ ID NO:1377, SEQ ID NO:1378, SEQ ID NO:1379, SEQ ID NO:1380, SEQ ID NO:1381, SEQ ID NO:1382, and SEQ ID NO:1383.

Examples of polypeptides are shown in the sequence listing that have HMM bit scores greater than 140 when fitted to an HMM generated from the amino acid sequences set forth in FIG. 46 are identified in the Sequence Listing of this application. Such polypeptides include SEQ ID NO:1385, SEQ ID NO:1387, SEQ ID NO:1389, SEQ ID NO:1390, SEQ ID NO:1391, SEQ ID NO:1393, SEQ ID NO:1394, SEQ ID NO:1395, SEQ ID NO:1396, SEQ ID NO:1398, SEQ ID NO:1400, SEQ ID NO:1401, SEQ ID NO:1402, SEQ ID NO:1403, SEQ ID NO:1404, SEQ ID NO:1405, and SEQ ID NO:1407.

Examples of polypeptides are shown in the sequence listing that have HMM bit scores greater than 150 when fitted to an HMM generated from the amino acid sequences set forth in FIG. 47 are identified in the Sequence Listing of this application. Such polypeptides include SEQ ID NO:1409, SEQ ID NO:1411, SEQ ID NO:1413, SEQ ID NO:1415, SEQ ID NO:1417, SEQ ID NO:1418, SEQ ID NO:1419, SEQ ID NO:1421, SEQ ID NO:1423, SEQ ID NO:1424, SEQ ID NO:1425, SEQ ID NO:1426.

Examples of polypeptides are shown in the sequence listing that have HMM bit scores greater than 190 when fitted to an HMM generated from the amino acid sequences set forth in FIG. 48 are identified in the Sequence Listing of this application. Such polypeptides include SEQ ID NO:1428, SEQ ID NO:1430, SEQ ID NO:1432, SEQ ID NO:1434, SEQ ID NO:1436, SEQ ID NO:1439, SEQ ID NO:1442, SEQ ID NO:1444, SEQ ID NO:1446, SEQ ID NO:1448, SEQ ID NO:1450, SEQ ID NO:1452, SEQ ID NO:1453, SEQ ID NO:1454, SEQ ID NO:1455, SEQ ID NO:1456, SEQ ID NO:1457, SEQ ID NO:1458, and SEQ ID NO:1459.

Examples of polypeptides are shown in the sequence listing that have HMM bit scores greater than 450 when fitted to an HMM generated from the amino acid sequences set forth in FIG. 49 are identified in the Sequence Listing of this application. Such polypeptides include SEQ ID NO:1463, SEQ ID NO:1465, SEQ ID NO:1467, SEQ ID NO:1469, SEQ ID NO:1471, SEQ ID NO:1473, SEQ ID NO:1474, SEQ ID NO:1475, SEQ ID NO:1476, and SEQ ID NO:1477.

Examples of polypeptides are shown in the sequence listing that have HMM bit scores greater than 580 when fitted to an HMM generated from the amino acid sequences set forth in FIG. 50 are identified in the Sequence Listing of this application. Such polypeptides include SEQ ID NO:1491, SEQ ID NO:1493, SEQ ID NO:1495, SEQ ID NO:1497, SEQ ID NO:1499, SEQ ID NO:1501, SEQ ID NO:1503, SEQ ID NO:1504, SEQ ID NO:1505, SEQ ID NO:1506, and SEQ ID NO:1508.

Examples of polypeptides are shown in the sequence listing that have HMM bit scores greater than 100 when fitted to an HMM generated from the amino acid sequences set forth in FIG. 51 are identified in the Sequence Listing of this application. Such polypeptides include SEQ ID NO:1510, SEQ ID NO:1512, SEQ ID NO:1514, SEQ ID NO:1516, SEQ ID NO:1518, SEQ ID NO:1520, SEQ ID NO:1522, and SEQ ID NO:1523.

Examples of polypeptides are shown in the sequence listing that have HMM bit scores greater than 800 when fitted to an HMM generated from the amino acid sequences set forth in FIG. 52 are identified in the Sequence Listing of this application. Such polypeptides include SEQ ID NO:1525, SEQ ID NO:1527, SEQ ID NO:1529, SEQ ID NO:1530, SEQ ID NO:1532, SEQ ID NO:1534, and SEQ ID NO:1535.

Examples of polypeptides are shown in the sequence listing that have HMM bit scores greater than 490 when fitted to an HMM generated from the amino acid sequences set forth in FIG. 53 are identified in the Sequence Listing of this application. Such polypeptides include SEQ ID NO:1537, SEQ ID NO:1539, SEQ ID NO:1540, SEQ ID NO:1541, SEQ ID NO:1543, SEQ ID NO:1545, SEQ ID NO:1547, SEQ ID NO:1548, SEQ ID NO:1550, SEQ ID NO:1552, SEQ ID NO:2386, SEQ ID NO:2388, SEQ ID NO:2390, SEQ ID NO:2391, and SEQ ID NO:2392.

Examples of polypeptides are shown in the sequence listing that have HMM bit scores greater than 690 when fitted to an HMM generated from the amino acid sequences set forth in FIG. 54 are identified in the Sequence Listing of this application. Such polypeptides include SEQ ID NO:1554, SEQ ID NO:1555, SEQ ID NO:1557, SEQ ID NO:1559, SEQ ID NO:1561, SEQ ID NO:1563, SEQ ID NO:1565, SEQ ID NO:1567, SEQ ID NO:1569, SEQ ID NO:1571, SEQ ID NO:1572, SEQ ID NO:1573, SEQ ID NO:1574, and SEQ ID NO:1575.

Examples of polypeptides are shown in the sequence listing that have HMM bit scores greater than 380 when fitted to an HMM generated from the amino acid sequences set forth in FIG. 55 are identified in the Sequence Listing of this application. Such polypeptides include SEQ ID NO:1035, SEQ ID NO:1036, SEQ ID NO:1037, SEQ ID NO:1040, SEQ ID NO:1041, SEQ ID NO:1043, SEQ ID NO:1044, SEQ ID NO:1046, SEQ ID NO:1047, SEQ ID NO:1048, SEQ ID NO:1050, SEQ ID NO:1440, SEQ ID NO:1480, SEQ ID NO:1481, SEQ ID NO:1482, SEQ ID NO:1483, SEQ ID NO:1484, SEQ ID NO:1485, SEQ ID NO:1486, SEQ ID NO:1487, SEQ ID NO:1488, SEQ ID NO:1577, SEQ ID NO:1578, SEQ ID NO:1580, SEQ ID NO:1582, SEQ ID NO:1584, SEQ ID NO:1586, SEQ ID NO:1588, SEQ ID NO:1590, SEQ ID NO:1592, SEQ ID NO:1594, SEQ ID NO:1596, SEQ ID NO:1598, SEQ ID NO:1599, SEQ ID NO:1601, SEQ ID NO:1602, SEQ ID NO:1605, SEQ ID NO:1607, SEQ ID NO:1608, SEQ ID NO:1609, SEQ ID NO:1611, SEQ ID NO:1613, SEQ ID NO:1615, SEQ ID NO:1617, SEQ ID NO:1619, SEQ ID NO:1621, SEQ ID NO:1622, SEQ ID NO:1623, SEQ ID NO:1624, SEQ ID NO:1625, SEQ ID NO:1627, SEQ ID NO:1629, SEQ ID NO:1631, SEQ ID NO:1633, SEQ ID NO:1635, SEQ ID NO:1637, SEQ ID NO:1639, SEQ ID NO:1643, SEQ ID NO:1645, SEQ ID NO:1648, SEQ ID NO:1649, SEQ ID NO:1651, and SEQ ID NO:1653.

Examples of polypeptides are shown in the sequence listing that have HMM bit scores greater than 870 when fitted to an HMM generated from the amino acid sequences set forth in FIG. 56 are identified in the Sequence Listing of this application. Such polypeptides include SEQ ID NO:173, SEQ ID NO:212, SEQ ID NO:361, SEQ ID NO:421, SEQ ID NO:443, SEQ ID NO:740, SEQ ID NO:744, SEQ ID NO:942, SEQ ID NO:1437, and SEQ ID NO:1461.

Examples of polypeptides are shown in the sequence listing that have HMM bit scores greater than 140 when fitted to an HMM generated from the amino acid sequences set forth in FIG. 57 are identified in the Sequence Listing of this application. Such polypeptides include SEQ ID NO:97, SEQ ID NO:2010, SEQ ID NO:2011, SEQ ID NO:2013, SEQ ID NO:2015, and SEQ ID NO:2017.

D. Percent Identity

In some embodiments, a low nitrogen tolerance-modulating polypeptide has an amino acid sequence with at least 20% sequence identity, e.g., at least 50%, 52%, 56%, 59%, 61%, 65%, 70%, 75%, 80%, 85%, 90%, 95%, 97%, 98%, or 99% sequence identity, to one of the amino acid sequences set forth in SEQ ID NO:3, SEQ ID NO:49, SEQ ID NO:77, SEQ ID NO:97, SEQ ID NO:100, SEQ ID NO:152, SEQ ID NO:166, SEQ ID NO:186, SEQ ID NO:208, SEQ ID NO:218, SEQ ID NO:234, SEQ ID NO:246, SEQ ID NO:300, SEQ ID NO:332, SEQ ID NO:368, SEQ ID NO:510, SEQ ID NO:533, SEQ ID NO:556, SEQ ID NO:558, SEQ ID NO:593, SEQ ID NO:613, SEQ ID NO:646, SEQ ID NO:687, SEQ ID NO:730, SEQ ID NO:746, SEQ ID NO:769, SEQ ID NO:792, SEQ ID NO:824, SEQ ID NO:828, SEQ ID NO:853, SEQ ID NO:855, SEQ ID NO:891, SEQ ID NO:917, SEQ ID NO:944, SEQ ID NO:976, SEQ ID NO:982, SEQ ID NO:1054, SEQ ID NO:1099, SEQ ID NO:1112, SEQ ID NO:1116, SEQ ID NO:1157, SEQ ID NO:1159, SEQ ID NO:1166, SEQ ID NO:1185, SEQ ID NO:1194, SEQ ID NO:1210, SEQ ID NO:1274, SEQ ID NO:1302, SEQ ID NO:1342, SEQ ID NO:1385, SEQ ID NO:1409, SEQ ID NO:1428, SEQ ID NO:1437, SEQ ID NO:1463, SEQ ID NO:1491, SEQ ID NO:1510, SEQ ID NO:1525, SEQ ID NO:1537, SEQ ID NO:1554, and SEQ ID NO:1577. Polypeptides having such a percent sequence identity often have a domain indicative of a low nitrogen tolerance-modulating polypeptide and/or have an HMM bit score that is greater than 20, as discussed above. Amino acid sequences of low nitrogen tolerance-modulating polypeptides having at least 20% sequence identity to one of the amino acid sequences set forth in SEQ ID NO:3, SEQ ID NO:49, SEQ ID NO:77, SEQ ID NO:97, SEQ ID NO:100, SEQ ID NO:152, SEQ ID NO:166, SEQ ID NO:186, SEQ ID NO:208, SEQ ID NO:218, SEQ ID NO:234, SEQ ID NO:246, SEQ ID NO:300, SEQ ID NO:332, SEQ ID NO:368, SEQ ID NO:510, SEQ ID NO:533, SEQ ID NO:556, SEQ ID NO:558, SEQ ID NO:593, SEQ ID NO:613, SEQ ID NO:646, SEQ ID NO:687, SEQ ID NO:730, SEQ ID NO:746, SEQ ID NO:769, SEQ ID NO:792, SEQ ID NO:824, SEQ ID NO:828, SEQ ID NO:853, SEQ ID NO:855, SEQ ID NO:891, SEQ ID NO:917, SEQ ID NO:944, SEQ ID NO:976, SEQ ID NO:982, SEQ ID NO:1054, SEQ ID NO:1099, SEQ ID NO:1112, SEQ ID NO:1116, SEQ ID NO:1157, SEQ ID NO:1159, SEQ ID NO:1166, SEQ ID NO:1185, SEQ ID NO:1194, SEQ ID NO:1210, SEQ ID NO:1274, SEQ ID NO:1302, SEQ ID NO:1342, SEQ ID NO:1385, SEQ ID NO:1409, SEQ ID NO:1428, SEQ ID NO:1437, SEQ ID NO:1463, SEQ ID NO:1491, SEQ ID NO:1510, SEQ ID NO:1525, SEQ ID NO:1537, SEQ ID NO:1554, and SEQ ID NO:1577 are provided in FIGS. 1-57 and in the Sequence Listing.

"Percent sequence identity" refers to the degree of sequence identity between any given reference sequence, e.g., SEQ ID NO:3, and a candidate low nitrogen tolerance-modulating sequence. A candidate sequence typically has a length that is from 80 percent to 200 percent of the length of the reference sequence, e.g., 82, 85, 87, 89, 90, 93, 95, 97, 99, 100, 105, 110, 115, 120, 130, 140, 150, 160, 170, 180, 190, or 200 percent of the length of the reference sequence. A percent identity for any candidate nucleic acid or polypeptide relative to a reference nucleic acid or polypeptide can be determined as follows. A reference sequence (e.g., a nucleic acid sequence or an amino acid sequence) is aligned to one or more candidate sequences using the computer program ClustalW (version 1.83, default parameters), which allows alignments of nucleic acid or polypeptide sequences to be carried out across their entire length (global alignment). Chenna et al. (2003) *Nucleic Acids Res.*, 31(13): 3497-500.

ClustalW calculates the best match between a reference and one or more candidate sequences, and aligns them so that identities, similarities and differences can be determined. Gaps of one or more residues can be inserted into a reference sequence, a candidate sequence, or both, to maximize sequence alignments. For fast pairwise alignment of nucleic acid sequences, the following default parameters are used: word size: 2; window size: 4; scoring method: percentage; number of top diagonals: 4; and gap penalty: 5. For multiple alignment of nucleic acid sequences, the following parameters are used: gap opening penalty: 10.0; gap extension penalty: 5.0; and weight transitions: yes. For fast pairwise alignment of protein sequences, the following parameters are used: word size: 1; window size: 5; scoring method: percentage; number of top diagonals: 5; gap penalty: 3. For multiple alignment of protein sequences, the following parameters are used: weight matrix: blosum; gap opening penalty: 10.0; gap extension penalty: 0.05; hydrophilic gaps: on; hydrophilic residues: Gly, Pro, Ser, Asn, Asp, Gln, Glu, Arg, and Lys; residue-specific gap penalties: on. The ClustalW output is a sequence alignment that reflects the relationship between sequences. ClustalW can be run, for example, at the Baylor College of Medicine Search Launcher site (searchlauncher.bcm.tmc.edu/multi-align/multi-align.html) and at the European Bioinformatics Institute site on the World Wide Web (ebi.ac.uk/clustalw).

To determine percent identity of a candidate nucleic acid or amino acid sequence to a reference sequence, the sequences are aligned using ClustalW, the number of identical matches in the alignment is divided by the length of the reference sequence, and the result is multiplied by 100. It is noted that the percent identity value can be rounded to the nearest tenth. For example, 78.11, 78.12, 78.13, and 78.14 are rounded down to 78.1, while 78.15, 78.16, 78.17, 78.18, and 78.19 are rounded up to 78.2.

In some cases, a low nitrogen tolerance-modulating polypeptide has an amino acid sequence with sequence similarity to the amino acid sequence set forth in SEQ ID NO:3, and preferably has at least 20% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:3. Amino acid sequences of polypeptides having greater than 20% sequence identity to the polypeptide set forth in SEQ ID NO:3 are provided in FIG. 1 and in the Sequence Listing. Examples of such polypeptides include SEQ ID NO:4, SEQ ID NO:6, SEQ ID NO:8, SEQ ID NO:10, SEQ ID NO:12, SEQ ID NO:14, SEQ ID NO:16, SEQ ID NO:17, SEQ ID NO:19, SEQ ID NO:20, SEQ ID NO:21, SEQ ID NO:22, SEQ ID NO:24, SEQ ID NO:25, SEQ ID NO:27, SEQ ID NO:29, SEQ ID NO:31, SEQ ID NO:33, SEQ ID NO:35, SEQ ID NO:36, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, and SEQ ID NO:47.

In some cases, a low nitrogen tolerance-modulating polypeptide has an amino acid sequence with sequence similarity to the amino acid sequence set forth in SEQ ID NO:49, and preferably has at least 20%, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:49. Amino acid sequences of polypeptides having greater than 45% sequence identity to the polypeptide set forth in SEQ ID NO:49 are provided in FIG. 2 and in the Sequence Listing. Examples of such polypeptides include SEQ ID NO:51, SEQ ID NO:53, SEQ ID NO:55, SEQ ID NO:56, SEQ ID NO:58, SEQ ID NO:60, SEQ ID NO:62, SEQ ID NO:63, SEQ ID NO:64, SEQ ID NO:65, SEQ ID NO:67, SEQ ID NO:69, SEQ ID NO:70, SEQ ID NO:71, SEQ ID NO:72, SEQ ID NO:73, and SEQ ID NO:75.

In some cases, a low nitrogen tolerance-modulating polypeptide has an amino acid sequence with sequence similarity to the amino acid sequence set forth in SEQ ID NO:77, and preferably has at least 20%, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:77. Amino acid sequences of polypeptides having greater than 45% sequence identity to the polypeptide set forth in SEQ ID NO:77 are provided in FIG. 3 and in the Sequence Listing. Examples of such polypeptides include SEQ ID NO:78, SEQ ID NO:80, SEQ ID NO:82, SEQ ID NO:84, SEQ ID NO:85, SEQ ID NO:87, SEQ ID NO:88, SEQ ID NO:90, SEQ ID NO:92, SEQ ID NO:93, SEQ ID NO:95, SEQ ID NO:1479.

In some cases, a low nitrogen tolerance-modulating polypeptide has an amino acid sequence with sequence similarity to the amino acid sequence set forth in SEQ ID NO:100, and preferably has at least 20%, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:100. Amino acid sequences of polypeptides having greater than 45% sequence identity to the polypeptide set forth in SEQ ID NO: 100 are provided in FIG. 4 and in the Sequence Listing. Examples of such polypeptides include SEQ ID NO:101, SEQ ID NO:102, SEQ ID NO:104, SEQ ID NO:106, SEQ ID NO:108, SEQ ID NO:110, SEQ ID NO:111, SEQ ID NO:113, SEQ ID NO:115, SEQ ID NO:116, SEQ ID NO:117, SEQ ID NO:118, SEQ ID NO:119, SEQ ID NO:120, SEQ ID NO:121, SEQ ID NO:122, SEQ ID NO:123, SEQ ID NO:125, SEQ ID NO:126, SEQ ID NO:128, SEQ ID NO:129, SEQ ID NO:130, SEQ ID NO:131, SEQ ID NO:132, SEQ ID NO:133, SEQ ID NO:134, SEQ ID NO:135, SEQ ID NO:137, SEQ ID NO:139, SEQ ID NO:141, SEQ ID NO:142, SEQ ID NO:144, SEQ ID NO:145, SEQ ID NO:146, SEQ ID NO:147, SEQ ID NO:148, SEQ ID NO:149, and SEQ ID NO:150.

In some cases, a low nitrogen tolerance-modulating polypeptide has an amino acid sequence with sequence similarity to the amino acid sequence set forth in SEQ ID NO:152, and preferably has at least 20%, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:152. Amino acid sequences of polypeptides having greater than 45% sequence identity to the polypeptide set forth in SEQ ID NO:152 are provided in FIG. 5 and in the Sequence Listing. Examples of such polypeptides include SEQ ID NO:154, SEQ ID NO:156, SEQ ID NO:158, SEQ ID NO:160, SEQ ID NO:162, and SEQ ID NO:164.

In some cases, a low nitrogen tolerance-modulating polypeptide has an amino acid sequence with sequence similarity to the amino acid sequence set forth in SEQ ID NO:166, and preferably has at least 20%, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:166. Amino acid sequences of polypeptides having greater than 45% sequence identity to the polypeptide set forth in SEQ ID NO:166 are provided in FIG. 6 and in the Sequence Listing. Examples of such polypeptides include SEQ ID NO:166, SEQ ID NO:168, SEQ ID NO:170, SEQ ID NO:172, SEQ ID NO:174, SEQ ID NO:177, SEQ ID NO:179, SEQ ID NO:181, SEQ ID NO:182, SEQ ID NO:183, SEQ ID NO:184.

In some cases, a low nitrogen tolerance-modulating polypeptide has an amino acid sequence with sequence similarity to the amino acid sequence set forth in SEQ ID NO:186, and preferably has at least 20%, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:186. Amino acid sequences of polypeptides having greater than 45% sequence identity to the polypeptide set forth in SEQ ID NO:186 are provided in FIG. 7 and in the Sequence Listing. Examples of such polypeptides include SEQ ID NO:188, SEQ ID NO:190, SEQ ID NO:191, SEQ ID NO:193, SEQ ID NO:194, SEQ ID NO:196, SEQ ID NO:197, SEQ ID NO:199, SEQ ID NO:201, SEQ ID NO:203, SEQ ID NO:204, SEQ ID NO:205, and SEQ ID NO:206.

In some cases, a low nitrogen tolerance-modulating polypeptide has an amino acid sequence with sequence similarity to the amino acid sequence set forth in SEQ ID NO:208, and preferably has at least 20%, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:208. Amino acid sequences of polypeptides having greater than 45% sequence identity to the polypeptide set forth in SEQ ID NO:208 are provided in FIG. 8 and in the Sequence Listing. Examples of such polypeptides include SEQ ID NO:209, SEQ ID NO:210, SEQ ID NO:214, and SEQ ID NO:216.

In some cases, a low nitrogen tolerance-modulating polypeptide has an amino acid sequence with sequence similarity to the amino acid sequence set forth in SEQ ID NO:218, and preferably has at least 20%, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:218. Amino acid sequences of polypeptides having greater than 45% sequence identity to the polypeptide set forth in SEQ ID NO:218 are provided in FIG. 9 and in the Sequence Listing. Examples of such polypeptides include SEQ ID NO:218, SEQ ID NO:220, SEQ ID NO:222, SEQ ID NO:223, SEQ ID NO:225, SEQ ID NO:227, SEQ ID NO:229, SEQ ID NO:230, SEQ ID NO:231, SEQ ID NO:232, SEQ ID NO:1039, SEQ ID NO:1049, and SEQ ID NO:1052.

In some cases, a low nitrogen tolerance-modulating polypeptide has an amino acid sequence with sequence similarity to the amino acid sequence set forth in SEQ ID NO:234, and preferably has at least 20%, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:234. Amino acid sequences of polypeptides having greater than 45% sequence identity to the polypeptide set forth in SEQ ID NO:234 are provided in FIG. 10 and in the Sequence Listing. Examples of such polypeptides include SEQ ID NO:236, SEQ ID NO:238, SEQ ID NO:239, SEQ ID NO:241, SEQ ID NO:242, SEQ ID NO:243, and SEQ ID NO:244.

In some cases, a low nitrogen tolerance-modulating polypeptide has an amino acid sequence with sequence similarity to the amino acid sequence set forth in SEQ ID NO:246, and preferably has at least 20%, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:246. Amino acid sequences of polypeptides having greater than 45% sequence identity to the polypeptide set forth in SEQ ID NO:246 are provided in FIG. 11 and in the Sequence Listing. Examples of such polypeptides include SEQ ID NO:248, SEQ ID NO:249, SEQ ID NO:251, SEQ ID NO:253, SEQ ID NO:255, SEQ ID NO:257, SEQ ID NO:259, SEQ ID NO:260, SEQ ID NO:262, SEQ ID NO:264, SEQ ID NO:265, SEQ ID NO:267, SEQ ID NO:268, SEQ ID NO:270, SEQ ID NO:272, SEQ ID NO:274, SEQ ID NO:276, SEQ ID NO:277, SEQ ID NO:279, SEQ ID NO:281, SEQ ID NO:283, SEQ ID NO:285, SEQ ID NO:286, SEQ ID NO:287, SEQ ID NO:288, SEQ ID NO:290, SEQ ID NO:291, SEQ ID NO:292, SEQ ID NO:293, SEQ ID NO:296, and SEQ ID NO:298.

In some cases, a low nitrogen tolerance-modulating polypeptide has an amino acid sequence with sequence similarity to the amino acid sequence set forth in SEQ ID NO:300, and preferably has at least 20%, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:300. Amino acid sequences of polypeptides having greater than 45% sequence identity to the polypeptide set forth in SEQ ID NO:300 are provided in FIG. 12 and in the Sequence Listing. Examples of such polypeptides include SEQ ID NO:302, SEQ ID NO:304, SEQ ID NO:306, SEQ ID NO:308, SEQ ID NO:310, SEQ ID NO:312, SEQ ID NO:314, SEQ ID NO:316, SEQ ID NO:318, SEQ ID NO:319, SEQ ID NO:320, SEQ ID NO:321, SEQ ID NO:322, SEQ ID NO:323, SEQ ID NO:325, SEQ ID NO:327, and SEQ ID NO:329.

In some cases, a low nitrogen tolerance-modulating polypeptide has an amino acid sequence with sequence similarity to the amino acid sequence set forth in SEQ ID NO:332, and preferably has at least 20%, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:332. Amino acid sequences of polypeptides having greater than 45% sequence identity to the polypeptide set forth in SEQ ID NO:332 are provided in FIG. 13 and in the Sequence Listing. Examples of such polypeptides include SEQ ID NO:332, SEQ ID NO:334, SEQ ID NO:335, SEQ ID NO:336, SEQ ID NO:338, SEQ ID NO:339, SEQ ID NO:341, SEQ ID NO:342, SEQ ID NO:343, SEQ ID NO:344, SEQ ID NO:345, SEQ ID NO:346, SEQ ID NO:347, SEQ ID NO:348, SEQ ID NO:349, SEQ ID NO:351, SEQ ID NO:352, SEQ ID NO:353, SEQ ID NO:354, SEQ ID NO:355, SEQ ID NO:356, SEQ ID NO:357, SEQ ID NO:358, SEQ ID NO:359, SEQ ID NO:360, SEQ ID NO:362, SEQ ID NO:363, SEQ ID NO:364, SEQ ID NO:365, SEQ ID NO:366, SEQ ID NO:2541, SEQ ID NO:2542, SEQ ID NO:2543, SEQ ID NO:2544, SEQ ID NO:2546, SEQ ID NO:2548, SEQ ID NO:2549, SEQ ID NO:2550, SEQ ID NO:2551, SEQ ID NO:2552, and SEQ ID NO:2553.

In some cases, a low nitrogen tolerance-modulating polypeptide has an amino acid sequence with sequence similarity to the amino acid sequence set forth in SEQ ID NO:368, and preferably has at least 20%, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:368. Amino acid sequences of polypeptides having greater than 45% sequence identity to the polypeptide set forth in SEQ ID NO:368 are provided in FIG. 14 and in the Sequence Listing. Examples of such polypeptides include SEQ ID NO:369, SEQ ID NO:370, SEQ ID NO:371, SEQ ID NO:372, SEQ ID NO:373, SEQ ID NO:374, SEQ ID NO:376, SEQ ID NO:378, SEQ ID NO:380, SEQ ID NO:382, SEQ ID NO:384, SEQ ID NO:386, SEQ ID NO:388, SEQ ID NO:390, SEQ ID NO:392, SEQ ID NO:394, SEQ ID NO:396, SEQ ID NO:398, SEQ ID NO:399, SEQ ID NO:401, SEQ ID NO:403, SEQ ID NO:404, SEQ ID NO:406, SEQ ID NO:408, SEQ ID NO:410, SEQ ID NO:412, SEQ ID NO:414, SEQ ID NO:416, SEQ ID NO:418, SEQ ID NO:419, SEQ ID NO:420, SEQ ID NO:422, SEQ ID NO:423, SEQ ID NO:425, SEQ ID NO:427, SEQ ID NO:428, SEQ ID NO:430, SEQ ID NO:432, SEQ ID NO:433, SEQ ID NO:434, SEQ ID NO:435, SEQ ID NO:436, SEQ ID NO:437, SEQ ID NO:438, SEQ ID NO:439, SEQ ID NO:440, SEQ ID NO:441, SEQ ID NO:444, SEQ ID NO:445, SEQ ID NO:446, SEQ ID NO:447, SEQ ID NO:448, SEQ ID NO:449, SEQ ID NO:450, SEQ ID NO:451, SEQ ID NO:452, SEQ ID NO:453, SEQ ID NO:454, SEQ ID NO:455, SEQ ID NO:456, SEQ ID NO:458, SEQ ID NO:459, SEQ ID NO:461, SEQ ID NO:463, SEQ ID NO:465, SEQ ID NO:467, SEQ ID NO:469, SEQ ID NO:471, SEQ ID NO:473, SEQ ID NO:474, SEQ ID NO:475, SEQ ID NO:477, SEQ ID NO:479, SEQ ID NO:481, SEQ ID NO:483, SEQ ID NO:485, SEQ ID NO:487, SEQ ID NO:488, SEQ ID NO:489, SEQ ID NO:490, SEQ ID NO:491, SEQ ID NO:492, SEQ ID NO:494, SEQ ID NO:495, SEQ ID NO:496, SEQ ID NO:497, SEQ ID NO:498, SEQ ID NO:499, SEQ ID NO:500, SEQ ID NO:501, SEQ ID NO:502, SEQ ID NO:504, SEQ ID NO:505, SEQ ID NO:506, SEQ ID NO:507, and SEQ ID NO:508.

In some cases, a low nitrogen tolerance-modulating polypeptide has an amino acid sequence with sequence similarity to the amino acid sequence set forth in SEQ ID NO:510, and preferably has at least 20%, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:510. Amino acid sequences of polypeptides having greater than 45% sequence identity to the polypeptide set forth in SEQ ID NO:510 are provided in FIG. 15 and in the Sequence Listing. Examples of such polypeptides include SEQ ID NO:511, SEQ ID NO:513, SEQ ID NO:515, SEQ ID NO:517, SEQ ID NO:521, SEQ ID NO:523, SEQ ID NO:525, SEQ ID NO:527, SEQ ID NO:529, SEQ ID NO:530, and SEQ ID NO:531.

In some cases, a low nitrogen tolerance-modulating polypeptide has an amino acid sequence with sequence similarity to the amino acid sequence set forth in SEQ ID NO:533, and preferably has at least 20%, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:533. Amino acid sequences of polypeptides having greater than 45% sequence identity to the polypeptide set forth in SEQ ID NO:533 are provided in FIG. 16 and in the Sequence Listing. Examples of such polypeptides include SEQ ID NO:535, SEQ ID NO:536, SEQ ID NO:538, SEQ ID NO:539, SEQ ID NO:541, SEQ ID NO:542, SEQ ID NO:543, SEQ ID NO:544, SEQ ID NO:545, SEQ ID NO:546, SEQ ID NO:547, SEQ ID NO:548, SEQ ID NO:550, SEQ ID NO:552, SEQ ID NO:553, and SEQ ID NO:554.

In some cases, a low nitrogen tolerance-modulating polypeptide has an amino acid sequence with sequence similarity to the amino acid sequence set forth in SEQ ID NO:558, and preferably has at least 20%, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:558. Amino acid sequences of polypeptides having greater than 45% sequence identity to the polypeptide set forth in SEQ ID NO:558 are provided in FIG. 17 and in the Sequence Listing. Examples of such polypeptides include SEQ ID NO:559, SEQ ID NO:560, SEQ ID NO:561, SEQ ID NO:562, SEQ ID NO:563, SEQ ID NO:564, SEQ ID NO:565, SEQ ID NO:566, SEQ ID NO:567, SEQ ID NO:569, SEQ ID NO:571, SEQ ID NO:572, SEQ ID NO:573, SEQ ID NO:575, SEQ ID NO:576, SEQ ID NO:577, SEQ ID NO:578, SEQ ID NO:579, SEQ ID NO:581, SEQ ID NO:583, SEQ ID NO:584, SEQ ID NO:585, SEQ ID NO:586, SEQ ID NO:588, SEQ ID NO:589, SEQ ID NO:590, and SEQ ID NO:591.

In some cases, a low nitrogen tolerance-modulating polypeptide has an amino acid sequence with sequence similarity to the amino acid sequence set forth in SEQ ID NO:593, and preferably has at least 20%, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:593. Amino acid sequences of polypeptides having greater than 45% sequence identity to the polypeptide set forth in SEQ ID NO:593 are provided in FIG. 18 and in the Sequence Listing. Examples of such polypeptides include SEQ ID NO:595, SEQ ID NO:597, SEQ ID NO:599, SEQ ID NO:601, SEQ ID NO:603, SEQ ID NO:605, SEQ ID NO:607, SEQ ID NO:609, SEQ ID NO:610, and SEQ ID NO:611.

In some cases, a low nitrogen tolerance-modulating polypeptide has an amino acid sequence with sequence similarity to the amino acid sequence set forth in SEQ ID NO:613, and preferably has at least 20%, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:613. Amino acid sequences of polypeptides having greater than 45% sequence identity to the polypeptide set forth in SEQ ID NO:613 are provided in FIG. 19 and in the Sequence Listing. Examples of such polypeptides include SEQ ID NO:615, SEQ ID NO:617, SEQ ID NO:618, SEQ ID NO:620, SEQ ID NO:622, SEQ ID NO:624, SEQ ID NO:626, SEQ ID NO:628, SEQ ID NO:630, SEQ ID NO:632, SEQ ID NO:634, SEQ ID NO:636, SEQ ID NO:638, SEQ ID NO:640, SEQ ID NO:642, SEQ ID NO:643, and SEQ ID NO:644.

In some cases, a low nitrogen tolerance-modulating polypeptide has an amino acid sequence with sequence similarity to the amino acid sequence set forth in SEQ ID NO:646, and preferably has at least 20%, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:646. Amino acid sequences of polypeptides having greater than 45% sequence identity to the polypeptide set forth in SEQ ID NO:646 are provided in FIG. 20 and in the Sequence Listing. Examples of such polypeptides include SEQ ID NO:648, SEQ ID NO:650, SEQ ID NO:652, SEQ ID NO:654, SEQ ID NO:656, SEQ ID NO:658, SEQ ID NO:660, SEQ ID NO:662, SEQ ID NO:664, SEQ ID NO:666, SEQ ID NO:668, SEQ ID NO:670, SEQ ID NO:672, SEQ ID NO:674, SEQ ID NO:676, SEQ ID NO:678, SEQ ID NO:679, SEQ ID NO:680, SEQ ID NO:681, SEQ ID NO:682, SEQ ID NO:683, and SEQ ID NO:685.

In some cases, a low nitrogen tolerance-modulating polypeptide has an amino acid sequence with sequence similarity to the amino acid sequence set forth in SEQ ID NO:687, and preferably has at least 20%, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:687. Amino acid sequences of polypeptides having greater than 45% sequence identity to the polypeptide set forth in SEQ ID NO:687 are provided in FIG. 21 and in the Sequence Listing. Examples of such polypeptides include SEQ ID NO:689, SEQ ID NO:691, SEQ ID NO:693, SEQ ID NO:694, SEQ ID NO:696, SEQ ID NO:697, SEQ ID NO:699, SEQ ID NO:701, SEQ ID NO:703, SEQ ID NO:705, SEQ ID NO:706, SEQ ID NO:708, SEQ ID NO:710, SEQ ID NO:712, SEQ ID NO:714, SEQ ID NO:716, SEQ ID NO:718, SEQ ID NO:720, SEQ ID NO:721, SEQ ID NO:722, SEQ ID NO:723, SEQ ID NO:724, SEQ ID NO:725, SEQ ID NO:726, SEQ ID NO:727, and SEQ ID NO:728.

In some cases, a low nitrogen tolerance-modulating polypeptide has an amino acid sequence with sequence similarity to the amino acid sequence set forth in SEQ ID NO:730, and preferably has at least 20%, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:730. Amino acid sequences of polypeptides having greater than 45% sequence identity to the polypeptide set forth in SEQ ID NO:730 are provided in FIG. 22 and in the Sequence Listing. Examples of such polypeptides include SEQ ID NO:732, SEQ ID NO:733, SEQ ID NO:735, SEQ ID NO:737, SEQ ID NO:738, and SEQ ID NO:742.

In some cases, a low nitrogen tolerance-modulating polypeptide has an amino acid sequence with sequence similarity to the amino acid sequence set forth in SEQ ID NO:746, and preferably has at least 20%, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:746. Amino acid sequences of polypeptides having greater than 45% sequence identity to the polypeptide set forth in SEQ ID NO:746 are provided in FIG. 23 and in the Sequence Listing. Examples of such polypeptides include SEQ ID NO:748, SEQ ID NO:750, SEQ ID NO:751, SEQ ID NO:753, SEQ ID NO:755, SEQ ID NO:757, SEQ ID NO:758, SEQ ID NO:760, SEQ ID NO:761, SEQ ID NO:762, SEQ ID NO:763, SEQ ID NO:765, and SEQ ID NO:767.

In some cases, a low nitrogen tolerance-modulating polypeptide has an amino acid sequence with sequence similarity to the amino acid sequence set forth in SEQ ID NO:769, and preferably has at least 20%, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:769. Amino acid sequences of polypeptides having greater than 45% sequence identity to the polypeptide set forth in SEQ ID NO:769 are provided in FIG. 24 and in the Sequence Listing. Examples of such polypeptides include SEQ ID NO:771, SEQ ID NO:773, SEQ ID NO:775, SEQ ID NO:777, SEQ ID NO:779, SEQ ID NO:781, SEQ ID NO:783, SEQ ID NO:785, SEQ ID NO:787, SEQ ID NO:789, and SEQ ID NO:790.

In some cases, a low nitrogen tolerance-modulating polypeptide has an amino acid sequence with sequence similarity to the amino acid sequence set forth in SEQ ID NO:792, and preferably has at least 20%, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:792. Amino acid sequences of polypeptides having greater than 20% sequence identity to the polypeptide set forth in SEQ ID NO:792 are provided in FIG. 25 and in the Sequence Listing. Examples of such polypeptides include SEQ ID NO:794, SEQ ID NO:796, SEQ ID NO:798, SEQ ID NO:799, SEQ ID NO:801, SEQ ID NO:803, SEQ ID NO:805, SEQ ID NO:807, SEQ ID NO:808, SEQ ID NO:810, SEQ ID NO:812, SEQ ID NO:814, SEQ ID NO:816, SEQ ID NO:818, SEQ ID NO:819, SEQ ID NO:820, SEQ ID NO:821, and SEQ ID NO:822.

In some cases, a low nitrogen tolerance-modulating polypeptide has an amino acid sequence with sequence similarity to the amino acid sequence set forth in SEQ ID NO:824, and preferably has at least 20%, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:824. Amino acid sequences of polypeptides having greater than 45% sequence identity to the polypeptide set forth in SEQ ID NO:824 are provided in FIG. 26 and in the Sequence Listing. Such polypeptides include, but not limited to, SEQ ID NO:826, SEQ ID NO:1696, SEQ ID NO:1698, SEQ ID NO:1700, SEQ ID NO:1702, SEQ ID NO:1704, SEQ ID NO:1706, SEQ ID NO:1708, SEQ ID NO:1710, SEQ ID NO:1711, SEQ ID NO:1713, SEQ ID NO:1714, SEQ ID NO:1715, and SEQ ID NO:1716.

In some cases, a low nitrogen tolerance-modulating polypeptide has an amino acid sequence with sequence similarity to the amino acid sequence set forth in SEQ ID NO:828, and preferably has at least 20%, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:828. Amino acid sequences of polypeptides having greater than 20% sequence identity to the polypeptide set forth in SEQ ID NO:828 are provided in FIG. 27 and in the Sequence Listing. Examples of such polypeptides include SEQ ID NO:830, SEQ ID NO:832, SEQ ID NO:834, SEQ ID NO:836, SEQ ID NO:837, SEQ ID NO:838, SEQ ID NO:839, SEQ ID NO:840, SEQ ID NO:842, SEQ ID NO:844, SEQ ID NO:845, SEQ ID NO:846, SEQ ID NO:847, SEQ ID NO:848, SEQ ID NO:849, SEQ ID NO:850, and SEQ ID NO:851.

In some cases, a low nitrogen tolerance-modulating polypeptide has an amino acid sequence with sequence similarity to the amino acid sequence set forth in SEQ ID NO:855, and preferably has at least 20%, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:855. Amino acid sequences of polypeptides having greater than 20% sequence identity to the polypeptide set forth in SEQ ID NO:855 are provided in FIG. 28 and in the Sequence Listing. Examples of such polypeptides include SEQ ID NO:856, SEQ ID NO:858, SEQ ID NO:860, SEQ ID NO:862, SEQ ID NO:864, SEQ ID NO:866, SEQ ID NO:868, SEQ ID NO:870, SEQ ID NO:872, SEQ ID NO:874, SEQ ID NO:876, SEQ ID NO:878, SEQ ID NO:880, SEQ ID NO:882, SEQ ID NO:884, SEQ ID NO:885, SEQ ID NO:886, SEQ ID NO:887, SEQ ID NO:888, and SEQ ID NO:889.

In some cases, a low nitrogen tolerance-modulating polypeptide has an amino acid sequence with sequence similarity to the amino acid sequence set forth in SEQ ID NO:891, and preferably has at least 20%, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:891. Amino acid sequences of polypeptides having greater than 20% sequence identity to the polypeptide set forth in SEQ ID NO:891 are provided in FIG. 29 and in the Sequence Listing. Examples of such polypeptides include SEQ ID NO:893, SEQ ID NO:894, SEQ ID NO:895, SEQ ID NO:896, SEQ ID NO:898, SEQ ID NO:900, SEQ ID NO:901, SEQ ID NO:902, SEQ ID NO:903, SEQ ID NO:904, SEQ ID NO:905, SEQ ID NO:907, SEQ ID NO:908, SEQ ID NO:909, SEQ ID NO:910, SEQ ID NO:911, SEQ ID NO:912, SEQ ID NO:913, SEQ ID NO:914, and SEQ ID NO:915.

In some cases, a low nitrogen tolerance-modulating polypeptide has an amino acid sequence with sequence similarity to the amino acid sequence set forth in SEQ ID NO:917, and preferably has at least 20%, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:917. Amino acid sequences of polypeptides having greater than 20% sequence identity to the polypeptide set forth in SEQ ID NO:917 are provided in FIG. 30 and in the Sequence Listing. Examples of such polypeptides include SEQ ID NO:919, SEQ ID NO:921, SEQ ID NO:923, SEQ ID NO:925, SEQ ID NO:927, SEQ ID NO:929, SEQ ID NO:931, SEQ ID NO:933, SEQ ID NO:935, SEQ ID NO:937, SEQ ID NO:939, and SEQ ID NO:940.

In some cases, a low nitrogen tolerance-modulating polypeptide has an amino acid sequence with sequence similarity to the amino acid sequence set forth in SEQ ID NO:944, and preferably has at least 20%, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:944. Amino acid sequences of polypeptides having greater than 20% sequence identity to the polypeptide set forth in SEQ ID NO:944 are provided in FIG. 31 and in the Sequence Listing. Examples of such polypeptides include SEQ ID NO:946, SEQ ID NO:947, SEQ ID NO:948, SEQ ID NO:950, SEQ ID NO:952, SEQ ID NO:954, SEQ ID NO:956, SEQ ID NO:958, SEQ ID NO:960, SEQ ID NO:962, SEQ ID NO:964, SEQ ID NO:966, SEQ ID NO:967, SEQ ID NO:968, SEQ ID NO:969, SEQ ID NO:970, SEQ ID NO:972, and SEQ ID NO:974.

In some cases, a low nitrogen tolerance-modulating polypeptide has an amino acid sequence with sequence similarity to the amino acid sequence set forth in SEQ ID NO:976, and preferably has at least 20%, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:976. Amino acid sequences of polypeptides having greater than 45% sequence identity to the polypeptide set forth in SEQ ID NO:976 are provided in FIG. 32 and in the Sequence Listing. Examples of such polypeptides include SEQ ID NO:978 and SEQ ID NO:980.

In some cases, a low nitrogen tolerance-modulating polypeptide has an amino acid sequence with sequence similarity to the amino acid sequence set forth in SEQ ID NO:982, and preferably has at least 20%, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:982. Amino acid sequences of polypeptides having greater than 20% sequence identity to the polypeptide set forth in SEQ ID NO:982 are provided in FIG. 33 and in the Sequence Listing. Examples of such polypeptides include SEQ ID NO:984, SEQ ID NO:985, SEQ ID NO:986, SEQ ID NO:987, SEQ ID NO:988, SEQ ID NO:989, SEQ ID NO:990, SEQ ID NO:991, SEQ ID NO:992, SEQ ID NO:993, SEQ ID NO:995, SEQ ID NO:996, SEQ ID NO:998, SEQ ID NO:1000, SEQ ID NO:1001, SEQ ID NO:1003, SEQ ID NO:1005, SEQ ID NO:1007, SEQ ID NO:1008, SEQ ID NO:1009, SEQ ID NO:1011, SEQ ID NO:1013, SEQ ID NO:1015, SEQ ID NO:1016, SEQ ID NO:1018, SEQ ID NO:1019, SEQ ID NO:1021, SEQ ID NO:1023, SEQ ID NO:1025, SEQ ID NO:1026, SEQ ID NO:1027, SEQ ID NO:1028, SEQ ID NO:1029, SEQ ID NO:1030, SEQ ID NO:1031, SEQ ID NO:1032, and SEQ ID NO:1033.

In some cases, a low nitrogen tolerance-modulating polypeptide has an amino acid sequence with sequence similarity to the amino acid sequence set forth in SEQ ID NO:1054, and preferably has at least 20%, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:1054. Amino acid sequences of polypeptides having greater than 20% sequence identity to the polypeptide set forth in SEQ ID NO:1054 are provided in FIG. 34 and in the Sequence Listing. Examples of such polypeptides include SEQ ID NO:1055, SEQ ID NO:1057, SEQ ID NO:1058, SEQ ID NO:1059, SEQ ID NO:1061, SEQ ID NO:1063, SEQ ID NO:1065, SEQ ID NO:1065, SEQ ID NO:1067, SEQ ID NO:1068, SEQ ID NO:1070, SEQ ID NO:1071, SEQ ID NO:1072, SEQ ID NO:1074, SEQ ID NO:1075, SEQ ID NO:1076, SEQ ID NO:1077, SEQ ID NO:1078, SEQ ID NO:1080, SEQ ID NO:1082, SEQ ID NO:1083, SEQ ID NO:1085, SEQ ID NO:1086, SEQ ID NO:1087, SEQ ID NO:1088, SEQ ID NO:1089, SEQ ID NO:1089, SEQ ID NO:1090, SEQ ID NO:1091, SEQ ID NO:1092, SEQ ID NO:1093, SEQ ID NO:1094, SEQ ID NO:1095, and SEQ ID NO:1097.

In some cases, a low nitrogen tolerance-modulating polypeptide has an amino acid sequence with sequence similarity to the amino acid sequence set forth in SEQ ID NO:1099, and preferably has at least 20%, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:1099. Amino acid sequences of polypeptides having greater than 20% sequence identity to the polypeptide set forth in SEQ ID NO:1099 are provided in FIG. 35 and in the Sequence Listing. Examples of such polypeptides include SEQ ID NO:1101, SEQ ID NO:1103, SEQ ID NO:1104, SEQ ID NO:1105, SEQ ID NO:1106, SEQ ID NO:1108, SEQ ID NO:1109, and SEQ ID NO:1110.

In some cases, a low nitrogen tolerance-modulating polypeptide has an amino acid sequence with sequence similarity to the amino acid sequence set forth in SEQ ID NO:1112, and preferably has at least 20%, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:1112. Amino acid sequences of polypeptides having greater than 20% sequence identity to the polypeptide set forth in SEQ ID NO:1112 are provided in FIG. 36 and in the Sequence Listing. Examples of such polypeptides include SEQ ID NO:1113 and SEQ ID NO:1114.

In some cases, a low nitrogen tolerance-modulating polypeptide has an amino acid sequence with sequence similarity to the amino acid sequence set forth in SEQ ID NO:1116, and preferably has at least 20%, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:1116. Amino acid sequences of polypeptides having greater than 20% sequence identity to the polypeptide set forth in SEQ ID NO:1116 are provided in FIG. 37 and in the Sequence Listing. Examples of such polypeptides include SEQ ID NO:1118, SEQ ID NO:1120, SEQ ID NO:1122, SEQ ID NO:1123, SEQ ID NO:1125, SEQ ID NO:1126, SEQ ID NO:1128, SEQ ID NO:1129, SEQ ID NO:1131, SEQ ID NO:1132, SEQ ID NO:1133, SEQ ID NO:1134, SEQ ID NO:1136, SEQ ID NO:1138, SEQ ID NO:1140, SEQ ID NO:1141, SEQ ID NO:1142, SEQ ID NO:1143, SEQ ID NO:1144, SEQ ID NO:1145, SEQ ID NO:1147, SEQ ID NO:1149, SEQ ID NO:1151, SEQ ID NO:1153, and SEQ ID NO:1155.

In some cases, a low nitrogen tolerance-modulating polypeptide has an amino acid sequence with sequence similarity to the amino acid sequence set forth in SEQ ID NO:1159, and preferably has at least 20%, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:1159. Amino acid sequences of polypeptides having greater than 20% sequence identity to the polypeptide set forth in SEQ ID NO:1159 are provided in FIG. 38 and in the Sequence Listing. Examples of such polypeptides include SEQ ID NO:1161, SEQ ID NO:1162, SEQ ID NO:1163, and SEQ ID NO:1164.

In some cases, a low nitrogen tolerance-modulating polypeptide has an amino acid sequence with sequence similarity to the amino acid sequence set forth in SEQ ID NO:1166, and preferably has at least 20%, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:1166. Amino acid sequences of polypeptides having greater than 20% sequence identity to the polypeptide set forth in SEQ ID NO:1166 are provided in FIG. 39 and in the Sequence Listing. Examples of such polypeptides include SEQ ID NO:1167, SEQ ID NO:1169, SEQ ID NO:1171, SEQ ID NO:1173, SEQ ID NO:1175, SEQ ID NO:1177, SEQ ID NO:1179, SEQ ID NO:1180, SEQ ID NO:1182, and SEQ ID NO:1183.

In some cases, a low nitrogen tolerance-modulating polypeptide has an amino acid sequence with sequence similarity to the amino acid sequence set forth in SEQ ID NO:1185, and preferably has at least 20%, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:1185. Amino acid sequences of polypeptides having greater than 20% sequence identity to the polypeptide set forth in SEQ ID NO:1185 are provided in FIG. 40 and in the Sequence Listing. Examples of such polypeptides include SEQ ID NO:1187, SEQ ID NO:1189, SEQ ID NO:1190, SEQ ID NO:1191, and SEQ ID NO:1192.

In some cases, a low nitrogen tolerance-modulating polypeptide has an amino acid sequence with sequence similarity to the amino acid sequence set forth in SEQ ID NO:1194, and preferably has at least 20%, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:1194. Amino acid sequences of polypeptides having greater than 20% sequence identity to the polypeptide set forth in SEQ ID NO:1194 are provided in FIG. 41 and in the Sequence Listing. Examples of such polypeptides include SEQ ID NO:1196, SEQ ID NO:1198, SEQ ID NO:1200, SEQ ID NO:1202, SEQ ID NO:1203, SEQ ID NO:1204, SEQ ID NO:1205, SEQ ID NO:1206, SEQ ID NO:1207, and SEQ ID NO:1208.

In some cases, a low nitrogen tolerance-modulating polypeptide has an amino acid sequence with sequence similarity to the amino acid sequence set forth in SEQ ID NO:1210, and preferably has at least 20%, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:1210. Amino acid sequences of polypeptides having greater than 20% sequence identity to the polypeptide set forth in SEQ ID NO:1210 are provided in FIG. 42 and in the Sequence Listing. Examples of such polypeptides include SEQ ID NO:1211, SEQ ID NO:1213, SEQ ID NO:1215, SEQ ID NO:1216, SEQ ID NO:1218, SEQ ID NO:1220, SEQ ID NO:1222, SEQ ID NO:1224, SEQ ID NO:1226, SEQ ID NO:1228, SEQ ID NO:1229, SEQ ID NO:1230, SEQ ID NO:1232, SEQ ID NO:1233, SEQ ID NO:1234, SEQ ID NO:1235, SEQ ID NO:1236, SEQ ID NO:1237, SEQ ID NO:1238, SEQ ID NO:1239, SEQ ID NO:1240, SEQ ID NO:1241, SEQ ID NO:1242, SEQ ID NO:1243, SEQ ID NO:1244, SEQ ID NO:1245, SEQ ID NO:1246, SEQ ID NO:1247, SEQ ID NO:1248, SEQ ID NO:1249, SEQ ID NO:1251, SEQ ID NO:1253, SEQ ID NO:1255, SEQ ID NO:1257, SEQ ID NO:1259, SEQ ID NO:1261, SEQ ID NO:1263, SEQ ID NO:1264, SEQ ID NO:1265, SEQ ID NO:1266, SEQ ID NO:1267, SEQ ID NO:1268, SEQ ID NO:1269, SEQ ID NO:1270, SEQ ID NO:1271, and SEQ ID NO:1272.

In some cases, a low nitrogen tolerance-modulating polypeptide has an amino acid sequence with sequence similarity to the amino acid sequence set forth in SEQ ID NO:1274, and preferably has at least 20%, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:1274. Amino acid sequences of polypeptides having greater than 20% sequence identity to the polypeptide set forth in SEQ ID NO:1274 are provided in FIG. 43 and in the Sequence Listing. Examples of such polypeptides include SEQ ID NO:1276, SEQ ID NO:1278, SEQ ID NO:1280, SEQ ID NO:1281, SEQ ID NO:1282, SEQ ID NO:1284, SEQ ID NO:1285, SEQ ID NO:1287, SEQ ID NO:1289, SEQ ID NO:1291, SEQ ID NO:1293, SEQ ID NO:1294, SEQ ID NO:1295, SEQ ID NO:1296, SEQ ID NO:1297, SEQ ID NO:1298, and SEQ ID NO:1300.

In some cases, a low nitrogen tolerance-modulating polypeptide has an amino acid sequence with sequence similarity to the amino acid sequence set forth in SEQ ID NO:1302, and preferably has at least 20%, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:1302. Amino acid sequences of polypeptides having greater than 20% sequence identity to the polypeptide set forth in SEQ ID NO:1302 are provided in FIG. 44 and in the Sequence Listing. Examples of such polypeptides include SEQ ID NO:1303, SEQ ID NO:1305, SEQ ID NO:1307, SEQ ID NO:1309, SEQ ID NO:1311, SEQ ID NO:1312, SEQ ID NO:1313, SEQ ID NO:1314, SEQ ID NO:1315, SEQ ID NO:1317, SEQ ID NO:1318, SEQ ID NO:1319, SEQ ID NO:1320, SEQ ID NO:1321, SEQ ID NO:1322, SEQ ID NO:1323, SEQ ID NO:1324, SEQ ID NO:1325, SEQ ID NO:1326, SEQ ID NO:1327, SEQ ID NO:1328, SEQ ID NO:1330, SEQ ID NO:1331, SEQ ID NO:1333, SEQ ID NO:1334, SEQ ID NO:1335, SEQ ID NO:1336, SEQ ID NO:1337, SEQ ID NO:1338, SEQ ID NO:1339, and SEQ ID NO:1340.

In some cases, a low nitrogen tolerance-modulating polypeptide has an amino acid sequence with sequence similarity to the amino acid sequence set forth in SEQ ID NO:1342, and preferably has at least 20%, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:1342. Amino acid sequences of polypeptides having greater than 20% sequence identity to the polypeptide set forth in SEQ ID NO:1342 are provided in FIG. 45 and in the Sequence Listing. Examples of such polypeptides include SEQ ID NO:1344, SEQ ID NO:1346, SEQ ID NO:1348, SEQ ID NO:1350, SEQ ID NO:1352, SEQ ID NO:1354, SEQ ID NO:1355, SEQ ID NO:1357, SEQ ID NO:1358, SEQ ID NO:1360, SEQ ID NO:1361, SEQ ID NO:1362, SEQ ID NO:1363, SEQ ID NO:1364, SEQ ID NO:1366, SEQ ID NO:1367, SEQ ID NO:1369, SEQ ID NO:1370, SEQ ID NO:1371, SEQ ID NO:1372, SEQ ID NO:1373, SEQ ID NO:1374, SEQ ID NO:1375, SEQ ID NO:1376, SEQ ID NO:1377, SEQ ID NO:1378, SEQ ID NO:1379, SEQ ID NO:1380, SEQ ID NO:1381, SEQ ID NO:1382, and SEQ ID NO:1383.

In some cases, a low nitrogen tolerance-modulating polypeptide has an amino acid sequence with sequence similarity to the amino acid sequence set forth in SEQ ID NO:1385, and preferably has at least 20%, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:1385. Amino acid sequences of polypeptides having greater than 20% sequence identity to the polypeptide set forth in SEQ ID NO:1385 are provided in FIG. 46 and in the Sequence Listing. Examples of such polypeptides include SEQ ID NO:1387, SEQ ID NO:1389, SEQ ID NO:1390, SEQ ID NO:1391, SEQ ID NO:1393, SEQ ID NO:1394, SEQ ID NO:1395, SEQ ID NO:1396, SEQ ID NO:1398, SEQ ID NO:1400, SEQ ID NO:1401, SEQ ID NO:1402, SEQ ID NO:1403, SEQ ID NO:1404, SEQ ID NO:1405, and SEQ ID NO:1407.

In some cases, a low nitrogen tolerance-modulating polypeptide has an amino acid sequence with sequence similarity to the amino acid sequence set forth in SEQ ID NO:1409, and preferably has at least 20%, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:1409. Amino acid sequences of polypeptides having greater than 20% sequence identity to the polypeptide set forth in SEQ ID NO:1409 are provided in FIG. 47 and in the Sequence Listing. Examples of such polypeptides include SEQ ID NO:1411, SEQ ID NO:1413, SEQ ID NO:1415, SEQ ID NO:1417, SEQ ID NO:1418, SEQ ID NO:1419, SEQ ID NO:1421, SEQ ID NO:1423, SEQ ID NO:1424, SEQ ID NO:1425, and SEQ ID NO:1426.

In some cases, a low nitrogen tolerance-modulating polypeptide has an amino acid sequence with sequence similarity to the amino acid sequence set forth in SEQ ID NO:1428, and preferably has at least 20%, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:1428. Amino acid sequences of polypeptides having greater than 20% sequence identity to the polypeptide set forth in SEQ ID NO:1428 are provided in FIG. 48 and in the Sequence Listing. Examples of such polypeptides include SEQ ID NO:1430, SEQ ID NO:1432, SEQ ID NO:1434, SEQ ID NO:1436, SEQ ID NO:1439, SEQ ID NO:1442, SEQ ID NO:1444, SEQ ID NO:1446, SEQ ID NO:1448, SEQ ID NO:1450, SEQ ID NO:1452, SEQ ID NO:1453, SEQ ID NO:1454, SEQ ID NO:1455, SEQ ID NO:1456, SEQ ID NO:1457, SEQ ID NO:1458, and SEQ ID NO:1459.

In some cases, a low nitrogen tolerance-modulating polypeptide has an amino acid sequence with sequence similarity to the amino acid sequence set forth in SEQ ID NO:1463, and preferably has at least 20%, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:1463. Amino acid sequences of polypeptides having greater than 20% sequence identity to the polypeptide set forth in SEQ ID NO:1463 are provided in FIG. 49 and in the Sequence Listing. Examples of such polypeptides include SEQ ID NO:1465, SEQ ID NO:1467, SEQ ID NO:1469, SEQ ID NO:1471, SEQ ID NO:1473, SEQ ID NO:1474, SEQ ID NO:1475, SEQ ID NO:1476, and SEQ ID NO:1477.

In some cases, a low nitrogen tolerance-modulating polypeptide has an amino acid sequence with sequence similarity to the amino acid sequence set forth in SEQ ID NO:1491, and preferably has at least 20%, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:1491. Amino acid sequences of polypeptides having greater than 20% sequence identity to the polypeptide set forth in SEQ ID NO:1491 are provided in FIG. 50 and in the Sequence Listing. Examples of such polypeptides include SEQ ID NO:1493, SEQ ID NO:1495, SEQ ID NO:1497, SEQ ID NO:1499, SEQ ID NO:1501, SEQ ID NO:1503, SEQ ID NO:1504, SEQ ID NO:1505, SEQ ID NO:1506, and SEQ ID NO:1508.

In some cases, a low nitrogen tolerance-modulating polypeptide has an amino acid sequence with sequence similarity to the amino acid sequence set forth in SEQ ID NO:1510, and preferably has at least 20%, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:1510. Amino acid sequences of polypeptides having greater than 20% sequence identity to the polypeptide set forth in SEQ ID NO:1510 are provided in FIG. 51 and in the Sequence Listing. Examples of such polypeptides include SEQ ID O:1512, SEQ ID NO:1514, SEQ ID NO:1516, SEQ ID NO:1518, SEQ ID NO:1520, SEQ ID NO:1522, and SEQ ID NO:1523.

In some cases, a low nitrogen tolerance-modulating polypeptide has an amino acid sequence with sequence similarity to the amino acid sequence set forth in SEQ ID NO:1525, and preferably has at least 20%, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:1525. Amino acid sequences of polypeptides having greater than 20% sequence identity to the polypeptide set forth in SEQ ID NO:1525 are provided in FIG. 52 and in the Sequence Listing. Examples of such polypeptides include SEQ ID NO:1527, SEQ ID NO:1529, SEQ ID NO:1530, SEQ ID NO:1532, SEQ ID NO:1534, and SEQ ID NO:1535.

In some cases, a low nitrogen tolerance-modulating polypeptide has an amino acid sequence with sequence similarity to the amino acid sequence set forth in SEQ ID NO:1537, and preferably has at least 20%, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:1537. Amino acid sequences of polypeptides having greater than 20% sequence identity to the polypeptide set forth in SEQ ID NO:1537 are provided in FIG. 53 and in the Sequence Listing. Examples of such polypeptides include SEQ ID NO:1539, SEQ ID NO:1540, SEQ ID NO:1541, SEQ ID NO:1543, SEQ ID NO:1545, SEQ ID NO:1547, SEQ ID NO:1548, SEQ ID NO:1550, SEQ ID NO:1552, SEQ ID NO:2386, SEQ ID NO:2388, SEQ ID NO:2390, SEQ ID NO:2391, and SEQ ID NO:2392.

In some cases, a low nitrogen tolerance-modulating polypeptide has an amino acid sequence with sequence similarity to the amino acid sequence set forth in SEQ ID NO:1554, and preferably has at least 20%, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:1554. Amino acid sequences of polypeptides having greater than 20% sequence identity to the polypeptide set forth in SEQ ID NO:1554 are provided in FIG. 54 and in the Sequence Listing. Examples of such polypeptides include SEQ ID NO:1555, SEQ ID NO:1557, SEQ ID NO:1559, SEQ ID NO:1561, SEQ ID NO:1563, SEQ ID NO:1565, SEQ ID NO:1567, SEQ ID NO:1569, SEQ ID NO:1571, SEQ ID NO:1572, SEQ ID NO:1573, SEQ ID NO:1574, and SEQ ID NO:1575.

In some cases, a low nitrogen tolerance-modulating polypeptide has an amino acid sequence with sequence similarity to the amino acid sequence set forth in SEQ ID NO:1577, and preferably has at least 20%, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:1577. Amino acid sequences of polypeptides having greater than 20% sequence identity to the polypeptide set forth in SEQ ID NO:1577 are provided in FIG. 55 and in the Sequence Listing. Examples of such polypeptides include SEQ ID NO:1035, SEQ ID NO:1036, SEQ ID NO:1037, SEQ ID NO:1040, SEQ ID NO:1041, SEQ ID NO:1043, SEQ ID NO:1044, SEQ ID NO:1046, SEQ ID NO:1047, SEQ ID NO:1048, SEQ ID NO:1050, SEQ ID NO:1440, SEQ ID NO:1480, SEQ ID NO:1481, SEQ ID NO:1482, SEQ ID NO:1483, SEQ ID NO:1484, SEQ ID NO:1485, SEQ ID NO:1486, SEQ ID NO:1487, SEQ ID NO:1488, SEQ ID NO:1578, SEQ ID NO:1580, SEQ ID NO:1582, SEQ ID NO:1584, SEQ ID NO:1586, SEQ ID NO:1588, SEQ ID NO:1590, SEQ ID NO:1592, SEQ ID NO:1594, SEQ ID NO:1596, SEQ ID NO:1598, SEQ ID NO:1599, SEQ ID NO:1601, SEQ ID NO:1602, SEQ ID NO:1605, SEQ ID NO:1607, SEQ ID NO:1608, SEQ ID NO:1609, SEQ ID NO:1611, SEQ ID NO:1613, SEQ ID NO:1615, SEQ ID NO:1617, SEQ ID NO:1619, SEQ ID NO:1621, SEQ ID NO:1622, SEQ ID NO:1623, SEQ ID NO:1624, SEQ ID NO:1625, SEQ ID NO:1627, SEQ ID NO:1629, SEQ ID NO:1631, SEQ ID NO:1633, SEQ ID NO:1635, SEQ ID NO:1637, SEQ ID NO:1639, SEQ ID NO:1643, SEQ ID NO:1645, SEQ ID NO:1648, SEQ ID NO:1649, SEQ ID NO:1651, SEQ ID NO:1653.

In some cases, a low nitrogen tolerance-modulating polypeptide has an amino acid sequence with sequence similarity to the amino acid sequence set forth in SEQ ID NO:1437, and preferably has at least 20%, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:1437. Amino acid sequences of polypeptides having greater than 20% sequence identity to the polypeptide set forth in SEQ ID NO:1437 are provided in FIG. 56 and in the Sequence Listing. Examples of such polypeptides include SEQ ID NO:173, SEQ ID NO:212, SEQ ID NO:361, SEQ ID NO:421, SEQ ID NO:443, SEQ ID NO:740, SEQ ID NO:744, SEQ ID NO:942, SEQ ID NO:1461.

In some cases, a low nitrogen tolerance-modulating polypeptide has an amino acid sequence with sequence similarity to the amino acid sequence set forth in SEQ ID NO:97, and preferably has at least 20%, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO:97. Amino acid sequences of polypeptides having greater than 20% sequence identity to the polypeptide set forth in SEQ ID NO:1437 are provided in FIG. 57 and in the Sequence Listing. Examples of such polypeptides include SEQ ID NO:2010, SEQ ID NO:2011, SEQ ID NO:2013, SEQ ID NO:2015, and SEQ ID NO:2017

E. Other Sequences

It should be appreciated that a low nitrogen tolerance-modulating polypeptide can include additional amino acids that are not involved in low nitrogen tolerance-modulation, and thus such a polypeptide can be longer than would otherwise be the case. For example, a low nitrogen tolerance-modulating polypeptide can include a purification tag, a chloroplast transit peptide, a mitochondrial transit peptide, an amyloplast peptide, or a leader sequence added to the amino or carboxy terminus. In some embodiments, a low nitrogen tolerance-modulating polypeptide includes an amino acid sequence that functions as a reporter, e.g., a green fluorescent protein or yellow fluorescent protein III. Nucleic Acids Nucleic acids described herein include nucleic acids that are effective to modulate low-nitrogen tolerance levels when transcribed in a plant or plant cell. Such nucleic acids include, without limitation, those that encode a low nitrogen tolerance-modulating polypeptide and those that can be used to inhibit expression of low nitrogen tolerance-modulating polypeptide via a nucleic acid based method.

A. Nucleic Acids Encoding Low Nitrogen Tolerance-modulating Polypeptides

Nucleic acids encoding low nitrogen tolerance-modulating polypeptides are described herein. Examples of such nucleic acids include SEQ ID NO:1, SEQ ID NO:48, SEQ ID NO:76, SEQ ID NO:96, SEQ ID NO:99, SEQ ID NO:151, SEQ ID NO:165, SEQ ID NO:175, SEQ ID NO:185, SEQ ID NO:207, SEQ ID NO:217, SEQ ID NO:233, SEQ ID NO:245, SEQ ID NO:299, SEQ ID NO:331, SEQ ID NO:367, SEQ ID NO:509, SEQ ID NO:532, SEQ ID NO:555, SEQ ID NO:557, SEQ ID NO:592, SEQ ID NO:612, SEQ ID NO:645, SEQ ID NO:686, SEQ ID NO:729, SEQ ID NO:745, SEQ ID NO:768, SEQ ID NO:791, SEQ ID NO:823, SEQ ID NO:827, SEQ ID NO:852, SEQ ID NO:854, SEQ ID NO:890, SEQ ID NO:916, SEQ ID NO:943, SEQ ID NO:975, SEQ ID NO:981, SEQ ID NO:1053, SEQ ID NO:1098, SEQ ID NO:1111, SEQ ID NO:1115, SEQ ID NO:1156, SEQ ID NO:1158, SEQ ID NO:1165, SEQ ID NO:1184, SEQ ID NO:1193, SEQ ID NO:1209, SEQ ID NO:1273, SEQ ID NO:1301, SEQ ID NO:1341, SEQ ID NO:1384, SEQ ID NO:1408, SEQ ID NO:1427, SEQ ID NO:1462, SEQ ID NO:1490, SEQ ID NO:1509, SEQ ID NO:1524, SEQ ID NO:1536, SEQ ID NO:1553, and SEQ ID NO:1576, as described in more detail below. A nucleic acid also can be a fragment that is at least 40% (e.g., at least 45, 50, 55, 60, 65, 70, 75, 80, 85, 90, 95, or 99%) of the length of the full-length nucleic acid set forth in SEQ ID NO:1, SEQ ID NO:48, SEQ ID NO:76, SEQ ID NO:96, SEQ ID NO:99, SEQ ID NO:151, SEQ ID NO:165, SEQ ID NO:175, SEQ ID NO:185, SEQ ID NO:207, SEQ ID NO:217, SEQ ID NO:233, SEQ ID NO:245, SEQ ID NO:299, SEQ ID NO:331, SEQ ID NO:367, SEQ ID NO:509, SEQ ID NO:532, SEQ ID NO:555, SEQ ID NO:557, SEQ ID NO:592, SEQ ID NO:612, SEQ ID NO:645, SEQ ID NO:686, SEQ ID NO:729, SEQ ID NO:745, SEQ ID NO:768, SEQ ID NO:791, SEQ ID NO:823, SEQ ID NO:827, SEQ ID NO:852, SEQ ID NO:854, SEQ ID NO:890, SEQ ID NO:916, SEQ ID NO:943, SEQ ID NO:975, SEQ ID NO:981, SEQ ID NO:1053, SEQ ID NO:1098, SEQ ID NO:1111, SEQ ID NO:1115, SEQ ID NO:1156, SEQ ID NO:1158, SEQ ID NO:1165, SEQ ID NO:1184, SEQ ID NO:1193, SEQ ID NO:1209, SEQ ID NO:1273, SEQ ID NO:1301, SEQ ID NO:1341, SEQ ID NO:1384, SEQ ID NO:1408, SEQ ID NO:1427, SEQ ID NO:1462, SEQ ID NO:1490, SEQ ID NO:1509, SEQ ID NO:1524, SEQ ID NO:1536, SEQ ID NO:1553, and SEQ ID NO:1576.

A low nitrogen tolerance-modulating nucleic acid can comprise the nucleotide sequence set forth in SEQ ID NO:1. Alternatively, a low nitrogen tolerance-modulating nucleic acid can be a variant of the nucleic acid having the nucleotide sequence set forth in SEQ ID NO:2. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:2.

A low nitrogen tolerance-modulating nucleic acid can comprise the nucleotide sequence set forth in SEQ ID NO: 48. Alternatively, a low nitrogen tolerance-modulating nucleic acid can be a variant of the nucleic acid having the nucleotide sequence set forth in SEQ ID NO: 48. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO: 48.

A low nitrogen tolerance-modulating nucleic acid can comprise the nucleotide sequence set forth in SEQ ID NO:76. Alternatively, a low nitrogen tolerance-modulating nucleic acid can be a variant of the nucleic acid having the nucleotide sequence set forth in SEQ ID NO:76. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:76.

A low nitrogen tolerance-modulating nucleic acid can comprise the nucleotide sequence set forth in SEQ ID NO:96. Alternatively, a low nitrogen tolerance-modulating nucleic acid can be a variant of the nucleic acid having the nucleotide sequence set forth in SEQ ID NO:96. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:96.

A low nitrogen tolerance-modulating nucleic acid can comprise the nucleotide sequence set forth in SEQ ID NO:99. Alternatively, a low nitrogen tolerance-modulating nucleic acid can be a variant of the nucleic acid having the nucleotide sequence set forth in SEQ ID NO:99. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:99.

A low nitrogen tolerance-modulating nucleic acid can comprise the nucleotide sequence set forth in SEQ ID NO:151. Alternatively, a low nitrogen tolerance-modulating nucleic acid can be a variant of the nucleic acid having the nucleotide sequence set forth in SEQ ID NO:151. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:151.

A low nitrogen tolerance-modulating nucleic acid can comprise the nucleotide sequence set forth in SEQ ID NO:165. Alternatively, a low nitrogen tolerance-modulating nucleic acid can be a variant of the nucleic acid having the nucleotide sequence set forth in SEQ ID NO:165. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:165.

A low nitrogen tolerance-modulating nucleic acid can comprise the nucleotide sequence set forth in SEQ ID NO:175. Alternatively, a low nitrogen tolerance-modulating nucleic acid can be a variant of the nucleic acid having the nucleotide sequence set forth in SEQ ID NO:175. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:175.

A low nitrogen tolerance-modulating nucleic acid can comprise the nucleotide sequence set forth in SEQ ID NO:185. Alternatively, a low nitrogen tolerance-modulating nucleic acid can be a variant of the nucleic acid having the nucleotide sequence set forth in SEQ ID NO:185. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:185.

A low nitrogen tolerance-modulating nucleic acid can comprise the nucleotide sequence set forth in SEQ ID NO:207. Alternatively, a low nitrogen tolerance-modulating nucleic acid can be a variant of the nucleic acid having the nucleotide sequence set forth in SEQ ID NO:207. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:207.

A low nitrogen tolerance-modulating nucleic acid can comprise the nucleotide sequence set forth in SEQ ID NO:217. Alternatively, a low nitrogen tolerance-modulating nucleic acid can be a variant of the nucleic acid having the nucleotide sequence set forth in SEQ ID NO:217. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:217.

A low nitrogen tolerance-modulating nucleic acid can comprise the nucleotide sequence set forth in SEQ ID NO:233. Alternatively, a low nitrogen tolerance-modulating nucleic acid can be a variant of the nucleic acid having the nucleotide sequence set forth in SEQ ID NO:233. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:233.

A low nitrogen tolerance-modulating nucleic acid can comprise the nucleotide sequence set forth in SEQ ID NO:245. Alternatively, a low nitrogen tolerance-modulating nucleic acid can be a variant of the nucleic acid having the nucleotide sequence set forth in SEQ ID NO:245. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:245.

A low nitrogen tolerance-modulating nucleic acid can comprise the nucleotide sequence set forth in SEQ ID NO:299. Alternatively, a low nitrogen tolerance-modulating nucleic acid can be a variant of the nucleic acid having the nucleotide sequence set forth in SEQ ID NO:299. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:299.

A low nitrogen tolerance-modulating nucleic acid can comprise the nucleotide sequence set forth in SEQ ID NO:331. Alternatively, a low nitrogen tolerance-modulating nucleic acid can be a variant of the nucleic acid having the nucleotide sequence set forth in SEQ ID NO:331. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:331.

A low nitrogen tolerance-modulating nucleic acid can comprise the nucleotide sequence set forth in SEQ ID NO:367. Alternatively, a low nitrogen tolerance-modulating nucleic acid can be a variant of the nucleic acid having the nucleotide sequence set forth in SEQ ID NO:367. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:367.

A low nitrogen tolerance-modulating nucleic acid can comprise the nucleotide sequence set forth in SEQ ID NO:509. Alternatively, a low nitrogen tolerance-modulating nucleic acid can be a variant of the nucleic acid having the nucleotide sequence set forth in SEQ ID NO:509. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:509.

A low nitrogen tolerance-modulating nucleic acid can comprise the nucleotide sequence set forth in SEQ ID NO:532. Alternatively, a low nitrogen tolerance-modulating nucleic acid can be a variant of the nucleic acid having the nucleotide sequence set forth in SEQ ID NO:532. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:532.

A low nitrogen tolerance-modulating nucleic acid can comprise the nucleotide sequence set forth in SEQ ID NO:555. Alternatively, a low nitrogen tolerance-modulating nucleic acid can be a variant of the nucleic acid having the nucleotide sequence set forth in SEQ ID NO:555. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:555.

A low nitrogen tolerance-modulating nucleic acid can comprise the nucleotide sequence set forth in SEQ ID NO:557. Alternatively, a low nitrogen tolerance-modulating nucleic acid can be a variant of the nucleic acid having the nucleotide sequence set forth in SEQ ID NO:557. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:557.

A low nitrogen tolerance-modulating nucleic acid can comprise the nucleotide sequence set forth in SEQ ID NO:592. Alternatively, a low nitrogen tolerance-modulating nucleic acid can be a variant of the nucleic acid having the nucleotide sequence set forth in SEQ ID NO:592. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:592.

A low nitrogen tolerance-modulating nucleic acid can comprise the nucleotide sequence set forth in SEQ ID NO:612. Alternatively, a low nitrogen tolerance-modulating nucleic acid can be a variant of the nucleic acid having the nucleotide sequence set forth in SEQ ID NO:612. For example, a low nitrogen tolerance-modulating nucleic acid can have a nucleotide sequence with at least 80% sequence A low nitrogen tolerance-modulating nucleic acid can comprise the nucleotide sequence set forth in SEQ ID NO:645. Alternatively, a low nitrogen tolerance-modulating nucleic acid can be a variant of the nucleic acid having the nucleotide sequence set forth in SEQ ID NO:645. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:645.

A low nitrogen tolerance-modulating nucleic acid can comprise the nucleotide sequence set forth in SEQ ID NO:686. Alternatively, a low nitrogen tolerance-modulating nucleic acid can be a variant of the nucleic acid having the nucleotide sequence set forth in SEQ ID NO:686. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:686.

A low nitrogen tolerance-modulating nucleic acid can comprise the nucleotide sequence set forth in SEQ ID NO:729. Alternatively, a low nitrogen tolerance-modulating nucleic acid can be a variant of the nucleic acid having the nucleotide sequence set forth in SEQ ID NO:729. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:729.

A low nitrogen tolerance-modulating nucleic acid can comprise the nucleotide sequence set forth in SEQ ID NO:745. Alternatively, a low nitrogen tolerance-modulating nucleic acid can be a variant of the nucleic acid having the nucleotide sequence set forth in SEQ ID NO:745. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:745.

A low nitrogen tolerance-modulating nucleic acid can comprise the nucleotide sequence set forth in SEQ ID NO:768. Alternatively, a low nitrogen tolerance-modulating nucleic acid can be a variant of the nucleic acid having the nucleotide sequence set forth in SEQ ID NO:768. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:768.

A low nitrogen tolerance-modulating nucleic acid can comprise the nucleotide sequence set forth in SEQ ID NO:791. Alternatively, a low nitrogen tolerance-modulating nucleic acid can be a variant of the nucleic acid having the nucleotide sequence set forth in SEQ ID NO:791. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:791.

A low nitrogen tolerance-modulating nucleic acid can comprise the nucleotide sequence set forth in SEQ ID NO:823. Alternatively, a low nitrogen tolerance-modulating nucleic acid can be a variant of the nucleic acid having the nucleotide sequence set forth in SEQ ID NO:823. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:823.

A low nitrogen tolerance-modulating nucleic acid can comprise the nucleotide sequence set forth in SEQ ID NO:827. Alternatively, a low nitrogen tolerance-modulating nucleic acid can be a variant of the nucleic acid having the nucleotide sequence set forth in SEQ ID NO:827. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:827.

A low nitrogen tolerance-modulating nucleic acid can comprise the nucleotide sequence set forth in SEQ ID NO:852. Alternatively, a low nitrogen tolerance-modulating nucleic acid can be a variant of the nucleic acid having the nucleotide sequence set forth in SEQ ID NO:852. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:852.

A low nitrogen tolerance-modulating nucleic acid can comprise the nucleotide sequence set forth in SEQ ID NO:854. Alternatively, a low nitrogen tolerance-modulating nucleic acid can be a variant of the nucleic acid having the nucleotide sequence set forth in SEQ ID NO:854. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:854.

A low nitrogen tolerance-modulating nucleic acid can comprise the nucleotide sequence set forth in SEQ ID NO:890. Alternatively, a low nitrogen tolerance-modulating nucleic acid can be a variant of the nucleic acid having the nucleotide sequence set forth in SEQ ID NO:890. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:890.

A low nitrogen tolerance-modulating nucleic acid can comprise the nucleotide sequence set forth in SEQ ID NO:916. Alternatively, a low nitrogen tolerance-modulating nucleic acid can be a variant of the nucleic acid having the nucleotide sequence set forth in SEQ ID NO:916. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:916.

A low nitrogen tolerance-modulating nucleic acid can comprise the nucleotide sequence set forth in SEQ ID NO:943. Alternatively, a low nitrogen tolerance-modulating nucleic acid can be a variant of the nucleic acid having the nucleotide sequence set forth in SEQ ID NO:943. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:943.

A low nitrogen tolerance-modulating nucleic acid can comprise the nucleotide sequence set forth in SEQ ID NO:975. Alternatively, a low nitrogen tolerance-modulating nucleic acid can be a variant of the nucleic acid having the nucleotide sequence set forth in SEQ ID NO:975. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:975.

A low nitrogen tolerance-modulating nucleic acid can comprise the nucleotide sequence set forth in SEQ ID NO:981. Alternatively, a low nitrogen tolerance-modulating nucleic acid can be a variant of the nucleic acid having the nucleotide sequence set forth in SEQ ID NO:981. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:981.

A low nitrogen tolerance-modulating nucleic acid can comprise the nucleotide sequence set forth in SEQ ID NO: 1034. Alternatively, a low nitrogen tolerance-modulating nucleic acid can be a variant of the nucleic acid having the nucleotide sequence set forth in SEQ ID NO: 1034. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO: 1034.

A low nitrogen tolerance-modulating nucleic acid can comprise the nucleotide sequence set forth in SEQ ID NO:1053. Alternatively, a low nitrogen tolerance-modulating nucleic acid can be a variant of the nucleic acid having the nucleotide sequence set forth in SEQ ID NO:1053. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:1053.

A low nitrogen tolerance-modulating nucleic acid can comprise the nucleotide sequence set forth in SEQ ID NO:1098. Alternatively, a low nitrogen tolerance-modulating nucleic acid can be a variant of the nucleic acid having the nucleotide sequence set forth in SEQ ID NO:1098. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:1098.

A low nitrogen tolerance-modulating nucleic acid can comprise the nucleotide sequence set forth in SEQ ID NO:1111. Alternatively, a low nitrogen tolerance-modulating nucleic acid can be a variant of the nucleic acid having the nucleotide sequence set forth in SEQ ID NO:1111. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:1111.

A low nitrogen tolerance-modulating nucleic acid can comprise the nucleotide sequence set forth in SEQ ID NO:1115. Alternatively, a low nitrogen tolerance-modulating nucleic acid can be a variant of the nucleic acid having the nucleotide sequence set forth in SEQ ID NO:1115. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:1115.

A low nitrogen tolerance-modulating nucleic acid can comprise the nucleotide sequence set forth in SEQ ID NO:1156. Alternatively, a low nitrogen tolerance-modulating nucleic acid can be a variant of the nucleic acid having the nucleotide sequence set forth in SEQ ID NO:1156. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:1156.

A low nitrogen tolerance-modulating nucleic acid can comprise the nucleotide sequence set forth in SEQ ID NO:1158. Alternatively, a low nitrogen tolerance-modulating nucleic acid can be a variant of the nucleic acid having the nucleotide sequence set forth in SEQ ID NO:1158. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:1158.

A low nitrogen tolerance-modulating nucleic acid can comprise the nucleotide sequence set forth in SEQ ID NO:1165. Alternatively, a low nitrogen tolerance-modulating nucleic acid can be a variant of the nucleic acid having the nucleotide sequence set forth in SEQ ID NO:1165. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:1165.

A low nitrogen tolerance-modulating nucleic acid can comprise the nucleotide sequence set forth in SEQ ID NO:1184. Alternatively, a low nitrogen tolerance-modulating nucleic acid can be a variant of the nucleic acid having the nucleotide sequence set forth in SEQ ID NO:1184. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:1184.

A low nitrogen tolerance-modulating nucleic acid can comprise the nucleotide sequence set forth in SEQ ID NO:1193. Alternatively, a low nitrogen tolerance-modulating nucleic acid can be a variant of the nucleic acid having the nucleotide sequence set forth in SEQ ID NO:1193. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:1193.

A low nitrogen tolerance-modulating nucleic acid can comprise the nucleotide sequence set forth in SEQ ID NO: 1209. Alternatively, a low nitrogen tolerance-modulating nucleic acid can be a variant of the nucleic acid having the nucleotide sequence set forth in SEQ ID NO: 1209. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO: 1209.

A low nitrogen tolerance-modulating nucleic acid can comprise the nucleotide sequence set forth in SEQ ID NO:1273. Alternatively, a low nitrogen tolerance-modulating nucleic acid can be a variant of the nucleic acid having the nucleotide sequence set forth in SEQ ID NO:1273. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:1273.

A low nitrogen tolerance-modulating nucleic acid can comprise the nucleotide sequence set forth in SEQ ID NO:1301. Alternatively, a low nitrogen tolerance-modulating nucleic acid can be a variant of the nucleic acid having the nucleotide sequence set forth in SEQ ID NO:1301. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:1301.

A low nitrogen tolerance-modulating nucleic acid can comprise the nucleotide sequence set forth in SEQ ID NO:1341. Alternatively, a low nitrogen tolerance-modulating nucleic acid can be a variant of the nucleic acid having the nucleotide sequence set forth in SEQ ID NO:1341. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:1341.

A low nitrogen tolerance-modulating nucleic acid can comprise the nucleotide sequence set forth in SEQ ID NO:1384. Alternatively, a low nitrogen tolerance-modulating nucleic acid can be a variant of the nucleic acid having the nucleotide sequence set forth in SEQ ID NO:1384. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:1384.

A low nitrogen tolerance-modulating nucleic acid can comprise the nucleotide sequence set forth in SEQ ID NO:1408. Alternatively, a low nitrogen tolerance-modulating nucleic acid can be a variant of the nucleic acid having the nucleotide sequence set forth in SEQ ID NO:1408. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:1408.

A low nitrogen tolerance-modulating nucleic acid can comprise the nucleotide sequence set forth in SEQ ID NO:1427. Alternatively, a low nitrogen tolerance-modulating nucleic acid can be a variant of the nucleic acid having the nucleotide sequence set forth in SEQ ID NO:1427. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:1427.

A low nitrogen tolerance-modulating nucleic acid can comprise the nucleotide sequence set forth in SEQ ID NO:1462. Alternatively, a low nitrogen tolerance-modulating nucleic acid can be a variant of the nucleic acid having the nucleotide sequence set forth in SEQ ID NO:1462. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:1462.

A low nitrogen tolerance-modulating nucleic acid can comprise the nucleotide sequence set forth in SEQ ID NO:1490. Alternatively, a low nitrogen tolerance-modulating nucleic acid can be a variant of the nucleic acid having the nucleotide sequence set forth in SEQ ID NO:1490. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:1490.

A low nitrogen tolerance-modulating nucleic acid can comprise the nucleotide sequence set forth in SEQ ID NO:1509. Alternatively, a low nitrogen tolerance-modulating nucleic acid can be a variant of the nucleic acid having the nucleotide sequence set forth in SEQ ID NO:1509. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:1509.

A low nitrogen tolerance-modulating nucleic acid can comprise the nucleotide sequence set forth in SEQ ID NO:1524. Alternatively, a low nitrogen tolerance-modulating nucleic acid can be a variant of the nucleic acid having the nucleotide sequence set forth in SEQ ID NO:1524. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:1524.

A low nitrogen tolerance-modulating nucleic acid can comprise the nucleotide sequence set forth in SEQ ID NO:1536. Alternatively, a low nitrogen tolerance-modulating nucleic acid can be a variant of the nucleic acid having the nucleotide sequence set forth in SEQ ID NO:1536. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:1536.

A low nitrogen tolerance-modulating nucleic acid can comprise the nucleotide sequence set forth in SEQ ID NO:1553. Alternatively, a low nitrogen tolerance-modulating nucleic acid can be a variant of the nucleic acid having the nucleotide sequence set forth in SEQ ID NO:1553. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:1553.

A low nitrogen tolerance-modulating nucleic acid can comprise the nucleotide sequence set forth in SEQ ID NO:1576. Alternatively, a low nitrogen tolerance-modulating nucleic acid can be a variant of the nucleic acid having the nucleotide sequence set forth in SEQ ID NO:1576. For example, a low nitrogen tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO:1576.

Isolated nucleic acid molecules can be produced by standard techniques. For example, polymerase chain reaction (PCR) techniques can be used to obtain an isolated nucleic acid containing a nucleotide sequence described herein. PCR can be used to amplify specific sequences from DNA as well as RNA, including sequences from total genomic DNA or total cellular RNA. Various PCR methods are described, for example, in *PCR Primer: A Laboratory Manual*, Dieffenbach and Dveksler, eds., Cold Spring Harbor Laboratory Press, 1995. Generally, sequence information from the ends of the region of interest or beyond is employed to design oligonucleotide primers that are identical or similar in sequence to opposite strands of the template to be amplified. Various PCR strategies also are available by which site-specific nucleotide sequence modifications can be introduced into a template nucleic acid. Isolated nucleic acids also can be chemically synthesized, either as a single nucleic acid molecule (e.g., using automated DNA synthesis in the 3' to 5' direction using phosphoramidite technology) or as a series of oligonucleotides. For example, one or more pairs of long oligonucleotides (e.g., >100 nucleotides) can be synthesized that contain the desired sequence, with each pair containing a short segment of complementarity (e.g., about 15 nucleotides) such that a duplex is formed when the oligonucleotide pair is annealed. DNA polymerase is used to extend the oligonucleotides, resulting in a single, double-stranded nucleic acid molecule per oligonucleotide pair, which then can be ligated into a vector. Isolated nucleic acids of the invention also can be obtained by mutagenesis of, e.g., a naturally occurring DNA.

B. Use of Nucleic Acids to Modulate Expression of Polypeptides i. Expression of a Low Nitrogen Tolerance-Modulating Polypeptide A nucleic acid encoding one of the low nitrogen tolerance-modulating polypeptides described herein can be used to express the polypeptide in a plant species of interest, typically by transforming a plant cell with a nucleic acid having the coding sequence for the polypeptide operably linked in sense orientation to one or more regulatory regions. It will be appreciated that because of the degeneracy of the genetic code, a number of nucleic acids can encode a particular low nitrogen tolerance-modulating polypeptide; i.e., for many amino acids, there is more than one nucleotide triplet that serves as the codon for the amino acid. Thus, codons in the coding sequence for a given low nitrogen tolerance-modulating polypeptide can be modified such that optimal expression in a particular plant species is obtained, using appropriate codon bias tables for that species.

In some cases, expression of a low nitrogen tolerance-modulating polypeptide inhibits one or more functions of an endogenous polypeptide. For example, a nucleic acid that encodes a dominant negative polypeptide can be used to inhibit protein function. A dominant negative polypeptide typically is mutated or truncated relative to an endogenous wild type polypeptide, and its presence in a cell inhibits one or more functions of the wild type polypeptide in that cell, i.e., the dominant negative polypeptide is genetically dominant and confers a loss of function. The mechanism by which a dominant negative polypeptide confers such a phenotype can vary but often involves a protein-protein interaction or a protein-DNA interaction. For example, a dominant negative polypeptide can be an enzyme that is truncated relative to a native wild type enzyme, such that the truncated polypeptide retains domains involved in binding a first protein but lacks domains involved in binding a second protein. The truncated polypeptide is thus unable to properly modulate the activity of the second protein. See, e.g., US 2007/0056058. As another example, a point mutation that results in a non-conservative amino acid substitution in a catalytic domain can result in a dominant negative polypeptide. See, e.g., US 2005/032221. As another example, a dominant negative polypeptide can be a transcription factor that is truncated relative to a native wild type transcription factor, such that the truncated polypeptide retains the DNA binding domain(s) but lacks the activation domain(s). Such a truncated polypeptide can inhibit the wild type transcription factor from binding DNA, thereby inhibiting transcription activation.

ii. Inhibition of Expression of a Low Nitrogen Tolerance-Modulating Polypeptide

Polynucleotides and recombinant constructs described herein can be used to inhibit expression of a low nitrogen tolerance-modulating polypeptide in a plant species of interest. See, e.g., Matzke and Birchler, *Nature Reviews Genetics* 6:24-35 (2005); Akashi et al., *Nature Reviews Mol. Cell Biology* 6:413-422 (2005); Mittal, *Nature Reviews Genetics* 5:355-365 (2004); Dorsett and Tuschl, *Nature Reviews Drug Discovery* 3: 318-329 (2004); and *Nature Reviews RNA interference collection*, October 2005 at nature.com/reviews/focus/mai. A number of nucleic acid based methods, including antisense RNA, ribozyme directed RNA cleavage, post-transcriptional gene silencing (PTGS), e.g., RNA interference (RNAi), and transcriptional gene silencing (TGS) are known to inhibit gene expression in plants. Suitable polynucleotides include full-length nucleic acids encoding low nitrogen tolerance-modulating polypeptides or fragments of such full-length nucleic acids. In some embodiments, a complement of the full-length nucleic acid or a fragment thereof can be used. Typically, a fragment is at least 10 nucleotides, e.g., at least 12, 13, 14, 15, 16, 17, 18, 19, 20, 21, 22, 23, 24, 25, 26, 27, 30, 35, 40, 50, 80, 100, 200, 500 nucleotides or more. Generally, higher homology can be used to compensate for the use of a shorter sequence.

Antisense technology is one well-known method. In this method, a nucleic acid of a gene to be repressed is cloned and operably linked to a regulatory region and a transcription termination sequence so that the antisense strand of RNA is transcribed. The recombinant construct is then transformed into plants, as described herein, and the antisense strand of RNA is produced. The nucleic acid need not be the entire sequence of the gene to be repressed, but typically will be substantially complementary to at least a portion of the sense strand of the gene to be repressed.

In another method, a nucleic acid can be transcribed into a ribozyme, or catalytic RNA, that affects expression of an mRNA. See, U.S. Pat. No. 6,423,885. Ribozymes can be designed to specifically pair with virtually any target RNA and cleave the phosphodiester backbone at a specific location, thereby functionally inactivating the target RNA. Heterologous nucleic acids can encode ribozymes designed to cleave particular mRNA transcripts, thus preventing expression of a polypeptide. Hammerhead ribozymes are useful for destroying particular mRNAs, although various ribozymes that cleave mRNA at site-specific recognition sequences can be used. Hammerhead ribozymes cleave mRNAs at locations dictated by flanking regions that form complementary base pairs with the target mRNA. The sole requirement is that the target RNA contains a 5'-UG-3' nucleotide sequence. The construction and production of hammerhead ribozymes is known in the art. See, for example, U.S. Pat. No. 5,254,678 and WO 02/46449 and references cited therein. Hammerhead ribozyme sequences can be embedded in a stable RNA such as a transfer RNA (tRNA) to increase cleavage efficiency in vivo. Perriman et al. (1995) *Proc. Natl. Acad. Sci. USA*, 92(13):6175-6179; de Feyter and Gaudron, Methods in Molecular Biology, Vol. 74, Chapter 43, "Expressing Ribozymes in Plants", Edited by Turner, P. C., Humana Press Inc., Totowa, N.J. RNA endoribonucleases which have been described, such as the one that occurs naturally in

*Tetrahymena thermophila*, can be useful. See, for example, U.S. Pat. Nos. 4,987,071 and 6,423,885.

PTGS, e.g., RNAi, can also be used to inhibit the expression of a gene. For example, a construct can be prepared that includes a sequence that is transcribed into an RNA that can anneal to itself, e.g., a double stranded RNA having a stem-loop structure. In some embodiments, one strand of the stem portion of a double stranded RNA comprises a sequence that is similar or identical to the sense coding sequence or a fragment thereof of a low nitrogen tolerance-modulating polypeptide, and that is from about 10 nucleotides to about 2,500 nucleotides in length. The length of the sequence that is similar or identical to the sense coding sequence can be from 10 nucleotides to 500 nucleotides, from 15 nucleotides to 300 nucleotides, from 20 nucleotides to 100 nucleotides, or from 25 nucleotides to 100 nucleotides. The other strand of the stem portion of a double stranded RNA comprises a sequence that is similar or identical to the antisense strand or a fragment thereof of the coding sequence of the low nitrogen tolerance-modulating polypeptide, and can have a length that is shorter, the same as, or longer than the corresponding length of the sense sequence. In some cases, one strand of the stem portion of a double stranded RNA comprises a sequence that is similar or identical to the 3' or 5' untranslated region, or a fragment thereof, of an mRNA encoding a low nitrogen tolerance-modulating polypeptide, and the other strand of the stem portion of the double stranded RNA comprises a sequence that is similar or identical to the sequence that is complementary to the 3' or 5' untranslated region, respectively, or a fragment thereof, of the mRNA encoding the low nitrogen tolerance-modulating polypeptide. In other embodiments, one strand of the stem portion of a double stranded RNA comprises a sequence that is similar or identical to the sequence of an intron, or a fragment thereof, in the pre-mRNA encoding a low nitrogen tolerance-modulating polypeptide, and the other strand of the stem portion comprises a sequence that is similar or identical to the sequence that is complementary to the sequence of the intron, or a fragment thereof, in the pre-mRNA.

The loop portion of a double stranded RNA can be from 3 nucleotides to 5,000 nucleotides, e.g., from 3 nucleotides to 25 nucleotides, from 15 nucleotides to 1,000 nucleotides, from 20 nucleotides to 500 nucleotides, or from 25 nucleotides to 200 nucleotides. The loop portion of the RNA can include an intron or a fragment thereof. A double stranded RNA can have zero, one, two, three, four, five, six, seven, eight, nine, ten, or more stem-loop structures.

A construct including a sequence that is operably linked to a regulatory region and a transcription termination sequence, and that is transcribed into an RNA that can form a double stranded RNA, is transformed into plants as described herein. Methods for using RNAi to inhibit the expression of a gene are known to those of skill in the art. See, e.g., U.S. Pat. Nos. 5,034,323; 6,326,527; 6,452,067; 6,573,099; 6,753,139; and 6,777,588. See also WO 97/01952; WO 98/53083; WO 99/32619; WO 98/36083; and U.S. Patent Publications 20030175965, 20030175783, 20040214330, and 20030180945.

Constructs containing regulatory regions operably linked to nucleic acid molecules in sense orientation can also be used to inhibit the expression of a gene. The transcription product can be similar or identical to the sense coding sequence, or a fragment thereof, of a low nitrogen tolerance-modulating polypeptide. The transcription product also can be unpolyadenylated, lack a 5' cap structure, or contain an unspliceable intron. Methods of inhibiting gene expression using a full-length cDNA as well as a partial cDNA sequence are known in the art. See, e.g., U.S. Pat. No. 5,231,020.

In some embodiments, a construct containing a nucleic acid having at least one strand that is a template for both sense and antisense sequences that are complementary to each other is used to inhibit the expression of a gene. The sense and antisense sequences can be part of a larger nucleic acid molecule or can be part of separate nucleic acid molecules having sequences that are not complementary. The sense or antisense sequence can be a sequence that is identical or complementary to the sequence of an mRNA, the 3' or 5' untranslated region of an mRNA, or an intron in a pre-mRNA encoding a low nitrogen tolerance-modulating polypeptide, or a fragment of such sequences. In some embodiments, the sense or antisense sequence is identical or complementary to a sequence of the regulatory region that drives transcription of the gene encoding a low nitrogen tolerance-modulating polypeptide. In each case, the sense sequence is the sequence that is complementary to the antisense sequence.

The sense and antisense sequences can be any length greater than about 10 nucleotides (e.g., 12, 13, 14, 15, 16, 17, 18, 19, 20, 21, 22, 23, 24, 25, 26, 27, 28, 29, 30, or more nucleotides). For example, an antisense sequence can be 21 or 22 nucleotides in length. Typically, the sense and antisense sequences range in length from about 15 nucleotides to about 30 nucleotides, e.g., from about 18 nucleotides to about 28 nucleotides, or from about 21 nucleotides to about 25 nucleotides.

In some embodiments, an antisense sequence is a sequence complementary to an mRNA sequence, or a fragment thereof, encoding a low nitrogen tolerance-modulating polypeptide described herein. The sense sequence complementary to the antisense sequence can be a sequence present within the mRNA of the low nitrogen tolerance-modulating polypeptide. Typically, sense and antisense sequences are designed to correspond to a 15-30 nucleotide sequence of a target mRNA such that the level of that target mRNA is reduced.

In some embodiments, a construct containing a nucleic acid having at least one strand that is a template for more than one sense sequence (e.g., 2, 3, 4, 5, 6, 7, 8, 9, 10 or more sense sequences) can be used to inhibit the expression of a gene. Likewise, a construct containing a nucleic acid having at least one strand that is a template for more than one antisense sequence (e.g., 2, 3, 4, 5, 6, 7, 8, 9, 10 or more antisense sequences) can be used to inhibit the expression of a gene. For example, a construct can contain a nucleic acid having at least one strand that is a template for two sense sequences and two antisense sequences. The multiple sense sequences can be identical or different, and the multiple antisense sequences can be identical or different. For example, a construct can have a nucleic acid having one strand that is a template for two identical sense sequences and two identical antisense sequences that are complementary to the two identical sense sequences. Alternatively, an isolated nucleic acid can have one strand that is a template for (1) two identical sense sequences 20 nucleotides in length, (2) one antisense sequence that is complementary to the two identical sense sequences 20 nucleotides in length, (3) a sense sequence 30 nucleotides in length, and (4) three identical antisense sequences that are complementary to the sense sequence 30 nucleotides in length. The constructs provided herein can be designed to have any arrangement of sense and antisense sequences. For example, two identical sense sequences can be followed by two identical antisense sequences or can be positioned between two identical antisense sequences.

A nucleic acid having at least one strand that is a template for one or more sense and/or antisense sequences can be operably linked to a regulatory region to drive transcription of an RNA molecule containing the sense and/or antisense sequence(s). In addition, such a nucleic acid can be operably linked to a transcription terminator sequence, such as the terminator of the nopaline synthase (nos) gene. In some cases, two regulatory regions can direct transcription of two transcripts: one from the top strand, and one from the bottom strand. See, for example, Yan et al., *Plant Physiol.*, 141: 1508-1518 (2006). The two regulatory regions can be the same or different. The two transcripts can form double-stranded RNA molecules that induce degradation of the target RNA. In some cases, a nucleic acid can be positioned within a T-DNA or plant-derived transfer DNA (P-DNA) such that the left and right T-DNA border sequences, or the left and right border-like sequences of the P-DNA, flank or are on either side of the nucleic acid. See, US 2006/0265788. The nucleic acid sequence between the two regulatory regions can be from about 15 to about 300 nucleotides in length. In some embodiments, the nucleic acid sequence between the two regulatory regions is from about 15 to about 200 nucleotides in length, from about 15 to about 100 nucleotides in length, from about 15 to about 50 nucleotides in length, from about 18 to about 50 nucleotides in length, from about 18 to about 40 nucleotides in length, from about 18 to about 30 nucleotides in length, or from about 18 to about 25 nucleotides in length.

In some nucleic-acid based methods for inhibition of gene expression in plants, a suitable nucleic acid can be a nucleic acid analog. Nucleic acid analogs can be modified at the base moiety, sugar moiety, or phosphate backbone to improve, for example, stability, hybridization, or solubility of the nucleic acid. Modifications at the base moiety include deoxyuridine for deoxythymidine, and 5-methyl-2'-deoxycytidine and 5-bromo-2'-deoxycytidine for deoxycytidine. Modifications of the sugar moiety include modification of the 2' hydroxyl of the ribose sugar to form 2'-O-methyl or 2'-O-allyl sugars. The deoxyribose phosphate backbone can be modified to produce morpholino nucleic acids, in which each base moiety is linked to a six-membered morpholino ring, or peptide nucleic acids, in which the deoxyphosphate backbone is replaced by a pseudopeptide backbone and the four bases are retained. See, for example, Summerton and Weller (1997) *Antisense Nucleic Acid Drug Dev.*, 7:187-195; Hyrup et al. (1996) *Bioorgan. Med. Chem.*, 4:5-23. In addition, the deoxyphosphate backbone can be replaced with, for example, a phosphorothioate or phosphorodithioate backbone, a phosphoroamidite, or an alkyl phosphotriester backbone.

C. Constructs/Vectors

Recombinant constructs provided herein can be used to transform plants or plant cells in order to modulate low-nitrogen tolerance levels. A recombinant nucleic acid construct can comprise a nucleic acid encoding a low nitrogen tolerance-modulating polypeptide as described herein, operably linked to a regulatory region suitable for expressing the low nitrogen tolerance-modulating polypeptide in the plant or cell. Thus, a nucleic acid can comprise a coding sequence that encodes any of the low nitrogen tolerance-modulating polypeptides as set forth in SEQ ID NO:3, SEQ ID NO:49, SEQ ID NO:77, SEQ ID NO:97, SEQ ID NO:100, SEQ ID NO:152, SEQ ID NO:166, SEQ ID NO:186, SEQ ID NO:208, SEQ ID NO:218, SEQ ID NO:234, SEQ ID NO:246, SEQ ID NO:300, SEQ ID NO:332, SEQ ID NO:368, SEQ ID NO:510, SEQ ID NO:533, SEQ ID NO:556, SEQ ID NO:558, SEQ ID NO:593, SEQ ID NO:613, SEQ ID NO:646, SEQ ID NO:687, SEQ ID NO:730, SEQ ID NO:746, SEQ ID NO:769, SEQ ID NO:792, SEQ ID NO:824, SEQ ID NO:828, SEQ ID NO:853, SEQ ID NO:855, SEQ ID NO:891, SEQ ID NO:917, SEQ ID NO:944, SEQ ID NO:976, SEQ ID NO:982, SEQ ID NO:1054, SEQ ID NO:1099, SEQ ID NO:1112, SEQ ID NO:1116, SEQ ID NO:1157, SEQ ID NO:1159, SEQ ID NO:1166, SEQ ID NO:1185, SEQ ID NO:1194, SEQ ID NO:1210, SEQ ID NO:1274, SEQ ID NO:1302, SEQ ID NO:1342, SEQ ID NO:1385, SEQ ID NO:1409, SEQ ID NO:1428, SEQ ID NO:1437, SEQ ID NO:1463, SEQ ID NO:1491, SEQ ID NO:1510, SEQ ID NO:1525, SEQ ID NO:1537, SEQ ID NO:1554, and SEQ ID NO:1577. Examples of nucleic acids encoding low nitrogen tolerance-modulating polypeptides are set forth in SEQ ID NO:1, SEQ ID NO:48, SEQ ID NO:76, SEQ ID NO:96, SEQ ID NO:99, SEQ ID NO:151, SEQ ID NO:165, SEQ ID NO:175, SEQ ID NO:185, SEQ ID NO:207, SEQ ID NO:217, SEQ ID NO:233, SEQ ID NO:245, SEQ ID NO:299, SEQ ID NO:331, SEQ ID NO:367, SEQ ID NO:509, SEQ ID NO:532, SEQ ID NO:555, SEQ ID NO:557, SEQ ID NO:592, SEQ ID NO:612, SEQ ID NO:645, SEQ ID NO:686, SEQ ID NO:729, SEQ ID NO:745, SEQ ID NO:768, SEQ ID NO:791, SEQ ID NO:823, SEQ ID NO:827, SEQ ID NO:852, SEQ ID NO:854, SEQ ID NO:890, SEQ ID NO:916, SEQ ID NO:943, SEQ ID NO:975, SEQ ID NO:981, SEQ ID NO:1053, SEQ ID NO:1098, SEQ ID NO:1111, SEQ ID NO:1115, SEQ ID NO:1156, SEQ ID NO:1158, SEQ ID NO:1165, SEQ ID NO:1184, SEQ ID NO:1193, SEQ ID NO:1209, SEQ ID NO:1273, SEQ ID NO:1301, SEQ ID NO:1341, SEQ ID NO:1384, SEQ ID NO:1408, SEQ ID NO:1427, SEQ ID NO:1462, SEQ ID NO:1490, SEQ ID NO:1509, SEQ ID NO:1524, SEQ ID NO:1536, SEQ ID NO:1553, and SEQ ID NO:1576. The low nitrogen tolerance-modulating polypeptide encoded by a recombinant nucleic acid can be a native low nitrogen tolerance-modulating polypeptide, or can be heterologous to the cell. In some cases, the recombinant construct contains a nucleic acid that inhibits expression of a low nitrogen tolerance-modulating polypeptide, operably linked to a regulatory region. Examples of suitable regulatory regions are described in the section entitled "Regulatory Regions."

Vectors containing recombinant nucleic acid constructs such as those described herein also are provided. Suitable vector backbones include, for example, those routinely used in the art such as plasmids, viruses, artificial chromosomes, BACs, YACs, or PACs. Suitable expression vectors include, without limitation, plasmids and viral vectors derived from, for example, bacteriophage, baculoviruses, and retroviruses. Numerous vectors and expression systems are commercially available from such corporations as Novagen (Madison, Wis.), Clontech (Palo Alto, Calif.), Stratagene (La Jolla, Calif.), and Invitrogen/Life Technologies (Carlsbad, Calif.).

The vectors provided herein also can include, for example, origins of replication, scaffold attachment regions (SARs), and/or markers. A marker gene can confer a selectable phenotype on a plant cell. For example, a marker can confer biocide resistance, such as resistance to an antibiotic (e.g., kanamycin, G418, bleomycin, or hygromycin), or an herbicide (e.g., glyphosate, chlorsulfuron or phosphinothricin). In addition, an expression vector can include a tag sequence designed to facilitate manipulation or detection (e.g., purification or localization) of the expressed polypeptide. Tag sequences, such as luciferase, β-glucuronidase (GUS), green fluorescent protein (GFP), glutathione S-transferase (GST), polyhistidine, c-myc, hemagglutinin, or Flag™ tag (Kodak, New Haven, Conn.) sequences typically are expressed as a fusion with the encoded polypeptide. Such tags can be inserted anywhere within the polypeptide, including at either the carboxyl or amino terminus.

D. Regulatory Regions

The choice of regulatory regions to be included in a recombinant construct depends upon several factors, including, but not limited to, efficiency, selectability, inducibility, desired expression level, and cell- or tissue-preferential expression. It is a routine matter for one of skill in the art to modulate the expression of a coding sequence by appropriately selecting and positioning regulatory regions relative to the coding sequence. Transcription of a nucleic acid can be modulated in a similar manner.

Some suitable regulatory regions initiate transcription only, or predominantly, in certain cell types. Methods for identifying and characterizing regulatory regions in plant genomic DNA are known, including, for example, those described in the following references: Jordano et al. (1989) *Plant Cell*, 1:855-866; Bustos et al. (1989) *Plant Cell*, 1:839-854; Green et al. (1988) *EMBO J.*, 7:4035-4044; Meier et al. (1991) *Plant Cell*, 3:309-316; and Zhang et al. (1996) *Plant Physiology*, 110:1069-1079.

Examples of various classes of regulatory regions are described below. Some of the regulatory regions indicated below as well as additional regulatory regions are described in more detail in U.S. Patent Application Ser. Nos. 60/505, 689; 60/518,075; 60/544,771; 60/558,869; 60/583,691; 60/619,181; 60/637,140; 60/757,544; 60/776,307; 10/957, 569; 11/058,689; 11/172,703; 11/208,308; 11/274,890; 60/583,609; 60/612,891; 11/097,589; 11/233,726; 11/408, 791; 11/414,142; 10/950,321; 11/360,017; PCT/US05/ 011105; PCT/US05/23639; PCT/US05/034308; PCT/US05/ 034343; and PCT/US06/038236; PCT/US06/040572; and PCT/US07/62762.

For example, the sequences of regulatory regions p326, YP0144, YP0190, p13879, YP0050, p32449, 21876, YP0158, YP0214, YP0380, PT0848, PT0633, YP0128, YP0275, PT0660, PT0683, PT0758, PT0613, PT0672, PT0688, PT0837, YP0092, PT0676, PT0708, YP0396, YP0007, YP0111, YP0103, YP0028, YP0121, YP0008, YP0039, YP0115, YP0119, YP0120, YP0374, YP0101, YP0102, YP0110, YP0117, YP0137, YP0285, YP0212, YP0097, YP0107, YP0088, YP0143, YP0156, PT0650, PT0695, PT0723, PT0838, PT0879, PT0740, PT0535, PT0668, PT0886, PT0585, YP0381, YP0337, PT0710, YP0356, YP0385, YP0384, YP0286, YP0377, PD1367, PT0863, PT0829, PT0665, PT0678, YP0086, YP0188, YP0263, PT0743 and YP0096 are set forth in the sequence listing of PCT/US06/040572; the sequence of regulatory region PT0625 is set forth in the sequence listing of PCT/ US05/034343; the sequences of regulatory regions PT0623, YP0388, YP0087, YP0093, YP0108, YP0022 and YP0080 are set forth in the sequence listing of U.S. patent application Ser. No. 11/172,703; the sequence of regulatory region PR0924 is set forth in the sequence listing of PCT/US07/ 62762; and the sequences of regulatory regions p530c10, pOsFIE2-2, pOsMEA, pOsYp102, and pOsYp285 are set forth in the sequence listing of PCT/US06/038236.

It will be appreciated that a regulatory region may meet criteria for one classification based on its activity in one plant species, and yet meet criteria for a different classification based on its activity in another plant species.

i. Broadly Expressing Promoters

A promoter can be said to be "broadly expressing" when it promotes transcription in many, but not necessarily all, plant tissues. For example, a broadly expressing promoter can promote transcription of an operably linked sequence in one or more of the shoot, shoot tip (apex), and leaves, but weakly or not at all in tissues such as roots or stems. As another example, a broadly expressing promoter can promote transcription of an operably linked sequence in one or more of the stem, shoot, shoot tip (apex), and leaves, but can promote transcription weakly or not at all in tissues such as reproductive tissues of flowers and developing seeds. Non-limiting examples of broadly expressing promoters that can be included in the nucleic acid constructs provided herein include the p326, YP0144, YP0190, p13879, YP0050, p32449, 21876, YP0158, YP0214, YP0380, PT0848, and PT0633 promoters. Additional examples include the cauliflower mosaic virus (CaMV) 35S promoter, the mannopine synthase (MAS) promoter, the 1' or 2' promoters derived from T-DNA of *Agrobacterium tumefaciens*, the figwort mosaic virus 34S promoter, actin promoters such as the rice actin promoter, and ubiquitin promoters such as the maize ubiquitin-1 promoter. In some cases, the CaMV 35S promoter is excluded from the category of broadly expressing promoters.

ii. Root Promoters

Root-active promoters confer transcription in root tissue, e.g., root endodermis, root epidermis, or root vascular tissues. In some embodiments, root-active promoters are root-preferential promoters, i.e., confer transcription only or predominantly in root tissue. Root-preferential promoters include the YP0128, YP0275, PT0625, PT0660, PT0683, and PT0758 promoters. Other root-preferential promoters include the PT0613, PT0672, PT0688, and PT0837 promoters, which drive transcription primarily in root tissue and to a lesser extent in ovules and/or seeds. Other examples of root-preferential promoters include the root-specific subdomains of the CaMV 35S promoter (Lam et al. (1989) *Proc. Natl. Acad. Sci. USA*, 86:7890-7894), root cell specific promoters reported by Conkling et al. (1990) *Plant Physiol.*, 93:1203-1211, and the tobacco RD2 promoter.

iii. Maturing Endosperm Promoters

In some embodiments, promoters that drive transcription in maturing endosperm can be useful. Transcription from a maturing endosperm promoter typically begins after fertilization and occurs primarily in endosperm tissue during seed development and is typically highest during the cellularization phase. Most suitable are promoters that are active predominantly in maturing endosperm, although promoters that are also active in other tissues can sometimes be used. Non-limiting examples of maturing endosperm promoters that can be included in the nucleic acid constructs provided herein include the napin promoter, the Arcelin-5 promoter, the phaseolin promoter (Bustos et al. (1989) *Plant Cell*, 1(9):839-853), the soybean trypsin inhibitor promoter (Riggs et al. (1989) *Plant Cell*, 1(6):609-621), the ACP promoter (Baerson et al. (1993) *Plant Mol. Biol.*, 22(2):255-267), the stearoyl-ACP desaturase promoter (Slocombe et al. (1994) *Plant Physiol.*, 104(4):167-176), the soybean α' subunit of β-conglycinin promoter (Chen et al. (1986) *Proc. Natl. Acad. Sci. USA*, 83:8560-8564), the oleosin promoter (Hong et al. (1997) *Plant Mol. Biol.*, 34(3):549-555), and zein promoters, such as the 15 kD zein promoter, the 16 kD zein promoter, 19 kD zein promoter, 22 kD zein promoter and 27 kD zein promoter. Also suitable are the Osgt-1 promoter from the rice glutelin-1 gene (Zheng et al. (1993) *Mol. Cell Biol.*, 13:5829-5842), the beta-amylase promoter, and the barley hordein promoter. Other maturing endosperm promoters include the YP0092, PT0676, and PT0708 promoters iv. Ovary Tissue Promoters Promoters that are active in ovary tissues such as the ovule wall and mesocarp can also be useful, e.g., a polygalacturonidase promoter, the banana TRX promoter, the melon actin promoter, YP0396, and PT0623. Examples of promoters that are active primarily in ovules include YP0007, YP0111, YP0092, YP0103, YP0028, YP0121, YP0008, YP0039, YP0115, YP0119, YP0120, and YP0374.

v. Embryo Sac/Early Endosperm Promoters

To achieve expression in embryo sac/early endosperm, regulatory regions can be used that are active in polar nuclei and/or the central cell, or in precursors to polar nuclei, but not in egg cells or precursors to egg cells. Most suitable are promoters that drive expression only or predominantly in polar nuclei or precursors thereto and/or the central cell. A pattern of transcription that extends from polar nuclei into early endosperm development can also be found with embryo sac/early endosperm-preferential promoters, although transcription typically decreases significantly in later endosperm development during and after the cellularization phase. Expression in the zygote or developing embryo typically is not present with embryo sac/early endosperm promoters.

Promoters that may be suitable include those derived from the following genes: *Arabidopsis* viviparous-1 (see, GenBank No. U93215); *Arabidopsis* atmycl (see, Urao (1996) *Plant Mol. Biol.*, 32:571-57; Conceicao (1994) *Plant*, 5:493-505); *Arabidopsis* FIE (GenBank No. AF129516); *Arabidopsis* MEA; *Arabidopsis* FIS2 (GenBank No. AF096096); and FIE 1.1 (U.S. Pat. No. 6,906,244). Other promoters that may be suitable include those derived from the following genes: maize MAC1 (see, Sheridan (1996) *Genetics*, 142: 1009-1020); maize Cat3 (see, GenBank No. L05934; Abler (1993) *Plant Mol. Biol.*, 22:10131-1038). Other promoters include the following *Arabidopsis* promoters: YP0039, YP0101, YP0102, YP0110, YP0117, YP0119, YP0137, DME, YP0285, and YP0212. Other promoters that may be useful include the following rice promoters: p530c10, pOs-FIE2-2, pOsMEA, pOsYp102, and pOsYp285.

vi. Embryo Promoters

Regulatory regions that preferentially drive transcription in zygotic cells following fertilization can provide embryo-preferential expression. Most suitable are promoters that preferentially drive transcription in early stage embryos prior to the heart stage, but expression in late stage and maturing embryos is also suitable. Embryo-preferential promoters include the barley lipid transfer protein (Ltp1) promoter (*Plant Cell Rep* (2001) 20:647-654), YP0097, YP0107, YP0088, YP0143, YP0156, PT0650, PT0695, PT0723, PT0838, PT0879, and PT0740.

vii. Photosynthetic Tissue Promoters

Promoters active in photosynthetic tissue confer transcription in green tissues such as leaves and stems. Most suitable are promoters that drive expression only or predominantly in such tissues. Examples of such promoters include the ribulose-1,5-bisphosphate carboxylase (RbcS) promoters such as the RbcS promoter from eastern larch (*Larix laricina*), the pine cab6 promoter (Yamamoto et al. (1994) *Plant Cell Physiol.*, 35:773-778), the Cab-1 promoter from wheat (Fejes et al. (1990) *Plant Mol. Biol.*, 15:921-932), the CAB-1 promoter from spinach (Lubberstedt et al. (1994) *Plant Physiol.*, 104:997-1006), the cab1R promoter from rice (Luan et al. (1992) *Plant Cell*, 4:971-981), the pyruvate orthophosphate dikinase (PPDK) promoter from corn (Matsuoka et al. (1993) *Proc. Natl. Acad. Sci. USA*, 90:9586-9590), the tobacco Lhcb1*2 promoter (Cerdan et al. (1997) *Plant Mol. Biol.*, 33:245-255), the *Arabidopsis thaliana* SUC2 sucrose-H+ symporter promoter (Truernit et al. (1995) *Planta*, 196:564-570), and thylakoid membrane protein promoters from spinach (psaD, psaF, psaE, PC, FNR, atpC, atpD, cab, rbcS). Other photosynthetic tissue promoters include PT0535, PT0668, PT0886, YP0144, YP0380 and PT0585.

viii. Vascular Tissue Promoters

Examples of promoters that have high or preferential activity in vascular bundles include YP0087, YP0093, YP0108, YP0022, and YP0080. Other vascular tissue-preferential promoters include the glycine-rich cell wall protein GRP 1.8 promoter (Keller and Baumgartner (1991) *Plant Cell*, 3(10): 1051-1061), the Commelina yellow mottle virus (CoYMV) promoter (Medberry et al. (1992) *Plant Cell*, 4(2):185-192), and the rice tungro bacilliform virus (RTBV) promoter (Dai et al. (2004) *Proc. Natl. Acad. Sci. USA*, 101(2):687-692).

ix. Inducible Promoters

Inducible promoters confer transcription in response to external stimuli such as chemical agents or environmental stimuli. For example, inducible promoters can confer transcription in response to hormones such as giberellic acid or ethylene, or in response to light or drought. Examples of drought-inducible promoters include YP0380, PT0848, YP0381, YP0337, PT0633, YP0374, PT0710, YP0356, YP0385, YP0396, YP0388, YP0384, PT0688, YP0286, YP0377, PD1367, and PD0901. Examples of nitrogen-inducible promoters include PT0863, PT0829, PT0665, and PT0886. Examples of shade-inducible promoters include PR0924 and PT0678. An example of a promoter induced by salt is rd29A (Kasuga et al. (1999) *Nature Biotech* 17: 287-291).

x. Basal Promoters

A basal promoter is the minimal sequence necessary for assembly of a transcription complex required for transcription initiation. Basal promoters frequently include a "TATA box" element that may be located between about 15 and about 35 nucleotides upstream from the site of transcription initiation. Basal promoters also may include a "CCAAT box" element (typically the sequence CCAAT) and/or a GGGCG sequence, which can be located between about 40 and about 200 nucleotides, typically about 60 to about 120 nucleotides, upstream from the transcription start site.

xi. Stem Promoters

A stem promoter may be specific to one or more stem tissues or specific to stem and other plant parts. Stem promoters may have high or preferential activity in, for example, epidermis and cortex, vascular cambium, procambium, or xylem. Examples of stem promoters include YP0018 which is disclosed in US20060015970 and CryIA (b) and CryIA(c) (Braga et al. 2003, Journal of New Seeds 5:209-221).

xii. Other Promoters

Other classes of promoters include, but are not limited to, shoot-preferential, callus-preferential, trichome cell-preferential, guard cell-preferential such as PT0678, tuber-preferential, parenchyma cell-preferential, and senescence-preferential promoters. Promoters designated YP0086, YP0188, YP0263, PT0758, PT0743, PT0829, YP0119, and YP0096, as described in the above-referenced patent applications, may also be useful.

xiii. Other Regulatory Regions

A 5' untranslated region (UTR) can be included in nucleic acid constructs described herein. A 5' UTR is transcribed, but is not translated, and lies between the start site of the transcript and the translation initiation codon and may include the +1 nucleotide. A 3' UTR can be positioned between the translation termination codon and the end of the transcript. UTRs can have particular functions such as increasing mRNA stability or attenuating translation. Examples of 3' UTRs include, but are not limited to, polyadenylation signals and transcription termination sequences, e.g., a nopaline synthase termination sequence.

It will be understood that more than one regulatory region may be present in a recombinant polynucleotide, e.g., introns, enhancers, upstream activation regions, transcription terminators, and inducible elements. Thus, for example, more than one regulatory region can be operably linked to the sequence of a polynucleotide encoding a low nitrogen tolerance-modulating polypeptide.

Regulatory regions, such as promoters for endogenous genes, can be obtained by chemical synthesis or by subcloning from a genomic DNA that includes such a regulatory region. A nucleic acid comprising such a regulatory region can also include flanking sequences that contain restriction enzyme sites that facilitate subsequent manipulation.

IV. Transgenic Plants and Plant Cells

A. Transformation

The invention also features transgenic plant cells and plants comprising at least one recombinant nucleic acid construct described herein. A plant or plant cell can be transformed by having a construct integrated into its genome, i.e., can be stably transformed. Stably transformed cells typically retain the introduced nucleic acid with each cell division. A plant or plant cell can also be transiently transformed such that the construct is not integrated into its genome. Transiently transformed cells typically lose all or some portion of the introduced nucleic acid construct with each cell division such that the introduced nucleic acid cannot be detected in daughter cells after a sufficient number of cell divisions. Both transiently transformed and stably transformed transgenic plants and plant cells can be useful in the methods described herein.

Transgenic plant cells used in methods described herein can constitute part or all of a whole plant. Such plants can be grown in a manner suitable for the species under consideration, either in a growth chamber, a greenhouse, or in a field. Transgenic plants can be bred as desired for a particular purpose, e.g., to introduce a recombinant nucleic acid into other lines, to transfer a recombinant nucleic acid to other species, or for further selection of other desirable traits. Alternatively, transgenic plants can be propagated vegetatively for those species amenable to such techniques. As used herein, a transgenic plant also refers to progeny of an initial transgenic plant provided the progeny inherits the transgene. Seeds produced by a transgenic plant can be grown and then selfed (or outcrossed and selfed) to obtain seeds homozygous for the nucleic acid construct.

Transgenic plants can be grown in suspension culture, or tissue or organ culture. For the purposes of this invention, solid and/or liquid tissue culture techniques can be used. When using solid medium, transgenic plant cells can be placed directly onto the medium or can be placed onto a filter that is then placed in contact with the medium. When using liquid medium, transgenic plant cells can be placed onto a flotation device, e.g., a porous membrane that contacts the liquid medium. A solid medium can be, for example, Murashige and Skoog (MS) medium containing agar and a suitable concentration of an auxin, e.g., 2,4-dichlorophenoxyacetic acid (2,4-D), and a suitable concentration of a cytokinin, e.g., kinetin.

When transiently transformed plant cells are used, a reporter sequence encoding a reporter polypeptide having a reporter activity can be included in the transformation procedure and an assay for reporter activity or expression can be performed at a suitable time after transformation. A suitable time for conducting the assay typically is about 1-21 days after transformation, e.g., about 1-14 days, about 1-7 days, or about 1-3 days. The use of transient assays is particularly convenient for rapid analysis in different species, or to confirm expression of a heterologous low nitrogen tolerance-modulating polypeptide whose expression has not previously been confirmed in particular recipient cells.

Techniques for introducing nucleic acids into monocotyledonous and dicotyledonous plants are known in the art, and include, without limitation, Agrobacterium-mediated transformation, viral vector-mediated transformation, electroporation and particle gun transformation, e.g., U.S. Pat. Nos. 5,538,880; 5,204,253; 6,329,571 and 6,013,863. If a cell or cultured tissue is used as the recipient tissue for transformation, plants can be regenerated from transformed cultures if desired, by techniques known to those skilled in the art.

B. Screening/Selection

A population of transgenic plants can be screened and/or selected for those members of the population that have a trait or phenotype conferred by expression of the transgene. For example, a population of progeny of a single transformation event can be screened for those plants having a desired level of expression of a low nitrogen tolerance-modulating polypeptide or nucleic acid. Physical and biochemical methods can be used to identify expression levels. These include Southern analysis or PCR amplification for detection of a polynucleotide; Northern blots, S1 RNase protection, primer-extension, or RT-PCR amplification for detecting RNA transcripts; enzymatic assays for detecting enzyme or ribozyme activity of polypeptides and polynucleotides; and protein gel electrophoresis, Western blots, immunoprecipitation, and enzyme-linked immunoassays to detect polypeptides. Other techniques such as in situ hybridization, enzyme staining, and immunostaining also can be used to detect the presence or expression of polypeptides and/or polynucleotides. Methods for performing all of the referenced techniques are known. As an alternative, a population of plants comprising independent transformation events can be screened for those plants having a desired trait, such as a modulated level of low-nitrogen tolerance. Selection and/or screening can be carried out over one or more generations, and/or in more than one geographic location. In some cases, transgenic plants can be grown and selected under conditions which induce a desired phenotype or are otherwise necessary to produce a desired phenotype in a transgenic plant. In addition, selection and/or screening can be applied during a particular developmental stage in which the phenotype is expected to be exhibited by the plant. Selection and/or screening can be carried out to choose those transgenic plants having a statistically significant difference in low nitrogen tolerance level relative to a control plant that lacks the transgene. Selected or screened transgenic plants have an altered phenotype as compared to a corresponding control plant, as described in the "Transgenic Plant Phenotypes" section herein.

C. Plant Species

The polynucleotides and vectors described herein can be used to transform a number of monocotyledonous and dicotyledonous plants and plant cell systems, including species from one of the following families: Acanthaceae, Alliaceae, Alstroemeriaceae, Amaryllidaceae, Apocynaceae, Arecaceae, Asteraceae, Berberidaceae, Bixaceae, Brassicaceae, Bromeliaceae, Cannabaceae, Caryophyllaceae, Cephalotaxaceae, Chenopodiaceae, Colchicaceae, Cucurbitaceae, Dioscoreaceae, Ephedraceae, Erythroxylaceae, Euphorbiaceae, Fabaceae, Lamiaceae, Linaceae, Lycopodiaceae, Malvaceae, Melanthiaceae, Musaceae, Myrtaceae, Nyssaceae, Papaveraceae, Pinaceae, Plantaginaceae, Poaceae, Rosaceae, Rubiaceae, Salicaceae, Sapindaceae, Solanaceae, Taxaceae, Theaceae, or Vitaceae.

Suitable species may include members of the genus *Abelmoschus, Abies, Acer, Agrostis, Allium, Alstroemeria, Ananas, Andrographis, Andropogon, Artemisia, Arundo, Atropa, Berberis, Beta, Bixa, Brassica, Calendula, Camellia, Camptotheca, Cannabis, Capsicum, Carthamus, Catharanthus, Cephalotaxus, Chrysanthemum, Cinchona, Citrullus, Coffea, Colchicum, Coleus, Cucumis, Cucurbita, Cynodon, Datura, Dianthus, Digitalis, Dioscorea, Elaeis, Ephedra, Erianthus, Erythroxylum, Eucalyptus, Festuca, Fragaria, Galanthus, Glycine, Gossypium, Helianthus, Hevea, Hordeum, Hyoscyamus, Jatropha, Lactuca, Linum, Lolium, Lupinus, Lycopersicon, Lycopodium, Manihot, Medicago, Mentha, Miscanthus, Musa, Nicotiana, Oryza, Panicum, Papaver, Parthenium, Pennisetum, Petunia, Phalaris, Phleum, Pinus, Poa, Poinsettia, Populus, Rauwolfia, Ricinus, Rosa, Saccharum, Salix, Sanguinaria, Scopolia, Secale, Solanum, Sorghum, Spartina, Spinacea, Tanacetum, Taxus, Theobroma, Triticosecale, Triticum, Uniola, Veratrum, Vinca, Vitis,* and *Zea.*

Suitable species include *Panicum* spp. or hybrid thereof, *Sorghum* spp. or hybrid thereof, sudangrass, *Miscanthus* spp. or hybrid thereof, *Saccharum* spp. or hybrid thereof, *Erianthus* spp., *Populus* spp., *Andropogon gerardii* (big bluestem), *Pennisetum purpureum* (elephant grass)) or hybrid thereof (e.g., *Pennisetum purpureum* x *Pennisetum typhoidum*), *Phalaris arundinacea* (reed canarygrass), *Cynodon dactylon* (bermudagrass), *Festuca arundinacea* (tall fescue), *Spartina pectinata* (prairie cord-grass), *Medicago sativa* (alfalfa), *Arundo donax* (giant reed) or hybrid thereof, *Secale cereale* (rye), *Salix* spp. (willow), *Eucalyptus* spp. (*eucalyptus*), Triticosecale (*triticum*—wheat X rye), *Tripsicum dactyloides* (Eastern gammagrass), *Leymus cinereus* (basin wildrye), *Leymus condensatus* (giant wildrye) and bamboo.

In some embodiments, a suitable species can be a wild, weedy, or cultivated *sorghum* species such as, but not limited to, *Sorghum almum, Sorghum amplum, Sorghum angustum, Sorghum arundinaceum, Sorghum bicolor* (such as bicolor, guinea, caudatum, kafir, and durra), *Sorghum brachypodum, Sorghum bulbosum, Sorghum burmahicum, Sorghum controversum, Sorghum drummondii, Sorghum ecarinatum, Sorghum exstans, Sorghum grande, Sorghum halepense, Sorghum interjectum, Sorghum intrans, Sorghum laxiflorum, Sorghum leiocladum, Sorghum macrospermum, Sorghum matarankense, Sorghum miliaceum, Sorghum nigrum, Sorghum nitidum, Sorghum plumosum, Sorghum propinquum, Sorghum purpureosericeum, Sorghum stipoideum, Sorghum sudanensese, Sorghum timorense, Sorghum trichocladum, Sorghum versicolor, Sorghum virgatum, Sorghum vulgare,* or hybrids such as *Sorghum* x *almum, Sorghum* x sudangrass or *Sorghum* x *drummondii*.

Suitable species also include *Helianthus annuus* (sunflower), *Carthamus tinctorius* (safflower), *Jatropha curcas* (jatropha), *Ricinus communis* (castor), *Elaeis guineensis* (palm), *Linum usitatissimum* (flax), and *Brassica juncea*.

Suitable species also include *Beta vulgaris* (sugarbeet), and *Manihot esculenta* (cassava).

Suitable species also include *Lycopersicon esculentum* (tomato), *Lactuca sativa* (lettuce), *Musa paradisiaca* (banana), *Solanum tuberosum* (potato), *Brassica oleracea* (broccoli, cauliflower, Brussels sprouts), *Camellia sinensis* (tea), *Fragaria ananassa* (strawberry), *Theobroma cacao* (cocoa), *Coffea arabica* (coffee), *Vitis vinifera* (grape), *Ananas comosus* (pineapple), *Capsicum annum* (hot & sweet pepper), *Allium cepa* (onion), *Cucumis melo* (melon), *Cucumis sativus* (cucumber), *Cucurbita maxima* (squash), *Cucurbita moschata* (squash), *Spinacea oleracea* (spinach), *Citrullus lanatus* (watermelon), *Abelmoschus esculentus* (okra), and *Solanum melongena* (eggplant).

Suitable species also include *Papaver somniferum* (opium poppy), *Papaver orientale, Taxus baccata, Taxus brevifolia, Artemisia annua, Cannabis sativa, Camptotheca acuminate, Catharanthus roseus, Vinca rosea, Cinchona officinalis, Colchicum autumnale, Veratrum californica, Digitalis lanata, Digitalis purpurea, Dioscorea* spp., *Andrographis paniculata, Atropa belladonna, Datura stomonium, Berberis* spp., *Cephalotaxus* spp., *Ephedra sinica, Ephedra* spp., *Erythroxylum coca, Galanthus wornorii, Scopolia* spp., *Lycopodium serratum* (=*Huperzia serrata*), *Lycopodium* spp., *Rauwolfia serpentina, Rauwolfia* spp., *Sanguinaria canadensis, Hyoscyamus* spp., *Calendula officinalis, Chrysanthemum parthenium, Coleus forskohlii,* and *Tanacetum parthenium.*

Suitable species also include *Parthenium argentatum* (guayule), *Hevea* spp. (rubber), *Mentha spicata* (mint), *Mentha piperita* (mint), *Bixa orellana,* and *Alstroemeria* spp.

Suitable species also include Rosa spp. (rose), *Dianthus caryophyllus* (carnation), *Petunia* spp. (*petunia*) and *Poinsettia pulcherrima* (poinsettia).

Suitable species also include *Nicotiana tabacum* (tobacco), *Lupinus albus* (lupin), *Uniola paniculata* (oats), bentgrass (*Agrostis* spp.), *Populus tremuloides* (aspen), *Pinus* spp. (pine), *Abies* spp. (fir), *Acer* spp. (maple), *Hordeum vulgare* (barley), *Poa pratensis* (bluegrass), *Lolium* spp. (ryegrass) and *Phleum pratense* (timothy).

Thus, the methods and compositions can be used over a broad range of plant species, including species from the dicot genera *Brassica, Carthamus, Glycine, Gossypium, Helianthus, Jatropha, Parthenium, Populus,* and *Ricinus*; and the monocot genera *Elaeis, Festuca, Hordeum, Lolium, Oryza, Panicum, Pennisetum, Phleum, Poa, Saccharum, Secale, Sorghum, Triticosecale, Triticum,* and *Zea.* In some embodiments, a plant is a member of the species *Panicum virgatum* (switchgrass), *Sorghum bicolor* (*sorghum*, sudangrass), *Miscanthus giganteus* (*miscanthus*), *Saccharum* sp. (energycane), *Populus balsamifera* (poplar), *Zea mays* (corn), *Glycine max* (soybean), *Brassica napus* (canola), *Triticum aestivum* (wheat), *Gossypium hirsutum* (cotton), *Oryza sativa* (rice), *Helianthus annuus* (sunflower), *Medicago sativa* (alfalfa), *Beta vulgaris* (sugarbeet), or *Pennisetum glaucum* (pearl millet).

In certain embodiments, the polynucleotides and vectors described herein can be used to transform a number of monocotyledonous and dicotyledenous plants and plant cell systems, wherein such plants are hybrids of different species or varieties of a specific species (e.g., *Saccharum* sp. X *Miscanthus* sp., *Panicum virgatum* x *Panicum amarum, Panicum virgatum* x *Panicum amarulum,* and *Pennisetum purpureum* x *Pennisetum typhoidum*).

D. Transgenic Plant Phenotypes

In some embodiments, a plant in which expression of a low nitrogen tolerance-modulating polypeptide is modulated can have increased levels of photosynthetic efficiency in seedlings. For example, a low nitrogen tolerance-modulating polypeptide described herein can be expressed in a transgenic plant, resulting in increased levels of photosynthetic efficiency in growth conditions with low nitrogen sources. The level of photosynthetic efficiency can be increased by at least 0.25 percent, e.g., 0.25, 1, 2, 3, 4, 5, 6, 7, 8, 9, 10, 11, 12, 13, 14, 15, 16, 17, 18, 19, 20, 25, 30, 35, 40, 45, 50, 55, 60, or more than 60 percent, as compared to the level of photosynthetic efficiency in a corresponding control plant that does not express the transgene. In some embodiments, a plant in which expression of a low nitrogen tolerance-modulating polypeptide is modulated can have decreased levels of photosynthetic efficiency. The level of photosynthetic efficiency can be decreased by at least 0.25 percent, e.g., 0.25, 1, 2, 3, 4, 5, 10, 15, 20, 25, 30, 35, or more than 35 percent, as compared to the level of photosynthetic in a corresponding control plant that does not express the transgene.

In some embodiments, a plant in which expression of a low nitrogen tolerance-modulating polypeptide is modulated can have increased or decreased levels of photosynthetic efficiency in one or more green tissues, e.g., leaves, stems, bulbs, flowers, fruits, young seeds. For example, the level of photosynthetic efficiency can be increased by at least 0.25 percent, e.g., 0.25, 1, 2, 3, 4, 5, 6, 7, 8, 9, 10, 11, 12, 13, 14, 15, 16, 17, 18, 19, 20, 25, 30, 35, 40, 45, 50, 55, 60, or more than 60 percent, as compared to the level of photosynthetic efficiency in a corresponding control plant that does not express the transgene. In some embodiments, a plant in which expression of a low nitrogen tolerance-modulating polypeptide is modulated can have decreased levels of photosynthetic efficiency in one or more green tissues. The level of photosynthetic efficiency can be decreased by at least 0.25 percent, e.g., 0.25, 1, 2, 3, 4, 5, 10, 15, 20, 25, 30, 35, or more than 35 percent, as compared to the level of photosynthetic efficiency in a corresponding control plant that does not express the transgene.

Increases in photosynthetic efficiency in low-nitrogen growth conditions in such plants can provide improved plant growth in geographic locales where plant's intake of nitrogenous fertilizers is often insufficient. Decreases in photosynthetic efficiency, and hence less tolerance to low-nitrogen growth conditions in such plants can be useful for removing weeds and such from the environment, by applying to weeds and such. For example, a plant capable of inducing the decrease in photosynthetic efficiency can be prepared to apply for land improvements and such.

Typically, a difference in the level of photosynthetic efficiency in a transgenic plant or cell relative to a control plant or cell is considered statistically significant at $p \leq 0.05$ with an appropriate parametric or non-parametric statistic, e.g., Chi-square test, Student's t-test, Mann-Whitney test, or F-test. In some embodiments, a difference in the level of photosynthetic is statistically significant at $p<0.01$, $p<0.005$, or $p<0.001$. A statistically significant difference in, for example, the level of photosynthetic efficiency in a transgenic plant compared to the amount in cells of a control plant indicates that the recombinant nucleic acid present in the transgenic plant results in altered levels of photosynthetic efficiency.

In some embodiments, a plant in which expression of a low nitrogen tolerance-modulating polypeptide is modulated can have increased growth rates in seedlings. For example, a low nitrogen tolerance-modulating polypeptide described herein can be expressed in a transgenic plant, resulting in increased growth rate in growth conditions of limiting nitrogen sources. The growth rate can be increased by at least 2 percent, e.g., 2, 3, 4, 5, 6, 7, 8, 9, 10, 11, 12, 13, 14, 15, 16, 17, 18, 19, 20, 25, 30, 35, 40, 45, 50, 55, 60, or more than 60 percent, as compared to the growth rate in a corresponding control plant that does not express the transgene. In some embodiments, a plant in which expression of a low nitrogen tolerance-modulating polypeptide is modulated can have decreased growth rates. The growth rate can be decreased by at least 2 percent, e.g., 2, 3, 4, 5, 10, 15, 20, 25, 30, 35, or more than 35 percent, as compared to the growth rate in a corresponding control plant that does not express the transgene. Growth rate can be measured in seedlings, developing, or mature plants and measured for periods of time such as about 1 hour, 3 hours, 6 hours, 12 hours, 1 day, 3 days, 5 days, 10 days, 1 month, 3 months, 6 months, 12 months, or the entire lifespan of a plant.

In some embodiments, a plant in which expression of a low nitrogen tolerance-modulating polypeptide is modulated can have increased or decreased growth rates in one or more vegetative and reproductive tissues, e.g., leaves, stems, flowers, bulbs, fruits, young seeds. For example, the growth rate can be increased by at least 2 percent, e.g., 2, 3, 4, 5, 6, 7, 8, 9, 10, 11, 12, 13, 14, 15, 16, 17, 18, 19, 20, 25, 30, 35, 40, 45, 50, 55, 60, or more than 60 percent, as compared to the growth rate in a corresponding control plant that does not express the transgene. In some embodiments, a plant in which expression of a low nitrogen tolerance-modulating polypeptide is modulated can have decreased levels of growth rate in one or more vegetative tissues. The growth rate can be decreased by at least 2 percent, e.g., 2, 3, 4, 5, 10, 15, 20, 25, 30, 35, or more than 35 percent, as compared to the growth rate in a corresponding control plant that does not express the transgene.

Increases in growth rate in low-nitrogen conditions in such plants can provide improved plant growth and initial establishment in geographic locales where plant's intake of nitrogenous fertilizers is often insufficient. Decreases in growth rate, and hence less tolerance to low-nitrogen growth conditions in such plants can be useful for engineering slow-growing plants, by applying to ornamentals and such. For example, a plant capable of inducing the decrease in growth rate can be prepared to apply for land improvements and such.

Typically, a difference in the growth rate of a transgenic plant or cell relative to a control plant or cell is considered statistically significant at $p \leq 0.05$ with an appropriate parametric or non-parametric statistic, e.g., Chi-square test, Student's t-test, Mann-Whitney test, or F-test. In some embodiments, a difference in the growth rate is statistically significant at $p<0.01$, $p<0.005$, or $p<0.001$. A statistically significant difference in, for example, the growth rate of a transgenic plant compared to the growth rate of a control plant indicates that the recombinant nucleic acid present in the transgenic plant results in altered growth rates.

The phenotype of a transgenic plant is evaluated relative to a control plant. A plant is said "not to express" a polypeptide when the plant exhibits less than 10%, e.g., less than 9%, 8%, 7%, 6%, 5%, 4%, 3%, 2%, 1%, 0.5%, 0.1%, 0.01%, or 0.001%, of the amount of polypeptide or mRNA encoding the polypeptide exhibited by the plant of interest. Expression can be evaluated using methods including, for example, RT-PCR, Northern blots, S1 RNase protection, primer extensions, Western blots, protein gel electrophoresis, immunoprecipitation, enzyme-linked immunoassays, chip assays, and mass spectrometry. It should be noted that if a polypeptide is expressed under the control of a tissue-preferential or broadly expressing promoter, expression can be evaluated in the entire plant or in a selected tissue.

Similarly, if a polypeptide is expressed at a particular time, e.g., at a particular time in development or upon induction, expression can be evaluated selectively at a desired time period.

V. Plant Breeding

Genetic polymorphisms are discrete allelic sequence differences in a population. Typically, an allele that is present at 1% or greater is considered to be a genetic polymorphism. The discovery that polypeptides disclosed herein can modulate photosynthetic efficiency and/or nitrogen content is useful in plant breeding, because genetic polymorphisms exhibiting a degree of linkage with loci for such polypeptides are more likely to be correlated with variation in a low-nitrogen tolerance trait. For example, genetic polymorphisms linked to the loci for such polypeptides are more likely to be useful in marker-assisted breeding programs to create lines having a desired modulation in the low-nitrogen tolerance trait.

Thus, one aspect of the invention includes methods of identifying whether one or more genetic polymorphisms are associated with variation in a low-nitrogen tolerance trait. Such methods involve determining whether genetic polymorphisms in a given population exhibit linkage with the locus for one of the polypeptides depicted in FIGS. 1-57, SEQ ID NO:556, SEQ ID NO:853, SEQ ID NO:1157 and/or a functional homolog thereof, such as, but not limited to those identified in the Sequence Listing of this application. The correlation is measured between variation in the low-nitrogen tolerance trait in plants of the population and the presence of the genetic polymorphism(s) in plants of the population, thereby identifying whether or not the genetic polymorphism(s) are associated with variation for the trait. If the presence of a particular allele is statistically significantly correlated with a desired modulation in the low-nitrogen tolerance trait, the allele is associated with variation for the trait and is useful as a marker for the trait. If, on the other hand, the presence of a particular allele is not significantly correlated with the desired modulation, the allele is not associated with variation for the trait and is not useful as a marker.

Such methods are applicable to populations containing the naturally occurring endogenous polypeptide rather than an exogenous nucleic acid encoding the polypeptide, i.e., populations that are not transgenic for the exogenous nucleic acid. It will be appreciated, however, that populations suitable for use in the methods may contain a transgene for another, different trait, e.g., herbicide resistance.

Genetic polymorphisms that are useful in such methods include simple sequence repeats (SSRs, or microsatellites), rapid amplification of polymorphic DNA (RAPDs), single nucleotide polymorphisms (SNPs), amplified fragment length polymorphisms (AFLPs) and restriction fragment length polymorphisms (RFLPs). SSR polymorphisms can be identified, for example, by making sequence specific probes and amplifying template DNA from individuals in the population of interest by PCR. If the probes flank an SSR in the population, PCR products of different sizes will be produced. See, e.g., U.S. Pat. No. 5,766,847. Alternatively, SSR polymorphisms can be identified by using PCR product(s) as a probe against Southern blots from different individuals in the population. See, U. H. Refseth et al. (1997) *Electrophoresis* 18: 1519. The identification of RFLPs is discussed, for example, in Alonso-Blanco et al. (Methods in Molecular Biology, vol. 82, "*Arabidopsis* Protocols", pp. 137-146, J. M. Martinez-Zapater and J. Salinas, eds., c. 1998 by Humana Press, Totowa, N.J.); Burr ("Mapping Genes with Recombinant Inbreds", pp. 249-254, in Freeling, M. and V. Walbot (Ed.), The Maize Handbook, c. 1994 by Springer-Verlag New York, Inc.: New York, N.Y., USA; Berlin Germany; Burr et al. (1998) *Genetics* 118: 519; and Gardiner, J. et al. (1993) *Genetics* 134: 917). The identification of AFLPs is discussed, for example, in EP 0 534 858 and U.S. Pat. No. 5,878,215.

In some embodiments, the methods are directed to breeding a plant line. Such methods use genetic polymorphisms identified as described above in a marker assisted breeding program to facilitate the development of lines that have a desired alteration in the low-nitrogen tolerance trait. Once a suitable genetic polymorphism is identified as being associated with variation for the trait, one or more individual plants are identified that possess the polymorphic allele correlated with the desired variation. Those plants are then used in a breeding program to combine the polymorphic allele with a plurality of other alleles at other loci that are correlated with the desired variation. Techniques suitable for use in a plant breeding program are known in the art and include, without limitation, backcrossing, mass selection, pedigree breeding, bulk selection, crossing to another population and recurrent selection. These techniques can be used alone or in combination with one or more other techniques in a breeding program. Thus, each identified plants is selfed or crossed a different plant to produce seed which is then germinated to form progeny plants. At least one such progeny plant is then selfed or crossed with a different plant to form a subsequent progeny generation. The breeding program can repeat the steps of selfing or outcrossing for an additional 0 to 5 generations as appropriate in order to achieve the desired uniformity and stability in the resulting plant line, which retains the polymorphic allele. In most breeding programs, analysis for the particular polymorphic allele will be carried out in each generation, although analysis can be carried out in alternate generations if desired.

In some cases, selection for other useful traits is also carried out, e.g., selection for fungal resistance or bacterial resistance. Selection for such other traits can be carried out before, during or after identification of individual plants that possess the desired polymorphic allele.

VI. Articles of Manufacture

Transgenic plants provided herein have various uses in the agricultural and energy production industries. For example, transgenic plants described herein can be used to make animal feed and food products. Such plants, however, are often particularly useful as a feedstock for energy production. Transgenic plants described herein often produce higher yields of grain and/or biomass per hectare, relative to control plants that lack the exogenous nucleic acid. In some embodiments, such transgenic plants provide equivalent or even increased yields of grain and/or biomass per hectare relative to control plants when grown under conditions of reduced inputs such as fertilizer and/or water. Thus, such transgenic plants can be used to provide yield stability at a lower input cost and/or under environmentally stressful conditions such as drought or limiting nitrogen sources. In some embodiments, plants described herein have a composition that permits more efficient processing into free sugars, and subsequently ethanol, for energy production. In some embodiments, such plants provide higher yields of ethanol, butanol, dimethyl ether, other biofuel molecules, and/or sugar-derived co-products per kilogram of plant material, relative to control plants. Such processing efficiencies are believed to be derived from the nitrogenous composition of the plant material. By providing higher yields at an equivalent or even decreased cost of production, the transgenic plants described herein improve profitability for farmers and processors as well as decrease costs to consumers.

Seeds from transgenic plants described herein can be conditioned and bagged in packaging material by means known in the art to form an article of manufacture. Packaging material such as paper and cloth are well known in the art. A package of seed can have a label, e.g., a tag or label secured to the packaging material, a label printed on the packaging material, or a label inserted within the package, that describes the nature of the seeds therein.

The invention will be further described in the following examples, which do not limit the scope of the invention described in the claims.

VII. Examples

Example 1

Transgenic *Arabidopsis* Plants

The following symbols are used in the Examples with respect to *Arabidopsis* transformation: $T_1$: first generation transformant; $T_2$: second generation, progeny of self-pollinated $T_1$ plants; $T_3$: third generation, progeny of self-pollinated $T_2$ plants; $T_4$: fourth generation, progeny of self-pollinated $T_3$ plants. Independent transformations are referred to as events.

The following is a list of nucleic acids that were isolated from *Arabidopsis thaliana* plants, CeresClone:29661 (SEQ ID NO:1), CeresClone:251343 (SEQ ID NO:48), CeresClone:19586 (SEQ ID NO:76), CeresClone:25136 (SEQ ID NO:96), CeresClone:1820 (SEQ ID NO:99), CeresClone: 13102 (SEQ ID NO:151), CeresClone:15457 (SEQ ID NO:165), Ceres Annot:859276 (SEQ ID NO:175), CeresClone:17883 (SEQ ID NO:185), CeresClone:251590 (SEQ ID NO:207), CeresClone:4898 (SEQ ID NO:217), CeresClone:148977 (SEQ ID NO:233), CeresClone:24255 (SEQ ID NO:245), CeresClone:38432 (SEQ ID NO:299), Ceres Annot:553243 (SEQ ID NO:331), CeresClone:1011900 (SEQ ID NO:367), CeresClone:5232 (SEQ ID NO:509), CeresClone:29302 (SEQ ID NO:532), CeresClone:93971 (SEQ ID NO:555), Ceres Annot:12669619_cDNA (SEQ ID NO:557), CeresClone:21608 (SEQ ID NO:592), CeresClone:2031 (SEQ ID NO:612), CeresClone:94503 (SEQ ID NO:645), CeresClone:21740 (SEQ ID NO:686), CeresClone:5609 (SEQ ID NO:729), CeresClone:3137 (SEQ ID NO:745), CeresClone:32430 (SEQ ID NO:768), CeresClone:101255 (SEQ ID NO:791), Ceres Annot:573161 (SEQ ID NO:854), Ceres Annot:552727 (SEQ ID NO:890), CeresClone:732 (SEQ ID NO:1193), CeresClone:2267 (SEQ ID NO:1209), CeresClone:39358 (SEQ ID NO:1273), CeresClone:115046 (SEQ ID NO:1301), Ceres Annot: 850581 (SEQ ID NO:1427), Ceres Annot:862321 (SEQ ID NO:1462), Ceres Annot:839064 (SEQ ID NO:1478), Ceres Annot:864666 (SEQ ID NO:1490), Ceres Annot:875012 (SEQ ID NO:1509), Ceres Annot:874016 (SEQ ID NO:1524), Ceres Annot:827304 (SEQ ID NO:1536), Ceres Annot:869192 (SEQ ID NO:1553), and Ceres Annot:876419 (SEQ ID NO:1576). The nucleic acid designated Ceres Clone: 968180 (SEQ ID NO:1115) was isolated from the species *Brassica napus*. The nucleic acid designated Ceres Clone: 1017441 (SEQ ID NO:224) was isolated from the species *Triticum aesticum*. The following is a list of nucleic acids that were isolated from *Zea mays* plants, CeresClone: 1387146 (SEQ ID NO:981), CeresClone:1408950 (SEQ ID NO:1098), CeresClone:208453 (SEQ ID NO:1111), CeresClone:208995 (SEQ ID NO:943), CeresClone:225681 (SEQ ID NO:975), CeresClone:239806 (SEQ ID NO:916), CeresClone:244306 (SEQ ID NO:1053), CeresClone:276809 (SEQ ID NO:823), CeresClone:324216 (SEQ ID NO:852), CeresClone:339439 (SEQ ID NO:1341), CeresClone: 424522 (SEQ ID NO:827), CeresClone:896483 (SEQ ID NO:1384), CeresClone:986438 (SEQ ID NO:1156), CeresClone:988083 (SEQ ID NO:1184), CeresClone:995409 (SEQ ID NO:1408), CeresClone:996227 (SEQ ID NO:1158), and CeresClone:996263 (SEQ ID NO:1165).

With the exception of Ceres Clone:29661 (SEQ ID NO:1), each isolated nucleic acid described above was cloned into a Ti plasmid vector, CRS338, containing a phosphinothricin acetyltransferase gene which confers FINALE™ resistance to transformed plants. Constructs were made using CRS338 that contained SEQ ID NO:48, SEQ ID NO:76, SEQ ID NO:96, SEQ ID NO:99, SEQ ID NO:151, SEQ ID NO:165, SEQ ID NO:175, SEQ ID NO:185, SEQ ID NO:207, SEQ ID NO:217, SEQ ID NO:233, SEQ ID NO:245, SEQ ID NO:299, SEQ ID NO:331, SEQ ID NO:367, SEQ ID NO:509, SEQ ID NO:532, SEQ ID NO:555, SEQ ID NO:557, SEQ ID NO:592, SEQ ID NO:612, SEQ ID NO:645, SEQ ID NO:686, SEQ ID NO:729, SEQ ID NO:745, SEQ ID NO:768, SEQ ID NO:791, SEQ ID NO:823, SEQ ID NO:827, SEQ ID NO:852, SEQ ID NO:854, SEQ ID NO:890, SEQ ID NO:916, SEQ ID NO:943, SEQ ID NO:975, SEQ ID NO:981, SEQ ID NO:1053, SEQ ID NO:1098, SEQ ID NO:1111, SEQ ID NO:1115, SEQ ID NO:1156, SEQ ID NO:1158, SEQ ID NO:1165, SEQ ID NO:1184, SEQ ID NO:1193, SEQ ID NO:1209, SEQ ID NO:1273, SEQ ID NO:1301, SEQ ID NO:1341, SEQ ID NO:1384, SEQ ID NO:1408, SEQ ID NO:1427, SEQ ID NO:1462, SEQ ID NO:1490, SEQ ID NO:1509, SEQ ID NO:1524, SEQ ID NO:1536, SEQ ID NO:1553, or SEQ ID NO:1576, each operably linked to a 35S promoter. Ceres Clone:29661 (SEQ ID NO:1) was cloned into a Ti plasmid vector, CRS 311, containing a phosphinothricin acetyltransferase gene, which confers FINALE™ resistance to transformed plants. SEQ ID NO:1 was operably linked to a p32449 promoter in the constructs made using the CRS 331 vector. Wild-type *Arabidopsis thaliana* ecotype Wassilewskija (Ws) plants were transformed separately with each construct. The transformations were performed essentially as described in Bechtold et al. (1993) *C.R. Acad. Sci. Paris*, 316:1194-1199.

Transgenic *Arabidopsis* lines containing SEQ ID NO:1, SEQ ID NO:48, SEQ ID NO:76, SEQ ID NO:96, SEQ ID NO:99, SEQ ID NO:151, SEQ ID NO:165, SEQ ID NO:185, SEQ ID NO:207, SEQ ID NO:217, SEQ ID NO:233, SEQ ID NO:245, SEQ ID NO:299, SEQ ID NO:331, SEQ ID NO:367, SEQ ID NO:509, SEQ ID NO:532, SEQ ID NO:555, SEQ ID NO:557, SEQ ID NO:592, SEQ ID NO:612, SEQ ID NO:645, SEQ ID NO:686, SEQ ID NO:729, SEQ ID NO:745, SEQ ID NO:768, SEQ ID NO:791, SEQ ID NO:823, SEQ ID NO:827, SEQ ID NO:852, SEQ ID NO:854, SEQ ID NO:890, SEQ ID NO:916, SEQ ID NO:943, SEQ ID NO:975, SEQ ID NO:981, SEQ ID NO:224, SEQ ID NO:1053, SEQ ID NO:1098, SEQ ID NO:1111, SEQ ID NO:1115, SEQ ID NO:1156, SEQ ID NO:1158, SEQ ID NO:1165, SEQ ID NO:1184, SEQ ID NO:1193, SEQ ID NO:1209, SEQ ID NO:1273, SEQ ID NO:1301, SEQ ID NO:1341, SEQ ID NO:1384, SEQ ID NO:1408, SEQ ID NO:1427, SEQ ID NO:1462, SEQ ID NO:1478, SEQ ID NO:1490, SEQ ID NO:1509, SEQ ID NO:1524, SEQ ID NO:1536, SEQ ID NO:1553, SEQ ID NO:1576, or SEQ ID NO:175 were designated ME00919, ME01312, ME01463, ME01821, ME01910, ME02538, ME02603, ME02613, ME02801, ME03123, ME04204, ME04477, ME04507, ME04587, ME04753, ME04772, ME04909, ME05033, ME05194, ME05267, ME05300, ME05341, ME05392, ME05429, ME05493, ME05885, ME07344, ME07859, ME08464, ME09939, ME11735, ME12910, ME12927, ME12929, ME12954, ME12970, ME13006, ME13021, ME13064, ME13071, ME13087, ME13106, ME13107, ME13108, ME13110, ME13125, ME13149, ME13151, ME13153, ME13177, ME13200, ME13204, ME14649, ME16546, ME17457, ME17567, ME17932, ME17936, ME18275, ME18924, ME19182, or ME20628, respectively. The presence of each vector containing a nucleic acid described above in the respective transgenic *Arabidopsis* line transformed with the vector was confirmed by FINALE™ resistance, PCR amplification from green leaf tissue extract, and/or sequencing of PCR products. As controls, wild-type *Arabidopsis* ecotype Ws plants were transformed with the empty vector, either CRS338 or CRS311.

Example 2

Screening for Transgenic Plants Tolerant to Low-nitrogen Growth Conditions

A low-nitrogen tolerance screen was carried out on seedlings in order to identify transgenic lines that showed increased photosynthesis efficiency or seedling size or greenness under limiting nitrogen conditions relative to the internal control plants. The media used for the low-nitrogen tolerance assay contained 0.5% sucrose, 0.5×MS without nitrogen media (PhytoTech), 0.05% MES Hydrate, and 0.8% Phytagar. In addition, for low ammonium nitrate assay, 240 µM $NH_4NO_3$ was used as nitrogen source. For low nitrate assay, nitrogen source was 300 µM $KNO_3$. pH of the media was adjusted to pH 5.7 using 10N KOH. Sterilized seeds were plated on agar plates and stratified for 2 days in the dark at 4° C. to promote uniform germination. Agar plates with germinating seedlings were placed horizontally in a CONVIRON® growth chamber set at 22° C., 16:8 hour light:dark cycle, 70% humidity with a combination of incandescent and fluorescent lamps emitting a light intensity of ~100 µEinsteins. The control plates were placed randomly within the set. Screen the seedlings daily starting at 14 days. In this screen, seedlings that were larger or greener relative to the internal controls on low nitrogen growth media were selected. As they were found each day, candidate seedlings were aseptically transplanted to standard MS germination plates for recovery. This intermediate recovery step was necessary before transplanting to soil to minimize the overall candidate mortality rate. The scoring and transplanting of candidates were continued until all remaining plants were small and yellowed from nitrogen stress. On the very last day of scoring, each plate was scanned for photosynthetic efficiency (Fv/Fm) on the chlorophyll fluorescence (CF) imager and scored as candidates and transplanted any extreme outliers on the high end of Fv/Fm scores. Fv/Fm ratio typically provides an estimate of the photosystem II (PSII) maximum efficiency within dark-adapted material where Fv is variable fluorescence, i.e. difference between minimum (Fo) and maximum (Fm) fluorescence signal, from dark-adapted material. This could be done visually by looking at the false color image for each seedling using the CF image analysis software (plants with high end Fv/Fm scores appear red). This step was typically done at ~24 days after germination. Seven days after being transferred to MS recovery plates, candidates were transplanted to soil (standard Sunshine:vermiculite 3:2 mix; Osmocote; Marathon).

Five days after being transplanted to soil, candidates were sprayed with FINALE® [5 mL FINALE®/48 oz. water] to eliminate non-transgenics from the population. Two days after spraying with FINALE®, cauline leaf tissue of each candidate was collected for genomic DNA extraction, PCR, and sequencing to determine the identity of the transgene for each candidate.

Example 3

Validation Plate Assay

This assay was designed to validate transgenic lines that showed increased photosynthesis or size under limiting nitrogen conditions relative to the internal control. The media used for the low-nitrogen tolerance assay contained 0.5% sucrose, 0.5×MS without nitrogen media (PhytoTech), 0.05% MES Hydrate, and 0.8% Phytagar. pH of the media was adjusted to pH 5.7 using 10N KOH. In addition, for low ammonium nitrate assay, 240 µM $NH_4NO_3$ was used as nitrogen source. For low nitrate assay, nitrogen source was 300 µM $KNO_3$. Sterilized seeds were plated on agar plates and stratified for 2 days in the dark at 4° C. to promote uniform germination. Agar plates with germinating seedlings were placed horizontally in a CONVIRON® growth chamber set at 22° C., 16:8 hour light:dark cycle, 70% humidity with a combination of incandescent and fluorescent lamps emitting a light intensity of ~100 µEinsteins. The control plates were placed randomly within the set. Plates were scanned every other day using the CF Imager (after 45 minute of dark-acclimation) and were completed after all wild-type plants have completely yellowed. After the plates were scanned on the last day, they were sprayed with FINALE® (10 mL FINALE® into 48 oz. full-strength MS liquid media). Two days after spraying, each plate was dark-acclimated for 45 minutes and scanned for Fv/Fm on the CF imager and scored for each of the plants at each time point. For each separate time point, the data for all the $T_2$ transgenic plants across an event was pooled and a one-tailed t-test was used to compare both the Fv/Fm ratios and rosette areas relative to the pooled non-transgenics across the same plate. Whenever possible, this process was repeated for the $T_3$ generation plants. A low nitrogen tolerant candidate was confirmed when the transgenic Fv/Fm ratio and/or rosette area was greater than the wild-type segregants with a p-value≤0.05 in 2 or more events in both generations Example 4

Validation Soil Assay

A Low, Medium, and High Nitrogen experiment on soil was carried out to assess phenotypic characteristics at a mature point in the life cycle of *Arabidopsis*, as compared to seedling screens. The lines to be tested were originally identified through superpool screens for low nitrate and low ammonium nitrate tolerance. These lines were later individually assayed as seedlings on low nitrate and low ammonium nitrate agar. For this assay, MetroMix200 soil was mixed with vermiculite and Marathon™ (MetroMix200: vermiculite 3:2 mix; Osmocote; Marathon) autoclaved and cooled before use. Experimental plants and controls were randomized across the flats. Prior to sowing seed, each flat was watered with 3 L filtered water. Flats with 24 wells were filled with the following 3:2 ratios of MetroMix200 to Thermorock vermiculite. At the beginning of the experiment no nitrogen was provided until 2 weeks after germination when ¼ Hoaglands supplemented with $KNO_3$ at 25 ppm, 250 ppm, and 1500 ppm were used to water the flats from beneath.

Seeds were stratified on soil and in the dark at 4° C. for 3 days. After the cold treatment, flats were transferred to the growth chamber. Plants were grown for approximately 5 weeks, or until full grown/mature. Plants were then dark-acclimated for one hour. Chlorophyll fluorescence images were taken using a CF-Imager (Technologica, UK) according to the manufacturer's protocol to measure the performance and efficiency of photosystem II: 1) Fv/Fm, maximum photosystem II efficiency 2) Fq'/Fm', operating efficiency and 3) non-photochemical quenching (NPQ).

One week after watering with ¼ Hoaglands supplemented with various $KNO_3$ concentrations, plant rosette area measurements were taken using the WhinRhizo imaging software (Reagent Instruments, Canada). The plants were then collected in manila envelopes, placed in a 125° C. drying oven for 1-2 days and weighed

Example 5

Analysis of ME00919 Events

ME00919 contains Ceres Clone:29661 (At3g61880, SEQ ID NO:1) from *Arabidopsis thaliana*, which encodes a 534 amino acid cytochrome P450 protein. Evaluation of low-nitrogen tolerance for ME00919 in $T_2$ and $T_3$ was conducted under the same conditions as described in Example 2. In this study, the seedling photosynthetic efficiency was measured as Fv/Fm comparing transgenic plants within an event to non-transgenic segregants pooled across the same plate. Two events, -01 and -03, showed significantly increased photosynthetic efficiency relative to the internal controls in both generations at p≤0.05 using a one-tailed t-test assuming unequal variance. A summary of photosynthetic efficiency of ME00919 seedlings on low ammonium nitrate-containing media are shown in Table 1. Events -01 and -03 segregated 15:1 and 3:1 (R:S), respectively, for FINALE™ resistance in the $T_2$ generation. ME00919 events were also tested for enhanced growth on the low ammonium nitrate media. No significant differences between the transgenics and the controls were observed.

Events -01 and -03 of ME00919 exhibited no statistically relevant negative phenotypes. That is, there was no detectable reduction in germination rate, the transgenic plants appeared wild type in all instances; there was no observable or statistical differences between transgenics and controls in days to flowering; there was no observable or statistical differences between transgenics and controls in the size of the rosette area 7 days post-bolting; and there was no observable or statistical differences between transgenics and controls in fertility (silique number and seed fill).

Example 6

Analysis of ME01312 Events

ME01312 contains Ceres Clone:251343 (At3g21270, SEQ ID NO:48) from *Arabidopsis thaliana*, which encodes a 204 amino acid Dof zinc finger protein. Ceres Clone: 251343 shares approximately 40% amino acid identity to the corn Dof1 gene, which when overexpressed in *Arabidopsis*, has shown to confer tolerance to plants receiving low nitrogen stress (Yanagisawa et al., 2004). Evaluation of low-nitrogen tolerance for ME01312 in $T_2$ and $T_3$ was conducted under the same conditions as described in Examples 2 and 3. In this study, the seedling photosynthetic efficiency was measured as Fv/Fm comparing transgenic plants within an event to non-transgenic segregants pooled across the same plate. Two events, -03 and -11, showed significantly enhanced photosynthetic efficiency on either low nitrate or low ammonium nitrate-containing media after 16 and 17 days compared to the internal controls in both generations at p≤0.05 using a one-tailed t-test assuming unequal variance. Event -03 had a slightly greater p-value than 0.05 in the $T_3$ generation for the low nitrate screen, significant at p≤0.10. A summary of photosynthetic efficiency of ME01312 seedlings on either low nitrate or low ammonium nitrate-containing media is shown in Table 2. Events -03 and -11 segregated 3:1 (R:S), respectively, for FINALE™ resistance in the $T_2$ generation.

TABLE 1 t-test comparison of seedling photosynthetic efficiency between transgenic seedlings and pooled non-transgenic segregants after 18 days of growth on low ammonium nitrate.

| | | Transgenic | | Pooled Non-Transgenics | | t-test |
|---|---|---|---|---|---|---|
| Line | Events | Fv/Fm | n | Fv/Fm | n | p-value |
| ME00919 | ME00919-01 ($T_2$) | 0.65641304 | 46 | 0.595818 | 11 | $2.48 \times 10^{-2}$ |
| ME00919 | ME00919-01 ($T_3$) | 0.66348780 | 41 | 0.595818 | 11 | $1.55 \times 10^{-2}$ |
| ME00919 | ME00919-03 ($T_2$) | 0.67212195 | 41 | 0.634026 | 38 | $3.35 \times 10^{-3}$ |
| ME00919 | ME00919-03 ($T_3$) | 0.69278947 | 19 | 0.634026 | 38 | $2.39 \times 10^{-5}$ |

TABLE 2A

T-test comparison of photosynthetic efficiency between transgenic seedlings and pooled non-transgenic segregants after 16 days of growth on low nitrate.

| | | Transgenic | | Pooled Non-Transgenics | | t-test |
|---|---|---|---|---|---|---|
| Line | Events | Fv/Fm | n | Fv/Fm | n | p-value |
| ME01312 | ME01312-03 ($T_2$) | 0.63 | 38 | 0.60 | 58 | 0.03 |
| ME01312 | ME01312-03 ($T_3$) | 0.63 | 38 | 0.60 | 58 | 0.07 |
| ME01312 | ME01312-11 ($T_2$) | 0.64 | 41 | 0.60 | 58 | 0.019 |
| ME01312 | ME01312-11 ($T_3$) | 0.64 | 47 | 0.60 | 58 | $9.89 \times 10^{-3}$ |

TABLE 2B

T-test comparison of photosynthetic efficiency between transgenic seedlings and pooled non-transgenic segregants after 17 days of growth on low ammonium nitrate

| Line | Events | Transgenic Fv/Fm | n | Pooled Non-Transgenics Fv/Fm | n | t-test p-value |
|---|---|---|---|---|---|---|
| ME01312 | ME01312-03 ($T_2$) | 0.64 | 36 | 0.61 | 88 | $2.64 \times 10^{-3}$ |
| ME01312 | ME01312-03 ($T_3$) | 0.66 | 27 | 0.61 | 88 | $1.87 \times 10^{-5}$ |
| ME01312 | ME01312-11 ($T_2$) | 0.65 | 35 | 0.61 | 88 | $7.06 \times 10^{-4}$ |
| ME01312 | ME01312-11 ($T_3$) | 0.64 | 37 | 0.61 | 88 | 0.011 |

Events -03-11 of ME01312 exhibited no statistically relevant negative phenotypes. That is, there was no detectable reduction in germination rate, the transgenic plants appeared wild type in all instances; there was no observable or statistical differences between transgenics and controls in days to flowering; there was no observable or statistical differences between transgenics and controls in the size of the rosette area 7 days post-bolting; and there was no observable or statistical differences between transgenics and controls in fertility (silique number and seed fill).

Example 7

Analysis of ME01463 Events

ME01463 contains Ceres Clone:19586 (At1g80600, SEQ ID NO:76) from *Arabidopsis thaliana*, which encodes a 457 acetylornithine aminotransferase, a member of the Class-III aminotransferase family. Evaluation of low-nitrogen tolerance for ME01463 in two generations was conducted under the same conditions as described in Examples 2 and 3. In this study, the seedling photosynthetic efficiency was measured as Fv/Fm comparing transgenic plants within an event to non-transgenic segregants pooled across the same plate. Three events, -02, -06, and -10, showed significantly increased photosynthetic efficiency on low ammonium nitrate containing-media relative to the internal controls in both generations at p≤0.05 using a one-tailed t-test assuming unequal variance. A summary of photosynthetic efficiency of ME01463 seedlings is shown in Table 3. Events -02, -06, and -10 segregated 2:1, 2:1 and 3:1 (R:S), respectively, for FINALE™ resistance in the $T_2$ generation. ME01463 events were also tested for enhanced growth on the low ammonium nitrate media. No significant differences between the transgenics and the controls were observed (data not shown).

TABLE 3

T-test comparison of seedling photosynthetic efficiency between transgenic seedlings and pooled non-transgenic segregants after 18 days of growth on low ammonium nitrate.

| Line | Events | Transgenic Fv/Fm | n | Pooled Non-Transgenics Fv/Fm | n | t-test p-value |
|---|---|---|---|---|---|---|
| ME01463 | ME01463-02 ($T_3$) | 0.6815 | 26 | 0.6376 | 122 | $2.47 \times 10^{-4}$ |
| ME01463 | ME01463-02 ($T_4$) | 0.6701 | 41 | 0.6376 | 122 | $1.57 \times 10^{-3}$ |
| ME01463 | ME01463-06 ($T_3$) | 0.6615 | 31 | 0.6376 | 122 | $2.37 \times 10^{-2}$ |
| ME01463 | ME01463-06 ($T_4$) | 0.6881 | 35 | 0.6376 | 122 | $5.85 \times 10^{-6}$ |
| ME01463 | ME01463-10 ($T_2$) | 0.6699 | 33 | 0.6376 | 122 | $2.25 \times 10^{-3}$ |
| ME01463 | ME01463-10 ($T_3$) | 0.6809 | 18 | 0.6376 | 122 | $4.60 \times 10^{-4}$ |

Events -02, -06, and -10 of ME01463 exhibited no statistically relevant negative phenotypes. That is, there was no detectable reduction in germination rate, the transgenic plants appeared wild type in all instances; there was no observable or statistical differences between transgenics and controls in days to flowering; there was no observable or statistical differences between transgenics and controls in the size of the rosette area 7 days post-bolting; and there was no observable or statistical differences between transgenics and controls in fertility (silique number and seed fill).

Example 8

Analysis of ME01821 Events

ME01821 contains Ceres Clone:25136 (At1g65500, SEQ ID NO:96) from *Arabidopsis thaliana*, which encodes a 86 amino acid protein of unknown function. Evaluation of low-nitrogen tolerance for ME01821 in $T_2$ generation was conducted under the same conditions as described in Examples 2 and 3. In this study, the seedling photosynthetic efficiency was measured as Fv/Fm comparing transgenic plants within an event to non-transgenic segregants pooled across the same plate. Three events, -01, -04 and -05, showed significantly increased photosynthetic efficiency on low nitrate-containing media relative to the internal controls in $T_2$ generation. Two events, -04 and -05, showed significantly increased photosynthetic efficiency on low ammonium nitrate-containing media relative to the internal controls in $T_2$ generation at p≤0.05 using a one-tailed t-test assuming unequal variance. A summary of photosynthetic efficiency of ME01821 seedlings is shown in Table 4.

TABLE 4A

T-test comparison of seedling photosynthetic efficiency between transgenic seedlings and pooled non-transgenic segregants after 14 days of growth on low nitrate.

| Line | Events | Transgenic | | Pooled Non-Transgenics | | t-test |
| --- | --- | --- | --- | --- | --- | --- |
| | | Fv/Fm | n | Fv/Fm | n | p-value |
| ME01821 | ME01821-01 ($T_2$) | 0.06745 | 15 | 0.6520 | 33 | $3.76 \times 10^{-2}$ |
| ME01821 | ME01821-04 ($T_2$) | 0.6826 | 17 | 0.6614 | 14 | $2.76 \times 10^{-2}$ |
| ME01821 | ME01821-05 ($T_2$) | 0.6826 | 20 | 0.6614 | 14 | $3.74 \times 10^{-2}$ |

TABLE 4B

T-test comparison of seedling photosynthetic efficiency between transgenic seedlings and pooled non-transgenic segregants after 18 days of growth on low ammonium nitrate.

| Line | Events | Transgenic | | Pooled Non-Transgenics | | t-test |
| --- | --- | --- | --- | --- | --- | --- |
| | | Fv/Fm | n | Fv/Fm | n | p-value |
| ME01821 | ME01821-04 ($T_2$) | 0.7422 | 13 | 0.7166 | 21 | $5.20 \times 10^{-3}$ |
| ME01821 | ME01821-05 ($T_2$) | 0.7426 | 19 | 0.7166 | 21 | $6.07 \times 10^{-3}$ |

A summary of the enhanced growth of ME01812 events on either low nitrate- or low ammonium nitrate-containing media is shown in Table 5. For two events -01 and -05, transgenic seedlings were found significantly larger than the pooled non-transgenic segregants after 14 days of growth on low nitrate-containing media (Table 5A). Transgenic seedlings of two events -02 and -05 were found significantly larger than the pooled non-transgenic segregants after 14 days of growth on low ammonium nitrate-containing media (Table 5B). In this study, the seedling area for transgenic plants within an event was compared to the seedling area for non-transgenic segregants pooled across the same line.

TABLE 5A

T-test comparison of seedling area between transgenic seedlings and pooled non-transgenic segregants after 14 days of growth on low nitrate.

| Line | Events | Transgenic | | Pooled Non-Transgenics | | t-test |
| --- | --- | --- | --- | --- | --- | --- |
| | | Area | n | Area | n | p-value |
| ME01821 | ME01821-01 ($T_2$) | 0.0608 | 15 | 0.0555 | 33 | $3.97 \times 10^{-2}$ |
| ME01821 | ME01821-05 ($T_2$) | 0.0666 | 20 | 0.0530 | 14 | $3.05 \times 10^{-6}$ |

TABLE 5B

T-test comparison of seedling area between transgenic seedlings and pooled non-transgenic segregants after 18 days of growth on low ammonium nitrate.

| Line | Events | Transgenic | | Pooled Non-Transgenics | | t-test |
| --- | --- | --- | --- | --- | --- | --- |
| | | Area | n | Area | n | p-value |
| ME01821 | ME01821-02 ($T_2$) | 0.0750 | 19 | 0.0567 | 21 | $8.94 \times 10^{-5}$ |
| ME01821 | ME01821-05 ($T_2$) | 0.0680 | 19 | 0.0567 | 21 | $7.89 \times 10^{-3}$ |

Example 9

Analysis of ME01910 Events

ME01910 contains Ceres Clone:1820 (At2g30620, SEQ ID NO:99) from *Arabidopsis thaliana*, which encodes a 273 amino acid linker histone H1 and H5 family protein. Evaluation of low-nitrogen tolerance for ME01910 in $T_2$ and $T_3$ was conducted under the same conditions as described in Examples 2 and 3. In this study, the seedling photosynthetic efficiency was measured as Fv/Fm comparing transgenic plants within an event to non-transgenic segregants pooled across the same plate. Two events, -01 and -02, showed significantly increased photosynthetic efficiency relative to the internal controls in both generations at $p \leq 0.05$ using a one-tailed t-test assuming unequal variance. A summary of photosynthetic efficiency of ME01910 seedlings is shown in Table 6. Events -01 and -02 segregated 3:1 (R:S) for FINALE™ resistance in the $T_2$ generation. ME01910 events were also tested for enhanced growth on the low ammonium nitrate media. No significant differences between the transgenics and the controls were observed.

TABLE 6 t-test comparison of seedling photosynthetic efficiency between transgenic seedlings and pooled non-transgenic segregants after 18 days of growth on low ammonium nitrate.

| Line | Events | Transgenic | | Pooled Non-Transgenics | | t-test |
| --- | --- | --- | --- | --- | --- | --- |
| | | Fv/Fm | n | Fv/Fm | n | p-value |
| ME01910 | ME01910-01 ($T_2$) | 0.60433 | 39 | 0.56396 | 27 | $2.03 \times 10^{-2}$ |
| ME01910 | ME01910-01 ($T_3$) | 0.61274 | 31 | 0.56396 | 27 | $9.23 \times 10^{-3}$ |
| ME01910 | ME01910-02 ($T_2$) | 0.62705 | 37 | 0.58083 | 29 | $7.39 \times 10^{-3}$ |
| ME01910 | ME01910-02 ($T_3$) | 0.64146 | 24 | 0.58083 | 29 | $9.23 \times 10^{-4}$ |

Events -01 and -02 of ME01910 exhibited no statistically relevant negative phenotypes. That is, there was no detectable reduction in germination rate, the transgenic plants appeared wild type in all instances; there was no observable or statistical differences between transgenics and controls in days to flowering; there was no observable or statistical differences between transgenics and controls in the size of the rosette area 7 days post-bolting; and there was no observable or statistical differences between transgenics and controls in fertility (silique number and seed fill).

Example 10

Analysis of ME02538 Events

ME02538 contains Ceres Clone:13102 (At1g67920, SEQ ID NO:151) from *Arabidopsis thaliana*, which encodes a 67 amino acid protein of unknown function. Evaluation of low-nitrogen tolerance for ME02538 in $T_2$ generation was conducted under the same conditions as described in Example 2. In this study, the seedling photosynthetic efficiency was measured as Fv/Fm comparing transgenic plants within an event to non-transgenic segregants pooled across the same plate. Two events, -04 and -05, showed significantly increased photosynthetic efficiency relative to the internal controls in $T_2$ generation on both low nitrate-containing and ammonium nitrate-containing media at $p\leq 0.05$ using a one-tailed t-test assuming unequal variance. A summary of photosynthetic efficiency of ME01821 seedlings is shown in Table 7.

TABLE 7A

T-test comparison of seedling photosynthetic efficiency between transgenic seedlings and pooled non-transgenic segregants after 14 days of growth on low nitrate.

| Line | Events | Transgenic Fv/Fm | n | Pooled Non-Transgenics Fv/Fm | n | t-test p-value |
|---|---|---|---|---|---|---|
| ME02538 | ME02538-04 ($T_2$) | 0.6686 | 15 | 0.6171 | 24 | $1.92 \times 10^{-4}$ |
| ME02538 | ME02538-05 ($T_2$) | 0.6420 | 20 | 0.6171 | 24 | $4.84 \times 10^{-2}$ |

TABLE 7B

T-test comparison of seedling photosynthetic efficiency between transgenic seedlings and pooled non-transgenic segregants after 18 days of growth on low ammonium nitrate.

| Line | Events | Transgenic Fv/Fm | n | Pooled Non-Transgenics Fv/Fm | n | t-test p-value |
|---|---|---|---|---|---|---|
| ME02538 | ME02538-04 ($T_2$) | 0.7345 | 13 | 0.7080 | 22 | $4.45 \times 10^{-3}$ |
| ME02538 | ME02538-05 ($T_2$) | 0.7356 | 20 | 0.7080 | 22 | $5.93 \times 10^{-3}$ |

ME02538 events were also tested for enhanced growth on the low ammonium nitrate media. A summary of the growth assay performed on ME01812 events is shown in Table 8. Transgenic seedlings of two events -01 and -02 were found significantly larger than the pooled non-transgenic segregants on both low nitrate- (Table 8A) and low ammonium nitrate-containing media (Table 8B).

TABLE 8A

T-test comparison of seedling area between transgenic seedlings and pooled non-transgenic segregants after 14 days of growth on low nitrate.

| Line | Events | Transgenic Area | n | Pooled Non-Transgenics Area | n | t-test p-value |
|---|---|---|---|---|---|---|
| ME02538 | ME02538-01 ($T_2$) | 0.0655 | 16 | 0.0558 | 36 | $2.80 \times 10^{-4}$ |
| ME02538 | ME02538-02 ($T_2$) | 0.0651 | 13 | 0.0601 | 20 | $1.32 \times 10^{-2}$ |

TABLE 8B

T-test comparison of seedling area between transgenic seedlings and pooled non-transgenic segregants after 18 days of growth on low ammonium nitrate.

| Line | Events | Transgenic Area | n | Pooled Non-Transgenics Area | n | t-test p-value |
|---|---|---|---|---|---|---|
| ME02538 | ME02538-01 ($T_2$) | 0.0856 | 15 | 0.0737 | 39 | $8.60 \times 10^{-3}$ |
| ME02538 | ME02538-02 ($T_2$) | 0.0864 | 14 | 0.0776 | 22 | $3.13 \times 10^{-2}$ |

Example 11

Analysis of ME02603 Events

ME02603 contains Ceres Clone:15457 (At5g47610, SEQ ID NO:165) from *Arabidopsis thaliana*, which encodes a 166 amino acid zinc ion binding protein. Evaluation of low-nitrogen tolerance for ME02603 in $T_2$ and $T_3$ was conducted under the same conditions as described in Examples 2 and 3. In this study, the seedling photosynthetic efficiency was measured as Fv/Fm comparing transgenic plants within an event to non-transgenic segregants pooled across the same plate. Two events, -01 and -04, showed significantly increased photosynthetic efficiency on low ammonium nitrate-containing media relative to the internal controls in both generations at $p\leq 0.05$ using a one-tailed t-test assuming unequal variance. A summary of photosynthetic efficiency of ME02603 seedlings is shown in Table 9. Events -01 and -04 segregated 3:1 (R:S) for FINALE™ resistance in the $T_2$ generation. Transgenic plants of two events -01 and -04—were also tested for enhanced photosynthetic efficiency on the low nitrate media. No significant differences between the transgenics and the controls were observed.

TABLE 9

T-test comparison of photosynthetic efficiency between transgenic seedlings and pooled non-transgenic segregants after 17 days (21 days for the $T_2$ generation of ME02603-01) of growth on low ammonium nitrate.

| Line | Events | Transgenic Fv/Fm | n | Pooled Non-Transgenics Fv/Fm | n | t-test p-value |
|---|---|---|---|---|---|---|
| ME02603 | ME02603-01 ($T_2$) | 0.61 | 10 | 0.54 | 32 | $9.00 \times 10^{-4}$ |
| ME02603 | ME02603-01 ($T_3$) | 0.67 | 28 | 0.65 | 62 | $6.11 \times 10^{-3}$ |
| ME02603 | ME02603-04 ($T_2$) | 0.69 | 25 | 0.65 | 62 | $4.45 \times 10^{-5}$ |
| ME02603 | ME02603-04 ($T_3$) | 0.68 | 24 | 0.65 | 62 | $7.53 \times 10^{-3}$ |

Events -01 and -04 of ME02603 exhibited no statistically relevant negative phenotypes. That is, there was no detectable reduction in germination rate, the transgenic plants appeared wild type in all instances; there was no observable or statistical differences between transgenics and controls in days to flowering; there was no observable or statistical differences between transgenics and controls in the size of the rosette area 7 days post-bolting; and there was no observable or statistical differences between transgenics and controls in fertility (silique number and seed fill).

Example 12

Analysis of ME02613 Events

ME02613 contains Ceres Clone:17883 (At3g13910, SEQ ID NO:185) from *Arabidopsis thaliana*, which encodes a 102 amino acid protein of unknown function. Evaluation of low-nitrogen tolerance for ME02613 in $T_2$ generation was conducted under the same conditions as described in Examples 2 and 3. In this study, the seedling photosynthetic efficiency was measured as Fv/Fm comparing transgenic plants within an event to non-transgenic segregants pooled across the same plate. In $T_2$ generation, two events, -01 and -04, showed significantly increased photosynthetic efficiency on low nitrate containing-media relative to the internal controls in $T_2$ generation at $p \leq 0.05$ using a one-tailed t-test assuming unequal variance. Two events, -03 and -04, showed significantly increased photosynthetic efficiency on low ammonium nitrate containing-media relative to the internal controls in $T_2$ generation at $p \leq 0.05$ using a one-tailed t-test assuming unequal variance. A summary of photosynthetic efficiency of ME02613 seedlings is shown in Table 10.

TABLE 10A

T-test comparison of seedling photosynthetic efficiency between transgenic seedlings and pooled non-transgenic segregants after 14 days of growth on low nitrate.

| | | Transgenic | | Pooled Non-Transgenics | | t-test |
|---|---|---|---|---|---|---|
| Line | Events | Fv/Fm | n | Fv/Fm | n | p-value |
| ME02613 | ME02613-01 ($T_2$) | 0.6979 | 16 | 0.6630 | 21 | $1.45 \times 10^{-2}$ |
| ME02613 | ME02613-04 ($T_2$) | 0.7046 | 13 | 0.6630 | 21 | $5.73 \times 10^{-4}$ |

TABLE 10B

T-test comparison of seedling photosynthetic efficiency between transgenic seedlings and pooled non-transgenic segregants after 18 days of growth on low ammonium nitrate.

| | | Transgenic | | Pooled Non-Transgenics | | t-test |
|---|---|---|---|---|---|---|
| Line | Events | Fv/Fm | n | Fv/Fm | n | p-value |
| ME02613 | ME02613-03 ($T_2$) | 0.7270 | 9 | 0.7068 | 29 | $4.34 \times 10^{-2}$ |
| ME02613 | ME02613-04 ($T_2$) | 0.7485 | 15 | 0.7068 | 29 | $7.09 \times 10^{-5}$ |

A summary of the enhanced growth of ME02613 events on either low nitrate- or low ammonium nitrate-containing media is shown in Table 11. For two events -01 and -03, transgenic seedlings were found significantly larger than the pooled non-transgenic segregants after 14 days of growth on low nitrate-containing media (Table 11A). Transgenic seedlings of two events -02 and -03 were found significantly larger than the pooled non-transgenic segregants after 14 days of growth on low ammonium nitrate-containing media (Table 11B).

TABLE 11A

T-test comparison of seedling area between transgenic seedlings and pooled non-transgenic segregants after 14 days of growth on low nitrate.

| | | Transgenic | | Pooled Non-Transgenics | | t-test |
|---|---|---|---|---|---|---|
| Line | Events | Area | n | Area | n | p-value |
| ME02613 | ME02613-01 ($T_2$) | 0.05706 | 16 | 0.05259 | 31 | $4.71 \times 10^{-2}$ |
| ME02613 | ME02613-03 ($T_2$) | 0.06236 | 12 | 0.05789 | 29 | $2.39 \times 10^{-2}$ |

TABLE 1

T-test comparison of seedling area between transgenic seedlings and pooled non-transgenic segregants after 18 days of growth on low ammonium nitrate.

| Line | Events | Transgenic Area | n | Pooled Non-Transgenics Area | n | t-test p-value |
|---|---|---|---|---|---|---|
| ME02613 | ME02613-02 ($T_2$) | 0.08324 | 14 | 0.07018 | 29 | $2.72 \times 10^{-4}$ |
| ME02613 | ME02613-03 ($T_2$) | 0.08273 | 9 | 0.07018 | 29 | $1.41 \times 10^{-2}$ |

Example 13

Analysis of ME02801 Events

ME02801 contains Ceres Clone:251590 (At3g53080, SEQ ID NO:207) from *Arabidopsis thaliana*, which encodes a 155 amino acid protein of unknown function. Evaluation of low-nitrogen tolerance for ME02801 in $T_2$ and $T_3$ was conducted under the same conditions as described in Example 2 and 3. In this study, the seedling photosynthetic efficiency was measured as Fv/Fm comparing transgenic plants within an event to non-transgenic segregants pooled across the same plate. Two events, -02 and -04, showed significantly increased photosynthetic efficiency on low nitrate-containing media relative to the internal controls in both generations at p≤0.05 using a one-tailed t-test assuming unequal variance. A summary of photosynthetic efficiency of ME02801 seedlings is shown in Table 12. Events -02 and -04 segregated 3:1 (R:S) for FINALE™ resistance in the $T_2$ generation. ME02801 events were also tested for enhanced growth on the low nitrate media and enhanced photosynthetic efficiency and growth on low ammonium nitrate media. No significant differences between the transgenics and the controls were observed.

TABLE 12 t-test comparison of seedling photosynthetic efficiency between transgenic seedlings and pooled non-transgenic segregants after 14 days of growth on low nitrate.

| Line | Events | Transgenic Fv/Fm | n | Pooled Non-Transgenics Fv/Fm | n | t-test p-value |
|---|---|---|---|---|---|---|
| ME02801 | ME02801-02 ($T_2$) | 0.536385 | 39 | 0.465903 | 113 | $5.49 \times 10^{-7}$ |
| ME02801 | ME02801-02 ($T_3$) | 0.536465 | 43 | 0.465903 | 113 | $5.11 \times 10^{-7}$ |
| ME02801 | ME02801-04 ($T_2$) | 0.532419 | 31 | 0.465903 | 113 | $1.28 \times 10^{-5}$ |
| ME02801 | ME02801-04 ($T_3$) | 0.510406 | 32 | 0.465903 | 113 | $1.74 \times 10^{-2}$ |

Events -02 and -04 of ME02801 exhibited no statistically relevant negative phenotypes. That is, there was no detectable reduction in germination rate, the transgenic plants appeared wild type in all instances; there was no observable or statistical differences between transgenics and controls in days to flowering; there was no observable or statistical differences between transgenics and controls in the size of the rosette area 7 days post-bolting; and there was no observable or statistical differences between transgenics and controls in fertility (silique number and seed fill).

Example 14

Analysis of ME03123 Events

ME03123 contains Ceres Clone:4898 (At1g29970, SEQ ID NO:217) from *Arabidopsis thaliana*, which encodes a 158 amino acid protein of unknown function. Evaluation of low-nitrogen tolerance for ME03123 in $T_2$ and/or $T_3$ was conducted under the same conditions as described in Examples 2 and 3. In this study, the seedling photosynthetic efficiency was measured as Fv/Fm comparing transgenic plants within an event to non-transgenic segregants pooled across the same plate. A summary of photosynthetic efficiency of ME03123 seedlings is shown in Table 13. Two events, -01 and -10, showed significantly increased photosynthetic efficiency on low nitrate- or low ammonium nitrate-containing media relative to the internal controls in $T_2$ or $T_3$ generation at p≤0.05 using a one-tailed t-test assuming unequal variance.

TABLE 13A

T-test comparison of seedling photosynthetic efficiency between transgenic seedlings and pooled non-transgenic segregants after 14 days of growth on low nitrate.

| Line | Events | Transgenic Fv/Fm | n | Pooled Non-Transgenics Fv/Fm | n | t-test p-value |
|---|---|---|---|---|---|---|
| ME03123 | ME03123-01 ($T_2$) | 0.6282 | 15 | 0.5732 | 26 | $6.60 \times 10^{-5}$ |
| ME03123 | ME03123-10 ($T_3$) | 0.6069 | 12 | 0.5732 | 26 | $1.05 \times 10^{-2}$ |

TABLE 13B

T-test comparison of seedling photosynthetic efficiency between transgenic seedlings and pooled non-transgenic segregants after 18 days of growth on low ammonium nitrate.

| Line | Events | Transgenic Fv/Fm | n | Pooled Non-Transgenics Fv/Fm | n | t-test p-value |
|---|---|---|---|---|---|---|
| ME03123 | ME03123-01 ($T_2$) | 0.6736 | 17 | 0.6315 | 16 | $1.74 \times 10^{-2}$ |
| ME03123 | ME03123-10 ($T_3$) | 0.6699 | 20 | 0.6315 | 16 | $1.60 \times 10^{-2}$ |

ME03123 events were also tested for enhanced growth on the low ammonium nitrate media. In this assay, transgenic seedlings of ME03123-02 and ME03123-04 ($T_2$) were significantly larger than the pooled non-transgenic segregants after 14 days of growth on low nitrate (Table 14).

TABLE 14

T-test comparison of seedling area between transgenic seedlings and pooled non-transgenic segregants after 14 days of growth on low nitrate.

| Line | Events | Transgenic Area | n | Pooled Non-Transgenics Area | n | t-test p-value |
|---|---|---|---|---|---|---|
| ME03123 | ME03123-02 ($T_2$) | 0.07235 | 19 | 0.05623 | 20 | $1.41 \times 10^{-6}$ |
| ME03123 | ME03123-04 ($T_3$) | 0.06571 | 7 | 0.05729 | 41 | $7.74 \times 10^{-3}$ |

Example 15

Analysis of ME04204 Events

ME04204 contains Ceres Clone:148977 (At1g78770, SEQ ID NO:233) from *Arabidopsis thaliana*, which encodes a 159 amino acid anaphase promoting complex/cyclosome subunit protein. However, it is also possible that this is a natural variant transcript produced by the plant, because multiple annotations for locus At1g78770 were found in public domain. Evaluation of low-nitrogen tolerance for ME04204 in $T_2$ and $T_3$ was conducted under the same conditions as described in Examples 2 and 3. In this study, the seedling photosynthetic efficiency was measured as Fv/Fm comparing transgenic plants within an event to non-transgenic segregants pooled across the same plate. Two events, -01 and -05, showed significantly increased photosynthetic efficiency relative to the internal controls in both generations at $p \leq 0.05$ using a one-tailed t-test assuming unequal variance. A summary of photosynthetic efficiency of ME04204 seedlings is shown in Table 15. Events -01 and -05 segregated 3:1 (R:S) for FINALE™ resistance in the $T_2$ generation. ME04204 events were also tested for enhanced growth on the low nitrate media. No significant differences between the transgenics and the controls were observed.

TABLE 15

T-test comparison of seedling photosynthetic efficiency between transgenic seedlings and pooled non-transgenic segregants after 14 days of growth on low nitrate.

| Line | Events | Transgenic Fv/Fm | n | Pooled Non-Transgenics Fv/Fm | n | t-test p-value |
|---|---|---|---|---|---|---|
| ME04204 | ME04204-01 ($T_2$) | 0.623676 | 34 | 0.585504 | 121 | $2.15 \times 10^{-4}$ |
| ME04204 | ME04204-01 ($T_3$) | 0.627706 | 17 | 0.585504 | 121 | $8.22 \times 10^{-5}$ |
| ME04204 | ME04204-05 ($T_2$) | 0.615857 | 35 | 0.585504 | 121 | $9.41 \times 10^{-3}$ |
| ME04204 | ME04204-05 ($T_3$) | 0.611419 | 43 | 0.585504 | 121 | $1.25 \times 10^{-2}$ |

Events -01 and -05 of ME04204 exhibited no statistically relevant negative phenotypes. That is, there was no detectable reduction in germination rate, the transgenic plants appeared wild type in all instances; there was no observable or statistical differences between transgenics and controls in days to flowering; there was no observable or statistical differences between transgenics and controls in the size of the rosette area 7 days post-bolting; and there was no observable or statistical differences between transgenics and controls in fertility (silique number and seed fill).

Example 16

Analysis of ME04477 Events

ME04477 contains Ceres Clone:24255 (At2g36320, SEQ ID NO:245) from *Arabidopsis thaliana*, which encodes a 161 amino acid DNA binding/zinc ion binding protein. Evaluation of low-nitrogen tolerance for ME04477 in $T_2$ and $T_3$ was conducted under the same conditions as described in Example 2. In this study, the seedling photosynthetic efficiency was measured as Fv/Fm comparing transgenic plants within an event to non-transgenic segregants pooled across the same plate. Two events, -01 and -05, showed significantly increased photosynthetic efficiency on low nitrate-containing media relative to the internal controls in both generations at $p \leq 0.05$ using a one-tailed t-test assuming unequal variance. A summary of photosynthetic efficiency of ME04477 seedlings is shown in Table 16. Events -01 and -05 segregated 3:1 (R:S) for FINALE™ resistance in the $T_2$ generation. ME04477 events were also tested for enhanced growth on the low nitrate media. No significant differences between the transgenics and the controls were observed.

TABLE 16

T-test comparison of seedling photosynthetic efficiency between transgenic seedlings and pooled non-transgenic segregants after 14 days of growth on low nitrate.

| Line | Events | Transgenic Fv/Fm | n | Pooled Non-Transgenics Fv/Fm | n | t-test p-value |
|---|---|---|---|---|---|---|
| ME04204 | ME04204-01 ($T_2$) | 0.623676 | 34 | 0.585504 | 121 | $2.15 \times 10^{-4}$ |
| ME04204 | ME04204-01 ($T_3$) | 0.627706 | 17 | 0.585504 | 121 | $8.22 \times 10^{-5}$ |
| ME04204 | ME04204-05 ($T_2$) | 0.615857 | 35 | 0.585504 | 121 | $9.41 \times 10^{-3}$ |
| ME04204 | ME04204-05 ($T_3$) | 0.611419 | 43 | 0.585504 | 121 | $1.25 \times 10^{-2}$ |

Events -01 and -05 of ME04477 exhibited no statistically relevant negative phenotypes. That is, there was no detectable reduction in germination rate, the transgenic plants appeared wild type in all instances; there was no observable or statistical differences between transgenics and controls in days to flowering; there was no observable or statistical differences between transgenics and controls in the size of the rosette area 7 days post-bolting; and there was no observable or statistical differences between transgenics and controls in fertility (silique number and seed fill).

Example 17

Analysis of ME04507 Events

ME04507 contains Ceres Clone:38432 (At4g38250, SEQ ID NO:299) from *Arabidopsis thaliana*, which encodes a 436 amino acid transmembrane amino acid transporter protein. Evaluation of low-nitrogen tolerance for ME04507 in $T_2$ and $T_3$ was conducted under the same conditions as described in Example 2. In this study, the seedling photosynthetic efficiency was measured as Fv/Fm comparing transgenic plants within an event to non-transgenic segregants pooled across the same plate. Two events, -03 and -04, showed significantly increased photosynthetic efficiency on low nitrate-containing media relative to the internal controls in both generations at p≤0.05 using a one-tailed t-test assuming unequal variance. A summary of photosynthetic efficiency of ME04507 seedlings is shown in Table 17. Events -03 and -04 segregated 15:1 and 3:1 (R:S), respectively, for FINALE™ resistance in the $T_2$ generation. ME04507 events were also tested for enhanced growth on the low nitrate media. No significant differences between the transgenics and the controls were observed.

TABLE 17

T-test comparison of seedling photosynthetic efficiency between transgenic seedlings and pooled non-transgenic segregants after 14 days of growth on low nitrate media.

| Line | Events | Transgenic Fv/Fm | n | Pooled Non-Transgenics Fv/Fm | n | t-test p-value |
|---|---|---|---|---|---|---|
| ME04507 | ME04507-03 ($T_2$) | 0.57753 | 40 | 0.53084 | 103 | $4.90 \times 10^{-4}$ |
| ME04507 | ME04507-03 ($T_3$) | 0.56318 | 39 | 0.53084 | 103 | $2.64 \times 10^{-2}$ |
| ME04507 | ME04507-04 ($T_2$) | 0.57708 | 38 | 0.53084 | 103 | $6.12 \times 10^{-3}$ |
| ME04507 | ME04507-04 ($T_3$) | 0.57277 | 22 | 0.53084 | 103 | $2.35 \times 10^{-2}$ |

Events -03 and -04 of ME04507 exhibited no statistically relevant negative phenotypes. That is, there was no detectable reduction in germination rate, the transgenic plants appeared wild type in all instances; there was no observable or statistical differences between transgenics and controls in days to flowering; there was no observable or statistical differences between transgenics and controls in the size of the rosette area 7 days post-bolting; and there was no observable or statistical differences between transgenics and controls in fertility (silique number and seed fill).

Example 18

Analysis of ME04587 Events

ME04587 contains Ceres Annot:553243 (At2g27010, SEQ ID NO:331) from *Arabidopsis thaliana*, which encodes a 516 amino acid cytochrome P450 protein. Evaluation of low-nitrogen tolerance for ME04587 in $T_2$ and $T_3$ was conducted under the same conditions as described in Example 2. In this study, the seedling photosynthetic efficiency was measured as Fv/Fm comparing transgenic plants within an event to non-transgenic segregants pooled across the same plate. Two events, -01 and -02, showed significantly increased photosynthetic efficiency on low ammonium nitrate-containing media relative to the internal controls in both generations at p≤0.05 using a one-tailed t-test assuming unequal variance. A summary of photosynthetic efficiency of ME04587 seedlings is shown in Table 18. In $T_2$ generation, events -01 and -02 segregated 1:1 and 47:1 respectively (R:S) for FINALE™ resistance. These two events segregated 2:1 and 7:1 respectively (R:S) for FINALE® resistance in the $T_3$ generation.

TABLE 18

T-test comparison of seedling photosynthetic efficiency between transgenic seedlings and pooled non-transgenic segregants after 18 days of growth on low ammonium nitrate.

| Line | Events | Transgenic Fv/Fm | n | Pooled Non-Transgenics Fv/Fm | n | t-test p-value |
|---|---|---|---|---|---|---|
| ME04587 | ME04587-01 ($T_2$) | 0.6424 | 10 | 0.5437 | 30 | $2.48 \times 10^{-3}$ |
| ME04587 | ME04587-01 ($T_3$) | 0.6165 | 25 | 0.5437 | 30 | $1.24 \times 10^{-2}$ |
| ME04587 | ME04587-02 ($T_2$) | 0.6022 | 47 | 0.5437 | 30 | $3.08 \times 10^{-2}$ |
| ME04587 | ME04587-02 ($T_3$) | 0.6310 | 43 | 0.5437 | 30 | $3.68 \times 10^{-3}$ |

ME04587 events were also tested for enhanced growth on the low ammonium nitrate media. In addition, these events were tested on low nitrate media for increased seedling area and photosynthetic efficiency. No statistically significant differences between the transgenics and the controls were observed.

Events -01 and -02 of ME04587 exhibited no statistically relevant negative phenotypes. That is, there was no detectable reduction in germination rate, the transgenic plants appeared wild type in all instances; there was no observable or statistical differences between transgenics and controls in days to flowering; there was no observable or statistical differences between transgenics and controls in the size of the rosette area 7 days post-bolting; and there was no observable or statistical differences between transgenics and controls in fertility (silique number and seed fill).

Example 19

Analysis of ME04753 Events

ME04753 contains Ceres Clone:1011900 (At2g21660, SEQ ID NO:367) from *Arabidopsis thaliana*, which encodes a 130 amino acid glycine-rich RNA binding protein. Evaluation of low-nitrogen tolerance for ME04753 in $T_2$ and $T_3$ was conducted under the same conditions as described in Examples 2 and 3. In this study, the seedling photosynthetic efficiency was measured as Fv/Fm comparing transgenic plants within an event to non-transgenic segregants pooled across the same plate. Two events, -01 and -02, showed significantly increased photosynthetic efficiency on low nitrate-containing media relative to the internal controls in both generations at $p \leq 0.05$ using a one-tailed t-test assuming unequal variance. A summary of photosynthetic efficiency of ME04753 seedlings is shown in Table 19. Events -01 and -02 segregated 3:1 and 2:1 respectively (R:S) for FINALE™ resistance in the $T_2$ generation. ME04753 events were also tested for enhanced growth on the low nitrate media. No significant differences between the transgenics and the controls were observed.

Events -01 and -02 of ME04753 exhibited no statistically relevant negative phenotypes. That is, there was no detectable reduction in germination rate, the transgenic plants appeared wild type in all instances; there was no observable or statistical differences between transgenics and controls in days to flowering; there was no observable or statistical differences between transgenics and controls in the size of the rosette area 7 days post-bolting; and there was no observable or statistical differences between transgenics and controls in fertility (silique number and seed fill).

Example 20

Analysis of ME04772 Events

ME04772 contains Ceres Clone:5232 (At1g13380, SEQ ID NO:509) from *Arabidopsis thaliana*, which encodes a 188 amino acid protein of unknown function. Evaluation of low-nitrogen tolerance for ME04772 in $T_2$ and $T_3$ was conducted under the same conditions as described in Example 2. In this study, the seedling photosynthetic efficiency was measured as Fv/Fm comparing transgenic plants within an event to non-transgenic segregants pooled across the same plate. Two events, -02 and -04, showed significantly increased photosynthetic efficiency on low nitrate-containing media relative to the internal controls in both generations at $p \leq 0.05$ using a one-tailed t-test assuming unequal variance. A summary of photosynthetic efficiency of ME04772 seedlings is shown in Table 20. Events -02 and -04 segregated 2:1 and 3:1 respectively (R:S) for FINALE™ resistance in the $T_2$ generation. ME04772 events were also tested for enhanced growth on the low nitrate media. No significant differences between the transgenics and the controls were observed.

TABLE 19

T-test comparison of seedling photosynthetic efficiency between transgenic seedlings and pooled non-transgenic segregants after 14 days of growth on low nitrate media.

| | | Transgenic | | Pooled Non-Transgenics | | t-test |
|---|---|---|---|---|---|---|
| Line | Events | Fv/Fm | n | Fv/Fm | n | p-value |
| ME04753 | ME04753-01 ($T_2$) | 0.49323 | 39 | 0.45917 | 66 | $3.17 \times 10^{-2}$ |
| ME04753 | ME04753-01 ($T_3$) | 0.50942 | 26 | 0.45917 | 66 | $1.80 \times 10^{-2}$ |
| ME04753 | ME04753-02 ($T_2$) | 0.49856 | 34 | 0.45917 | 66 | $2.43 \times 10^{-2}$ |
| ME04753 | ME04753-02 ($T_3$) | 0.51274 | 27 | 0.45917 | 66 | $1.15 \times 10^{-2}$ |

TABLE 20

T-test comparison of seedling photosynthetic efficiency between transgenic seedlings and pooled non-transgenic segregants after 14 days of growth on low nitrate media.

| Line | Events | Transgenic Fv/Fm | n | Pooled Non-Transgenics Fv/Fm | n | t-test p-value |
|---|---|---|---|---|---|---|
| ME04772 | ME04772-02 ($T_2$) | 0.53708 | 25 | 0.46204 | 53 | $3.36 \times 10^{-5}$ |
| ME04772 | ME04772-02 ($T_3$) | 0.53121 | 34 | 0.46204 | 53 | $1.27 \times 10^{-4}$ |
| ME04772 | ME04772-04 ($T_2$) | 0.52921 | 34 | 0.46204 | 53 | $3.71 \times 10^{-4}$ |
| ME04772 | ME04772-04 ($T_3$) | 0.50272 | 36 | 0.46204 | 53 | $2.73 \times 10^{-2}$ |

Events -02 and -04 of ME04772 exhibited no statistically relevant negative phenotypes. That is, there was no detectable reduction in germination rate, the transgenic plants appeared wild type in all instances; there was no observable or statistical differences between transgenics and controls in days to flowering; there was no observable or statistical differences between transgenics and controls in the size of the rosette area 7 days post-bolting; and there was no observable or statistical differences between transgenics and controls in fertility (silique number and seed fill).

Example 21

Analysis of ME04772 Events

ME04909 contains Ceres Clone:29302 (At1g49010, SEQ ID NO:532) from *Arabidopsis thaliana*, which encodes a 314 amino acid Myb-like DNA-binding domain protein. Evaluation of low-nitrogen tolerance for ME04909 in $T_2$ and $T_3$ was conducted under the same conditions as described in Examples 2 and 3. In this study, the seedling photosynthetic efficiency was measured as Fv/Fm comparing transgenic plants within an event to non-transgenic segregants pooled across the same plate. Two events, -01 and -03, showed significantly increased photosynthetic efficiency on low nitrate-containing media relative to the internal controls in both generations at p≤0.05 using a one-tailed t-test assuming unequal variance. A summary of photosynthetic efficiency of ME04909 seedlings is shown in Table 21. Events -01 and -03 segregated 15:1 (R:S) for FINALE™ resistance in the $T_2$ generation. ME04909 events were also tested for enhanced growth on the low nitrate media. No significant differences between the transgenics and the controls were observed.

TABLE 21 t-test comparison of seedling photosynthetic efficiency between transgenic seedlings and pooled non-transgenic segregants after 14 days of growth on low nitrate.

| Line | Events | Transgenic Fv/Fm | n | Pooled Non-Transgenics Fv/Fm | n | t-test p-value |
|---|---|---|---|---|---|---|
| ME04909 | ME04909-01 ($T_2$) | 0.587774 | 31 | 0.550342 | 111 | $1.36 \times 10^{-2}$ |
| ME04909 | ME04909-01 ($T_3$) | 0.607452 | 31 | 0.550342 | 111 | $1.28 \times 10^{-3}$ |
| ME04909 | ME04909-03 ($T_2$) | 0.581537 | 41 | 0.550342 | 111 | $1.8 \times 10^{-2}$ |
| ME04909 | ME04909-03 ($T_3$) | 0.609806 | 31 | 0.550342 | 111 | $4.3 \times 10^{-5}$ |

Events -01 and -03 of ME04909 exhibited no statistically relevant negative phenotypes. That is, there was no detectable reduction in germination rate, the transgenic plants appeared wild type in all instances; there was no observable or statistical differences between transgenics and controls in days to flowering; there was no observable or statistical differences between transgenics and controls in the size of the rosette area 7 days post-bolting; and there was no observable or statistical differences between transgenics and controls in fertility (silique number and seed fill).

Example 22

Analysis of ME05033 Events

ME05033 contains Ceres Clone:93971 (At4g19095, SEQ ID NO:555) from *Arabidopsis thaliana*, which encodes a 188 amino acid protein of unknown function. Evaluation of low-nitrogen tolerance for ME05033 in $T_2$ and $T_3$ was conducted under the same conditions as described in Example 2. In this study, the seedling photosynthetic efficiency was measured as Fv/Fm comparing transgenic plants within an event to non-transgenic segregants pooled across the same plate. Two events, -03 and -05, showed significantly increased photosynthetic efficiency on low nitrate-containing media relative to the internal controls in both generations at p≤0.05 using a one-tailed t-test assuming unequal variance. A summary of photosynthetic efficiency of ME05033 seedlings is shown in Table 22. Events -03 and -05 segregated 15:1 and 2:1 respectively (R:S) for FINALE™ resistance in the $T_2$ generation. ME05033 events were also tested for enhanced growth on the low nitrate media. No significant differences between the transgenics and the controls were observed.

TABLE 22

T-test comparison of seedling photosynthetic efficiency between transgenic seedlings and pooled non-transgenic segregants after 14 days of growth on low nitrate media.

| Line | Events | Transgenic Fv/Fm | n | Pooled Non-Transgenics Fv/Fm | n | t-test p-value |
|---|---|---|---|---|---|---|
| ME05033 | ME05033-03 ($T_2$) | 0.65717 | 46 | 0.62621 | 132 | $9.20 \times 10^{-5}$ |
| ME05033 | ME05033-03 ($T_3$) | 0.64956 | 39 | 0.62621 | 132 | $4.52 \times 10^{-3}$ |
| ME05033 | ME05033-05 ($T_2$) | 0.64448 | 29 | 0.62621 | 132 | $3.46 \times 10^{-2}$ |
| ME05033 | ME05033-05 ($T_3$) | 0.65537 | 30 | 0.62621 | 132 | $2.38 \times 10^{-4}$ |

Events -03 and -05 of ME05033 exhibited no statistically relevant negative phenotypes. That is, there was no detectable reduction in germination rate, the transgenic plants appeared wild type in all instances; there was no observable or statistical differences between transgenics and controls in days to flowering; there was no observable or statistical differences between transgenics and controls in the size of the rosette area 7 days post-bolting; and there was no observable or statistical differences between transgenics and controls in fertility (silique number and seed fill).

Example 23

Analysis of ME05194 Events

ME05194 contains Ceres cDNA:12669619 (At1g30710, SEQ ID NO:557) from *Arabidopsis thaliana*, which encodes a 531 amino acid electron carrier protein. Evaluation of low-nitrogen tolerance for ME05194 in $T_2$ and $T_3$ was conducted under the same conditions as described in Examples 2 and 3. Two events, -03 and -05, showed significantly enhanced growth on low nitrate-containing media relative to the internal controls in both generations at $p \leq 0.05$ using a one-tailed t-test assuming unequal variance. In this study, the seedling area at 14 days for transgenic plants within an event was compared to the seedling area for non-transgenic segregants pooled across the same line. A summary of enhanced growth under low nitrate growth conditions of ME05194 seedlings is shown in Table 23. Events -03 and -05 segregated 1:1 (R:S) for FINALE™ resistance in the $T_2$ generation. ME05194 events were also tested for increased photosynthetic efficiency on the low nitrate media. No significant differences between the transgenics and the controls were observed.

TABLE 23 t-test comparison of seedling area between transgenic seedlings and pooled non-transgenic segregants after 14 days of growth on low nitrate.

| Line | Events | Transgenic Area | n | Pooled Non-Transgenics Area | n | t-test p-value |
|---|---|---|---|---|---|---|
| ME05194 | ME05194-03 ($T_2$) | 0.051216 | 38 | 0.040874 | 82 | $2.54 \times 10^{-5}$ |
| ME05194 | ME05194-03 ($T_3$) | 0.047042 | 45 | 0.040874 | 82 | $2.61 \times 10^{-2}$ |
| ME05194 | ME05194-05 ($T_2$) | 0.048746 | 26 | 0.040874 | 82 | $6.15 \times 10^{-3}$ |
| ME05194 | ME05194-05 ($T_3$) | 0.048457 | 14 | 0.040874 | 82 | $3.03 \times 10^{-2}$ |

Events -03 and -05 of ME05194 exhibited no statistically relevant negative phenotypes. That is, there was no detectable reduction in germination rate, the transgenic plants appeared wild type in all instances; there was no observable or statistical differences between transgenics and controls in days to flowering; there was no observable or statistical differences between transgenics and controls in the size of the rosette area 7 days post-bolting; and there was no observable or statistical differences between transgenics and controls in fertility (silique number and seed fill).

Example 24

Analysis of ME05267 Events

ME05267 contains Ceres Clone:21608 (At5g49510, SEQ ID NO:592) from *Arabidopsis thaliana*, which encodes a 195 amino acid von Hippel-Lindau binding protein. Evaluation of low-nitrogen tolerance for ME05267 in $T_2$ and $T_3$ was conducted under the same conditions as described in Examples 2 and 3. Two events, -01 and -04, showed significantly enhanced growth on low nitrate-containing media relative to the internal controls in both generations at $p \leq 0.05$ using a one-tailed t-test assuming unequal variance. In this study, the seedling area at 14 days for transgenic plants within an event was compared to the seedling area for non-transgenic segregants pooled across the same line. A summary of enhanced growth under low nitrate growth conditions of ME05194 seedlings is shown in Table 24. Events -01 and -04 segregated 15:1 (R:S) for FINALE™ resistance in the $T_2$ generation. ME05267 events were also tested for increased photosynthetic efficiency on the low nitrate media. No significant differences between the transgenics and the controls were observed.

TABLE 24 t-test comparison of seedling area between transgenic seedlings and pooled non-transgenic segregants after 14 days of growth on low nitrate.

| Line | Events | Transgenic Area | n | Pooled Non-Transgenics Area | n | t-test p-value |
|---|---|---|---|---|---|---|
| ME05267 | ME05267-0 ($T_2$) | 0.053263 | 46 | 0.0450197 | 122 | $4.4 \times 10^{-5}$ |
| ME05267 | ME05267-01 ($T_3$) | 0.051135 | 26 | 0.0450197 | 122 | $5.0 \times 10^{-2}$ |

TABLE 24-continued t-test comparison of seedling area between
transgenic seedlings and pooled non-transgenic
segregants after 14 days of growth on low nitrate.

| Line | Events | Transgenic Area | n | Pooled Non-Transgenics Area | n | t-test p-value |
|---|---|---|---|---|---|---|
| ME05267 | ME05267-04 ($T_2$) | 0.049977 | 44 | 0.0450197 | 122 | $6.4 \times 10^{-3}$ |
| ME05267 | ME05267-04 ($T_3$) | 0.053084 | 38 | 0.0450197 | 122 | $8.4 \times 10^{-4}$ |

Events -01 and -04 of ME05267 exhibited no statistically relevant negative phenotypes. That is, there was no detectable reduction in germination rate, the transgenic plants appeared wild type in all instances; there was no observable or statistical differences between transgenics and controls in days to flowering; there was no observable or statistical differences between transgenics and controls in the size of the rosette area 7 days post-bolting; and there was no observable or statistical differences between transgenics and controls in fertility (silique number and seed fill).

Example 25

Analysis of ME05300 Events

ME05300 contains Ceres Clone:2031 (At1g72020, SEQ ID NO:612) from *Arabidopsis thaliana*, which encodes a 97 amino acid protein of unknown function. Evaluation of low-nitrogen tolerance for ME05300 in $T_2$ generation was conducted under the same conditions as described in Examples 2 and 3. A summary of photosynthetic efficiency of ME05300 seedlings is shown in Table 25. Two events, -04 and -05, showed significantly increased photosynthetic efficiency on low nitrate- and low ammonium nitrate-containing media relative to the internal controls in $T_2$ generation at $p \leq 0.05$ using a one-tailed t-test assuming unequal variance. In this study, the seedling photosynthetic efficiency was measured as Fv/Fm comparing transgenic plants within an event to non-transgenic segregants pooled across the same plate. In addition, two events, -01 and -05, showed significantly enhanced growth on low nitrate- and low ammonium nitrate-containing media relative to the internal controls in $T_2$ generation at $p \leq 0.05$ using a one-tailed t-test assuming unequal variance. In this study, the seedling area for transgenic plants within an event was compared to the seedling area for non-transgenic segregants pooled across the same line. A summary of enhanced growth under low nitrate and low ammonium nitrate growth conditions of ME05300 seedlings is shown in Table 26.

TABLE 25A

T-test comparison of seedling photosynthetic efficiency
between transgenic seedlings and pooled non-transgenic
segregants after 14 days of growth on low nitrate.

| Line | Events | Transgenic Fv/Fm | n | Pooled Non-Transgenics Fv/Fm | n | t-test p-value |
|---|---|---|---|---|---|---|
| ME05300 | ME05300-04 ($T_2$) | 0.6867 | 7 | 0.6488 | 27 | $1.65 \times 10^{-2}$ |
| ME05300 | ME05300-05 ($T_2$) | 0.6839 | 16 | 0.6488 | 27 | $2.50 \times 10^{-3}$ |

TABLE 25B

T-test comparison of seedling photosynthetic efficiency
between transgenic seedlings and pooled non-transgenic
segregants after 18 days of growth on low ammonium nitrate.

| Line | Events | Transgenic Fv/Fm | n | Pooled Non-Transgenics Fv/Fm | n | t-test p-value |
|---|---|---|---|---|---|---|
| ME05300 | ME05300-04 ($T_2$) | 0.6767 | 6 | 0.6323 | 32 | $1.68 \times 10^{-2}$ |
| ME05300 | ME05300-05 ($T_2$) | 0.6934 | 11 | 0.6323 | 32 | $7.04 \times 10^{-4}$ |

TABLE 26A

T-test comparison of seedling area between
transgenic seedlings and pooled non-transgenic
segregants after 14 days of growth on low nitrate.

| Line | Events | Transgenic Area | n | Pooled Non-Transgenics Area | n | t-test p-value |
|---|---|---|---|---|---|---|
| ME05300 | ME05300-01 ($T_2$) | 0.0737 | 18 | 0.0588 | 21 | $3.80 \times 10^{-3}$ |
| ME05300 | ME05300-05 ($T_2$) | 0.0655 | 16 | 0.0570 | 27 | $1.59 \times 10^{-2}$ |

TABLE 26B

T-test comparison of seedling area between transgenic
seedlings and pooled non-transgenic segregants
after 18 days of growth on low ammonium nitrate.

| Line | Events | Transgenic Area | n | Pooled Non-Transgenics Area | n | t-test p-value |
|---|---|---|---|---|---|---|
| ME05300 | ME05300-01 ($T_2$) | 0.0987 | 17 | 0.0776 | 29 | $3.89 \times 10^{-3}$ |
| ME05300 | ME05300-05 ($T_2$) | 0.1082 | 11 | 0.0776 | 29 | $1.57 \times 10^{-3}$ |

Example 26

Analysis of ME05341 Events

ME05341 contains Ceres Clone:94503 (At4g14420, SEQ ID NO:645) from *Arabidopsis thaliana*, which encodes a 158 amino acid elicitor-like protein. Evaluation of low-nitrogen tolerance for ME05341 in $T_2$ and $T_3$ was conducted under the same conditions as described in Examples 2 and 3. Two events, -01 and -02, showed significantly enhanced growth on low nitrate-containing media relative to the internal controls in both generations at $p \leq 0.05$ using a one-tailed t-test assuming unequal variance. In this study, the seedling area at 14 days for transgenic plants within an event was compared to the seedling area for non-transgenic segregants pooled across the same line. A summary of photosynthetic efficiency of ME05341 seedlings is shown in Table 27. Events -01 and -02 segregated 15:1 (R:S) for FINALE™ resistance in the $T_2$ generation. ME05341 events were also tested for increased photosynthetic efficiency on the low nitrate media. No significant differences between the transgenics and the controls were observed.

TABLE 27 t-test comparison of seedling area between transgenic seedlings and pooled non-transgenic segregants after 14 days of growth on low nitrate.

| Line | Events | Transgenic Area | n | Pooled Non-Transgenics Area | n | t-test p-value |
|---|---|---|---|---|---|---|
| ME05341 | ME05341-01 ($T_2$) | 0.06253 | 46 | 0.04988 | 143 | $4.17 \times 10^{-10}$ |
| ME05341 | ME05341-01 ($T_3$) | 0.05876 | 38 | 0.04988 | 143 | $4.13 \times 10^{-4}$ |
| ME05341 | ME05341-02 ($T_2$) | 0.06152 | 46 | 0.04988 | 143 | $2.91 \times 10^{-7}$ |
| ME05341 | ME05341-02 ($T_3$) | 0.05572 | 48 | 0.04988 | 143 | $2.90 \times 10^{-3}$ |

Events -01 and -02 of ME05341 exhibited no statistically relevant negative phenotypes. That is, there was no detectable reduction in germination rate, the transgenic plants appeared wild type in all instances; there was no observable or statistical differences between transgenics and controls in days to flowering; there was no observable or statistical differences between transgenics and controls in the size of the rosette area 7 days post-bolting; and there was no observable or statistical differences between transgenics and controls in fertility (silique number and seed fill).

Example 27

Analysis of ME05392 Events

ME05392 contains Ceres Clone:21740 (At5g01610, SEQ ID NO:686) from *Arabidopsis thaliana*, which encodes a 170 amino acid protein of unknown function. Evaluation of low-nitrogen tolerance for ME05392 in $T_2$ and $T_3$ was conducted under the same conditions as described in Examples 2 and 3. In this study, the seedling photosynthetic efficiency was measured as Fv/Fm comparing transgenic plants within an event to non-transgenic segregants pooled across the same plate. Two events, -01 and -03, showed significantly increased photosynthetic efficiency on low nitrate-containing media relative to the internal controls in both generations at p≤0.05 using a one-tailed t-test assuming unequal variance. A summary of photosynthetic efficiency of ME05392 seedlings is shown in Table 20. Events -01 and -03 segregated 2:1 (R:S) for FINALE™ resistance in the $T_2$ generation. ME05392 events were also tested for enhanced growth on the low nitrate media. No significant differences between the transgenics and the controls were observed.

TABLE 28

T-test comparison of seedling photosynthetic efficiency between transgenic seedlings and pooled non-transgenic segregants after 14 days of growth on low nitrate media.

| Line | Events | Transgenic Fv/Fm | n | Pooled Non-Transgenics Fv/Fm | n | t-test p-value |
|---|---|---|---|---|---|---|
| ME05392 | ME05392-01 ($T_2$) | 0.61759 | 32 | 0.60093 | 107 | $3.70 \times 10^{-2}$ |
| ME05392 | ME05392-01 ($T_3$) | 0.63388 | 40 | 0.60093 | 107 | $5.05 \times 10^{-5}$ |
| ME05392 | ME05392-03 ($T_2$) | 0.64335 | 23 | 0.60093 | 107 | $5.81 \times 10^{-5}$ |
| ME05392 | ME05392-03 ($T_3$) | 0.63397 | 36 | 0.60093 | 107 | $4.30 \times 10^{-5}$ |

Events -01 and -03 of ME05392 exhibited no statistically relevant negative phenotypes. That is, there was no detectable reduction in germination rate, the transgenic plants appeared wild type in all instances; there was no observable or statistical differences between transgenics and controls in days to flowering; there was no observable or statistical differences between transgenics and controls in the size of the rosette area 7 days post-bolting; and there was no observable or statistical differences between transgenics and controls in fertility (silique number and seed fill).

Example 28

Analysis of ME05429 Events

ME05429 contains Ceres Clone:5609 (At3g60480, SEQ ID NO:729) from *Arabidopsis thaliana*, which encodes a 188 amino acid protein of unknown function. Evaluation of low-nitrogen tolerance for ME05429 in $T_2$ and $T_3$ was conducted under the same conditions as described in Examples 2 and 3. In this study, the seedling photosynthetic efficiency was measured as Fv/Fm comparing transgenic plants within an event to non-transgenic segregants pooled across the same plate. Two events, -06 and -08, showed significantly increased photosynthetic efficiency on low ammonium nitrate-containing media relative to the internal controls in both generations at p≤0.05 using a one-tailed t-test assuming unequal variance. A summary of photosynthetic efficiency of ME05429 seedlings is shown in Table 29. Events -06 and -08 segregated 3:1 and 2:1 respectively (R:S) for FINALE™ resistance in the $T_2$ generation. ME05429 events were tested for enhanced growth on the low ammonium nitrate media. In addition, these events were also tested for enhanced growth and photosynthetic efficiency on low nitrate media. No significant differences between the transgenics and the controls were observed.

TABLE 29 t-test comparison of seedling photosynthetic efficiency between transgenic seedlings and pooled non-transgenic segregants after 18 days of growth on low ammonium nitrate.

| Line | Events | Transgenic Fv/Fm | n | Pooled Non-Transgenics Fv/Fm | n | t-test p-value |
|---|---|---|---|---|---|---|
| ME05429 | ME05429-06 ($T_2$) | 0.62521 | 28 | 0.59991 | 78 | $2.85 \times 10^{-2}$ |
| ME05429 | ME05429-06 ($T_3$) | 0.63031 | 39 | 0.59991 | 78 | $8.49 \times 10^{-3}$ |
| ME05429 | ME05429-08 ($T_2$) | 0.64526 | 23 | 0.59991 | 78 | $1.67 \times 10^{-3}$ |
| ME05429 | ME05429-08 ($T_3$) | 0.65076 | 17 | 0.59991 | 78 | $2.76 \times 10^{-4}$ |

Events -06 and -08 of ME05429 exhibited no statistically relevant negative phenotypes. That is, there was no detectable reduction in germination rate, the transgenic plants appeared wild type in all instances; there was no observable or statistical differences between transgenics and controls in days to flowering; there was no observable or statistical differences between transgenics and controls in the size of the rosette area 7 days post-bolting; and there was no observable or statistical differences between transgenics and controls in fertility (silique number and seed fill).

Example 29

Analysis of ME05493 Events

ME05493 contains Ceres Clone:3137 (At3g43430, SEQ ID NO:745) from *Arabidopsis thaliana*, which encodes a 169 amino acid zinc finger family protein. Evaluation of low-nitrogen tolerance for ME05493 in $T_2$ and $T_3$ was conducted under the same conditions as described in Examples 2 and 3. In this study, the seedling photosynthetic efficiency was measured as Fv/Fm comparing transgenic plants within an event to non-transgenic segregants pooled across the same plate. Two events, -01 and -05, showed significantly increased photosynthetic efficiency on low nitrate-containing media relative to the internal controls in both generations at p≤0.05 using a one-tailed t-test assuming unequal variance. A summary of photosynthetic efficiency of ME05493 seedlings is shown in Table 30. Events -01 and -05 segregated 15:1 (R:S) for FINALE™ resistance in the $T_2$ generation. ME05493 events were also tested for enhanced growth on the low nitrate media. No significant differences between the transgenics and the controls were observed.

TABLE 30 t-test comparison of seedling photosynthetic efficiency between transgenic seedlings and pooled non-transgenic segregants after 14 days of growth on low nitrate media.

| Line | Events | Transgenic Fv/Fm | n | Pooled Non-Transgenics Fv/Fm | n | t-test p-value |
|---|---|---|---|---|---|---|
| ME05493 | ME05493-01 ($T_2$) | 0.64121 | 32 | 0.61097 | 92 | $1.13 \times 10^{-3}$ |
| ME05493 | ME05493-01 ($T_3$) | 0.64250 | 46 | 0.61097 | 92 | $3.03 \times 10^{-4}$ |
| ME05493 | ME05493-05 ($T_2$) | 0.62865 | 43 | 0.61097 | 92 | $1.75 \times 10^{-2}$ |
| ME05493 | ME05493-05 ($T_3$) | 0.63936 | 42 | 0.61097 | 92 | $1.21 \times 10^{-4}$ |

Events -01 and -05 of ME05493 exhibited no statistically relevant negative phenotypes. That is, there was no detectable reduction in germination rate, the transgenic plants appeared wild type in all instances; there was no observable or statistical differences between transgenics and controls in days to flowering; there was no observable or statistical differences between transgenics and controls in the size of the rosette area 7 days post-bolting; and there was no observable or statistical differences between transgenics and controls in fertility (silique number and seed fill).

Example 30

Analysis of ME05885 Event

ME05885 contains Ceres Clone:32430 (At1g16170, SEQ ID NO:768) from *Arabidopsis thaliana*, which encodes a 92 amino acid protein of unknown function. Evaluation of low-nitrogen tolerance for ME05885 in $T_3$ generation was conducted under the same conditions as described in Examples 2 and 3. A summary of photosynthetic efficiency of ME05885 seedlings is shown in Table 31. In this study, the seedling photosynthetic efficiency was measured as Fv/Fm comparing transgenic plants within an event to non-transgenic segregants pooled across the same plate. Two events, -01 and -05, showed significantly increased photosynthetic efficiency on low nitrate-containing media and low ammonium nitrate-containing media relative to the internal controls in $T_3$ generation at p≤0.05 using a one-tailed t-test assuming unequal variance.

TABLE 31A

T-test comparison of seedling photosynthetic efficiency between transgenic seedlings and pooled non-transgenic segregants after 14 days of growth on low nitrate.

| Line | Events | Transgenic Fv/Fm | n | Pooled Non-Transgenics Fv/Fm | n | t-test p-value |
|---|---|---|---|---|---|---|
| ME05885 | ME05885-01 ($T_3$) | 0.6759 | 12 | 0.6533 | 28 | $4.32 \times 10^{-2}$ |
| ME05885 | ME05885-05 ($T_3$) | 0.6831 | 7 | 0.6530 | 52 | $3.68 \times 10^{-6}$ |

TABLE 31B

T-test comparison of seedling photosynthetic efficiency between transgenic seedlings and pooled non-transgenic segregants after 18 days of growth on low ammonium nitrate.

| Line | Events | Transgenic Fv/Fm | n | Pooled Non-Transgenics Fv/Fm | n | t-test p-value |
|---|---|---|---|---|---|---|
| ME05885 | ME05885-01 ($T_3$) | 0.6490 | 13 | 0.6135 | 30 | $3.06 \times 10^{-2}$ |
| ME05885 | ME05885-05 ($T_3$) | 0.6810 | 9 | 0.6133 | 43 | $6.77 \times 10^{-5}$ |

ME05885 events were also tested for enhanced growth on the low nitrate and low ammonium nitrate media. A summary of enhanced growth under low nitrate and low ammonium nitrate growth conditions of ME05885 seedlings in $T_3$ generation is shown in Table 32. Two events, -03 and -05, showed significantly enhanced growth on low nitrate-containing media. Two events, -02 and -05, showed significantly enhanced growth on low ammonium nitrate-containing media relative to the internal controls at p≤0.05 using a one-tailed t-test assuming unequal variance. In this study, the seedling area for transgenic plants within an event was compared to the seedling area for non-transgenic segregants pooled across the same line.

TABLE 32A

T-test comparison of seedling area between transgenic seedlings and pooled non-transgenic segregants after 14 days of growth on low nitrate.

| Line | Events | Transgenic Area | n | Pooled Non-Transgenics Area | n | t-test p-value |
|---|---|---|---|---|---|---|
| ME05885 | ME05885-03 ($T_3$) | 0.06245 | 6 | 0.05286 | 14 | $1.42 \times 10^{-2}$ |
| ME05885 | ME05885-05 ($T_3$) | 0.05893 | 7 | 0.04725 | 12 | $5.61 \times 10^{-3}$ |

TABLE 32B

T-test comparison of seedling area between transgenic seedlings and pooled non-transgenic segregants after 18 days of growth on low ammonium nitrate.

| Line | Events | Transgenic Area | n | Pooled Non-Transgenics Area | n | t-test p-value |
|---|---|---|---|---|---|---|
| ME05885 | ME05885-02 ($T_3$) | 0.0744 | 14 | 0.05595 | 6 | $3.28 \times 10^{-5}$ |
| ME05885 | ME05885-05 ($T_3$) | 0.0753 | 9 | 0.06179 | 11 | $5.08 \times 10^{-3}$ |

Example 31

Analysis of ME07344 Events

ME07344 contains Ceres Clone:101255 (At2g19810, SEQ ID NO:791) from *Arabidopsis thaliana*, which encodes a 359 amino acid CCCH-type zinc finger protein. Evaluation of low-nitrogen tolerance for ME07344 in $T_2$ and $T_3$ was conducted under the same conditions as described in Example 4. In this study, the $4^{th}$ true leaf from each plant was collected on day 38 and analyzed on the CF imager for its Fv/Fm value. Transgenic plants within an event were compared to all non-transgenic plants, including the non-transgenic segregants and external controls. Two events, -02 and -03, showed significantly increased photosynthetic efficiency relative to the internal controls in both generations at $p \leq 0.05$ using a one-tailed t-test assuming unequal variance. A summary of photosynthetic efficiency of ME07344 seedlings is shown in Table 33. Events -02 and -03 segregated 3:1 (R:S) for FINALE™ resistance in the $T_2$ generation. ME07344 events were also tested for enhanced growth on the low nitrate media. No significant differences between the transgenics and the controls were observed.

TABLE 33

T-test comparison of photosynthetic efficiency between transgenic plants and non-transgenic controls after 38 days of growth on nitrogen-depleted soil.

| Line | Events | Transgenic Fv/Fm | n | Non-Transgenic Controls Fv/Fm | n | t-test p-value |
|---|---|---|---|---|---|---|
| ME07344 | ME07344-02 ($T_2$) | 0.752 | 17 | 0.729 | 50 | $2.86 \times 10^{-4}$ |
| ME07344 | ME07344-02 ($T_3$) | 0.750 | 16 | 0.729 | 50 | $1.11 \times 10^{-4}$ |
| ME07344 | ME07344-03 ($T_2$) | 0.741 | 13 | 0.729 | 50 | 0.018 |
| ME07344 | ME07344-03 ($T_3$) | 0.754 | 17 | 0.729 | 50 | $4.62 \times 10^{-6}$ |

Events -02 and -03 of ME07344 exhibited no statistically relevant negative phenotypes. That is, there was no detectable reduction in germination rate, the transgenic plants appeared wild type in all instances; there was no observable or statistical differences between transgenics and controls in days to flowering; there was no observable or statistical differences between transgenics and controls in the size of the rosette area 7 days post-bolting; and there was no observable or statistical differences between transgenics and controls in fertility (silique number and seed fill).

Example 32

Analysis of ME07859 Events

ME07859 contains Ceres Clone:276809 (SEQ ID NO:823) from *Zea mays*, which encodes a 135 amino acid sterol desaturase protein. Evaluation of low-nitrogen tolerance for ME07859 in $T_2$ and $T_3$ was conducted under the same conditions as described in Examples 2 and 3. In this study, the seedling photosynthetic efficiency was measured as Fv/Fm comparing transgenic plants within an event to non-transgenic segregants pooled across the same plate. Two events, -02 and -04, showed significantly increased photosynthetic efficiency on low nitrate-containing media relative to the internal controls in both generations at $p \leq 0.05$ using a one-tailed t-test assuming unequal variance. A summary of photosynthetic efficiency of ME07859 seedlings is shown in Table 34. Events -02 and -04 segregated 1:1 and 2:1 respectively (R:S) for FINALE™ resistance in the $T_2$ generation. ME07859 events were also tested for enhanced growth on the low nitrate media as well as for enhanced growth and photosynthetic efficiency on low ammonium nitrate media. No significant differences between the transgenics and the controls were observed.

TABLE 34 t-test comparison of seedling photosynthetic efficiency between transgenic seedlings and pooled non-transgenic segregants after 14 days of growth on low nitrate media.

| Line | Events | Transgenic Fv/Fm | n | Pooled Non-Transgenics Fv/Fm | n | t-test p-value |
|---|---|---|---|---|---|---|
| ME07859 | ME07859-02 ($T_2$) | 0.6598 | 24 | 0.6378 | 127 | 0.03 |
| ME07859 | ME07859-02 ($T_3$) | 0.6825 | 14 | 0.6378 | 127 | $1.3 \times 10^{-3}$ |
| ME07859 | ME07859-04 ($T_2$) | 0.6539 | 33 | 0.6378 | 127 | 0.05 |
| ME07859 | ME07859-04 ($T_3$) | 0.6601 | 17 | 0.6378 | 127 | 0.05 |

Events -02 and -04 of ME07859 exhibited no statistically relevant negative phenotypes. That is, there was no detectable reduction in germination rate, the transgenic plants appeared wild type in all instances; there was no observable or statistical differences between transgenics and controls in days to flowering; there was no observable or statistical differences between transgenics and controls in the size of the rosette area 7 days post-bolting; and there was no observable or statistical differences between transgenics and controls in fertility (silique number and seed fill).

Example 33

Analysis of ME08464 Events

ME08464 contains Ceres Clone:424522 (SEQ ID NO:827) from *Zea mays*, which encodes a 500 amino acid unknown protein. Evaluation of low-nitrogen tolerance for ME08464 in $T_2$ and $T_3$ was conducted under the same conditions as described in Examples 2 and 3. In this study, the seedling photosynthetic efficiency was measured as Fv/Fm comparing transgenic plants within an event to non-transgenic segregants pooled across the same plate. Two events, -02 and -03, showed significantly increased photosynthetic efficiency on low ammonium nitrate-containing media relative to the internal controls in both generations at $p \leq 0.05$ using a one-tailed t-test assuming unequal variance. A summary of photosynthetic efficiency of ME07859 seedlings is shown in Table 35. Events -02 and -03 segregated 3:1 (R:S) for FINALE™ resistance in the $T_2$ generation. ME08464 events were also tested for increased photosynthetic efficiency on the low nitrate media. No significant differences between the transgenics and the controls were observed.

TABLE 35

T-test comparison of photosynthetic efficiency between transgenic seedlings and pooled non-transgenic segregants after 15 days of growth on low ammonium nitrate.

| Line | Events | Transgenic Fv/Fm | n | Pooled Non-Transgenics Fv/Fm | n | t-test p-value |
|---|---|---|---|---|---|---|
| ME08464 | ME08464-02 ($T_2$) | 0.65 | 41 | 0.62 | 40 | 0.015 |
| ME08464 | ME08464-02 ($T_3$) | 0.67 | 32 | 0.62 | 40 | $2.32 \times 10^{-4}$ |
| ME08464 | ME08464-03 ($T_2$) | 0.65 | 43 | 0.62 | 40 | 0.013 |
| ME08464 | ME08464-03 ($T_3$) | 0.65 | 42 | 0.62 | 40 | $6.85 \times 10^{-3}$ |

Events -02 and -03 of ME08464 exhibited no statistically relevant negative phenotypes. That is, there was no detectable reduction in germination rate, the transgenic plants appeared wild type in all instances; there was no observable or statistical differences between transgenics and controls in days to flowering; there was no observable or statistical differences between transgenics and controls in the size of the rosette area 7 days post-bolting; and there was no observable or statistical differences between transgenics and controls in fertility (silique number and seed fill)

Example 34

Analysis of ME09939 Events

ME09939 contains Ceres Clone:324216 (SEQ ID NO:852) from *Zea mays*, which encodes a 38 amino acid protein of unknown function. Evaluation of low-nitrogen tolerance for ME09939 in $T_2$ and $T_3$ was conducted under the same conditions as described in Examples 2 and 3. In this study, the seedling photosynthetic efficiency was measured as Fv/Fm comparing transgenic plants within an event to non-transgenic segregants pooled across the same plate. Two events, -04 and -05, showed significantly increased photosynthetic efficiency on low ammonium nitrate-containing media relative to the internal controls in both generations at p≤0.05 using a one-tailed t-test assuming unequal variance. A summary of photosynthetic efficiency of ME09939 seedlings is shown in Table 36. Events -04 and -05 segregated 15:1 and 3:1 respectively (R:S) for FINALE™ resistance in the $T_2$ generation. ME09939 events were also tested for enhanced growth on the low ammonium nitrate media. No significant differences between the transgenics and the controls were observed.

Events -04 and -05 of ME09939 exhibited no statistically relevant negative phenotypes. That is, there was no detectable reduction in germination rate, the transgenic plants appeared wild type in all instances; there was no observable or statistical differences between transgenics and controls in days to flowering; there was no observable or statistical differences between transgenics and controls in the size of the rosette area 7 days post-bolting; and there was no observable or statistical differences between transgenics and controls in fertility (silique number and seed fill).

Example 35

Analysis of ME11735 Events

ME11735 contains Ceres Annot:573161 (At5g43260, SEQ ID NO:854) from *Arabidopsis thaliana*, which encodes a 97 amino acid DnaJ-related chaperone protein. Evaluation of low-nitrogen tolerance for ME11735 in $T_2$ and $T_3$ was conducted under the same conditions as described in Example 2 and 3. A summary of the enhanced growth of ME11735 events on low nitrate-containing media is shown in Table 37. In this study, the seedling area for transgenic plants within an event was compared to the seedling area for non-transgenic segregants pooled across the same line. Two events, -04 and -05, were found significantly larger than the pooled non-transgenic segregants after 14 days of growth on low nitrate-containing media relative to the internal controls in both generations at p≤0.05 using a one-tailed t-test assuming unequal variance. ME11735 events were also tested for increased photosynthetic efficiency on the low nitrate media. No significant differences between the transgenics and the controls were observed. Events -04 and -05 segregated 40:1 and 4:1 respectively (R:S) for FINALE™ resistance in the $T_2$ generation.

TABLE 36

T-test comparison of seedling photosynthetic efficiency between transgenic seedlings and pooled non-transgenic segregants after 18 days of growth on low ammonium nitrate.

| Line | Events | Transgenic Fv/Fm | n | Pooled Non-Transgenics Fv/Fm | n | t-test p-value |
|---|---|---|---|---|---|---|
| ME09939 | ME09939-04 ($T_2$) | 0.49285 | 40 | 0.38571 | 7 | 0.05 |
| ME09939 | ME09939-04 ($T_3$) | 0.50697 | 34 | 0.38571 | 7 | $3.50 \times 10^{-2}$ |
| ME09939 | ME09939-05 ($T_2$) | 0.53487 | 39 | 0.47492 | 24 | $1.19 \times 10^{-2}$ |
| ME09939 | ME09939-05 ($T_3$) | 0.55341 | 32 | 0.47492 | 24 | $1.82 \times 10^{-3}$ |

TABLE 37 t-test comparison of seedling area between transgenic seedlings and pooled non-transgenic segregants after 14 days of growth on low nitrate.

| Line | Events | Transgenic Area | n | Pooled Non-Transgenics Area | n | t-test p-value |
|---|---|---|---|---|---|---|
| ME11735 | ME11735-04 ($T_2$) | 0.05820 | 41 | 0.04994 | 127 | $5.91 \times 10^{-5}$ |
| ME11735 | ME11735-04 ($T_3$) | 0.05553 | 42 | 0.04994 | 127 | $1.26 \times 10^{-2}$ |
| ME11735 | ME11735-05 ($T_2$) | 0.05788 | 37 | 0.04994 | 127 | $1.59 \times 10^{-3}$ |
| ME11735 | ME11735-05 ($T_3$) | 0.06011 | 13 | 0.04994 | 127 | $1.64 \times 10^{-2}$ |

Events -04 and -05 of ME11735 exhibited no statistically relevant negative phenotypes. That is, there was no detectable reduction in germination rate, the transgenic plants appeared wild type in all instances; there was no observable or statistical differences between transgenics and controls in days to flowering; there was no observable or statistical differences between transgenics and controls in the size of the rosette area 7 days post-bolting; and there was no observable or statistical differences between transgenics and controls in fertility (silique number and seed fill).

Example 36

Analysis of ME12910 Events

ME12910 contains Ceres Annot:552727 (At2g22930, SEQ ID NO:890) from *Arabidopsis thaliana*, which encodes a 442 amino acid UDP-glucoronosyl and UDP-glucosyl transferase family protein. Evaluation of low-nitrogen tolerance for ME12910 in $T_2$ and $T_3$ was conducted under the same conditions as described in Examples 2 and 3. In this study, the seedling photosynthetic efficiency was measured as Fv/Fm comparing transgenic plants within an event to non-transgenic segregants pooled across the same plate. Two events, -03 and -05, showed significantly increased photosynthetic efficiency on low ammonium nitrate-containing media relative to the internal controls in both generations at $p \leq 0.05$ using a one-tailed t-test assuming unequal variance. A summary of photosynthetic efficiency of ME12910 seedlings is shown in Table 38. ME12910 events were also tested for enhanced growth on the low ammonium nitrate media. No significant differences between the transgenics and the controls were observed.

Events -03 and -05 segregated 3:1 and 15:1 respectively (R:S) for FINALE™ resistance in the $T_2$ generation.

Events -03 and -05 of ME12910 exhibited no statistically relevant negative phenotypes. That is, there was no detectable reduction in germination rate, the transgenic plants appeared wild type in all instances; there was no observable or statistical differences between transgenics and controls in days to flowering; there was no observable or statistical differences between transgenics and controls in the size of the rosette area 7 days post-bolting; and there was no observable or statistical differences between transgenics and controls in fertility (silique number and seed fill)

Example 37

Analysis of ME12927 Event

ME12927 contains Ceres Clone:239806 (SEQ ID NO:916) from *Zea mays*, which encodes a 201 amino acid lipoprotein amino terminal region. Evaluation of low-nitrogen tolerance for ME12927 in $T_2$ and $T_3$ was conducted under the same conditions as described in Examples 2 and 3. In this study, the seedling photosynthetic efficiency was measured as Fv/Fm comparing transgenic plants within an event to non-transgenic segregants pooled across the same plate. Three events, -02, -03 and -05, showed significantly increased photosynthetic efficiency on low ammonium nitrate-containing media relative to the internal controls in both generations at $p \leq 0.05$, using a one-tailed t-test assuming unequal variance. A summary of photosynthetic efficiency of ME12927 seedlings is shown in Table 39.

TABLE 38 t-test comparison of seedling photosynthetic efficiency between transgenic seedlings and pooled non-transgenic segregants after 18 days of growth on low ammonium nitrate.

| Line | Events | Transgenic Fv/Fm | n | Pooled Non-Transgenics Fv/Fm | n | t-test p-value |
|---|---|---|---|---|---|---|
| ME12910 | ME12910-03 ($T_2$) | 0.5851 | 39 | 0.5191 | 29 | $1.54 \times 10^{-3}$ |
| ME12910 | ME12910-03 ($T_3$) | 0.5861 | 22 | 0.5191 | 29 | $2.17 \times 10^{-3}$ |
| ME12910 | ME12910-05 ($T_2$) | 0.5523 | 44 | 0.4251 | 7 | $1.23 \times 10^{-2}$ |
| ME12910 | ME12910-05 ($T_3$) | 0.5600 | 42 | 0.4251 | 7 | $9.62 \times 10^{-3}$ |

TABLE 39 t-test comparison of seedling photosynthetic efficiency between transgenic seedlings and pooled non-transgenic segregants after 18 days of growth on low ammonium nitrate.

| Line | Events | Transgenic Fv/Fm | n | Pooled Non-Transgenics Fv/Fm | n | t-test p-value |
|---|---|---|---|---|---|---|
| ME12927 | ME12927-02 ($T_2$) | 0.60843 | 44 | 0.47813 | 8 | $4.88 \times 10^{-3}$ |
| ME12927 | ME12927-02 ($T_3$) | 0.60867 | 36 | 0.47813 | 8 | $5.23 \times 10^{-3}$ |
| ME12927 | ME12927-03 ($T_2$) | 0.61906 | 32 | 0.57929 | 38 | $8.96 \times 10^{-3}$ |
| ME12927 | ME12927-03 ($T_3$) | 0.63437 | 19 | 0.57929 | 38 | $5.35 \times 10^{-4}$ |
| ME12927 | ME12927-05 ($T_2$) | 0.60581 | 43 | 0.53982 | 22 | $7.26 \times 10^{-3}$ |
| ME12927 | ME12927-05 ($T_3$) | 0.63145 | 29 | 0.53982 | 22 | $5.83 \times 10^{-4}$ |

ME12927 events were also tested for enhanced growth on the low ammonium nitrate media. A summary of the enhanced growth of ME11735 events on low ammonium nitrate-containing media is shown in Table 40. In this study, the seedling area for transgenic plants within an event was compared to the seedling area for non-transgenic segregants pooled across the same line. Three events, -02, -03 and -05, were found significantly larger than the pooled non-transgenic segregants after 18 days of growth on low ammonium nitrate-containing media relative to the internal controls in both generations at p≤0.05, using a one-tailed t-test assuming unequal variance.

TABLE 40 t-test comparison of seedling area between transgenic seedlings and pooled non-transgenic segregants after 18 days of growth on low ammonium nitrate.

| Line | Events | Transgenic Area | n | Pooled Non-Transgenics Area | n | t-test p-value |
|---|---|---|---|---|---|---|
| ME12927 | ME12927-02 ($T_2$) | 0.066920 | 44 | 0.056585 | 117 | $1.65 \times 10^{-4}$ |
| ME12927 | ME12927-02 ($T_3$) | 0.062119 | 36 | 0.056585 | 117 | $3.51 \times 10^{-2}$ |
| ME12927 | ME12927-03 ($T_2$) | 0.068972 | 32 | 0.056585 | 117 | $1.18 \times 10^{-5}$ |
| ME12927 | ME12927-03 ($T_3$) | 0.063716 | 19 | 0.056585 | 117 | $1.98 \times 10^{-2}$ |
| ME12927 | ME12927-05 ($T_2$) | 0.069972 | 43 | 0.056585 | 117 | $4.25 \times 10^{-6}$ |
| ME12927 | ME12927-05 ($T_3$) | 0.064014 | 29 | 0.056585 | 117 | $8.49 \times 10^{-3}$ |

Events 02, -03 and -05 segregated 15:1, 2:1 and 15:1 respectively (R:S) for FINALE™ resistance in the $T_2$ generation.

Events 02, -03 and -05 of ME12927 exhibited no statistically relevant negative phenotypes. That is, there was no detectable reduction in germination rate, the transgenic plants appeared wild type in all instances; there was no observable or statistical differences between transgenics and controls in days to flowering; there was no observable or statistical differences between transgenics and controls in the size of the rosette area 7 days post-bolting; and there was no observable or statistical differences between transgenics and controls in fertility (silique number and seed fill) in $T_1$ generation.

Example 38

Analysis of ME12929 Events

ME12929 contains Ceres Clone:208995 (SEQ ID NO:943) from *Zea mays*, which encodes a 94 amino acid protein of unknown function. Evaluation of low-nitrogen tolerance for ME12929 in $T_2$ and $T_3$ was conducted under the same conditions as described in Examples 2 and 3. In this study, the seedling photosynthetic efficiency was measured as Fv/Fm comparing transgenic plants within an event to non-transgenic segregants pooled across the same plate. Two events, -03 and -04, showed significantly increased photosynthetic efficiency on low ammonium nitrate-containing media relative to the internal controls in both generations at p≤0.05 using a one-tailed t-test assuming unequal variance. A summary of photosynthetic efficiency of ME12929 seedlings is shown in Table 41. ME12929 events were also tested for enhanced growth on the low ammonium nitrate media. No significant differences between the transgenics and the controls were observed. Events -03 and -04 segregated 1:1 and 3:1 respectively (R:S) for FINALE™ resistance in the $T_2$ generation.

TABLE 41 t-test comparison of seedling photosynthetic efficiency between transgenic seedlings and pooled non-transgenic segregants after 14 days of growth on low ammonium nitrate.

| Line | Events | Transgenic Fv/Fm | n | Pooled Non-Transgenics Fv/Fm | n | t-test p-value |
|---|---|---|---|---|---|---|
| ME12929 | ME12929-03 ($T_2$) | 0.6410 | 33 | 0.5736 | 24 | $9.44 \times 10^{-4}$ |
| ME12929 | ME12929-03 ($T_3$) | 0.6610 | 41 | 0.5736 | 24 | $4.38 \times 10^{-5}$ |
| ME12929 | ME12929-04 ($T_2$) | 0.6544 | 47 | 0.5790 | 9 | $3.68 \times 10^{-2}$ |
| ME12929 | ME12929-04 ($T_3$) | 0.6663 | 43 | 0.5790 | 9 | $2.15 \times 10^{-2}$ |

Events -03 and -04 of ME12929 exhibited no statistically relevant negative phenotypes. That is, there was no detectable reduction in germination rate, the transgenic plants appeared wild type in all instances; there was no observable or statistical differences between transgenics and controls in days to flowering; there was no observable or statistical differences between transgenics and controls in the size of the rosette area 7 days post-bolting; and there was no observable or statistical differences between transgenics and controls in fertility (silique number and seed fill)

Example 39

0020Analysis of ME12954 Events

ME12954 contains Ceres Clone:225681 (SEQ ID NO:975) from *Zea mays*, which encodes a 286 amino acid protein of unknown function. Evaluation of low-nitrogen tolerance for ME12954 in $T_2$ and $T_3$ was conducted under the same conditions as described in Examples 2 and 3. Two events, -04 and -05, showed significantly increased photosynthetic efficiency on low ammonium nitrate-containing media relative to the internal controls in both generations at p≤0.05 using a one-tailed t-test assuming unequal variance. In this study, the seedling photosynthetic efficiency was measured as Fv/Fm comparing transgenic plants within an event to non-transgenic segregants pooled across the same plate. A summary of photosynthetic efficiency of ME12954 seedlings is shown in Table 42.

TABLE 42 t-test comparison of seedling photosynthetic efficiency between transgenic seedlings and pooled non-transgenic segregants after 18 days of growth on low ammonium nitrate.

| Line | Events | Transgenic Fv/Fm | n | Pooled Non-Transgenics Fv/Fm | n | t-test p-value |
|---|---|---|---|---|---|---|
| ME12954 | ME12954-04 ($T_2$) | 0.6236 | 40 | 0.5973 | 152 | $6.61 \times 10^{-3}$ |
| ME12954 | ME12954-04 ($T_3$) | 0.6200 | 39 | 0.5973 | 152 | $1.97 \times 10^{-2}$ |
| ME12954 | ME12954-05 ($T_2$) | 0.6280 | 45 | 0.5973 | 152 | $1.79 \times 10^{-2}$ |
| ME12954 | ME12954-05 ($T_3$) | 0.6315 | 35 | 0.5973 | 152 | $2.85 \times 10^{-2}$ |

ME12954 events were also tested for enhanced growth on the low ammonium nitrate media. A summary of the enhanced growth of ME12954 events on low ammonium nitrate-containing media is shown in Table 43. In this study, the seedling area for transgenic plants within an event was compared to the seedling area for non-transgenic segregants pooled across the same line. Two events, -02 and -04, were found significantly larger than the pooled non-transgenic segregants after 18 days of growth on low ammonium nitrate-containing media relative to the internal controls in both generations at p≤0.05, using a one-tailed t-test assuming unequal variance.

TABLE 43 t-test comparison of seedling area between transgenic seedlings and pooled non-transgenic segregants after 18 days of growth on low ammonium nitrate.

| Line | Events | Transgenic Area | n | Pooled Non-Transgenics Area | n | t-test p-value |
|---|---|---|---|---|---|---|
| ME12954 | ME12954-02 ($T_2$) | 0.06883 | 31 | 0.05579 | 152 | $1.86 \times 10^{-5}$ |
| ME12954 | ME12954-02 ($T_3$) | 0.06604 | 26 | 0.05579 | 152 | $1.48 \times 10^{-3}$ |

TABLE 43-continued t-test comparison of seedling area between transgenic seedlings and pooled
non-transgenic segregants after 18 days of growth on low ammonium nitrate.

| Line | Events | Transgenic | | Pooled Non-Transgenics | | t-test |
|---|---|---|---|---|---|---|
| | | Area | n | Area | n | p-value |
| ME12954 | ME12954-04 ($T_2$) | 0.06469 | 40 | 0.05579 | 152 | $1.95 \times 10^{-4}$ |
| ME12954 | ME12954-04 ($T_3$) | 0.06301 | 39 | 0.05579 | 152 | $3.32 \times 10^{-3}$ |

Events -02, -04 and -05 segregated 2:1, 3:1 and 15:1 respectively (R:S) for FINALE™ resistance in the T2 generation.

Events -02, -04 and -05 of ME12954 exhibited no statistically relevant negative phenotypes. That is, there was no detectable reduction in germination rate, the transgenic plants appeared wild type in all instances; there was no observable or statistical differences between transgenics and controls in days to flowering; there was no observable or statistical differences between transgenics and controls in the size of the rosette area 7 days post-bolting; and there was no observable or statistical differences between transgenics and controls in fertility (silique number and seed fill).

Example 40

Analysis of ME12970 Events

ME12970 contains Ceres Clone:1387146 (SEQ ID NO:981) from *Zea mays*, which encodes a 147 amino acid C2 domain-containing protein. Evaluation of low-nitrogen tolerance for ME12970 in $T_2$ and $T_3$ was conducted under the same conditions as described in Examples 2 and 3. Two events, -02 and -03, showed significantly increased photosynthetic efficiency on low ammonium nitrate-containing media relative to the internal controls in both generations at p≤0.05 using a one-tailed t-test assuming unequal variance. In this study, the seedling photosynthetic efficiency was measured as Fv/Fm comparing transgenic plants within an event to non-transgenic segregants pooled across the same plate. A summary of photosynthetic efficiency of ME12970 seedlings is shown in Table 44. ME12970 events were also tested for enhanced growth on the low ammonium nitrate media. No significant differences between the transgenics and the controls were observed.

Events -02 and -03 segregated 15:1 and 3:1 respectively (R:S) for FINALE™ resistance in the T2 generation.

Events -02 and -03 of ME12970 exhibited no statistically relevant negative phenotypes. That is, there was no detectable reduction in germination rate, the transgenic plants appeared wild type in all instances; there was no observable or statistical differences between transgenics and controls in days to flowering; there was no observable or statistical differences between transgenics and controls in the size of the rosette area 7 days post-bolting; and there was no observable or statistical differences between transgenics and controls in fertility (silique number and seed fill).

Example 41

Analysis of ME13006 Events

ME13006 contains Ceres Clone:1017441 (SEQ ID NO:224) from *Triticum aestivum*, which encodes a 143 amino acid polypeptide, predicted to be a homolog of Ceres Clone:4898 (ME03123, SEQ ID NO:217). Evaluation of low-nitrogen tolerance for ME13006 in $T_2$ and $T_3$ was conducted under the same conditions as described in Examples 2 and 3. In this study, the seedling photosynthetic efficiency was measured as Fv/Fm comparing transgenic plants within an event to non-transgenic segregants pooled across the same plate. Two events, -01 and -03, showed significantly increased photosynthetic efficiency on low ammonium nitrate-containing media relative to the internal controls in both generations at p≤0.05 using a one-tailed t-test assuming unequal variance. A summary of photosynthetic efficiency of ME13006 seedlings is shown in Table 45. ME13006 events were also tested for enhanced growth on the low nitrate media. No significant differences between the transgenics and the controls were observed.

TABLE 44 t-test comparison of seedling photosynthetic efficiency between transgenic
seedlings and pooled non-transgenic segregants after 18 days
of growth on low ammonium nitrate.

| Line | Events | Transgenic | | Pooled Non-Transgenics | | t-test |
|---|---|---|---|---|---|---|
| | | Fv/Fm | n | Fv/Fm | n | p-value |
| ME12970 | ME12970-02 ($T_2$) | 0.55136 | 44 | 0.52401 | 108 | $3.78 \times 10^{-2}$ |
| ME12970 | ME12970-02 ($T_3$) | 0.58305 | 43 | 0.52401 | 108 | $1.89 \times 10^{-5}$ |
| ME12970 | ME12970-03 ($T_2$) | 0.58759 | 37 | 0.52401 | 108 | $2.14 \times 10^{-6}$ |
| ME12970 | ME12970-03 ($T_3$) | 0.59131 | 29 | 0.52401 | 108 | $3.05 \times 10^{-6}$ |

TABLE 45 t-test comparison of seedling area between transgenic seedlings and pooled
non-transgenic segregants after 14 days of growth on low ammonium nitrate.

| Line | Events | Transgenic | | Pooled Non-Transgenics | | t-test |
|---|---|---|---|---|---|---|
| | | Area | n | Area | n | p-value |
| ME13006 | ME13006-01 ($T_2$) | 0.0777 | 42 | 0.0648 | 7 | $3.29 \times 10^{-2}$ |
| ME13006 | ME13006-01 ($T_3$) | 0.0660 | 28 | 0.0540 | 19 | $1.49 \times 10^{-3}$ |
| ME13006 | ME13006-03 ($T_2$) | 0.0706 | 21 | 0.0601 | 29 | $4.83 \times 10^{-3}$ |
| ME13006 | ME13006-03 ($T_3$) | 0.0758 | 14 | 0.0617 | 33 | $2.60 \times 10^{-3}$ |

Events -01 and -03 segregated 3:1 and 1:1 respectively (R:S) for FINALE™ resistance in the $T_2$ generation.

Events -01 and -03 of ME13006 exhibited no statistically relevant negative phenotypes. That is, there was no detectable reduction in germination rate, the transgenic plants appeared wild type in all instances; there was no observable or statistical differences between transgenics and controls in days to flowering; there was no observable or statistical differences between transgenics and controls in the size of the rosette area 7 days post-bolting; and there was no observable or statistical differences between transgenics and controls in fertility (silique number and seed fill).

Example 42

Analysis of ME13021 Events

ME13021 contains Ceres Clone:244306 (SEQ ID NO:1053) from *Zea mays*, which encodes a 572 amino acid TCP-1/cpn60 chaperonin family protein. Evaluation of low-nitrogen tolerance for ME13021 in $T_2$ and $T_3$ was conducted under the same conditions as described in Examples 2 and 3. In this study, the seedling photosynthetic efficiency was measured as Fv/Fm comparing transgenic plants within an event to non-transgenic segregants pooled across the same plate. Two events, -04 and -05, showed significantly increased photosynthetic efficiency on low ammonium nitrate-containing media relative to the internal controls in both generations at p≤0.05 using a one-tailed t-test assuming unequal variance. A summary of photosynthetic efficiency of ME13021 seedlings is shown in Table 46. ME13021 events were also tested for enhanced growth on the low ammonium nitrate media. No significant differences between the transgenics and the controls were observed.

Events -04 and -05 segregated 3:1 and 2:1 respectively (R:S) for FINALE™ resistance in the T2 generation.

Events -04 and -05 of ME13021 exhibited no statistically relevant negative phenotypes. That is, there was no detectable reduction in germination rate, the transgenic plants appeared wild type in all instances; there was no observable or statistical differences between transgenics and controls in days to flowering; there was no observable or statistical differences between transgenics and controls in the size of the rosette area 7 days post-bolting; and there was no observable or statistical differences between transgenics and controls in fertility (silique number and seed fill) in T1 generation.

Example 43

Analysis of ME13064 Events

ME13064 contains Ceres Clone:1408950 (SEQ ID NO:1098) from *Zea mays*, which encodes a 152 amino acid protein of unknown function. Evaluation of low-nitrogen tolerance for ME13064 in $T_2$ and $T_3$ was conducted under the same conditions as described in Examples 2 and 3. In this study, the seedling photosynthetic efficiency was measured as Fv/Fm comparing transgenic plants within an event to non-transgenic segregants pooled across the same plate. Two events, -03 and -04, showed significantly increased photosynthetic efficiency on low ammonium nitrate-containing media relative to the internal controls in both generations at p≤0.05 using a one-tailed t-test assuming unequal variance. A summary of photosynthetic efficiency of ME13064 seedlings is shown in Table 47. ME13064 events were also tested for enhanced growth on the low ammonium nitrate media. No significant differences between the transgenics and the controls were observed.

TABLE 46 t-test comparison of seedling photosynthetic efficiency between transgenic
seedlings and pooled non-transgenic segregants after 18 days
of growth on low ammonium nitrate.

| Line | Events | Transgenic | | Pooled Non-Transgenics | | t-test |
|---|---|---|---|---|---|---|
| | | Fv/Fm | n | Fv/Fm | n | p-value |
| ME13021 | ME13021-04 ($T_2$) | 0.56697 | 39 | 0.49440 | 10 | $2.47 \times 10^{-2}$ |
| ME13021 | ME13021-04 ($T_3$) | 0.59916 | 37 | 0.48685 | 13 | $1.54 \times 10^{-3}$ |
| ME13021 | ME13021-05 ($T_2$) | 0.60575 | 32 | 0.50344 | 18 | $6.05 \times 10^{-4}$ |
| ME13021 | ME13021-05 ($T_3$) | 0.64400 | 23 | 0.55638 | 26 | $3.86 \times 10^{-6}$ |

TABLE 47 t-test comparison of seedling photosynthetic efficiency between transgenic seedlings and pooled non-transgenic segregants after 18 days of growth on low ammonium nitrate.

| Line | Events | Transgenic | | Pooled Non-Transgenics | | t-test |
|---|---|---|---|---|---|---|
| | | Fv/Fm | n | Fv/Fm | n | p-value |
| ME13064 | ME13064-03 ($T_2$) | 0.59444 | 27 | 0.54793 | 28 | $5.84 \times 10^{-3}$ |
| ME13064 | ME13064-03 ($T_3$) | 0.59676 | 29 | 0.54793 | 28 | $1.25 \times 10^{-2}$ |
| ME13064 | ME13064-04 ($T_2$) | 0.58577 | 31 | 0.51053 | 40 | $2.05 \times 10^{-3}$ |
| ME13064 | ME13064-04 ($T_3$) | 0.59128 | 25 | 0.51053 | 40 | $8.93 \times 10^{-4}$ |

Events -03 and -04 segregated 2:1 (R:S) for FINALE™ resistance in the T2 generation.

Events -03 and -04 of ME13064 exhibited no statistically relevant negative phenotypes. That is, there was no detectable reduction in germination rate, the transgenic plants appeared wild type in all instances; there was no observable or statistical differences between transgenics and controls in days to flowering; there was no observable or statistical differences between transgenics and controls in the size of the rosette area 7 days post-bolting; and there was no observable or statistical differences between transgenics and controls in fertility (silique number and seed fill) in T1 generation.

Example 44

Analysis of ME13071 Events

ME13071 contains Ceres Clone:208453 (SEQ ID NO:1111) from *Zea mays*, which encodes a 74 amino acid protein of unknown function. Evaluation of low-nitrogen tolerance for ME13071 in $T_2$ and $T_3$ was conducted under the same conditions as described in Examples 2 and 3. Two events, -03 and -05, showed significantly enhanced growth on low nitrate- and low ammonium nitrate-containing media relative to the internal controls in $T_2$ generation at p≤0.05 using a one-tailed t-test assuming unequal variance. In this study, the seedling area for transgenic plants within an event was compared to the seedling area for non-transgenic segregants pooled across the same line. A summary of enhanced growth under low ammonium nitrate growth conditions of ME13071 seedlings is shown in Table 48. ME13071 events were also tested for photosynthetic efficiency on the low ammonium nitrate media. No significant differences between the transgenics and the controls were observed.

Events -03 and -05 segregated 1:1 and 2:1 respectively (R:S) for FINALE™ resistance in the T2 generation.

Events -03 and -05 of ME13071 exhibited no statistically relevant negative phenotypes. That is, there was no detectable reduction in germination rate, the transgenic plants appeared wild type in all instances; there was no observable or statistical differences between transgenics and controls in days to flowering; there was no observable or statistical differences between transgenics and controls in the size of the rosette area 7 days post-bolting; and there was no observable or statistical differences between transgenics and controls in fertility (silique number and seed fill).

Example 45

Analysis of ME13087 Events

ME13087 contains Ceres Clone:968180 (SEQ ID NO:1115) from *Brassica napus*, which encodes a 159 amino acid zinc finger protein. Evaluation of low-nitrogen tolerance for ME13087 in $T_2$ and $T_3$ was conducted under the same conditions as described in Examples 2 and 3. In this study, the seedling photosynthetic efficiency was measured as Fv/Fm comparing transgenic plants within an event to non-transgenic segregants pooled across the same plate. Four events, -01, -02, -03 and -04, showed significantly increased photosynthetic efficiency on low ammonium nitrate-containing media relative to the internal controls in both generations at p≤0.05 using a one-tailed t-test assuming unequal variance. A summary of photosynthetic efficiency of ME13087 seedlings is shown in Table 49. ME13087 events were also tested for enhanced growth on the low ammonium nitrate media. No significant differences between the transgenics and the controls were observed.

TABLE 48 t-test comparison of seedling area between transgenic seedlings and pooled non-transgenic segregants after 18 days of growth on low ammonium nitrate.

| Line | Events | Transgenic | | Pooled Non-Transgenics | | t-test |
|---|---|---|---|---|---|---|
| | | Area | n | Area | n | p-value |
| ME13071 | ME13071-03 ($T_2$) | 0.06694 | 26 | 0.05915 | 19 | $3.55 \times 10^{-3}$ |
| ME13071 | ME13071-03 ($T_3$) | 0.07787 | 24 | 0.07040 | 22 | $3.65 \times 10^{-2}$ |
| ME13071 | ME13071-05 ($T_2$) | 0.06232 | 32 | 0.05491 | 16 | $2.07 \times 10^{-3}$ |
| ME13071 | ME13071-05 ($T_3$) | 0.06335 | 22 | 0.05626 | 28 | $1.09 \times 10^{-2}$ |

TABLE 49 t-test comparison of seedling photosynthetic efficiency between transgenic seedlings and pooled non-transgenic segregants after 18 days of growth on low ammonium nitrate.

| Line | Events | Transgenic Fv/Fm | n | Pooled Non-Transgenics Fv/Fm | n | t-test p-value |
|---|---|---|---|---|---|---|
| ME13087 | ME13087-01 ($T_2$) | 0.59761 | 23 | 0.56163 | 38 | $9.61 \times 10^{-3}$ |
| ME13087 | ME13087-01 ($T_3$) | 0.61247 | 15 | 0.56163 | 38 | $5.99 \times 10^{-4}$ |
| ME13087 | ME13087-02 ($T_2$) | 0.63400 | 39 | 0.58532 | 34 | $9.30 \times 10^{-3}$ |
| ME13087 | ME13087-02 ($T_3$) | 0.63442 | 26 | 0.58532 | 34 | $1.22 \times 10^{-2}$ |
| ME13087 | ME13087-03 ($T_2$) | 0.61429 | 38 | 0.55533 | 24 | $5.04 \times 10^{-3}$ |
| ME13087 | ME13087-03 ($T_3$) | 0.62283 | 35 | 0.55533 | 24 | $3.31 \times 10^{-3}$ |
| ME13087 | ME13087-04 ($T_2$) | 0.62714 | 28 | 0.60068 | 56 | $3.02 \times 10^{-2}$ |
| ME13087 | ME13087-04 ($T_3$) | 0.64543 | 7 | 0.60068 | 56 | $9.04 \times 10^{-3}$ |

Events -01, -02, -03 and -04 segregated 2:1, 3:1, 3:1 and 2:1 respectively (R:S) for FINALE™ resistance in the T2 generation.

Events -01, -02, -03 and -04 of ME13087 exhibited no statistically relevant negative phenotypes. That is, there was no detectable reduction in germination rate, the transgenic plants appeared wild type in all instances; there was no observable or statistical differences between transgenics and controls in days to flowering; there was no observable or statistical differences between transgenics and controls in the size of the rosette area 7 days post-bolting; and there was no observable or statistical differences between transgenics and controls in fertility (silique number and seed fill) in T1 generation Example 46

Analysis of ME13106 Events

ME13106 contains Ceres Clone:986438 (SEQ ID NO:1156) from *Zea mays*, which encodes a 188 amino acid protein of unknown function. Evaluation of low-nitrogen tolerance for ME13106 in $T_2$ and $T_3$ was conducted under the same conditions as described in Examples 2 and 3. In this study, the seedling photosynthetic efficiency was measured as Fv/Fm comparing transgenic plants within an event to non-transgenic segregants pooled across the same plate. Two events, -03 and -04, showed significantly increased photosynthetic efficiency on low ammonium nitrate-containing media relative to the internal controls in both generations at p≤0.05 using a one-tailed t-test assuming unequal variance. A summary of photosynthetic efficiency of ME13106 seedlings is shown in Table 50. ME13106 events were also tested for enhanced growth on the low ammonium nitrate media. No significant differences between the transgenics and the controls were observed.

TABLE 50 t-test comparison of seedling photosynthetic efficiency between transgenic seedlings and pooled non-transgenic segregants after 18 days of growth on low ammonium nitrate.

| Line | Events | Transgenic Fv/Fm | n | Pooled Non-Transgenics Fv/Fm | n | t-test p-value |
|---|---|---|---|---|---|---|
| ME13106 | ME13106-03 ($T_2$) | 0.62726 | 27 | 0.58600 | 43 | $1.50 \times 10^{-2}$ |
| ME13106 | ME13106-03 ($T_3$) | 0.65163 | 30 | 0.58600 | 43 | $1.69 \times 10^{-4}$ |
| ME13106 | ME13106-04 ($T_2$) | 0.60836 | 36 | 0.55876 | 25 | $2.62 \times 10^{-2}$ |
| ME13106 | ME13106-04 ($T_3$) | 0.64250 | 38 | 0.55876 | 25 | $5.01 \times 10^{-4}$ |

Events -03 and -04 segregated 1:1 and 3:1 respectively (R:S) for FINALE™ resistance in the $T_2$ generation.

Events -03 and -04 of ME13106 exhibited no statistically relevant negative phenotypes. That is, there was no detectable reduction in germination rate, the transgenic plants appeared wild type in all instances; there was no observable or statistical differences between transgenics and controls in days to flowering; there was no observable or statistical differences between transgenics and controls in the size of the rosette area 7 days post-bolting; and there was no observable or statistical differences between transgenics and controls in fertility (silique number and seed fill)

Example 47

Analysis of ME13107 Events

ME13107 contains Ceres Clone:996227 (SEQ ID NO:1158) from *Zea mays*, which encodes a 240 amino acid zein seed storage protein. Evaluation of low-nitrogen tolerance for ME13107 in $T_2$ and $T_3$ was conducted under the same conditions as described in Examples 2 and 3. In this study, the seedling photosynthetic efficiency was measured as Fv/Fm comparing transgenic plants within an event to non-transgenic segregants pooled across the same plate. Three events, -02, -04 and -05, showed significantly increased photosynthetic efficiency on low ammonium nitrate-containing media relative to the internal controls in both generations at p≤0.05 using a one-tailed t-test assuming unequal variance. A summary of photosynthetic efficiency of ME13107 seedlings is shown in Table 51.

TABLE 51 t-test comparison of seedling photosynthetic efficiency between transgenic seedlings and pooled non-transgenic segregants after 18 days of growth on low ammonium nitrate.

| Line | Events | Transgenic Fv/Fm | n | Pooled Non-Transgenics Fv/Fm | n | t-test p-value |
|---|---|---|---|---|---|---|
| ME13107 | ME13107-02 ($T_2$) | 0.63122 | 37 | 0.56643 | 21 | $1.07 \times 10^{-2}$ |
| ME13107 | ME13107-02 ($T_3$) | 0.63848 | 29 | 0.56643 | 21 | $6.03 \times 10^{-3}$ |
| ME13107 | ME13107-04 ($T_2$) | 0.62948 | 27 | 0.55918 | 50 | $2.07 \times 10^{-5}$ |
| ME13107 | ME13107-04 ($T_3$) | 0.63019 | 21 | 0.55918 | 50 | $6.72 \times 10^{-5}$ |
| ME13107 | ME13107-05 ($T_2$) | 0.61952 | 29 | 0.54440 | 48 | $7.85 \times 10^{-5}$ |
| ME13107 | ME13107-05 ($T_3$) | 0.62185 | 20 | 0.54440 | 48 | $4.02 \times 10^{-5}$ |

ME13107 events were also tested for enhanced growth on the low ammonium nitrate media. Two events, -02 and -04, showed significantly enhanced growth on low ammonium nitrate-containing media relative to the internal controls in $T_2$ generation at $p \leq 0.05$ using a one-tailed t-test assuming unequal variance. In this study, the seedling area for transgenic plants within an event was compared to the seedling area for non-transgenic segregants pooled across the same line. A summary of enhanced growth under low ammonium nitrate growth conditions of ME13071 seedlings is shown in Table 52.

TABLE 52 t-test comparison of seedling area between transgenic seedlings and pooled non-transgenic segregants after 18 days of growth on low ammonium nitrate.

| Line | Events | Transgenic Area | n | Pooled Non-Transgenics Area | n | t-test p-value |
|---|---|---|---|---|---|---|
| ME13107 | ME13107-02 ($T_2$) | 0.07738 | 37 | 0.06919 | 203 | $3.63 \times 10^{-2}$ |
| ME13107 | ME13107-02 ($T_3$) | 0.07688 | 29 | 0.06919 | 203 | $4.60 \times 10^{-2}$ |
| ME13107 | ME13107-04 ($T_2$) | 0.07514 | 27 | 0.06919 | 203 | $3.18 \times 10^{-2}$ |
| ME13107 | ME13107-04 ($T_3$) | 0.07585 | 21 | 0.06919 | 203 | $2.27 \times 10^{-2}$ |

Events -02, -04 and -05 segregated 3:1, 1:1 and 2:1 respectively (R:S) for FINALE™ resistance in the $T_2$ generation.

Events -02, -04 and -05 of ME13107 exhibited no statistically relevant negative phenotypes. That is, there was no detectable reduction in germination rate, the transgenic plants appeared wild type in all instances; there was no observable or statistical differences between transgenics and controls in days to flowering; there was no observable or statistical differences between transgenics and controls in the size of the rosette area 7 days post-bolting; and there was no observable or statistical differences between transgenics and controls in fertility (silique number and seed fill).

Example 48

Analysis of ME13108 Events

ME13108 contains Ceres Clone:996263 (SEQ ID NO:1165) from *Zea mays*, which encodes an 84 amino acid BRICK1 protein. Evaluation of low-nitrogen tolerance for ME13108 in $T_2$ and $T_3$ was conducted under the same conditions as described in Examples 2 and 3. In this study, the seedling photosynthetic efficiency was measured as Fv/Fm comparing transgenic plants within an event to non-transgenic segregants pooled across the same plate. Three events, -01, -04 and -05, showed significantly increased photosynthetic efficiency on low ammonium nitrate-containing media relative to the internal controls in both generations at $p \leq 0.05$ using a one-tailed t-test assuming unequal variance. A summary of photosynthetic efficiency of ME13108 seedlings is shown in Table 53. ME13108 events were also tested for enhanced growth on the low ammonium nitrate media. No significant differences between the transgenics and the controls were observed.

TABLE 53 t-test comparison of seedling photosynthetic efficiency between transgenic seedlings and pooled non-transgenic segregants after 18 days of growth on low ammonium nitrate.

| Line | Events | Transgenic Fv/Fm | n | Pooled Non-Transgenics Fv/Fm | n | t-test p-value |
|---|---|---|---|---|---|---|
| ME13108 | ME13108-01 ($T_2$) | 0.56703 | 36 | 0.53932 | 195 | $1.97 \times 10^{-2}$ |
| ME13108 | ME13108-01 ($T_3$) | 0.59250 | 26 | 0.53932 | 195 | $3.64 \times 10^{-4}$ |
| ME13108 | ME13108-04 ($T_2$) | 0.60032 | 37 | 0.53932 | 195 | $3.37 \times 10^{-7}$ |
| ME13108 | ME13108-04 ($T_3$) | 0.60463 | 30 | 0.53932 | 195 | $4.10 \times 10^{-5}$ |
| ME13108 | ME13108-05 ($T_2$) | 0.60727 | 30 | 0.53932 | 195 | $4.97 \times 10^{-9}$ |
| ME13108 | ME13108-05 ($T_3$) | 0.61850 | 32 | 0.53932 | 195 | $2.35 \times 10^{-9}$ |

Events -01, -04 and -05 segregated 3:1 (R:S) for FINALE™ resistance in the $T_2$ generation.

Events -01, -04 and -05 of ME13108 exhibited no statistically relevant negative phenotypes. That is, there was no detectable reduction in germination rate, the transgenic plants appeared wild type in all instances; there was no observable or statistical differences between transgenics and controls in days to flowering; there was no observable or statistical differences between transgenics and controls in the size of the rosette area 7 days post-bolting; and there was no observable or statistical differences between transgenics and controls in fertility (silique number and seed fill).

Example 49

Analysis of ME13110 Events

ME13110 contains Ceres Clone:988083 (SEQ ID NO:1184) from *Zea mays*, which encodes a 188 amino acid protein of unknown function. Evaluation of low-nitrogen tolerance for ME13110 in $T_2$ and $T_3$ was conducted under the same conditions as described in Examples 2 and 3. In this study, the seedling photosynthetic efficiency was measured as Fv/Fm comparing transgenic plants within an event to non-transgenic segregants pooled across the same plate. Three events, -03, -04 and -05, showed significantly increased photosynthetic efficiency on low ammonium nitrate-containing media relative to the internal controls in both generations at $p \leq 0.05$ using a one-tailed t-test assuming unequal variance. A summary of photosynthetic efficiency of ME13110 seedlings is shown in Table 54. ME13110 events were also tested for enhanced growth on the low ammonium nitrate media. No significant differences between the transgenics and the controls were observed.

TABLE 54 t-test comparison of seedling photosynthetic efficiency
between transgenic seedlings and pooled non-transgenic
segregants after 18 days of growth on low ammonium nitrate.

| | | Transgenic | | Pooled Non-Transgenics | | t-test |
|---|---|---|---|---|---|---|
| Line | Events | Fv/Fm | n | Fv/Fm | n | p-value |
| ME13110 | ME13110-03 ($T_2$) | 0.5721 | 34 | 0.3948 | 16 | $8.92 \times 10^{-3}$ |
| ME13110 | ME13110-03 ($T_3$) | 0.5773 | 24 | 0.4583 | 26 | $4.58 \times 10^{-4}$ |
| ME13110 | ME13110-04 ($T_2$) | 0.5651 | 35 | 0.4243 | 15 | $4.34 \times 10^{-2}$ |
| ME13110 | ME13110-04 ($T_3$) | 0.6000 | 10 | 0.4594 | 40 | $3.29 \times 10^{-3}$ |
| ME13110 | ME13110-05 ($T_2$) | 0.5143 | 28 | 0.3809 | 22 | $2.24 \times 10^{-2}$ |
| ME13110 | ME13110-05 ($T_3$) | 0.5278 | 28 | 0.3688 | 21 | $1.28 \times 10^{-2}$ |

Events -03, -04 and -05 segregated 3:1, 1:1 and 3:1 respectively (R:S) for FINALE™ resistance in the $T_2$ generation.

Events -03, -04 and -05 of ME13110 exhibited no statistically relevant negative phenotypes. That is, there was no detectable reduction in germination rate, the transgenic plants appeared wild type in all instances; there was no observable or statistical differences between transgenics and controls in days to flowering; there was no observable or statistical differences between transgenics and controls in the size of the rosette area 7 days post-bolting; and there was no observable or statistical differences between transgenics and controls in fertility (silique number and seed fill).

Example 50

Analysis of ME13125 Events

ME13125 contains Ceres Clone:732 (At3g50880, SEQ ID NO:1193) from *Arabidopsis thaliana*, which encodes a 188 amino acid protein of unknown function. Evaluation of low-nitrogen tolerance for ME13125 in $T_2$ and $T_3$ was conducted under the same conditions as described in Examples 2 and 3. In this study, the seedling photosynthetic efficiency was measured as Fv/Fm comparing transgenic plants within an event to non-transgenic segregants pooled across the same plate. Three events, -01, -03 and -05, showed significantly increased photosynthetic efficiency on low ammonium nitrate-containing media relative to the internal controls in both generations at p≤0.05 using a one-tailed t-test assuming unequal variance. A summary of photosynthetic efficiency of ME13125 seedlings is shown in Table 55. ME13125 events were also tested for enhanced growth on the low ammonium nitrate media. No significant differences between the transgenics and the controls were observed.

TABLE 55 t-test comparison of seedling photosynthetic efficiency
between transgenic seedlings and pooled non-transgenic
segregants after 18 days of growth on low ammonium nitrate.

| | | Transgenic | | Pooled Non-Transgenics | | t-test |
|---|---|---|---|---|---|---|
| Line | Events | Fv/Fm | n | Fv/Fm | n | p-value |
| ME13125 | ME13125-01 ($T_2$) | 0.61129 | 42 | 0.53829 | 125 | $4.82 \times 10^{-7}$ |
| ME13125 | ME13125-01 ($T_3$) | 0.61929 | 38 | 0.53829 | 125 | $1.96 \times 10^{-7}$ |
| ME13125 | ME13125-03 ($T_2$) | 0.63360 | 45 | 0.53829 | 125 | $3.05 \times 10^{-13}$ |
| ME13125 | ME13125-03 ($T_3$) | 0.62218 | 44 | 0.53829 | 125 | $3.81 \times 10^{-9}$ |
| ME13125 | ME13125-05 ($T_2$) | 0.61565 | 31 | 0.53829 | 125 | $4.12 \times 10^{-8}$ |
| ME13125 | ME13125-05 ($T_3$) | 0.58469 | 16 | 0.53829 | 125 | 0.05 |

Events -01, -03 and -05 segregated 3:1, 15:1 and 2:1 respectively (R:S) for FINALE™ resistance in the $T_2$ generation.

Events -01, -03 and -05 of ME13125 exhibited no statistically relevant negative phenotypes. That is, there was no detectable reduction in germination rate, the transgenic plants appeared wild type in all instances; there was no observable or statistical differences between transgenics and controls in days to flowering; there was no observable or statistical differences between transgenics and controls in the size of the rosette area 7 days post-bolting; and there was no observable or statistical differences between transgenics and controls in fertility (silique number and seed fill).

Example 51

Analysis of ME13149 Events

ME13149 contains Ceres Clone:2267 (At2g24765, SEQ ID NO:1209) from *Arabidopsis thaliana*, which encodes a 182 amino acid ADP-ribosylation factor 3 protein. Evaluation of low-nitrogen tolerance for ME13149 in $T_2$ and $T_3$ was conducted under the same conditions as described in Examples 2 and 3. In this study, the seedling photosynthetic efficiency was measured as Fv/Fm comparing transgenic plants within an event to non-transgenic segregants pooled across the same plate. Two events, -02 and -03, showed significantly increased photosynthetic efficiency on low ammonium nitrate-containing media relative to the internal controls in both generations at p≤0.05 using a one-tailed t-test assuming unequal variance. A summary of photosynthetic efficiency of ME13149 seedlings is shown in Table 56. ME13149 events were also tested for enhanced growth on the low ammonium nitrate media. No significant differences between the transgenics and the controls were observed.

TABLE 56 t-test comparison of seedling photosynthetic efficiency
between transgenic seedlings and pooled non-transgenic
segregants after 18 days of growth on low ammonium nitrate.

| | | Transgenic | | Pooled Non-Transgenics | | t-test |
|---|---|---|---|---|---|---|
| Line | Events | Fv/Fm | n | Fv/Fm | n | p-value |
| ME13149 | ME13149-02 ($T_2$) | 0.55623 | 30 | 0.51138 | 55 | $2.29 \times 10^{-2}$ |
| ME13149 | ME13149-02 ($T_3$) | 0.54818 | 17 | 0.51138 | 55 | $4.56 \times 10^{-2}$ |
| ME13149 | ME13149-03 ($T_2$) | 0.55998 | 42 | 0.51138 | 55 | $5.11 \times 10^{-3}$ |
| ME13149 | ME13149-03 ($T_3$) | 0.58450 | 24 | 0.51138 | 55 | $2.77 \times 10^{-4}$ |

Events -02 and -03 segregated 2:1 and 15:1 respectively (R:S) for FINALE™ resistance in the $T_2$ generation.

Events -02 and -03 of ME13149 exhibited no statistically relevant negative phenotypes. That is, there was no detectable reduction in germination rate, the transgenic plants appeared wild type in all instances; there was no observable or statistical differences between transgenics and controls in days to flowering; there was no observable or statistical differences between transgenics and controls in the size of the rosette area 7 days post-bolting; and there was no observable or statistical differences between transgenics and controls in fertility (silique number and seed fill).

Example 52

Analysis of ME13151 Events

ME13151 contains Ceres Clone:39358 (At3g25150, SEQ ID NO:1273) from *Arabidopsis thaliana*, which encodes a 488 amino acid nuclear transport factor 2 (NTF2) domain protein. Evaluation of low-nitrogen tolerance for ME13151 in $T_2$ and $T_3$ was conducted under the same conditions as described in Examples 2 and 3. In this study, the seedling photosynthetic efficiency was measured as Fv/Fm comparing transgenic plants within an event to non-transgenic segregants pooled across the same plate. Two events, -01 and -02, showed significantly increased photosynthetic efficiency on low ammonium nitrate-containing media relative to the internal controls in both generations at $p \leq 0.05$ using a one-tailed t-test assuming unequal variance. A summary of photosynthetic efficiency of ME13151 seedlings is shown in Table 57. ME13151 events were also tested for enhanced growth on the low ammonium nitrate media. No significant differences between the transgenics and the controls were observed.

TABLE 57

T-test comparison of seedling photosynthetic efficiency between transgenic seedlings and pooled non-transgenic segregants after 18 days of growth on low ammonium nitrate.

| Line | Events | Transgenic Fv/Fm | n | Pooled Non-Transgenics Fv/Fm | n | t-test p-value |
|---|---|---|---|---|---|---|
| ME13151 | ME13151-01 ($T_2$) | 0.62593 | 44 | 0.53141 | 17 | $8.58 \times 10^{-4}$ |
| ME13151 | ME13151-01 ($T_3$) | 0.59936 | 33 | 0.53141 | 17 | $1.21 \times 10^{-2}$ |
| ME13151 | ME13151-02 ($T_2$) | 0.59879 | 39 | 0.46956 | 16 | $3.08 \times 10^{-5}$ |
| ME13151 | ME13151-02 ($T_3$) | 0.59566 | 32 | 0.46956 | 16 | $4.28 \times 10^{-5}$ |

Events -01 and -02 segregated 9:1 and 6:1 respectively (R:S) for FINALE™ resistance in the T2 generation.

Events -01 and -02 of ME13151 exhibited no statistically relevant negative phenotypes. That is, there was no detectable reduction in germination rate, the transgenic plants appeared wild type in all instances; there was no observable or statistical differences between transgenics and controls in days to flowering; there was no observable or statistical differences between transgenics and controls in the size of the rosette area 7 days post-bolting; and there was no observable or statistical differences between transgenics and controls in fertility (silique number and seed fill).

Example 53

Analysis of ME13153 Events

ME13153 contains Ceres Clone:115046 (At3g17760, SEQ ID NO:1301) from *Arabidopsis thaliana*, which encodes a 494 amino acid glutamate decarboxylase. Evaluation of low-nitrogen tolerance for ME13153 in $T_2$ and $T_3$ was conducted under the same conditions as described in Examples 2 and 3. In this study, the seedling photosynthetic efficiency was measured as Fv/Fm comparing transgenic plants within an event to non-transgenic segregants pooled across the same plate. Two events, -03 and -04, showed significantly increased photosynthetic efficiency on low ammonium nitrate-containing media relative to the internal controls in both generations at $p \leq 0.05$ using a one-tailed t-test assuming unequal variance. A summary of photosynthetic efficiency of ME13153 seedlings is shown in Table 58. ME13153 events were also tested for increased photosynthetic efficiency on the low nitrate media. No significant differences between the transgenics and the controls were observed.

TABLE 58

T-test comparison of seedling photosynthetic efficiency between transgenic seedlings and non-transgenic segregants after 14 days of growth on low ammonium nitrate.

| Line | Events | Transgenic Fv/Fm | n | Pooled Non-Transgenics Fv/Fm | n | t-test p-value |
|---|---|---|---|---|---|---|
| ME13153 | ME13153-03 ($T_2$) | 0.62 | 34 | 0.56 | 16 | $3.0 \times 10^{-2}$ |
| ME13153 | ME13153-03 ($T_3$) | 0.60 | 19 | 0.54 | 22 | $2.9 \times 10^{-2}$ |
| ME13153 | ME13153-04 ($T_2$) | 0.57 | 32 | 0.50 | 18 | $4.3 \times 10^{-2}$ |
| ME13153 | ME13153-04 ($T_3$) | 0.61 | 24 | 0.55 | 24 | $2.1 \times 10^{-2}$ |

Events -03 and -04 segregated 3:1 (R:S) for FINALE™ resistance in the $T_2$ generation.

Events -03 and -04 of ME13153 exhibited no statistically relevant negative phenotypes. That is, there was no detectable reduction in germination rate, the transgenic plants appeared wild type in all instances; there was no observable or statistical differences between transgenics and controls in days to flowering; there was no observable or statistical differences between transgenics and controls in the size of the rosette area 7 days post-bolting. Events -03 and -04 yielded slightly less seed per plant compared to the controls, but these differences are not significant at $p \leq 0.10$.

Example 54

Analysis of ME13177 Events

ME13177 contains Ceres Clone:339439 (SEQ ID NO:1341) from *Zea mays*, which encodes a 345 amino acid cyclin C-terminal domain protein. Evaluation of low-nitrogen tolerance for ME13177 in $T_2$ and $T_3$ was conducted under the same conditions as described in Examples 2 and 3. In this study, the seedling photosynthetic efficiency was measured as Fv/Fm comparing transgenic plants within an event to non-transgenic segregants pooled across the same plate. Two events, -01 and -02, showed significantly increased photosynthetic efficiency on low ammonium nitrate-containing media relative to the internal controls in both generations at $p \leq 0.05$ using a one-tailed t-test assuming unequal variance. A summary of photosynthetic efficiency of ME13177 seedlings is shown in Table 59. ME13177 events were also tested for enhanced growth on the low ammonium nitrate media. No significant differences between the transgenics and the controls were observed.

TABLE 59 t-test comparison of seedling photosynthetic efficiency between transgenic seedlings and pooled non-transgenic segregants after 18 days of growth on low ammonium nitrate.

| Line | Events | Transgenic Fv/Fm | n | Pooled Non-Transgenics Fv/Fm | n | t-test p-value |
|---|---|---|---|---|---|---|
| ME13177 | ME13177-01 ($T_2$) | 0.6315 | 32 | 0.6112 | 175 | $2.43 \times 10^{-2}$ |
| ME13177 | ME13177-01 ($T_3$) | 0.6407 | 29 | 0.6112 | 175 | $7.33 \times 10^{-3}$ |
| ME13177 | ME13177-02 ($T_2$) | 0.6400 | 41 | 0.6112 | 175 | $1.23 \times 10^{-3}$ |
| ME13177 | ME13177-02 ($T_3$) | 0.6499 | 20 | 0.6112 | 175 | $6.47 \times 10^{-3}$ |

Events -01 and -02 segregated 2:1 and 3:1 respectively (R:S) for FINALE™ resistance in the $T_2$ generation.

Events -01 and -02 of ME13177 exhibited no statistically relevant negative phenotypes. That is, there was no detectable reduction in germination rate, the transgenic plants appeared wild type in all instances; there was no observable or statistical differences between transgenics and controls in days to flowering; there was no observable or statistical differences between transgenics and controls in the size of the rosette area 7 days post-bolting; and there was no observable or statistical differences between transgenics and controls in fertility (silique number and seed fill).

Example 55

Analysis of ME13200 Events

ME13200 contains Ceres Clone:896483 (SEQ ID NO:1384) from Zea mays, which encodes an 85 amino acid myb family transcription factor. Evaluation of low-nitrogen tolerance for ME13200 in $T_2$ and $T_3$ was conducted under the same conditions as described in Examples 2 and 3. A summary of the enhanced growth of ME13200 events on low ammonium nitrate-containing media is shown in Table 60. In this study, the seedling area for transgenic plants within an event was compared to the seedling area for non-transgenic segregants pooled across the same line. Two events, -03 and -04, were found significantly larger than the pooled non-transgenic segregants after 18 days of growth on low ammonium nitrate-containing media relative to the internal controls in both generations at p≤0.05 using a one-tailed t-test assuming unequal variance. ME13200 events were also tested for increased photosynthetic efficiency on the low ammonium nitrate media as well as for enhanced photosynthesis and growth on low nitrate media. No significant differences between the transgenics and the controls were observed.

TABLE 60 t-test comparison of seedling area between transgenic seedlings and pooled non-transgenic segregants after 18 days of growth on low ammonium nitrate.

| Line | Events | Transgenic Area | n | Pooled Non-Transgenics Area | n | t-test p-value |
|---|---|---|---|---|---|---|
| ME13200 | ME13200-03 ($T_2$) | 0.07366 | 43 | 0.06342 | 35 | $4.09 \times 10^{-4}$ |
| ME13200 | ME13200-03 ($T_3$) | 0.08193 | 34 | 0.06342 | 35 | $2.37 \times 10^{-5}$ |
| ME13200 | ME13200-04 ($T_2$) | 0.07377 | 48 | 0.06342 | 35 | $4.87 \times 10^{-4}$ |
| ME13200 | ME13200-04 ($T_3$) | 0.07530 | 47 | 0.06342 | 35 | $1.88 \times 10^{-4}$ |

Events -03 and -04 segregated 3:1 and 15:1 respectively (R:S) for FINALE™ resistance in the $T_2$ generation.

Events -03 and -04 of ME13200 exhibited no statistically relevant negative phenotypes. That is, there was no detectable reduction in germination rate, the transgenic plants appeared wild type in all instances; there was no observable or statistical differences between transgenics and controls in days to flowering; there was no observable or statistical differences between transgenics and controls in the size of the rosette area 7 days post-bolting; and there was no observable or statistical differences between transgenics and controls in fertility (silique number and seed fill).

Example 56

Analysis of ME13204 Events

ME13204 contains Ceres Clone:995409 (SEQ ID NO:1408) from Zea mays, which encodes a 178 amino acid protein of unknown function. Evaluation of low-nitrogen tolerance for ME13204 in $T_2$ and $T_3$ was conducted under the same conditions as described in Examples 2 and 3. In this study, the seedling photosynthetic efficiency was measured as Fv/Fm comparing transgenic plants within an event to non-transgenic segregants pooled across the same plate. Two events, -01 and -05, showed significantly increased photosynthetic efficiency on low nitrate-containing media relative to the internal controls in both generations at p≤0.05 using a one-tailed t-test assuming unequal variance. A summary of photosynthetic efficiency of ME13204 seedlings is shown in Table 61. ME13204 events were also tested for enhanced growth on the low nitrate media as well as for enhanced growth and photosynthetic efficiency on low ammonium nitrate media. No significant differences between the transgenics and the controls were observed.

TABLE 61

T-test comparison of seedling photosynthetic efficiency between transgenic seedlings and pooled non-transgenic segregants after 14 days of growth on low nitrate media.

| Line | Events | Transgenic Fv/Fm | n | Pooled Non-Transgenics Fv/Fm | n | t-test p-value |
|---|---|---|---|---|---|---|
| ME13204 | ME13204-01 ($T_2$) | 0.5874 | 45 | 0.5354 | 46 | $1.41 \times 10^{-2}$ |
| ME13204 | ME13204-01 ($T_3$) | 0.5932 | 36 | 0.5354 | 46 | $9.85 \times 10^{-3}$ |
| ME13204 | ME13204-05 ($T_2$) | 0.5855 | 34 | 0.5354 | 46 | $2.00 \times 10^{-2}$ |
| ME13204 | ME13204-05 ($T_3$) | 0.5998 | 20 | 0.5354 | 46 | $5.58 \times 10^{-3}$ |

Events -01 and -05 segregated 9:1 and 3:1 respectively (R:S) for FINALE™ resistance in the $T_2$ generation.

Events -01 and -05 of ME13204 exhibited no statistically relevant negative phenotypes. That is, there was no detectable reduction in germination rate, the transgenic plants appeared wild type in all instances; there was no observable or statistical differences between transgenics and controls in days to flowering; there was no observable or statistical differences between transgenics and controls in the size of the rosette area 7 days post-bolting; and there was no observable or statistical differences between transgenics and controls in fertility (silique number and seed fill).

Example 57

Analysis of ME14649 Events

ME14649 contains Ceres Annot:850581 (At5g01880, SEQ ID NO:1427) from *Arabidopsis thaliana*, which encodes a 159 amino acid zinc finger protein. Evaluation of low-nitrogen tolerance for ME14649 in $T_2$ and $T_3$ was conducted under the same conditions as described in Examples 2 and 3. In this study, the seedling photosynthetic efficiency was measured as Fv/Fm comparing transgenic plants within an event to non-transgenic segregants pooled across the same plate. Two events, -02 and -03, showed significantly increased photosynthetic efficiency on low ammonium nitrate-containing media relative to the internal controls in both generations at $p \leq 0.05$ using a one-tailed t-test assuming unequal variance. A summary of photosynthetic efficiency of ME14649 seedlings is shown in Table 62. ME14649 events were also tested for enhanced growth on the low ammonium nitrate media. No significant differences between the transgenics and the controls were observed.

TABLE 62 t-test comparison of seedling photosynthetic efficiency between transgenic seedlings and pooled non-transgenic segregants after 18 days of growth on low ammonium nitrate.

| | | Transgenic | | Pooled Non-Transgenics | | t-test |
|---|---|---|---|---|---|---|
| Line | Events | Fv/Fm | n | Fv/Fm | n | p-value |
| ME14649 | ME14649-02 ($T_2$) | 0.59789 | 35 | 0.54533 | 30 | $1.54 \times 10^{-4}$ |
| ME14649 | ME14649-02 ($T_3$) | 0.58154 | 26 | 0.54533 | 30 | $3.42 \times 10^{-2}$ |
| ME14649 | ME14649-03 ($T_2$) | 0.61875 | 28 | 0.56539 | 33 | $2.03 \times 10^{-3}$ |
| ME14649 | ME14649-03 ($T_3$) | 0.62630 | 27 | 0.56539 | 33 | $9.18 \times 10^{-4}$ |

Events -02 and -03 segregated 3:1 and 2:1 respectively (R:S) for FINALE™ resistance in the $T_2$ generation.

Events -02 and -03 of ME14649 exhibited no statistically relevant negative phenotypes. That is, there was no detectable reduction in germination rate, the transgenic plants appeared wild type in all instances; there was no observable or statistical differences between transgenics and controls in days to flowering; there was no observable or statistical differences between transgenics and controls in the size of the rosette area 7 days post-bolting; and there was no observable or statistical differences between transgenics and controls in fertility (silique number and seed fill) in T1 generation.

Example 58

Analysis of ME16546 Events

ME16546 contains Ceres Annot:862321 (At2g45360, SEQ ID NO:1462) from *Arabidopsis thaliana*, which encodes a 215 amino acid protein of unknown function. Evaluation of low-nitrogen tolerance for ME16546 in $T_2$ and $T_3$ was conducted under the same conditions as described in Examples 2 and 3. In this study, the seedling photosynthetic efficiency was measured as Fv/Fm comparing transgenic plants within an event to non-transgenic segregants pooled across the same plate. Two events, -04 and -05, showed significantly increased photosynthetic efficiency on low ammonium nitrate-containing media relative to the internal controls in both generations at $p \leq 0.05$ using a one-tailed t-test assuming unequal variance. A summary of photosynthetic efficiency of ME16546 seedlings is shown in Table 63. ME16546 events were also tested for enhanced growth on the low ammonium nitrate media. No significant differences between the transgenics and the controls were observed.

TABLE 63 t-test comparison of seedling photosynthetic efficiency between transgenic seedlings and pooled non-transgenic segregants after 18 days of growth on low ammonium nitrate.

| | | Transgenic | | Pooled Non-Transgenics | | t-test |
|---|---|---|---|---|---|---|
| Line | Events | Fv/Fm | n | Fv/Fm | n | p-value |
| ME16546 | ME16546-04 ($T_2$) | 0.59891 | 33 | 0.56124 | 130 | $2.21 \times 10^{-4}$ |
| ME16546 | ME16546-04 ($T_3$) | 0.57924 | 41 | 0.56124 | 130 | $3.77 \times 10^{-2}$ |
| ME16546 | ME16546-05 ($T_2$) | 0.58861 | 36 | 0.56124 | 130 | $7.17 \times 10^{-3}$ |
| ME16546 | ME16546-05 ($T_3$) | 0.61763 | 27 | 0.56124 | 130 | $3.25 \times 10^{-6}$ |

Events -04 and -05 segregated 2:1 and 3:1 respectively (R:S) for FINALE™ resistance in the $T_2$ generation.

Events -04 and -05 of ME16546 exhibited no statistically relevant negative phenotypes. That is, there was no detectable reduction in germination rate, the transgenic plants appeared wild type in all instances; there was no observable or statistical differences between transgenics and controls in days to flowering; there was no observable or statistical differences between transgenics and controls in the size of the rosette area 7 days post-bolting; and there was no observable or statistical differences between transgenics and controls in fertility (silique number and seed fill).

Example 59

Analysis of ME17457 Events

ME17457 contains Ceres Annot:839064 (At1g80600, SEQ ID NO:1478) from *Arabidopsis thaliana*, which encodes a 457 acetylornithine aminotransferase, a member of the Class-III aminotransferase family. This is a homolog of Ceres Clone:19586 (ME01463, SEQ ID NO:76). Evaluation of low-nitrogen tolerance for ME17457 in $T_2$ and $T_3$ was conducted under the same conditions as described in Examples 2 and 3. In this study, the seedling photosynthetic efficiency was measured as Fv/Fm comparing transgenic plants within an event to non-transgenic segregants pooled across the same plate. Four events, -02, -03, -05 and -06, showed significantly increased photosynthetic efficiency on low ammonium nitrate-containing media relative to the internal controls in both generations at $p \leq 0.05$ using a one-tailed t-test assuming unequal variance. A summary of photosynthetic efficiency of ME17457 seedlings is shown in Table 64. ME17457 events were also tested for enhanced growth on the low ammonium nitrate media. No significant differences between the transgenics and the controls were observed.

TABLE 64 t-test comparison of seedling photosynthetic efficiency between transgenic seedlings and pooled non-transgenic segregants after 18 days of growth on low ammonium nitrate.

| Line | Events | Transgenic Fv/Fm | n | Pooled Non-Transgenics Fv/Fm | n | t-test p-value |
|---|---|---|---|---|---|---|
| ME17457 | ME17457-02 ($T_2$) | 0.60800 | 21 | 0.50878 | 46 | $6.99 \times 10^{-4}$ |
| ME17457 | ME17457-02 ($T_3$) | 0.59539 | 18 | 0.50878 | 46 | $9.02 \times 10^{-3}$ |
| ME17457 | ME17457-03 ($T_2$) | 0.55164 | 11 | 0.49673 | 45 | $3.45 \times 10^{-2}$ |
| ME17457 | ME17457-03 ($T_3$) | 0.57356 | 18 | 0.49673 | 45 | $2.49 \times 10^{-3}$ |
| ME17457 | ME17457-05 ($T_2$) | 0.52928 | 18 | 0.42672 | 32 | $2.23 \times 10^{-3}$ |
| ME17457 | ME17457-05 ($T_3$) | 0.56660 | 25 | 0.42672 | 32 | $5.97 \times 10^{-5}$ |
| ME17457 | ME17457-06 ($T_2$) | 0.54088 | 33 | 0.47350 | 30 | $3.59 \times 10^{-4}$ |
| ME17457 | ME17457-06 ($T_3$) | 0.52210 | 21 | 0.47350 | 30 | $2.03 \times 10^{-2}$ |

Events -02, -03 and -05 segregated 1:1, and Event -06 segregated 3:1 (R:S) for FINALE™ resistance in the $T_2$ generation.

Events -02, -03, -05 and -06 of ME17457 exhibited no statistically relevant negative phenotypes. That is, there was no detectable reduction in germination rate, the transgenic plants appeared wild type in all instances; there was no observable or statistical differences between transgenics and controls in days to flowering; there was no observable or statistical differences between transgenics and controls in the size of the rosette area 7 days post-bolting; and there was no observable or statistical differences between transgenics and controls in fertility (silique number and seed fill).

Example 60

Analysis of ME17567 Events

ME17567 contains Ceres Annot:864666 (At1g16320, SEQ ID NO:1490) from *Arabidopsis thaliana*, which encodes a 273 amino acid protein of unknown function. Evaluation of low-nitrogen tolerance for ME17567 in $T_2$ and $T_3$ was conducted under the same conditions as described in Examples 2 and 3. In this study, the seedling photosynthetic efficiency was measured as Fv/Fm comparing transgenic plants within an event to non-transgenic segregants pooled across the same plate. Two events, -01 and -04, showed significantly increased photosynthetic efficiency on low nitrate-containing media relative to the internal controls in both generations at p≤0.05 using a one-tailed t-test assuming unequal variance. A summary of photosynthetic efficiency of ME17567 seedlings is shown in Table 65. ME17567 events were also tested for enhanced growth on the low nitrate media as well as enhanced photosynthetic efficiency and growth on low ammonium nitrate media. No significant differences between the transgenics and the controls were observed.

TABLE 65 t-test comparison of seedling photosynthetic efficiency between transgenic seedlings and pooled non-transgenic segregants after 14 days of growth on low nitrate.

| Line | Events | Transgenic Fv/Fm | n | Pooled Non-Transgenics Fv/Fm | n | t-test p-value |
|---|---|---|---|---|---|---|
| ME17567 | ME17567-01 ($T_2$) | 0.605455 | 33 | 0.474791 | 67 | $9.69 \times 10^{-10}$ |
| ME17567 | ME17567-01 ($T_3$) | 0.6244 | 20 | 0.474791 | 67 | $6.79 \times 10^{-13}$ |
| ME17567 | ME17567-04 ($T_2$) | 0.57727 | 37 | 0.474791 | 67 | $1.22 \times 10^{-7}$ |
| ME17567 | ME17567-04 ($T_3$) | 0.615143 | 35 | 0.474791 | 67 | $5.95 \times 10^{-13}$ |

Events -01 and -04 segregated 2:1 and 3:1 respectively (R:S) for FINALE™ resistance in the $T_2$ generation.

Events -01 and -04 of ME17567 exhibited no statistically relevant negative phenotypes. That is, there was no detectable reduction in germination rate, the transgenic plants appeared wild type in all instances; there was no observable or statistical differences between transgenics and controls in days to flowering; there was no observable or statistical differences between transgenics and controls in the size of the rosette area 7 days post-bolting; and there was no observable or statistical differences between transgenics and controls in fertility (silique number and seed fill).

Example 61

Analysis of ME17932 Events

ME17932 contains Ceres Annot:875012 (At3g53560, SEQ ID NO:1509) from *Arabidopsis thaliana*, which encodes a 340 amino acid chloroplast lumen common family protein. Evaluation of low-nitrogen tolerance for ME17932 in $T_2$ and $T_3$ was conducted under the same conditions as described in Examples 2 and 3. In this study, the seedling photosynthetic efficiency was measured as Fv/Fm comparing transgenic plants within an event to non-transgenic segregants pooled across the same plate. Four events, -01, -02, -03 and -05, showed significantly increased photosynthetic efficiency on low ammonium nitrate-containing media relative to the internal controls in both generations at p≤0.05 using a one-tailed t-test assuming unequal variance. A summary of photosynthetic efficiency of ME17932 seedlings is shown in Table 66. ME17932 events were also tested for enhanced growth on the low ammonium nitrate media. No significant differences between the transgenics and the controls were observed.

TABLE 66 t-test comparison of seedling photosynthetic efficiency between transgenic seedlings and pooled non-transgenic segregants after 18 days of growth on low ammonium nitrate.

| Line | Events | Transgenic Fv/Fm | n | Pooled Non-Transgenics Fv/Fm | n | t-test p-value |
|---|---|---|---|---|---|---|
| ME17932 | ME17932-01 ($T_2$) | 0.6292 | 36 | 0.6094 | 194 | 0.050 |
| ME17932 | ME17932-01 ($T_3$) | 0.6640 | 22 | 0.6094 | 194 | $2.82 \times 10^{-6}$ |
| ME17932 | ME17932-02 ($T_2$) | 0.6351 | 32 | 0.6094 | 194 | $1.05 \times 10^{-2}$ |
| ME17932 | ME17932-02 ($T_3$) | 0.6373 | 20 | 0.6094 | 194 | $2.82 \times 10^{-2}$ |

TABLE 66-continued t-test comparison of seedling photosynthetic efficiency between transgenic seedlings and pooled non-transgenic segregants after 18 days of growth on low ammonium nitrate.

| Line | Events | Transgenic Fv/Fm | n | Pooled Non-Transgenics Fv/Fm | n | t-test p-value |
|---|---|---|---|---|---|---|
| ME17932 | ME17932-03 ($T_2$) | 0.6504 | 45 | 0.6094 | 194 | $1.80 \times 10^{-5}$ |
| ME17932 | ME17932-03 ($T_3$) | 0.6708 | 20 | 0.6094 | 194 | $8.38 \times 10^{-4}$ |
| ME17932 | ME17932-05 ($T_2$) | 0.6349 | 24 | 0.6094 | 194 | $3.23 \times 10^{-2}$ |
| ME17932 | ME17932-05 ($T_3$) | 0.6615 | 11 | 0.6094 | 194 | $1.16 \times 10^{-3}$ |

Events -01, -02, -03 and -05 segregated 3:1, 2:1, 15:1 and 1:1 respectively (R:S) for FINALE™ resistance in the $T_2$ generation.

Events -01, -02, -03 and -05 of ME17932 exhibited no statistically relevant negative phenotypes. That is, there was no detectable reduction in germination rate, the transgenic plants appeared wild type in all instances; there was no observable or statistical differences between transgenics and controls in days to flowering; there was no observable or statistical differences between transgenics and controls in the size of the rosette area 7 days post-bolting; and there was no observable or statistical differences between transgenics and controls in fertility (silique number and seed fill).

Example 62

Analysis of ME17936 Events

ME17936 contains Ceres Annot:874016 (At3g42800, SEQ ID NO:1524) from *Arabidopsis thaliana*, which encodes a 341 amino acid protein of unknown function. Evaluation of low-nitrogen tolerance for ME17936 in $T_2$ and $T_3$ was conducted under the same conditions as described in Examples 2 and 3. In this study, the seedling photosynthetic efficiency was measured as Fv/Fm comparing transgenic plants within an event to non-transgenic segregants pooled across the same plate. Two events, -01 and -05, showed significantly increased photosynthetic efficiency on low nitrate-containing media relative to the internal controls in both generations at p≤0.05 using a one-tailed t-test assuming unequal variance. A summary of photosynthetic efficiency of ME17936 seedlings is shown in Table 67. ME17936 events were also tested for enhanced growth on the low nitrate media as well as for increased photosynthetic efficiency and enhanced growth on low ammonium nitrate media. No significant differences between the transgenics and the controls were observed.

TABLE 67 t-test comparison of seedling photosynthetic efficiency between transgenic seedlings and pooled non-transgenic segregants after 14 days of growth on low nitrate media.

| Line | Events | Transgenic Fv/Fm | n | Pooled Non-Transgenics Fv/Fm | n | t-test p-value |
|---|---|---|---|---|---|---|
| ME17936 | ME17936-01 ($T_2$) | 0.64778 | 36 | 0.61762 | 39 | $4.68 \times 10^{-3}$ |
| ME17936 | ME17936-01 ($T_3$) | 0.66081 | 21 | 0.61762 | 39 | $4.33 \times 10^{-5}$ |

TABLE 67-continued t-test comparison of seedling photosynthetic efficiency between transgenic seedlings and pooled non-transgenic segregants after 14 days of growth on low nitrate media.

| Line | Events | Transgenic Fv/Fm | n | Pooled Non-Transgenics Fv/Fm | n | t-test p-value |
|---|---|---|---|---|---|---|
| ME17936 | ME17936-05 ($T_2$) | 0.63189 | 35 | 0.61444 | 50 | $2.73 \times 10^{-2}$ |
| ME17936 | ME17936-05 ($T_3$) | 0.64257 | 14 | 0.61444 | 50 | $2.56 \times 10^{-2}$ |

Events -01 and -05 segregated 3:1 (R:S) for FINALE™ resistance in the $T_2$ generation.

Events -01 and -05 of ME17936 exhibited no statistically relevant negative phenotypes. That is, there was no detectable reduction in germination rate, the transgenic plants appeared wild type in all instances; there was no observable or statistical differences between transgenics and controls in days to flowering; there was no observable or statistical differences between transgenics and controls in the size of the rosette area 7 days post-bolting; and there was no observable or statistical differences between transgenics and controls in fertility (silique number and seed fill).

Example 63

Analysis of ME18275 Events

ME18275 contains Ceres Annot:827304 (At2g18300, SEQ ID NO:1536) from *Arabidopsis thaliana*, which encodes a 335 amino acid helix-loop-helix DNA-binding domain. Evaluation of low-nitrogen tolerance for ME18275 in $T_2$ and $T_3$ was conducted under the same conditions as described in Examples 2 and 3. A summary of the enhanced growth of ME18275 events on low nitrate-containing media is shown in Table 68. In this study, the seedling area for transgenic plants within an event was compared to the seedling area for non-transgenic segregants pooled across the same line. Three events, -01, -02 and -03, were found significantly larger than the pooled non-transgenic segregants after 14 days of growth on low nitrate-containing media relative to the internal controls in both generations at p≤0.05, using a one-tailed t-test assuming unequal variance. ME18275 events were also tested for photosynthetic efficiency on the low nitrate media as well as for increased photosynthetic efficiency and enhanced growth on low ammonium nitrate media. No significant differences between the transgenics and the controls were observed.

TABLE 68 t-test comparison of seedling area between transgenic seedlings and pooled non-transgenic segregants after 14 days of growth on low nitrate.

| Line | Events | Transgenic Area | n | Pooled Non-Transgenics Area | n | t-test p-value |
|---|---|---|---|---|---|---|
| ME18275 | ME18275-01 ($T_2$) | 0.09574 | 40 | 0.05961 | 10 | $3.24 \times 10^{-10}$ |
| ME18275 | ME18275-01 ($T_3$) | 0.07807 | 32 | 0.05142 | 15 | $3.71 \times 10^{-4}$ |
| ME18275 | ME18275-02 ($T_2$) | 0.11903 | 33 | 0.05884 | 16 | $6.21 \times 10^{-14}$ |
| ME18275 | ME18275-02 ($T_3$) | 0.08552 | 22 | 0.04208 | 24 | $2.82 \times 10^{-5}$ |
| ME18275 | ME18275-03 ($T_2$) | 0.10281 | 39 | 0.06789 | 9 | $9.48 \times 10^{-8}$ |
| ME18275 | ME18275-03 ($T_3$) | 0.09136 | 20 | 0.05646 | 26 | $9.46 \times 10^{-4}$ |

Events -01, -02 and -03 segregated 3:1 (R:S) for FINALE™ resistance in the $T_2$ generation.

Events -01, -02 and -03 of ME18275 exhibited no statistically relevant negative phenotypes. That is, there was no detectable reduction in germination rate, the transgenic plants appeared wild type in all instances; there was no observable or statistical differences between transgenics and controls in days to flowering; there was no observable or statistical differences between transgenics and controls in the size of the rosette area 7 days post-bolting; and there was no observable or statistical differences between transgenics and controls in fertility (silique number and seed fill).

Example 64

Analysis of ME18924 Events

ME18924 contains Ceres Annot:869192 (At1g72160, SEQ ID NO:1553) from *Arabidopsis thaliana*, which encodes a 490 amino acid emp24/gp25L/p24 family protein. Evaluation of low-nitrogen tolerance for ME18924 in $T_2$ and $T_3$ was conducted under the same conditions as described in Examples 2 and 3. A summary of photosynthetic efficiency of ME18924 seedlings is shown in Table 69. In this study, the seedling photosynthetic efficiency was measured as Fv/Fm comparing transgenic plants within an event to non-transgenic segregants pooled across the same plate. Three events, -02, -04 and -05, showed significantly increased photosynthetic efficiency on low ammonium nitrate-containing media relative to the internal controls in both generations at p≤0.05, using a one-tailed t-test assuming unequal variance.

TABLE 69 t-test comparison of seedling photosynthetic efficiency between transgenic seedlings and pooled non-transgenic segregants after 18 days of growth on low ammonium nitrate.

| Line | Events | Transgenic | | Pooled Non-Transgenics | | t-test |
|---|---|---|---|---|---|---|
| | | Fv/Fm | n | Fv/Fm | n | p-value |
| ME18924 | ME18924-02 ($T_2$) | 0.6515 | 46 | 0.6223 | 138 | $6.43 \times 10^{-3}$ |
| ME18924 | ME18924-02 ($T_3$) | 0.6639 | 45 | 0.6223 | 138 | $1.52 \times 10^{-4}$ |
| ME18924 | ME18924-04 ($T_2$) | 0.6489 | 33 | 0.6223 | 138 | $2.72 \times 10^{-3}$ |
| ME18924 | ME18924-04 ($T_3$) | 0.6517 | 21 | 0.6223 | 138 | $1.58 \times 10^{-2}$ |
| ME18924 | ME18924-05 ($T_2$) | 0.6602 | 35 | 0.6223 | 138 | $5.55 \times 10^{-5}$ |
| ME18924 | ME18924-05 ($T_3$) | 0.6488 | 31 | 0.6223 | 138 | $4.25 \times 10^{-2}$ |

ME18924 events were also tested for enhanced growth on the low ammonium nitrate media. A summary of the enhanced growth of ME18924 events on low nitrate-containing media is shown in Table 70. In this study, the seedling area for transgenic plants within an event was compared to the seedling area for non-transgenic segregants pooled across the same line. Two events, -01 and -04, were found significantly larger than the pooled non-transgenic segregants after 18 days of growth on low ammonium nitrate-containing media relative to the internal controls in both generations at p≤0.05, using a one-tailed t-test assuming unequal variance.

TABLE 70 t-test comparison of seedling area between transgenic seedlings and pooled non-transgenic segregants after 18 days of growth on low ammonium nitrate.

| Line | Events | Transgenic | | Pooled Non-Transgenics | | t-test |
|---|---|---|---|---|---|---|
| | | Area | n | Area | n | p-value |
| ME18924 | ME18924-01 ($T_2$) | 0.06881 | 37 | 0.06311 | 138 | $1.31 \times 10^{-2}$ |
| ME18924 | ME18924-01 ($T_3$) | 0.07164 | 34 | 0.06311 | 138 | $7.43 \times 10^{-3}$ |
| ME18924 | ME18924-04 ($T_2$) | 0.08401 | 33 | 0.06311 | 138 | $5.64 \times 10^{-8}$ |
| ME18924 | ME18924-04 ($T_3$) | 0.07365 | 21 | 0.06311 | 138 | $3.82 \times 10^{-2}$ |

Events -01, -02, -04 and -05 segregated 3:1, 15:1, 2:1 and 2:1 respectively (R:S) for FINALE™ resistance in the $T_2$ generation.

Events -01, -02, -04 and -05 of ME18924 exhibited no statistically relevant negative phenotypes. That is, there was no detectable reduction in germination rate, the transgenic plants appeared wild type in all instances; there was no observable or statistical differences between transgenics and controls in days to flowering; there was no observable or statistical differences between transgenics and controls in the size of the rosette area 7 days post-bolting; and there was no observable or statistical differences between transgenics and controls in fertility (silique number and seed fill).

Example 65

Analysis of ME19182 Events

ME19182 contains Ceres Annot:876419 (At4g01480, SEQ ID NO:1576) from *Arabidopsis thaliana*, which encodes a 216 amino acid inorganic pyrophosphatase protein. Evaluation of low-nitrogen tolerance for ME19182 in $T_2$ and $T_3$ was conducted under the same conditions as described in Examples 2 and 3. In this study, the seedling photosynthetic efficiency was measured as Fv/Fm comparing transgenic plants within an event to non-transgenic segregants pooled across the same plate. Two events, -01 and -03, showed significantly increased photosynthetic efficiency on low ammonium nitrate-containing media relative to the internal controls in both generations at p≤0.05 using a one-tailed t-test assuming unequal variance. A summary of photosynthetic efficiency of ME19182 seedlings is shown in Table 71. ME19182 events were also tested for enhanced growth on the low ammonium nitrate media. No significant differences between the transgenics and the controls were observed.

TABLE 71 t-test comparison of seedling photosynthetic efficiency between transgenic seedlings and pooled non-transgenic segregants after 18 days of growth on low ammonium nitrate.

| Line | Events | Transgenic | | Pooled Non-Transgenics | | t-test |
|---|---|---|---|---|---|---|
| | | Fv/Fm | n | Fv/Fm | n | p-value |
| ME19182 | ME19182-01 ($T_2$) | 0.64938 | 24 | 0.61988 | 154 | $2.47 \times 10^{-2}$ |
| ME19182 | ME19182-01 ($T_3$) | 0.65546 | 13 | 0.61988 | 154 | $1.08 \times 10^{-2}$ |
| ME19182 | ME19182-03 ($T_2$) | 0.64797 | 37 | 0.61988 | 154 | $3.84 \times 10^{-3}$ |
| ME19182 | ME19182-03 ($T_3$) | 0.65388 | 26 | 0.61988 | 154 | $3.15 \times 10^{-3}$ |

Events -01 and -03 segregated 2:1 and 3:1 respectively (R:S) for FINALE™ resistance in the T2 generation.

Events -01 and -03 of ME19182 exhibited no statistically relevant negative phenotypes. That is, there was no detectable reduction in germination rate, the transgenic plants appeared wild type in all instances; there was no observable or statistical differences between transgenics and controls in days to flowering; there was no observable or statistical differences between transgenics and controls in the size of the rosette area 7 days post-bolting; and there was no observable or statistical differences between transgenics and controls in fertility (silique number and seed fill).

Example 66

Analysis of ME20628 Events

ME20628 contains Ceres Annot:859276 (At2g21230, SEQ ID NO:175) from *Arabidopsis thaliana*, which encodes a 188 amino acid protein of unknown function. Evaluation of low-nitrogen tolerance for ME20628 in $T_2$ and $T_3$ was conducted under the same conditions as described in Examples 2 and 3. In this study, the seedling photosynthetic efficiency was measured as Fv/Fm comparing transgenic plants within an event to non-transgenic segregants pooled across the same plate. Two events, -03 and -04, showed significantly increased photosynthetic efficiency on low nitrate-containing media relative to the internal controls in both generations at p≤0.05 using a one-tailed t-test assuming unequal variance. A summary of photosynthetic efficiency of ME20628 seedlings is shown in Table 72. ME20628 events were also tested for enhanced growth on the low nitrate media as well as for increased photosynthetic efficiency and enhanced growth on low ammonium nitrate media. No significant differences between the transgenics and the controls were observed.

TABLE 72 t-test comparison of seedling photosynthetic efficiency between transgenic seedlings and pooled non-transgenic segregants after 14 days of growth on low nitrate media.

| Line | Events | Transgenic Fv/Fm | n | Pooled Non-Transgenics Fv/Fm | n | t-test p-value |
|---|---|---|---|---|---|---|
| ME20628 | ME20628-03 ($T_2$) | 0.62771 | 42 | 0.58957 | 7 | $9.94 \times 10^{-3}$ |
| ME20628 | ME20628-03 ($T_3$) | 0.64375 | 20 | 0.61914 | 28 | $2.97 \times 10^{-2}$ |
| ME20628 | ME20628-04 ($T_2$) | 0.62439 | 38 | 0.59667 | 12 | $4.78 \times 10^{-2}$ |
| ME20628 | ME20628-04 ($T_3$) | 0.64768 | 22 | 0.61360 | 25 | $9.93 \times 10^{-4}$ |

Events -03 and -04 segregated 3:1 (R:S) for FINALE™ resistance in the $T_2$ generation.

Events -03 and -04 of ME20628 exhibited no statistically relevant negative phenotypes. That is, there was no detectable reduction in germination rate, the transgenic plants appeared wild type in all instances; there was no observable or statistical differences between transgenics and controls in days to flowering; there was no observable or statistical differences between transgenics and controls in the size of the rosette area 7 days post-bolting; and there was no observable or statistical differences between transgenics and controls in fertility (silique number and seed fill).

Example 67

Determination of Functional Homologs by Reciprocal BLAST

A candidate sequence was considered a functional homolog of a reference sequence if the candidate and reference sequences encoded proteins having a similar function and/or activity. A process known as Reciprocal BLAST (Rivera et al. (1998) *Proc. Natl. Acad. Sci. USA*, 95:6239-6244) was used to identify potential functional homolog sequences from databases consisting of all available public and proprietary peptide sequences, including NR from NCBI and peptide translations from Ceres clones.

Before starting a Reciprocal BLAST process, a specific reference polypeptide was searched against all peptides from its source species using BLAST in order to identify polypeptides having BLAST sequence identity of 80% or greater to the reference polypeptide and an alignment length of 85% or greater along the shorter sequence in the alignment. The reference polypeptide and any of the aforementioned identified polypeptides were designated as a cluster.

The BLASTP version 2.0 program from Washington University at Saint Louis, Mo., USA was used to determine BLAST sequence identity and E-value. The BLASTP version 2.0 program includes the following parameters: 1) an E-value cutoff of 1.0e-5; 2) a word size of 5; and 3) the -postsw option. The BLAST sequence identity was calculated based on the alignment of the first BLAST HSP (High-scoring Segment Pairs) of the identified potential functional homolog sequence with a specific reference polypeptide. The number of identically matched residues in the BLAST HSP alignment was divided by the HSP length, and then multiplied by 100 to get the BLAST sequence identity. The HSP length typically included gaps in the alignment, but in some cases gaps were excluded.

The main Reciprocal BLAST process consists of two rounds of BLAST searches; forward search and reverse search. In the forward search step, a reference polypeptide sequence, "polypeptide A," from source species SA was BLASTed against all protein sequences from a species of interest. Top hits were determined using an E-value cutoff of $10^{-5}$ and a sequence identity cutoff of 35%. Among the top hits, the sequence having the lowest E-value was designated as the best hit, and considered a potential functional homolog or ortholog. Any other top hit that had a sequence identity of 80% or greater to the best hit or to the original reference polypeptide was considered a potential functional homolog or ortholog as well. This process was repeated for all species of interest.

In the reverse search round, the top hits identified in the forward search from all species were BLASTed against all protein sequences from the source species SA. A top hit from the forward search that returned a polypeptide from the aforementioned cluster as its best hit was also considered as a potential functional homolog.

Functional homologs were identified by manual inspection of potential functional homolog sequences. Representative functional homologs for SEQ ID NO:3, SEQ ID NO:49, SEQ ID NO:77, SEQ ID NO:100, SEQ ID NO:152, SEQ ID NO:166, SEQ ID NO:186, SEQ ID NO:208, SEQ ID NO:218, SEQ ID NO:234, SEQ ID NO:246, SEQ ID NO:300, SEQ ID NO:332, SEQ ID NO:368, SEQ ID NO:510, SEQ ID NO:533, SEQ ID NO:558, SEQ ID NO:593, SEQ ID NO:613, SEQ ID NO:646, SEQ ID NO:687, SEQ ID NO:730, SEQ ID NO:746, SEQ ID NO:769, SEQ ID NO:792, SEQ ID NO:824, SEQ ID NO:828, SEQ ID NO:855, SEQ ID NO:891, SEQ ID NO:917, SEQ ID NO:944, SEQ ID NO:976, SEQ ID NO:982, SEQ ID NO:1054, SEQ ID NO:1099, SEQ ID NO:1112, SEQ ID NO:1116, SEQ ID NO:1159, SEQ ID NO:1166, SEQ ID NO:1185, SEQ ID NO:1194, SEQ ID NO:1210, SEQ ID NO:1274, SEQ ID NO:1302, SEQ ID NO:1342, SEQ ID NO:1385, SEQ ID NO:1409, SEQ ID NO:1428, SEQ ID NO:1463, SEQ ID NO:1491, SEQ ID NO:1510, SEQ ID NO:1525, SEQ ID NO:1537, SEQ ID NO:1554, SEQ ID NO:1577, and SEQ ID NO:1437 are shown in FIGS. 1-57, respectively. Additional exemplary homologs are correlated to certain Figures in the Sequence Listing.

Example 68

Determination of Functional Homologs by Hidden Markov Models

Hidden Markov Models (HMMs) were generated by the program HMMER 2.3.2. To generate each HMM, the default HMMER 2.3.2 program parameters, configured for global alignments, were used.

An HMM was generated using the sequences shown in FIG. 1 as input. These sequences were fitted to the model and a representative HMM bit score for each sequence is shown in the Sequence Listing. Additional sequences were fitted to the model, and representative HMM bit scores for any such additional sequences are shown in the Sequence Listing. The results indicate that these additional sequences are functional homologs of SEQ ID NO:3.

The procedure above was repeated and an HMM was generated for each group of sequences shown in FIGS. 2-57, using the sequences shown in each Figure as input for that HMM. A representative bit score for each sequence is shown in the Sequence Listing. Additional sequences were fitted to certain HMMs, and representative HMM bit scores for such additional sequences are shown in the Sequence Listing. The results indicate that these additional sequences are functional homologs of the sequences used to generate that HMM.

VIII. Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US10428344B2). An electronic copy of the "Sequence Listing" will also be available from the USPTO upon request and payment of the fee set forth in 37 CFR 1.19(b)(3).

What is claimed is:

1. A method of producing a plant, said method comprising growing a plant cell comprising an exogenous nucleic acid molecule, said exogenous nucleic acid molecule comprising a regulatory region operably linked to a nucleotide sequence encoding a polypeptide, said polypeptide comprising an amino acid sequence having 80 percent or greater sequence identity to the amino acid sequence of SEQ ID NO:5752, and wherein said plant has a difference in the level of low-nitrogen tolerance as compared to the corresponding level of low-nitrogen tolerance of a control plant that does not comprise said nucleic acid molecule.

2. A method of producing a plant, said method comprising growing a plant cell comprising an exogenous nucleic acid molecule, said exogenous nucleic acid molecule comprising a regulatory region operably linked to a nucleotide sequence encoding a polypeptide, the nucleotide sequence comprising a nucleic acid sequence having 80 percent or greater sequence identity to the nucleic acid sequence of SEQ ID NO:5751, wherein a plant produced from said plant cell has a difference in the level of low-nitrogen tolerance as compared to the corresponding level of low-nitrogen tolerance of a control plant that does not comprise said nucleic acid molecule.

3. The method of claim 1 or 2, wherein the polypeptide comprises a SRF-type transcription factor domain.

4. The method of claim 1, wherein the polypeptide comprises the amino acid sequence of SEQ ID NO:5752, wherein a tissue of a plant produced from said plant cell has a difference in the level of low-nitrogen tolerance as compared to the corresponding level of low-nitrogen tolerance of a control plant that does not comprise said nucleic acid molecule.

5. A method of modulating the level of low-nitrogen tolerance in a plant, said method comprising introducing into a plant cell an exogenous nucleic acid molecule, said exogenous nucleic acid molecule comprising a regulatory region operably linked to a nucleotide sequence encoding a polypeptide, said polypeptide comprising an amino acid sequence having 80 percent or greater sequence identity to the amino acid sequence of SEQ ID NO:5752, and wherein a tissue of a plant produced from said plant cell has a difference in the level of low-nitrogen tolerance as compared to the corresponding level of low-nitrogen tolerance of a control plant that does not comprise said exogenous nucleic acid molecule.

6. A method of modulating the level of low-nitrogen tolerance in a plant, said method comprising introducing into a plant cell an exogenous nucleic acid molecule, said exogenous nucleic acid molecule comprising a regulatory region operably linked to a nucleotide sequence encoding a polypeptide, the nucleotide sequence comprising a nucleic acid sequence having 80 percent or greater sequence identity to the nucleic acid sequence of SEQ ID NO: 5751, wherein a tissue of a plant produced from said plant cell has a difference in the level of low-nitrogen tolerance as compared to the corresponding level of low-nitrogen tolerance of a control plant that does not comprise said nucleic acid molecule.

7. The method of claim 5, wherein said polypeptide comprises the amino acid sequence of SEQ ID NO:5752.

8. The method of claim 6, wherein the nucleic acid molecule comprises the nucleic acid sequence of SEQ ID NO: 5751.

9. A plant cell comprising an exogenous nucleic acid molecule, said exogenous nucleic acid molecule comprising a regulatory region operably linked to a nucleotide sequence encoding a polypeptide, said polypeptide comprising an amino acid sequence having 80 percent or greater sequence identity to the amino acid sequence of SEQ ID NO:5752, and wherein said plant cell has a difference in the level of low-nitrogen tolerance as compared to the corresponding level of low-nitrogen tolerance of a control plant that does not comprise said nucleic acid molecule.

10. A plant cell comprising an exogenous nucleic acid molecule said exogenous nucleic acid molecule comprising a regulatory region operably linked to a nucleotide sequence encoding a polypeptide, the nucleotide sequence comprising a nucleic acid sequence having 80 percent or greater sequence identity to the nucleic acid sequence of SEQ ID NO: 5751, wherein a tissue of a plant produced from said plant cell has a difference in the level of low-nitrogen tolerance as compared to the corresponding level of low-nitrogen tolerance of a control plant that does not comprise said nucleic acid molecule.

11. A transgenic plant comprising the plant cell of claim 9 or 10.

12. The transgenic plant of claim 11, wherein said plant is a member of a species selected from the group consisting of *Panicum virgatum* (switchgrass), *Sorghum bicolor* (sorghum, sudangrass), *Miscanthus giganteus* (miscanthus), *Saccharum* sp. (energycane), *Populus balsamifera* (poplar), *Zea mays* (corn), *Glycine max* (soybean), *Brassica napus* (canola), *Triticum aestivum* (wheat), *Gossypium hirsutum* (cotton), *Oryza sativa* (rice), *Helianthus annuus* (sunflower), *Medicago sativa* (alfalfa), *Beta vulgaris* (sugarbeet), or *Pennisetum glaucum* (pearl millet).

13. A product comprising plant tissue from a transgenic plant according to claims 12.

14. The plant cell of claim 9, wherein the polypeptide comprises the amino acid sequence of SEQ ID NO:5752.

15. The plant cell of claim 10, wherein the nucleotide sequence comprises the nucleic acid sequence of SEQ ID NO: 5751.

* * * * *